United States Patent
Wang

(10) Patent No.: US 8,669,361 B2
(45) Date of Patent: Mar. 11, 2014

(54) PYRAZOL-4-YL-HETEROCYCLYL-CARBOXAMIDE COMPOUNDS AND METHODS OF USE

(71) Applicant: Genentech, Inc., South San Francisco, CA (US)

(72) Inventor: Xiaojing Wang, Foster City, CA (US)

(73) Assignee: F. Hoffmann-La Roche AG, Basel (CH)

( * ) Notice: Subject to any disclaimer, the term of this patent is extended or adjusted under 35 U.S.C. 154(b) by 0 days.

(21) Appl. No.: 13/834,316

(22) Filed: Mar. 15, 2013

(65) Prior Publication Data

US 2013/0203732 A1 Aug. 8, 2013

Related U.S. Application Data

(62) Division of application No. 13/080,762, filed on Apr. 6, 2011, now Pat. No. 8,436,001.

(60) Provisional application No. 61/321,588, filed on Apr. 7, 2010.

(51) Int. Cl.
C07D 239/00 (2006.01)
(52) U.S. Cl.
USPC ...... 544/333; 544/405; 546/275.4; 548/364.1
(58) Field of Classification Search
USPC ........................................ 548/364.1
See application file for complete search history.

(56) References Cited

U.S. PATENT DOCUMENTS

| | | |
|---|---|---|
| 2009/0163486 A1 | 6/2009 | Ulrich et al. |
| 2009/0197866 A1 | 8/2009 | Cherrier et al. |
| 2009/0203715 A1 | 8/2009 | Bothe et al. |
| 2009/0263398 A1 | 10/2009 | Lyons et al. |
| 2009/0318430 A1 | 12/2009 | Pike et al. |
| 2010/0004232 A1 | 1/2010 | Berdini et al. |
| 2010/0021420 A1 | 1/2010 | Lyons et al. |
| 2010/0130465 A1 | 5/2010 | Shipps et al. |
| 2010/0249088 A1 | 9/2010 | Sugasawa et al. |

FOREIGN PATENT DOCUMENTS

| | | |
|---|---|---|
| WO | 2008/054749 A1 | 5/2008 |
| WO | 2008/090382 A1 | 7/2008 |
| WO | 2008/106692 A1 | 9/2008 |
| WO | 2009/074246 A1 | 6/2009 |
| WO | 2009/074247 A1 | 6/2009 |
| WO | 2009/077954 A1 | 6/2009 |
| WO | 2009/093012 A1 | 7/2009 |
| WO | 2009/109576 A1 | 9/2009 |
| WO | 2011/003065 A2 | 1/2011 |
| WO | 2011/050305 A1 | 4/2011 |
| WO | 2011/089132 A1 | 7/2011 |
| WO | 2011/154327 A1 | 12/2011 |

OTHER PUBLICATIONS

Anizon et al., "Fighting tumor cell survival: advances in the design and evaluation of Pim inhibitors" Curr Med Chem. 17:4114-33 ( 2010).
CAS Registry Database, Accession No. 0017538818, Mar. 9, 2011.
CAS Registry Database, Accession No. 0017578774, Mar. 9, 2011.
CAS Registry Database, Accession No. 0059896570, Mar. 9, 2011.
CAS Registry Database, Accession No. 0060579904, Apr. 9, 2011.
CAS Registry Database, Accession No. 0064871203, Mar. 9, 2011.
Velaparthi et al., "5-tert-butyl-N-pyrazol-4-yl-4,5,6,7-tetrahydrobenzo[d]isoxazole-3-carboxamide derivatives as novel potent inhibitors of Mycobacterium tuberculosis pantothenate synthetase: initiating a quest for new antitubercular drugs" J Med Chem. 51:1999-2002 ( 2008).
Warmuth et al., "Ba/F3 cells and their use in kinase drug discovery" Curr Opin Oncol 19(1):55-60 (Jan. 2007).

Primary Examiner — Brian McDowell
(74) Attorney, Agent, or Firm — Alex Andrus; Genentech, Inc.

(57) ABSTRACT

Pyrazol-4-yl-heterocyclyl-carboxamide compounds of Formula I, including stereoisomers, geometric isomers, tautomers, and pharmaceutically acceptable salts thereof, wherein X is a thiazolyl, picolinyl, pyridinyl, or pyrimidinyl, are useful for inhibiting Pim kinase, and for treating disorders such as cancer mediated by Pim kinase. Methods of using compounds of Formula I for in vitro, in situ, and in vivo diagnosis, prevention or treatment of such disorders in mammalian cells, or associated pathological conditions, are disclosed.

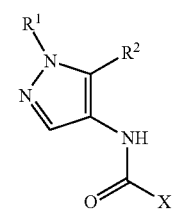

16 Claims, 3 Drawing Sheets

PYRAZOL-4-YL-HETEROCYCLYL-CARBOXAMIDE COMPOUNDS AND METHODS OF USE

CROSS REFERENCE TO RELATED APPLICATIONS

This application is a divisional of U.S. Ser. No. 13/080,762 filed on 6 Apr. 2011, and claims the benefit under 35 USC §119(e) of U.S. Provisional Application Ser. No. 61/321,588 filed on 7 Apr. 2010, which is incorporated by reference in entirety

FIELD OF THE INVENTION

The invention relates generally to pyrazol-4-yl-heterocyclyl-carboxamide compounds for treating disorders mediated by Pim kinase (Pim-1, Pim-2, and/or Pim-3) inhibitors, thus useful as cancer therapeutics. The invention also relates to compositions, more specifically pharmaceutical compositions comprising these compounds and methods of using the same, either alone or in combination, to treat various forms of cancer and hyperproliferative disorders, as well as methods of using the compounds for in vitro, in situ, and in vivo diagnosis or treatment of mammalian cells, or associated pathological conditions.

BACKGROUND OF THE INVENTION

Pim kinases are family of three highly-related serine and threonine protein kinases encoded by the genes Pim-1, Pim-2, and Pim-3. The gene names are derived from the phrase Proviral Insertion, Moloney, frequent integration sites for murine moloney virus wherein the insertions lead to overexpression of Pim kinases and either de novo T-cell lymphomas, or dramatic acceleration of tumorigenesis in a transgenic Myc-driven lymphoma model (Cuypers et al. (1984) Cell, vol. 37 (1) pp. 141-50; Selten et al. (1985) EMBO J. vol. 4 (7) pp. 1793-8; van der Lugt et al. (1995) EMBO J. vol. 14 (11) pp. 2536-44; Mikkers et al. (2002) Nature Genetics, vol. 32 (1) pp. 153-9; van Lohuizen et al. (1991) Cell, vol. 65 (5) pp. 737-52). These experiments reveal synergy with the oncogene c-Myc, and suggest that inhibition of the Pim kinases may have therapeutic benefit.

Mouse genetics suggests that antagonizing Pim kinases may have an acceptable safety profile; a Pim 1–/–; Pim-2–/–, Pim-3–/– mouse knockout is viable although slightly smaller than wild type littermates (Mikkers et al. (2004) Mol Cell Biol vol. 24 (13) pp. 6104-154). The three genes give rise to six protein isoforms including a protein kinase domain, and apparently without recognizable regulatory domains. All six isoforms are constitutively active protein kinases that do not require post-translational modification for activity, thus Pim kinases are regulated primarily at the transcriptional level (Qian et al. (2005) J Biol Chem, vol. 280 (7) pp. 6130-7). Pim kinase expression is highly inducible by cytokines and growth factors receptors and Pims are direct transcriptional targets of the Stat proteins, including Stat3 and Stat5. Pim-1, for example, is required for the l30-mediated Stat3 proliferation signal (Aksoy et al. (2007) Stem Cells, vol. 25 (12) pp. 2996-3004; Hirano et al. (2000) Oncogene vol. 19 (21) pp. 2548-56; Shirogane et al. (1999) Immunity vol. 11 (6) pp. 709-19).

Pim kinases function in cellular proliferation and survival pathways parallel to the PI3k/Akt/mTOR signaling axis (Hammerman et al. (2005) Blood vol. 105 (11) pp. 4477-83). Indeed, several of the phosphorylation targets of the PI3k axis including Bad and eIF4E-BP1 are cell growth and apoptosis regulators and are also phosphorylation targets of the Pim kinases (Fox et al. (2003) Genes Dev vol. 17 (15) pp. 1841-54; Macdonald et al. (2006) Cell Biol vol. 7 pp. 1; Aho et al. (2004) FEBS Letters vol. 571 (1-3) pp. 43-9; Tamburini et al. (2009) Blood vol. 114 (8) pp. 1618-27). Pim kinase may affect cell survival since phosphorylation of Bad increases Bcl-2 activity and therefore promotes cell survival. Likewise, phosphorylation of eIF4E-BP1 by mTOR or Pim kinases causes depression of eIF4E, promoting mRNA translation and cellular growth. In addition, Pim-1 has been recognized to promote cell cycle progression through phosphorylation of CDC25A, p21, and Cdc25C (Mochizuki et al. (1999) J Biol Chem vol. 274 (26) pp. 18659-66; Bachmann et al. (2006) Int J Biochem Cell Biol vol. 38 (3) pp. 430-43; Wang et al. (2002) Biochim Biophys Acta vol. 1593 (1) pp. 45-55.

Pim kinases show synergy in transgenic mouse models with c-Myc-driven and Akt-driven tumors (Verbeek et al. (1991) Mol Cell Biol vol. 11 (2) pp. 1176-9; Allen et al. Oncogene (1997) vol. 15 (10) pp. 1133-41; Hammerman et al. (2005) Blood vol. 105 (11) pp. 4477-83). Pim Kinases are involved in transforming activity of oncogenes identified in acute myeloid leukemia (AML) including Flt3-ITD, BCR-abl, and Tel-Jak2. Expression of these oncogenes in BaF3 cells results in upregulation of Pim-1 and Pim-2 expression, resulting in IL-3 independent growth, and subsequent Pim inhibition results in apoptosis and cell growth arrest (Adam et al. (2006) Cancer Research vol. 66 (7) pp. 3828-35). Pim overexpression and dysregulation has also been noted as a frequent event in many hematopoietic cancers, including leukemias and lymphoma (Amson et al. (1989) Proc Natl Acad Sci USA vol. 86 (22) pp. 8857-61); Cohen et al. (2004) Leuk Lymphoma vol. 45 (5) pp. 951-5; Hiittmann et al. (2006) Leukemia vol. 20 (10) pp. 1774-82) as well as multiple myeloma (Claudio et al. (2002) Blood vol. 100 (6) pp. 2175-86. Pim 1 has been shown to be overexpressed and correlated to prostate cancer progression (Cibull et al. (2006) J Clin Pathol vol. 59 (3) pp. 285-8; Dhanasekaran et al. (2001) Nature vol. 412 (6849) pp. 822-6). Pim 1 expression increases in mouse models with disease progression (Kim et al. (2002) Proc Natl Acad Sci USA vol. 99 (5) pp. 2884-9). Pim-1 has been reported to be the most highly overexpressed mRNA in the subset of human prostate tumor samples which have a c-Myc-driven gene signature (Ellwood-Yen et al. (2003) Cancer Cell vol. 4 (3) pp. 223-38). Pim-3 has been also been shown to be overexpressed and to have a functional role in pancreatic cancer and hepatocellular carcinoma (Li et al. (2006) Cancer Research vol. 66 (13) pp. 6741-7; Fujii et al. (2005) Int J Cancer, vol. 114 (2) pp. 209-18.

Beyond oncology therapeutic and diagnostic applications, Pim kinases could play an important role in normal immune system function and Pim inhibition could be therapeutic for a number of different immunologic pathologies including inflammation, autoimmune conditions, allergy, and immune suppression for organ transplantation (Aho et al. Expression of human Pim family genes is selectively up-regulated by cytokines promoting T helper type 1, but not T helper type 2, cell differentiation. Immunology (2005) vol. 116 (1) pp. 82-8).

SUMMARY OF THE INVENTION

The invention relates to pyrazol-4-yl-heterocyclyl-carboxamide compounds for treating disorders mediated by Pim kinase (Pim-1, Pim-2, and/or Pim-3) inhibitors Formula I compounds.

Formula I compounds have the structure:

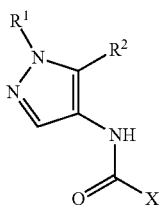

I and stereoisomers, geometric isomers, tautomers, and pharmaceutically acceptable salts thereof. The various substituents, including $R^1$, $R^2$, $R^3$, $R^4$, $R^5$, $R^6$, $R^7$, and X are as defined herein.

Formula I compounds include compounds Formula Ia, Ib, Ic, and Id, having the structures:

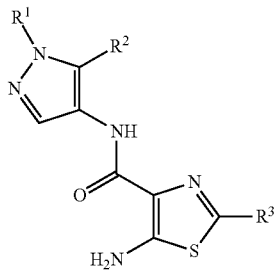

Ia

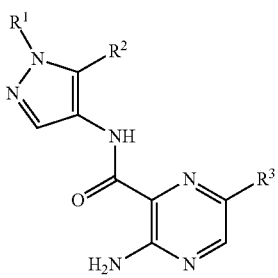

Ib

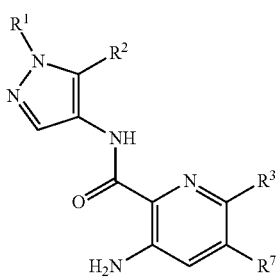

Ic

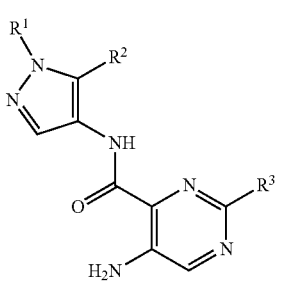

Id

One aspect of the invention is a pharmaceutical composition comprised of a Formula I compound and a pharmaceutically acceptable carrier, glidant, diluent, or excipient. The pharmaceutical composition may further comprise a second chemotherapeutic agent.

Another aspect of the invention is a process for making a pharmaceutical composition which comprises combining a Formula I compound with a pharmaceutically acceptable carrier.

The invention includes a method of treating a disease or disorder which method comprises administering a therapeutically effective amount of a Formula I compound to a patient with a disease or disorder selected from cancer, immune disorders, cardiovascular disease, viral infection, inflammation, metabolism/endocrine function disorders and neurological disorders, and mediated by Pim kinase. The method includes further administering an additional therapeutic agent selected from a chemotherapeutic agent, an anti-inflammatory agent, an immunomodulatory agent, a neurotropic factor, an agent for treating cardiovascular disease, an agent for treating liver disease, an anti-viral agent, an agent for treating blood disorders, an agent for treating diabetes, and an agent for treating immunodeficiency disorders.

The invention includes a kit for treating a condition mediated by Pim kinase, comprising: a) a first pharmaceutical composition comprising a Formula I compound; and b) instructions for use.

The invention includes a Formula I compound for use as a medicament, and for use in treating a disease or disorder selected from cancer, immune disorders, cardiovascular disease, viral infection, inflammation, metabolism/endocrine function disorders and neurological disorders, and mediated by Pim kinase.

The invention includes use of a Formula I compound in the manufacture of a medicament for the treatment of cancer, immune disorders, cardiovascular disease, viral infection, inflammation, metabolism/endocrine function disorders and neurological disorders, and where the medicament mediates Pim kinase.

The invention includes methods of making a Formula I compound.

DETAILED DESCRIPTION OF EXEMPLARY EMBODIMENTS

Figure 1:
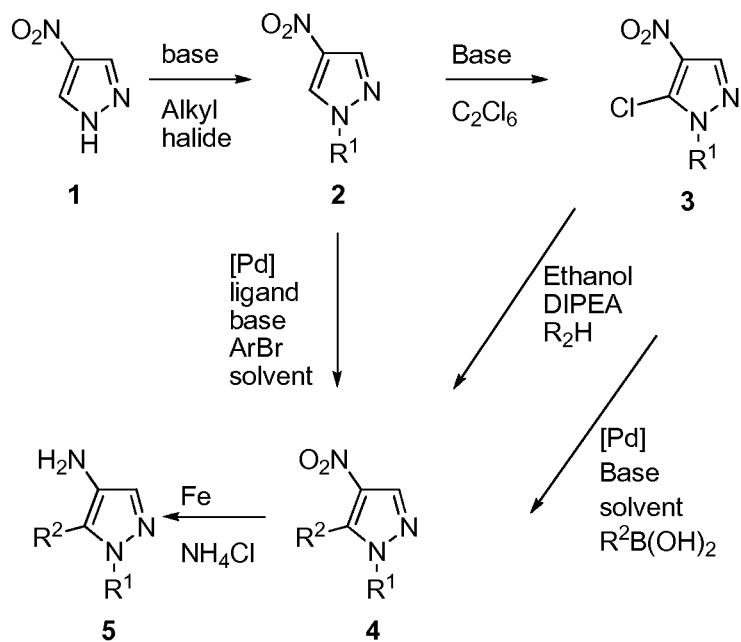
FIG. 1 shows an exemplary synthesis of 4-aminopyrazole compounds 5 from nitro-1H-pyrazole 1.

Reference will now be made in detail to certain embodiments of the invention, examples of which are illustrated in the accompanying structures and formulas. While the invention will be described in conjunction with the enumerated embodiments, it will be understood that they are not intended to limit the invention to those embodiments. On the contrary, the invention is intended to cover all alternatives, modifications, and equivalents which may be included within the scope of the present invention as defined by the claims. One skilled in the art will recognize many methods and materials similar or equivalent to those described herein, which could be used in the practice of the present invention. The present invention is in no way limited to the methods and materials described. In the event that one or more of the incorporated literature, patents, and similar materials differs from or contradicts this application, including but not limited to defined terms, term usage, described techniques, or the like, this application controls.

DEFINITIONS

The term "alkyl" as used herein refers to a saturated linear or branched-chain monovalent hydrocarbon radical of one to twelve carbon atoms ($C_1$-$C_{12}$), wherein the alkyl radical may be optionally substituted independently with one or more substituents described below. In another embodiment, an alkyl radical is one to eight carbon atoms ($C_1$-$C_8$), or one to six carbon atoms ($C_1$-$C_6$). Examples of alkyl groups include, but are not limited to, methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —$CH(CH_3)_2$), 1-butyl (n-Bu, n-butyl, —$CH_2CH_2CH_2CH_3$), 2-methyl-1-propyl (i-Bu, i-butyl, —$CH_2CH(CH_3)_2$), 2-butyl (s-Bu, s-butyl, —$CH(CH_3)$ $CH_2CH_3$), 2-methyl-2-propyl (t-Bu, t-butyl, —$C(CH_3)_3$), 1-pentyl (n-pentyl, —$CH_2CH_2CH_2CH_2CH_3$), 2-pentyl (—$CH(CH_3)CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)CH(CH_3)_2$), 3-methyl-1-butyl (—$CH_2CH_2CH$ $(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—$CH$ $(CH_3)CH_2CH_2CH_2CH_3$), 3-hexyl (—$CH(CH_2CH_3)$ $(CH_2CH_2CH_3)$), 2-methyl-2-pentyl (—$C(CH_3)_2$ $CH_2CH_2CH_3$), 3-methyl-2-pentyl (—$CH(CH_3)CH(CH_3)$ $CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C$ $(CH_3)_2CH(CH_3)_2$), 3,3-dimethyl-2-butyl (—$CH(CH_3)C$ $(CH_3)_3$, 1-heptyl, 1-octyl, and the like.

The term "alkylene" as used herein refers to a saturated linear or branched-chain divalent hydrocarbon radical of one to twelve carbon atoms ($C_1$-$C_{12}$), wherein the alkylene radical may be optionally substituted independently with one or more substituents described below. In another embodiment, an alkylene radical is one to eight carbon atoms ($C_1$-$C_8$), or one to six carbon atoms ($C_1$-$C_6$). Examples of alkylene groups include, but are not limited to, methylene (—$CH_2$—), ethylene (—$CH_2CH_2$—), propylene (—$CH_2CH_2CH_2$—), and the like.

The term "alkenyl" refers to linear or branched-chain monovalent hydrocarbon radical of two to eight carbon atoms ($C_2$-$C_8$) with at least one site of unsaturation, i.e., a carbon-carbon, $sp^2$ double bond, wherein the alkenyl radical may be optionally substituted independently with one or more substituents described herein, and includes radicals having "cis" and "trans" orientations, or alternatively, "E" and "Z" orientations. Examples include, but are not limited to, ethylenyl or vinyl (—$CH=CH_2$), allyl (—$CH_2CH=CH_2$), and the like.

The term "alkenylene" refers to linear or branched-chain divalent hydrocarbon radical of two to eight carbon atoms ($C_2$-$C_8$) with at least one site of unsaturation, i.e., a carbon-carbon, $sp^2$ double bond, wherein the alkenylene radical may be optionally substituted substituted independently with one or more substituents described herein, and includes radicals having "cis" and "trans" orientations, or alternatively, "E" and "Z" orientations. Examples include, but are not limited to, ethylenylene or vinylene (—$CH=CH$—), allyl (—$CH_2CH=CH$—), and the like.

The term "alkynyl" refers to a linear or branched monovalent hydrocarbon radical of two to eight carbon atoms ($C_2$-$C_8$) with at least one site of unsaturation, i.e., a carbon-carbon, sp triple bond, wherein the alkynyl radical may be optionally substituted independently with one or more substituents described herein. Examples include, but are not limited to, ethynyl (—$C≡CH$), propynyl (propargyl, —$CH_2C≡CH$), and the like.

The term "alkynylene" refers to a linear or branched divalent hydrocarbon radical of two to eight carbon atoms ($C_2$-$C_8$) with at least one site of unsaturation, i.e., a carbon-carbon, sp triple bond, wherein the alkynylene radical may be optionally substituted independently with one or more substituents described herein. Examples include, but are not limited to, ethynylene (—$C≡C$—), propynylene (propargylene, —$CH_2C≡C$—), and the like.

The terms "carbocycle", "carbocyclyl", "carbocyclic ring" and "cycloalkyl" refer to a monovalent non-aromatic, saturated or partially unsaturated ring having 3 to 12 carbon atoms ($C_3$-$C_{12}$) as a monocyclic ring or 7 to 12 carbon atoms as a bicyclic ring. Bicyclic carbocycles having 7 to 12 atoms can be arranged, for example, as a bicyclo[4,5], [5,5], [5,6] or [6,6] system, and bicyclic carbocycles having 9 or 10 ring atoms can be arranged as a bicyclo[5,6] or [6,6] system, or as bridged systems such as bicyclo[2.2.1]heptane, bicyclo [2.2.2]octane and bicyclo[3.2.2]nonane. Spiro moieties are also included within the scope of this definition. Examples of monocyclic carbocycles include, but are not limited to, cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl, cyclododecyl, and the like. Carbocyclyl groups are optionally substituted independently with one or more substituents described herein.

"Aryl" means a monovalent aromatic hydrocarbon radical of 6-20 carbon atoms ($C_6$-$C_{20}$) derived by the removal of one hydrogen atom from a single carbon atom of a parent aromatic ring system. Some aryl groups are represented in the exemplary structures as "Ar". Aryl includes bicyclic radicals comprising an aromatic ring fused to a saturated, partially unsaturated ring, or aromatic carbocyclic ring. Typical aryl groups include, but are not limited to, radicals derived from benzene (phenyl), substituted benzenes, naphthalene, anthracene, biphenyl, indenyl, indanyl, 1,2-dihydronaphthalene, 1,2,3,4-tetrahydronaphthyl, and the like. Aryl groups are optionally substituted independently with one or more substituents described herein.

"Arylene" means a divalent aromatic hydrocarbon radical of 6-20 carbon atoms ($C_6$-$C_{20}$) derived by the removal of two hydrogen atom from a two carbon atoms of a parent aromatic ring system. Some arylene groups are represented in the exemplary structures as "Ar". Arylene includes bicyclic radicals comprising an aromatic ring fused to a saturated, partially unsaturated ring, or aromatic carbocyclic ring. Typical arylene groups include, but are not limited to, radicals derived from benzene (phenylene), substituted benzenes, naphthalene, anthracene, biphenylene, indenylene, indanylene, 1,2-dihydronaphthalene, 1,2,3,4-tetrahydronaphthyl, and the like. Arylene groups are optionally substituted with one or more substituents described herein.

The terms "heterocycle," "heterocyclyl" and "heterocyclic ring" are used interchangeably herein and refer to a saturated or a partially unsaturated (i.e., having one or more double and/or triple bonds within the ring) carbocyclic radical of 3 to about 20 ring atoms in which at least one ring atom is a heteroatom selected from nitrogen, oxygen, phosphorus and sulfur, the remaining ring atoms being C, where one or more ring atoms is optionally substituted independently with one or more substituents described below. A heterocycle may be a monocycle having 3 to 7 ring members (2 to 6 carbon atoms and 1 to 4 heteroatoms selected from N, O, P, and S) or a bicycle having 7 to 10 ring members (4 to 9 carbon atoms and 1 to 6 heteroatoms selected from N, O, P, and S), for example: a bicyclo[4,5], [5,5], [5,6], or [6,6] system. Heterocycles are described in Paquette, Leo A.; "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and J. Am. Chem. Soc. (1960) 82:5566. "Heterocyclyl" also includes radicals where heterocycle radicals are fused with a saturated, partially unsaturated ring, or aromatic carbocyclic or heterocyclic ring. Examples of heterocyclic rings include, but are not limited to, morpholin-4-yl, piperidin-1-yl, piperazinyl, piperazin-4-yl-2-one, piperazin-4-yl-3-one, pyrrolidin-1-yl, thiomorpholin-4-yl, S-dioxothiomorpholin-4-yl, azocan-1-yl, azetidin-1-yl, octahydropyrido[1,2-a]pyrazin-2-yl, [1,4]diazepan-1-yl, pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, homopiperazinyl, azetidinyl, oxetanyl, thietanyl, homopiperidinyl, oxepanyl, thiepanyl, oxazepinyl, diazepinyl, thiazepinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinylimidazolinyl, imidazolidinyl, 3-azabicyco[3.1.0]hexanyl, 3-azabicyclo[4.1.0]heptanyl, azabicyclo[2.2.2]hexanyl, 3H-indolyl quinolizinyl and N-pyridyl ureas. Spiro moieties are also included within the scope of this definition. Examples of a heterocyclic group wherein 2 ring atoms are substituted with oxo (=O) moieties are pyrimidinonyl and 1,1-dioxo-thiomorpholinyl. The heterocycle groups herein are optionally substituted independently with one or more substituents described herein.

The term "heteroaryl" refers to a monovalent aromatic radical of 5-, 6-, or 7-membered rings, and includes fused ring systems (at least one of which is aromatic) of 5-20 atoms, containing one or more heteroatoms independently selected from nitrogen, oxygen, and sulfur. Examples of heteroaryl groups are pyridinyl (including, for example, 2-hydroxypyridinyl), imidazolyl, imidazopyridinyl, pyrimidinyl (including, for example, 4-hydroxypyrimidinyl), pyrazolyl, triazolyl, pyrazinyl, tetrazolyl, furyl, thienyl, isoxazolyl, thiazolyl, oxadiazolyl, oxazolyl, isothiazolyl, pyrrolyl, quinolinyl, isoquinolinyl, tetrahydroisoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, triazolyl, thiadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. Heteroaryl groups are optionally substituted independently with one or more substituents described herein.

The heterocycle or heteroaryl groups may be carbon (carbon-linked), or nitrogen (nitrogen-linked) bonded where such is possible. By way of example and not limitation, carbon bonded heterocycles or heteroaryls are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline.

By way of example and not limitation, nitrogen bonded heterocycles or heteroaryls are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or β-carboline.

The terms "treat" and "treatment" refer to both therapeutic treatment and prophylactic or preventative measures, wherein the object is to prevent or slow down (lessen) an undesired physiological change or disorder, such as the development or spread of cancer. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

The phrase "therapeutically effective amount" means an amount of a compound of the present invention that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the drug may prevent growth and/or kill existing cancer cells, it may be cytostatic and/or cytotoxic. For cancer therapy, efficacy can be measured, for example, by assessing the time to disease progression (TTP) and/or determining the response rate (RR).

The terms "cancer" refers to or describe the physiological condition in mammals that is typically characterized by unregulated cell growth. A "tumor" comprises one or more cancerous cells. Examples of cancer include, but are not limited to, carcinoma, lymphoma, blastoma, sarcoma, and leukemia or lymphoid malignancies. More particular examples of such cancers include squamous cell cancer (e.g., epithelial squamous cell cancer), lung cancer including small-cell lung cancer, non-small cell lung cancer ("NSCLC"), adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, as well as head and neck cancer.

A "chemotherapeutic agent" is a chemical compound useful in the treatment of cancer, regardless of mechanism of action. Classes of chemotherapeutic agents include, but are not limited to: alkylating agents, antimetabolites, spindle poison plant alkaloids, cytotoxic/antitumor antibiotics, topoisomerase inhibitors, antibodies, photosensitizers, and kinase inhibitors. Chemotherapeutic agents include compounds used in "targeted therapy" and conventional chemotherapy. Examples of chemotherapeutic agents include: erlotinib (TARCEVA®, Genentech/OSI Pharm.), docetaxel (TAXOTERE®, Sanofi-Aventis), 5-FU (fluorouracil, 5-fluorouracil, CAS No. 51-21-8), gemcitabine (GEMZAR®, Lilly), PD-0325901 (CAS No. 391210-10-9, Pfizer), cisplatin (cis-diamine, dichloroplatinum(II), CAS No. 15663-27-1), carboplatin (CAS No. 41575-94-4), paclitaxel (TAXOL®, Bristol-Myers Squibb Oncology, Princeton, N.J.), trastuzumab (HERCEPTIN®, Genentech), temozolomide (4-methyl-5-oxo-2,3,4,6,8-pentazabicyclo[4.3.0]nona-2,7,9-triene-9-carboxamide, CAS No. 85622-93-1, TEMODAR®, TEMODAL®, Schering Plough), tamoxifen ((Z)-2-[4-(1,2-diphenylbut-1-enyl)phenoxy]-N,N-dimethylethanamine, NOLVADEX®, ISTUBAL®, VALODEX®), and doxorubicin (ADRIAMYCIN®), Akti-1/2, HPPD, and rapamycin.

More examples of chemotherapeutic agents include: oxaliplatin (ELOXATIN®, Sanofi), bortezomib (VELCADE®, Millennium Pharm.), sutent (SUNITINIB®, SU11248, Pfizer), letrozole (FEMARA®, Novartis), imatinib mesylate (GLEEVEC®, Novartis), XL-518 (Mek inhibitor, Exelixis, WO 2007/044515), ARRY-886 (Mek inhibitor, AZD6244, Array BioPharma, Astra Zeneca), SF-1126 (PI3K inhibitor, Semafore Pharmaceuticals), BEZ-235 (PI3K inhibitor, Novartis), XL-147 (PI3K inhibitor, Exelixis), PTK787/ZK 222584 (Novartis), fulvestrant (FASLODEX®, AstraZeneca), leucovorin (folinic acid), rapamycin (sirolimus, RAPAMUNE®, Wyeth), lapatinib (TYKERB®, GSK572016, Glaxo Smith Kline), lonafarnib (SARASAR™, SCH 66336, Schering Plough), sorafenib (NEXAVAR®, BAY43-9006, Bayer Labs), gefitinib (IRESSA®, AstraZeneca), irinotecan (CAMPTOSAR®, CPT-11, Pfizer), tipifarnib (ZARNESTRA™, Johnson & Johnson), ABRAXANE™ (Cremophor-free), albumin-engineered nanoparticle formulations of paclitaxel (American Pharmaceutical Partners, Schaumberg, Il), vandetanib (rINN, ZD6474, ZACTIMA®, AstraZeneca), chloranmbucil, AG1478, AG1571 (SU 5271; Sugen), temsirolimus (TORISEL®, Wyeth), pazopanib (GlaxoSmithKline), canfosfamide (TELCYTA®, Telik), thiotepa and cyclosphosphamide (CYTOXAN®, NEOSAR®); alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including the synthetic analog topotecan); bryostatin; callystatin; CC-1065 (including its adozelesin, carzelesin and bizelesin synthetic analogs); cryptophycins (particularly cryptophycin 1 and cryptophycin 8); dolastatin; duocarmycin (including the synthetic analogs, KW-2189 and CB1-TM1); eleutherobin; pancratistatin; a sarcodictyin; spongistatin; nitrogen mustards such as chlorambucil, chlornaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics (e.g., calicheamicin, calicheamicin gamma1I, calicheamicin omega1I (Angew Chem. Intl. Ed. Engl. (1994) 33:183-186); dynemicin, dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, morpholino-doxorubicin, cyanomorpholino-doxorubicin, 2-pyrrolino-doxorubicin and deoxydoxorubicin), epirubicin, esorubicin, idarubicin, nemorubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; 6-thioguanine; mercaptopurine; methotrexate; platinum analogs such as cisplatin and carboplatin; vinblastine; etoposide (VP-16); ifosfamide; mitoxantrone; vincristine; vinorelbine (NAVELBINE®); novantrone; teniposide; edatrexate; daunomycin; aminopterin; capecitabine (XELODA®, Roche); ibandronate; CPT-11; topoisomerase inhibitor RFS 2000; difluoromethylornithine (DMFO); retinoids such as retinoic acid; and pharmaceutically acceptable salts, acids and derivatives of any of the above.

Also included in the definition of "chemotherapeutic agent" are: (i) anti-hormonal agents that act to regulate or inhibit hormone action on tumors such as anti-estrogens and selective estrogen receptor modulators (SERMs), including, for example, tamoxifen (including NOLVADEX®; tamoxifen citrate), raloxifene, droloxifene, 4-hydroxytamoxifen, trioxifene, keoxifene, LY117018, onapristone, and FARESTON® (toremifine citrate); (ii) aromatase inhibitors that inhibit the enzyme aromatase, which regulates estrogen production in the adrenal glands, such as, for example, 4(5)- imidazoles, aminoglutethimide, MEGASE® (megestrol acetate), AROMASIN® (exemestane; Pfizer), formestanie, fadrozole, RIVISOR® (vorozole), FEMARA® (letrozole; Novartis), and ARIMIDEX® (anastrozole; AstraZeneca); (iii) anti-androgens such as flutamide, nilutamide, bicalutamide, leuprolide, and goserelin; as well as troxacitabine (a 1,3-dioxolane nucleoside cytosine analog); (iv) protein kinase inhibitors such as MEK inhibitors (WO 2007/044515); (v) lipid kinase inhibitors; (vi) antisense oligonucleotides, particularly those which inhibit expression of genes in signaling pathways implicated in aberrant cell proliferation, for example, PKC-alpha, Raf and H-Ras, such as oblimersen (GENASENSE®, Genta Inc.); (vii) ribozymes such as VEGF expression inhibitors (e.g., ANGIOZYME®) and HER2 expression inhibitors; (viii) vaccines such as gene therapy vaccines, for example, ALLOVECTIN®, LEUVECTIN®, and VAXID®; PROLEUKIN® rIL-2; topoisomerase 1 inhibitors such as LURTOTECAN®; ABARELIX® rmRH; (ix) anti-angiogenic agents such as bevacizumab (AVASTIN®, Genentech); and pharmaceutically acceptable salts, acids and derivatives of any of the above.

Also included in the definition of "chemotherapeutic agent" are therapeutic antibodies such as alemtuzumab (Campath), bevacizumab (AVASTIN®, Genentech); cetuximab (ERBITUX®, Imclone); panitumumab (VECTIBIX®, Amgen), rituximab (RITUXAN®, Genentech/Biogen Idec), pertuzumab (OMNITARG™, 2C4, Genentech), trastuzumab (HERCEPTIN®, Genentech), tositumomab (Bexxar, Corixia), and the antibody drug conjugate, gemtuzumab ozogamicin (MYLOTARG®, Wyeth).

Humanized monoclonal antibodies with therapeutic potential as chemotherapeutic agents in combination with the PI3K inhibitors of the invention include: alemtuzumab, apolizumab, aselizumab, atlizumab, bapineuzumab, bevacizumab, bivatuzumab mertansine, cantuzumab mertansine, cedelizumab, certolizumab pegol, cidfusituzumab, cidtuzumab, daclizumab, eculizumab, efalizumab, epratuzumab, erlizumab, felvizumab, fontolizumab, gemtuzumab ozogamicin, inotuzumab ozogamicin, ipilimumab, labetuzumab, lintuzumab, matuzumab, mepolizumab, motavizumab, motovizumab, natalizumab, nimotuzumab, nolovizumab, numavizumab, ocrelizumab, omalizumab, palivizumab, pascolizumab, pecfusituzumab, pectuzumab, pertuzumab, pexelizumab, ralivizumab, ranibizumab, reslivizumab, reslizumab, resyvizumab, rovelizumab, ruplizumab, sibrotuzumab, siplizumab, sontuzumab, tacatuzumab tetraxetan, tadocizumab, talizumab, tefibazumab, tocilizumab, toralizumab, trastuzumab, tucotuzumab celmoleukin, tucusituzumab, umavizumab, urtoxazumab, and visilizumab.

A "metabolite" is a product produced through metabolism in the body of a specified compound or salt thereof. Metabolites of a compound may be identified using routine techniques known in the art and their activities determined using tests such as those described herein. Such products may result for example from the oxidation, reduction, hydrolysis, amidation, deamidation, esterification, deesterification, enzymatic cleavage, and the like, of the administered compound. Accordingly, the invention includes metabolites of compounds of the invention, including compounds produced by a process comprising contacting a Formula I compound of this invention with a mammal for a period of time sufficient to yield a metabolic product thereof.

The term "package insert" is used to refer to instructions customarily included in commercial packages of therapeutic products, that contain information about the indications, usage, dosage, administration, contraindications and/or warnings concerning the use of such therapeutic products.

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

"Diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers may separate under high resolution analytical procedures such as electrophoresis and chromatography.

"Enantiomers" refer to two stereoisomers of a compound which are non-superimposable mirror images of one another.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., "Stereochemistry of Organic Compounds", John Wiley & Sons, Inc., New York, 1994. The compounds of the invention may contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

The phrase "pharmaceutically acceptable salt" as used herein, refers to pharmaceutically acceptable organic or inorganic salts of a compound of the invention. Exemplary salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate "mesylate", ethanesulfonate, benzenesulfonate, p-toluenesulfonate, and pamoate (i.e., 1,1'-methylene-bis(2-hydroxy-3-naphthoate)) salts. A pharmaceutically acceptable salt may involve the inclusion of another molecule such as an acetate ion, a succinate ion or other counter ion.

The counter ion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counter ion.

If the compound of the invention is a base, the desired pharmaceutically acceptable salt may be prepared by any suitable method available in the art, for example, treatment of the free base with an inorganic acid, such as hydrochloric acid, hydrobromic acid, sulfuric acid, nitric acid, methanesulfonic acid, phosphoric acid and the like, or with an organic acid, such as acetic acid, trifluoroacetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

If the compound of the invention is an acid, the desired pharmaceutically acceptable salt may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include, but are not limited to, organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

The phrase "pharmaceutically acceptable" indicates that the substance or composition must be compatible chemically and/or toxicologically, with the other ingredients comprising a formulation, and/or the mammal being treated therewith.

A "solvate" refers to an association or complex of one or more solvent molecules and a compound of the invention. Examples of solvents that form solvates include, but are not limited to, water, isopropanol, ethanol, methanol, DMSO, ethylacetate, acetic acid, and ethanolamine.

The terms "compound of this invention," and "compounds of the present invention" and "compounds of Formula I" include compounds of Formulas I and stereoisomers, geometric isomers, tautomers, solvates, metabolites, and pharmaceutically acceptable salts and prodrugs thereof.

Any formula or structure given herein, including Formula I compounds, is also intended to represent hydrates, solvates, and polymorphs of such compounds, and mixtures thereof.

Any formula or structure given herein, including Formula I compounds, is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as, but not limited to 2H (deuterium, D), 3H (tritium), 11C, 13C, 14C, 15N, 18F, 31P, 32P, 35S, 36Cl, and 125I. Various isotopically labeled compounds of the present invention, for example those into which radioactive isotopes such as 3H, 13C, and 14C are incorporated. Such isotopically labelled compounds may be useful in metabolic studies, reaction kinetic studies, detection or imaging techniques, such as positron emission tomography (PET) or single-photon emission computed tomography (SPECT) including drug or substrate tissue distribution assays, or in radioactive treatment of patients. Deuterium labelled or substituted therapeutic compounds of the invention may have improved DMPK (drug metabolism and pharmacokinetics) properties, relating to distribution, metabolism, and excretion (ADME). Substitution with heavier isotopes such as deuterium may afford certain therapeutic advantages resulting from greater metabolic stability, for example increased in vivo half-life or reduced dosage requirements. An 18F labeled compound may be useful for PET or SPECT studies. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent. Further, substitution with heavier isotopes, particularly deuterium (i.e., 2H or D) may afford certain therapeutic advantages resulting from greater metabolic stability, for example increased in vivo half-life or reduced dosage requirements or an improvement in therapeutic index. It is understood that deuterium in this context is regarded as a substituent in the compound of the formula (I). The concentration of such a heavier isotope, specifically deuterium, may be defined by an isotopic enrichment factor. In the compounds of this invention any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Accordingly, in the compounds of this invention any atom specifically designated as a deuterium (D) is meant to represent deuterium.

Pyrazol-4-Yl-Heterocyclyl-Carboxamide Compounds

The present invention provides pyrazol-4-yl-heterocyclyl-carboxamide compounds of Formula I, including Formulas Ia, Ib, Ic and Id, and pharmaceutical formulations thereof, which are potentially useful in the treatment of diseases, conditions and/or disorders modulated by Pim kinases.

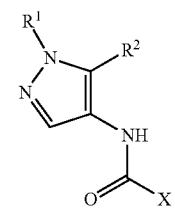

I and stereoisomers, geometric isomers, tautomers, or pharmaceutically acceptable salts thereof, wherein:

$R^1$ is H, $C_1$-$C_{12}$ alkyl, $C_2$-$C_{12}$ alkenyl, $C_2$-$C_{12}$ alkynyl, $C_6$-$C_{20}$ aryl, $C_3$-$C_{12}$ carbocyclyl, $C_2$-$C_{20}$ heterocyclyl, or $C_1$-$C_{20}$ heteroaryl;

$R^2$ is H, $C_1$-$C_{12}$ alkyl, $C_2$-$C_{12}$ alkenyl, $C_2$-$C_{12}$ alkynyl, $C_2$-$C_{20}$ heterocyclyl, $C_1$-$C_{20}$ heteroaryl, —($C_1$-$C_{20}$ heteroaryl)-($C_2$-$C_{20}$ heterocyclyl), $C_6$-$C_{20}$ aryl, $C_3$-$C_{12}$ carbocyclyl, $NR^4R^5$ or $OR^4$;

or $R^1$ and $R^2$ together form $C_2$-$C_{20}$ heterocyclyl or $C_1$-$C_{20}$ heteroaryl;

X is selected from the structures:

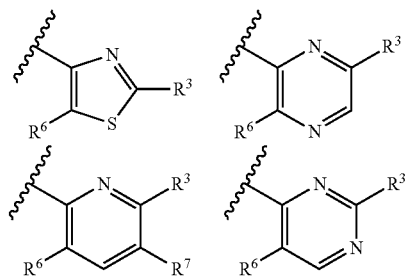

where the wavy line indicates the site of attachment;

$R^3$ is H, Cl, Br, $C_1$-$C_{12}$ alkyl, —($C_1$-$C_{12}$ alkylene)-($C_3$-$C_{12}$ carbocyclyl), —($C_1$-$C_{12}$ alkylene)-($C_2$-$C_{20}$ heterocyclyl), —($C_2$-$C_8$ alkenylene)-($C_3$-$C_{12}$ carbocyclyl), —($C_2$-$C_8$ alkenylene)-($C_2$-$C_{20}$ heterocyclyl), $C_6$-$C_{20}$ aryl, —($C_6$-$C_{20}$ arylene)-($C_2$-$C_{20}$ heterocyclyl), —($C_6$-$C_{20}$ arylene)-($C_1$-$C_{12}$ alkylene)-($C_2$-$C_{20}$ heterocyclyl), $C_3$-$C_{12}$ carbocyclyl, $C_2$-$C_{20}$ heterocyclyl, or $C_1$-$C_{20}$ heteroaryl;

$R^4$ and $R^5$ are independently selected from H, $C_1$-$C_{12}$ alkyl, $C_6$-$C_{20}$ aryl, $C_3$-$C_{12}$ carbocyclyl, $C_2$-$C_{20}$ heterocyclyl, $C_1$-$C_{20}$ heteroaryl, —($C_1$-$C_{12}$ alkylene)-($C_6$-$C_{20}$ aryl), —($C_1$-$C_{12}$ alkylene)-($C_3$-$C_{12}$ carbocyclyl), —($C_1$-$C_{12}$ alkylene)-($C_2$-$C_{20}$ heterocyclyl), —($C_1$-$C_{12}$ alkylene)-($C_1$-$C_{20}$ heteroaryl); or $R^4$ and $R^5$ together form $C_2$-$C_{20}$ heterocyclyl or $C_1$-$C_{20}$ heteroaryl;

$R^6$ is H or —$NH_2$;

$R^7$ is H, F, $CH_2F$, $CHF_2$, and $CF_3$; and where alkyl, alkenyl, alkynyl, alkylene, carbocyclyl, heterocyclyl, aryl, and heteroaryl are optionally substituted with one or more groups independently selected from F, Cl, Br, I, —$CH_3$, —$CH_2CH_3$, —$CH(CH_3)_2$, —$CH_2CH(CH_3)_2$, —$CH_2NH_2$, —$CH_2CH_2NH_2$, —$CH_2CHCH_2NH_2$, —$CH_2CH(CH_3)NH_2$, —$CH_2OH$, —$CH_2CH_2OH$, —$C(CH_3)_2OH$, —$CH(OH)CH(CH_3)_2$, —$C(CH_3)_2CH_2OH$, —$CH_2CH_2SO_2CH_3$, —CN, —$CF_3$, —$CO_2H$, —$COCH_3$, —$CO_2CH_3$, —$CO_2C(CH_3)_3$, —$COCH(OH)CH_3$, —$CONH_2$, —$CONHCH_3$, —$CON(CH_3)_2$, —$C(CH_3)_2CONH_2$, —$NO_2$, —$NH_2$, —$NHCH_3$, —$N(CH_3)_2$, —$NHCOCH_3$, —$N(CH_3)COCH_3$, —$NHS(O)_2CH_3$, —$N(CH_3)C(CH_3)_2CONH_2$, —$N(CH_3)CH_2CH_2S(O)_2CH_3$, =O, —OH, —$OCH_3$, —$S(O)_2N(CH_3)_2$, —$SCH_3$, —$CH_2OCH_3$, —$S(O)_2CH_3$, cyclopropyl, cyclobutyl, cyclopentyl, cyclohexyl, cycloheptyl, azetidinyl, azepanyl, oxetanyl, pyrrolidinyl, piperazinyl, piperidinyl, (piperidin-4-yl)ethyl), pyranyl, (piperidin-4-ylmethyl), morpholinomethyl, and morpholino.

Exemplary embodiments of Formula I compounds include wherein $R^1$ is $C_1$-$C_{12}$ alkyl.

Exemplary embodiments of Formula I compounds include wherein $R^2$ is $NR^4R^5$ and together form $C_2$-$C_{20}$ heterocyclyl or $C_1$-$C_{20}$ heteroaryl.

Exemplary embodiments of Formula I compounds include wherein $R^2$ is selected from the structures:

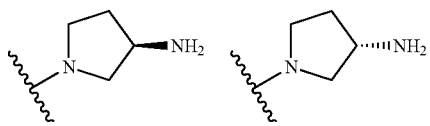

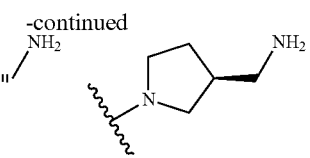

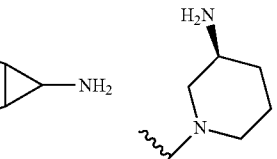

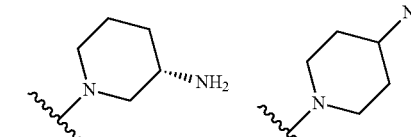

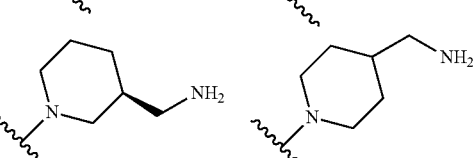

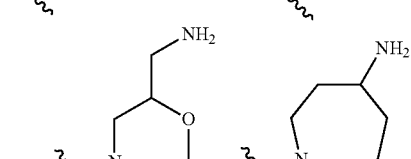

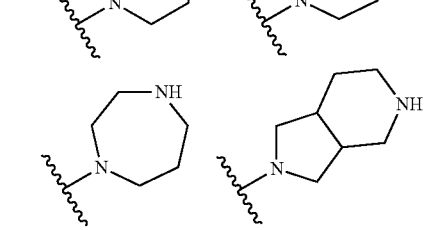

where the wavy line indicates the site of attachment.

Exemplary embodiments of Formula I compounds include wherein $R^2$ is selected from the structures:

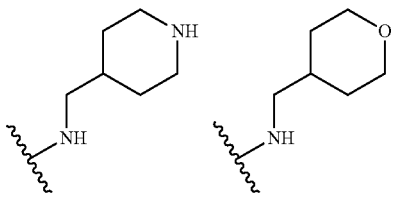

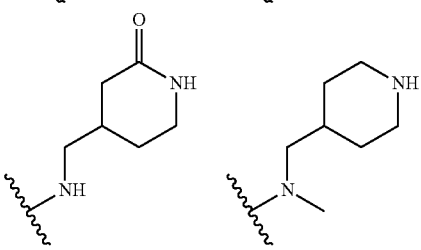

where the wavy line indicates the site of attachment.

Exemplary embodiments of Formula I compounds include wherein $R^2$ is $OR^4$.

Exemplary embodiments of Formula I compounds include wherein R² is selected from the structures:

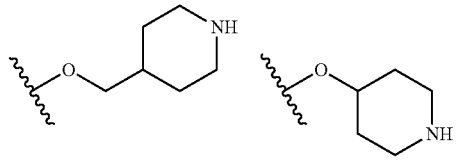 [SMILES: *OCC1CCNCC1 ; *OC1CCNCC1]

where the wavy line indicates the site of attachment.

Exemplary embodiments of Formula I compounds include wherein R¹ and R² together form $C_2$-$C_{20}$ heterocyclyl or $C_1$-$C_{20}$ heteroaryl selected from the structures:

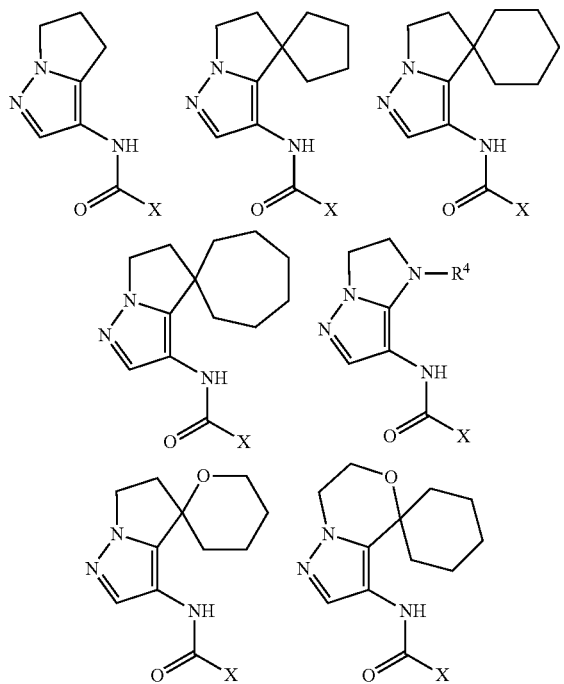

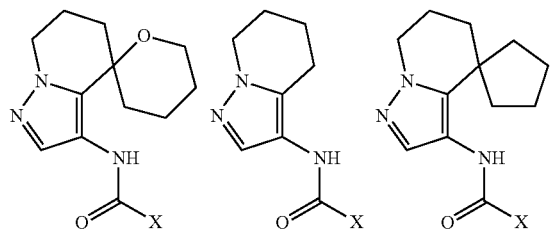

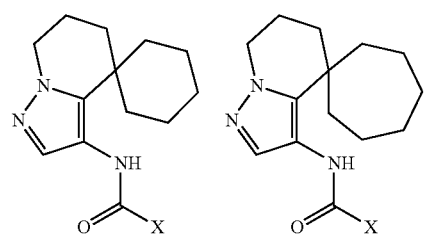

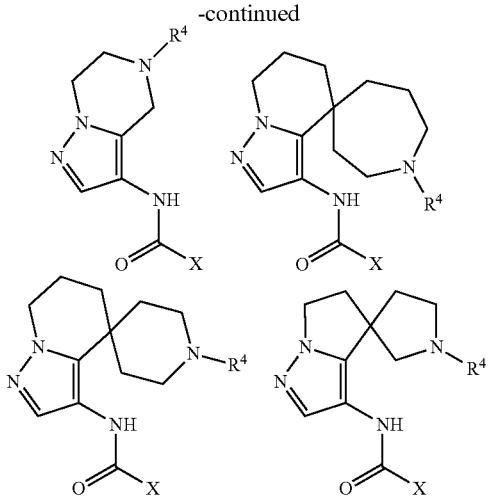

where the $C_2$-$C_{20}$ heterocyclyl or $C_1$-$C_{20}$ heteroaryl formed by R¹ and R² is optionally substituted with one or more groups independently selected from F, Cl, Br, I, —$CH_3$, —$CH_2CH_3$, —$CH_2CH(CH_3)_2$, —$CH_2NH_2$, —$CH_2CH_2NH_2$, —$CH_2CH(CH_3)NH_2$, —$CH_2OH$, —$CH_2CH_2OH$, —$C(CH_3)_2OH$, —$CH(OH)CH(CH_3)_2$, —$C(CH_3)_2CH_2OH$, —$CH_2CH_2SO_2CH_3$, —CN, —$CF_3$, —$CO_2H$, —$COCH_3$, —$CO_2CH_3$, —$CO_2C(CH_3)_3$, —COCH(OH)$CH_3$, —$CONH_2$, —$CONHCH_3$, —$CON(CH_3)_2$, —$C(CH_3)_2CONH_2$, —$NO_2$, —$NH_2$, —$NHCH_3$, —$N(CH_3)_2$, —$NHCOCH_3$, —$N(CH_3)COCH_3$, —$NHS(O)_2CH_3$, —$N(CH_3)C(CH_3)_2CONH_2$, —$N(CH_3)CH_2CH_2S(O)_2CH_3$, =O, —OH, —$OCH_3$, —$S(O)_2N(CH_3)_2$, —$SCH_3$, —$CH_2OCH_3$, —$S(O)_2CH_3$, cyclopropyl, azetidinyl, oxetanyl, pyrrolidinyl, and morpholino.

Exemplary embodiments of Formula I compounds include wherein R³ is $C_6$-$C_{20}$ aryl, including where phenyl substituted with one or more F.

Exemplary embodiments of Formula I compounds include the structures of Formula Ia, Ib, Ic, and Id:

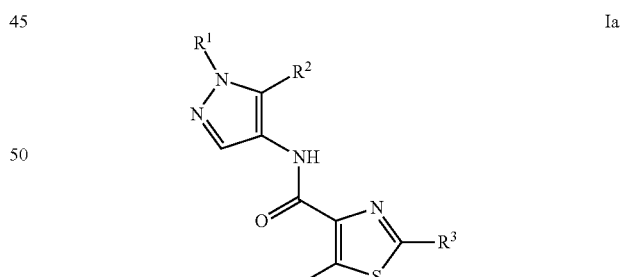

Ia

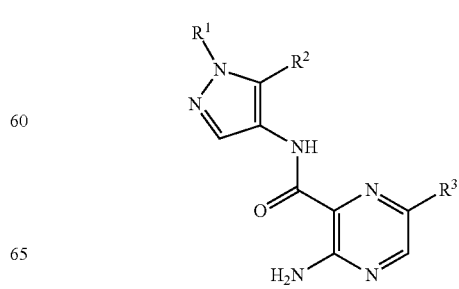

Ib

-continued

Ic
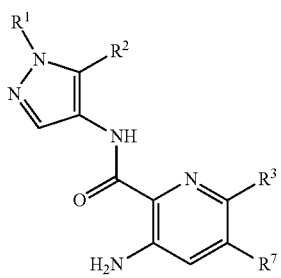

Id
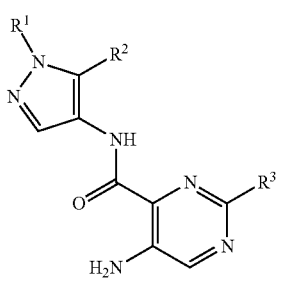

Where R¹ is H, it will be understood that Formula I compounds include pyrazole tautomers, such as:

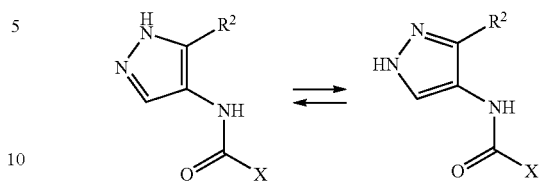

Biological Evaluation

Determination of the Pim kinase activity of a Formula I compound is possible by a number of direct and indirect detection methods. Certain exemplary compounds described herein were assayed for their Pim kinase binding activity, including isoforms Pim-1, Pim-2, and Pim-3, (Example 901) and in vitro activity against tumor cells (Example 902). Certain exemplary compounds of the invention had Pim binding activity $IC_{50}$ values less than about 1 micromolar (μM). Certain compounds of the invention had tumor cell-based activity $EC_{50}$ values less than about 1 micromolar (μM).

Exemplary Formula I compounds in Table 1 and Table 2 were made, characterized, and tested for inhibition of Pim kinase according to the methods of this invention, and have the following structures and corresponding names (ChemBioDraw Ultra, Version 11.0, CambridgeSoft Corp., Cambridge Mass.).

TABLE 1

| No. | Structure | Name |
|---|---|---|
| 101 | 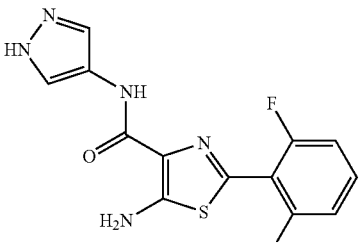 | 5-amino-2-(2,6-difluorophenyl)-N-(1H-pyrazol-4-yl)thiazole-4-carboxamide |
| 102 | 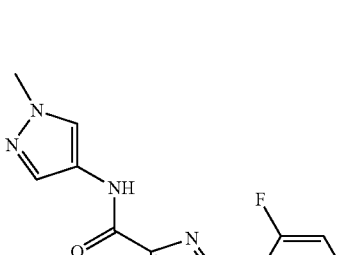 | 5-amino-2-(2,6-difluorophenyl)-N-(1-methyl-1H-pyrazol-4-yl)thiazole-4-carboxamide |

TABLE 1-continued

| No. | Structure | Name |
|---|---|---|
| 103 | 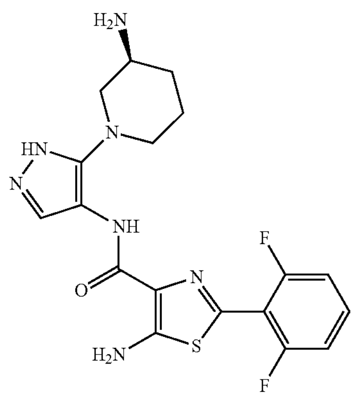 [SMILES: Nc1sc(-c2c(F)cccc2F)nc1C(=O)Nc1cn[nH]c1N1CCC[C@H](N)C1] | (S)-5-amino-N-(5-(3-aminopiperidin-1-yl)-1H-pyrazol-4-yl)-2-(2,6-difluorophenyl)thiazole-4-carboxamide |
| 104 | 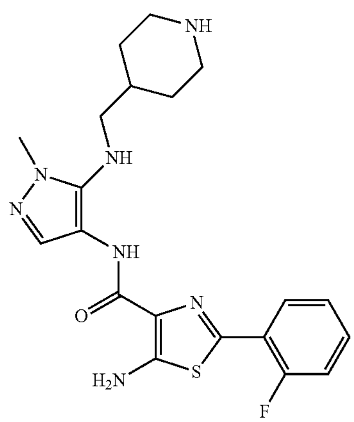 [SMILES: Cn1ncc(NC(=O)c2nc(-c3ccccc3F)sc2N)c1NCC1CCNCC1] | 5-amino-2-(2-fluorophenyl)-N-(1-methyl-5-(piperidin-4-ylmethylamino)-1H-pyrazol-4-yl)thiazole-4-carboxamide |
| 105 | 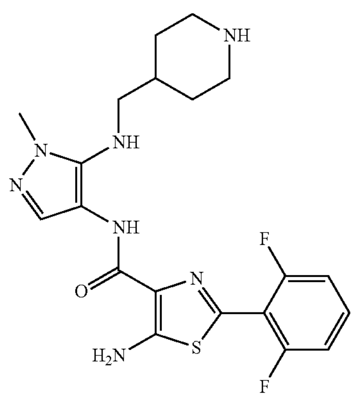 | 5-amino-2-(2,6-difluorophenyl)-N-(1-methyl-5-(piperidin-4-ylmethylamino)-1H-pyrazol-4-yl)thiazole-4-carboxamide |
| 106 | 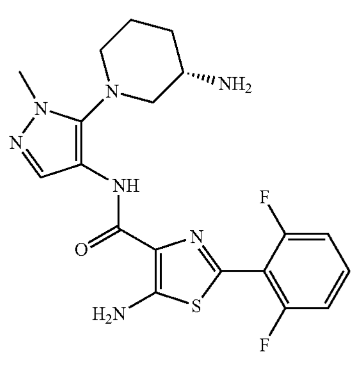 [SMILES: Cn1ncc(NC(=O)c2nc(-c3c(F)cccc3F)sc2N)c1N1CCC[C@H](N)C1] | (S)-5-amino-N-(5-(3-aminopiperidin-1-yl)-1-methyl-1H-pyrazol-4-yl)-2-(2,6-difluorophenyl)thiazole-4-carboxamide |

TABLE 1-continued

| No. | Name |
|---|---|
| 107 | (S)-5-amino-N-(5-(3-aminopiperidin-1-yl)-1-methyl-1H-pyrazol-4-yl)-2-(2-fluorophenyl)thiazole-4-carboxamide |
| 108 | 5-amino-N-(5-(4-aminopiperidin-1-yl)-1-methyl-1H-pyrazol-4-yl)-2-(2,6-difluorophenyl)thiazole-4-carboxamide |
| 109 | 3-amino-N-(5-(4-aminopiperidin-1-yl)-1-methyl-1H-pyrazol-4-yl)-6-phenylpicolinamide |
| 110 | 3-amino-N-(5-(4-aminopiperidin-1-yl)-1-methyl-1H-pyrazol-4-yl)-6-(2-fluorophenyl)picolinamide |

TABLE 1-continued

| No. | Structure | Name |
|---|---|---|
| 111 | 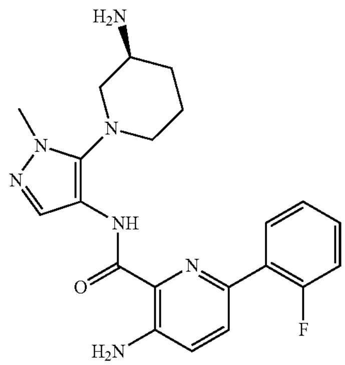 | (S)-3-amino-N-(5-(3-aminopiperidin-1-yl)-1-methyl-1H-pyrazol-4-yl)-6-(2-fluorophenyl)picolinamide |
| 112 | 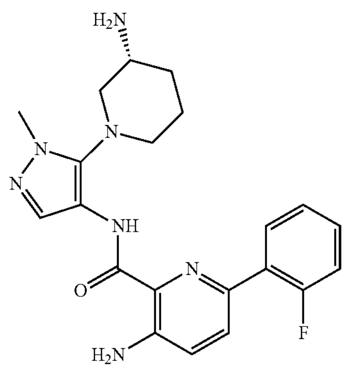 [SMILES: Cn1ncc(NC(=O)c2nc(-c3ccccc3F)ccc2N)c1N1CCC[C@@H](N)C1] | (R)-3-amino-N-(5-(3-aminopiperidin-1-yl)-1-methyl-1H-pyrazol-4-yl)-6-(2-fluorophenyl)picolinamide |
| 113 | 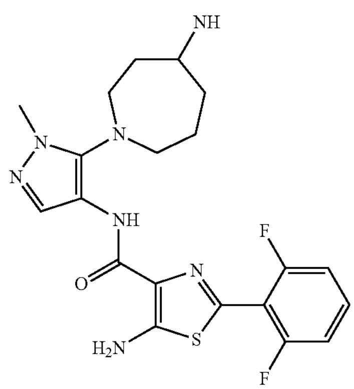 [SMILES: Cn1ncc(NC(=O)c2nc(-c3c(F)cccc3F)sc2N)c1N1CCCC(N)CC1] | 5-amino-N-(5-(4-aminoazepan-1-1-methyl-1H-pyrazol-4-yl)-2-(2,6 difluorophenyl)thiazole-4-carboxamide |
| 114 | 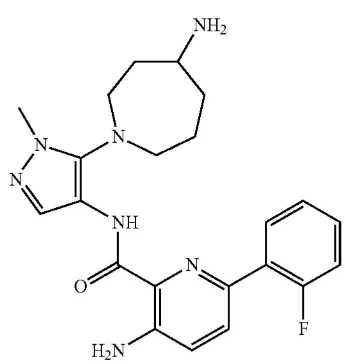 [SMILES: Cn1ncc(NC(=O)c2nc(-c3ccccc3F)ccc2N)c1N1CCCC(N)CC1] | 3-amino-N-(5-(4-aminoazepan-1-yl)-1-methyl-1H-pyrazol-4-yl)-6-(2-fluorophenyl)picolinamide |

TABLE 1-continued

| No. | Structure | Name |
|---|---|---|
| 115 | 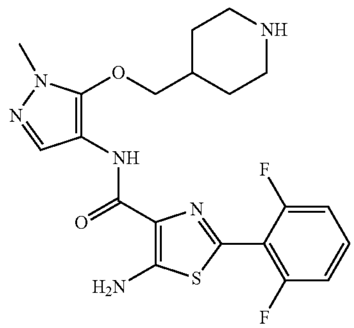 [SMILES: Cn1ncc(NC(=O)c2nc(-c3c(F)cccc3F)sc2N)c1OCC1CCNCC1] | 5-amino-2-(2,6-difluorophenyl)-N-(1-methyl-5-(piperidin-4-ylmethoxy)-1H-pyrazol-4-yl)thiazole-4-carboxamide |
| 116 | 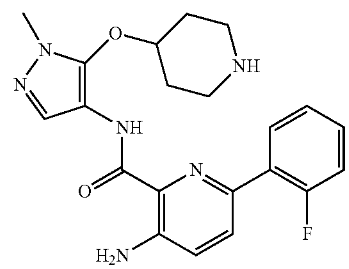 [SMILES: Cn1ncc(NC(=O)c2nc(-c3ccccc3F)ccc2N)c1OC1CCNCC1] | 3-amino-6-(2-fluorophenyl)-N-(1-methyl-5-(piperidin-4-yloxy)-1H-pyrazol-4-yl)picolinamide |
| 117 | 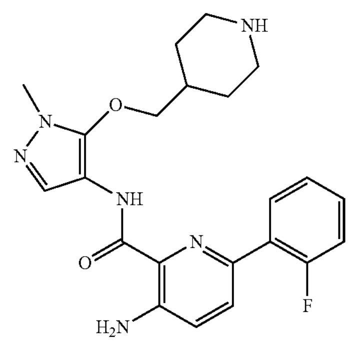 [SMILES: Cn1ncc(NC(=O)c2nc(-c3ccccc3F)ccc2N)c1OCC1CCNCC1] | 3-amino-6-(2-fluorophenyl)-N-(1-methyl-5-(piperidin-4-ylmethoxy)-1H-pyrazol-4-yl)picolinamide |
| 118 | 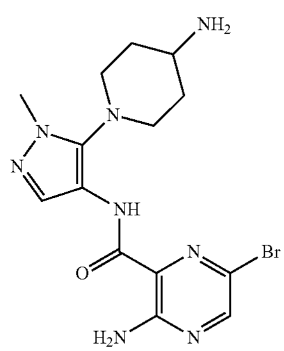 [SMILES: Cn1ncc(NC(=O)c2nc(Br)cnc2N)c1N1CCC(N)CC1] | 3-amino-N-(5-(4-aminopiperidin-1-yl)-1-methyl-1H-pyrazol-4-yl)-6-bromopyrazine-2-carboxamide |

TABLE 1-continued

| No. | Structure | Name |
|---|---|---|
| 119 | 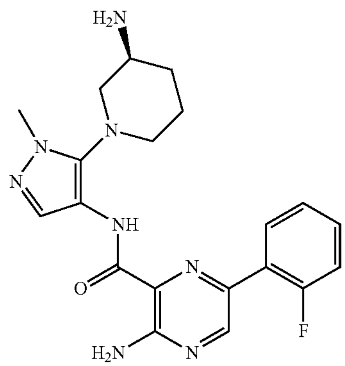 [SMILES: Cn1ncc(NC(=O)c2nc(-c3ccccc3F)cnc2N)c1N1CCC[C@H](N)C1] | (S)-3-amino-N-(5-(3-aminopiperidin-1-yl)-1-methyl-1H-pyrazol-4-yl)-6-(2-fluorophenyl)pyrazine-2-carboxamide |
| 120 | 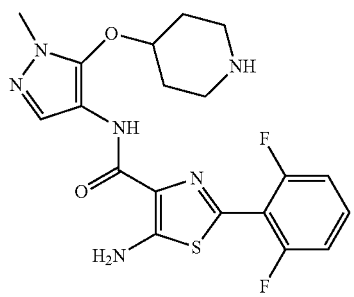 [SMILES: Cn1ncc(NC(=O)c2nc(-c3c(F)cccc3F)sc2N)c1OC1CCNCC1] | 5-amino-2-(2,6-difluorophenyl)-N-(1-methyl-5-(piperidin-4-yloxy)-1H-pyrazol-4-yl)thiazole-4-carboxamide |
| 121 | 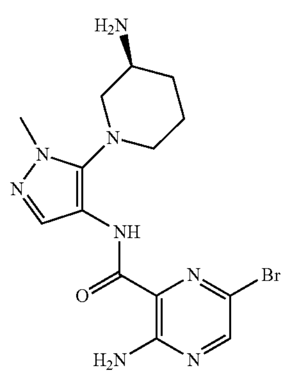 [SMILES: Cn1ncc(NC(=O)c2nc(Br)cnc2N)c1N1CCC[C@H](N)C1] | (S)-3-amino-N-(5-(3-aminopiperidin-1-yl)-1-methyl-1H-pyrazol-4-yl)-6-bromopyrazine-2-carboxamide |
| 122 | 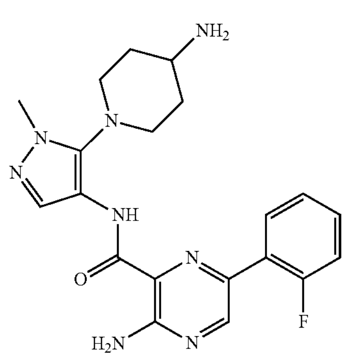 [SMILES: Cn1ncc(NC(=O)c2nc(-c3ccccc3F)cnc2N)c1N1CCC(N)CC1] | 3-amino-N-(5-(4-aminopiperidin-1-yl)-1-methyl-1H-pyrazol-4-yl)-6-(2-fluorophenyl)pyrazine-2-carboxamide |

TABLE 1-continued

| No. | Structure | Name |
|---|---|---|
| 123 | 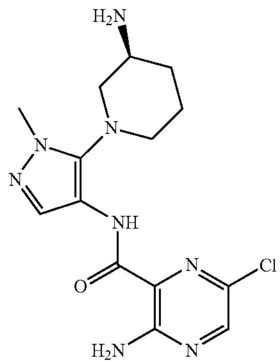 [SMILES: Cn1ncc(NC(=O)c2nc(Cl)cnc2N)c1N1CCC[C@H](N)C1] | (S)-3-amino-N-(5-(3-aminopiperidin-1-yl)-1-methyl-1H-pyrazol-4-yl)-6-chloropyrazine-2-carboxamide |
| 124 | 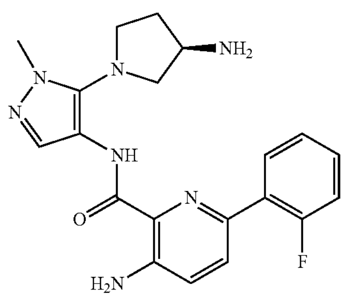 [SMILES: Cn1ncc(NC(=O)c2nc(-c3ccccc3F)ccc2N)c1N1CC[C@@H](N)C1] | (R)-3-amino-N-(5-(3-aminopyrrolidin-1-yl)-1-methyl-1H-pyrazol-4-yl)-6-(2-fluorophenyl)picolinamide |
| 125 | 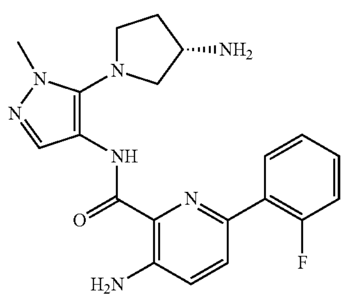 [SMILES: Cn1ncc(NC(=O)c2nc(-c3ccccc3F)ccc2N)c1N1CC[C@H](N)C1] | (S)-3-amino-N-(5-(3-aminopyrrolidin-1-yl)-1-methyl-1H-pyrazol-4-yl)-6-(2-fluorophenyl)picolinamide |
| 126 | 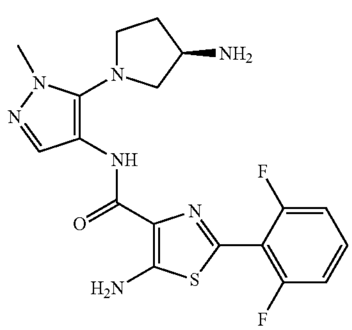 [SMILES: Cn1ncc(NC(=O)c2nc(-c3c(F)cccc3F)sc2N)c1N1CC[C@@H](N)C1] | (R)-5-amino-N-(5-(3-aminopyrrolidin-1-yl)-1-methyl-1H-pyrazol-4-yl)-2-(2,6-difluorophenyl)thiazole-4-carboxamide |
| 127 | 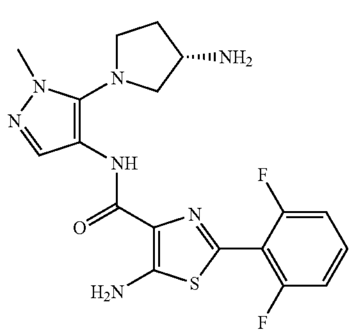 [SMILES: Cn1ncc(NC(=O)c2nc(-c3c(F)cccc3F)sc2N)c1N1CC[C@H](N)C1] | (S)-5-amino-N-(5-(3-aminopyrrolidin-1-yl)-1-methyl-1H-pyrazol-4-yl)-2-(2,6-difluorophenyl)thiazole-4-carboxamide |

TABLE 1-continued

| No. | Structure | Name |
|---|---|---|
| 128 | 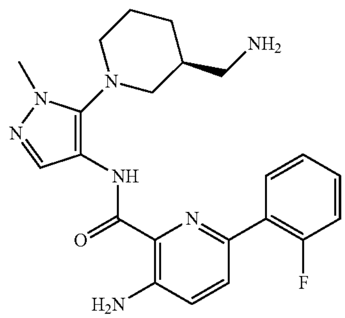 [SMILES: Cn1ncc(NC(=O)c2nc(-c3ccccc3F)ccc2N)c1N1CCC[C@@H](CN)C1] | (S)-3-amino-N-(5-(3-(aminomethyl)piperidin-1-yl)-1-methyl-1H-pyrazol-4-yl)-6-(2-fluorophenyl)picolinamide |
| 129 | 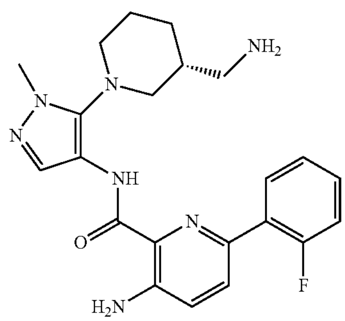 [SMILES: Cn1ncc(NC(=O)c2nc(-c3ccccc3F)ccc2N)c1N1CCC[C@H](CN)C1] | (R)-3-amino-N-(5-(3-(aminomethyl)piperidin-1-yl)-1-methyl-1H-pyrazol-4-yl)-6-(2-fluorophenyl)picolinamide |
| 130 | 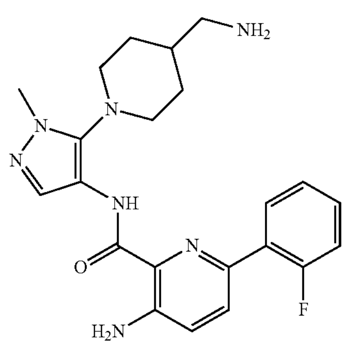 [SMILES: Cn1ncc(NC(=O)c2nc(-c3ccccc3F)ccc2N)c1N1CCC(CN)CC1] | 3-amino-N-(5-(4-(aminomethyl)piperidin-1-yl)-1-methyl-1H-pyrazol-4-yl)-6-(2-fluorophenyl)picolinamide |
| 131 | 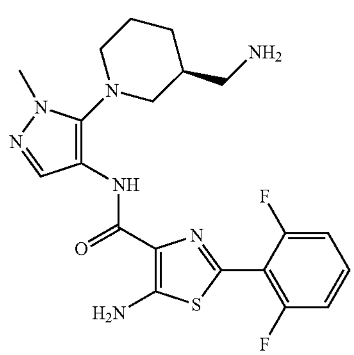 [SMILES: Cn1ncc(NC(=O)c2nc(-c3c(F)cccc3F)sc2N)c1N1CCC[C@@H](CN)C1] | (S)-5-amino-N-(5-(3-(aminomethyl)piperidin-1-yl)-1-methyl-1H-pyrazol-4-yl)-2-(2,6-difluorophenyl)thiazole-4-carboxamide |

TABLE 1-continued

| No. | Structure | Name |
|---|---|---|
| 132 | 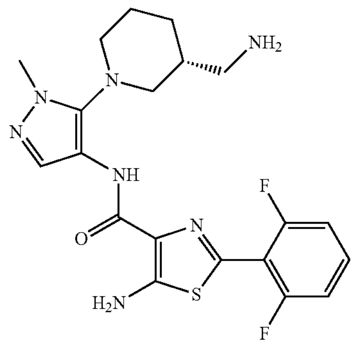 [SMILES: Cn1ncc(NC(=O)c2nc(-c3c(F)cccc3F)sc2N)c1N1CCC[C@H](CN)C1] | (R)-5-amino-N-(5-(3-(aminomethyl)piperidin-1-yl)-1-methyl-1H-pyrazol-4-yl)-2-(2,6-difluorophenyl)thiazole-4-carboxamide |
| 133 | 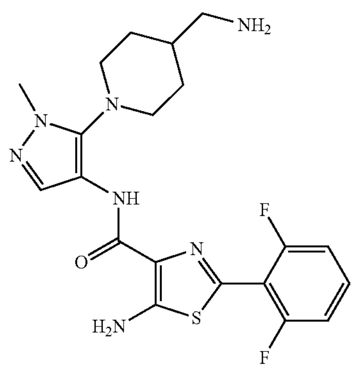 [SMILES: Cn1ncc(NC(=O)c2nc(-c3c(F)cccc3F)sc2N)c1N1CCC(CN)CC1] | 5-amino-N-(5-(4-(aminomethyl)piperidin-1-yl)-1-methyl-1H-pyrazol-4-yl)-2-(2,6-difluorophenyl)thiazole-4-carboxamide |
| 134 | 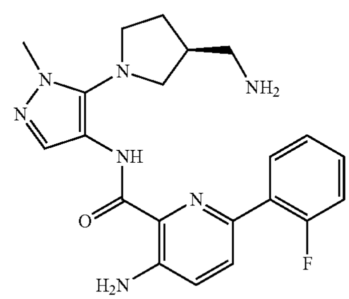 [SMILES: Cn1ncc(NC(=O)c2nc(-c3ccccc3F)ccc2N)c1N1CC[C@@H](CN)C1] | (S)-3-amino-N-(5-(3-(aminomethyl)pyrrolidin-1-yl)-1-methyl-1H-pyrazol-4-yl)-6-(2-fluorophenyl)picolinamide |
| 135 | 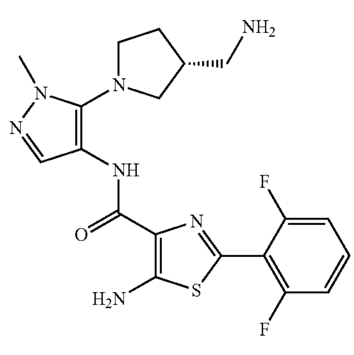 [SMILES: Cn1ncc(NC(=O)c2nc(-c3c(F)cccc3F)sc2N)c1N1CC[C@H](CN)C1] | (R)-5-amino-N-(5-(3-(aminomethyl)pyrrolidin-1-yl)-1-methyl-1H-pyrazol-4-yl)-2-(2,6-difluorophenyl)thiazole-4-carboxamide |

TABLE 1-continued

| No. | Structure | Name |
|---|---|---|
| 136 | 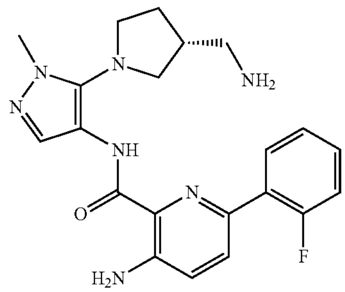 [SMILES: Cn1ncc(NC(=O)c2nc(-c3ccccc3F)ccc2N)c1N1CC[C@H](CN)C1] | (R)-3-amino-N-(5-(3-(aminomethyl)pyrrolidin-1-yl)-1-methyl-1H-pyrazol-4-yl)-6-(2-fluorophenyl)picolinamide |
| 137 | 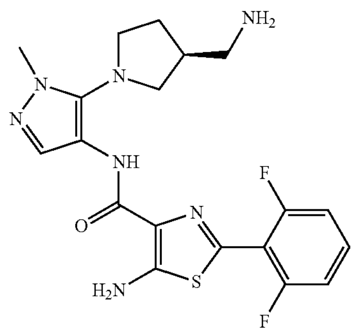 [SMILES: Cn1ncc(NC(=O)c2nc(-c3c(F)cccc3F)sc2N)c1N1CC[C@@H](CN)C1] | (S)-5-amino-N-(5-(3-(aminomethyl)pyrrolidin-1-yl)-1-methyl-1H-pyrazol-4-yl)-2-(2,6-difluorophenyl)thiazole-4-carboxamide |
| 138 | 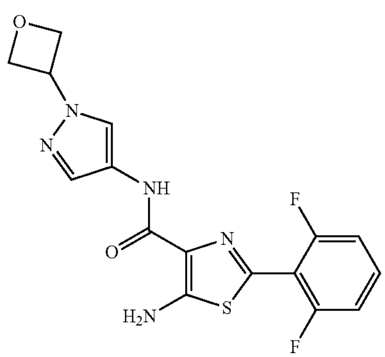 [SMILES: Nc1sc(-c2c(F)cccc2F)nc1C(=O)Nc1cnn(C2COC2)c1] | 5-amino-2-(2,6-difluorophenyl)-N-(1-(oxetan-3-yl)-1H-pyrazol-4-yl)thiazole-4-carboxamide |
| 139 | 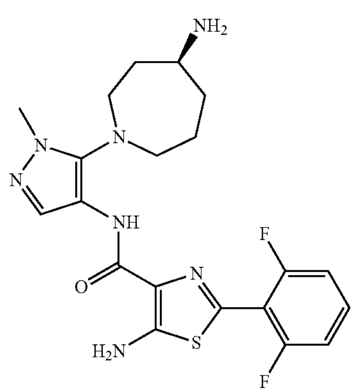 [SMILES: Cn1ncc(NC(=O)c2nc(-c3c(F)cccc3F)sc2N)c1N1CCC[C@H](N)CC1] | (S)-5-amino-N-(5-(4-aminoazepan-1-yl)-1-methyl-1H-pyrazol-4-yl)-2-(2,6-difluorophenyl)thiazole-4-carboxamide |

TABLE 1-continued

| No. | Structure | Name |
|---|---|---|
| 140 | 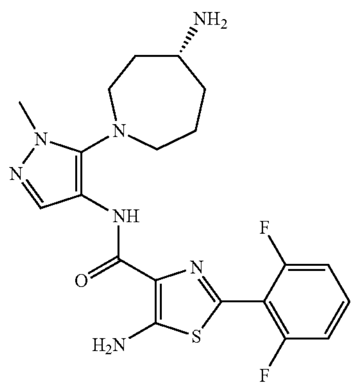 [SMILES: Cn1ncc(NC(=O)c2nc(-c3c(F)cccc3F)sc2N)c1N1CCC[C@@H](N)CC1] | (R)-5-amino-N-(5-(4-aminoazepan-1-yl)-1-methyl-1H-pyrazol-4-yl)-2-(2,6-difluorophenyl)thiazole-4-carboxamide |
| 141 | 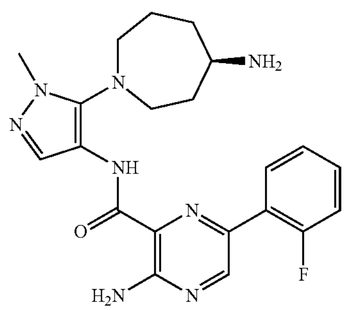 [SMILES: Cn1ncc(NC(=O)c2nc(-c3ccccc3F)cnc2N)c1N1CCC[C@@H](N)CC1] | (R)-3-amino-N-(5-(4-aminoazepan-1-yl)-1-methyl-1H-pyrazol-4-yl)-6-(2-fluorophenyl)pyrazine-2-carboxamide |
| 142 | 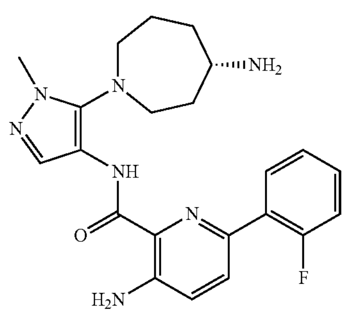 | (S)-3-amino-N-(5-(4-aminoazepan-1-yl)-1-methyl-1H-pyrazol-4-yl)-6-(2-fluorophenyl)picolinamide |
| 143 | 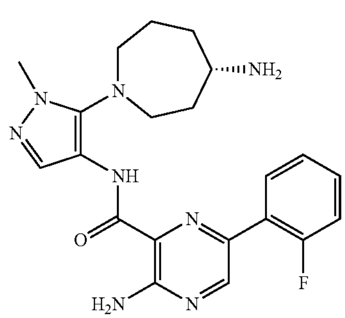 [SMILES: Cn1ncc(NC(=O)c2nc(-c3ccccc3F)cnc2N)c1N1CCC[C@H](N)CC1] | (S)-3-amino-N-(5-(4-aminoazepan-1-yl)-1-methyl-1H-pyrazol-4-yl)-6-(2-fluorophenyl)pyrazine-2-carboxamide |

TABLE 1-continued

| No. | Structure | Name |
|---|---|---|
| 144 | 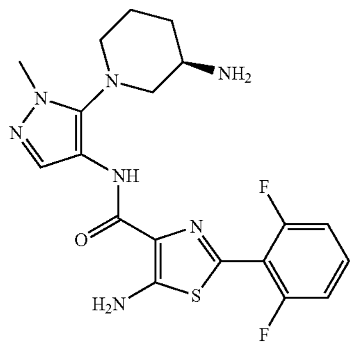 [SMILES: Cn1ncc(NC(=O)c2nc(-c3c(F)cccc3F)sc2N)c1N1CCC[C@@H](N)C1] | (R)-5-amino-N-(5-(3-aminopiperidin-1-yl)-1-methyl-1H-pyrazol-4-yl)-2-(2,6-difluorophenyl)thiazole-4-carboxamide |
| 145 | 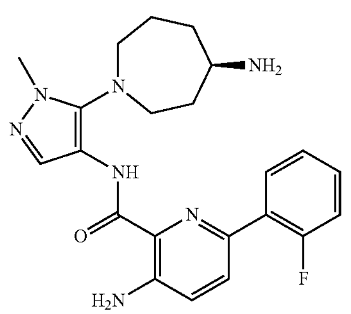 [SMILES: Cn1ncc(NC(=O)c2nc(-c3ccccc3F)ccc2N)c1N1CCC[C@@H](N)CC1] | (R)-3-amino-N-(5-(4-aminoazepan-1-yl)-1-methyl-1H-pyrazol-4-yl)-6-(2-fluorophenyl)picolinamide |
| 146 | 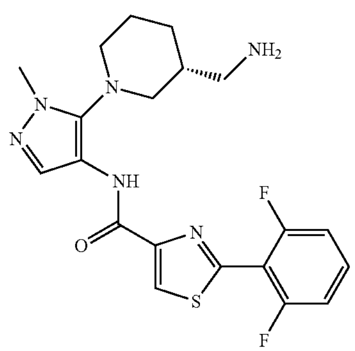 [SMILES: Cn1ncc(NC(=O)c2csc(-c3c(F)cccc3F)n2)c1N1CCC[C@H](CN)C1] | (R)-N-(5-(3-(aminomethyl)piperidin-1-yl)-1-methyl-1H-pyrazol-4-yl)-2-(2,6-difluorophenyl)thiazole-4-carboxamide |
| 147 | 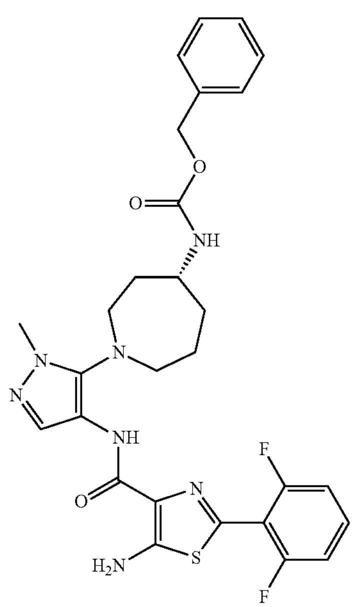 [SMILES: Cn1ncc(NC(=O)c2nc(-c3c(F)cccc3F)sc2N)c1N1CCC[C@@H](NC(=O)OCc2ccccc2)CC1] | (R)-benzyl 1-(4-(5-amino-2-(2,6-difluorophenyl)thiazole-4-carboxamido)-1-methyl-1H-pyrazol-5-yl)azepan-4-ylcarbamate |

TABLE 1-continued

| No. | Structure | Name |
|---|---|---|
| 148 | 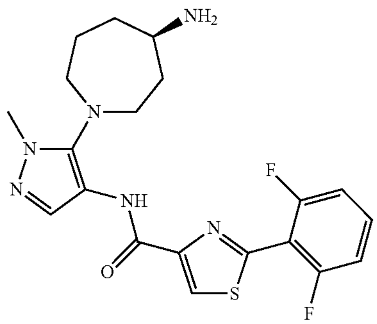 [SMILES: Cn1ncc(NC(=O)c2csc(-c3c(F)cccc3F)n2)c1N1CCC[C@@H](N)CC1] | (R)-N-(5-(4-aminoazepan-1-yl)-1-methyl-1H-pyrazol-4-yl)-2-(2,6-difluorophenyl)thiazole-4-carboxamide |
| 149 | 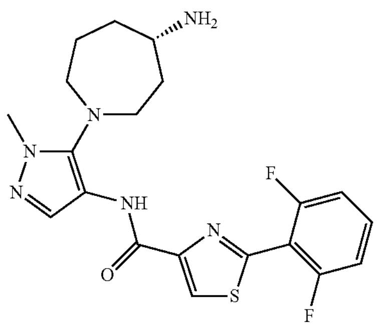 [SMILES: Cn1ncc(NC(=O)c2csc(-c3c(F)cccc3F)n2)c1N1CCC[C@H](N)CC1] | (S)-N-(5-(4-aminoazepan-1-yl)-1-methyl-1H-pyrazol-4-yl)-2-(2,6-difluorophenyl)thiazole-4-carboxamide |
| 150 | 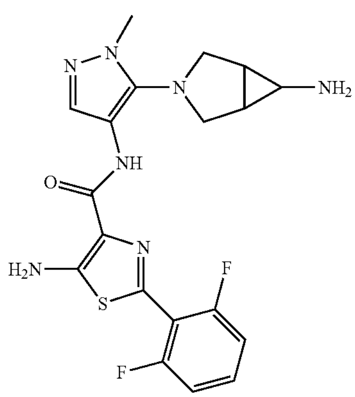 [SMILES: Cn1ncc(NC(=O)c2nc(-c3c(F)cccc3F)sc2N)c1N1CC2C(N)C2C1] | 5-amino-N-(5-(6-amino-3-azabicyclo[3.1.0]hexan-3-yl)-1-methyl-1H-pyrazol-4-yl)-2-(2,6-difluorophenyl)thiazole-4-carboxamide |
| 151 | 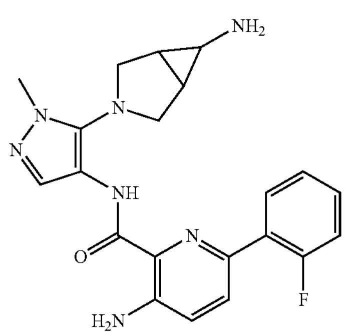 [SMILES: Cn1ncc(NC(=O)c2nc(-c3ccccc3F)ccc2N)c1N1CC2C(N)C2C1] | 3-amino-N-(5-(6-amino-3-azabicyclo[3.1.0]hexan-3-yl)-1-methyl-1H-pyrazol-4-yl)-6-(2-fluorophenyl)picolinamide |

TABLE 1-continued

| No. | Structure | Name |
|---|---|---|
| 152 | 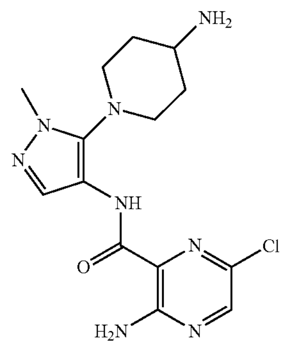 [SMILES: Cn1ncc(NC(=O)c2nc(Cl)cnc2N)c1N1CCC(N)CC1] | 3-amino-N-(5-(4-aminopiperidin-1-yl)-1-methyl-1H-pyrazol-4-yl)-6-chloropyrazine-2-carboxamide |
| 153 | 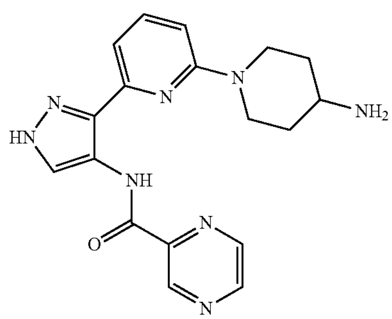 [SMILES: NC1CCN(c2cccc(-c3n[nH]cc3NC(=O)c3cnccn3)n2)CC1] | N-(3-(6-(4-aminopiperidin-1-yl)yridine-2-yl)-1H-pyrazol-4-yl)pyrazine-2-carboxamide |
| 154 | 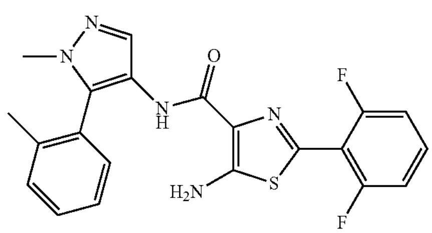 [SMILES: Cc1ccccc1-c1c(NC(=O)c2nc(-c3c(F)cccc3F)sc2N)cnn1C] | 5-amino-2-(2,6-difluorophenyl)-N-(1-methyl-5-o-tolyl-1H-pyrazol-4-yl)thiazole-4-carboxamide |
| 155 | 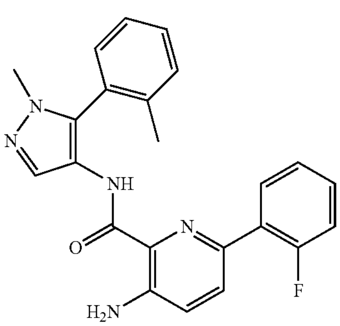 [SMILES: Cc1ccccc1-c1c(NC(=O)c2nc(-c3ccccc3F)ccc2N)cnn1C] | 3-amino-6-(2-fluorophenyl)-N-(1-methyl-5-o-tolyl-1H-pyrazol-4-yl)picolinamide |
| 156 | 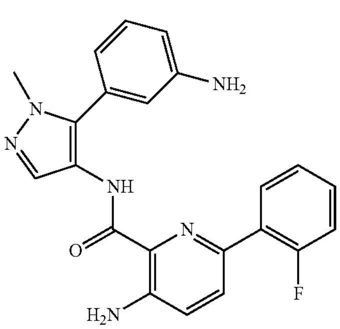 [SMILES: Cn1ncc(NC(=O)c2nc(-c3ccccc3F)ccc2N)c1-c1cccc(N)c1] | 3-amino-N-(5-(3-aminophenyl)-1-methyl-1H-pyrazol-4-yl)-6-(2-fluorophenyl)picolinamide |

TABLE 1-continued

| No. | Structure | Name |
|---|---|---|
| 157 | 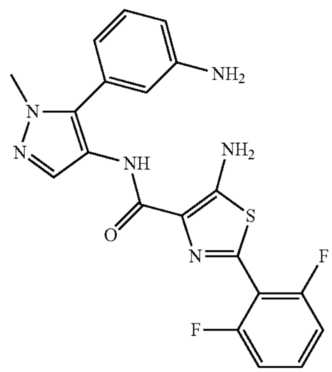 [SMILES: Cn1ncc(NC(=O)c2nc(-c3c(F)cccc3F)sc2N)c1-c1cccc(N)c1] | 5-amino-N-(5-(3-aminophenyl)-1-methyl-1H-pyrazol-4-yl)-2-(2,6-difluorophenyl)thiazole-4-carboxamide |

TABLE 2

| No. | Structure | Name |
|---|---|---|
| 158 | 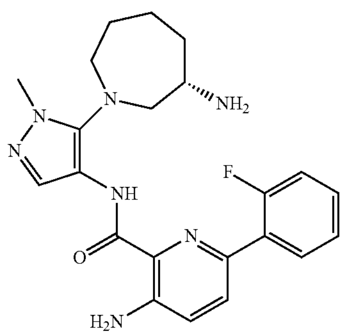 [SMILES: Cn1ncc(NC(=O)c2nc(-c3ccccc3F)ccc2N)c1N1CCCC[C@H](N)C1] | (S)-3-amino-N-(5-(3-aminoazepan-1-yl)-1-methyl-1H-pyrazol-4-yl)-6-(2-fluorophenyl)picolinamide |
| 159 | 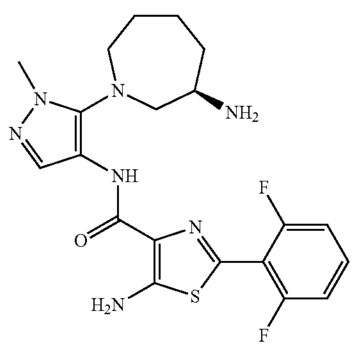 [SMILES: Cn1ncc(NC(=O)c2nc(-c3c(F)cccc3F)sc2N)c1N1CCCC[C@@H](N)C1] | (R)-5-amino-N-(5-(3-aminoazepan-1-yl)-1-methyl-1H-pyrazol-4-yl)-2-(2,6-difluorophenyl)thiazole-4-carboxamide |
| 160 | 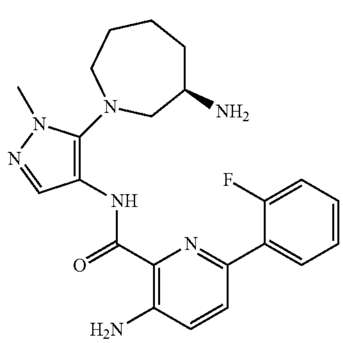 [SMILES: Cn1ncc(NC(=O)c2nc(-c3ccccc3F)ccc2N)c1N1CCCC[C@@H](N)C1] | (R)-3-amino-N-(5-(3-aminoazepan-1-yl)-1-methyl-1H-pyrazol-4-yl)-6-(2-fluorophenyl)picolinamide |

TABLE 2-continued

| No. | Structure | Name |
|---|---|---|
| 161 | 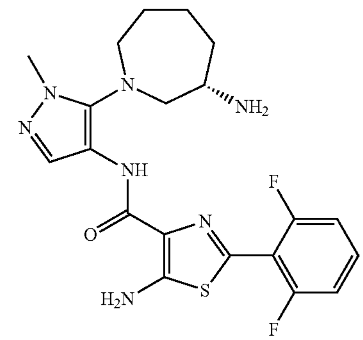 [SMILES: Cn1ncc(NC(=O)c2nc(-c3c(F)cccc3F)sc2N)c1N1CCCC[C@H](N)C1] | (S)-5-amino-N-(5-(3-aminoazepan-1-yl)-1-methyl-1H-pyrazol-4-yl)-2-(2,6-difluorophenyl)thiazole-4-carboxamide |
| 162 | 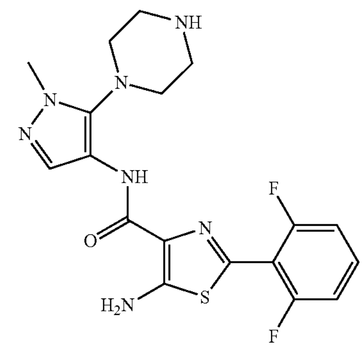 [SMILES: Cn1ncc(NC(=O)c2nc(-c3c(F)cccc3F)sc2N)c1N1CCNCC1] | 5-amino-2-(2,6-difluorophenyl)-N-(1-methyl-5-(piperazin-1-yl)-1H-pyrazol-4-yl)thiazole-4-carboxamide |
| 163 | 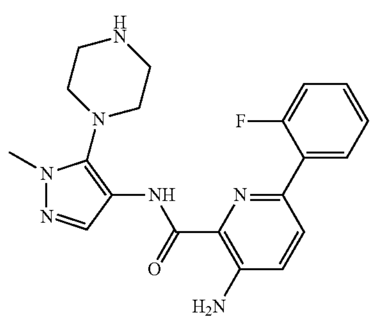 [SMILES: Cn1ncc(NC(=O)c2nc(-c3ccccc3F)ccc2N)c1N1CCNCC1] | 3-amino-6-(2-fluorophenyl)-N-(1-methyl-5-(piperazin-1-yl)-1H-pyrazol-4-yl)picolinamide |
| 164 | 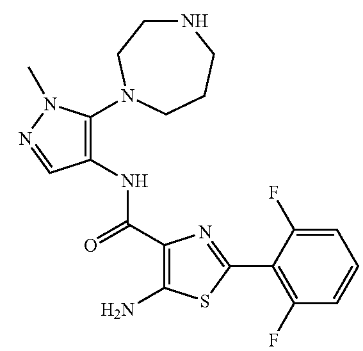 [SMILES: Cn1ncc(NC(=O)c2nc(-c3c(F)cccc3F)sc2N)c1N1CCCNCC1] | N-(5-(1,4-diazepan-1-yl)-1-methyl-1H-pyrazol-4-yl)-5-amino-2-(2,6-difluorophenyl)thiazole-4-carboxamide |

TABLE 2-continued

| No. | Structure | Name |
|---|---|---|
| 165 | 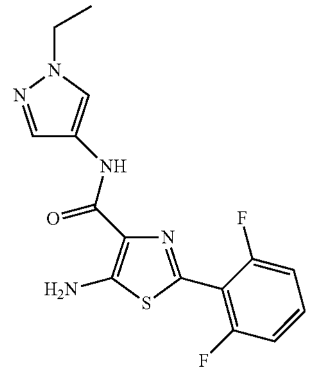 [SMILES: CCn1cc(NC(=O)c2nc(-c3c(F)cccc3F)sc2N)cn1] | 5-amino-2-(2,6-difluorophenyl)-N-(1-ethyl-1H-pyrazol-4-yl)thiazole-4-carboxamide |
| 166 | 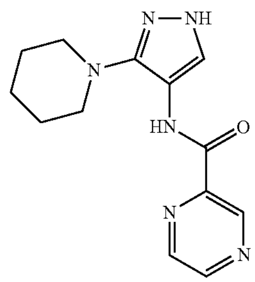 [SMILES: O=C(Nc1c[nH]nc1N1CCCCC1)c1cnccn1] | N-(3-(piperidin-1-yl)-1H-pyrazol-4-yl)pyrazine-2-carboxamide |
| 167 | 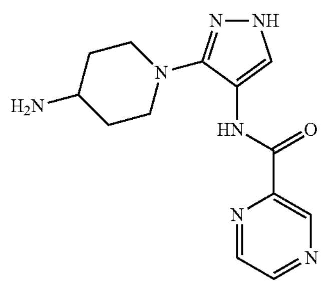 [SMILES: NC1CCN(c2n[nH]cc2NC(=O)c2cnccn2)CC1] | N-(3-(4-aminopiperidin-1-yl)-1H-pyrazol-4-yl)pyrazine-2-carboxamide |
| 168 | 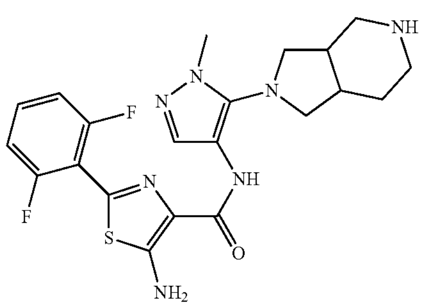 [SMILES: Cn1ncc(NC(=O)c2nc(-c3c(F)cccc3F)sc2N)c1N1CC2CCNCC2C1] | 5-amino-2-(2,6-difluorophenyl)-N-(1-methyl-5-(1H-pyrrolo[3,4-c]pyridin-2(3H,3aH,4H,5H,6H,7H,7aH)-yl)-1H-pyrazol-4-yl)thiazole-4-carboxamide |
| 169 | 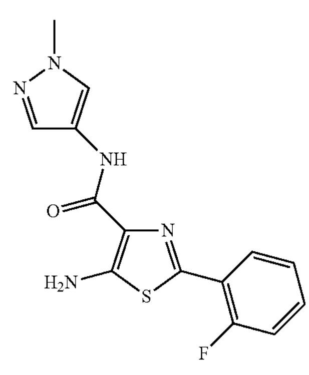 [SMILES: Cn1cc(NC(=O)c2nc(-c3ccccc3F)sc2N)cn1] | 5-amino-2-(2-fluorophenyl)-N-(1-methyl-1H-pyrazol-4-yl)thiazole-4-carboxamide |

TABLE 2-continued

| No. | Structure | Name |
|---|---|---|
| 170 | 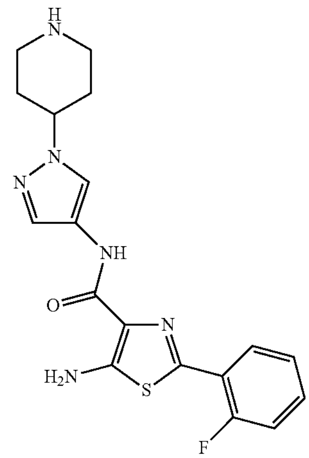 [SMILES: Nc1sc(-c2ccccc2F)nc1C(=O)Nc1cnn(C2CCNCC2)c1] | 5-amino-2-(2-fluorophenyl)-N-(1-(piperidin-4-yl)-1H-pyrazol-4-yl)thiazole-4-carboxamide |
| 171 | 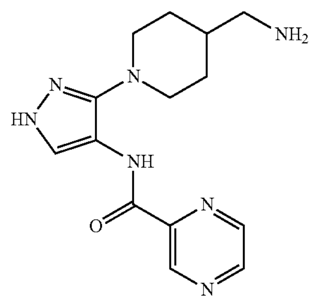 [SMILES: NCC1CCN(c2n[nH]cc2NC(=O)c2cnccn2)CC1] | N-(3-(4-(aminomethyl)piperidin-1-yl)-1H-pyrazol-4-yl)pyrazine-2-carboxamide |
| 172 | 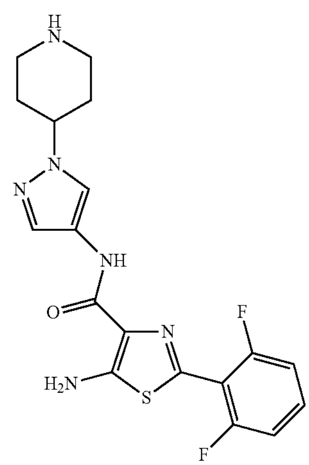 [SMILES: Nc1sc(-c2c(F)cccc2F)nc1C(=O)Nc1cnn(C2CCNCC2)c1] | 5-amino-2-(2,6-difluorophenyl)-N-(1-(piperidin-4-yl)-1H-pyrazol-4-yl)thiazole-4-carboxamide |
| 173 | 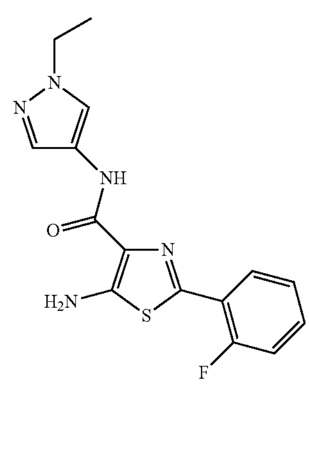 [SMILES: CCn1cc(NC(=O)c2nc(-c3ccccc3F)sc2N)cn1] | 5-amino-N-(1-ethyl-1H-pyrazol-4-yl)-2-(2-fluorophenyl)thiazole-4-carboxamide |

TABLE 2-continued

| No. | Structure | Name |
|---|---|---|
| 174 | 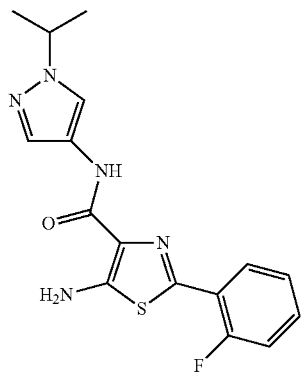 [SMILES: CC(C)n1cc(NC(=O)c2nc(-c3ccccc3F)sc2N)cn1] | 5-amino-2-(2-fluorophenyl)-N-(1-isopropyl-1H-pyrazol-4-yl)thiazole-4-carboxamide |
| 175 | 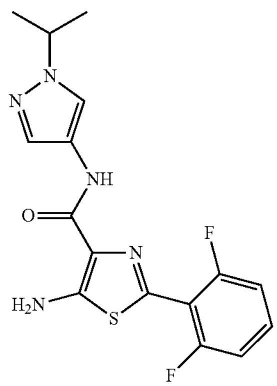 [SMILES: CC(C)n1cc(NC(=O)c2nc(-c3c(F)cccc3F)sc2N)cn1] | 5-amino-2-(2,6-difluorophenyl)-N-(1-isopropyl-1H-pyrazol-4-yl)thiazole-4-carboxamide |
| 176 | 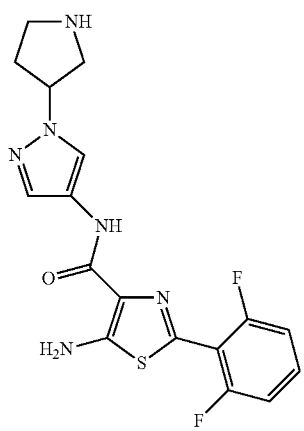 [SMILES: Nc1sc(-c2c(F)cccc2F)nc1C(=O)Nc1cnn(C2CCNC2)c1] | 5-amino-2-(2,6-difluorophenyl)-N-(1-(pyrrolidin-3-yl)-1H-pyrazol-4-yl)thiazole-4-carboxamide |
| 177 | 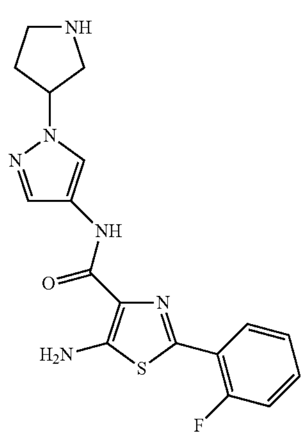 [SMILES: Nc1sc(-c2ccccc2F)nc1C(=O)Nc1cnn(C2CCNC2)c1] | 5-amino-2-(2-fluorophenyl)-N-(1-(pyrrolidin-3-yl)-1H-pyrazol-4-yl)thiazole-4-carboxamide |

TABLE 2-continued

| No. | Structure | Name |
|---|---|---|
| 178 | 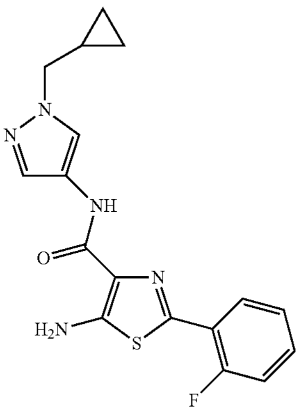 [SMILES: Nc1sc(-c2ccccc2F)nc1C(=O)Nc1cnn(CC2CC2)c1] | 5-amino-N-(1-(cyclopropylmethyl)-1H-pyrazol-4-yl)-2-(2-fluorophenyl)thiazole-4-carboxamide |
| 179 | 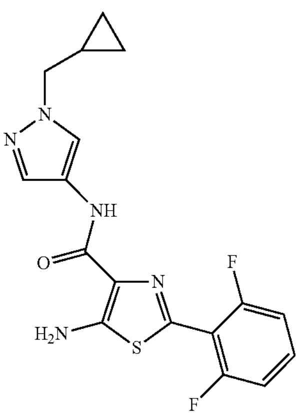 [SMILES: Nc1sc(-c2c(F)cccc2F)nc1C(=O)Nc1cnn(CC2CC2)c1] | 5-amino-N-(1-(cyclopropylmethyl)-1H-pyrazol-4-yl)-2-(2,6-difluorophenyl)thiazole-4-carboxamide |
| 180 | 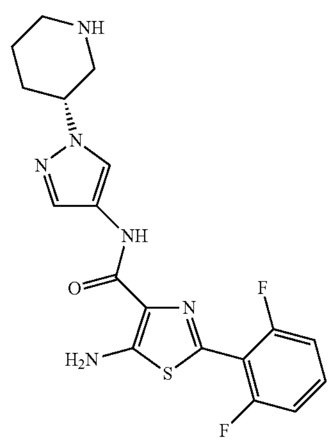 [SMILES: Nc1sc(-c2c(F)cccc2F)nc1C(=O)Nc1cnn([C@@H]2CCCNC2)c1] | (R)-5-amino-2-(2,6-difluorophenyl)-N-(1-(piperidin-3-yl)-1H-pyrazol-4-yl)thiazole-4-carboxamide |
| 181 | 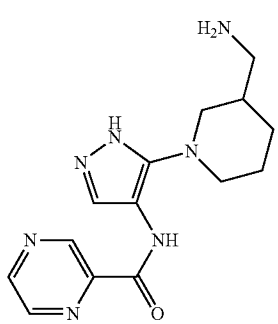 [SMILES: NCC1CCCN(c2[nH]ncc2NC(=O)c2cnccn2)C1] | N-(5-(3-(aminomethyl)piperidin-1-yl)-1H-pyrazol-4-yl)pyrazine-2-carboxamide |

TABLE 2-continued

| No. | Structure | Name |
|---|---|---|
| 182 | 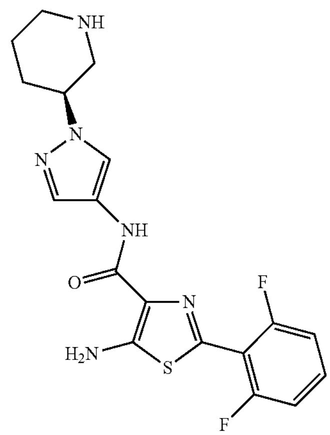 [SMILES: Nc1sc(-c2c(F)cccc2F)nc1C(=O)Nc1cnn([C@H]2CCCNC2)c1] | (S)-5-amino-2-(2,6-difluorophenyl)-N-(1-(piperidin-3-yl)-1H-pyrazol-4-yl)thiazole-4-carboxamide |
| 183 | 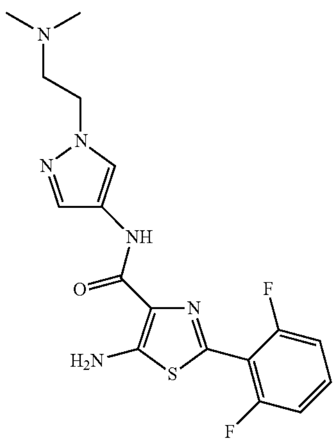 [SMILES: CN(C)CCn1cc(NC(=O)c2nc(-c3c(F)cccc3F)sc2N)cn1] | 5-amino-2-(2,6-difluorophenyl)-N-(1-(2-(dimethylamino)ethyl)-1H-pyrazol-4-yl)thiazole-4-carboxamide |
| 184 | 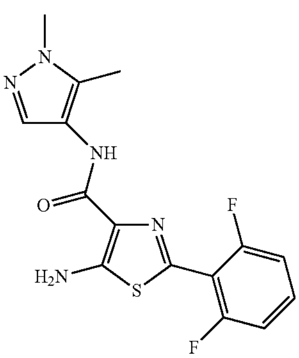 [SMILES: Cc1c(NC(=O)c2nc(-c3c(F)cccc3F)sc2N)cnn1C] | 5-amino-2-(2,6-difluorophenyl)-N-(1,5-dimethyl-1H-pyrazol-4-yl)thiazole-4-carboxamide |
| 185 | 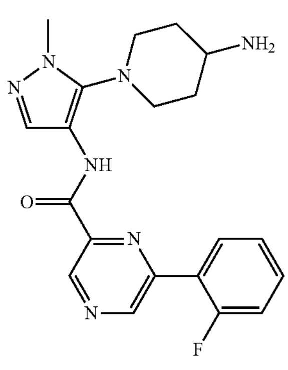 [SMILES: Cn1ncc(NC(=O)c2cncc(-c3ccccc3F)n2)c1N1CCC(N)CC1] | N-(5-(4-aminopiperidin-1-yl)-1-methyl-1H-pyrazol-4-yl)-6-(2-fluorophenyl)pyrazine-2-carboxamide |

TABLE 2-continued

| No. | Structure | Name |
|---|---|---|
| 186 | 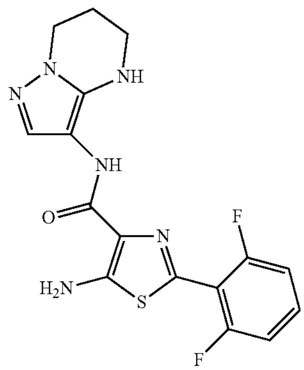 [SMILES: Nc1sc(-c2c(F)cccc2F)nc1C(=O)Nc1cnn2c1NCCC2] | 5-amino-2-(2,6-difluorophenyl)-N-(4,5,6,7-tetrahydropyrazolo[1,5-a]pyrimidin-3-yl)thiazole-4-carboxamide |
| 187 | 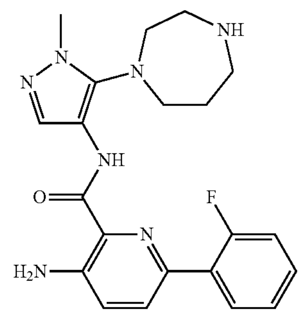 [SMILES: Cn1ncc(NC(=O)c2nc(-c3ccccc3F)ccc2N)c1N1CCCNCC1] | N-(5-(1,4-diazepan-1-yl)-1-methyl-1H-pyrazol-4-yl)-3-amino-6-(2-fluorophenyl)picolinamide |
| 188 | 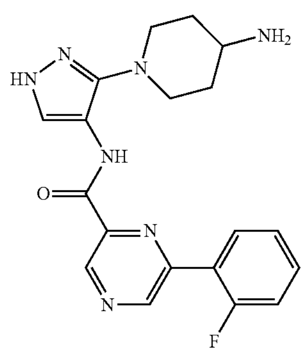 [SMILES: NC1CCN(c2n[nH]cc2NC(=O)c2cncc(-c3ccccc3F)n2)CC1] | N-(3-(4-aminopiperidin-1-yl)-1H-pyrazol-4-yl)-6-(2-fluorophenyl)pyrazine-2-carboxamide |
| 189 | 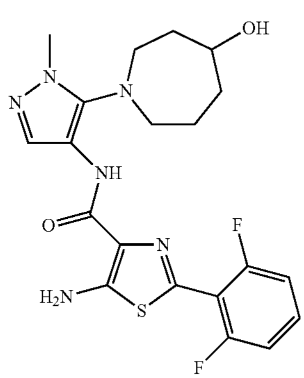 [SMILES: Cn1ncc(NC(=O)c2nc(-c3c(F)cccc3F)sc2N)c1N1CCCC(O)CC1] | 5-amino-2-(2,6-difluorophenyl)-N-(5-(4-hydroxyazepan-1-yl)-1-methyl-1H-pyrazol-4-yl)thiazole-4-carboxamide |

TABLE 2-continued

| No. | Structure | Name |
|---|---|---|
| 190 | 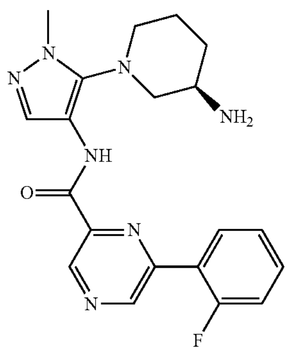 [SMILES: Cn1ncc(NC(=O)c2cncc(-c3ccccc3F)n2)c1N1CCC[C@@H](N)C1] | (R)-N-(5-(3-aminopiperidin-1-yl)-1-methyl-1H-pyrazol-4-yl)-6-(2-fluorophenyl)pyrazine-2-carboxamide |
| 191 | 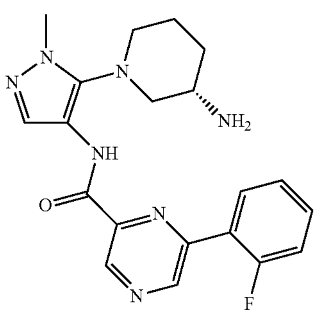 [SMILES: Cn1ncc(NC(=O)c2cncc(-c3ccccc3F)n2)c1N1CCC[C@H](N)C1] | (S)-N-(5-(3-aminopiperidin-1-yl)-1-methyl-1H-pyrazol-4-yl)-6-(2-fluorophenyl)pyrazine-2-carboxamide |
| 192 | 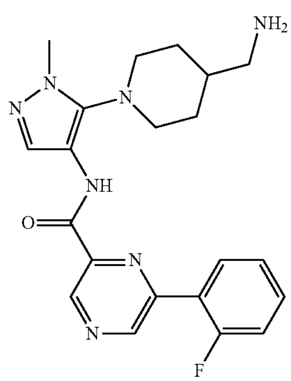 [SMILES: Cn1ncc(NC(=O)c2cncc(-c3ccccc3F)n2)c1N1CCC(CN)CC1] | N-(5-(4-(aminomethyl)piperidin-1-yl)-1-methyl-1H-pyrazol-4-yl)-6-(2-fluorophenyl)pyrazine-2-carboxamide |
| 193 | 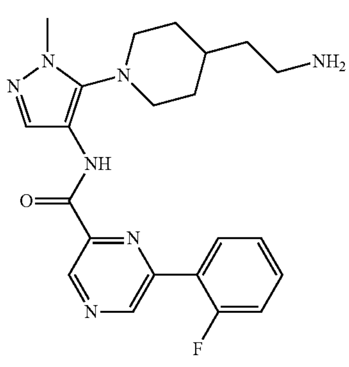 [SMILES: Cn1ncc(NC(=O)c2cncc(-c3ccccc3F)n2)c1N1CCC(CCN)CC1] | N-(5-(4-(2-aminoethyl)piperidin-1-yl)-1-methyl-1H-pyrazol-4-yl)-6-(2-fluorophenyl)pyrazine-2-carboxamide |

TABLE 2-continued

| No. | Structure | Name |
|---|---|---|
| 194 | 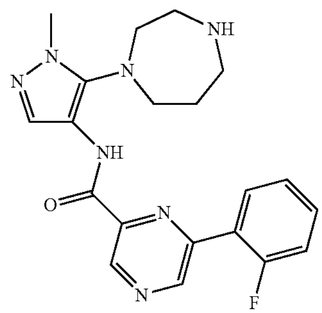 [SMILES: Cn1ncc(NC(=O)c2cncc(-c3ccccc3F)n2)c1N1CCCNCC1] | N-(5-(1,4-diazepan-1-yl)-1-methyl-1H-pyrazol-4-yl)-6-(2-fluorophenyl)pyrazine-2-carboxamide |
| 195 | 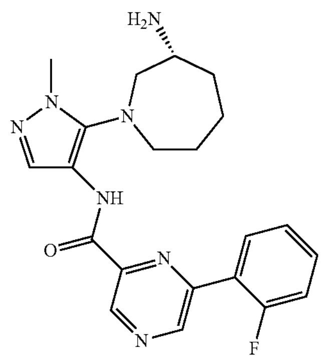 [SMILES: Cn1ncc(NC(=O)c2cncc(-c3ccccc3F)n2)c1N1CCCC[C@@H](N)C1] | (R)-N-(5-(3-aminoazepan-1-yl)-1-methyl-1H-pyrazol-4-yl)-6-(2-fluorophenyl)pyrazine-2-carboxamide |
| 196 | 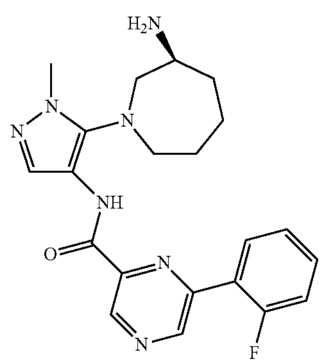 [SMILES: Cn1ncc(NC(=O)c2cncc(-c3ccccc3F)n2)c1N1CCCC[C@H](N)C1] | (S)-N-(5-(3-aminoazepan-1-yl)-1-methyl-1H-pyrazol-4-yl)-6-(2-fluorophenyl)pyrazine-2-carboxamide |
| 197 | 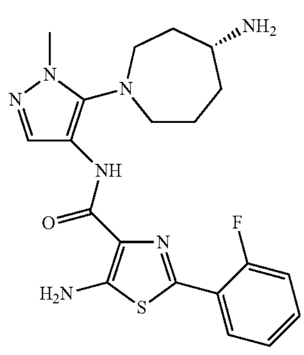 [SMILES: Cn1ncc(NC(=O)c2nc(-c3ccccc3F)sc2N)c1N1CCC[C@@H](N)CC1] | (R)-5-amino-N-(5-(4-aminoazepan-1-yl)-1-methyl-1H-pyrazol-4-yl)-2-(2-fluorophenyl)thiazole-4-carboxamide |

TABLE 2-continued

| No. | Structure | Name |
|---|---|---|
| 198 | 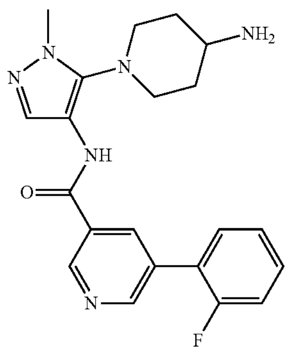 [SMILES: Cn1ncc(NC(=O)c2cncc(-c3ccccc3F)c2)c1N1CCC(N)CC1] | N-(5-(4-aminopiperidin-1-yl)-1-methyl-1H-pyrazol-4-yl)-5-(2-fluorophenyl)nicotinamide |
| 199 | 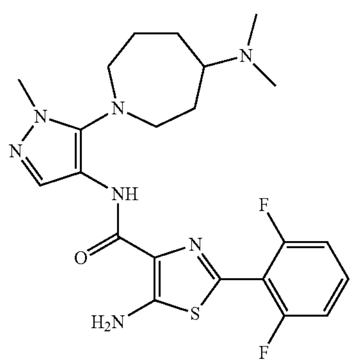 [SMILES: CN(C)C1CCCN(c2c(NC(=O)c3nc(-c4c(F)cccc4F)sc3N)cnn2C)CC1] | 5-amino-2-(2,6-difluorophenyl)-N-(5-(4-(dimethylamino)azepan-1-yl)-1-methyl-1H-pyrazol-4-yl)thiazole-4-carboxamide |
| 200 | 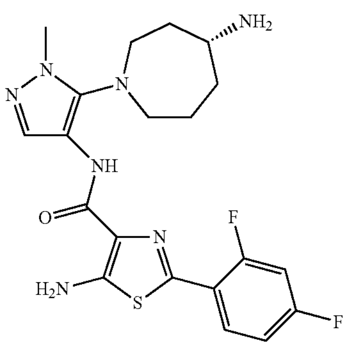 [SMILES: Cn1ncc(NC(=O)c2nc(-c3ccc(F)cc3F)sc2N)c1N1CCC[C@@H](N)CC1] | (R)-5-amino-N-(5-(4-aminoazepan-1-yl)-1-methyl-1H-pyrazol-4-yl)-2-(2,4-difluorophenyl)thiazole-4-carboxamide |
| 201 | 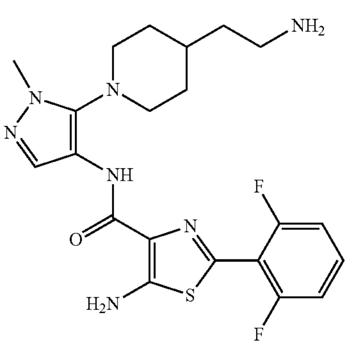 [SMILES: Cn1ncc(NC(=O)c2nc(-c3c(F)cccc3F)sc2N)c1N1CCC(CCN)CC1] | 5-amino-N-(5-(4-(2-aminoethyl)piperidin-1-yl)-1-methyl-1H-pyrazol-4-yl)-2-(2,6-difluorophenyl)thiazole-4-carboxamide |

TABLE 2-continued

| No. | Structure | Name |
|---|---|---|
| 202 | 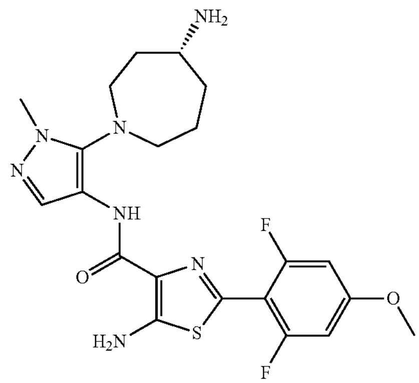 [SMILES: COc1cc(F)c(-c2nc(C(=O)Nc3cnn(C)c3N3CCC[C@@H](N)CC3)c(N)s2)c(F)c1] | (R)-5-amino-N-(5-(4-aminoazepan-1-yl)-1-methyl-1H-pyrazol-4-yl)-2-(2,6-difluoro-4-methoxyphenyl)thiazole-4-carboxamide |
| 203 | 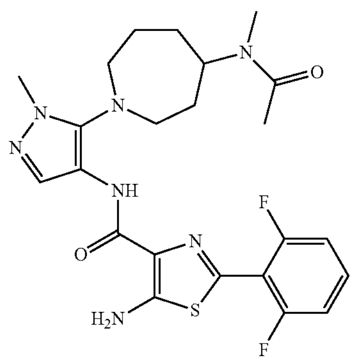 [SMILES: CC(=O)N(C)C1CCCN(c2c(NC(=O)c3nc(-c4c(F)cccc4F)sc3N)cnn2C)CC1] | 5-amino-2-(2,6-difluorophenyl)-N-(1-methyl-5-(4-(N-methylacetamido)azepan-1-yl)-1H-pyrazol-4-yl)thiazole-4-carboxamide |
| 204 | 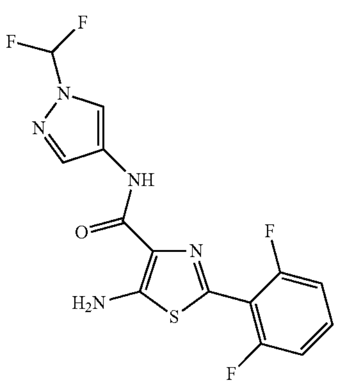 [SMILES: Nc1sc(-c2c(F)cccc2F)nc1C(=O)Nc1cnn(C(F)F)c1] | 5-amino-N-(1-(difluoromethyl)-1H-pyrazol-4-yl)-2-(2,6-difluorophenyl)thiazole-4-carboxamide |
| 205 | 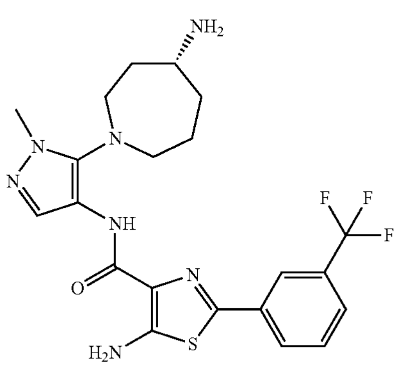 [SMILES: Cn1ncc(NC(=O)c2nc(-c3cccc(C(F)(F)F)c3)sc2N)c1N1CCC[C@@H](N)CC1] | (R)-5-amino-N-(5-(4-aminoazepan-1-yl)-1-methyl-1H-pyrazol-4-yl)-2-(3-(trifluoromethyl)phenyl)thiazole-4-carboxamide |

TABLE 2-continued

| No. | Structure | Name |
|---|---|---|
| 206 | 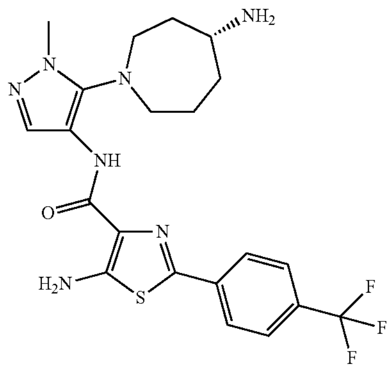 [SMILES: Cn1ncc(NC(=O)c2nc(-c3ccc(C(F)(F)F)cc3)sc2N)c1N1CCC[C@@H](N)CC1] | (R)-5-amino-N-(5-(4-aminoazepan-1-yl)-1-methyl-1H-pyrazol-4-yl)-2-(4-(trifluoromethyl)phenyl)thiazole-4-carboxamide |
| 207 | 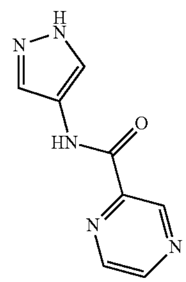 [SMILES: O=C(Nc1cn[nH]c1)c1cnccn1] | N-(1H-pyrazol-4-yl)pyrazine-2-carboxamide |
| 208 | 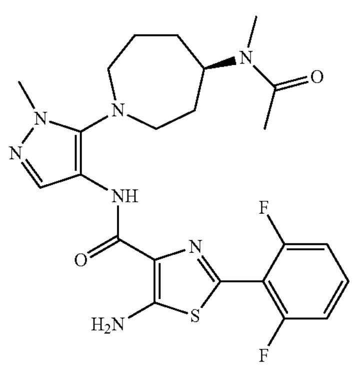 [SMILES: CC(=O)N(C)[C@@H]1CCCN(c2c(NC(=O)c3nc(-c4c(F)cccc4F)sc3N)cnn2C)CC1] | (R)-5-amino-2-(2,6-difluorophenyl)-N-(1-methyl-5-(4-(N-methylacetamido)azepan-1-yl)-1H-pyrazol-4-yl)thiazole-4-carboxamide |
| 209 | 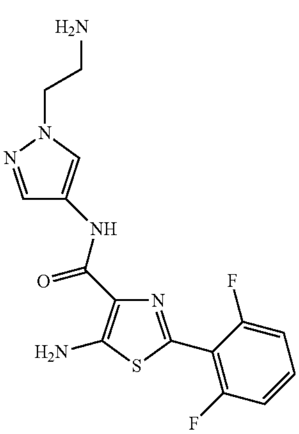 [SMILES: NCCn1cc(NC(=O)c2nc(-c3c(F)cccc3F)sc2N)cn1] | 5-amino-N-(1-(2-aminoethyl)-1H-pyrazol-4-yl)-2-(2,6-difluorophenyl)thiazole-4-carboxamide |

TABLE 2-continued

| No. | Structure | Name |
|---|---|---|
| 210 | 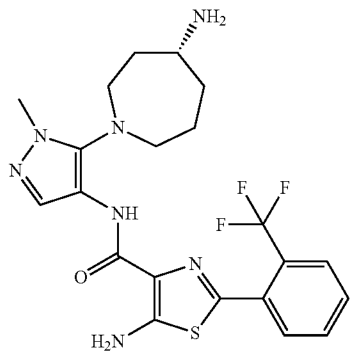 [SMILES: Cn1ncc(NC(=O)c2nc(-c3ccccc3C(F)(F)F)sc2N)c1N1CCC[C@@H](N)CC1] | (R)-5-amino-N-(5-(4-aminoazepan-1-yl)-1-methyl-1H-pyrazol-4-yl)-2-(2-(trifluoromethyl)phenyl)thiazole-4-carboxamide |
| 211 | 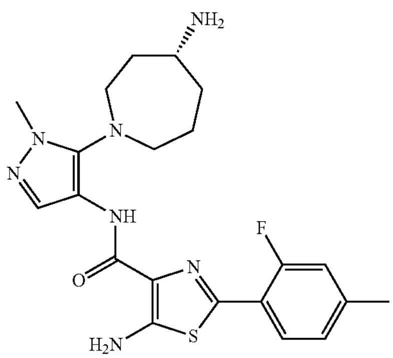 [SMILES: Cc1ccc(-c2nc(C(=O)Nc3cnn(C)c3N3CCC[C@@H](N)CC3)c(N)s2)c(F)c1] | (R)-5-amino-N-(5-(4-aminoazepan-1-yl)-1-methyl-1H-pyrazol-4-yl)-2-(2-fluoro-4-methylphenyl)thiazole-4-carboxamide |
| 212 | 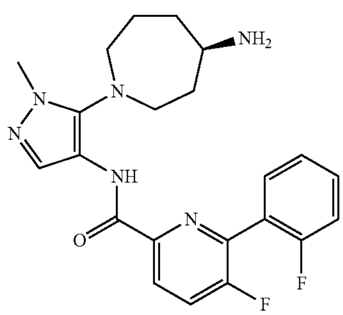 [SMILES: Cn1ncc(NC(=O)c2ccc(F)c(-c3ccccc3F)n2)c1N1CCC[C@@H](N)CC1] | (R)-N-(5-(4-aminoazepan-1-yl)-1-methyl-1H-pyrazol-4-yl)-5-fluoro-6-(2-fluorophenyl)picolinamide |
| 213 | 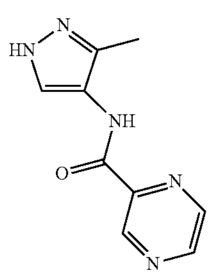 | N-(3-methyl-1H-pyrazol-4-yl)pyrazine-2-carboxamide |

TABLE 2-continued

| No. | Structure | Name |
|---|---|---|
| 214 | 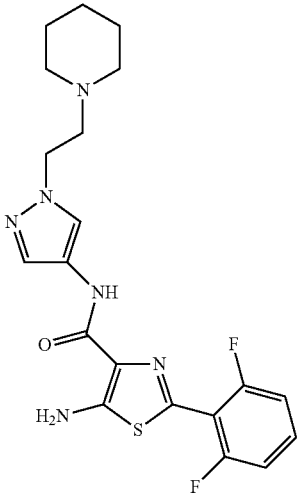 [SMILES: Nc1sc(-c2c(F)cccc2F)nc1C(=O)Nc1cnn(CCN2CCCCC2)c1] | 5-amino-2-(2,6-difluorophenyl)-N-(1-(2-(piperidin-1-yl)ethyl)-1H-pyrazol-4-yl)thiazole-4-carboxamide |
| 215 | 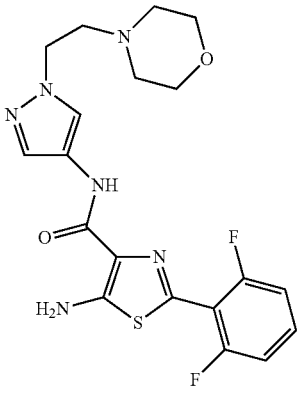 [SMILES: Nc1sc(-c2c(F)cccc2F)nc1C(=O)Nc1cnn(CCN2CCOCC2)c1] | 5-amino-2-(2,6-difluorophenyl)-N-(1-(2-morpholinoethyl)-1H-pyrazol-4-yl)thiazole-4-carboxamide |
| 216 | 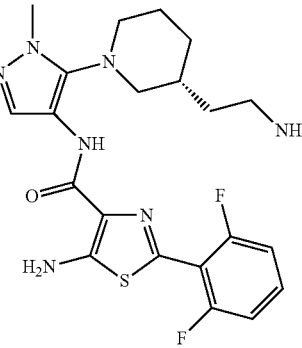 | (R)-5-amino-N-(5-(3-(2-aminoethyl)piperidin-1-yl)-1-methyl-1H-pyrazol-4-yl)-2-(2,6-difluorophenyl)thiazole-4-carboxamide |
| 217 | 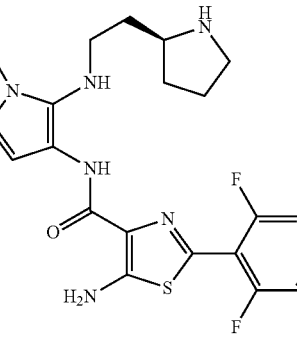 | (S)-5-amino-2-(2,6-difluorophenyl)-N-(1-methyl-5-(2-(pyrrolidin-2-yl)ethylamino)-1H-pyrazol-4-yl)thiazole-4-carboxamide |

TABLE 2-continued
| No. | Structure | Name |
|---|---|---|
| 218 | 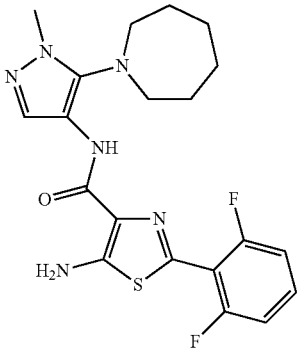 [SMILES: Cn1ncc(NC(=O)c2nc(-c3c(F)cccc3F)sc2N)c1N1CCCCCC1] | 5-amino-N-(5-(azepan-1-yl)-1-methyl-1H-pyrazol-4-yl)-2-(2,6-difluorophenyl)thiazole-4-carboxamide |
| 219 | 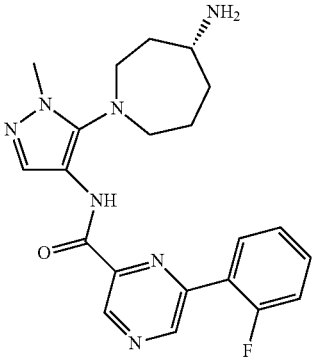 [SMILES: Cn1ncc(NC(=O)c2cncc(-c3ccccc3F)n2)c1N1CCC[C@@H](N)CC1] | (R)-N-(5-(4-aminoazepan-1-yl)-1-methyl-1H-pyrazol-4-yl)-6-(2-fluorophenyl)pyrazine-2-carboxamide |
| 220 | 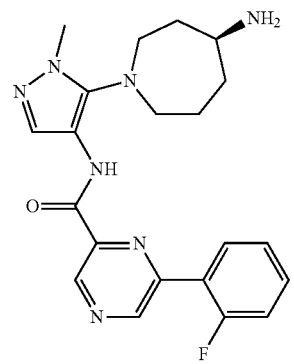 [SMILES: Cn1ncc(NC(=O)c2cncc(-c3ccccc3F)n2)c1N1CCC[C@H](N)CC1] | (S)-N-(5-(4-aminoazepan-1-yl)-1-methyl-1H-pyrazol-4-yl)-6-(2-fluorophenyl)pyrazine-2-carboxamide |
| 221 | 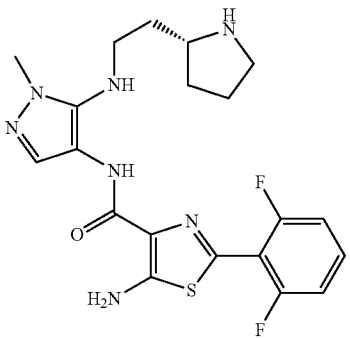 [SMILES: Cn1ncc(NC(=O)c2nc(-c3c(F)cccc3F)sc2N)c1NCC[C@H]1CCCN1] | (R)-5-amino-2-(2,6-difluorophenyl)-N-(1-methyl-5-(2-(pyrrolidin-2-yl)ethylamino)-1H-pyrazol-4-yl)thiazole-4-carboxamide |

TABLE 2-continued

| No. | Structure | Name |
|---|---|---|
| 222 | 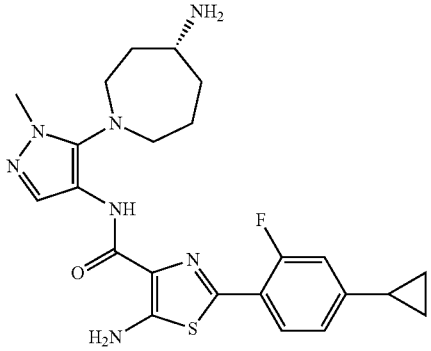 [SMILES: Cn1ncc(NC(=O)c2nc(-c3ccc(C4CC4)cc3F)sc2N)c1N1CCC[C@@H](N)CC1] | (R)-5-amino-N-(5-(4-aminoazepan-1-yl)-1-methyl-1H-pyrazol-4-yl)-2-(4-cyclopropyl-2-fluorophenyl)thiazole-4-carboxamide |
| 223 | 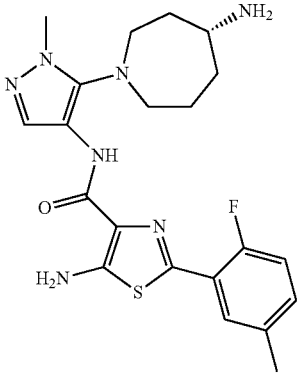 [SMILES: Cc1ccc(F)c(-c2nc(C(=O)Nc3cnn(C)c3N3CCC[C@@H](N)CC3)c(N)s2)c1] | (R)-5-amino-N-(5-(4-aminoazepan-1-yl)-1-methyl-1H-pyrazol-4-yl)-2-(2-fluoro-5-methylphenyl)thiazole-4-carboxamide |
| 224 | 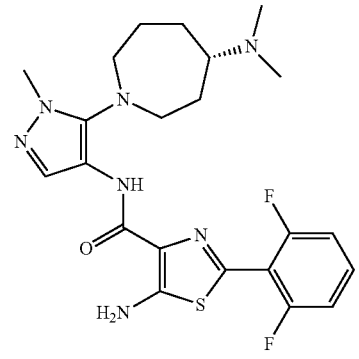 [SMILES: CN(C)[C@H]1CCCN(c2c(NC(=O)c3nc(-c4c(F)cccc4F)sc3N)cnn2C)CC1] | (S)-5-amino-2-(2,6-difluorophenyl)-N-(5-(4-(dimethylamino)azepan-1-yl)-1-methyl-1H-pyrazol-4-yl)thiazole-4-carboxamide |
| 225 | 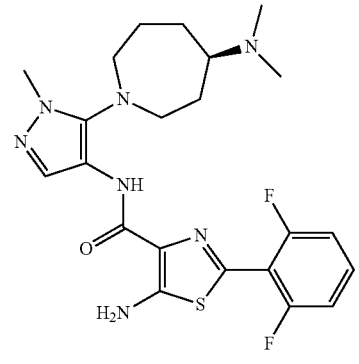 [SMILES: CN(C)[C@@H]1CCCN(c2c(NC(=O)c3nc(-c4c(F)cccc4F)sc3N)cnn2C)CC1] | (R)-5-amino-2-(2,6-difluorophenyl)-N-(5-(4-(dimethylamino)azepan-1-yl)-1-methyl-1H-pyrazol-4-yl)thiazole-4-carboxamide |

TABLE 2-continued

| No. | Structure | Name |
|---|---|---|
| 226 | 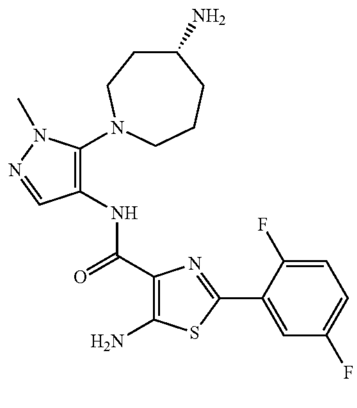 [SMILES: Cn1ncc(NC(=O)c2nc(-c3cc(F)ccc3F)sc2N)c1N1CCC[C@@H](N)CC1] | (R)-5-amino-N-(5-(4-aminoazepan-1-yl)-1-methyl-1H-pyrazol-4-yl)-2-(2,5-difluorophenyl)thiazole-4-carboxamide |
| 227 | 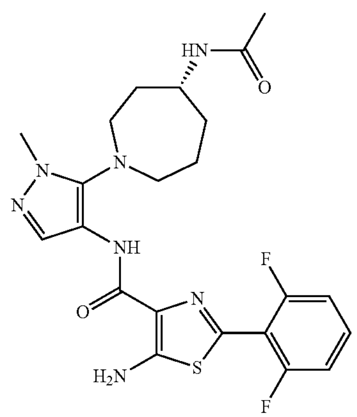 [SMILES: CC(=O)N[C@@H]1CCCN(c2c(NC(=O)c3nc(-c4c(F)cccc4F)sc3N)cnn2C)CC1] | (R)-N-(5-(4-acetamidoazepan-1-yl)-1-methyl-1H-pyrazol-4-yl)-5-amino-2-(2,6-difluorophenyl)thiazole-4-carboxamide |
| 228 | 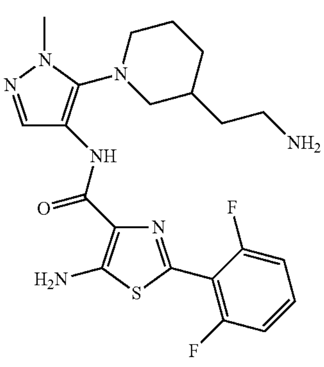 [SMILES: Cn1ncc(NC(=O)c2nc(-c3c(F)cccc3F)sc2N)c1N1CCCC(CCN)C1] | 5-amino-N-(5-(3-(2-aminoethyl)piperidin-1-yl)-1-methyl-1H-pyrazol-4-yl)-2-(2,6-difluorophenyl)thiazole-4-carboxamide |
| 229 | 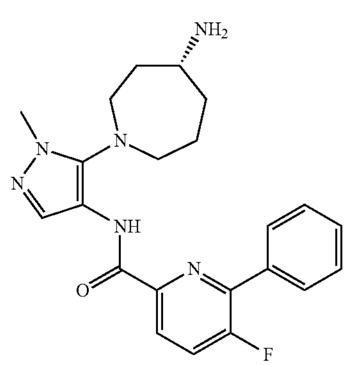 [SMILES: Cn1ncc(NC(=O)c2ccc(F)c(-c3ccccc3)n2)c1N1CCC[C@@H](N)CC1] | (R)-N-(5-(4-aminoazepan-1-yl)-1-methyl-1H-pyrazol-4-yl)-5-fluoro-6-phenylpicolinamide |

TABLE 2-continued

| No. | Structure | Name |
|---|---|---|
| 230 | 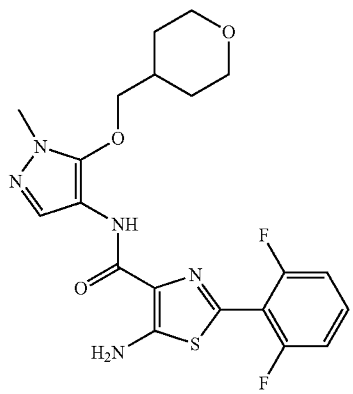 [SMILES: Cn1ncc(NC(=O)c2nc(-c3c(F)cccc3F)sc2N)c1OCC1CCOCC1] | 5-amino-2-(2,6-difluorophenyl)-N-(1-methyl-5-((tetrahydro-2H-pyran-4-yl)methoxy)-1H-pyrazol-4-yl)thiazole-4-carboxamide |
| 231 | 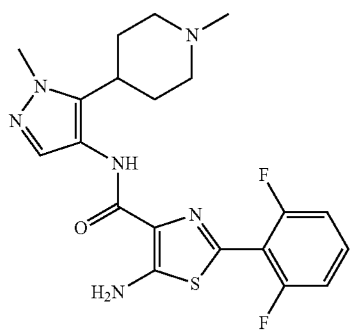 [SMILES: CN1CCC(c2c(NC(=O)c3nc(-c4c(F)cccc4F)sc3N)cnn2C)CC1] | 5-amino-2-(2,6-difluorophenyl)-N-(1-methyl-5-(1-methylpiperidin-4-yl)-1H-pyrazol-4-yl)thiazole-4-carboxamide |
| 232 | 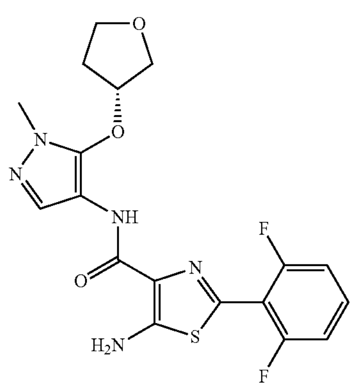 [SMILES: Cn1ncc(NC(=O)c2nc(-c3c(F)cccc3F)sc2N)c1O[C@@H]1CCOC1] | (R)-5-amino-2-(2,6-difluorophenyl)-N-(1-methyl-5-(tetrahydrofuran-3-yloxy)-1H-pyrazol-4-yl)thiazole-4-carboxamide |
| 233 | 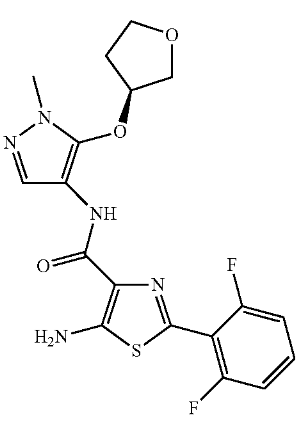 [SMILES: Cn1ncc(NC(=O)c2nc(-c3c(F)cccc3F)sc2N)c1O[C@H]1CCOC1] | (S)-5-amino-2-(2,6-difluorophenyl)-N-(1-methyl-5-(tetrahydrofuran-3-yloxy)-1H-pyrazol-4-yl)thiazole-4-carboxamide |

TABLE 2-continued

| No. | Structure | Name |
|---|---|---|
| 234 | 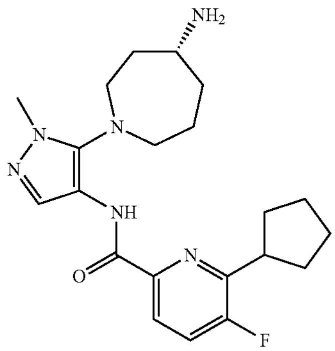 [SMILES: Cn1ncc(NC(=O)c2ccc(F)c(C3CCCC3)n2)c1N1CCC[C@@H](N)CC1] | (R)-N-(5-(4-aminoazepan-1-yl)-1-methyl-1H-pyrazol-4-yl)-6-cyclopentyl-5-fluoropicolinamide |
| 235 | 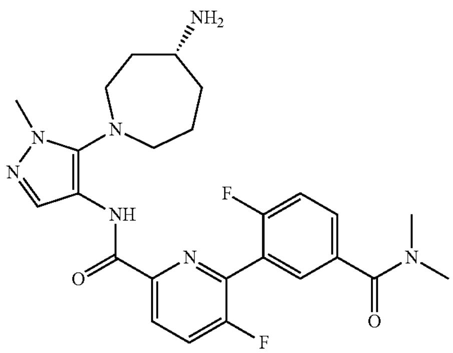 [SMILES: CN(C)C(=O)c1ccc(F)c(-c2nc(C(=O)Nc3cnn(C)c3N3CCC[C@@H](N)CC3)ccc2F)c1] | (R)-N-(5-(4-aminoazepan-1-yl)-1-methyl-1H-pyrazol-4-yl)-6-(5-(dimethylcarbamoyl)-2-fluorophenyl)-5-fluoropicolinamide |
| 236 | 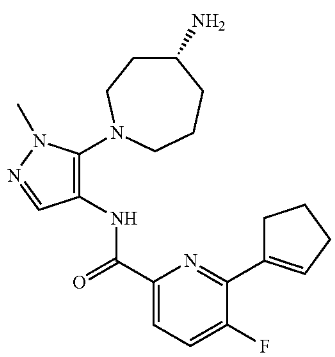 [SMILES: Cn1ncc(NC(=O)c2ccc(F)c(C3=CCCC3)n2)c1N1CCC[C@@H](N)CC1] | (R)-N-(5-(4-aminoazepan-1-yl)-1-methyl-1H-pyrazol-4-yl)-6-cyclopentenyl-5-fluoropicolinamide |
| 237 | 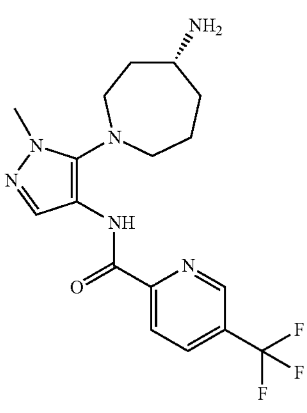 [SMILES: Cn1ncc(NC(=O)c2ccc(C(F)(F)F)cn2)c1N1CCC[C@@H](N)CC1] | (R)-N-(5-(4-aminoazepan-1-yl)-1-methyl-1H-pyrazol-4-yl)-5-(trifluoromethyl)picolinamide |

TABLE 2-continued
| No. | Structure | Name |
|---|---|---|
| 238 | 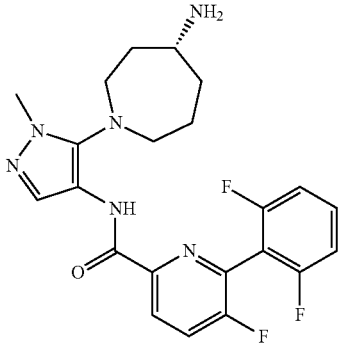 [SMILES: Cn1ncc(NC(=O)c2ccc(F)c(-c3c(F)cccc3F)n2)c1N1CCC[C@@H](N)CC1] | (R)-N-(5-(4-aminoazepan-1-yl)-1-methyl-1H-pyrazol-4-yl)-6-(2,6-difluorophenyl)-5-fluoropicolinamide |
| 239 | 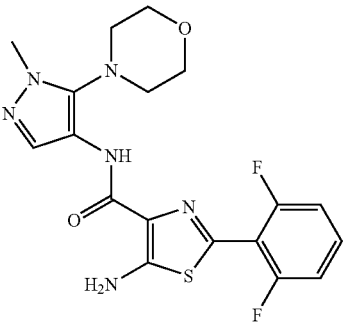 | 5-amino-2-(2,6-difluorophenyl)-N-(1-methyl-5-morpholino-1H-pyrazol-4-yl)thiazole-4-carboxamide |
| 240 | 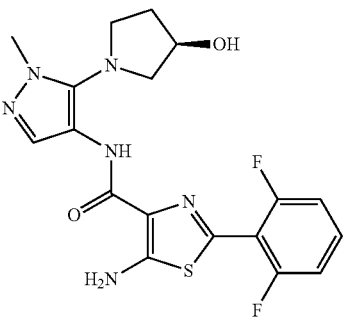 | (R)-5-amino-2-(2,6-difluorophenyl)-N-(5-(3-hydroxypyrrolidin-1-yl)-1-methyl-1H-pyrazol-4-yl)thiazole-4-carboxamide |
| 241 | 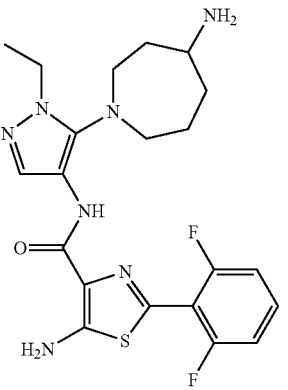 [SMILES: CCn1ncc(NC(=O)c2nc(-c3c(F)cccc3F)sc2N)c1N1CCCC(N)CC1] | 5-amino-N-(5-(4-aminoazepan-1-yl)-1-ethyl-1H-pyrazol-4-yl)-2-(2,6-difluorophenyl)thiazole-4-carboxamide |

TABLE 2-continued

| No. | Structure | Name |
|---|---|---|
| 242 | 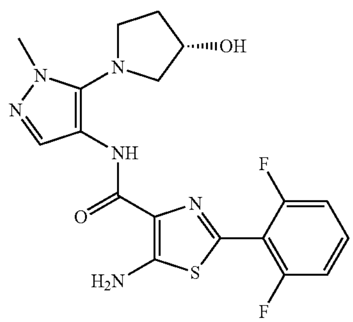 [SMILES: Cn1ncc(NC(=O)c2nc(-c3c(F)cccc3F)sc2N)c1N1CC[C@H](O)C1] | (S)-5-amino-2-(2,6-difluorophenyl)-N-(5-(3-hydroxypyrrolidin-1-yl)-1-methyl-1H-pyrazol-4-yl)thiazole-4-carboxamide |
| 243 | 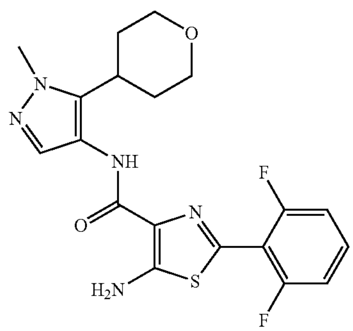 [SMILES: Cn1ncc(NC(=O)c2nc(-c3c(F)cccc3F)sc2N)c1C1CCOCC1] | 5-amino-2-(2,6-difluorophenyl)-N-(1-methyl-5-(tetrahydro-2H-pyran-4-yl)-1H-pyrazol-4-yl)thiazole-4-carboxamide |
| 244 | 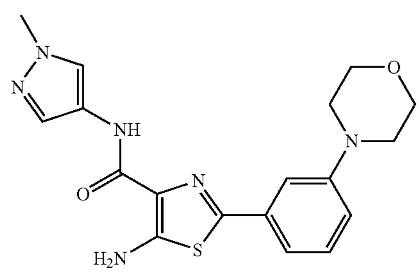 [SMILES: Cn1cc(NC(=O)c2nc(-c3cccc(N4CCOCC4)c3)sc2N)cn1] | 5-amino-N-(1-methyl-1H-pyrazol-4-yl)-2-(3-morpholinophenyl)thiazole-4-carboxamide |
| 245 | 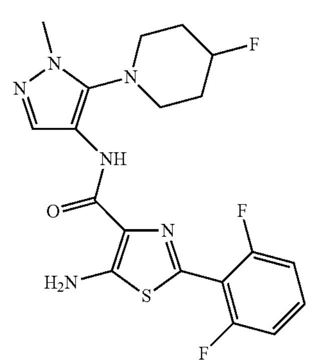 [SMILES: Cn1ncc(NC(=O)c2nc(-c3c(F)cccc3F)sc2N)c1N1CCC(F)CC1] | 5-amino-2-(2,6-difluorophenyl)-N-(5-(4-fluoropiperidin-1-yl)-1-methyl-1H-pyrazol-4-yl)thiazole-4-carboxamide |

TABLE 2-continued

| No. | Structure | Name |
|---|---|---|
| 246 | 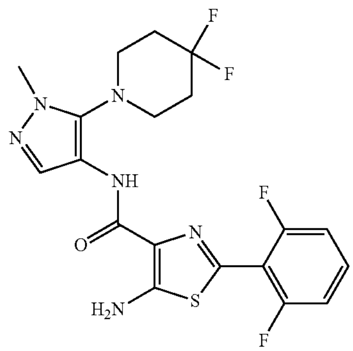 [SMILES: Cn1ncc(NC(=O)c2nc(-c3c(F)cccc3F)sc2N)c1N1CCC(F)(F)CC1] | 5-amino-2-(2,6-difluorophenyl)-N-(5-(4,4-difluoropiperidin-1-yl)-1-methyl-1H-pyrazol-4-yl)thiazole-4-carboxamide |
| 247 | 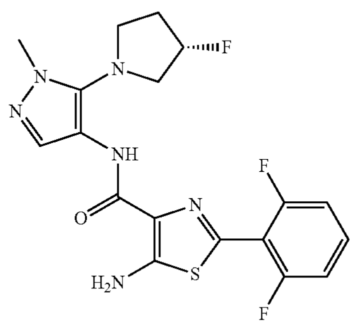 [SMILES: Cn1ncc(NC(=O)c2nc(-c3c(F)cccc3F)sc2N)c1N1CC[C@H](F)C1] | (S)-5-amino-2-(2,6-difluorophenyl)-N-(5-(3-fluoropyrrolidin-1-yl)-1-methyl-1H-pyrazol-4-yl)thiazole-4-carboxamide |
| 248 | 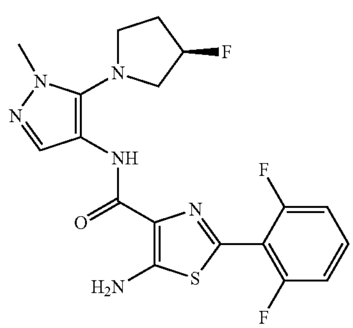 [SMILES: Cn1ncc(NC(=O)c2nc(-c3c(F)cccc3F)sc2N)c1N1CC[C@@H](F)C1] | (R)-5-amino-2-(2,6-difluorophenyl)-N-(5-(3-fluoropyrrolidin-1-yl)-1-methyl-1H-pyrazol-4-yl)thiazole-4-carboxamide |
| 249 | 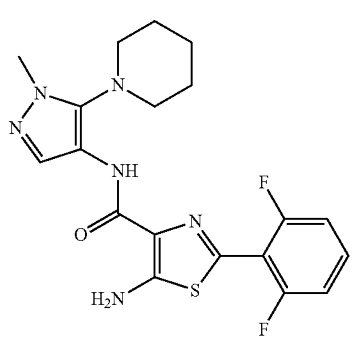 [SMILES: Cn1ncc(NC(=O)c2nc(-c3c(F)cccc3F)sc2N)c1N1CCCCC1] | 5-amino-2-(2,6-difluorophenyl)-N-(1-methyl-5-(piperidin-1-yl)-1H-pyrazol-4-yl)thiazole-4-carboxamide |

TABLE 2-continued

| No. | Structure | Name |
|---|---|---|
| 250 | 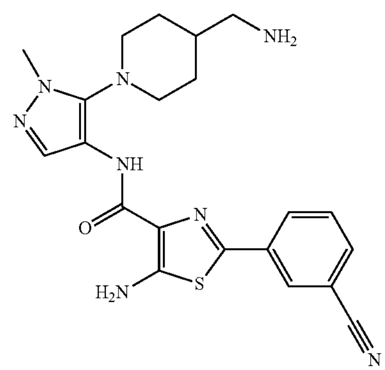 [SMILES: Cn1ncc(NC(=O)c2nc(-c3cccc(C#N)c3)sc2N)c1N1CCC(CN)CC1] | 5-amino-N-(5-(4-(aminomethyl)piperidin-1-yl)-1-methyl-1H-pyrazol-4-yl)-2-(3-cyanophenyl)thiazole-4-carboxamide |
| 251 | 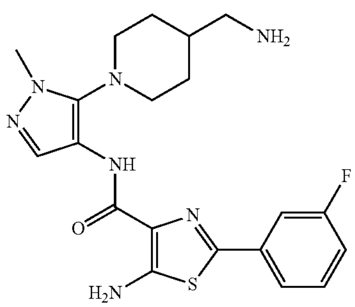 [SMILES: Cn1ncc(NC(=O)c2nc(-c3cccc(F)c3)sc2N)c1N1CCC(CN)CC1] | 5-amino-N-(5-(4-(aminomethyl)piperidin-1-yl)-1-methyl-1H-pyrazol-4-yl)-2-(3-fluorophenyl)thiazole-4-carboxamide |
| 252 | 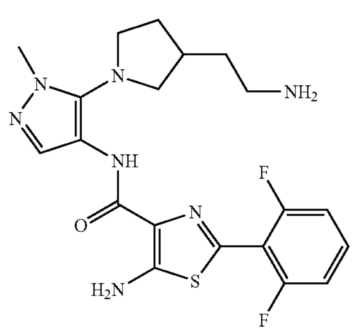 [SMILES: Cn1ncc(NC(=O)c2nc(-c3c(F)cccc3F)sc2N)c1N1CCC(CCN)C1] | 5-amino-N-(5-(3-(2-aminoethyl)pyrrolidin-1-yl)-1-methyl-1H-pyrazol-4-yl)-2-(2,6-difluorophenyl)thiazole-4-carboxamide |
| 253 | 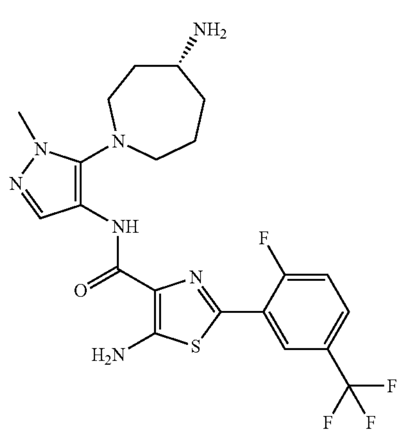 [SMILES: Cn1ncc(NC(=O)c2nc(-c3cc(C(F)(F)F)ccc3F)sc2N)c1N1CCC[C@@H](N)CC1] | (R)-5-amino-N-(5-(4-aminoazepan-1-yl)-1-methyl-1H-pyrazol-4-yl)-2-(2-fluoro-5-(trifluoromethyl)phenyl)thiazole-4-carboxamide |

TABLE 2-continued

| No. | Structure | Name |
|---|---|---|
| 254 | 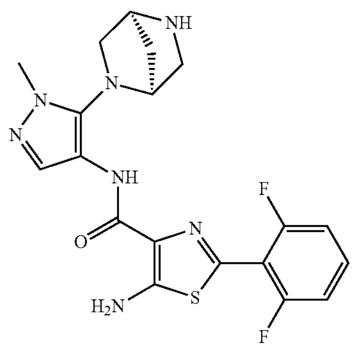 [SMILES: Cn1ncc(NC(=O)c2nc(-c3c(F)cccc3F)sc2N)c1N1C[C@@H]2C[C@H]1CN2] | N-(5-((1S,4S)-2,5-diazabicyclo[2.2.1]heptan-2-yl)-1-methyl-1H-pyrazol-4-yl)-5-amino-2-(2,6-difluorophenyl)thiazole-4-carboxamide |
| 255 | 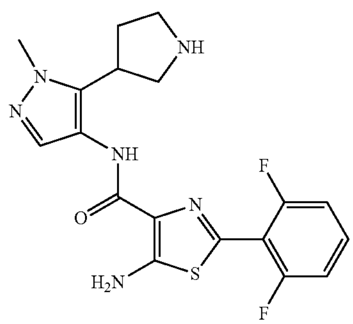 [SMILES: Cn1ncc(NC(=O)c2nc(-c3c(F)cccc3F)sc2N)c1C1CCNC1] | 5-amino-2-(2,6-difluorophenyl)-N-(1-methyl-5-(pyrrolidin-3-yl)-1H-pyrazol-4-yl)thiazole-4-carboxamide |
| 256 | 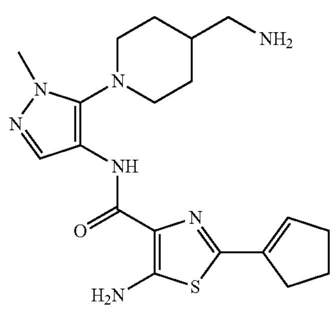 [SMILES: Cn1ncc(NC(=O)c2nc(C3=CCCC3)sc2N)c1N1CCC(CN)CC1] | 5-amino-N-(5-(4-(aminomethyl)piperidin-1-yl)-1-methyl-1H-pyrazol-4-yl)-2-cyclopentenylthiazole-4-carboxamide |
| 257 | 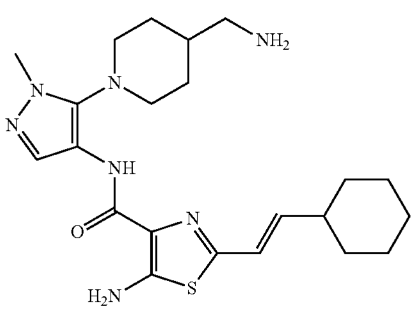 [SMILES: Cn1ncc(NC(=O)c2nc(/C=C/C3CCCCC3)sc2N)c1N1CCC(CN)CC1] | (E)-5-amino-N-(5-(4-(aminomethyl)piperidin-1-yl)-1-methyl-1H-pyrazol-4-yl)-2-(2-cyclohexylvinyl)thiazole-4-carboxamide |
| 258 | 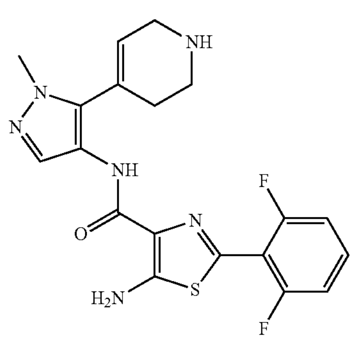 [SMILES: Cn1ncc(NC(=O)c2nc(-c3c(F)cccc3F)sc2N)c1C1=CCNCC1] | 5-amino-2-(2,6-difluorophenyl)-N-(1-methyl-5-(1,2,3,6-tetrahydropyridin-4-yl)-1H-pyrazol-4-yl)thiazole-4-carboxamide |

TABLE 2-continued

| No. | Structure | Name |
|---|---|---|
| 259 | 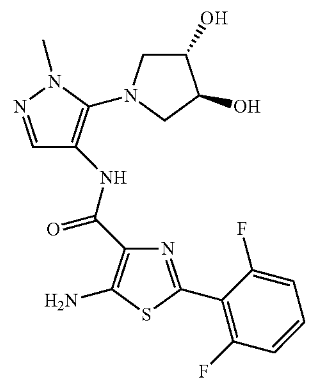 [SMILES: Cn1ncc(NC(=O)c2nc(-c3c(F)cccc3F)sc2N)c1N1C[C@H](O)[C@@H](O)C1] | 5-amino-2-(2,6-difluorophenyl)-N-(5-((3S,4S)-3,4-dihydroxypyrrolidin-1-yl)-1-methyl-1H-pyrazol-4-yl)thiazole-4-carboxamide |
| 260 | 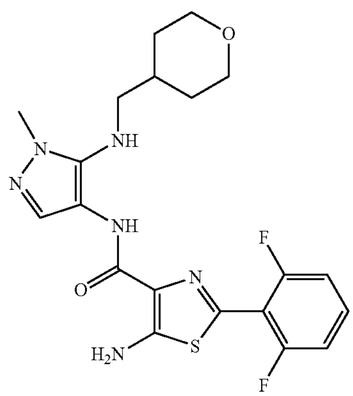 [SMILES: Cn1ncc(NC(=O)c2nc(-c3c(F)cccc3F)sc2N)c1NCC1CCOCC1] | 5-amino-2-(2,6-difluorophenyl)-N-(1-methyl-5-((tetrahydro-2H-pyran-4-yl)methylamino)-1H-pyrazol-4-yl)thiazole-4-carboxamide |
| 261 | 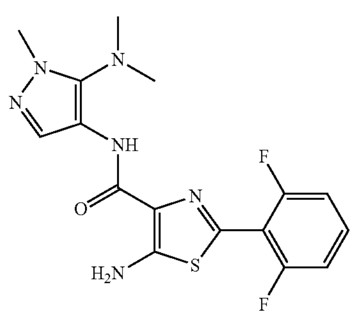 [SMILES: CN(C)c1c(NC(=O)c2nc(-c3c(F)cccc3F)sc2N)cnn1C] | 5-amino-2-(2,6-difluorophenyl)-N-(5-(dimethylamino)-1-methyl-1H-pyrazol-4-yl)thiazole-4-carboxamide |
| 262 | 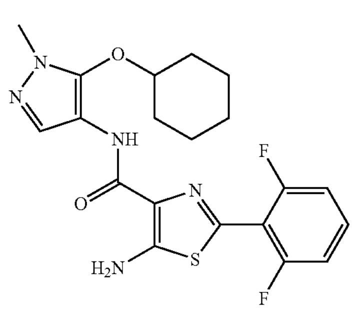 [SMILES: Cn1ncc(NC(=O)c2nc(-c3c(F)cccc3F)sc2N)c1OC1CCCCC1] | 5-amino-N-(5-(cyclohexyloxy)-1-methyl-1H-pyrazol-4-yl)-2-(2,6-difluorophenyl)thiazole-4-carboxamide |

TABLE 2-continued

| No. | Structure | Name |
|---|---|---|
| 263 | 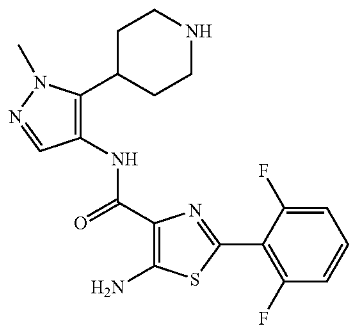 [SMILES: Cn1ncc(NC(=O)c2nc(-c3c(F)cccc3F)sc2N)c1C1CCNCC1] | 5-amino-2-(2,6-difluorophenyl)-N-(1-methyl-5-(piperidin-4-yl)-1H-pyrazol-4-yl)thiazole-4-carboxamide |
| 264 | 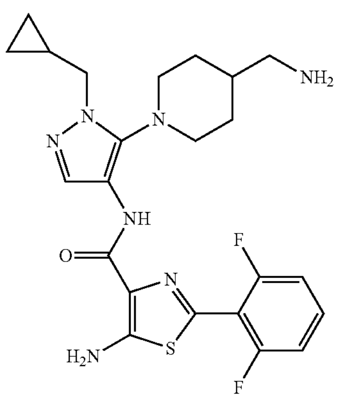 [SMILES: NCC1CCN(c2c(NC(=O)c3nc(-c4c(F)cccc4F)sc3N)cnn2CC2CC2)CC1] | 5-amino-N-(5-(4-(aminomethyl)piperidin-1-yl)-1-(cyclopropylmethyl)-1H-pyrazol-4-yl)-2-(2,6-difluorophenyl)thiazole-4-carboxamide |
| 265 | 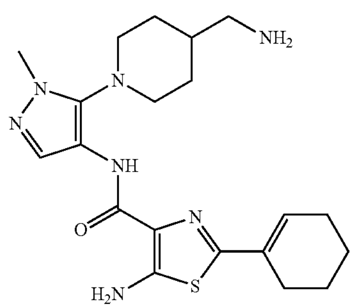 [SMILES: Cn1ncc(NC(=O)c2nc(C3=CCCCC3)sc2N)c1N1CCC(CN)CC1] | 5-amino-N-(5-(4-(aminomethyl)piperidin-1-yl)-1-methyl-1H-pyrazol-4-yl)-2-cyclohexenylthiazole-4-carboxamide |
| 266 | 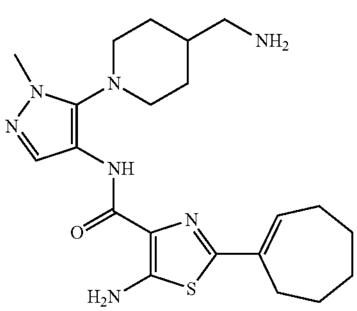 [SMILES: Cn1ncc(NC(=O)c2nc(C3=CCCCCC3)sc2N)c1N1CCC(CN)CC1] | 5-amino-N-(5-(4-(aminomethyl)piperidin-1-yl)-1-methyl-1H-pyrazol-4-yl)-2-cycloheptenylthiazole-4-carboxamide |

TABLE 2-continued

| No. | Structure | Name |
|---|---|---|
| 267 | 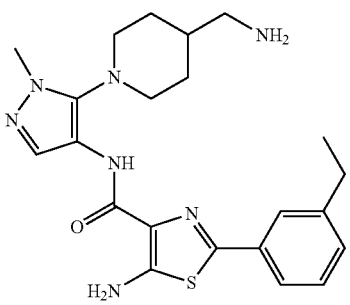 [SMILES: CCc1cccc(-c2nc(C(=O)Nc3cnn(C)c3N3CCC(CN)CC3)c(N)s2)c1] | 5-amino-N-(5-(4-(aminomethyl)piperidin-1-yl)-1-methyl-1H-pyrazol-4-yl)-2-(3-ethylphenyl)thiazole-4-carboxamide |
| 268 | 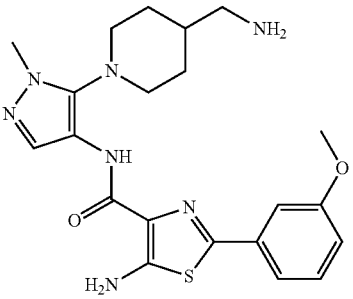 [SMILES: COc1cccc(-c2nc(C(=O)Nc3cnn(C)c3N3CCC(CN)CC3)c(N)s2)c1] | 5-amino-N-(5-(4-(aminomethyl)piperidin-1-yl)-1-methyl-1H-pyrazol-4-yl)-2-(3-methoxyphenyl)thiazole-4-carboxamide |
| 269 | 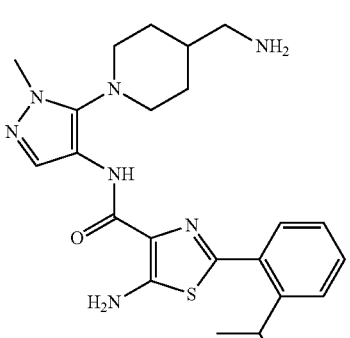 | 5-amino-N-(5-(4-(aminomethyl)piperidin-1-yl)-1-methyl-1H-pyrazol-4-yl)-2-(2-isopropylphenyl)thiazole-4-carboxamide |
| 270 | 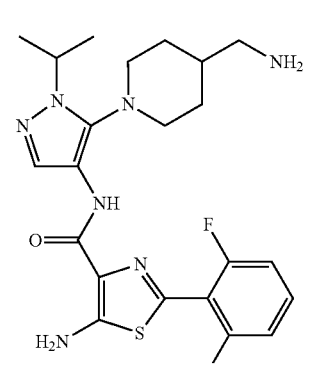 | 5-amino-N-(5-(4-(aminomethyl)piperidin-1-yl)-1-isopropyl-1H-pyrazol-4-yl)-2-(2,6-difluorophenyl)thiazole-4-carboxamide |

TABLE 2-continued

| No. | Structure | Name |
|---|---|---|
| 271 | 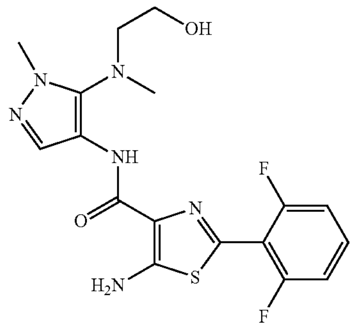 [SMILES: CN(CCO)c1c(NC(=O)c2nc(-c3c(F)cccc3F)sc2N)cnn1C] | 5-amino-2-(2,6-difluorophenyl)-N-(5-((2-hydroxyethyl)(methyl)amino)-1-methyl-1H-pyrazol-4-yl)thiazole-4-carboxamide |
| 272 | 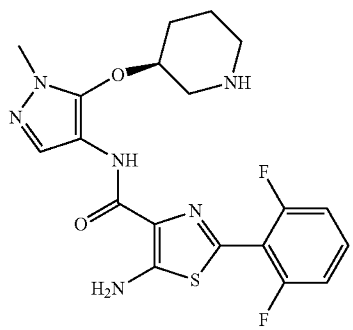 [SMILES: Cn1ncc(NC(=O)c2nc(-c3c(F)cccc3F)sc2N)c1O[C@H]1CCCNC1] | (S)-5-amino-2-(2,6-difluorophenyl)-N-(1-methyl-5-(piperidin-3-yloxy)-1H-pyrazol-4-yl)thiazole-4-carboxamide |
| 273 | 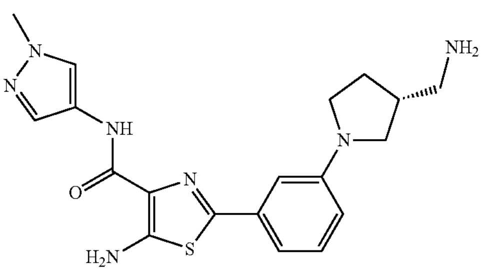 [SMILES: Cn1cc(NC(=O)c2nc(-c3cccc(N4CC[C@H](CN)C4)c3)sc2N)cn1] | (R)-5-amino-2-(3-(3-(aminomethyl)pyrrolidin-1-yl)phenyl)-N-(1-methyl-1H-pyrazol-4-yl)thiazole-4-carboxamide |
| 274 | 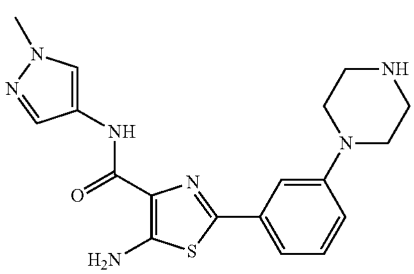 [SMILES: Cn1cc(NC(=O)c2nc(-c3cccc(N4CCNCC4)c3)sc2N)cn1] | 5-amino-N-(1-methyl-1H-pyrazol-4-yl)-2-(3-(piperazin-1-yl)phenyl)thiazole-4-carboxamide |
| 275 | 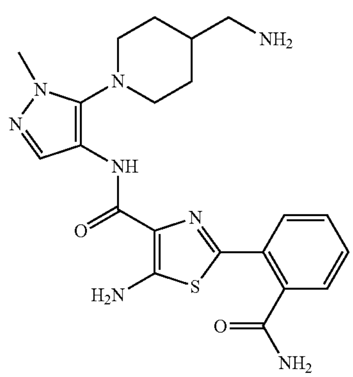 [SMILES: Cn1ncc(NC(=O)c2nc(-c3ccccc3C(N)=O)sc2N)c1N1CCC(CN)CC1] | 5-amino-N-(5-(4-(aminomethyl)piperidin-1-yl)-1-methyl-1H-pyrazol-4-yl)-2-(2-carbamoylphenyl)thiazole-4-carboxamide |

TABLE 2-continued

| No. | Structure | Name |
|---|---|---|
| 276 | 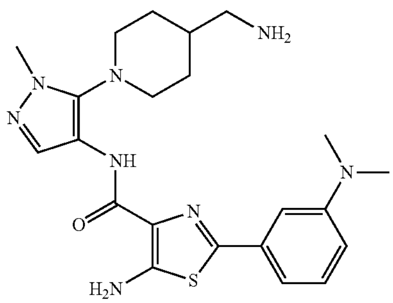 | 5-amino-N-(5-(4-(aminomethyl)piperidin-1-yl)-1-methyl-1H-pyrazol-4-yl)-2-(3-(dimethylamino)phenyl)thiazole-4-carboxamide |
| 277 | 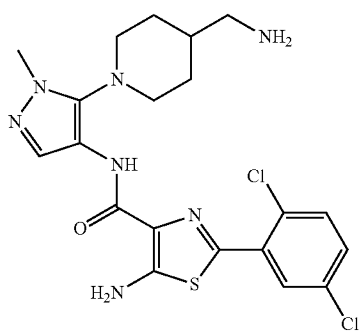 [SMILES: Cn1ncc(NC(=O)c2nc(-c3cc(Cl)ccc3Cl)sc2N)c1N1CCC(CN)CC1] | 5-amino-N-(5-(4-(aminomethyl)piperidin-1-yl)-1-methyl-1H-pyrazol-4-yl)-2-(2,5-dichlorophenyl)thiazole-4-carboxamide |
| 278 | 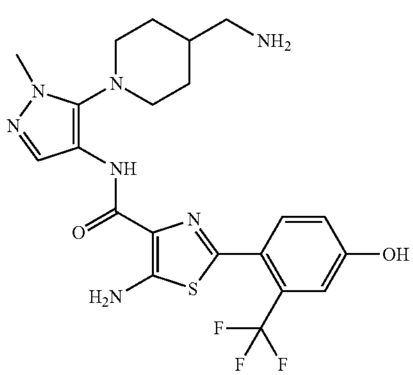 [SMILES: Cn1ncc(NC(=O)c2nc(-c3ccc(O)cc3C(F)(F)F)sc2N)c1N1CCC(CN)CC1] | 5-amino-N-(5-(4-(aminomethyl)piperidin-1-yl)-1-methyl-1H-pyrazol-4-yl)-2-(4-hydroxy-2-(trifluoromethyl)phenyl)thiazole-4-carboxamide |
| 279 | 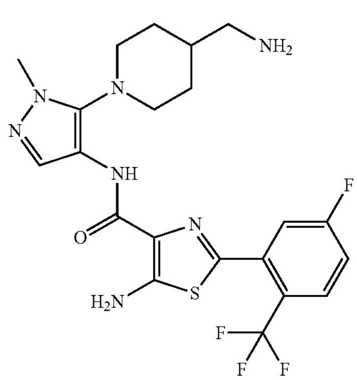 [SMILES: Cn1ncc(NC(=O)c2nc(-c3cc(F)ccc3C(F)(F)F)sc2N)c1N1CCC(CN)CC1] | 5-amino-N-(5-(4-(aminomethyl)piperidin-1-yl)-1-methyl-1H-pyrazol-4-yl)-2-(5-fluoro-2-(trifluoromethyl)phenyl)thiazole-4-carboxamide |

TABLE 2-continued

| No. | Structure | Name |
|---|---|---|
| 280 | 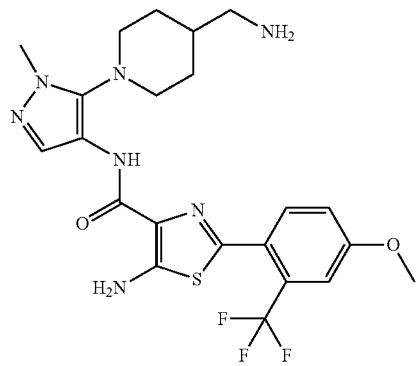 [SMILES: COc1ccc(-c2nc(C(=O)Nc3cnn(C)c3N3CCC(CN)CC3)c(N)s2)c(C(F)(F)F)c1] | 5-amino-N-(5-(4-(aminomethyl)piperidin-1-yl)-1-methyl-1H-pyrazol-4-yl)-2-(4-methoxy-2-(trifluoromethyl)phenyl)thiazole-4-carboxamide |
| 281 | 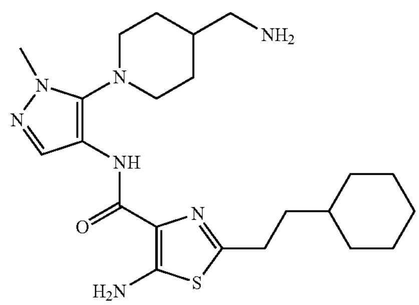 | 5-amino-N-(5-(4-(aminomethyl)piperidin-1-yl)-1-methyl-1H-pyrazol-4-yl)-2-(2-cyclohexylethyl)thiazole-4-carboxamide |
| 282 | 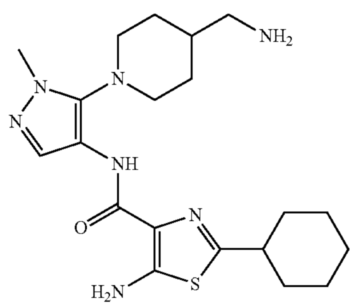 [SMILES: Cn1ncc(NC(=O)c2nc(C3CCCCC3)sc2N)c1N1CCC(CN)CC1] | 5-amino-N-(5-(4-(aminomethyl)piperidin-1-yl)-1-methyl-1H-pyrazol-4-yl)-2-cyclohexylthiazole-4-carboxamide |
| 283 | 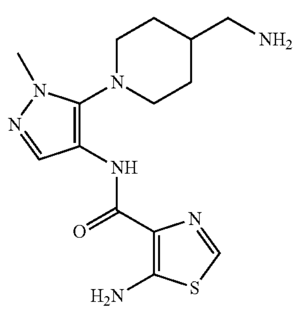 [SMILES: Cn1ncc(NC(=O)c2ncsc2N)c1N1CCC(CN)CC1] | 5-amino-N-(5-(4-(aminomethyl)piperidin-1-yl)-1-methyl-1H-pyrazol-4-yl)thiazole-4-carboxamide |
| 284 | 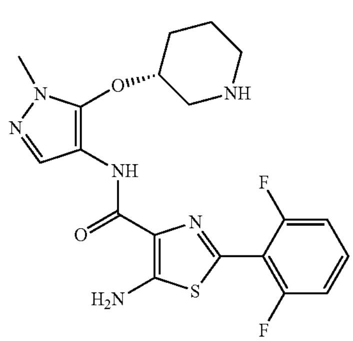 [SMILES: Cn1ncc(NC(=O)c2nc(-c3c(F)cccc3F)sc2N)c1O[C@@H]1CCCNC1] | (R)-5-amino-2-(2,6-difluorophenyl)-N-(1-methyl-5-(piperidin-3-yloxy)-1H-pyrazol-4-yl)thiazole-4-carboxamide |

TABLE 2-continued

| No. | Structure | Name |
| --- | --- | --- |
| 285 | 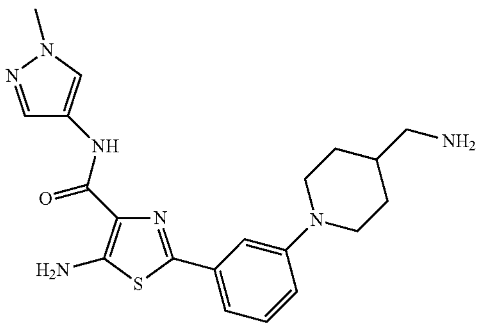 [SMILES: Cn1cc(NC(=O)c2nc(-c3cccc(N4CCC(CN)CC4)c3)sc2N)cn1] | 5-amino-2-(3-(4-(aminomethyl)piperidin-1-yl)phenyl)-N-(1-methyl-1H-pyrazol-4-yl)thiazole-4-carboxamide |
| 286 | 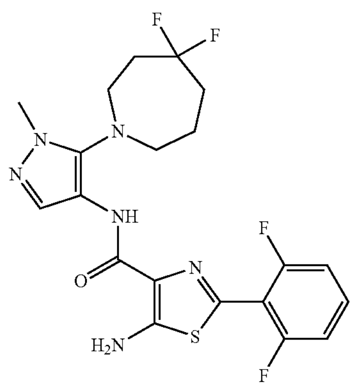 [SMILES: Cn1ncc(NC(=O)c2nc(-c3c(F)cccc3F)sc2N)c1N1CCCC(F)(F)CC1] | 5-amino-N-(5-(4,4-difluoroazepan-1-yl)-1-methyl-1H-pyrazol-4-yl)-2-(2,6-difluorophenyl)thiazole-4-carboxamide |
| 287 | 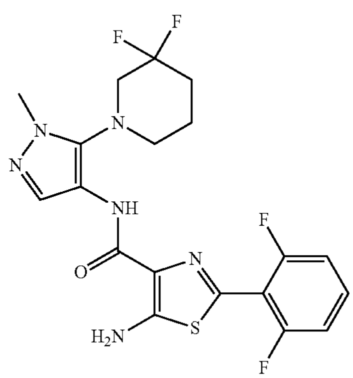 [SMILES: Cn1ncc(NC(=O)c2nc(-c3c(F)cccc3F)sc2N)c1N1CCCC(F)(F)C1] | 5-amino-2-(2,6-difluorophenyl)-N-(5-(3,3-difluoropiperidin-1-yl)-1-methyl-1H-pyrazol-4-yl)thiazole-4-carboxamide |
| 288 | 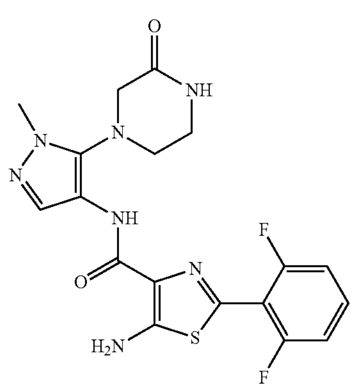 [SMILES: Cn1ncc(NC(=O)c2nc(-c3c(F)cccc3F)sc2N)c1N1CCNC(=O)C1] | 5-amino-2-(2,6-difluorophenyl)-N-(1-methyl-5-(3-oxopiperazin-1-yl)-1H-pyrazol-4-yl)thiazole-4-carboxamide |

TABLE 2-continued

| No. | Structure | Name |
|---|---|---|
| 289 | 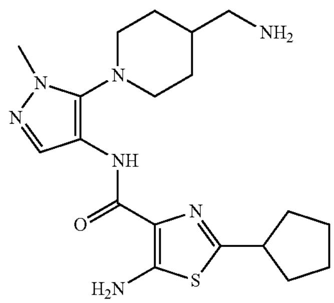 [SMILES: Cn1ncc(NC(=O)c2nc(C3CCCC3)sc2N)c1N1CCC(CN)CC1] | 5-amino-N-(5-(4-(aminomethyl)piperidin-1-yl)-1-methyl-1H-pyrazol-4-yl)-2-cyclopentylthiazole-4-carboxamide |
| 290 | 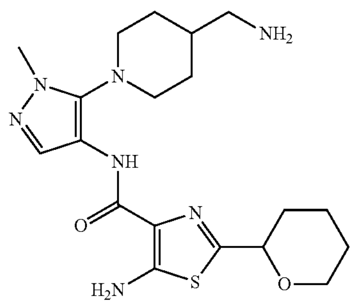 [SMILES: Cn1ncc(NC(=O)c2nc(C3CCCCO3)sc2N)c1N1CCC(CN)CC1] | 5-amino-N-(5-(4-(aminomethyl)piperidin-1-yl)-1-methyl-1H-pyrazol-4-yl)-2-(tetrahydro-2H-pyran-2-yl)thiazole-4-carboxamide |
| 291 | 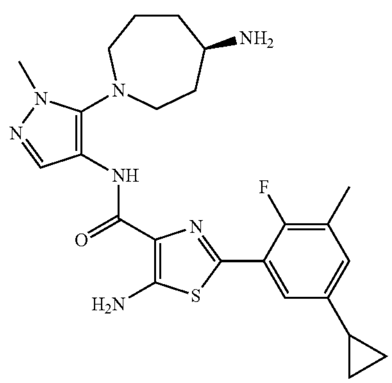 [SMILES: Cc1cc(C2CC2)cc(-c2nc(C(=O)Nc3cnn(C)c3N3CCC[C@@H](N)CC3)c(N)s2)c1F] | (R)-5-amino-N-(5-(4-aminoazepan-1-yl)-1-methyl-1H-pyrazol-4-yl)-2-(5-cyclopropyl-2-fluoro-3-methylphenyl)thiazole-4-carboxamide |
| 292 | 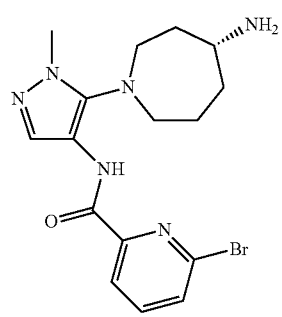 [SMILES: Cn1ncc(NC(=O)c2cccc(Br)n2)c1N1CCC[C@@H](N)CC1] | (R)-N-(5-(4-aminoazepan-1-yl)-1-methyl-1H-pyrazol-4-yl)-6-bromopicolinamide |
| 293 | 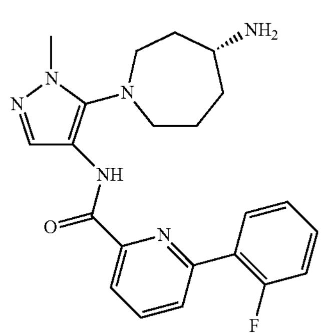 [SMILES: Cn1ncc(NC(=O)c2cccc(-c3ccccc3F)n2)c1N1CCC[C@@H](N)CC1] | (R)-N-(5-(4-aminoazepan-1-yl)-1-methyl-1H-pyrazol-4-yl)-6-(2-fluorophenyl)picolinamide |

… TABLE 2-continued

| No. | Structure | Name |
|---|---|---|
| 294 | 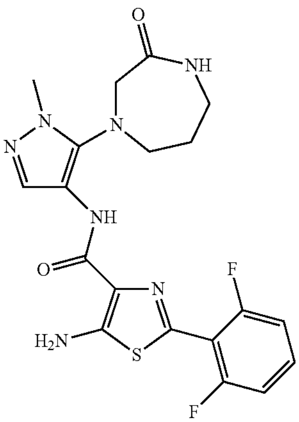 [SMILES: Cn1ncc(NC(=O)c2nc(-c3c(F)cccc3F)sc2N)c1N1CCCNC(=O)C1] | 5-amino-2-(2,6-difluorophenyl)-N-(1-methyl-5-(3-oxo-1,4-diazepan-1-yl)-1H-pyrazol-4-yl)thiazole-4-carboxamide |
| 295 | 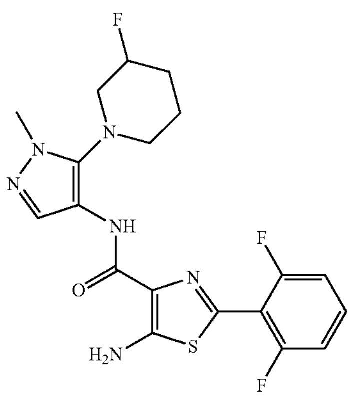 [SMILES: Cn1ncc(NC(=O)c2nc(-c3c(F)cccc3F)sc2N)c1N1CCCC(F)C1] | 5-amino-2-(2,6-difluorophenyl)-N-(5-(3-fluoropiperidin-1-yl)-1-methyl-1H-pyrazol-4-yl)thiazole-4-carboxamide |
| 296 | 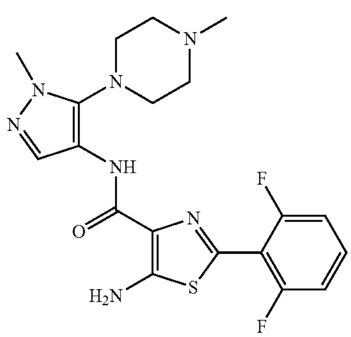 [SMILES: CN1CCN(c2c(NC(=O)c3nc(-c4c(F)cccc4F)sc3N)cnn2C)CC1] | 5-amino-2-(2,6-difluorophenyl)-N-(1-methyl-5-(4-methylpiperazin-1-yl)-1H-pyrazol-4-yl)thiazole-4-carboxamide |
| 297 | 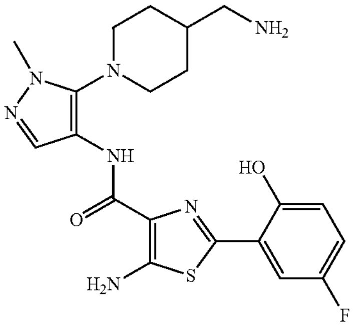 [SMILES: Cn1ncc(NC(=O)c2nc(-c3cc(F)ccc3O)sc2N)c1N1CCC(CN)CC1] | 5-amino-N-(5-(4-(aminomethyl)piperidin-1-yl)-1-methyl-1H-pyrazol-4-yl)-2-(5-fluoro-2-hydroxyphenyl)thiazole carboxamide |

TABLE 2-continued

| No. | Structure | Name |
|---|---|---|
| 298 | 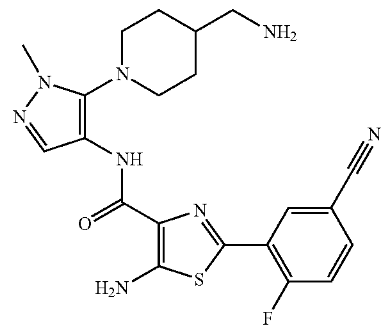 [SMILES: Cn1ncc(NC(=O)c2nc(-c3cc(C#N)ccc3F)sc2N)c1N1CCC(CN)CC1] | 5-amino-N-(5-(4-(aminomethyl)piperidin-1-yl)-1-methyl-1H-pyrazol-4-yl)-2-(5-cyano-2-fluorophenyl)thiazole-4-carboxamide |
| 299 | 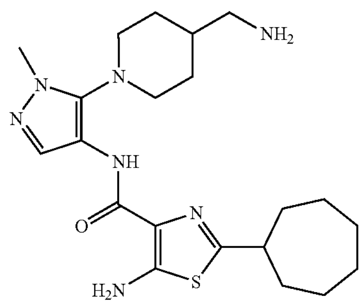 [SMILES: Cn1ncc(NC(=O)c2nc(C3CCCCCC3)sc2N)c1N1CCC(CN)CC1] | 5-amino-N-(5-(4-(aminomethyl)piperidin-1-yl)-1-methyl-1H-pyrazol-4-yl)-2-cycloheptylthiazole-4-carboxamide |
| 300 | 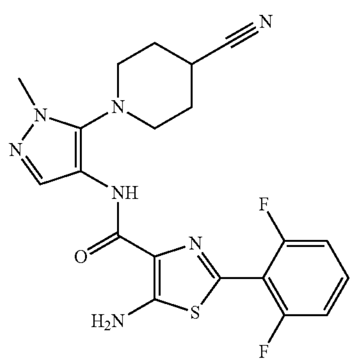 [SMILES: Cn1ncc(NC(=O)c2nc(-c3c(F)cccc3F)sc2N)c1N1CCC(C#N)CC1] | 5-amino-N-(5-(4-cyanopiperidin-1-yl)-1-methyl-1H-pyrazol-4-yl)-2-(2,6-difluorophenyl)thiazole-4-carboxamide |
| 301 | 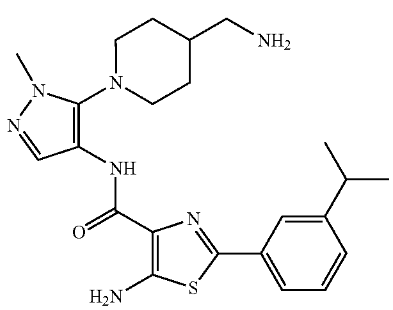 [SMILES: CC(C)c1cccc(-c2nc(C(=O)Nc3cnn(C)c3N3CCC(CN)CC3)c(N)s2)c1] | 5-amino-N-(5-(4-(aminomethyl)piperidin-1-yl)-1-methyl-1H-pyrazol-4-yl)-2-(3-isopropylphenyl)thiazole-4-carboxamide |

TABLE 2-continued

| No. | Structure | Name |
|---|---|---|
| 302 | 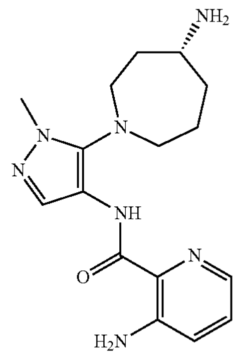 [SMILES: Cn1ncc(NC(=O)c2ncccc2N)c1N1CCC[C@@H](N)CC1] | (R)-3-amino-N-(5-(4-aminoazepan-1-yl)-1-methyl-1H-pyrazol-4-yl)picolinamide |
| 303 | 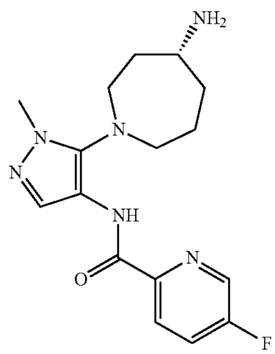 [SMILES: Cn1ncc(NC(=O)c2ccc(F)cn2)c1N1CCC[C@@H](N)CC1] | (R)-N-(5-(4-aminoazepan-1-yl)-1-methyl-1H-pyrazol-4-yl)-5-fluoropicolinamide |
| 304 | 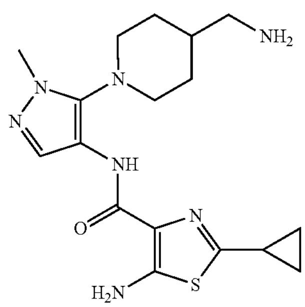 [SMILES: Cn1ncc(NC(=O)c2nc(C3CC3)sc2N)c1N1CCC(CN)CC1] | 5-amino-N-(5-(4-(aminomethyl)piperidin-1-yl)-1-methyl-1H-pyrazol-4-yl)-2-cyclopropylthiazole-4-carboxamide |
| 305 | 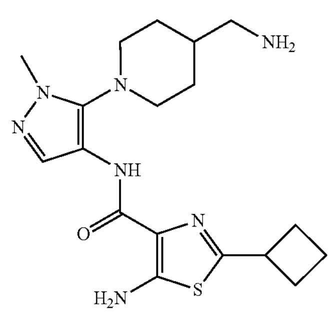 [SMILES: Cn1ncc(NC(=O)c2nc(C3CCC3)sc2N)c1N1CCC(CN)CC1] | 5-amino-N-(5-(4-(aminomethyl)piperidin-1-yl)-1-methyl-1H-pyrazol-4-yl)-2-cyclobutylthiazole-4-carboxamide |
| 306 | 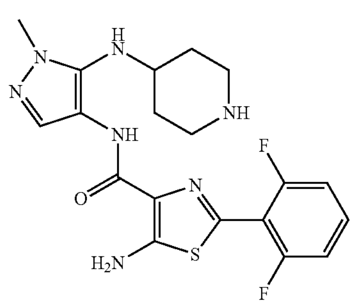 [SMILES: Cn1ncc(NC(=O)c2nc(-c3c(F)cccc3F)sc2N)c1NC1CCNCC1] | 5-amino-2-(2,6-difluorophenyl)-N-(1-methyl-5-(piperidin-4-ylamino)-1H-pyrazol-4-yl)thiazole-4-carboxamide |

TABLE 2-continued

| No. | Structure | Name |
|-----|-----------|------|
| 307 | 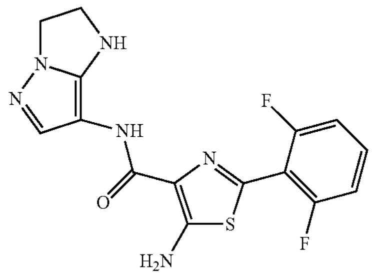 [SMILES: Nc1sc(-c2c(F)cccc2F)nc1C(=O)Nc1cnn2c1NCC2] | 5-amino-2-(2,6-difluorophenyl)-N-(2,3-dihydro-1H-imidazo[1,2-b]pyrazol-7-yl)thiazole-4-carboxamide |
| 308 | 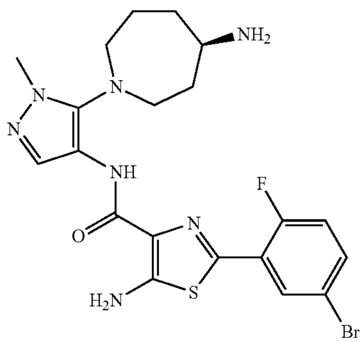 [SMILES: Cn1ncc(NC(=O)c2nc(-c3cc(Br)ccc3F)sc2N)c1N1CCC[C@@H](N)CC1] | (R)-5-amino-N-(5-(4-aminoazepan-1-yl)-1-methyl-1H-pyrazol-4-yl)-2-(5-bromo-2-fluorophenyl)thiazole-4-carboxamide |
| 309 | 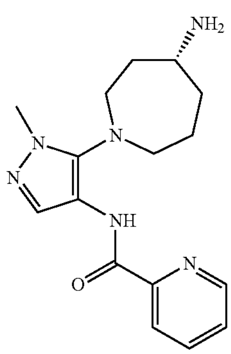 [SMILES: Cn1ncc(NC(=O)c2ccccn2)c1N1CCC[C@@H](N)CC1] | (R)-N-(5-(4-aminoazepan-1-yl)-1-methyl-1H-pyrazol-4-yl)picolinamide |
| 310 | 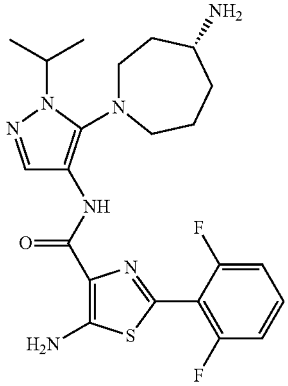 [SMILES: CC(C)n1ncc(NC(=O)c2nc(-c3c(F)cccc3F)sc2N)c1N1CCC[C@@H](N)CC1] | (R)-5-amino-N-(5-(4-aminoazepan-1-yl)-1-isopropyl-1H-pyrazol-4-yl)-2-(2,6-difluorophenyl)thiazole-4-carboxamide |

TABLE 2-continued

| No. | Structure | Name |
|---|---|---|
| 311 | 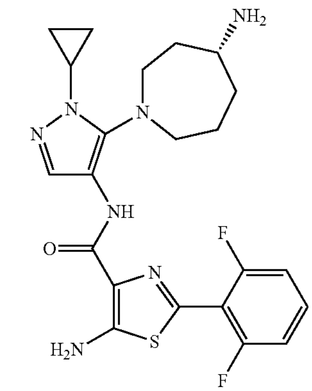 [SMILES: Nc1sc(-c2c(F)cccc2F)nc1C(=O)Nc1cnn(C2CC2)c1N1CCC[C@@H](N)CC1] | (R)-5-amino-N-(5-(4-aminoazepan-1-yl)-1-cyclopropyl-1H-pyrazol-4-yl)-2-(2,6-difluorophenyl)thiazole-4-carboxamide |
| 312 | 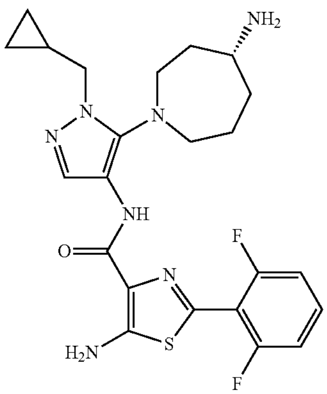 [SMILES: Nc1sc(-c2c(F)cccc2F)nc1C(=O)Nc1cnn(CC2CC2)c1N1CCC[C@@H](N)CC1] | (R)-5-amino-N-(5-(4-aminoazepan-1-yl)-1-(cyclopropylmethyl)-1H-pyrazol-4-yl)-2-(2,6-difluorophenyl)thiazole-4-carboxamide |
| 313 | 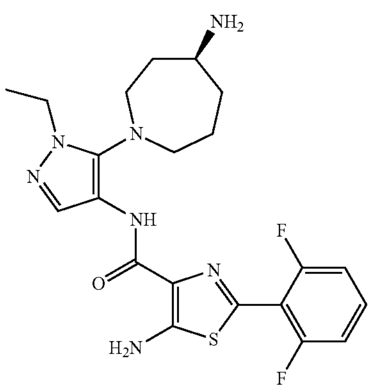 [SMILES: CCn1ncc(NC(=O)c2nc(-c3c(F)cccc3F)sc2N)c1N1CCC[C@H](N)CC1] | (S)-5-amino-N-(5-(4-aminoazepan-1-yl)-1-ethyl-1H-pyrazol-4-yl)-2-(2,6-difluorophenyl)thiazole-4-carboxamide |
| 314 | 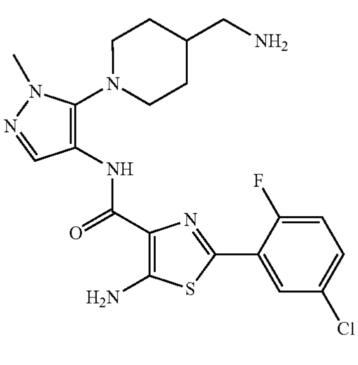 [SMILES: Cn1ncc(NC(=O)c2nc(-c3cc(Cl)ccc3F)sc2N)c1N1CCC(CN)CC1] | 5-amino-N-(5-(4-(aminomethyl)piperidin-1-yl)-1-methyl-1H-pyrazol-4-yl)-2-(5-chloro-2-fluorophenyl)thiazole-4-carboxamide |

TABLE 2-continued

| No. | Structure | Name |
|---|---|---|
| 315 | 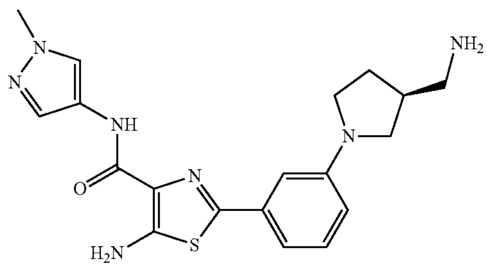 [SMILES: Cn1cc(NC(=O)c2nc(-c3cccc(N4CC[C@@H](CN)C4)c3)sc2N)cn1] | (S)-5-amino-2-(3-(3-(aminomethyl)pyrrolidin-1-yl)phenyl)-N-(1-methyl-1H-pyrazol-4-yl)thiazole-4-carboxamide |
| 316 | 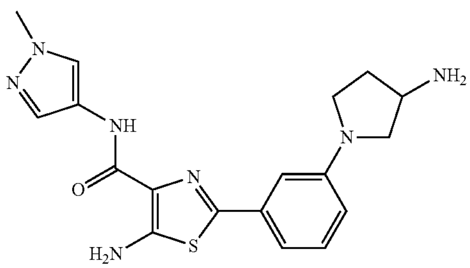 [SMILES: Cn1cc(NC(=O)c2nc(-c3cccc(N4CCC(N)C4)c3)sc2N)cn1] | 5-amino-2-(3-(3-aminopyrrolidin-1-yl)phenyl)-N-(1-methyl-1H-pyrazol-4-yl)thiazole-4-carboxamide |
| 317 | 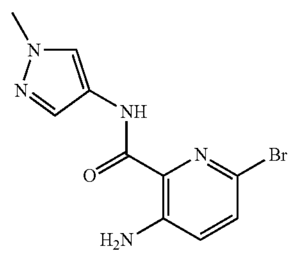 [SMILES: Cn1cc(NC(=O)c2nc(Br)ccc2N)cn1] | 3-amino-6-bromo-N-(1-methyl-1H-pyrazol-4-yl)picolinamide |
| 318 | 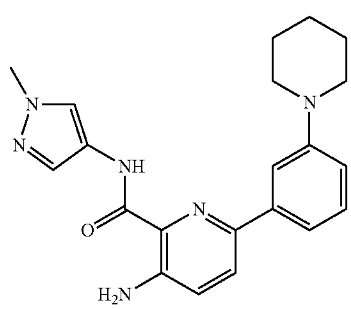 [SMILES: Cn1cc(NC(=O)c2nc(-c3cccc(N4CCCCC4)c3)ccc2N)cn1] | 3-amino-N-(1-methyl-1H-pyrazol-4-yl)-6-(3-(piperidin-1-yl)phenyl)picolinamide |
| 319 | 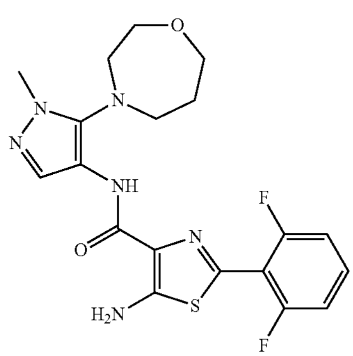 [SMILES: Cn1ncc(NC(=O)c2nc(-c3c(F)cccc3F)sc2N)c1N1CCCOCC1] | 5-amino-2-(2,6-difluorophenyl)-N-(1-methyl-5-(1,4-oxazepan-4-yl)-1H-pyrazol-4-yl)thiazole-4-carboxamide |

TABLE 2-continued

| No. | Structure | Name |
|---|---|---|
| 320 | 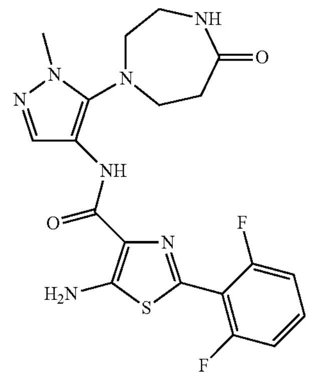 [SMILES: Cn1ncc(NC(=O)c2nc(-c3c(F)cccc3F)sc2N)c1N1CCNC(=O)CC1] | 5-amino-2-(2,6-difluorophenyl)-N-(1-methyl-5-(5-oxo-1,4-diazepan-1-yl)-1H-pyrazol-4-yl)thiazole-4-carboxamide |
| 321 | 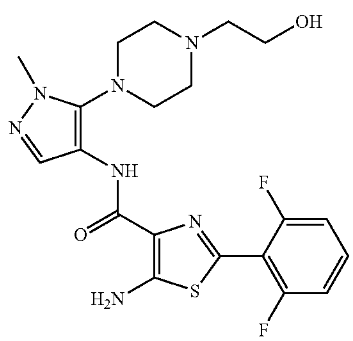 [SMILES: Cn1ncc(NC(=O)c2nc(-c3c(F)cccc3F)sc2N)c1N1CCN(CCO)CC1] | 5-amino-2-(2,6-difluorophenyl)-N-(5-(4-(2-hydroxyethyl)piperazin-1-yl)-1-methyl-1H-pyrazol-4-yl)thiazole-4-carboxamide |
| 322 | 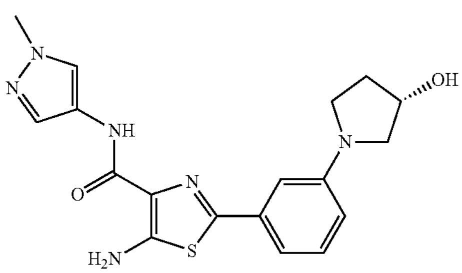 [SMILES: Cn1cc(NC(=O)c2nc(-c3cccc(N4CC[C@H](O)C4)c3)sc2N)cn1] | (S)-5-amino-2-(3-(3-hydroxypyrrolidin-1-yl)phenyl)-N-(1-methyl-1H-pyrazol-4-yl)thiazole-4-carboxamide |
| 323 | 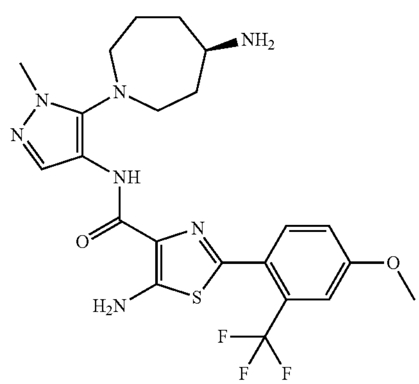 [SMILES: COc1ccc(-c2nc(C(=O)Nc3cnn(C)c3N3CCC[C@@H](N)CC3)c(N)s2)c(C(F)(F)F)c1] | (R)-5-amino-N-(5-(4-aminoazepan-1-yl)-1-methyl-1H-pyrazol-4-yl)-2-(4-methoxy-2-(trifluoromethyl)phenyl)thiazole-4-carboxamide |

TABLE 2-continued

| No. | Structure | Name |
|---|---|---|
| 324 | 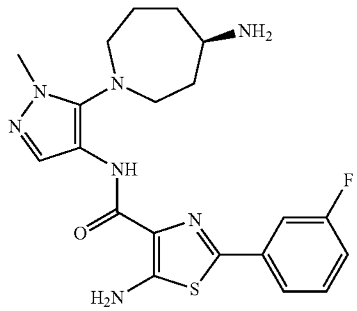 [SMILES: Cn1ncc(NC(=O)c2nc(-c3cccc(F)c3)sc2N)c1N1CCC[C@@H](N)CC1] | (R)-5-amino-N-(5-(4-aminoazepan-1-yl)-1-methyl-1H-pyrazol-4-yl)-2-(3-fluorophenyl)thiazole-4-carboxamide |
| 325 | 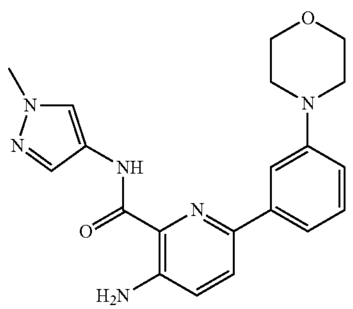 [SMILES: Cn1cc(NC(=O)c2nc(-c3cccc(N4CCOCC4)c3)ccc2N)cn1] | 3-amino-N-(1-methyl-1H-pyrazol-4-yl)-6-(3-morpholinophenyl)picolinamide |
| 326 | 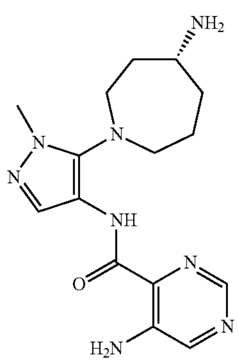 [SMILES: Cn1ncc(NC(=O)c2ncncc2N)c1N1CCC[C@@H](N)CC1] | (R)-5-amino-N-(5-(4-aminoazepan-1-yl)-1-methyl-1H-pyrazol-4-yl)pyrimidine-4-carboxamide |
| 327 | 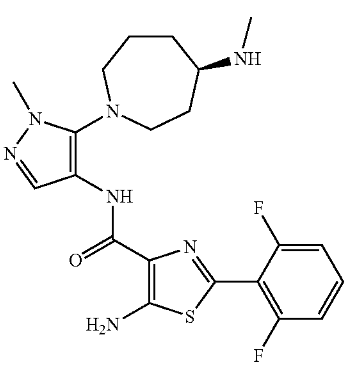 [SMILES: CN[C@@H]1CCCN(c2c(NC(=O)c3nc(-c4c(F)cccc4F)sc3N)cnn2C)CC1] | (R)-5-amino-2-(2,6-difluorophenyl)-N-(1-methyl-5-(4-(methylamino)azepan-1-yl)-1H-pyrazol-4-yl)thiazole-4-carboxamide |

TABLE 2-continued

| No. | Structure | Name |
|---|---|---|
| 328 | 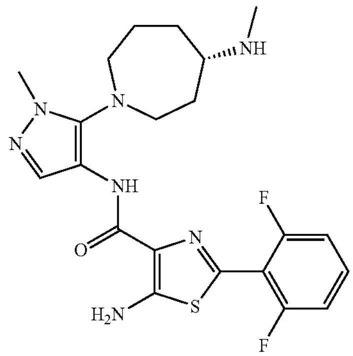 [SMILES: CN[C@H]1CCCN(c2c(NC(=O)c3nc(-c4c(F)cccc4F)sc3N)cnn2C)CC1] | (S)-5-amino-2-(2,6-difluorophenyl)-N-(1-methyl-5-(4-(methylamino)azepan-1-yl)-1H-pyrazol-4-yl)thiazole-4-carboxamide |
| 329 | 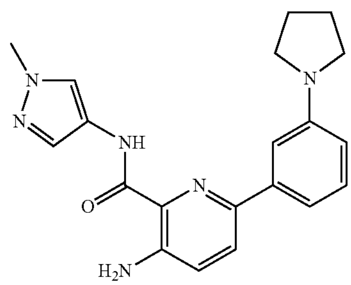 [SMILES: Cn1cc(NC(=O)c2nc(-c3cccc(N4CCCC4)c3)ccc2N)cn1] | 3-amino-N-(1-methyl-1H-pyrazol-4-yl)-6-(3-(pyrrolidin-1-yl)phenyl)picolinamide |
| 330 | 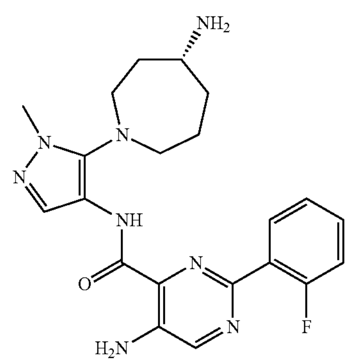 [SMILES: Cn1ncc(NC(=O)c2nc(-c3ccccc3F)ncc2N)c1N1CCC[C@@H](N)CC1] | (R)-5-amino-N-(5-(4-aminoazepan-1-yl)-1-methyl-1H-pyrazol-4-yl)-2-(2-fluorophenyl)pyrimidine-4-carboxamide |
| 331 | 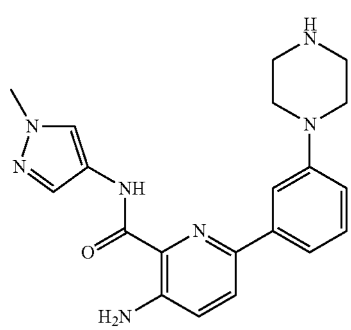 [SMILES: Cn1cc(NC(=O)c2nc(-c3cccc(N4CCNCC4)c3)ccc2N)cn1] | 3-amino-N-(1-methyl-1H-pyrazol-4-yl)-6-(3-(piperazin-1-yl)phenyl)picolinamide |

TABLE 2-continued

| No. | Structure | Name |
|---|---|---|
| 332 | 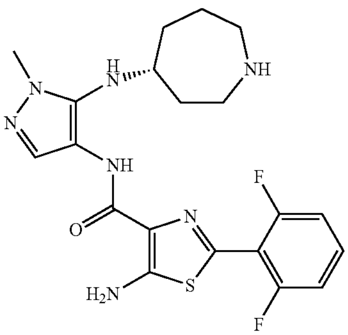 [SMILES: Cn1ncc(NC(=O)c2nc(-c3c(F)cccc3F)sc2N)c1N[C@@H]1CCCNCC1] | (R)-5-amino-N-(5-(azepan-4-ylamino)-1-methyl-1H-pyrazol-4-yl)-2-(2,6-difluorophenyl)thiazole-4-carboxamide |
| 333 | 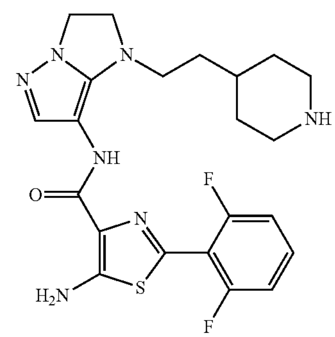 [SMILES: Nc1sc(-c2c(F)cccc2F)nc1C(=O)Nc1cnn2c1N(CCC1CCNCC1)CC2] | 5-amino-2-(2,6-difluorophenyl)-N-(1-(2-(piperidin-4-yl)ethyl)-2,3-dihydro-1H-imidazo[1,2-b]pyrazol-7-yl)thiazole-4-carboxamide |
| 334 | 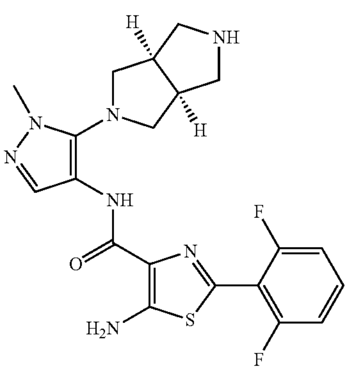 [SMILES: Cn1ncc(NC(=O)c2nc(-c3c(F)cccc3F)sc2N)c1N1C[C@H]2CNC[C@H]2C1] | 5-amino-2-(2,6-difluorophenyl)-N-(5-((3aR,6aS)-hexahydropyrrolo[3,4-c]pyrrol-2(1H)-yl)-1-methyl-1H-pyrazol-4-yl)thiazole-4-carboxamide |
| 335 | 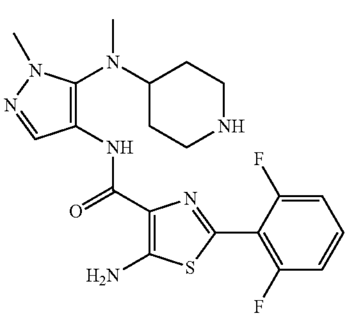 [SMILES: CN(c1c(NC(=O)c2nc(-c3c(F)cccc3F)sc2N)cnn1C)C1CCNCC1] | 5-amino-2-(2,6-difluorophenyl)-N-(1-methyl-5-(methyl(piperidin-4-yl)amino)-1H-pyrazol-4-yl)thiazole-4-carboxamide |

TABLE 2-continued

| No. | Structure | Name |
|---|---|---|
| 336 | 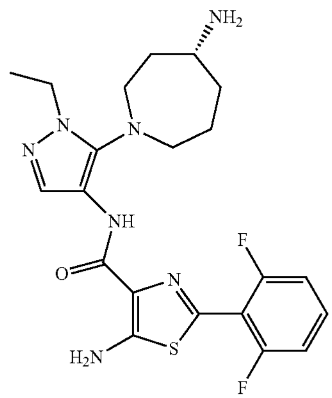 [SMILES: CCn1ncc(NC(=O)c2nc(-c3c(F)cccc3F)sc2N)c1N1CCC[C@@H](N)CC1] | (R)-5-amino-N-(5-(4-aminoazepan-1-yl)-1-ethyl-1H-pyrazol-4-yl)-2-(2,6-difluorophenyl)thiazole-4-carboxamide |
| 337 | 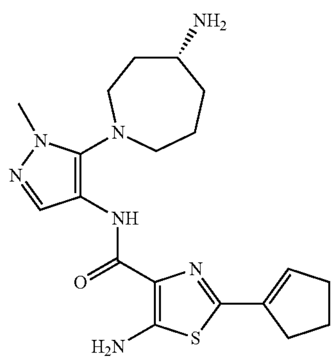 [SMILES: Cn1ncc(NC(=O)c2nc(C3=CCCC3)sc2N)c1N1CCC[C@@H](N)CC1] | (R)-5-amino-N-(5-(4-aminoazepan-1-yl)-1-methyl-1H-pyrazol-4-yl)-2-cyclopentenylthiazole-4-carboxamide |
| 338 | 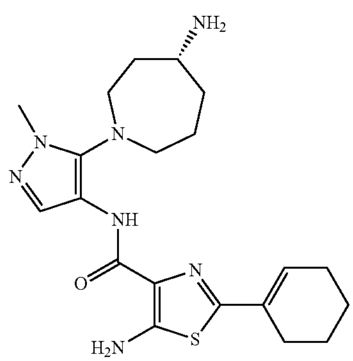 [SMILES: Cn1ncc(NC(=O)c2nc(C3=CCCCC3)sc2N)c1N1CCC[C@@H](N)CC1] | (R)-5-amino-N-(5-(4-aminoazepan-1-yl)-1-methyl-1H-pyrazol-4-yl)-2-cyclohexenylthiazole-4-carboxamide |
| 339 | 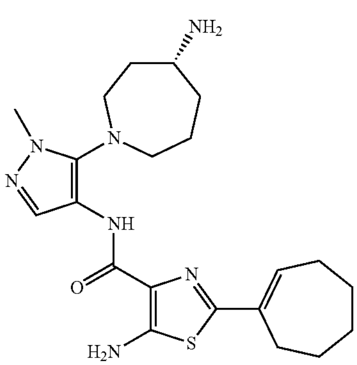 [SMILES: Cn1ncc(NC(=O)c2nc(C3=CCCCCC3)sc2N)c1N1CCC[C@@H](N)CC1] | (R)-5-amino-N-(5-(4-aminoazepan-1-yl)-1-methyl-1H-pyrazol-4-yl)-2-cycloheptenylthiazole-4-carboxamide |

TABLE 2-continued

| No. | Structure | Name |
|---|---|---|
| 340 | 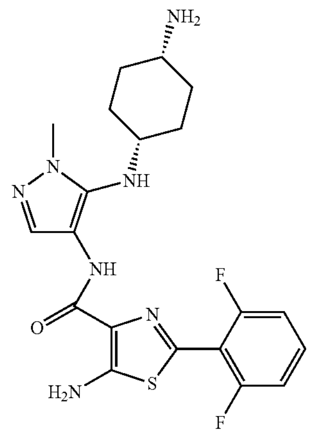 [SMILES: Cn1ncc(NC(=O)c2nc(-c3c(F)cccc3F)sc2N)c1N[C@H]1CC[C@@H](N)CC1] | 5-amino-N-(5-((1s,4s)-4-aminocyclohexylamino)-1-methyl-1H-pyrazol-4-yl)-2-(2,6-difluorophenyl)thiazole-4-carboxamide |
| 341 | 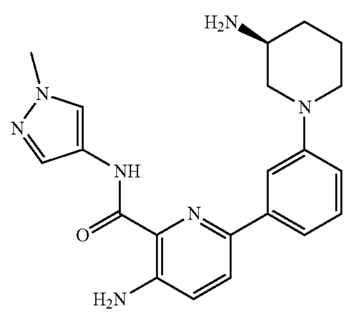 [SMILES: Cn1cc(NC(=O)c2nc(-c3cccc(N4CCC[C@H](N)C4)c3)ccc2N)cn1] | (S)-3-amino-6-(3-(3-aminopiperidin-1-yl)phenyl)-N-(1-methyl-1H-pyrazol-4-yl)picolinamide |
| 342 | 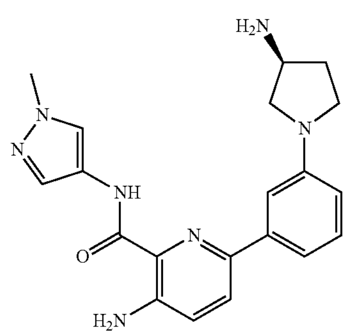 [SMILES: Cn1cc(NC(=O)c2nc(-c3cccc(N4CC[C@H](N)C4)c3)ccc2N)cn1] | (S)-3-amino-6-(3-(3-aminopyrrolidin-1-yl)phenyl)-N-(1-methyl-1H-pyrazol-4-yl)picolinamide |
| 343 | 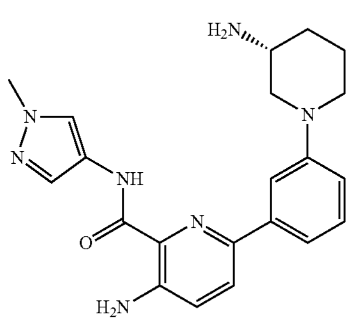 [SMILES: Cn1cc(NC(=O)c2nc(-c3cccc(N4CCC[C@@H](N)C4)c3)ccc2N)cn1] | (R)-3-amino-6-(3-(3-aminopiperidin-1-yl)phenyl)-N-(1-methyl-1H-pyrazol-4-yl)picolinamide |

TABLE 2-continued

| No. | Structure | Name |
|---|---|---|
| 344 | 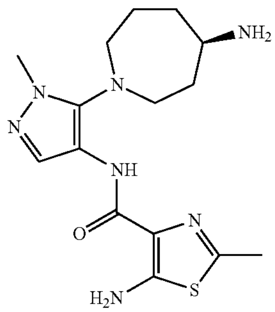 [SMILES: Cc1nc(C(=O)Nc2cnn(C)c2N2CCC[C@@H](N)CC2)c(N)s1] | (R)-5-amino-N-(5-(4-aminoazepan-1-yl)-1-methyl-1H-pyrazol-4-yl)-2-methylthiazole-4-carboxamide |
| 345 | 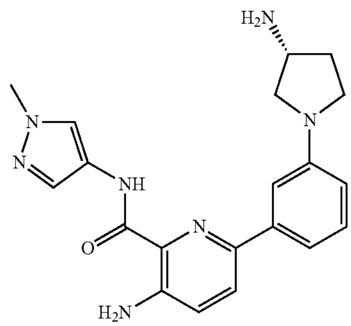 [SMILES: Cn1cc(NC(=O)c2nc(-c3cccc(N4CC[C@@H](N)C4)c3)ccc2N)cn1] | (R)-3-amino-6-(3-(3-aminopyrrolidin-1-yl)phenyl)-N-(1-methyl-1H-pyrazol-4-yl)picolinamide |
| 346 | 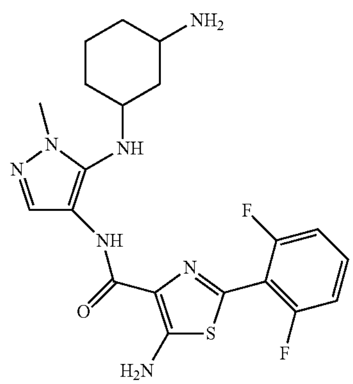 [SMILES: Cn1ncc(NC(=O)c2nc(-c3c(F)cccc3F)sc2N)c1NC1CCCC(N)C1] | 5-amino-N-(5-((cis-3-aminocyclohexylamino)-1-methyl-1H-pyrazol-4-yl)-2-(2,6-difluorophenyl)thiazole-4-carboxamide |
| 347 | 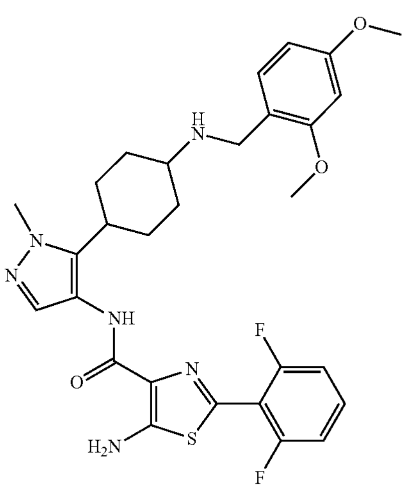 [SMILES: COc1ccc(CNC2CCC(c3c(NC(=O)c4nc(-c5c(F)cccc5F)sc4N)cnn3C)CC2)c(OC)c1] | 5-amino-2-(2,6-difluorophenyl)-N-(5-(4-(2,4-dimethoxybenzylamino)cyclohexyl)-1-methyl-1H-pyrazol-4-yl)thiazole-4-carboxamide |

TABLE 2-continued

| No. | Structure | Name |
|---|---|---|
| 348 | 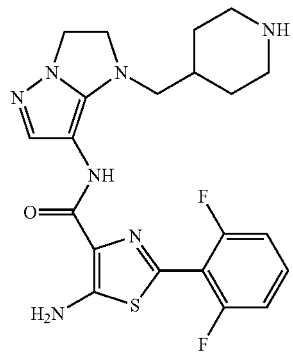 [SMILES: Nc1sc(-c2c(F)cccc2F)nc1C(=O)Nc1cnn2c1N(CC1CCNCC1)CC2] | 5-amino-2-(2,6-difluorophenyl)-N-(1-(piperidin-4-ylmethyl)-2,3-dihydro-1H-imidazo[1,2-b]pyrazol-7-yl)thiazole-4-carboxamide |
| 349 | 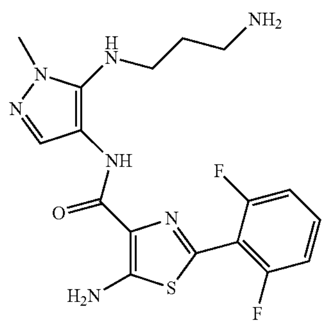 [SMILES: Cn1ncc(NC(=O)c2nc(-c3c(F)cccc3F)sc2N)c1NCCCN] | 5-amino-N-(5-(3-aminopropylamino)-1-methyl-1H-pyrazol-4-yl)-2-(2,6-difluorophenyl)thiazole-4-carboxamide |
| 350 | 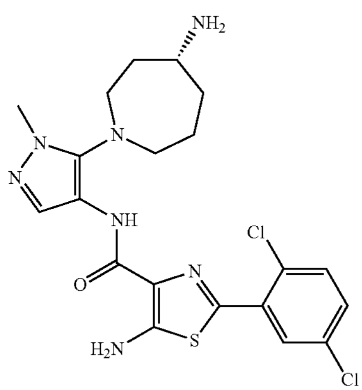 [SMILES: Cn1ncc(NC(=O)c2nc(-c3cc(Cl)ccc3Cl)sc2N)c1N1CCC[C@@H](N)CC1] | (R)-5-amino-N-(5-(4-aminoazepan-1-yl)-1-methyl-1H-pyrazol-4-yl)-2-(2,5-dichlorophenyl)thiazole-4-carboxamide |
| 351 | 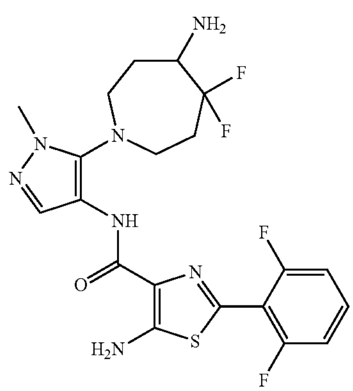 [SMILES: Cn1ncc(NC(=O)c2nc(-c3c(F)cccc3F)sc2N)c1N1CCC(N)C(F)(F)CC1] | 5-amino-N-(5-(5-amino-4,4-difluoroazepan-1-yl)-1-methyl-1H-pyrazol-4-yl)-2-(2,6-difluorophenyl)thiazole-4-carboxamide |

TABLE 2-continued

| No. | Structure | Name |
|---|---|---|
| 352 | 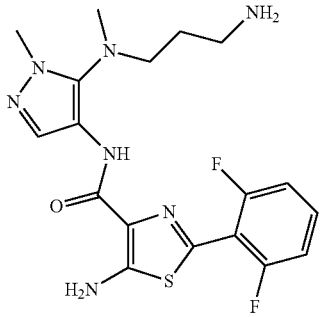 [SMILES: CN(CCCN)c1c(NC(=O)c2nc(-c3c(F)cccc3F)sc2N)cnn1C] | 5-amino-N-(5-((3-aminopropyl)(methyl)amino)-1-methyl-1H-pyrazol-4-yl)-2-(2,6-difluorophenyl)thiazole-4-carboxamide |
| 353 | 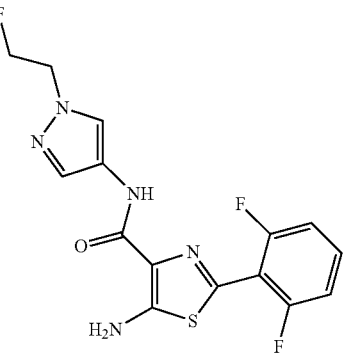 | 5-amino-2-(2,6-difluorophenyl)-N-(1-(2-fluoroethyl)-1H-pyrazol-4-yl)thiazole-4-carboxamide |
| 354 | 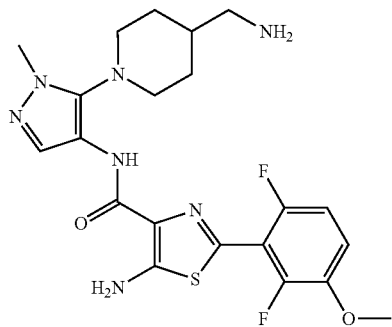 [SMILES: COc1ccc(F)c(-c2nc(C(=O)Nc3cnn(C)c3N3CCC(CN)CC3)c(N)s2)c1F] | 5-amino-N-(5-(4-(aminomethyl)piperidin-1-yl)-1-methyl-1H-pyrazol-4-yl)-2-(2,6-difluoro-3-methoxyphenyl)thiazole-4-carboxamide |
| 355 | 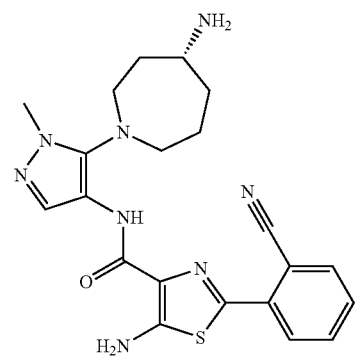 [SMILES: Cn1ncc(NC(=O)c2nc(-c3ccccc3C#N)sc2N)c1N1CCC[C@@H](N)CC1] | (R)-5-amino-N-(5-(4-aminoazepan-1-yl)-1-methyl-1H-pyrazol-4-yl)-2-(2-cyanophenyl)thiazole-4-carboxamide |

TABLE 2-continued

| No. | Structure | Name |
|---|---|---|
| 356 | 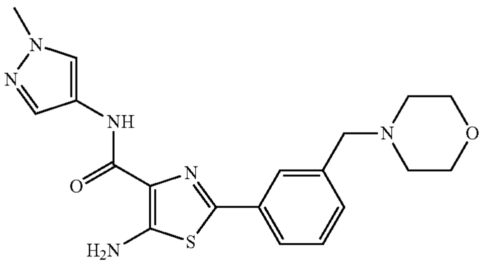 [SMILES: Cn1cc(NC(=O)c2nc(-c3cccc(CN4CCOCC4)c3)sc2N)cn1] | 5-amino-N-(1-methyl-1H-pyrazol-4-yl)-2-(3-(morpholinomethyl)phenyl)thiazole-4-carboxamide |
| 357 | 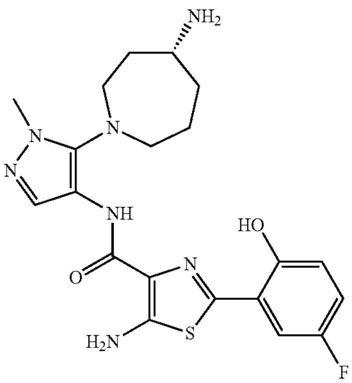 [SMILES: Cn1ncc(NC(=O)c2nc(-c3cc(F)ccc3O)sc2N)c1N1CCC[C@@H](N)CC1] | (R)-5-amino-N-(5-(4-aminoazepan-1-yl)-1-methyl-1H-pyrazol-4-yl)-2-(5-fluoro-2-hydroxyphenyl)thiazole-4-carboxamide |
| 358 | 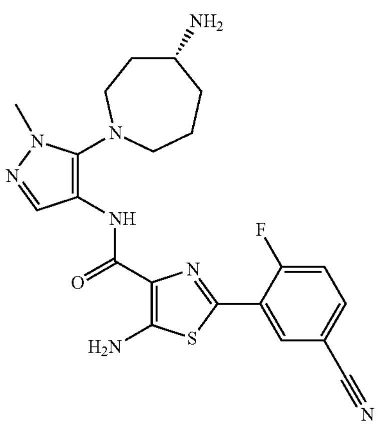 [SMILES: Cn1ncc(NC(=O)c2nc(-c3cc(C#N)ccc3F)sc2N)c1N1CCC[C@@H](N)CC1] | (R)-5-amino-N-(5-(4-aminoazepan-1-yl)-1-methyl-1H-pyrazol-4-yl)-2-(5-cyano-2-fluorophenyl)thiazole-4-carboxamide |
| 359 | 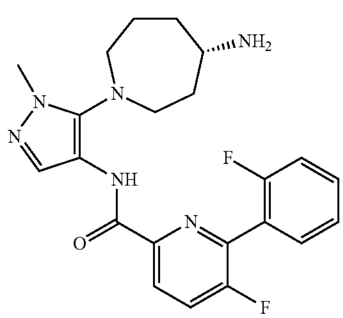 [SMILES: Cn1ncc(NC(=O)c2ccc(F)c(-c3ccccc3F)n2)c1N1CCC[C@H](N)CC1] | (S)-N-(5-(4-aminoazepan-1-yl)-1-methyl-1H-pyrazol-4-yl)-5-fluoro-6-(2-fluorophenyl)picolinamide |

TABLE 2-continued

| No. | Structure | Name |
|---|---|---|
| 360 | 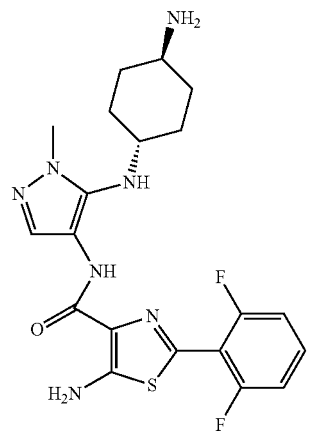 [SMILES: Cn1ncc(NC(=O)c2nc(-c3c(F)cccc3F)sc2N)c1N[C@H]1CC[C@H](N)CC1] | 5-amino-N-(5-((1r,4r)-4-aminocyclohexylamino)-1-methyl-1H-pyrazol-4-yl)-2-(2,6-difluorophenyl)thiazole-4-carboxamide |
| 361 | 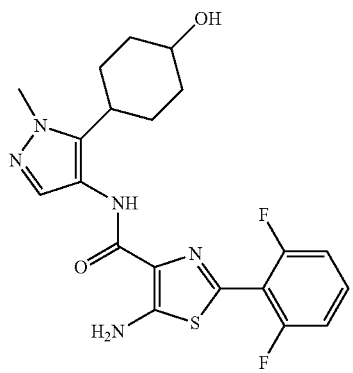 [SMILES: Cn1ncc(NC(=O)c2nc(-c3c(F)cccc3F)sc2N)c1C1CCC(O)CC1] | 5-amino-2-(2,6-difluorophenyl)-N-(5-(4-hydroxycyclohexyl)-1-methyl-1H-pyrazol-4-yl)thiazole-4-carboxamide |
| 362 | 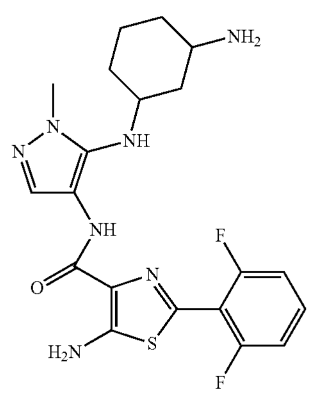 [SMILES: Cn1ncc(NC(=O)c2nc(-c3c(F)cccc3F)sc2N)c1NC1CCCC(N)C1] | 5-amino-N-(5-((trans-3-aminocyclohexylamino)-1-methyl-1H-pyrazol-4-yl)-2-(2,6-difluorophenyl)thiazole-4-carboxamide |
| 363 | 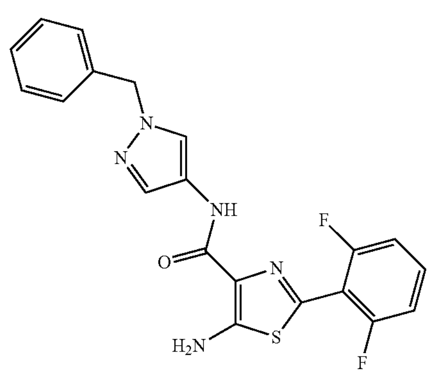 [SMILES: Nc1sc(-c2c(F)cccc2F)nc1C(=O)Nc1cnn(Cc2ccccc2)c1] | 5-amino-N-(1-benzyl-1H-pyrazol-4-yl)-2-(2,6-difluorophenyl)thiazole-4-carboxamide |

TABLE 2-continued

| No. | Structure | Name |
|---|---|---|
| 364 | 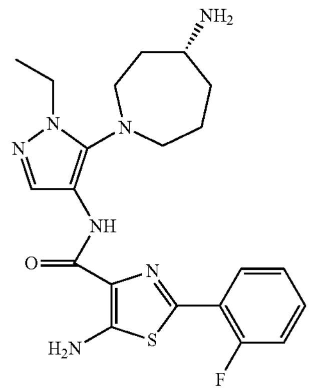 [SMILES: CCn1ncc(NC(=O)c2nc(-c3ccccc3F)sc2N)c1N1CCC[C@@H](N)CC1] | (R)-5-amino-N-(5-(4-aminoazepan-1-yl)-1-ethyl-1H-pyrazol-4-yl)-2-(2-fluorophenyl)thiazole-4-carboxamide |
| 365 | 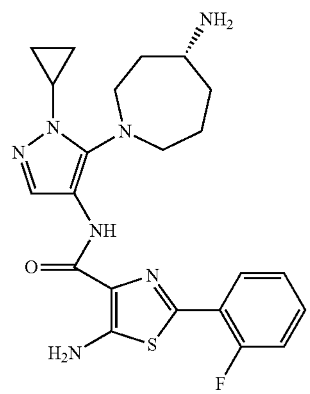 [SMILES: Nc1sc(-c2ccccc2F)nc1C(=O)Nc1cnn(C2CC2)c1N1CCC[C@@H](N)CC1] | (R)-5-amino-N-(5-(4-aminoazepan-1-yl)-1-cyclopropyl-1H-pyrazol-4-yl)-2-(2-fluorophenyl)thiazole-4-carboxamide |
| 366 | 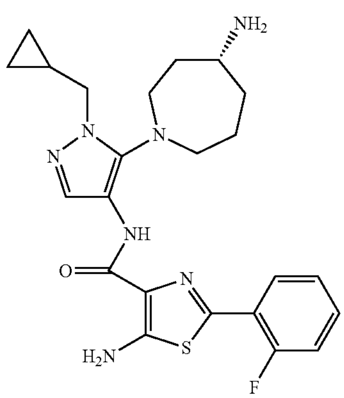 [SMILES: Nc1sc(-c2ccccc2F)nc1C(=O)Nc1cnn(CC2CC2)c1N1CCC[C@@H](N)CC1] | (R)-5-amino-N-(5-(4-aminoazepan-1-yl)-1-(cyclopropylmethyl)-1H-pyrazol-4-yl)-2-(2-fluorophenyl)thiazole-4-carboxamide |
| 367 | 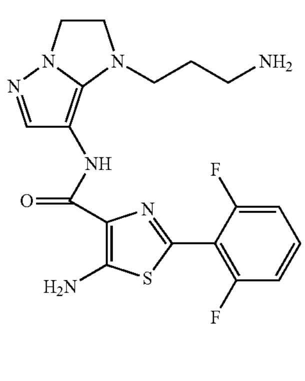 [SMILES: NCCCN1CCn2ncc(NC(=O)c3nc(-c4c(F)cccc4F)sc3N)c21] | 5-amino-N-(1-(3-aminopropyl)-2,3-dihydro-1H-imidazo[1,2-b]pyrazol-7-yl)-2-(2,6-difluorophenyl)thiazole-4-carboxamide |

TABLE 2-continued

| No. | Structure | Name |
|---|---|---|
| 368 | 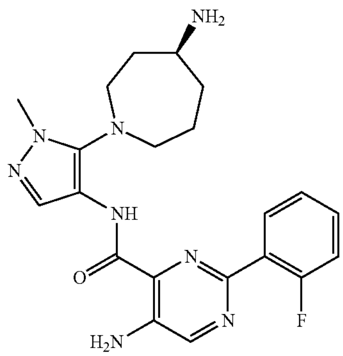 [SMILES: Cn1ncc(NC(=O)c2nc(-c3ccccc3F)ncc2N)c1N1CCC[C@H](N)CC1] | (S)-5-amino-N-(5-(4-aminoazepan-1-yl)-1-methyl-1H-pyrazol-4-yl)-2-(2-fluorophenyl)pyrimidine-4-carboxamide |
| 369 | 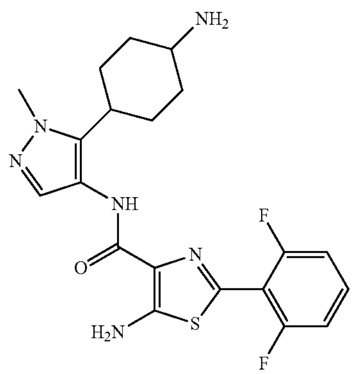 [SMILES: Cn1ncc(NC(=O)c2nc(-c3c(F)cccc3F)sc2N)c1C1CCC(N)CC1] | 5-amino-N-(5-(4-aminocyclohexyl)-1-methyl-1H-pyrazol-4-yl)-2-(2,6-difluorophenyl)thiazole-4-carboxamide |
| 370 | 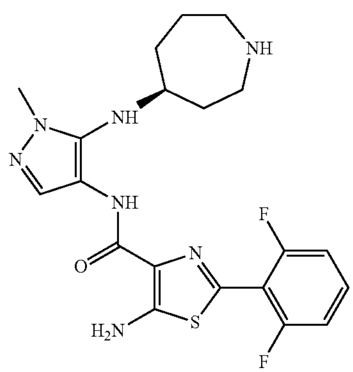 [SMILES: Cn1ncc(NC(=O)c2nc(-c3c(F)cccc3F)sc2N)c1N[C@H]1CCCNCC1] | (S)-5-amino-N-(5-(azepan-4-ylamino)-1-methyl-1H-pyrazol-4-yl)-2-(2,6-difluorophenyl)thiazole-4-carboxamide |
| 371 | 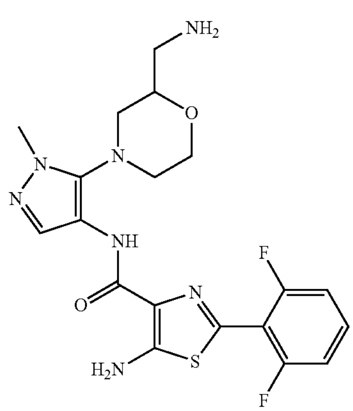 [SMILES: Cn1ncc(NC(=O)c2nc(-c3c(F)cccc3F)sc2N)c1N1CCOC(CN)C1] | 5-amino-N-(5-(2-(aminomethyl)morpholino)-1-methyl-1H-pyrazol-4-yl)-2-(2,6-difluorophenyl)thiazole-4-carboxamide |

TABLE 2-continued

| No. | Structure | Name |
|---|---|---|
| 372 | 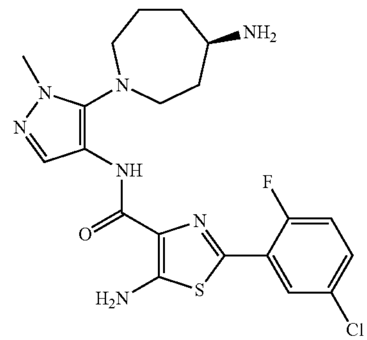 | (R)-5-amino-N-(5-(4-aminoazepan-1-yl)-1-methyl-1H-pyrazol-4-yl)-2-(5-chloro-2-fluorophenyl)thiazole-4-carboxamide |
| 373 | 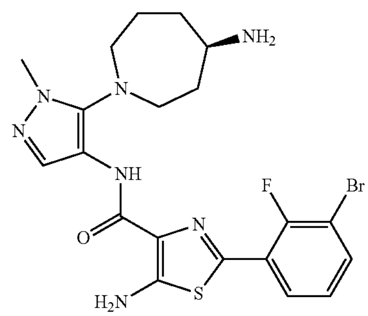 [SMILES: Cn1ncc(NC(=O)c2nc(-c3cccc(Br)c3F)sc2N)c1N1CCC[C@@H](N)CC1] | (R)-5-amino-N-(5-(4-aminoazepan-1-yl)-1-methyl-1H-pyrazol-4-yl)-2-(3-bromo-2-fluorophenyl)thiazole-4-carboxamide |
| 374 | 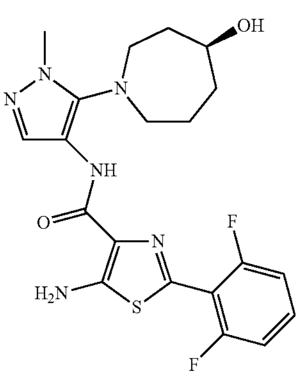 [SMILES: Cn1ncc(NC(=O)c2nc(-c3c(F)cccc3F)sc2N)c1N1CCC[C@H](O)CC1] | (S)-5-amino-2-(2,6-difluorophenyl)-N-(5-(4-hydroxyazepan-1-yl)-1-methyl-1H-pyrazol-4-yl)thiazole-4-carboxamide |
| 375 | 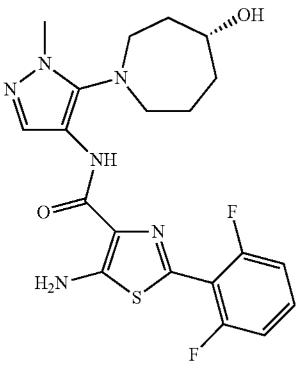 [SMILES: Cn1ncc(NC(=O)c2nc(-c3c(F)cccc3F)sc2N)c1N1CCC[C@@H](O)CC1] | (R)-5-amino-2-(2,6-difluorophenyl)-N-(5-(4-hydroxyazepan-1-yl)-1-methyl-1H-pyrazol-4-yl)thiazole-4-carboxamide |

TABLE 2-continued

| No. | Structure | Name |
|---|---|---|
| 376 | 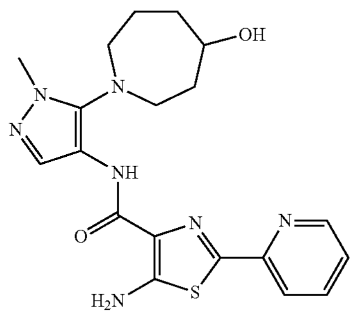 [SMILES: Cn1ncc(NC(=O)c2nc(-c3ccccn3)sc2N)c1N1CCCC(O)CC1] | 5-amino-N-(5-(4-hydroxyazepan-1-yl)-1-methyl-1H-pyrazol-4-yl)-2-(pyridin-2-yl)thiazole-4-carboxamide |
| 377 | 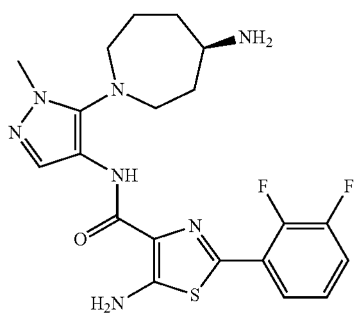 [SMILES: Cn1ncc(NC(=O)c2nc(-c3cccc(F)c3F)sc2N)c1N1CCC[C@@H](N)CC1] | (R)-5-amino-N-(5-(4-aminoazepan-1-yl)-1-methyl-1H-pyrazol-4-yl)-2-(2,3-difluorophenyl)thiazole-4-carboxamide |
| 378 | 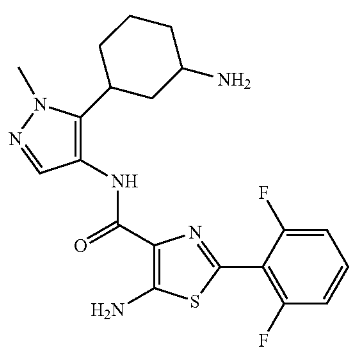 [SMILES: Cn1ncc(NC(=O)c2nc(-c3c(F)cccc3F)sc2N)c1C1CCCC(N)C1] | 5-amino-N-(5-(trans-3-aminocyclohexyl)-1-methyl-1H-pyrazol-4-yl)-2-(2,6-difluorophenyl)thiazole-4-carboxamide |
| 379 | 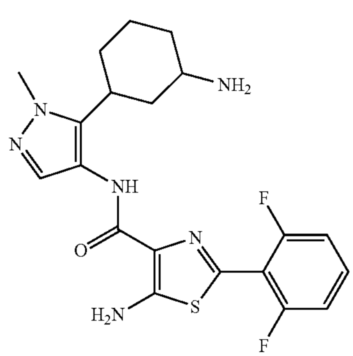 [SMILES: Cn1ncc(NC(=O)c2nc(-c3c(F)cccc3F)sc2N)c1C1CCCC(N)C1] | 5-amino-N-(5-(cis-3-aminocyclohexyl)-1-methyl-1H-pyrazol-4-yl)-2-(2,6-difluorophenyl)thiazole-4-carboxamide |

TABLE 2-continued

| No. | Structure | Name |
|---|---|---|
| 380 | 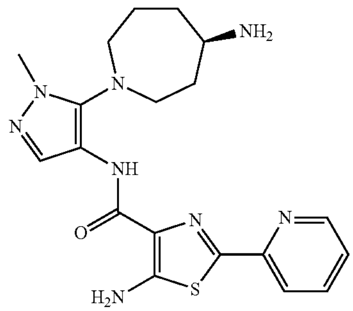 [SMILES: Cn1ncc(NC(=O)c2nc(-c3ccccn3)sc2N)c1N1CCC[C@@H](N)CC1] | (R)-5-amino-N-(5-(4-aminoazepan-1-yl)-1-methyl-1H-pyrazol-4-yl)-2-(pyridin-2-yl)thiazole-4-carboxamide |
| 381 | 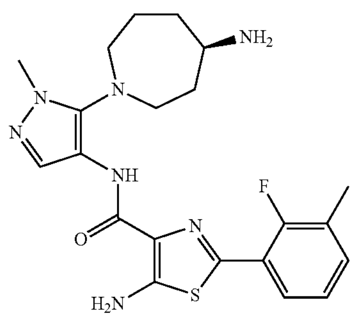 [SMILES: Cc1cccc(-c2nc(C(=O)Nc3cnn(C)c3N3CCC[C@@H](N)CC3)c(N)s2)c1F] | (R)-5-amino-N-(5-(4-aminoazepan-1-yl)-1-methyl-1H-pyrazol-4-yl)-2-(2-fluoro-3-methylphenyl)thiazole-4-carboxamide |
| 382 | 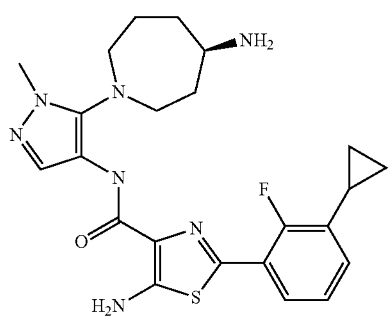 [SMILES: Cn1ncc(NC(=O)c2nc(-c3cccc(C4CC4)c3F)sc2N)c1N1CCC[C@@H](N)CC1] | (R)-5-amino-N-(5-(4-aminoazepan-1-yl)-1-methyl-1H-pyrazol-4-yl)-2-(3-cyclopropyl-2-fluorophenyl)thiazole-4-carboxamide |
| 383 | 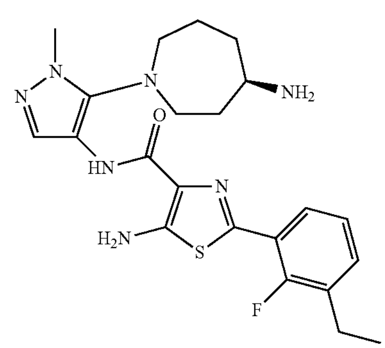 [SMILES: CCc1cccc(-c2nc(C(=O)Nc3cnn(C)c3N3CCC[C@@H](N)CC3)c(N)s2)c1F] | (R)-5-amino-N-(5-(4-aminoazepan-1-yl)-1-methyl-1H-pyrazol-4-yl)-2-(3-ethyl-2-fluorophenyl)thiazole-4-carboxamide |

TABLE 2-continued

| No. | Structure | Name |
|---|---|---|
| 384 | 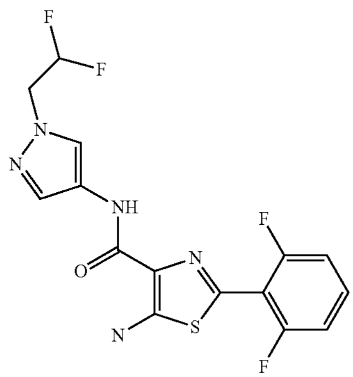 [SMILES: Nc1sc(-c2c(F)cccc2F)nc1C(=O)Nc1cnn(CC(F)F)c1] | 5-amino-N-(1-(2,2-difluoroethyl)-1H-pyrazol-4-yl)-2-(2,6-difluorophenyl)thiazole-4-carboxamide |
| 385 | 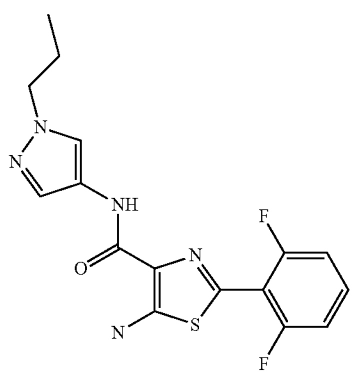 [SMILES: CCCn1cc(NC(=O)c2nc(-c3c(F)cccc3F)sc2N)cn1] | 5-amino-2-(2,6-difluorophenyl)-N-(1-propyl-1H-pyrazol-4-yl)thiazole-4-carboxamide |
| 386 | 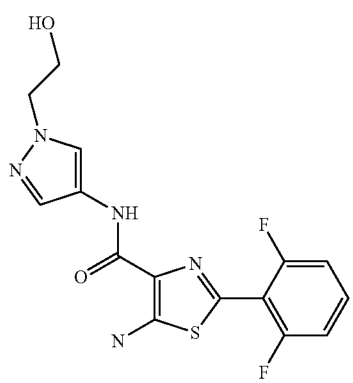 [SMILES: Nc1sc(-c2c(F)cccc2F)nc1C(=O)Nc1cnn(CCO)c1] | 5-amino-2-(2,6-difluorophenyl)-N-(1-(2-hydroxyethyl)-1H-pyrazol-4-yl)thiazole-4-carboxamide |
| 387 | 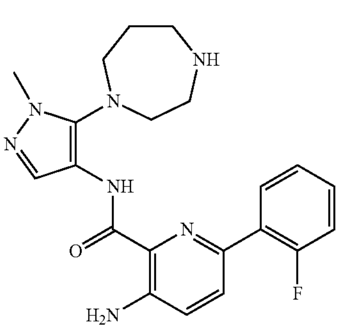 [SMILES: Cn1ncc(NC(=O)c2nc(-c3ccccc3F)ccc2N)c1N1CCCNCC1] | N-(5-(1,4-diazepan-1-yl)-1-methyl-1H-pyrazol-4-yl)-3-amino-6-(2-fluorophenyl)picolinamide |

TABLE 2-continued

| No. | Structure | Name |
|---|---|---|
| 388 | 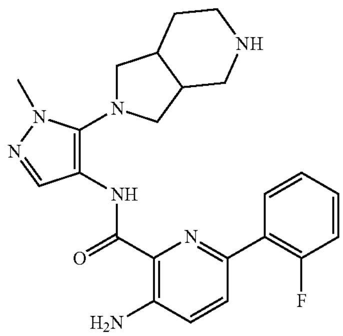 [SMILES: Cn1ncc(NC(=O)c2nc(-c3ccccc3F)ccc2N)c1N1CC2CCNCC2C1] | 3-amino-6-(2-fluorophenyl)-N-(1-methyl-5-(1H-pyrrolo[3,4-c]pyridin-2(3H,3aH,4H,5H,6H,7H,7aH)-yl)-1H-pyrazol-4-yl)picolinamide |
| 389 | 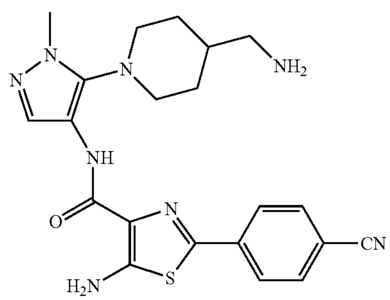 [SMILES: Cn1ncc(NC(=O)c2nc(-c3ccc(C#N)cc3)sc2N)c1N1CCC(CN)CC1] | 5-Amino-N-(5-(4-(aminomethyl)piperidin-1-yl)-1-methyl-1H-pyrazol-4-yl)-2-(4-cyanophenyl)thiazole-4-carboxamide |
| 390 | 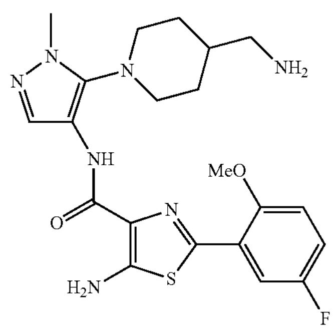 [SMILES: COc1ccc(F)cc1-c1nc(C(=O)Nc2cnn(C)c2N2CCC(CN)CC2)c(N)s1] | 5-Amino-N-(5-(4-(aminomethyl)piperidin-1-yl)-1-methyl-1H-pyrazol-4-yl)-2-(5-fluoro-2-methoxyphenyl)thiazole-4-carboxamide |
| 391 | 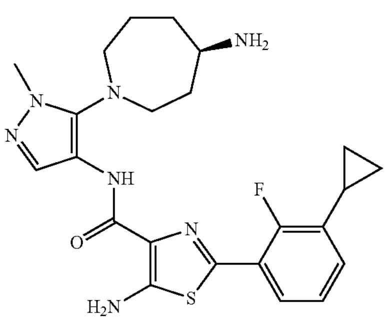 | (R)-5-amino-N-(5-(4-aminoazepan-1-yl)-1-methyl-1H-pyrazol-4-yl)-2-(3-cyclopropyl-2-fluorophenyl)thiazole-4-carboxamide |

TABLE 2-continued

| No. | Structure | Name |
|---|---|---|
| 392 | 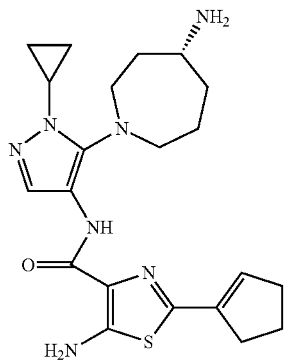 [SMILES: Nc1sc(C2=CCCC2)nc1C(=O)Nc1cnn(C2CC2)c1N1CCC[C@@H](N)CC1] | (R)-5-amino-N-(5-(4-aminoazepan-1-yl)-1-cyclopropyl-1H-pyrazol-4-yl)-2-cyclopentenylthiazole-4-carboxamide |
| 393 | 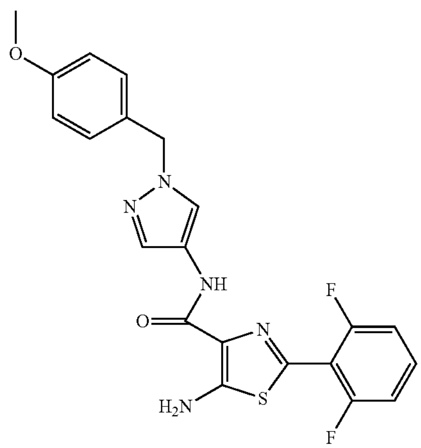 [SMILES: COc1ccc(Cn2cc(NC(=O)c3nc(-c4c(F)cccc4F)sc3N)cn2)cc1] | 5-amino-2-(2,6-difluorophenyl)-N-(1-(4-methoxybenzyl)-1H-pyrazol-4-yl)thiazole-4-carboxamide |
| 394 | 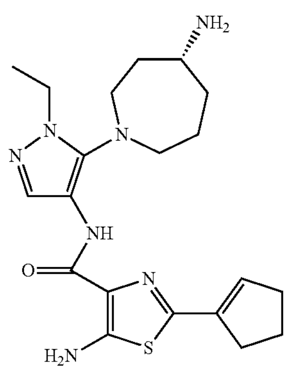 [SMILES: CCn1ncc(NC(=O)c2nc(C3=CCCC3)sc2N)c1N1CCC[C@@H](N)CC1] | (R)-5-amino-N-(5-(4-aminoazepan-1-yl)-1-ethyl-1H-pyrazol-4-yl)-2-cyclopentenylthiazole-4-carboxamide |
| 395 | 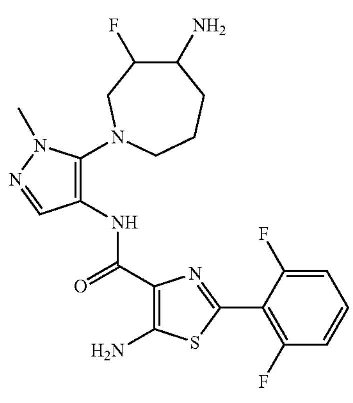 [SMILES: Cn1ncc(NC(=O)c2nc(-c3c(F)cccc3F)sc2N)c1N1CCCC(N)C(F)C1] | 5-amino-N-(5-(4-amino-3-fluoroazepan-1-yl)-1-methyl-1H-pyrazol-4-yl)-2-(2,6-difluorophenyl)thiazole-4-carboxamide |

TABLE 2-continued

| No. | Structure | Name |
|---|---|---|
| 396 | 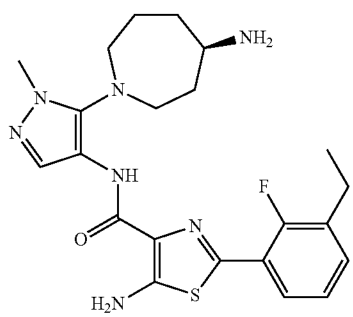 [SMILES: CCc1cccc(-c2nc(C(=O)Nc3cnn(C)c3N3CCC[C@@H](N)CC3)c(N)s2)c1F] | (R)-5-amino-N-(5-(4-aminoazepan-1-yl)-1-methyl-1H-pyrazol-4-yl)-2-(3-ethyl-2-fluorophenyl)thiazole-4-carboxamide |
| 397 | 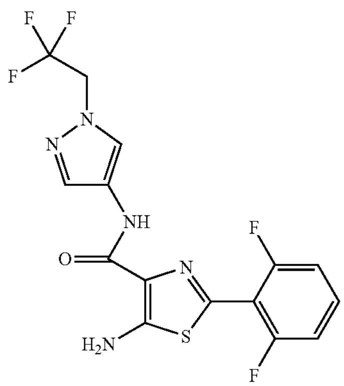 [SMILES: Nc1sc(-c2c(F)cccc2F)nc1C(=O)Nc1cnn(CC(F)(F)F)c1] | 5-amino-2-(2,6-difluorophenyl)-N-(1-(2,2,2-trifluoroethyl)-1H-pyrazol-4-yl)thiazole-4-carboxamide |
| 398 | 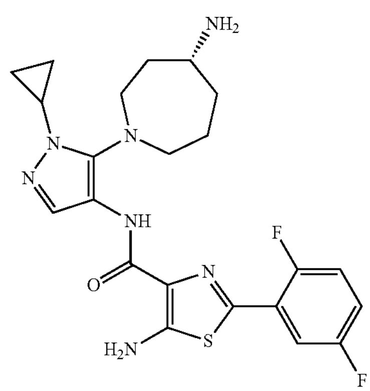 [SMILES: Nc1sc(-c2cc(F)ccc2F)nc1C(=O)Nc1cnn(C2CC2)c1N1CCC[C@@H](N)CC1] | (R)-5-amino-N-(5-(4-aminoazepan-1-yl)-1-cyclopropyl-1H-pyrazol-4-yl)-2-(2,5-difluorophenyl)thiazole-4-carboxamide |
| 399 | 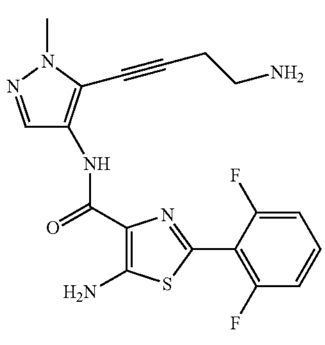 [SMILES: Cn1ncc(NC(=O)c2nc(-c3c(F)cccc3F)sc2N)c1C#CCCN] | 5-amino-N-(5-(4-aminobut-1-ynyl)-1-methyl-1H-pyrazol-4-yl)-2-(2,6-difluorophenyl)thiazole-4-carboxamide |

TABLE 2-continued

| No. | Structure | Name |
|---|---|---|
| 400 | 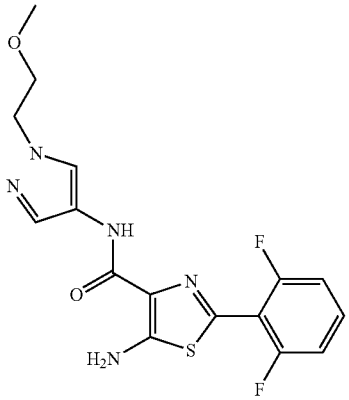 [SMILES: COCCN/C=C(\C=N)NC(=O)c1nc(-c2c(F)cccc2F)sc1N] | 5-amino-2-(2,6-difluorophenyl)-N-(1-(2-methoxyethyl)-1H-pyrazol-4-yl)thiazole-4-carboxamide |
| 401 | 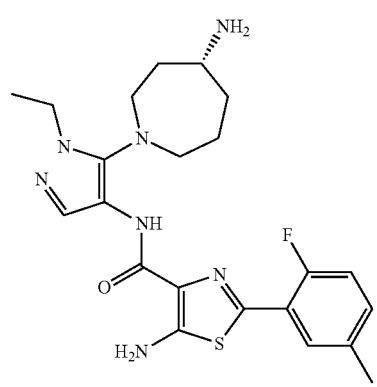 [SMILES: CCN/C(=C(\C=N)NC(=O)c1nc(-c2cc(C)ccc2F)sc1N)N1CCC[C@@H](N)CC1] | (R)-5-amino-N-(5-(4-aminoazepan-1-yl)-1-ethyl-1H-pyrazol-4-yl)-2-(2-fluoro-5-methylphenyl)thiazole-4-carboxamide |
| 402 | 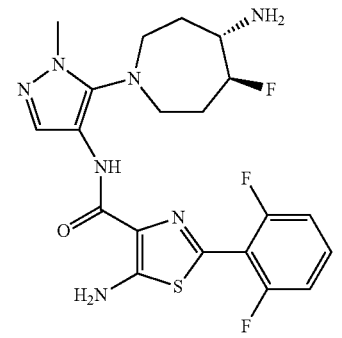 [SMILES: Cn1ncc(NC(=O)c2nc(-c3c(F)cccc3F)sc2N)c1N1CC[C@H](N)[C@@H](F)CC1] | 5-amino-N-(5-((4S,5S)-4-amino-5-fluoroazepan-1-yl)-1-methyl-1H-pyrazol-4-yl)-2-(2,6-difluorophenyl)thiazole-4-carboxamide |
| 403 | 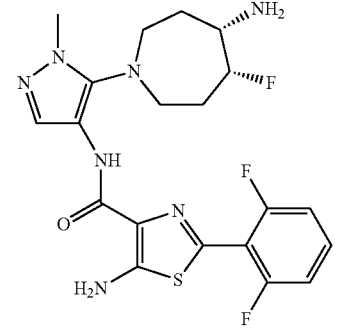 [SMILES: Cn1ncc(NC(=O)c2nc(-c3c(F)cccc3F)sc2N)c1N1CC[C@@H](F)[C@@H](N)CC1] | 5-amino-N-(5-((4S,5R)-4-amino-5-fluoroazepan-1-yl)-1-methyl-1H-pyrazol-4-yl)-2-(2,6-difluorophenyl)thiazole-4-carboxamide |

TABLE 2-continued

| No. | Structure | Name |
|---|---|---|
| 404 | 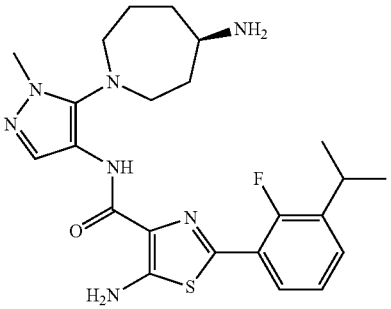 [SMILES: CC(C)c1cccc(-c2nc(C(=O)Nc3cnn(C)c3N3CCC[C@@H](N)CC3)c(N)s2)c1F] | (R)-5-amino-N-(5-(4-aminoazepan-1-yl)-1-methyl-1H-pyrazol-4-yl)-2-(2-fluoro-3-isopropylphenyl)thiazole-4-carboxamide |
| 405 | 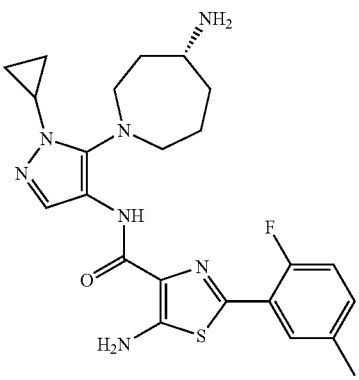 [SMILES: Cc1ccc(F)c(-c2nc(C(=O)Nc3cnn(C4CC4)c3N3CCC[C@@H](N)CC3)c(N)s2)c1] | (R)-5-amino-N-(5-(4-aminoazepan-1-yl)-1-cyclopropyl-1H-pyrazol-4-yl)-2-(2-fluoro-5-methylphenyl)thiazole-4-carboxamide |
| 406 | 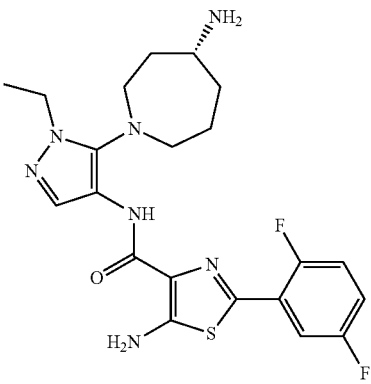 [SMILES: CCn1ncc(NC(=O)c2nc(-c3cc(F)ccc3F)sc2N)c1N1CCC[C@@H](N)CC1] | (R)-5-amino-N-(5-(4-aminoazepan-1-yl)-1-ethyl-1H-pyrazol-4-yl)-2-(2,5-difluorophenyl)thiazole-4-carboxamide |
| 407 | 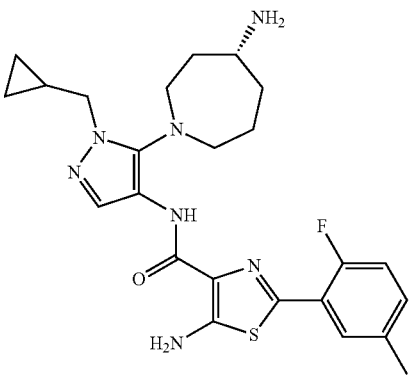 [SMILES: Cc1ccc(F)c(-c2nc(C(=O)Nc3cnn(CC4CC4)c3N3CCC[C@@H](N)CC3)c(N)s2)c1] | (R)-5-amino-N-(5-(4-aminoazepan-1-yl)-1-(cyclopropylmethyl)-1H-pyrazol-4-yl)-2-(2-fluoro-5-methylphenyl)thiazole-4-carboxamide |

TABLE 2-continued

| No. | Structure | Name |
|---|---|---|
| 408 | 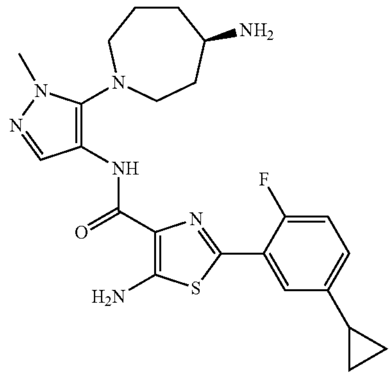 [SMILES: Cn1ncc(NC(=O)c2nc(-c3cc(C4CC4)ccc3F)sc2N)c1N1CCC[C@@H](N)CC1] | (R)-5-amino-N-(5-(4-aminoazepan-1-yl)-1-methyl-1H-pyrazol-4-yl)-2-(5-cyclopropyl-2-fluorophenyl)thiazole-4-carboxamide |
| 409 | 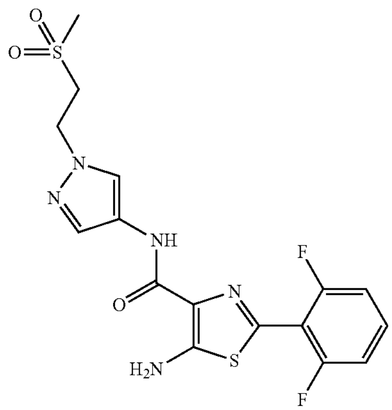 [SMILES: CS(=O)(=O)CCn1cc(NC(=O)c2nc(-c3c(F)cccc3F)sc2N)cn1] | 5-amino-2-(2,6-difluorophenyl)-N-(1-(2-(methylsulfonyl)ethyl)-1H-pyrazol-4-yl)thiazole-4-carboxamide |
| 410 | 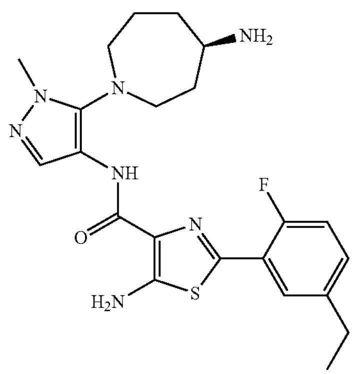 [SMILES: CCc1ccc(F)c(-c2nc(C(=O)Nc3cnn(C)c3N3CCC[C@@H](N)CC3)c(N)s2)c1] | (R)-5-amino-N-(5-(4-aminoazepan-1-yl)-1-methyl-1H-pyrazol-4-yl)-2-(5-ethyl-2-fluorophenyl)thiazole-4-carboxamide |
| 411 | 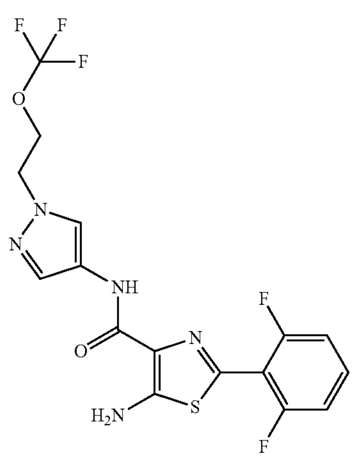 [SMILES: Nc1sc(-c2c(F)cccc2F)nc1C(=O)Nc1cnn(CCOC(F)(F)F)c1] | 5-amino-2-(2,6-difluorophenyl)-N-(1-(2-(trifluoromethoxy)ethyl)-1H-pyrazol-4-yl)thiazole-4-carboxamide |

| No. | Structure | Name |
| --- | --- | --- |
| 412 | 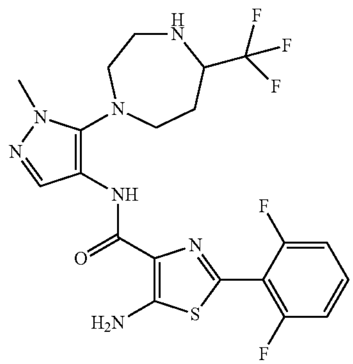 [SMILES: Cn1ncc(NC(=O)c2nc(-c3c(F)cccc3F)sc2N)c1N1CCNC(C(F)(F)F)CC1] | 5-amino-2-(2,6-difluorophenyl)-N-(1-methyl-5-(5-(trifluoromethyl)-1,4-diazepan-1-yl)-1H-pyrazol-4-yl)thiazole-4-carboxamide |
| 413 | 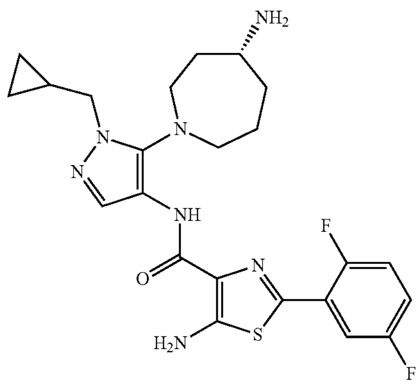 [SMILES: Nc1sc(-c2cc(F)ccc2F)nc1C(=O)Nc1cnn(CC2CC2)c1N1CCC[C@@H](N)CC1] | (R)-5-amino-N-(5-(4-aminoazepan-1-yl)-1-(cyclopropylmethyl)-1H-pyrazol-4-yl)-2-(2,5-difluorophenyl)thiazole-4-carboxamide |
| 414 | 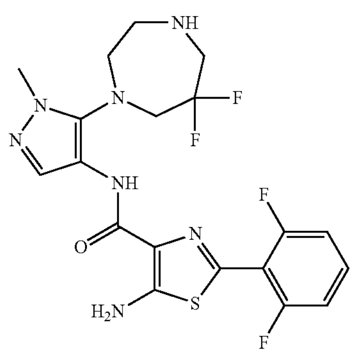 [SMILES: Cn1ncc(NC(=O)c2nc(-c3c(F)cccc3F)sc2N)c1N1CCNCC(F)(F)C1] | 5-amino-N-(5-(6,6-difluoro-1,4-diazepan-1-yl)-1-methyl-1H-pyrazol-4-yl)-2-(2,6-difluorophenyl)thiazole-4-carboxamide |
| 415 | 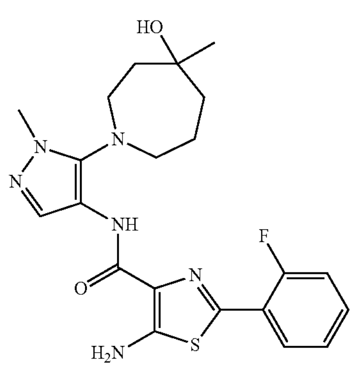 [SMILES: Cn1ncc(NC(=O)c2nc(-c3ccccc3F)sc2N)c1N1CCCC(C)(O)CC1] | 5-amino-2-(2-fluorophenyl)-N-(5-(4-hydroxy-4-methylazepan-1-yl)-1-methyl-1H-pyrazol-4-yl)thiazole-4-carboxamide |

TABLE 2-continued

| No. | Structure | Name |
|---|---|---|
| 416 | 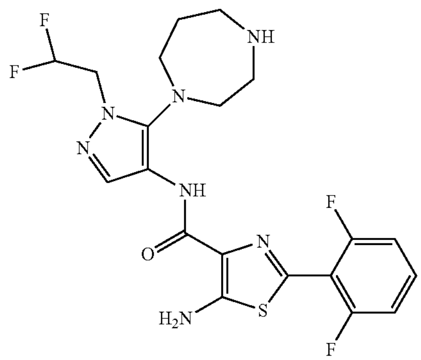 [SMILES: Nc1sc(-c2c(F)cccc2F)nc1C(=O)Nc1cnn(CC(F)F)c1N1CCCNCC1] | N-(5-(1,4-diazepan-1-yl)-1-(2,2-difluoroethyl)-1H-pyrazol-4-yl)-5-amino-2-(2,6-difluorophenyl)thiazole-4-carboxamide |
| 417 | 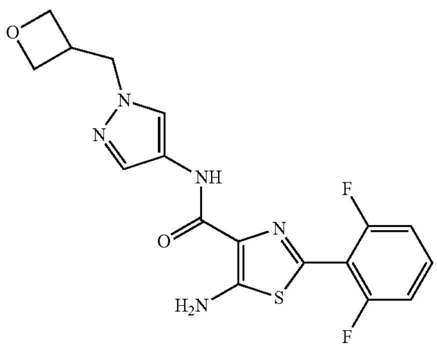 [SMILES: Nc1sc(-c2c(F)cccc2F)nc1C(=O)Nc1cnn(CC2COC2)c1] | 5-amino-2-(2,6-difluorophenyl)-N-(1-(oxetan-3-ylmethyl)-1H-pyrazol-4-yl)thiazole-4-carboxamide |
| 418 | 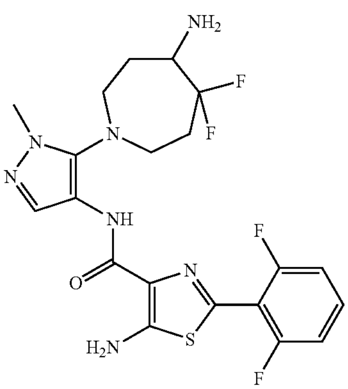 [SMILES: Cn1ncc(NC(=O)c2nc(-c3c(F)cccc3F)sc2N)c1N1CCC(N)C(F)(F)CC1] | 5-amino-N-(5-(5-amino-4,4-difluoroazepan-1-yl)-1-methyl-1H-pyrazol-4-yl)-2-(2,6-difluorophenyl)thiazole-4-carboxamide |
| 419 | 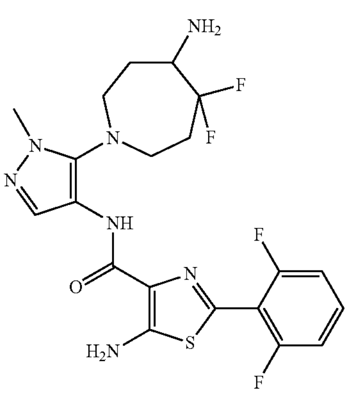 [SMILES: Cn1ncc(NC(=O)c2nc(-c3c(F)cccc3F)sc2N)c1N1CCC(N)C(F)(F)CC1] | 5-amino-N-(5-(5-amino-4,4-difluoroazepan-1-yl)-1-methyl-1H-pyrazol-4-yl)-2-(2,6-difluorophenyl)thiazole-4-carboxamide |

TABLE 2-continued

| No. | Structure | Name |
|---|---|---|
| 420 | 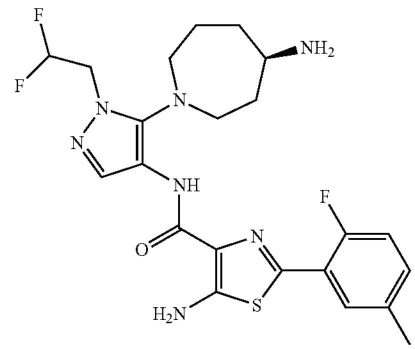 [SMILES: Cc1ccc(F)c(-c2nc(C(=O)Nc3cnn(CC(F)F)c3N3CCC[C@@H](N)CC3)c(N)s2)c1] | (R)-5-amino-N-(5-(4-aminoazepan-1-yl)-1-(2,2-difluoroethyl)-1H-pyrazol-4-yl)-2-(2-fluoro-5-methylphenyl)thiazole-4-carboxamide |
| 421 | 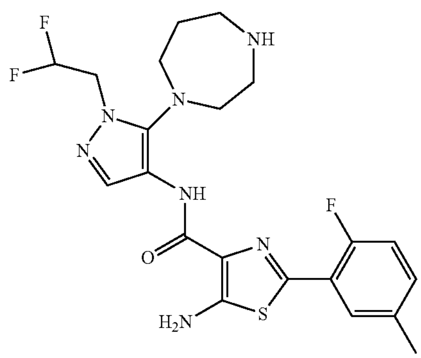 [SMILES: Cc1ccc(F)c(-c2nc(C(=O)Nc3cnn(CC(F)F)c3N3CCCNCC3)c(N)s2)c1] | N-(5-(1,4-diazepan-1-yl)-1-(2,2-difluoroethyl)-1H-pyrazol-4-yl)-5-amino-2-(2-fluoro-5-methylphenyl)thiazole-4-carboxamide |
| 422 | 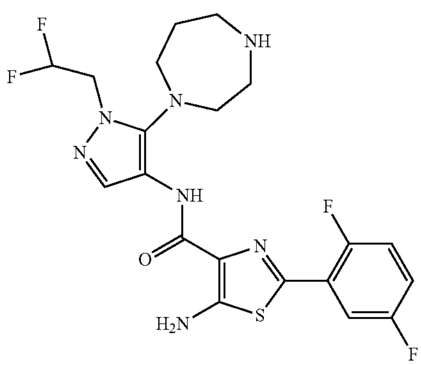 [SMILES: Nc1sc(-c2cc(F)ccc2F)nc1C(=O)Nc1cnn(CC(F)F)c1N1CCCNCC1] | N-(5-(1,4-diazepan-1-yl)-1-(2,2-difluoroethyl)-1H-pyrazol-4-yl)-5-amino-2-(2,5-difluorophenyl)thiazole-4-carboxamide |
| 423 | 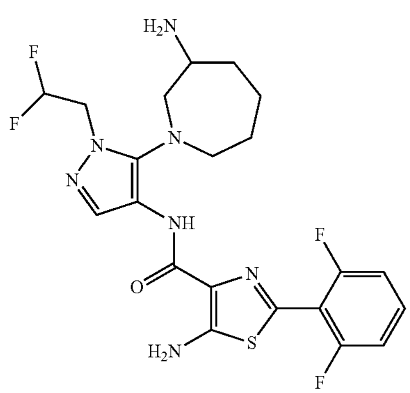 [SMILES: Nc1sc(-c2c(F)cccc2F)nc1C(=O)Nc1cnn(CC(F)F)c1N1CCCCC(N)C1] | 5-amino-N-(5-(3-aminoazepan-1-yl)-1-(2,2-difluoroethyl)-1H-pyrazol-4-yl)-2-(2,6-difluorophenyl)thiazole-4-carboxamide |

TABLE 2-continued

| No. | Structure | Name |
|---|---|---|
| 424 | 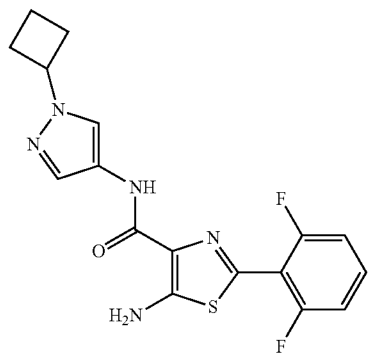 [SMILES: Nc1sc(-c2c(F)cccc2F)nc1C(=O)Nc1cnn(C2CCC2)c1] | 5-amino-N-(1-cyclobutyl-1H-pyrazol-4-yl)-2-(2,6-difluorophenyl)thiazole-4-carboxamide |
| 425 | 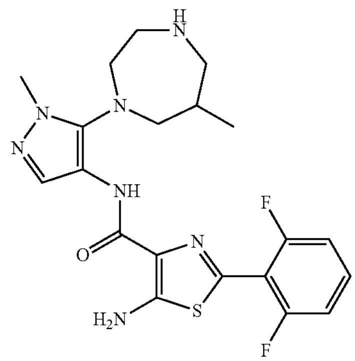 [SMILES: CC1CNCCN(c2c(NC(=O)c3nc(-c4c(F)cccc4F)sc3N)cnn2C)C1] | 5-amino-2-(2,6-difluorophenyl)-N-(1-methyl-5-(6-methyl-1,4-diazepan-1-yl)-1H-pyrazol-4-yl)thiazole-4-carboxamide |

The compounds of the present invention were tested for their capacity to inhibit Pim kinase activity and for their biological effects on growing cells as described below in Examples 901 and 902. Formula I compounds having $Ki/IC_{50}/EC_{50}$ of less than 1 µM in assays described in Examples 901 and 902, may be useful therapeutically as Pim kinase inhibitors (Pim-1, Pim-2 and/or Pim-3).

The present invention includes a composition (e.g., a pharmaceutical composition) comprising a compound of Formula I, and/or solvates, hydrates and/or salts thereof, and a carrier (a pharmaceutically acceptable carrier). The present invention also includes a composition (e.g., a pharmaceutical composition) comprising a compound of Formula I and/or solvates, hydrates and/or salts thereof, and a carrier (a pharmaceutically acceptable carrier), further comprising a second chemotherapeutic agent such as those described herein. The present compositions are useful for inhibiting abnormal cell growth or treating a hyperproliferative disorder such as cancer in a mammal (e.g., human). For example, the present compounds and compositions are useful for treating multiple myeloma, lymphoma, acute myeloid leukemia, prostate cancer, breast cancer, hepatocellular carcinoma, pancreatic cancer, and/or colorectal cancer in a mammal (e.g., human).

The present invention includes a method of inhibiting abnormal cell growth or treating a hyperproliferative disorder such as cancer in a mammal (e.g., human) comprising administering to said mammal a therapeutically effective amount of a compound of Formula I, and/or solvates, hydrates and/or salts thereof, or a composition thereof. For example, the present invention includes a method of treating multiple myeloma, lymphoma, acute myeloid leukemia, prostate cancer, breast cancer, hepatocellular carcinoma, pancreatic cancer, and/or colorectal cancer in a mammal (e.g., human), comprising administering to said mammal a therapeutically effective amount of a compound of Formula I, and/or solvates, hydrates and/or salts thereof) or a composition thereof.

The present invention includes a method of inhibiting abnormal cell growth or treating a hyperproliferative disorder such as cancer in a mammal (e.g., human) comprising administering to said mammal a therapeutically effective amount of a compound of Formula I, and/or solvates, hydrates and/or salts thereof, or a composition thereof, in combination with a second chemotherapeutic agent such as those described herein. For example, the present invention includes a method of treating multiple myeloma, lymphoma, acute myeloid leukemia, prostate cancer, breast cancer, hepatocellular carcinoma, pancreatic cancer, and/or colorectal cancer in a mammal (e.g., human), comprising administering to said mammal a therapeutically effective amount of a compound of Formula I, and/or solvates, hydrates and/or salts thereof, or a composition thereof, in combination with a second chemotherapeutic agent such as those described herein.

The present invention includes a method of treating lymphoma in a mammal (e.g., human) comprising administering to said mammal a therapeutically effective amount of a compound of Formula I, and/or solvates, hydrates and/or salts thereof, or a composition thereof, either alone or in combination with a second chemotherapeutic agent such as an anti-B-cell antibody therapeutic (e.g., Rituxan and/or Dacetuzumab), gemcitabine, corticosteroids (e.g., prednisolone and/or dexamethasone), chemotherapy cocktails (e.g., CHOP (cyclophosphamide, doxorubicin, vincristine, prednisolone) and/or ICE (isfosfamide, cytoxan, etoposide)), a combination of biologics and chemotherapy (e.g., Rituxan-ICE, Dacetuzumab-Rituxan-ICE, R-Gem, and/or D-R-Gem), an Akt inhibitor, a PI3K inhibitor (e.g, GDC-0941 (Genentech) and/or GDC-0980 (Genentech)), rapamycin, a MEK inhibitor (GDC-0973), a Bcl-2 inhibitor (ABT-263), and lymphoma directed antibody drug conjugate (e.g., antiCD22 antibody drug conjugate including but not limited to antiCD22-vcM-MAE, and/or antiCD79b-antibody drug conjugate including but not limited to antiCD79b-vcMMAE).

The present invention includes a method of treating multiple myeloma in a mammal (e.g., human) comprising administering to said mammal a therapeutically effective amount of a compound of Formula I, and/or solvates, hydrates and/or salts thereof, or a composition thereof, either alone or in combination with a second chemotherapeutic agent such as melphalan, "Imids" (e.g., thalidomide, lenalidomide, and/or pomolidamide), corticosteroids (e.g., dexamethasone and/or prednisolone), and bortezomib or other proteasome inhibitor.

The present invention includes a method of treating multiple myeloma, chronic lymphocytic leukemia (CLL), or acute myeloid leukemia (AML) in a mammal (e.g., human) comprising administering to said mammal a therapeutically effective amount of a compound of Formula I, and/or solvates, hydrates and/or salts thereof, or a composition thereof, either alone or in combination with a second chemotherapeutic agent such as cytarabine (araC), anthracyclines (e.g., daunorubicin and/or idarubicin), anti-myeloid antibody therapeutics (e.g., SGN-33), anti-myeloid antibody-drug conjugates (e.g., MYLOTARG®).

The present invention includes a method of treating chronic lymphocytic leukemia (CLL) in a mammal (e.g., human) comprising administering to said mammal a therapeutically effective amount of a compound of Formula I, and/or solvates, hydrates and/or salts thereof, or a composition thereof, either alone or in combination with a second chemotherapeutic agent such as fludarabine, cyclophosphamide, anti-B-cell antibody therapeutics (e.g., Rituxan and/or Dacetuzumab).

The present invention includes a method of treating chronic myeloid leukemia (CML) in a mammal (e.g., human) comprising administering to said mammal a therapeutically effective amount of a compound of Formula I, and/or solvates, hydrates and/or salts thereof, or a composition thereof, either alone or in combination with a second chemotherapeutic agent such as a BCR-abl inhibitor (e.g., imatinib, nilotinib, and/or dasatinib).

The present invention includes a method of treating myelodysplastic diseases (MDS) and myeloproliferative disorders including polycythemia vera (PV), essential thrombocytosis (ET) or myelofibrosis (MF), in a mammal (e.g., human) comprising administering to said mammal a therapeutically effective amount of a compound of Formula I, and/or solvates, hydrates and/or salts thereof, or a composition thereof, either alone or in combination.

The present invention includes a method of using the present compounds for in vitro, in situ, and in vivo diagnosis or treatment of mammalian cells, organisms, or associated pathological conditions.

Administration of the compounds of the present invention (hereinafter the "active compound(s)") can be effected by any method that enables delivery of the compounds to the site of action. These methods include oral routes, intraduodenal routes, parenteral injection (including intravenous, subcutaneous, intramuscular, intravascular or infusion), topical, inhalation and rectal administration.

The amount of the active compound administered will be dependent on the subject being treated, the severity of the disorder or condition, the rate of administration, the disposition of the compound and the discretion of the prescribing physician. However, an effective dosage is in the range of about 0.001 to about 100 mg per kg body weight per day, preferably about 1 to about 35 mg/kg/day, in single or divided doses. For a 70 kg human, this would amount to about 0.05 to 7 g/day, preferably about 0.05 to about 2.5 g/day. In some instances, dosage levels below the lower limit of the aforesaid range may be more than adequate, while in other cases still larger doses may be employed without causing any harmful side effect, provided that such larger doses are first divided into several small doses for administration throughout the day.

The active compound may be applied as a sole therapy or in combination with one or more chemotherapeutic agents, for example those described herein. Such conjoint treatment may be achieved by way of the simultaneous, sequential or separate dosing of the individual components of treatment.

The pharmaceutical composition may, for example, be in a form suitable for oral administration as a tablet, capsule, pill, powder, sustained release formulations, solution, suspension for parenteral injection as a sterile solution, suspension or emulsion for topical administration as an ointment or cream or for rectal administration as a suppository. The pharmaceutical composition may be in unit dosage forms suitable for single administration of precise dosages. The pharmaceutical composition will include a conventional pharmaceutical carrier or excipient and a compound according to the invention as an active ingredient. In addition, it may include other medicinal or pharmaceutical agents, carriers, adjuvants, etc.

Exemplary parenteral administration forms include solutions or suspensions of Formula I compounds in sterile aqueous solutions, for example, aqueous propylene glycol or dextrose solutions. Such dosage forms can be suitably buffered, if desired.

Suitable pharmaceutical carriers include inert diluents or fillers, water and various organic solvents. The pharmaceutical compositions may, if desired, contain additional ingredients such as flavorings, binders, excipients and the like. Thus for oral administration, tablets containing various excipients, such as citric acid may be employed together with various disintegrants such as starch, alginic acid and certain complex silicates and with binding agents such as sucrose, gelatin and acacia. Additionally, lubricating agents such as magnesium stearate, sodium lauryl sulfate and talc are often useful for tabletting purposes. Solid compositions of a similar type may also be employed in soft and hard filled gelatin capsules. Preferred materials, therefore, include lactose or milk sugar and high molecular weight polyethylene glycols. When aqueous suspensions or elixirs are desired for oral administration the active compound therein may be combined with various sweetening or flavoring agents, coloring matters or dyes and, if desired, emulsifying agents or suspending agents, together with diluents such as water, ethanol, propylene glycol, glycerin, or combinations thereof.

Methods of preparing various pharmaceutical compositions with a specific amount of active compound are known, or will be apparent, to those skilled in this art. For examples, see Remington's Pharmaceutical Sciences, Mack Publishing Company, Ester, Pa., 15.sup.th Edition (1975).

Administration of Formula I Compounds

The Formula I compounds of the invention may be administered by any route appropriate to the condition to be treated. Suitable routes include oral, parenteral (including subcutaneous, intramuscular, intravenous, intraarterial, intradermal, intrathecal and epidural), transdermal, rectal, nasal, topical (including buccal and sublingual), vaginal, intraperitoneal, intrapulmonary and intranasal. For local immunosuppressive treatment, the compounds may be administered by intralesional administration, including perfusing or otherwise contacting the graft with the inhibitor before transplantation. It will be appreciated that the preferred route may vary with for example the condition of the recipient. Where the compound is administered orally, it may be formulated as a pill, capsule, tablet, etc. with a pharmaceutically acceptable carrier or excipient. Where the compound is administered parenterally, it may be formulated with a pharmaceutically acceptable parenteral vehicle and in a unit dosage injectable form, as detailed below.

A dose to treat human patients may range from about 10 mg to about 1000 mg of Formula I compound. A typical dose may be about 100 mg to about 300 mg of the compound. A dose may be administered once a day (QID), twice per day (BID), or more frequently, depending on the pharmacokinetic and pharmacodynamic properties, including absorption, distribution, metabolism, and excretion of the particular compound. In addition, toxicity factors may influence the dosage and administration regimen. When administered orally, the pill, capsule, or tablet may be ingested daily or less frequently for a specified period of time. The regimen may be repeated for a number of cycles of therapy.

Methods of Treatment with Formula I Compounds

Compounds of the present invention are useful for treating hyperproliferative diseases, conditions and/or disorders including, but not limited to, those characterized by over expression of Pim kinases, e.g. Pim-1, Pim-2 and Pim-3 kinases. Accordingly, another aspect of this invention includes methods of treating or preventing diseases or conditions that can be treated or prevented by inhibiting Pim kinase. In one embodiment, the method comprises administering to a mammal in need thereof a therapeutically effective amount of a compound of Formula I, or a stereoisomer, geometric isomer, tautomer, or pharmaceutically acceptable salt thereof. In one embodiment, a human patient is treated with a compound of Formula I and a pharmaceutically acceptable carrier, adjuvant, or vehicle, wherein said compound of Formula I is present in an amount to detectably inhibit Pim kinase activity.

Cancers which can be treated according to the methods of this invention include, but are not limited to, breast, ovary, cervix, prostate, testis, genitourinary tract, esophagus, larynx, glioblastoma, neuroblastoma, stomach, skin, keratoacanthoma, lung, epidermoid carcinoma, large cell carcinoma, non-small cell lung carcinoma (NSCLC), small cell carcinoma, lung adenocarcinoma, bone, colon, adenoma, pancreas, adenocarcinoma, thyroid, follicular carcinoma, undifferentiated carcinoma, papillary carcinoma, seminoma, melanoma, sarcoma, bladder carcinoma, liver carcinoma and biliary passages, kidney carcinoma, myeloid disorders, lymphoid disorders, hairy cells, buccal cavity and pharynx (oral), lip, tongue, mouth, pharynx, small intestine, colon-rectum, large intestine, rectum, brain and central nervous system, Hodgkin's and leukemia.

Another aspect of this invention provides a compound of this invention for use in the treatment of the diseases or conditions described herein in a mammal, for example, a human, suffering from such disease or condition. Also provided is the use of a compound of this invention in the preparation of a medicament for the treatment of the diseases and conditions described herein in a warm-blooded animal, such as a mammal, for example a human, suffering from such disorder.

Pharmaceutical Formulations

In order to use a Formula I compound for the therapeutic treatment (including prophylactic treatment) of mammals including humans, it is normally formulated in accordance with standard pharmaceutical practice as a pharmaceutical composition. According to this aspect of the invention there is provided a pharmaceutical composition comprising a compound of this invention in association with a pharmaceutically acceptable diluent or carrier.

A typical formulation is prepared by mixing a Formula I compound and a carrier, diluent or excipient. Suitable carriers, diluents and excipients are well known to those skilled in the art and include materials such as carbohydrates, waxes, water soluble and/or swellable polymers, hydrophilic or hydrophobic materials, gelatin, oils, solvents, water and the like. The particular carrier, diluent or excipient used will depend upon the means and purpose for which the compound of the present invention is being applied. Solvents are generally selected based on solvents recognized by persons skilled in the art as safe (GRAS) to be administered to a mammal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG 400, PEG 300), etc. and mixtures thereof. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the drug (i.e., a compound of the present invention or pharmaceutical composition thereof) or aid in the manufacturing of the pharmaceutical product (i.e., medicament).

The formulations may be prepared using conventional dissolution and mixing procedures. For example, the bulk drug substance (i.e., compound of the present invention or stabilized form of the Formula I compound (e.g., complex with a cyclodextrin derivative or other known complexation agent) is dissolved in a suitable solvent in the presence of one or more of the excipients described above. The compound of the present invention is typically formulated into pharmaceutical dosage forms to provide an easily controllable dosage of the drug and to enable patient compliance with the prescribed regimen.

The pharmaceutical composition (or formulation) for application may be packaged in a variety of ways depending upon the method used for administering the drug. Generally, an article for distribution includes a container having deposited therein the pharmaceutical formulation in an appropriate form. Suitable containers are well known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

Pharmaceutical formulations of the compounds of the present invention may be prepared for various routes and types of administration. For example, a compound of Formula I having the desired degree of purity may optionally be mixed with pharmaceutically acceptable diluents, carriers, excipients or stabilizers (Remington's Pharmaceutical Sciences (1980) 16$^{th}$ edition, Osol, A. Ed.), in the form of a lyophilized formulation, milled powder, or an aqueous solution. Formulation may be conducted by mixing at ambient temperature at the appropriate pH, and at the desired degree of purity, with physiologically acceptable carriers, i.e., carriers that are non-toxic to recipients at the dosages and concentrations employed. The pH of the formulation depends mainly on the particular use and the concentration of compound, but may range from about 3 to about 8. Formulation in an acetate buffer at pH 5 is a suitable embodiment.

The compound of this invention for use herein is preferably sterile. In particular, formulations to be used for in vivo administration must be sterile. Such sterilization is readily accomplished by filtration through sterile filtration membranes.

The compound ordinarily can be stored as a solid composition, a lyophilized formulation or as an aqueous solution.

The pharmaceutical compositions of the invention comprising a Formula I compound will be formulated, dosed and administered in a fashion, i.e., amounts, concentrations, schedules, course, vehicles and route of administration, consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "therapeutically effective amount" of the compound to be administered will be governed by such considerations, and is the minimum amount necessary to prevent, ameliorate, or treat the coagulation factor mediated disorder. Such amount is preferably below the amount that is toxic to the host or renders the host significantly more susceptible to bleeding.

As a general proposition, the initial pharmaceutically effective amount of the Formula I compound administered parenterally per dose will be in the range of about 0.01-100 mg/kg, namely about 0.1 to 20 mg/kg of patient body weight per day, with the typical initial range of compound used being 0.3 to 15 mg/kg/day.

Acceptable diluents, carriers, excipients and stabilizers are nontoxic to recipients at the dosages and concentrations employed, and include buffers such as phosphate, citrate and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG). The active pharmaceutical ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16$^{th}$ edition, Osol, A. Ed. (1980).

Sustained-release preparations of Formula I compounds may be prepared. Suitable examples of sustained-release preparations include semipermeable matrices of solid hydrophobic polymers containing a compound of Formula I, which matrices are in the form of shaped articles, e.g., films, or microcapsules. Examples of sustained-release matrices include polyesters, hydrogels (for example, poly(2-hydroxyethyl-methacrylate), or poly(vinyl alcohol)), polylactides (U.S. Pat. No. 3,773,919), copolymers of L-glutamic acid and gamma-ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate) and poly-D-(−)-3-hydroxybutyric acid.

The formulations include those suitable for the administration routes detailed herein. The formulations may conveniently be presented in unit dosage form and may be prepared by any of the methods well known in the art of pharmacy. Techniques and formulations generally are found in *Remington's Pharmaceutical Sciences* (Mack Publishing Co., Easton, Pa.). Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations of a compound of Formula I suitable for oral administration may be prepared as discrete units such as pills, capsules, cachets or tablets each containing a predetermined amount of a compound of Formula I.

Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered active ingredient moistened with an inert liquid diluent. The tablets may optionally be coated or scored and optionally are formulated so as to provide slow or controlled release of the active ingredient therefrom.

Tablets, troches, lozenges, aqueous or oil suspensions, dispersible powders or granules, emulsions, hard or soft capsules, e.g., gelatin capsules, syrups or elixirs may be prepared for oral use. Formulations of compounds of Formula I intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

For treatment of the eye or other external tissues, e.g., mouth and skin, the formulations are preferably applied as a topical ointment or cream containing the active ingredient(s) in an amount of, for example, 0.075 to 20% w/w. When formulated in an ointment, the active ingredients may be employed with either a paraffinic or a water-miscible ointment base. Alternatively, the active ingredients may be formulated in a cream with an oil-in-water cream base.

If desired, the aqueous phase of the cream base may include a polyhydric alcohol, i.e., an alcohol having two or more hydroxyl groups such as propylene glycol, butane 1,3-diol, mannitol, sorbitol, glycerol and polyethylene glycol (including PEG 400) and mixtures thereof. The topical formulations may desirably include a compound which enhances absorption or penetration of the active ingredient through the skin or other affected areas. Examples of such dermal penetration enhancers include dimethyl sulfoxide and related analogs.

The oily phase of the emulsions of this invention may be constituted from known ingredients in a known manner. While the phase may comprise merely an emulsifier, it desirably comprises a mixture of at least one emulsifier with a fat or oil, or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations. Emulsifiers and emulsion stabilizers suitable for use in the formulation of the invention include Tween® 60, Span® 80, cetostearyl alcohol, benzyl alcohol, myristyl alcohol, glyceryl mono-stearate and sodium lauryl sulfate.

Aqueous suspensions of Formula I compounds contain the active materials in admixture with excipients suitable for the manufacture of aqueous suspensions. Such excipients include a suspending agent, such as sodium carboxymethylcellulose, croscarmellose, povidone, methylcellulose, hydroxypropyl methylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxybenzoate, one or more coloring agents, one or more flavoring agents and one or more sweetening agents, such as sucrose or saccharin.

The pharmaceutical compositions of compounds of Formula I may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as a solution in 1,3-butanediol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The amount of active ingredient that may be combined with the carrier material to produce a single dosage form will vary depending upon the host treated and the particular mode of administration. For example, a time-release formulation intended for oral administration to humans may contain approximately 1 to 1000 mg of active material compounded with an appropriate and convenient amount of carrier material which may vary from about 5 to about 95% of the total compositions (weight:weight). The pharmaceutical composition can be prepared to provide easily measurable amounts for administration. For example, an aqueous solution intended for intravenous infusion may contain from about 3 to 500 μg of the active ingredient per milliliter of solution in order that infusion of a suitable volume at a rate of about 30 mL/hr can occur.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

Formulations suitable for topical administration to the eye also include eye drops wherein the active ingredient is dissolved or suspended in a suitable carrier, especially an aqueous solvent for the active ingredient. The active ingredient is preferably present in such formulations in a concentration of about 0.5 to 20% w/w, for example about 0.5 to 10% w/w, for example about 1.5% w/w.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for intrapulmonary or nasal administration have a particle size for example in the range of 0.1 to 500 microns (including particle sizes in a range between 0.1 and 500 microns in increments microns such as 0.5, 1, 30 microns, 35 microns, etc.), which is administered by rapid inhalation through the nasal passage or by inhalation through the mouth so as to reach the alveolar sacs. Suitable formulations include aqueous or oily solutions of the active ingredient. Formulations suitable for aerosol or dry powder administration may be prepared according to conventional methods and may be delivered with other therapeutic agents such as compounds heretofore used in the treatment or prophylaxis disorders as described below.

Formulations suitable for vaginal administration may be presented as pessaries, tampons, creams, gels, pastes, foams or spray formulations containing in addition to the active ingredient such carriers as are known in the art to be appropriate.

The formulations may be packaged in unit-dose or multi-dose containers, for example sealed ampoules and vials, and may be stored in a freeze-dried (lyophilized) condition requiring only the addition of the sterile liquid carrier, for example water, for injection immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

The invention further provides veterinary compositions comprising at least one active ingredient as above defined together with a veterinary carrier therefore. Veterinary carriers are materials useful for the purpose of administering the composition and may be solid, liquid or gaseous materials which are otherwise inert or acceptable in the veterinary art and are compatible with the active ingredient. These veterinary compositions may be administered parenterally, orally or by any other desired route.

Combination Therapy

The compounds of Formula I may be employed alone or in combination with other therapeutic agents for the treatment of a disease or disorder described herein, such as a hyperproliferative disorder (e.g., cancer). In certain embodiments, a compound of Formula I is combined in a pharmaceutical combination formulation, or dosing regimen as combination therapy, with a second compound that has anti-hyperproliferative properties or that is useful for treating a hyperproliferative disorder (e.g., cancer). The second compound of the pharmaceutical combination formulation or dosing regimen preferably has complementary activities to the compound of Formula I such that they do not adversely affect each other. Such compounds are suitably present in combination in amounts that are effective for the purpose intended. In one embodiment, a composition of this invention comprises a compound of Formula I, in combination with a chemotherapeutic agent such as described herein.

The combination therapy may be administered as a simultaneous or sequential regimen. When administered sequentially, the combination may be administered in two or more administrations. The combined administration includes coadministration, using separate formulations or a single pharmaceutical formulation, and consecutive administration in either order, wherein preferably there is a time period while both (or all) active agents simultaneously exert their biological activities.

Suitable dosages for any of the above coadministered agents are those presently used and may be lowered due to the combined action (synergy) of the newly identified agent and other chemotherapeutic agents or treatments.

The combination therapy may provide "synergy" and prove "synergistic", i.e., the effect achieved when the active ingredients used together is greater than the sum of the effects that results from using the compounds separately. A synergistic effect may be attained when the active ingredients are: (1) co-formulated and administered or delivered simultaneously in a combined, unit dosage formulation; (2) delivered by alternation or in parallel as separate formulations; or (3) by some other regimen. When delivered in alternation therapy, a synergistic effect may be attained when the compounds are administered or delivered sequentially, e.g., by different injections in separate syringes, separate pills or capsules, or separate infusions. In general, during alternation therapy, an effective dosage of each active ingredient is administered sequentially, i.e., serially, whereas in combination therapy, effective dosages of two or more active ingredients are administered together.

In a particular embodiment of anti-cancer therapy, a compound of Formula I, or a stereoisomer, geometric isomer, tautomer, solvate, metabolite, or pharmaceutically acceptable salt or prodrug thereof, may be combined with other chemotherapeutic, hormonal or antibody agents such as those described herein, as well as combined with surgical therapy and radiotherapy. Combination therapies according to the present invention thus comprise the administration of at least one compound of Formula I, or a stereoisomer, geometric isomer, tautomer, solvate, metabolite, or pharmaceutically acceptable salt or prodrug thereof, and the use of at least one other cancer treatment method. The amounts of the compound(s) of Formula I and the other pharmaceutically active chemotherapeutic agent(s) and the relative timings of administration will be selected in order to achieve the desired combined therapeutic effect.

Metabolites of Formula I Compounds

Also falling within the scope of this invention are the in vivo metabolic products of Formula I described herein. Such products may result for example from the oxidation, reduction, hydrolysis, amidation, deamidation, esterification, deesterification, enzymatic cleavage, and the like, of the administered compound. Accordingly, the invention includes metabolites of compounds of Formula I, including compounds produced by a process comprising contacting a compound of this invention with a mammal for a period of time sufficient to yield a metabolic product thereof.

Metabolite products typically are identified by preparing a radiolabelled (e.g., $^{14}C$ or $^{3}H$) isotope of a compound of the invention, administering it parenterally in a detectable dose (e.g., greater than about 0.5 mg/kg) to an animal such as rat, mouse, guinea pig, monkey, or to man, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g., by MS, LC/MS or NMR analysis. In general, analysis of metabolites is done in the same way as conventional drug metabolism studies well known to those skilled in the art. The metabolite products, so long as they are not otherwise found in vivo, may be useful in diagnostic assays for therapeutic dosing of the compounds of the invention.

Articles of Manufacture

In another embodiment of the invention, an article of manufacture, or "kit", containing materials useful for the treatment of the diseases and disorders described above is provided. The kit comprises a container comprising a compound of Formula I. The kit may further comprise a label or package insert, on or associated with the container. The term "package insert" is used to refer to instructions customarily included in commercial packages of therapeutic products, that contain information about the indications, usage, dosage, administration, contraindications and/or warnings concerning the use of such therapeutic products. Suitable containers include, for example, bottles, vials, syringes, blister pack, etc. The container may be formed from a variety of materials such as glass or plastic. The container may hold a compound of Formula I or II or a formulation thereof which is effective for treating the condition and may have a sterile access port (for example, the container may be an intravenous solution bag or a vial having a stopper pierceable by a hypodermic injection needle). At least one active agent in the composition is a compound of Formula I. The label or package insert indicates that the composition is used for treating the condition of choice, such as cancer. In addition, the label or package insert may indicate that the patient to be treated is one having a disorder such as a hyperproliferative disorder, neurodegeneration, cardiac hypertrophy, pain, migraine or a neurotraumatic disease or event. In one embodiment, the label or package inserts indicates that the composition comprising a compound of Formula I can be used to treat a disorder resulting from abnormal cell growth. The label or package insert may also indicate that the composition can be used to treat other disorders. Alternatively, or additionally, the article of manufacture may further comprise a second container comprising a pharmaceutically acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

The kit may further comprise directions for the administration of the compound of Formula I and, if present, the second pharmaceutical formulation. For example, if the kit comprises a first composition comprising a compound of Formula I, and a second pharmaceutical formulation, the kit may further comprise directions for the simultaneous, sequential or separate administration of the first and second pharmaceutical compositions to a patient in need thereof.

In another embodiment, the kits are suitable for the delivery of solid oral forms of a compound of Formula I, such as tablets or capsules. Such a kit preferably includes a number of unit dosages. Such kits can include a card having the dosages oriented in the order of their intended use. An example of such a kit is a "blister pack". Blister packs are well known in the packaging industry and are widely used for packaging pharmaceutical unit dosage forms. If desired, a memory aid can be provided, for example in the form of numbers, letters, or other markings or with a calendar insert, designating the days in the treatment schedule in which the dosages can be administered.

According to one embodiment, a kit may comprise (a) a first container with a compound of Formula I contained therein; and optionally (b) a second container with a second pharmaceutical formulation contained therein, wherein the second pharmaceutical formulation comprises a second compound with anti-hyperproliferative activity. Alternatively, or additionally, the kit may further comprise a third container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

In certain other embodiments wherein the kit comprises a composition of Formula I and a second therapeutic agent, the kit may comprise a container for containing the separate compositions such as a divided bottle or a divided foil packet, however, the separate compositions may also be contained within a single, undivided container. Typically, the kit comprises directions for the administration of the separate components. The kit form is particularly advantageous when the separate components are preferably administered in different dosage forms (e.g., oral and parenteral), are administered at different dosage intervals, or when titration of the individual components of the combination is desired by the prescribing physician.

Preparation of Formula I Compounds

Compounds of Formula I may be synthesized by synthetic routes that include processes analogous to those well-known in the chemical arts, particularly in light of the description contained herein, and those for other heterocycles described in: Comprehensive Heterocyclic Chemistry II, Editors Katritzky and Rees, Elsevier, 1997, e.g. Volume 3; Liebigs Annalen der Chemie, (9):1910-16, (1985); Helvetica Chimica Acta, 41:1052-60, (1958); Arzneimittel-Forschung, 40(12):1328-31, (1990), each of which are expressly incorporated by reference. Starting materials are generally available from commercial sources such as Aldrich Chemicals (Milwaukee, Wis.) or are readily prepared using methods well known to those skilled in the art (e.g., prepared by methods generally described in Louis F. Fieser and Mary Fieser, *Reagents for Organic Synthesis*, v. 1-23, Wiley, N.Y. (1967-2006 ed.), or *Beilsteins Handbuch der organischen Chemie*, 4, Aufl. ed. Springer-Verlag, Berlin, including supplements (also available via the Beilstein online database).

Synthetic chemistry transformations and protecting group methodologies (protection and deprotection) useful in synthesizing Formula I compounds and necessary reagents and intermediates are known in the art and include, for example, those described in R. Larock, Comprehensive Organic Transformations, VCH Publishers (1989); T. W. Greene and P. G. M. Wuts, Protective Groups in Organic Synthesis, $3^{rd}$ Ed., John Wiley and Sons (1999); and L. Paquette, ed., Encyclopedia of Reagents for Organic Synthesis, John Wiley and Sons (1995) and subsequent editions thereof.

Compounds of Formula I may be prepared singly or as compound libraries comprising at least 2, for example 5 to 1,000 compounds, or 10 to 100 compounds. Libraries of compounds of Formula I may be prepared by a combinatorial 'split and mix' approach or by multiple parallel syntheses using either solution phase or solid phase chemistry, by procedures known to those skilled in the art. Thus according to a further aspect of the invention there is provided a compound library comprising at least 2 compounds, or pharmaceutically acceptable salts thereof.

The General Procedures and Examples provide exemplary methods for preparing Formula I compounds. Those skilled in the art will appreciate that other synthetic routes may be used to synthesize the Formula I compounds. Although specific starting materials and reagents are depicted and discussed in the Figures, General Procedures, and Examples, other starting materials and reagents can be easily substituted to provide a variety of derivatives and/or reaction conditions. In addition, many of the exemplary compounds prepared by the described methods can be further modified in light of this disclosure using conventional chemistry well known to those skilled in the art.

In preparing compounds of Formulas I, protection of remote functionality (e.g., primary or secondary amine) of intermediates may be necessary. The need for such protection will vary depending on the nature of the remote functionality and the conditions of the preparation methods. Suitable amino-protecting groups include acetyl, trifluoroacetyl, t-butoxycarbonyl (BOC), benzyloxycarbonyl (CBz) and 9-fluorenylmethyleneoxycarbonyl (Fmoc). The need for such protection is readily determined by one skilled in the art. For a general description of protecting groups and their use, see T. W. Greene, Protective Groups in Organic Synthesis, John Wiley & Sons, New York, 1991.

Methods of Separation

In the methods of preparing Formula I compounds, it may be advantageous to separate reaction products from one another and/or from starting materials. The desired products of each step or series of steps is separated and/or purified to the desired degree of homogeneity by the techniques common in the art. Typically such separations involve multiphase extraction, crystallization from a solvent or solvent mixture, distillation, sublimation, or chromatography. Chromatography can involve any number of methods including, for example: reverse-phase and normal phase; size exclusion; ion exchange; high, medium and low pressure liquid chromatography methods and apparatus; small scale analytical; simulated moving bed (SMB) and preparative thin or thick layer chromatography, as well as techniques of small scale thin layer and flash chromatography.

Another class of separation methods involves treatment of a mixture with a reagent selected to bind to or render otherwise separable a desired product, unreacted starting material, reaction by product, or the like. Such reagents include adsorbents or absorbents such as activated carbon, molecular sieves, ion exchange media, or the like. Alternatively, the reagents can be acids in the case of a basic material, bases in the case of an acidic material, binding reagents such as antibodies, binding proteins, selective chelators such as crown ethers, liquid/liquid ion extraction reagents (LIX), or the like. Selection of appropriate methods of separation depends on the nature of the materials involved, such as, boiling point and molecular weight in distillation and sublimation, presence or absence of polar functional groups in chromatography, stability of materials in acidic and basic media in multiphase extraction, and the like.

Diastereomeric mixtures can be separated into their individual diastereomers on the basis of their physical chemical differences by methods well known to those skilled in the art, such as by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereoisomers to the corresponding pure enantiomers. Also, some of the compounds of the present invention may be atropisomers (e.g., substituted biaryls) and are considered as part of this invention. Enantiomers can also be separated by use of a chiral HPLC column.

A single stereoisomer, e.g., an enantiomer, substantially free of its stereoisomer may be obtained by resolution of the racemic mixture using a method such as formation of diastereomers using optically active resolving agents (Eliel, E. and Wilen, S. "Stereochemistry of Organic Compounds," John Wiley & Sons, Inc., New York, 1994; Lochmuller, C. H., (1975) J. Chromatogr., 113(3):283-302). Racemic mixtures of chiral compounds of the invention can be separated and isolated by any suitable method, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure stereoisomers, and (3) separation of the substantially pure or enriched stereoisomers directly under chiral conditions. See: "Drug Stereochemistry, Analytical Methods and Pharmacology," Irving W. Wainer, Ed., Marcel Dekker, Inc., New York (1993).

Under method (1), diastereomeric salts can be formed by reaction of enantiomerically pure chiral bases such as brucine, quinine, ephedrine, strychnine, α-methyl-β-phenylethylamine (amphetamine), and the like with asymmetric compounds bearing acidic functionality, such as carboxylic acid and sulfonic acid. The diastereomeric salts may be induced to separate by fractional crystallization or ionic chromatography. For separation of the optical isomers of amino compounds, addition of chiral carboxylic or sulfonic acids, such as camphorsulfonic acid, tartaric acid, mandelic acid, or lactic acid can result in formation of the diastereomeric salts.

Alternatively, by method (2), the substrate to be resolved is reacted with one enantiomer of a chiral compound to form a diastereomeric pair (E. and Wilen, S. "Stereochemistry of Organic Compounds", John Wiley & Sons, Inc., 1994, p. 322). Diastereomeric compounds can be formed by reacting asymmetric compounds with enantiomerically pure chiral derivatizing reagents, such as menthyl derivatives, followed by separation of the diastereomers and hydrolysis to yield the pure or enriched enantiomer. A method of determining optical purity involves making chiral esters, such as a menthyl ester, e.g., (−) menthyl chloroformate in the presence of base, or Mosher ester, α-methoxy-α-(trifluoromethyl)phenyl acetate (Jacob III. J. Org. Chem. (1982) 47:4165), of the racemic mixture, and analyzing the $^1$H NMR spectrum for the presence of the two atropisomeric enantiomers or diastereomers. Stable diastereomers of atropisomeric compounds can be separated and isolated by normal- and reverse-phase chromatography following methods for separation of atropisomeric naphthyl-isoquinolines (WO 96/15111). By method (3), a racemic mixture of two enantiomers can be separated by chromatography using a chiral stationary phase ("Chiral Liquid Chromatography" (1989) W. J. Lough, Ed., Chapman and Hall, New York; Okamoto, J. Chromatogr., (1990) 513:375-378). Enriched or purified enantiomers can be distinguished by methods used to distinguish other chiral molecules with asymmetric carbon atoms, such as optical rotation and circular dichroism.

General Preparative Procedures

FIG. 1 shows an exemplary synthesis of 4-aminopyrazole compounds 5. 4-nitro-1H-pyrazole 1 is converted to 2 by treatment with a base in a suitable solvent or neat, followed by the addition of an alkylation reagent such as dimethyl sulfate. Compound 2 may be converted to compound 3 by treatment with a base such as lithium hexamethyldisilazide, or nBuLi in a suitable solvent at an appropriate temperature, such as THF at −78° C. Compound 3 may be converted to compound 4 by direct SnAr or Suzuki conditions described in the literature. Compound 5 may be synthesized from 4 by a suitable reduction method, such as by ion in the presence of a weak Lewis acid such as ammonium chloride in a suitable solvent such as ethanol or water, or by treatment with zinc powder and ammonium formate in tetrahydrofuran, or hydrogenation with $H_2$ and transitional metal catalysts such as palladium on carbon.

Figure 2:
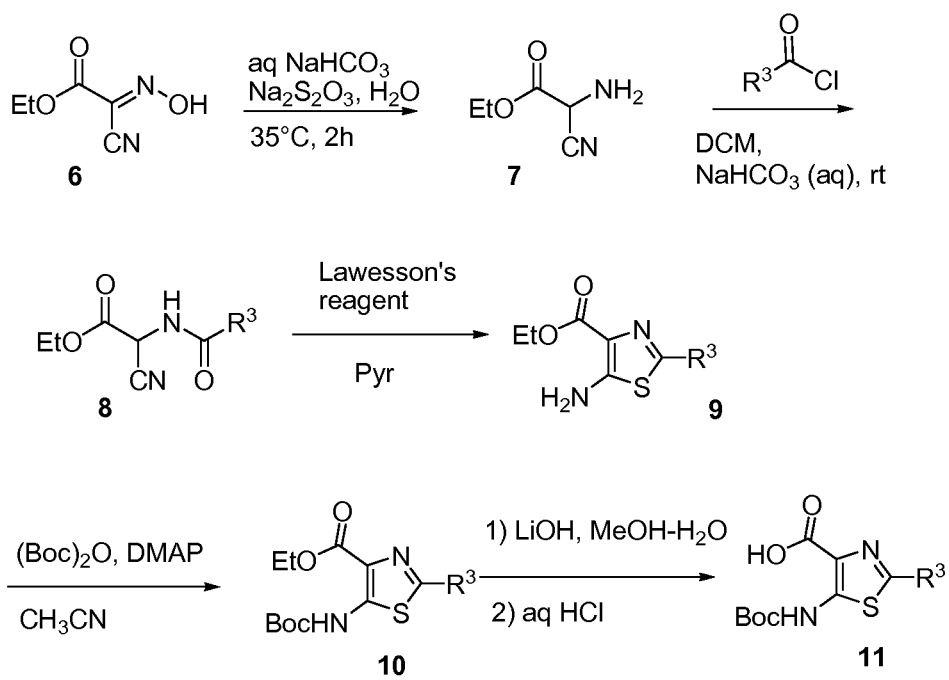
FIG. 2 shows an exemplary synthesis of 4-carboxy-thiazoles 11 from hydroxamide compounds 6.

FIG. 2 shows an exemplary synthesis of 4-carboxy-thiazoles 11 from hydroxamide compounds 6. Reduction of 6 by a reducing reagent in a suitable solvent such as $Na_2S_2O_3$ in water gives 7, which may be converted to 8 by an acylating reagent in a suitable solvent with a suitable base such as benzoyl chloride in dichloromethane with sodium bicarbonate. Compound 8 may be converted to 9 by a sulfur containing reagent in a suitable reagent such as Lawesson's reagent in pyridine, and protected to 10 by a suitable Boc-protecting group. Ester hydrolysis of 10 using a suitable base and solvent, such as LiOH in methanol and water gives 11.

Figure 3:
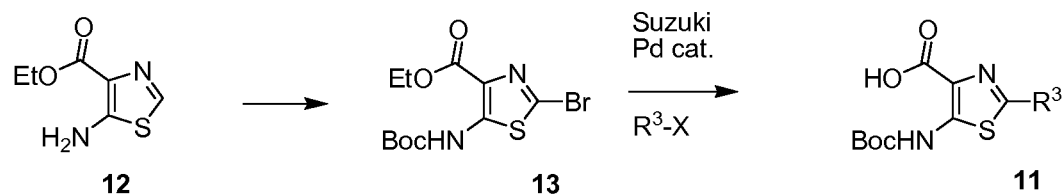
FIG. 3 shows an exemplary synthesis of 2-substituted, 4-carboxy-5-aminothiazoles 11 by C-2 bromination of 12 followed by Suzuki reaction of 13.

FIG. 3 shows an exemplary synthesis of 2-substituted, 4-carboxy-5-aminothiazoles 11 by C-2 bromination of 12 followed by Suzuki reaction of 13.

The Suzuki-type coupling reaction is useful to attach a heterocycle or a heteroaryl by displacing a halide at the 2-position of the thiazole, pyridyl, or picolinyl ring in the synthesis of a Formula I compound. For example, 2-bromo (or chloro) thiazole 11 may be reacted with about 1.5 equivalents of a aryl, heterocyclyl or heteroaryl boronic acid or ester reagent and an excess of aqueous sodium carbonate in acetonitrile. A catalytic amount, or more, of a low valent palladium reagent, such as bis(triphenylphosphine)palladium(II) dichloride, is added. A variety of boronic acids or boronic esters can be used. Boronic esters included pinacole esters (4,4,5,5-tetramethyl-1,3,2-dioxaborolan-2-yl). Also, a nitrogen of a heterocycle or heteroaryl may be protected, for example as N-THP. In some cases potassium acetate is used in place of sodium carbonate to adjust the pH of the aqueous layer. The reaction may be heated to about 140-150° C. under pressure in a microwave reactor such as the Biotage Optimizer (Biotage, Inc.) for 10 to 30 minutes. The contents are extracted with ethyl acetate, or another organic solvent. After evaporation of the organic layer the Suzuki coupling product may be purified on silica or by reverse phase HPLC.

A variety of palladium catalysts can be used during the Suzuki coupling step to form exemplary Formula I compounds. Low valent, Pd(II) and Pd(0) catalysts may be used in the Suzuki coupling reaction, including PdCl2(PPh₃)₂, Pd(t-Bu)₃, PdCl₂ dppf CH₂Cl₂, Pd(PPh₃)₄, Pd(Oac)/PPh₃, Cl₂Pd [(Pet₃)]₂, Pd(DIPHOS)₂, Cl₂Pd(Bipy), [PdCl (Ph₂PCH₂PPh₂)]₂, Cl₂Pd[P(o-tol)₃]₂, Pd₂(dba)₃/P(o-tol)₃, Pd₂(dba)/P(furyl)₃, Cl₂Pd[P(furyl)₃]₂, Cl₂Pd(PmePh₂)₂, Cl₂Pd[P(4-F-Ph)₃]₂, Cl₂Pd[P(C₆F₆)₃]₂, Cl₂Pd[P(2-COOH-Ph)(Ph)₂]₂, Cl₂Pd[P(4-COOH-Ph)(Ph)₂]₂, and encapsulated catalysts Pd EnCat™ 30, Pd EnCat™ TPP30, and Pd(II) EnCat™ BINAP30 (US 2004/0254066).

Figure 4:
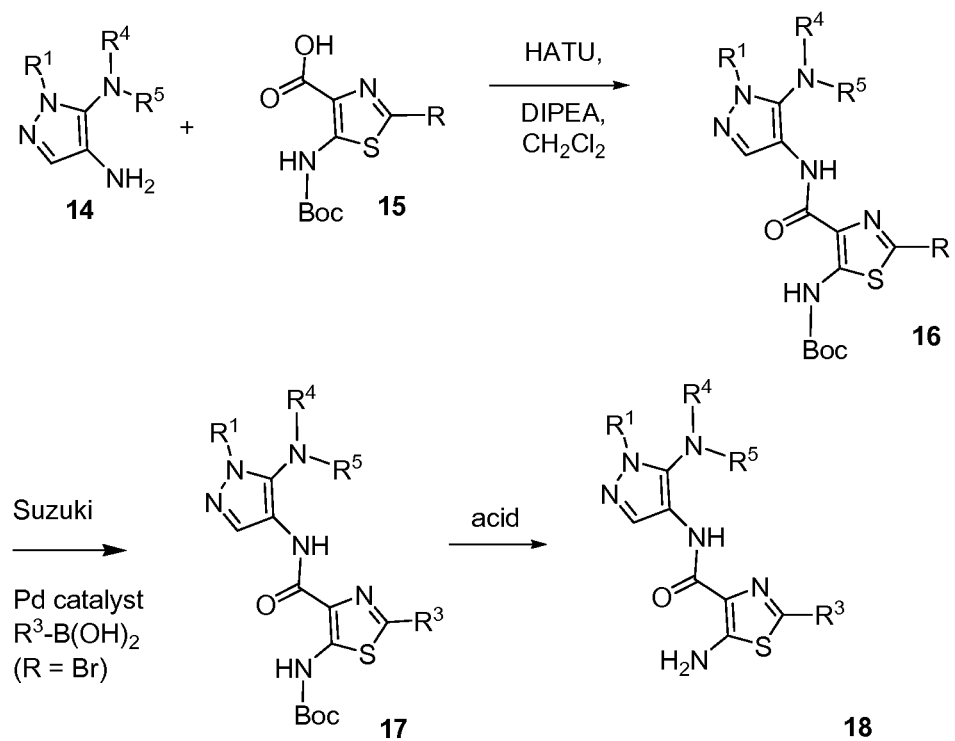
FIG. 4 shows an exemplary synthesis of 5-amino-N-(pyrazol-4-yl)thiazole-carboxamide compounds 18 made from coupling of 3,4-diaminopyrazole compounds 14 and 2-substituted, 4-carboxy-5-aminothiazoles 11.

FIG. 4 shows an exemplary synthesis of 5-amino-N-(pyrazol-4-yl)thiazole-carboxamide compounds 18 from coupling of 3,4-diaminopyrazole compounds 14 and 2-substituted, 4-carboxy-5-aminothiazoles 11.

Figure 5:
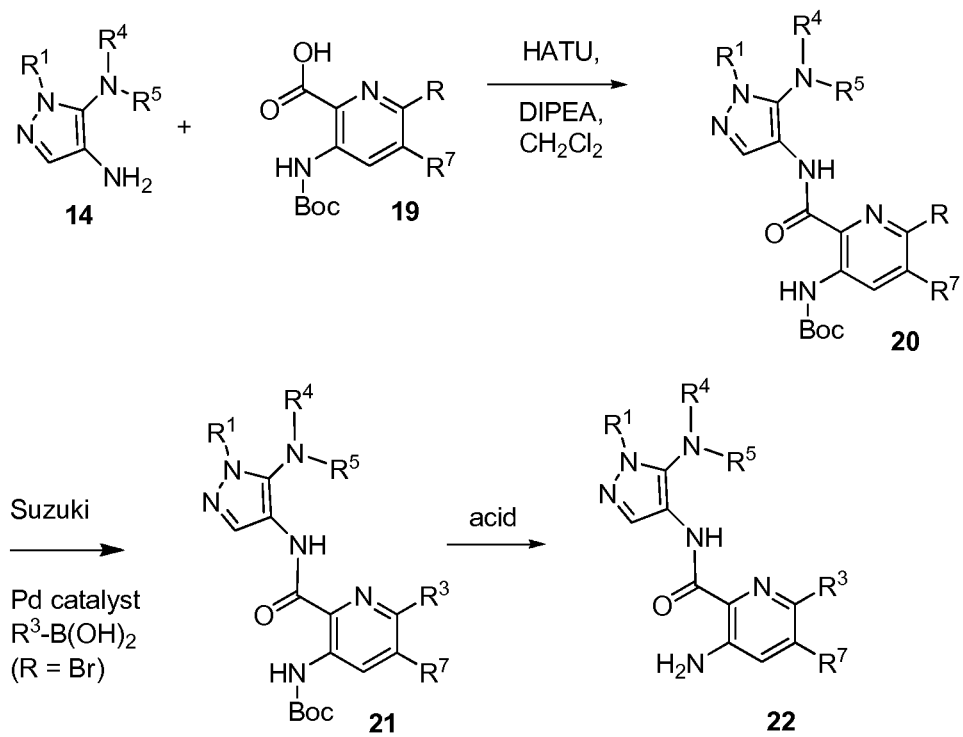
FIG. 5 shows an exemplary synthesis of 6-amino-N-(pyrazol-4-yl)pyridyl-carboxamide compounds 22 made from coupling of 3,4-diaminopyrazole compounds 14 and 6-substituted, 2-carboxy-3-aminopyridyl compounds 19.

FIG. 5 shows an exemplary synthesis of 6-amino-N-(pyrazol-4-yl)pyridyl-carboxamide compounds 22 from coupling of 3,4-diaminopyrazole compounds 14 and 6-substituted, 2-carboxy-3-aminopyridyl compounds 19.

Figure 6:
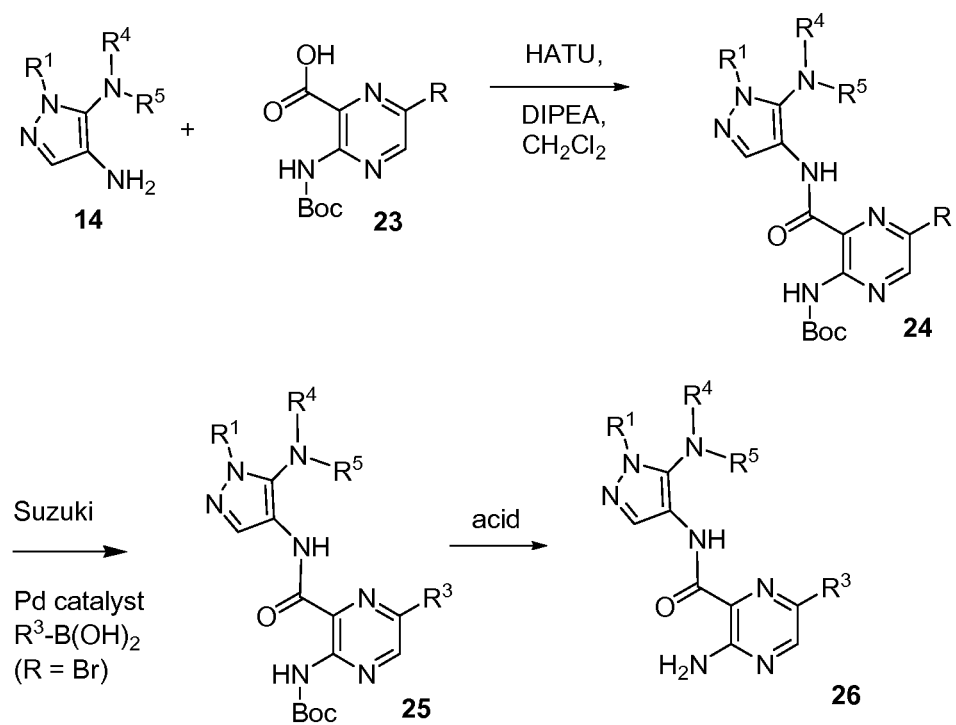
FIG. 6 shows an exemplary synthesis of 6-amino-N-(pyrazol-4-yl)picolinic-carboxamide compounds 26 from coupling of 3,4-diaminopyrazole compounds 14 and 5-substituted, 3-carboxy-2-aminopicolinyl compounds 23.

FIG. 6 shows an exemplary synthesis of 6-amino-N-(pyrazol-4-yl)picolinic-carboxamide compounds 26 from coupling of 3,4-diaminopyrazole compounds 14 and 5-substituted, 3-carboxy-2-aminopicolinyl compounds 23.

EXAMPLES

Intermediates

Example 1

5-chloro-1-methyl-4-nitro-1H-pyrazole

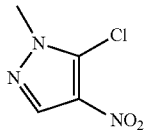

To a 500 mL round bottom flask containing 4-nitro-1-H-pyrazole (5 g, 44.2 mmol) was added sodium hydroxide (1M, 200 mL) and dimethyl sulfate (31 mL, 330 mmol). The mixture was stirred at room temperature for 72 h and the mixture was extracted with CH₂Cl₂ (2×150 mL). The organic layer was separated and the solvent was distilled off to yield 1-methyl-4-nitro-1H-pyrazole as a white solid (4.30 g, 76%).

Following WO 2007/99326, to a 500 mL 3-neck-round bottom flask was added 1-methyl-4-nitro-1H-pyrazole (4.30 g, 33.8 mmol) and THF (12 mL). The mixture was cooled to −78° C. and lithium hexamethyldisilazide in THF (1M, 88.4 mL, 90 mmol) was added dropwise via an addition funnel over 20 min. The brown mixture was stirred for 30 min and warmed to −45 C over 30 min. The mixture was cooled back down to −78° C. and hexachloroethane (10.5 g, 44.2 mmol) dissolved in THF (20 mL) was added via an addition funnel over 15 min. The mixture was stirred for 2.5 h, warmed from −78 C to −40 C and the reaction was monitored by LCMS. Upon completion of the reaction, the reaction was quenched with a solution of saturated NH₄Cl (150 mL), and ethyl acetate (100 mL) was added. The organic layer was separated and the aqueous layer was extracted with ethyl acetate (100 mL). The combined organic layer was washed with water (150 mL), dried over Na₂SO₄ and the organic solvent was distilled off. The crude product was purified via flash chromatography (CH₂Cl₂/7% MeOH) to yield 5-chloro-1-methyl-4-nitro-1H-pyrazole as a white solid (1.40 g, 20%). ¹H NMR (400 MHz, CDCl₃) δ 8.13 (s, 1H), 3.92 (s, 3H); ESIMS m/z=162.0 (M+1)

Example 2 tert-butyl 1-(4-amino-1-methyl-1H-pyrazol-5-yl) azepan-4-ylcarbamate

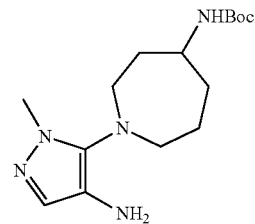

To a 10 mL microwave vial was added 5-chloro-1-methyl-4-nitro-1H-pyrazole (150 mg, 0.93 mmol), tert-butyl azepan-4-ylcarbamate (220 mg, 1.02 mmol). Ethanol (4 mL) and diisopropylethylamine (1.00 mL, 8.00 mmol) were added and the mixture was irradiated with a microwave for 60 min at 130° C. The mixture was cooled, concentrated and purified via flash chromatography, heptane/ethyl acetate 20% to 80% to afford yellow oil (306 mg, 97%).

To a 50 mL round bottom flask was added the nitro compound (306 mg, 0.90 mmol), iron (202 mg, 3.61 mmol), ammonium chloride (241 mg, 4.5 mmol), ethanol (10 mL) and water (1.5 mL). The mixture was stirred for 1 h at 60° C. and the reaction was monitored by LCMS. Upon completion of the reaction, the mixture was filtered through a pad of Celite and was washed with ethyl acetate (30 mL) and a 10% aqueous solution of K₃PO₄ (30 mL). The organic layer was washed with water (30 mL), dried over Na₂SO₄ and the organic solvent was distilled off to yield tert-butyl 1-(4-amino-1-methyl-1H-pyrazol-5-yl)azepan-4-ylcarbamate as a brown oil with a purity of >98% (264 mg, 95%). ESIMS m/z=310.1 (M+1).

Example 3 tert-butyl 1-(1-methyl-4-amino-1H-pyrazol-5-yl) piperidin-4-ylcarbamate

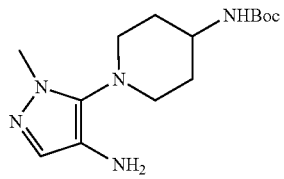 [SMILES: Cn1ncc(N)c1N1CCC(NC(=O)OC(C)(C)C)CC1]

Following the procedures as described in Example 2 and starting with tert-butyl piperidin-4-ylcarbamate, tert-butyl 1-(1-methyl-4-amino-1H-pyrazol-5-yl)piperidin-4-ylcarbamate was obtained as a brown oil (173 mg, 70%) over two steps. ESIMS m/z=296.1 (M+1).

Example 4

(S)-tert-butyl 1-(1-methyl-4-amino-1H-pyrazol-5-yl)piperidin-3-ylcarbamate

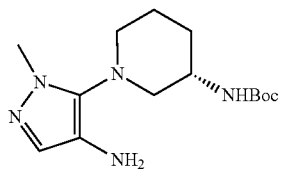 [SMILES: Cn1ncc(N)c1N1CCC[C@H](NC(=O)OC(C)(C)C)C1]

Following the procedures as described in Example 2 and starting with (S)-tert-butyl piperidin-3-ylcarbamate, (S)-tert-butyl 1-(1-methyl-4-amino-1H-pyrazol-5-yl)piperidin-3-ylcarbamate was obtained as a brown oil (206 mg, 75%) over two steps. ESIMS m/z=296.1 (M+1).

Example 5

(S)-tert-butyl 1-(4-amino-1-methyl-1H-pyrazol-5-yl)pyrrolidin-3-ylcarbamate

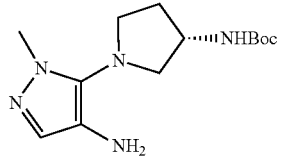 [SMILES: Cn1ncc(N)c1N1CC[C@H](NC(=O)OC(C)(C)C)C1]

Following the procedures as described in Example 2 and starting with (S)-tert-butyl pyrrolidin-3-ylcarbamate, (S)-tert-butyl 1-(4-amino-1-methyl-1H-pyrazol-5-yl)pyrrolidin-3-ylcarbamate was obtained as a brown oil (162 mg, 62%) over two steps. ESIMS m/z=282.1 (M+1).

Example 6 tert-butyl 4-((4-amino-1-methyl-1H-pyrazol-5-yloxy)methyl)piperidine-1-carboxylate

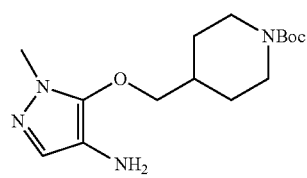

To a 50 mL round bottom flask was added 5-chloro-1-methyl-4-nitro-1H-pyrazole (100 mg, 0.60 mmol), tert-butyl 4-(hydroxymethyl)piperidine-1-carboxylate (200 mg, 0.93 mmol) and DMF (10 mL). NaH (37 mg, 1.55 mmol) was added slowly and the mixture was stirred for 1 h. The mixture concentrated and purified via flash chromatography, heptane/ethyl acetate 20% to 80% to afford an oil (150 mg, 70%).

To a 50 mL round bottom flask was added the nitro compound (150 mg, 0.44 mmol), iron (173 mg, 3.10 mmol), ammonium chloride (199 mg, 3.71 mmol), ethanol (10 mL) and water (1.5 mL). The mixture was stirred for 1 h at 60° C. and the reaction was monitored by LCMS. Upon completion of the reaction, the mixture was filtered through a pad of Celite and was washed with ethyl acetate (30 mL) and a 10% aqueous solution of $K_3PO_4$ (30 mL). The organic layer was washed with water (30 mL), dried over $Na_2SO_4$ and the organic solvent was distilled off to yield tert-butyl 4-((4-amino-1-methyl-1H-pyrazol-5-yloxy)methyl)piperidine-1-carboxylate as a brown oil with a purity of >98% (135 mg, 99%). ESIMS m/z=311.1 (M+1).

Example 7

(R)-tert-butyl 1-(1-methyl-4-amino-1H-pyrazol-5-yl)piperidin-3-ylcarbamate

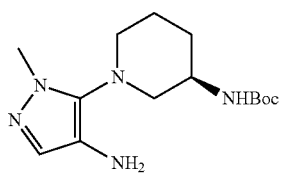 [SMILES: Cn1ncc(N)c1N1CCC[C@@H](NC(=O)OC(C)(C)C)C1]

Following the procedures as described in Example 2 and starting with (R)-tert-butyl piperidin-3-ylcarbamate, (R)-tert-butyl 1-(1-methyl-4-amino-1H-pyrazol-5-yl)piperidin-3-ylcarbamate was obtained as a brown oil (187 mg, 68%) over two steps. ESIMS m/z=296.1 (M+1).

Example 8 tert-butyl 4-(4-amino-1-methyl-1H-pyrazol-5-yloxy)piperidine-1-carboxylate

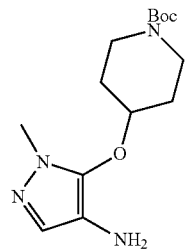 [SMILES: Cn1ncc(N)c1OC1CCN(C(=O)OC(C)(C)C)CC1]

Following the procedures as described in Example 6 and starting with tert-butyl 4-hydroxypiperidine-1-carboxylate, tert-butyl 4-(4-amino-1-methyl-1H-pyrazol-5-yloxy)piperidine-1-carboxylate was obtained as a brown oil (102 mg, 50%) over two steps. ESIMS m/z=297.1 (M+1)

Example 9

(R)-tert-butyl 1-(4-amino-1-methyl-1H-pyrazol-5-yl)pyrrolidin-3-ylcarbamate

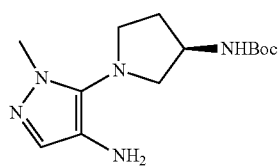

Following the procedures as described in Example 2 and starting with (R)-tert-butyl pyrrolidin-3-ylcarbamate, (R)-tert-butyl 1-(4-amino-1-methyl-1H-pyrazol-5-yl)pyrrolidin-3-ylcarbamate was obtained as a brown oil (159 mg, 61%) over two steps. ESIMS m/z=282.1 (M+1).

Example 10 tert-butyl 4-((4-amino-1-methyl-1H-pyrazol-5-ylamino)methyl)piperidine-1-carboxylate

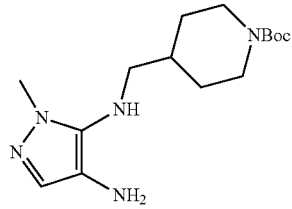 [SMILES: Cn1ncc(N)c1NCC1CCN(C(=O)OC(C)(C)C)CC1]

Following the procedures as described in Example 2 and starting with tert-butyl 4-(aminomethyl)piperidine-1-carboxylate, tert-butyl 4-((4-amino-1-methyl-1H-pyrazol-5-ylamino)methyl)piperidine-1-carboxylate was obtained as a brown oil (124 mg, 43%) over two steps. ESIMS m/z=310.1 (M+1).

Example 11

(S)-tert-butyl (1-(4-amino-1-methyl-1H-pyrazol-5-yl)pyrrolidin-3-yl)methylcarbamate

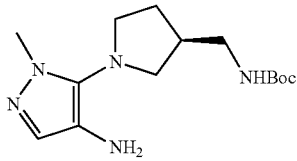 [SMILES: Cn1ncc(N)c1N1CC[C@@H](CNC(=O)OC(C)(C)C)C1]

Following the procedures as described in Example 2 and starting with (R)-tert-butyl pyrrolidin-3-ylmethylcarbamate, (S)-tert-butyl (1-(4-amino-1-methyl-1H-pyrazol-5-yl)pyrrolidin-3-yl)methylcarbamate was obtained as a brown oil (230 mg, 84%) over two steps. ESIMS m/z=296.1 (M+1)

Example 12

(R)-tert-butyl (1-(4-amino-1-methyl-1H-pyrazol-5-yl)pyrrolidin-3-yl)methylcarbamate

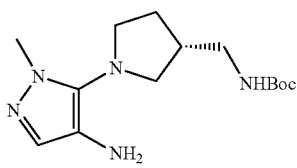

Following the procedures as described in Example 2 and starting with (S)-tert-butyl pyrrolidin-3-ylmethylcarbamate, (R)-tert-butyl (1-(4-amino-1-methyl-1H-pyrazol-5-yl)pyrrolidin-3-yl)methylcarbamate was obtained as a brown oil (200 mg, 73%) over two steps. ESIMS m/z=296.1 (M+1).

Example 13 tert-butyl (1-(4-amino-1H-pyrazol-5-yl)piperidin-4-yl)methylcarbamate

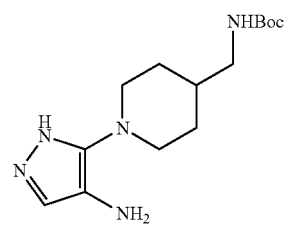 [SMILES: CC(C)(C)OC(=O)NCC1CCN(c2[nH]ncc2N)CC1]

Following the procedures as described in Example 2 and starting with tert-butyl piperidin-4-ylmethylcarbamate, tert-butyl (1-(4-amino-1H-pyrazol-5-yl)piperidin-4-yl)methylcarbamate was obtained as a brown oil (270 mg, 98%) over two steps. ESIMS m/z=310.1 (M+1).

Example 14

(S)-tert-butyl (1-(4-amino-1-methyl-1H-pyrazol-5-yl)piperidin-3-yl)methylcarbamate

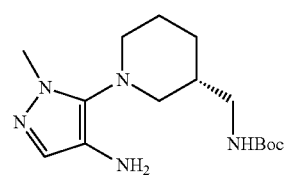

Following the procedures as described in Example 2 and starting with (R)-tert-butyl piperidin-3-ylmethylcarbamate, (S)-tert-butyl (1-(4-amino-1-methyl-1H-pyrazol-5-yl)piperidin-3-yl)methylcarbamate was obtained as a brown oil (270 mg, 98%) over two steps. ESIMS m/z=310.1 (M+1).

Example 15

(R)-tert-butyl (1-(4-amino-1-methyl-1H-pyrazol-5-yl)piperidin-3-yl)methylcarbamate

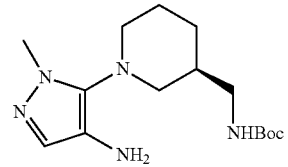 [SMILES: Cn1ncc(N)c1N1CCC[C@@H](CNC(=O)OC(C)(C)C)C1]

Following the procedures as described in Example 2 and starting with (S)-tert-butyl piperidin-3-ylmethylcarbamate, (R)-tert-butyl (1-(4-amino-1-methyl-1H-pyrazol-5-yl)piperidin-3-yl)methylcarbamate was obtained as a brown oil (268 mg, 98%) over two steps. ESIMS m/z=310.1 (M+1)

Example 16

(R)-benzyl 1-(4-amino-1-methyl-1H-pyrazol-5-yl)azepan-4-ylcarbamate

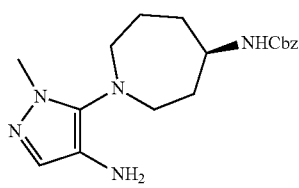 [SMILES: Cn1ncc(N)c1N1CCC[C@@H](NC(=O)OCc2ccccc2)CC1]

Following the procedures as described in Example 2 and starting with (R)-benzyl azepan-4-ylcarbamate, (R)-benzyl 1-(4-amino-1-methyl-1H-pyrazol-5-yl)azepan-4-ylcarbamate was obtained as a brown oil (191 mg, 60%) over two steps. ESIMS m/z=344.1 (M+1).

Example 17

(S)-benzyl 1-(4-amino-1-methyl-1H-pyrazol-5-yl)azepan-4-ylcarbamate

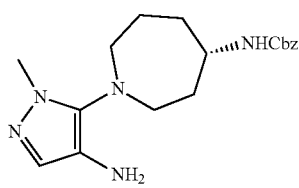 [SMILES: Cn1ncc(N)c1N1CCC[C@H](NC(=O)OCc2ccccc2)CC1]

Following the procedures as described in Example 2 and starting with (S)-benzyl azepan-4-ylcarbamate, (S)-benzyl 1-(4-amino-1-methyl-1H-pyrazol-5-yl)azepan-4-ylcarbamate was obtained as a brown oil (220 mg, 63%) over two steps. ESIMS m/z=344.1 (M+1).

Example 18 tert-butyl 3-(4-amino-1-methyl-1H-pyrazol-5-yl)-3-azabicyclo[3.1.0]hexan-6-ylcarbamate

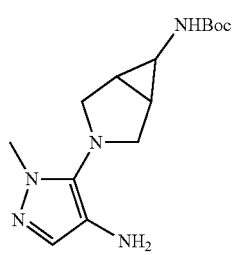 [SMILES: Cn1ncc(N)c1N1CC2C(C1)C2NC(=O)OC(C)(C)C]

Following the procedures as described in Example 2 and starting tert-butyl 3-azabicyclo[3.1.0]hexan-6-ylcarbamate, tert-butyl 3-(4-amino-1-methyl-1H-pyrazol-5-yl)-3-azabicy- clo[3.1.0]hexan-6-ylcarbamate was obtained as a brown oil (130 mg, 48%) over two steps. ESIMS m/z=294.1 (M+1).

Example 19 ethyl 2-amino-2-cyanoacetate

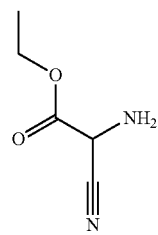

To a stirred solution of (E)-ethyl 2-cyano-2-(hydroxy-imino)acetate (20 g, 0.14 mol) in water (250 mL) was added a saturated solution of NaHCO$_3$ in water (160 mL), followed by the addition of Na$_2$S$_2$O$_4$ (60 g, 0.423 mol). The reaction mixture was warmed up to 35° C. and stirred for additional 2 hr. It was then saturated with NaCl (150 g) and extracted with DCM (3×350 mL). Combined organic layers were washed with brine, dried over Na$_2$SO$_4$, filtered and concentrated in vacuo to give ethyl 2-amino-2-cyanoacetate as a red oil (7.8 g, 43%) that was used at the next step without additional purification. $^1$H-NMR (CDCl$_3$, 500 MHz) δ (ppm): 4.45 (s, 1H), 4.34 (q, J=7.0 Hz, 2H), 1.36 (t, J=7.0 Hz, 3H); MS (ESI) m/z: 129 [M+H$^+$].

Example 20 ethyl 2-benzamido-2-cyanoacetate

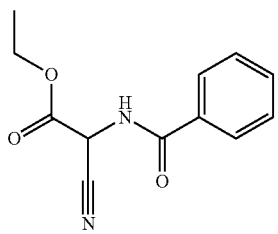 [SMILES: CCOC(=O)C(C#N)NC(=O)c1ccccc1]

To a stirred solution of compound ethyl 2-amino-2-cyanoacetate (0.64 g, 5 mmol) in DCM (15 mL) was added a saturate solution of NaHCO$_3$ in water (15 mL). With vigorously stirring, benzoyl chloride (0.84 g, 6 mmol) was added. The reaction mixture was stirred at ambient temperature for additional 30 min at which time it was extracted with DCM (3×15 mL). Combined organic layers were washed with brine (20 mL) and dried over Na$_2$SO$_4$, filtered, concentrated in vacuo. Resulted residue was purified by silica gel column chromatography (5:1 PE/EtOAc) to afford ethyl 2-benzamido-2-cyanoacetate (0.25 g, 22%) as white solid: $^1$H-NMR (CDCl$_3$, 500 MHz) δ (ppm): 7.83-7.85 (m, 2H), 7.59 (t, J=7.5 Hz, 1H), 7.49 (t, J=7.5 Hz, 2H), 7.02 (d, J=7.0 Hz, 1H), 5.72

(d, J=7.5 Hz, 1H), 4.40 (q, J=7.5 Hz, 2H), 1.39 (t, J=7.0 Hz, 3H); MS (ESI) m/z: 233 [M+H⁺].

Example 21 ethyl 5-amino-2-phenylthiazole-4-carboxylate

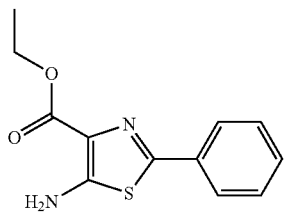 [SMILES: CCOC(=O)c1nc(-c2ccccc2)sc1N]

To a stirred solution of compound ethyl 2-benzamido-2-cyanoacetate (0.46 g, 2 mmol) in pyridine (20 mL) was added Lawesson's reagent (0.81 g, 2 mmol). The reaction mixture was heated at reflux for 15 hr. It was then concentrated and diluted with EtOAc (40 mL). The diluted mixture was washed with water (3×20 mL), brine (10 mL), dried over Na$_2$SO$_4$, filtered, and concentrated in vacuo. The residue was purified by silica gel column chromatography (10:1 PE/EtOAc) to afford ethyl 5-amino-2-phenylthiazole-4-carboxylate (0.2 g, 40%) as yellow solid: ¹H-NMR (CDCl$_3$, 500 MHz) δ (ppm): 7.80 (d, J=6.5 Hz, 1H), 7.36-7.41 (m, 3H), 4.43 (q, J=7.0 Hz, 2H), 1.44 (t, J=7.0 Hz, 3H); MS (ESI) m/z: 249 [M+H⁺].

Example 22 ethyl 5-(tert-butoxycarbonylamino)-2-phenylthiazole-4-carboxylate

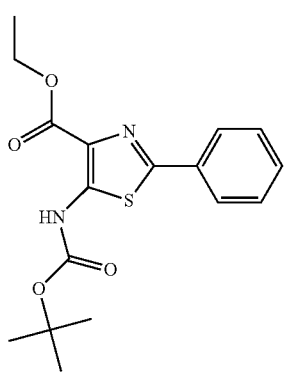 [SMILES: CCOC(=O)c1nc(-c2ccccc2)sc1NC(=O)OC(C)(C)C]

To a solution of compound ethyl 5-amino-2-phenylthiazole-4-carboxylate (248 mg, 1 mmol) in CH$_3$CN (10 mL) was added DMAP (6 mg, 0.05 mmol) followed by (Boc)$_2$O (262 mg, 1.2 mmol). The reaction mixture was maintained at ambient temperature for additional 30 min. The mixture was then evaporated in vacuo to give ethyl 5-(tert-butoxycarbonylamino)-2-phenylthiazole-4-carboxylate as a red solid (340 mg, 95%) that was used at the next step without further purification.

Example 23

5-(tert-butoxycarbonylamino)-2-phenylthiazole-4-carboxylic acid

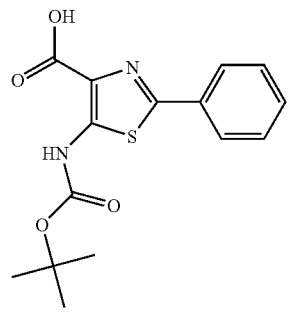 [SMILES: CC(C)(C)OC(=O)Nc1sc(-c2ccccc2)nc1C(=O)O]

To a solution of compound ethyl 5-(tert-butoxycarbonylamino)-2-phenylthiazole-4-carboxylate (348 mg, 1 mmol) in MeOH/H$_2$O (10 mL, 1:1) was added LiOH.H$_2$O (20 mg, 5 mmol). The reaction mixture was heated at 50-55° C. until starting material disappeared from TLC. It was cooled at about 0-4° C. and conc. HCl added dropwise until pH of about 5. The resulted mixture was then extracted with DCM (3×20 mL). Combined organic layers were washed with brine (2×20 mL), dried over Na$_2$SO$_4$, filtered, and concentrated in vacuo. The residue was purified by silica gel column chromatography (50:1 DCM:MeOH) to give the 5-(tert-butoxycarbonylamino)-2-phenylthiazole-4-carboxylic acid (0.22 g, 68%) as white solid: ¹H-NMR (CDCl$_3$, 500 MHz) δ (ppm): 9.69 (s, 1H), 7.89-7.91 (m, 2H), 7.46-7.47 (m, 3H), 1.57 (s, 9H); MS (ESI) m/z: 321 [M+H⁺]

Example 24

5-(tert-butoxycarbonylamino)-2-(2-fluorophenyl) thiazole-4-carboxylic acid

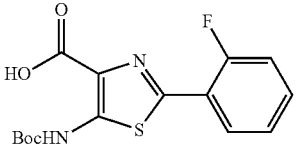 [SMILES: CC(C)(C)OC(=O)Nc1sc(-c2ccccc2F)nc1C(=O)O]

Following procedures from Examples 19-23 and shown in FIG. 2, 2-fluorobenzoyl chloride was converted to 5-(tert-butoxycarbonylamino)-2-(2-fluorophenyl)thiazole-4-carboxylic acid: ¹H-NMR (CDCl$_3$, 500 MHz) δ (ppm): 9.70 (s, 1H), 8.19-8.23 (m, 1H), 7.42-7.45 (m, 1H), 7.20-7.30 (m, 2H), 1.57 (s, 9H); MS (ESI) m/z: 339 [M+H⁺]

Example 25

5-(tert-butoxycarbonylamino)-2-(2,6-difluorophenyl) thiazole-4-carboxylic acid

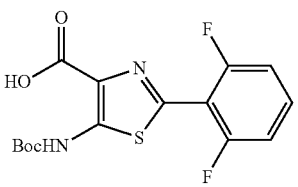 [SMILES: CC(C)(C)OC(=O)Nc1sc(-c2c(F)cccc2F)nc1C(=O)O]

Following procedures from Examples 19-23 and shown in FIG. 2, 2,6-difluorobenzoyl chloride was converted to 5-(tert-butoxycarbonylamino)-2-(2,6-difluorophenyl)thiazole-4-carboxylic acid: $^1$H-NMR (CD$_3$OD, 500 MHz) δ (ppm): 7.42-7.46 (m, 1H), 7.06 (t, J=8.5 Hz, 2H), 1.47 (s, 9H); MS (ESI) m/z: 355 [M+H$^+$].

Example 26

5-(tert-butoxycarbonylamino)-2-(2-chlorophenyl)thiazole-4-carboxylic acid

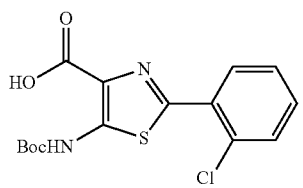 [SMILES: CC(C)(C)OC(=O)Nc1sc(-c2ccccc2Cl)nc1C(=O)O]

Following procedures from Examples 19-23 and shown in FIG. 2, 2-chlorobenzoyl chloride was converted to 5-(tert-butoxycarbonylamino)-2-(2-chlorophenyl)thiazole-4-carboxylic acid: $^1$H-NMR (DMSO, 500 MHz) δ (ppm): 13.57 (s, 1H), 10.05 (s, 1H), 8.14-8.17 (m, 1H), 7.63-7.65 (m, 1H), 7.49-7.51 (m, 2H), 1.53 (s, 9H); MS (ESI) m/z: 355 [M+H$^+$].

Example 27

2-(5-bromo-2-fluorophenyl)-5-(tert-butoxycarbonylamino)thiazole-4-carboxylic acid

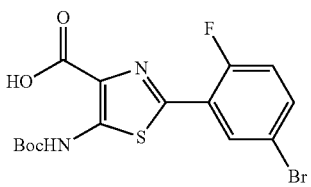 [SMILES: CC(C)(C)OC(=O)Nc1sc(-c2cc(Br)ccc2F)nc1C(=O)O]

Following procedures from Examples 19-23 and shown in FIG. 2, 5-bromo-2-fluorobenzoyl chloride was converted to 2-(5-bromo-2-fluorophenyl)-5-(tert-butoxycarbonylamino)thiazole-4-carboxylic acid: $^1$H-NMR (CDCl$_3$, 500 MHz) δ (ppm): 9.70 (s, 1H), 8.32-8.34 (m, 1H), 7.49-7.52 (m, 1H), 7.09-7.13 (m, 1H), 1.57 (s, 9H); MS (ESI) m/z: 418 [M+H$^+$].

Example 28

2-(5-bromo-2-chlorophenyl)-5-(tert-butoxycarbonylamino)thiazole-4-carboxylic acid

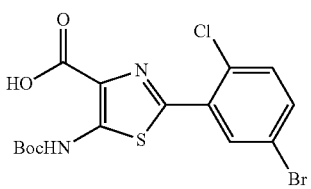 [SMILES: CC(C)(C)OC(=O)Nc1sc(-c2cc(Br)ccc2Cl)nc1C(=O)O]

Following procedures from Examples 19-23 and shown in FIG. 2, 5-bromo-2-chlorobenzoyl chloride was converted to 2-(5-bromo-2-chlorophenyl)-5-(tert-butoxycarbonylamino)thiazole-4-carboxylic acid: $^1$H-NMR (CDCl$_3$, 500 MHz) δ (ppm): 9.70 (s, 1H), 8.31 (d, J=2.5 Hz, 1H), 7.47 (dd, J=2.5 Hz, J=8.5 Hz, 1H), 7.35 (d, J=9.0 Hz, 1H), 1.57 (s, 9H); MS (ESI) m/z: 433 [M+H$^+$].

Example 29

2-(3-bromophenyl)-5-(tert-butoxycarbonylamino)thiazole-4-carboxylic acid

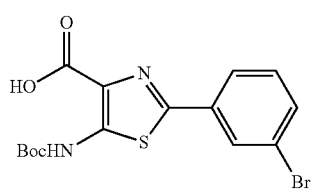 [SMILES: CC(C)(C)OC(=O)Nc1sc(-c2cccc(Br)c2)nc1C(=O)O]

Following procedures from Examples 19-23 and shown in FIG. 2, 3-bromobenzoyl chloride was converted to 2-(3-bromophenyl)-5-(tert-butoxycarbonylamino)thiazole-4-carboxylic acid: $^1$H-NMR (CDCl$_3$, 500 MHz) δ (ppm): 9.68 (s, 1H), 8.08 (s, 1H), 7.78 (d, J=8.0 Hz, 1H), 7.56 (d, J=8.0 Hz, 1H), 7.32 (t, J=8.0 Hz, 1H), 1.57 (s, 9H); MS (ESI) m/z: 399 [M+H$^+$]

Example 30

2-(4-bromo-2-fluorophenyl)-5-(tert-butoxycarbonylamino)thiazole-4-carboxylic acid

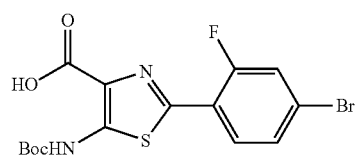 [SMILES: CC(C)(C)OC(=O)Nc1sc(-c2ccc(Br)cc2F)nc1C(=O)O]

Following procedures from Examples 19-23 and shown in FIG. 2, 4-bromo-2-fluorobenzoyl chloride was converted to 2-(4-bromo-2-fluorophenyl)-5-(tert-butoxycarbonylamino)thiazole-4-carboxylic acid: $^1$H-NMR (CDCl$_3$, 500 MHz) δ (ppm): 9.67 (s, 1H), 8.07 (t, J=8.0 Hz, 1H), 7.42 (d, J=9.5 Hz, 1H), 1.57 (s, 9H); MS (ESI) m/z: 417 [M+H$^+$]

Example 31

5-(tert-butoxycarbonylamino)-2-(yridine-2-yl)thiazole-4-carboxylic acid

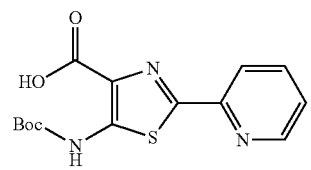 [SMILES: CC(C)(C)OC(=O)Nc1sc(-c2ccccn2)nc1C(=O)O]

To a solution of picolinic acid (1.23 g, 10 mmol), EDC.HCl (1.91 g, 10 mmol) and HOBT (1.35 g, 10 mmol) in THF (80 mL) was added DIPEA (3.6 g, 30 mmol) at ambient temperature. The reaction mixture was maintained at the same temperature for 1 hr at which time a solution of ethyl 2-amino-2-cyanoacetate (1.28 g, 10 mmol) in THF (5 mL) was added. The reaction mixture was stirred at ambient temperature for additional 6 hr. It was then concentrated, and the residue was purified by silica gel column chromatography (5:1 PE/EtOAc) to give ethyl 2-cyano-2-(picolinamido)acetate (0.7 g, 30%) as yellow solid.

Following procedures from Examples 19-23 and shown in FIG. 2, ethyl 2-cyano-2-(picolinamido)acetate was converted to 5-(tert-butoxycarbonylamino)-2-(yridine-2-yl)thiazole-4-carboxylic acid: $^1$H-NMR (CDCl$_3$, 500 MHz) δ (ppm): 9.72 (s, 1H), 8.61 (d, J=4.5 Hz, 1H), 8.09 (d, J=8.0 Hz, 1H), 7.81 (t, J=7.5 Hz, 1H), 7.34 (dd, J=5.5 Hz, J=7.0 Hz, 1H), 1.57 (s, 9H); MS (ESI) m/z: 322 [M+H$^+$].

Example 32

5-(tert-butoxycarbonylamino)-2-isopropylthiazole-4-carboxylic acid

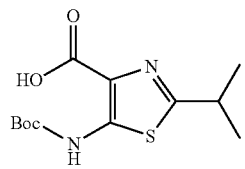 [SMILES: CC(C)c1nc(C(=O)O)c(NC(=O)OC(C)(C)C)s1]

Following procedures from Examples 19-23 and shown in FIG. 2, isobutyryl chloride was converted to 5-(tert-butoxycarbonylamino)-2-isopropylthiazole-4-carboxylic acid: $^1$H-NMR (CDCl$_3$, 500 MHz) δ (ppm): 9.54 (s, 1H), 3.16-3.21 (m, 1H), 1.54 (s, 9H), 1.37 (d, J=7.0 Hz, 6H); MS (ESI) m/z: 287 [M+H$^+$].

Example 33

5-(tert-butoxycarbonylamino)-2-cyclohexylthiazole-4-carboxylic acid

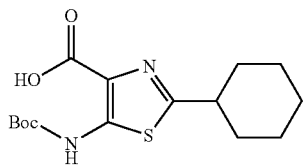 [SMILES: CC(C)(C)OC(=O)Nc1sc(C2CCCCC2)nc1C(=O)O]

Following procedures from Examples 19-23 and shown in FIG. 2, cyclohexanecarboxylic acid chloride was converted to 5-(tert-butoxycarbonylamino)-2-cyclohexylthiazole-4-carboxylic acid: $^1$H-NMR (CDCl$_3$, 500 MHz) δ (ppm): 9.53 (s, 1H), 2.84-2.89 (m, 1H), 2.08-2.12 (m, 2H), 1.84 (dd, J=3.5 Hz, J=10.0 Hz, 2H), 1.73 (d, J=13.0 Hz, 1H), 1.53 (s, 9H), 1.35-1.50 (m, 4H), 1.25-1.27 (m, 1H); MS (ESI) m/z: 327 [M+H$^+$].

Example 34

5-(tert-butoxycarbonylamino)-2-o-tolylthiazole-4-carboxylic acid

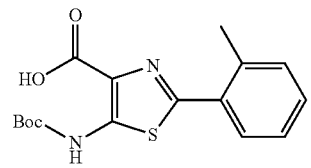 [SMILES: Cc1ccccc1-c1nc(C(=O)O)c(NC(=O)OC(C)(C)C)s1]

Following procedures from Examples 19-23 and shown in FIG. 2, 2-methylbenzoyl chloride was converted to 5-(tert-butoxycarbonylamino)-2-o-tolylthiazole-4-carboxylic acid: $^1$H-NMR (CD$_3$OD, 500 MHz) δ (ppm): 7.34 (s, 1H), 7.13-7.22 (m, 3H), 2.32 (s, 3H), 1.43 (s, 9H); MS (ESI) m/z: 335 [M+H$^+$].

Example 35

5-(tert-butoxycarbonylamino)-2-(2-methoxyphenyl)thiazole-4-carboxylic acid

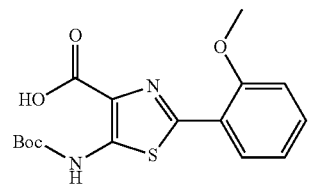 [SMILES: COc1ccccc1-c1nc(C(=O)O)c(NC(=O)OC(C)(C)C)s1]

Following procedures from Examples 19-23 and shown in FIG. 2, 2-methoxybenzoyl chloride was converted to 5-(tert-butoxycarbonylamino)-2-(2-methoxyphenyl)thiazole-4-carboxylic acid: $^1$H-NMR (CD$_3$OD, 500 MHz) δ (ppm): 9.63 (s, 1H), 8.27 (d, J=7.5 Hz, 1H), 7.42 (t, J=8.0 Hz, 1H), 7.09 (t, J=7.5 Hz, 1H), 7.04 (d, J=9.0 Hz, 1H), 1.57 (s, 9H); MS (ESI) m/z: 351 [M+$^+$]

Example 36

5-(tert-butoxycarbonylamino)-2-(2-(trifluoromethyl)phenyl)thiazole-4-carboxylic acid

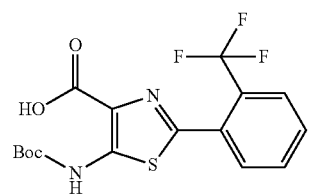 [SMILES: CC(C)(C)OC(=O)Nc1sc(-c2ccccc2C(F)(F)F)nc1C(=O)O]

Following procedures from Examples 19-23 and shown in FIG. 2, 2-(trifluoromethyl)benzoyl chloride was converted to 5-(tert-butoxycarbonylamino)-2-(2-(trifluoromethyl)phenyl)thiazole-4-carboxylic acid: $^1$H-NMR (CD$_3$OD, 500 MHz) δ (ppm): 7.76 (d, J=7.5 Hz, 1H), 7.58-7.64 (m, 3H), 1.46 (s, 9H); MS (ESI) m/z: 389 [M+H$^+$].

Example 37

5-(tert-butoxycarbonylamino)-2-methylthiazole-4-carboxylic acid

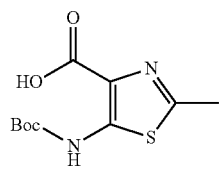

Following procedures from Examples 19-23 and shown in FIG. 2, acetyl chloride was converted to 5-(tert-butoxycarbonylamino)-2-methylthiazole-4-carboxylic acid: $^1$H-NMR (CDCl$_3$, 500 MHz) δ (ppm): 9.62 (s, 1H), 2.62 (s, 3H), 1.54 (s, 9H); MS (ESI) m/z: 259 [M+H$^+$]

Example 38

5-(tert-butoxycarbonylamino)thiazole-4-carboxylic acid

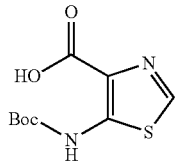

Under N$_2$, HCOOH (2.44 g, 53 mmol) was added to Ac$_2$O (6.48 g, 63.6 mmol) at 0° C. After it was allowed to warm to ambient temperature the reaction was heated at 50° C. for 15 hr. It was allowed to cool to ambient temperature. This mixed acid anhydride was then added dropwise to a solution of ethyl 2-amino-2-cyanoacetate (128 mg, 1 mmol) in dry THF (5 mL) at 0° C. After the cooling bath was removed, the reaction was maintained at ambient temperature for additional 1 hr. The reaction mixture was concentrated and purified by silica gel column chromatography (5:1 PE/EtOAc) to afford ethyl 2-cyano-2-formamidoacetate (110 mg, 70%) as a white solid.

Following procedures from Examples 19-23 and shown in FIG. 2, ethyl 2-cyano-2-formamidoacetate was converted to 5-(tert-butoxycarbonylamino)thiazole-4-carboxylic acid: $^1$H-NMR (CDCl$_3$, 500 MHz) δ (ppm): 9.70 (s, 1H), 8.29 (s, 1H), 1.55 (s, 9H); MS (ESI) m/z: 245 [M+H$^+$]

Example 39

2-bromo-5-(tert-butoxycarbonylamino)thiazole-4-carboxylic acid

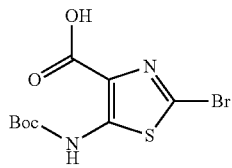

To a solution of 5-(tert-butoxycarbonylamino)thiazole-4-carboxylic acid (1.72 g, 10 mmol) in DCM (50 mL) was added in three portions NBS (1.95 g, 11 mmol); the reaction mixture was stirred at ambient temperature for 1 h. Reaction was concentrated in vacuo; resulted residue was purified by silica gel column chromatography (6:1 Pet-ether-EtOAc) to afford 2-bromo-5-(tert-butoxycarbonylamino)thiazole-4-carboxylic acid (1.75 g, 70%) as white solid: $^1$H-NMR (CDCl$_3$, 500 MHz) δ (ppm): 13.65 (s, 1H), 10.03 (s, 1H), 1.49 (s, 9H). MS (ESI) m/z: 324 [M+H$^+$]

Example 40

5-(tert-butoxycarbonylamino)-2-(2,5-difluorophenyl)thiazole-4-carboxylic acid

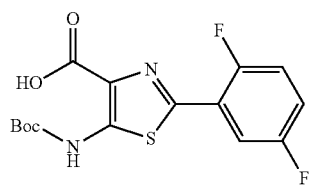 [SMILES: CC(C)(C)OC(=O)Nc1sc(-c2cc(F)ccc2F)nc1C(=O)O]

Following procedures from Examples 19-23 and shown in FIG. 2, 2,5-difluorobenzoyl chloride was converted to 5-(tert-butoxycarbonylamino)-2-(2,5-difluorophenyl)thiazole-4-carboxylic acid: $^1$H-NMR (CDCl$_3$, 500 MHz) δ (ppm): 9.68 (s, 1H), 7.87-7.91 (m, 1H), 7.15-7.26 (m, 1H), 7.08-7.13 (m, 1H), 1.57 (s, 9H); MS (ESI) m/z: 357 [M+H$^+$]

Example 41

5-(tert-butoxycarbonylamino)-2-(2,4-difluorophenyl)thiazole-4-carboxylic acid

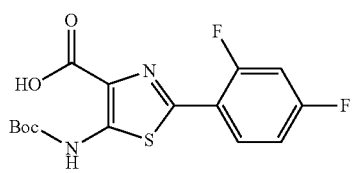 [SMILES: CC(C)(C)OC(=O)Nc1sc(-c2ccc(F)cc2F)nc1C(=O)O]

Following procedures from Examples 19-23 and shown in FIG. 2, 2,4-difluorobenzoyl chloride was converted to 5-(tert-butoxycarbonylamino)-2-(2,4-difluorophenyl)thiazole-4-carboxylic acid: $^1$H-NMR (CDCl$_3$, 500 MHz) δ (ppm): 9.66 (s, 1H), 8.16-8.21 (m, 1H), 6.95-7.04 (m, 2H), 1.62 (s, 9H); MS (ESI) m/z: 357 [M+H$^+$]

Example 42

5-(tert-butoxycarbonylamino)-2-(2,3-difluorophenyl)thiazole-4-carboxylic acid

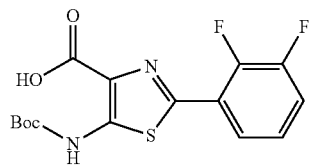 [SMILES: CC(C)(C)OC(=O)Nc1sc(-c2cccc(F)c2F)nc1C(=O)O]

Following procedures from Examples 19-23 and shown in FIG. 2, 2,3-difluorobenzoyl chloride was converted to 5-(tert-butoxycarbonylamino)-2-(2,3-difluorophenyl)thiazole-4-carboxylic acid: $^1$H-NMR (CD$_3$OD, 400 MHz) δ (ppm): 7.45 (s, 1H), 7.07-7.16 (m, 2H), 1.42 (s, 9H); MS (ESI) m/z: 357 [M+H$^+$].

Example 43

2-benzyl-5-(tert-butoxycarbonylamino)thiazole-4-carboxylic acid

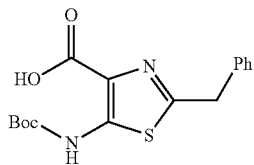 [SMILES: CC(C)(C)OC(=O)Nc1sc(Cc2ccccc2)nc1C(=O)O]

Following procedures from Examples 19-23 and shown in FIG. 2, 2-phenylacetyl chloride was converted to 2-benzyl-5-(tert-butoxycarbonylamino)thiazole-4-carboxylic acid: $^1$H-NMR (CDCl$_3$, 500 MHz) δ (ppm): 9.63 (s, 1H), 7.27-7.35 (m, 5H), 4.25 (s, 2H), 1.50 (s, 9H); MS (ESI) m/z: 335 [M+H$^+$].

Example 44

5-(tert-butoxycarbonylamino)-2-(quinolin-7-yl)thiazole-4-carboxylic acid

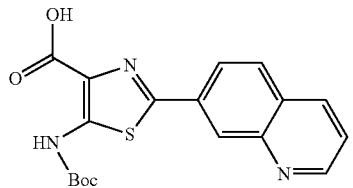 [SMILES: CC(C)(C)OC(=O)Nc1sc(-c2ccc3cccnc3c2)nc1C(=O)O]

Following procedures from Examples 19-23 and shown in FIG. 2, quinoline-7-carbonyl chloride was converted to 5-(tert-butoxycarbonylamino)-2-(quinolin-7-yl)thiazole-4-carboxylic acid: $^1$H-NMR (DMSO, 500 MHz) δ (ppm): 10.14 (s, 1H), 9.11 (d, J=5 Hz, 1h), 8.68 (s, 1H), 8.55 (s, 1H), 8.21-8.25 (m, 2H), 7.75-7.77 (m, 1H), 1.54 (s, 9H); MS (ESI) m/z: 372 [M+H$^+$]

Example 45

5-(tert-butoxycarbonylamino)-2-(imidazo[1,2-a]yridine-2-yl)thiazole-4-carboxylic acid

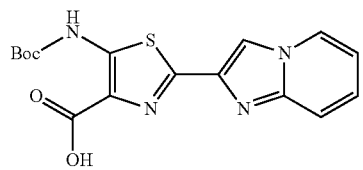 [SMILES: CC(C)(C)OC(=O)Nc1sc(-c2cn3ccccc3n2)nc1C(=O)O]

Following procedures from Examples 19-23 and shown in FIG. 2, imidazo[1,2-a]pyridine-2-carbonyl chloride was converted to 5-(tert-butoxycarbonylamino)-2-(imidazo[1,2-a]pyridine-2-yl)thiazole-4-carboxylic acid: $^1$H-NMR (DMSO, 500 MHz) δ (ppm): 10.12 (s, 1H), 8.58 (d, 5 Hz, 1H), 8.45 (s, 1H), 7.61 (d, 5 Hz, 1H), 7.31-7.34 (m, 1H), 6.97-6.99 (m, 1H), 1.53 (s, 9H); MS (ESI) m/z: 361 [M+H$^+$].

Example 46

5-(tert-butoxycarbonylamino)-2-tert-butylthiazole-4-carboxylic acid

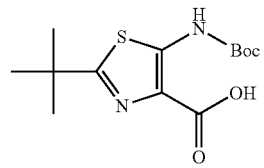 [SMILES: CC(C)(C)OC(=O)Nc1sc(C(C)(C)C)nc1C(=O)O]

Following procedures from Examples 19-23 and shown in FIG. 2, pivaloyl chloride was converted to 5-(tert-butoxycarbonylamino)-2-tert-butylthiazole-4-carboxylic acid: $^1$H-NMR (CDCl$_3$, 500 MHz) δ (ppm): 9.55 (s, 1H), 1.55 (s, 9H), 1.42 (s, 9H); MS (ESI) m/z: 301 [M+H$^+$].

Example 47

5-(tert-butoxycarbonylamino)-2-(3-chlorophenyl)thiazole-4-carboxylic acid

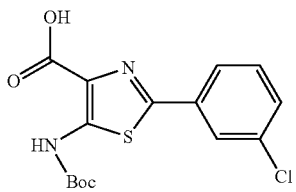 [SMILES: CC(C)(C)OC(=O)Nc1sc(-c2cccc(Cl)c2)nc1C(=O)O]

Following procedures from Examples 19-23 and shown in FIG. 2, 3-chlorobenzoyl chloride was converted to 5-(tert-butoxycarbonylamino)-2-(3-chlorophenyl)thiazole-4-carboxylic acid: $^1$H-NMR (DMSO, 500 MHz) δ (ppm): 9.67 (s, 1H), 7.91 (s, 1H), 7.72 (d, J=7 Hz, 1H), 7.38-7.40 (m, 2H), 1.56 s, 9H); MS (ESI) m/z: 355 [M+H$^+$].

Example 48

5-(tert-butoxycarbonylamino)-2-(4-chlorophenyl)thiazole-4-carboxylic acid

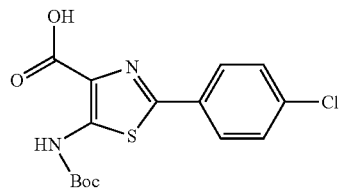 [SMILES: CC(C)(C)OC(=O)Nc1sc(-c2ccc(Cl)cc2)nc1C(=O)O]

Following procedures from Examples 19-23 and shown in FIG. 2, 4-chlorobenzoyl chloride was converted to 5-(tert-butoxycarbonylamino)-2-(4-chlorophenyl)thiazole-4-carboxylic acid: $^1$H-NMR (DMSO, 500 MHz) δ (ppm): 9.66 (s, 1H), 7.81 (d, J=8.5 Hz, 2H), 7.42 (d, J=8.5 Hz, 2H), 1.56 (s, 9H); MS (ESI) m/z: 355 [M+H$^+$].

Example 49

5-amino-N-(1-methyl-1H-pyrazol-4-yl)thiazole-4-carboxamide

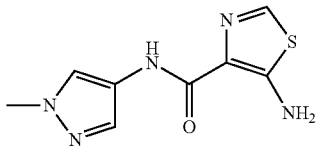

Following the procedures as described in Example 113, 1-methyl-1H-pyrazol-4-amine, 5-(tert-butoxycarbonylamino)thiazole-4-carboxylic acid were reacted to give 5-amino-N-(1-methyl-1H-pyrazol-4-yl)thiazole-4-carboxamide as a white solid (13 mg, 32%) over two steps. ESIMS m/z=336.1 (M+1)

Example 50 tert-butyl 3-(4-amino-1-methyl-1H-pyrazol-5-yl)phenyl carbamate

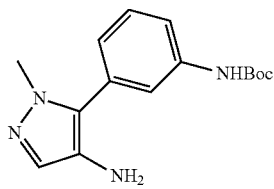 [SMILES: Cn1ncc(N)c1-c1cccc(NC(=O)OC(C)(C)C)c1]

To a 10 mL microwave vial was added 5-chloro-1-methyl-4-nitro-1H-pyrazole (150 mg, 0.93 mmol), 3-(tert-butoxycarbonylamino)phenylboronic acid (440 mg, 1.86 mmol), dichloro[1,1'-bis(diphenylphosphino)ferrocene]palladium (II) (152 mg, 0.019 mmol), a 1:1 M solution of Na$_2$CO$_3$/KOAc (1 mL) and acetonitrile (4 mL). The mixture was irradiated to 130° C. with a microwave for 40 min and the mixture was cooled, concentrated and purified via flash chromatography, heptane/ethyl acetate 20% to 95% to afford a yellow oil. To a 50 mL round bottom flask was added the nitro compound (120 mg, 0.90 mmol), iron (156 mg, 2.8 mmol), ammonium chloride (200 mg, 3.7 mmol), ethanol (10 mL) and water (1.5 mL). The mixture was stirred for 1 h and the reaction was monitored by LCMS. Upon completion of the reaction, the mixture was filtered through a pad of Celite and was washed with ethyl acetate (30 mL) and a 10% aqueous solution of K$_3$PO$_4$ (30 mL). The organic layer was washed with water (30 mL), dried over Na$_2$SO$_4$ and the organic solvent was distilled off to yield tert-butyl 3-(4-amino-1-methyl-1H-pyrazol-5-yl)phenylcarbamate as a brown oil with a purity of >98% (120 mg, 45%) over two steps. ESIMS m/z=289.1 (M+1)

Example 51

1-methyl-5-o-tolyl-1H-pyrazol-4-amine

Following the procedures as described in Example 2 and starting with o-tolylboronic acid, 1-methyl-5-o-tolyl-1H-pyrazol-4-amine was obtained as a brown oil (148 mg, 85%) over two steps. ESIMS m/z=188.1 (M+1)

Example 51

2-(4-Cyclopropyl-2-fluorophenyl)-4,4,5,5-tetramethyl-1,3,2-dioxaborolane

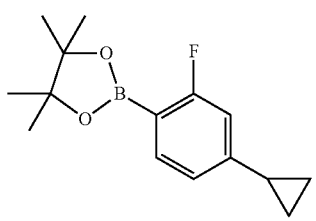 [SMILES: CC1(C)OB(c2ccc(C3CC3)cc2F)OC1(C)C]

Step 1: Preparation of 3-fluoro-4-nitrophenyl trifluoromethanesulfonate

To a stirred solution of 3-fluoro-4-nitrophenol (10.00 g, 63.65 mmol) and trifluoromethanesulfonic anhydride (20.0 mL, 119 mmol, 1.87 eq.) in anhydrous DCM (100.0 mL) at 0° C. was added dropwise triethylamine (33.27 mL, 238.7 mmol, 3.75 eq.). The resultant brown reaction mixture was stirred at 0° C. for 2 h and then stirred at ambient temperature for 16 h. The reaction mixture was slowly quenched with water and extracted with DCM (3×100 mL). The combined organic layers were washed with brine (1×), dried over Na$_2$SO$_4$, filtered, and concentrated under reduced pressure. The crude oil was purified via flash column chromatography eluted with 0 to 65% DCM/hexane to give 15.67 g (85.1%) of 3-fluoro-4-nitrophenyl trifluoromethanesulfonate as an oil. $^1$H NMR (500 MHz, CDCl$_3$) δ 8.23 (t, J=8.52 Hz, 1H), 7.34-7.27 (m, 2H).

Step 2: Preparation of 4-cyclopropyl-2-fluoro-1-nitrobenzene

A mixture of 3-fluoro-4-nitrophenyl trifluoromethanesulfonate (7.15 g, 24.73 mmol), cyclopropylboronic acid (2.55 g, 29.67 mmol), [1,1'-bis(diphenylphosphino)-ferrocene]dichloropalladium(II), complexed with dichloromethane (1:1) (1.62 g, 1.98 mmol), and 2M cesium carbonate in water (19.8 mL, 39.56 mmol) in toluene (39.5 mL) was degassed for 20 min. The reaction mixture was stirred at 90° C. under $N_2$ for 2.5 h. The reaction was cooled to RT, diluted with ethyl acetate (200 mL), and filtered through a pad of Celite. The filtrate was washed with brine, dried over $Na_2SO_4$, filtered, and concentrated under reduced pressure. The crude residue was purified via flash column chromatography eluted with 0 to 75% DCM/hexane to give 4.11 g (91.7%) of 4-cyclopropyl-2-fluoro-1-nitrobenzene as an oil. $^1$H NMR (400 MHz, MeOD) δ 7.98 (dd, J=10.2, 6.6 Hz, 1H), 7.12-7.02 (m, 2H), 2.11-1.97 (m, 1H), 1.20-1.11 (m, 2H), 0.89-0.82 (m, 2H).

Step 3: Preparation of 4-cyclopropyl-2-fluoroaniline

A mixture of 4-cyclopropyl-2-fluoro-1-nitrobenzene (3.36 g, 18.55 mmol), powdered iron (4.35 g, 77.9 mmol), and 2M ammonium chloride in water (19.8 mL) and 3:2:1 v/v EtOH:THF:$H_2O$ (86 mL) was stirred at reflux under $N_2$ for 17 h. The reaction mixture was cooled to RT and filtered through a pad of Celite. The Celite pad was rinsed well with ethyl acetate (~50 mL). Saturated aqueous $NaHCO_3$ solution was slowly added to the filtrate to neutralize the reaction mixture. The reaction mixture was extracted with ethyl acetate (3×200 mL). The combined organic layers were washed with water and brine, dried over $Na_2SO_4$, filtered, and concentrated under reduced pressure. The crude residue was purified via flash column chromatography eluted with 0 to 75% ethyl acetate/hexane to give 2.80 g (99%) of an orange oil, which solidified at 20° C. $^1$H NMR (400 MHz, CDCl$_3$) δ 6.75-6.63 (m, 3H), 3.57 (s, 2H), 1.87-1.72 (m, 1H), 0.93-0.83 (m, 2H), 0.64-0.51 (m, 2H); MS (ESI) m/z: 152.3 [M+H]$^+$.

Step 4: Preparation of 4-cyclopropyl-2-fluoro-1-iodobenzene

To a stirred mixture of 4-cyclopropyl-2-fluoroaniline (1.63 g, 10.78 mmol) in water (20 mL) at 0° C. was added concentrated sulfuric acid (8.6 mL, 15.0 eq.) dropwise, while keeping the temperature constant at 0° C. A solution of sodium nitrite (781.0 mg, 11.32 mmol, 1.05 eq.) in water (2.7 mL) was added and stirred for 5 minutes. This resulting reaction mixture was then added to a solution of potassium iodide (3.76 g, 22.64 mmol, 2.1 eq.) in water (9.7 mL), and the reaction mixture was stirred at 60° C. for 3 h. DCM (400 mL) was added to the cooled reaction. The biphasic layers were separated, and the aqueous layer was extracted with DCM (2×150 mL). The combined organic layers were washed with saturated aqueous $Na_2S_2O_4$, water, and brine, dried over $Na_2SO_4$, filtered, and concentrated under reduced pressure. The crude residue was purified via flash column chromatography eluted with 100% heptane to give 2.01 g (71.28%) of 4-cyclopropyl-2-fluoro-1-iodobenzene as a clear oil. $^1$H NMR (400 MHz, CDCl$_3$) δ 7.57 (dd, J=8.0, 6.9 Hz, 1H), 6.76 (dd, J=9.4, 1.9 Hz, 1H), 6.64 (dd, J=8.2, 1.9 Hz, 1H), 1.94-1.77 (m, 1H), 1.09-0.95 (m, 2H), 0.79-0.56 (m, 2H).

Step 5

In a high pressure tube was placed 4-cyclopropyl-2-fluoro-1-iodobenzene (1.32 g, 5.04 mmol), bispinacol ester boronate (1.53 g, 6.04 mmol), potassium acetate (1.98 g, 20.15 mmol), [1,1'-bis(diphenylphosphino)ferrocene]dichloropalladium (II) (368.5 mg, 0.50 mmol), and N,N-dimethylformamide (35 mL). The reaction mixture was degassed with $N_2$ for 15 minutes. The vessel was sealed and the reaction mixture was stirred at 90° C. for 16 h. The cooled reaction mixture was diluted with ethyl acetate (75 mL) and water (25 mL) and then filtered through a pad of Celite. The biphasic layers were separated and the organic layer was washed with water and brine, dried over $Na_2SO_4$, filtered, and concentrated under reduced pressure. The crude residue was purified via flash column chromatography eluted with 0 to 75% EA/heptane to give 859.0 mg (65.1%) of 2-(4-cyclopropyl-2-fluorophenyl)-4,4,5,5-tetramethyl-1,3,2-dioxaborolane as a clear oil. $^1$H NMR (400 MHz, CDCl$_3$) δ 7.58 (s, 1H), 6.83 (d, J=7.7 Hz, 1H), 6.68 (d, J=10.8 Hz, 1H), 1.91-1.81 (m, 1H), 1.33 (s, 12H), 0.98 (dd, J=8.3, 2.0 Hz, 2H), 0.74-0.66 (m, 2H)

Example 53

((R)-1-{4-[(2-Bromo-5-tert-butoxycarbonylamino-thiazole-4-carbonyl)-amino]-2-methyl-2H-pyrazol-3-yl}-perhydro-azepin-4-yl)-carbamic acid benzyl ester

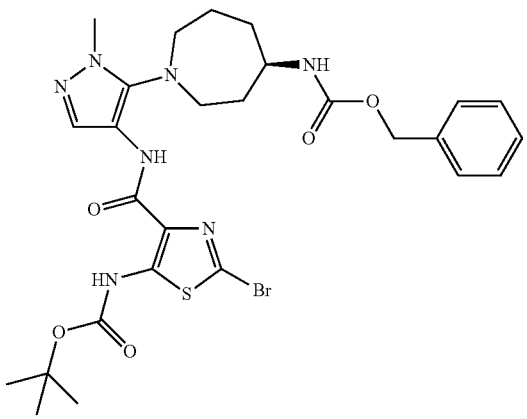 [SMILES: Cn1ncc(NC(=O)c2nc(Br)sc2NC(=O)OC(C)(C)C)c1N1CCC[C@@H](NC(=O)OCc2ccccc2)CC1]

To a stirred solution of 2-bromo-5-(isopropoxycarbonylamino)-thiazole-4-carboxylic acid (650.0 mg, 2.01 mmol) and [(R)-1-(4-amino-2-methyl-2H-pyrazol-3-yl)-azepan-4-yl]-carbamic acid benzyl ester (828.9 mg, 2.41 mmol, 1.2 eq.) in anhydrous N,N-dimethylformamide (22 mL) was added HATU (1.07 g, 2.81 mmol, 1.4 eq.) followed by N,N-diisopropylethylamine (0.88 mL, 5.03 mmol, 2.5 eq.), and the reaction mixture was stirred at RT under $N_2$ for 7 days. The reaction mixture was diluted with ethyl acetate (150 mL). The organic layer was washed with 50% brine/water, water and brine, dried over $Na_2SO_4$, filtered, and concentrated under reduced pressure. The crude was purified via flash column chromatography eluted with 45 to 100% ethyl acetate/heptane to give 1.30 g (79.7%) of ((R)-1-{4-[(2-Bromo-5-tert-butoxycarbonylamino-thiazole-4-carbonyl)-amino]-2-methyl-2H-pyrazol-3-yl}-perhydro-azepin-4-yl)-carbamic acid benzyl ester as a tacky gel. $^1$H NMR (400 MHz, CDCl$_3$) δ 10.28 (s, 1H), 8.39 (s, 1H), 7.74 (s, 1H), 7.33 (s, 5H), 5.09 (s, 2H), 4.98 (s, 1H), 3.89 (s, 1H), 3.72 (s, 3H), 3.36-3.21 (m, 2H), 3.16-3.03 (m, 2H), 2.19-2.01 (m, 2H), 2.00-1.61 (m, 4H), 1.51 (s, 9H)

Example 54

N-(5,5-Difluoro-1-(1-methyl-4-nitro-1H-pyrazol-5-yl)azepan-4-yl)-2,2,2-trifluoroacetamide

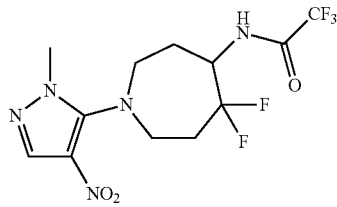 [SMILES: Cn1ncc([N+](=O)[O-])c1N1CCC(NC(=O)C(F)(F)F)C(F)(F)CC1]

Dess Martin periodinane (2.3 g, 5.4 mmol) was added portionwise to a solution of benzyl 4-azido-5-hydroxyazepane-1-carboxylate (1.3 g, 4.5 mmol) in DCM (25 mL). After stirring at room temperature for 18 hr, the mixture was diluted with DCM and quenched with aqueous NaHCO$_3$ (40 mL) followed by aqueous Na$_2$S$_2$O$_3$ (20%, 40 mL). The resulting mixture was stirred for 20 min. The organic layer was separated, dried over Na$_2$SO$_4$ and the solvent removed under reduced pressure. Purification via silica gel column chromatography (0-50% EtOAc/isohexane) gave benzyl 4-azido-5-oxoazepane-1-carboxylate (1.10 g, 84%) as a clear oil. To a solution of this oil (1.10 g, 3.8 mmol) in DCM (10 mL) was added deoxo-Fluor® (50% in THF, 3.5 mL, 9.5 mmol) and the mixture was stirred at room temperature for 18 hr. The mixture was diluted with DCM, cooled in an ice/water bath and quenched by dropwise addition of saturated aqueous NaHCO$_3$ (20 mL). Effervescence was observed. The resulting mixture was stirred for 10 min. The organic layer was separated, dried over Na$_2$SO$_4$ and the solvent removed under reduced pressure. The crude product was purified via silica gel column chromatography (0-40% EtOAc/isohexane) to give benzyl 5-azido-4,4-difluoroazepane-1-carboxylate (0.65 g, 56%) as a clear oil. This oil was dissolved in THF (10 mL) and water (2 mL) and triphenylphosphine (0.58 g, 2.2 mmol) added. After stirring and heating at 60° C. for 18 hr, the mixture was concentrated under reduced pressure. The crude product was dissolved in DCM and the organic layer was washed with water, separated, dried over Na$_2$SO$_4$ and the solvent removed under reduced pressure. To the crude product in DCM (20 mL), cooled in a water/ice bath, was added DIPEA (1.1 mL, 6.36 mmol) followed by trifluoroacetic anhydride (0.75 mL, 5.3 mmol) dropwise. The mixture was allowed to warm to room temperature, stirred for 18 hr and diluted with DCM. Water was added and the organic layer was separated, dried over Na$_2$SO$_4$ and the solvent was removed under reduced pressure. The residue was purified via silica gel column chromatography (0-60% EtOAc/isohexane) to yield benzyl 4,4-difluoro5-(2,2,2-trifluoroacetamido) azepane-1-carboxylate (0.59 g, 73%) as a clear oil. This trifluoroacetamide (0.57 g, 1.5 mmol) was dissolved in MeOH (50 mL) and passed through the H-Cube® (Full H$_2$ Mode, 70° C., flow rate: 1 mL/min, 30 mm 10% Pd/C cartridge). The solvent was removed under reduced pressure to give crude N-(5,5-difluoroazepan-4-yl)-2,2,2-trifluoroacetamide. To a solution of the azepane (0.37 g, 1.5 mmol) in EtOH (4 mL) was added 5-chloro-1-methyl-4-nitro-1H-pyrazole (0.73 g, 4.5 mmol) and DIPEA (0.65 mL, 3.8 mmol). The mixture was heated at 130° C. in a microwave for 6 hr. The solvent was removed under reduced pressure and the crude product was purified via silica gel column chromatography (0-50% EtOAc/isohexane) to yield N-(5,5-difluoro-1-(1-methyl-4-nitro-1H-pyrazol-5-yl)azepan-4-yl)-2,2,2-trifluoroacetamide as a pale yellow oil (0.31 g, 56%). $^1$H NMR (400 MHz, CDCl$_3$) δ 8.05 (s, 1H), 6.77 (d, J=9.0 Hz, 1H), 4.72-4.58 (m, 1H), 3.80 (s, 3H), 3.55-3.39 (m, 2H), 3.33-3.18 (m, 2H), 2.52-2.17 (m, 3H), 2.14-2.04 (m, 1H).

Example 55 tert-Butyl 4-(5-(4,4-difluoro-5-(2,2,2-trifluoroacetamido)azepan-1-yl)-1-methyl-1H-pyrazol-4-ylcarbamoyl)-2-(2,6-difluorophenyl)thiazol-5-ylcarbamate

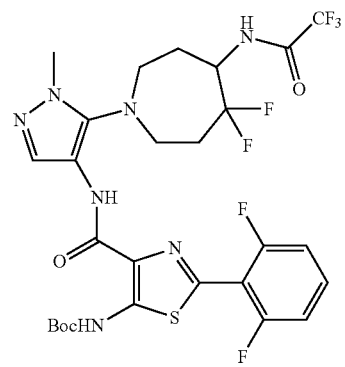 [SMILES: Cn1ncc(NC(=O)c2nc(-c3c(F)cccc3F)sc2NC(=O)OC(C)(C)C)c1N1CCC(NC(=O)C(F)(F)F)C(F)(F)CC1]

A solution of N-(5,5-difluoro-1-(1-methyl-4-nitro-1H-pyrazol-5-yl)azepan-4-yl)-2,2,2-trifluoroacetamide (0.29 g, 0.78 mmol) in MeOH (20 mL) was passed through the H-Cube® (Full H$_2$ Mode, 70° C., flow rate: 1 mL/min, 30 mm 10% Pd/C cartridge). The solvent was removed under reduced pressure to give the crude amine. To a solution of this amine (0.26 g, 0.78 mmol) in DCM (15 mL) was added DIPEA (0.68 mL, 3.9 mmol), PyBOP (0.61 g, 1.17 mmol) and 5-(tert-butoxycarbonylamino)-2-(2,6-difluorophenyl)thiazole-4-carboxylic acid (0.30 g, 0.86 mmol) and the mixture was stirred at room temperature for 18 hr. The mixture was diluted with DCM and washed with water. The organic layer was separated, dried over Na$_2$SO$_4$ and the solvent removed under reduced pressure. Purification via silica gel column chromatography (0-80% EtOAc/isohexane) gave tert-butyl 4-(5-(4,4-difluoro-5-(2,2,2-trifluoroacetamido)-azepan-1-yl)-1-methyl-1H-pyrazol-4-ylcarbamoyl)-2-(2,6-difluorophenyl)thiazol-5-ylcarbamate as a white solid (0.37 g, 69%). $^1$H NMR (400 MHz, CDCl$_3$) δ 10.28 (s, 1H), 8.71 (s, 1H), 7.82 (s, 1H), 7.42-7.33 (m, 1H), 7.11-7.01 (m, 2H), 6.72 (d, J=9.0 Hz, 1H), 4.73-4.57 (m, 1H), 3.77 (s, 3H), 3.51-3.37 (m, 2H), 3.36-3.25 (m, 2H), 2.49-2.36 (m, 2H), 2.25-2.03 (m, 2H), 1.55 (s, 9H).

Example 56

3,3-Difluoro-1-(1-methyl-4-nitro-1H-pyrazol-5-yl)piperidine

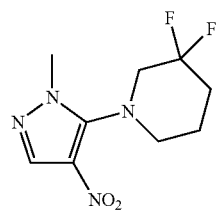 [SMILES: Cn1ncc([N+](=O)[O-])c1N1CCCC(F)(F)C1]

A mixture of 5-chloro-1-methyl-4-nitro-1H-pyrazole (0.1 g, 4.5 mmol), 3,3-difluoropiperidine hydrochloride (0.14 g, 0.93 mmol) and DIPEA (0.5 mL, 2.8 mmol) in EtOH (3 mL) was heated at 130° C. in a microwave for 1 hr. Additional DIPEA (0.5 mL, 2.8 mmol) and 3,3-difluoropiperidine hydrochloride (0.29 g, 1.8 mmol) were added and the mixture was heated at 130° C. in a microwave for 2 hr. The solvent was removed under reduced pressure and the crude product was purified via silica gel column chromatography (0-60% EtOAc/isohexane) to yield 3,3-difluoro-1-(1-methyl-4-nitro-1H-pyrazol-5-yl)piperidine as a yellow oil (127 mg, 83%). $^1$H NMR (400 MHz, CDCl$_3$) δ 8.04 (s, 1H), 3.80 (s, 3H), 3.41-3.29 (m, 2H), 3.26-3.04 (m, 2H), 2.17-2.03 (m, 2H), 1.97-1.88 (m, 2H).

Example 57 tert-Butyl 2-(2,6-difluorophenyl)-4-(5-(3,3-difluoropiperidin-1-yl)-1-methyl-1H-pyrazol-4-ylcarbamoyl)thiazol-5-ylcarbamate

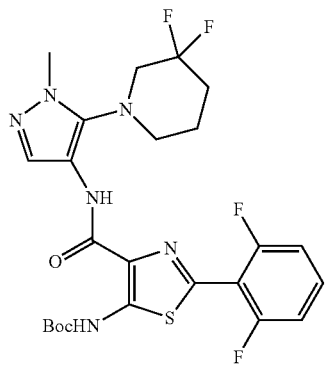 [SMILES: Cn1ncc(NC(=O)c2nc(-c3c(F)cccc3F)sc2NC(=O)OC(C)(C)C)c1N1CCCC(F)(F)C1]

Following the procedure for Example 55, starting with 3,3-difluoro-1-(1-methyl-4-nitro-1H-pyrazol-5-yl)piperidine and 5-(tert-butoxycarbonylamino)-2-(2,6-difluorophenyl)thiazole-4-carboxylic acid, gave tert-butyl 2-(2,6-difluorophenyl)-4-(5-(3,3-difluoropiperidin-1-yl)-1-methyl-1H-pyrazol-4-ylcarbamoyl)thiazol-5-ylcarbamate as a cream solid (57 mg, 20%). $^1$H NMR (400 MHz, CDCl$_3$) δ 10.33 (s, 1H), 8.67 (s, 1H), 7.71 (s, 1H), 7.41-7.32 (m, 1H), 7.11-7.01 (m, 2H), 3.76 (s, 3H), 3.32 (t, J=11.0 Hz, 2H), 3.19-3.13 (m, 2H), 2.10-1.97 (m, 2H), 1.94-1.85 (m, 2H), 1.53 (s, 9H).

Example 58 tert-Butyl 3-(methyl(1-methyl-4-nitro-1H-pyrazol-5-yl)amino)propylcarbamate

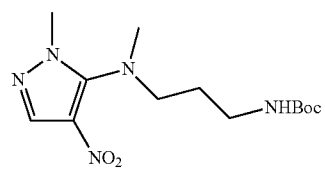 [SMILES: CN(CCCNC(=O)OC(C)(C)C)c1c([N+](=O)[O-])cnn1C]

A mixture of 5-chloro-1-methyl-4-nitro-1H-pyrazole (0.81 g, 5 mmol), tert-butyl 3-aminopropylcarbamate (0.85 g, 4.88 mmol) and DIPEA (1.8 mL, 10.5 mmol) in EtOH (5 mL) was heated at 130° C. in the microwave for 90 min. On cooling the reaction mixture was concentrated under reduced pressure and the residue purified via silica gel column chromatography (0-100% EtOAc/isohexane) to afford tert-butyl 3-(1-methyl-4-nitro-1H-pyrazol-5-ylamino)propylcarbamate as a yellow gum (1.27 g, 85%). A mixture of this gum (0.3 g, 1 mmol), K$_2$CO$_3$ (0.41 g, 3 mmol) and methyl iodide (0.1 mL, 1.58 mmol) in DMF (5 mL) was stirred at 60° C. for 18 hr. More methyl iodide (0.1 mL, 1.58 mmol) was added and stirring at 60° C. was continued for 24 hr. The reaction mixture was cooled and concentrated under reduced pressure. The residue was triturated in DCM (100 mL), filtered and the filtrate concentrated under reduced pressure. Purification via silica gel column chromatography (0-100% EtOAc/isohexane) gave tert-butyl 3-(methyl(1-methyl-4-nitro-1H-pyrazol-5-yl)amino)propylcarbamate as a pale yellow gum (0.122 g, 38%). $^1$H-NMR (400 MHz, CDCl$_3$) δ 8.03 (s, 1H), 4.60 (s, 1H), 3.77 (s, 3H), 3.20-3.14 (m, 4H), 2.86 (s, 3H), 1.72-1.61 (m, 2H), 1.42 (s, 9H).

Example 59 tert-Butyl 2-(2,6-difluorophenyl)-4-(5-(tert-butyl-(3-methylamino)propylcarbamoyl-3-yl)-1-methyl-1H-pyrazol-4-ylcarbamoyl)thiazol-5-ylcarbamate

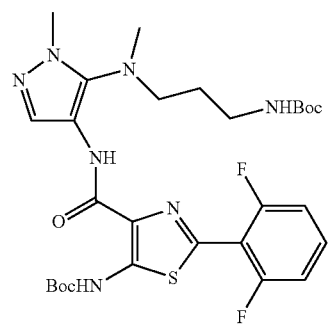 [SMILES: CN(CCCNC(=O)OC(C)(C)C)c1c(NC(=O)c2nc(-c3c(F)cccc3F)sc2NC(=O)OC(C)(C)C)cnn1C]

A solution of tert-butyl 3-(methyl(1-methyl-4-nitro-1H-pyrazol-5-yl)amino)propylcarbamate (122 mg, 0.39 mmol) in MeOH (15 mL) was passed through the H-Cube® (Full H$_2$ Mode, 50° C., flow rate: 1 mL/min, 30 mm 10% Pd/C cartridge). The solvent was removed under reduced pressure to afford a red oil (0.12 g). To a solution of this oil in DCM (10 mL) was added 5-(tert-butoxycarbonylamino)-2-(2,6-difluorophenyl)thiazole-4-carboxylic acid (166 mg, 0.47 mmol), PyBOP (0.33 g, 0.64 mmol) and DIPEA (0.5 mL, 2.86 mmol) and the mixture was stirred at room temperature for 66 hr. Water (20 ml) was added and stirring continued for 30 min. The layers were separated and the aqueous layer extracted with DCM. The combined organic layers were passed through a phase separation cartridge and the solvent removed under reduced pressure. Purification via silica gel column chromatography (0-100% EtOAc/isohexane) gave tert-butyl 2-(2,6-difluorophenyl)-4-(5-(tert-butyl-(3-methylamino)propylcarbamoyl-3-yl)-1-methyl-1H-pyrazol-4-ylcarbamoyl)thiazol-5-ylcarbamate as a white solid (207 mg, 90%). $^1$H-NMR (400 MHz, CDCl$_3$) δ 10.37 (s, 1H), 8.74 (s, 1H), 7.87 (s, 1H), 7.42-7.32 (m, 1H), 7.10-7.02 (m, 2H), 4.65 (s, 1H), 3.75 (s, 3H), 3.20-3.14 (m, 2H), 3.10 (t, J=7 Hz, 2H), 2.85 (s, 3H), 1.76-1.66 (m, 2H), 1.55 (s, 9H), 1.39 (s, 9H).

Example 60

5-Chloro-1-ethyl-4-nitro-1H-pyrazole

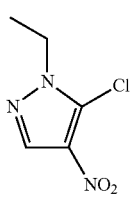

Following the procedure for Example 1 starting with 1-ethyl-4-nitropyrazole gave 5-chloro-1-ethyl-4-nitro-1H-pyrazole as a colourless solid (1.3 g, 74%). $^1$H-NMR (400 MHz, CDCl$_3$) δ 8.16 (s, 1H), 4.26 (q, J=7 Hz, 2H), 1.50 (t, J=7 Hz, 3H).

Example 61

5-Chloro-1-cyclopropylmethyl-4-nitro-1H-pyrazole

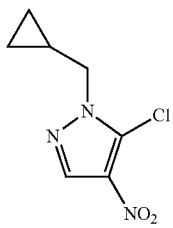 [SMILES: O=[N+]([O-])c1cnn(CC2CC2)c1Cl]

Following the procedure for Example 1 starting with 1-cyclopropylmethyl-4-nitropyrazole gave 5-chloro-1-cyclopropylmethyl-4-nitro-1H-pyrazole as a colourless oil (1.16 g, 56%). $^1$H-NMR (400 MHz, CDCl$_3$) δ 8.17 (s, 1H), 4.07 (d, J=7 Hz, 2H), 1.39-1.28 (m, 1H), 0.66-0.59 (m, 2H), 0.50-0.40 (m, 2H).

Example 62

5-Chloro-1-cyclopropyl-4-nitro-1H-pyrazole

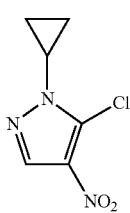 [SMILES: O=[N+]([O-])c1cnn(C2CC2)c1Cl]

Following the procedure for Example 1 starting with 1-cyclopropyl-4-nitropyrazole gave 5-chloro-1-cyclopropyl-4-nitro-1H-pyrazole as a colourless solid (0.23 g, 63%). $^1$H-NMR (400 MHz, CDCl$_3$) δ 8.09 (s, 1H), 3.62-3.54 (m, 1H), 1.38-1.28 (m, 2H), 1.25-1.13 (m, 2H).

Example 63

(R)—N-(Azepan-4-yl)-2,2,2-trifluoroacetamide

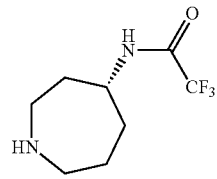

A solution of (R)-tert-butyl 4-(benzyloxycarbonylamino)azepane-1-carboxylate (3.25 g, 0.33 mmol) in MeOH (100 mL) was stirred at room temperature under an atmospheric pressure of hydrogen gas in the presence of 10% Pd/C (1 g) for 1.5 hr. The mixture was filtered through celite and the solvent removed under reduced pressure to afford (R)-tert-butyl 4-(2,2,2-trifluoroacetamido)azepane-1-carboxylate as a pale grey oil (2 g, 100%). To a stirred solution of this oil (1.8 g, 8.4 mmol) and DIPEA (3 mL, 17.18 mmol) in DCM (100 mL) at room temperature was added trifluoroacetic anhydride (1.31 mL, 9.27 mmol) dropwise over 5 min and the resultant pale yellow solution was stirred for 18 hr. Saturated aqueous sodium hydrogen carbonate (150 mL) was added and stirring continued for 1 hr. The layers were separated, the organics passed through a phase separation cartridge and the solvent removed under reduced pressure to give (R)-tert-butyl 4-(2,2,2-trifluoroacetamido)azepane-1-carboxylate as a pale yellow oil (2.61 g, 100%). To a solution of this oil (2.6 g, 8.38 mmol) in DCM (50 mL) at room temperature was added trifluoroacetic acid (25 mL) and the mixture stirred for 2 hr. The solvent was removed under reduced pressure and the residue dissolved in DCM and passed through an SCX column washing with DCM and MeOH and eluting with 1 N ammonia in MeOH. The solvent was removed under reduced pressure to afford (R)—N-(azepan-4-yl)-2,2,2-trifluoroacetamide as a pale yellow oil (1.3 g, 74%). $^1$H-NMR (400 MHz, CDCl$_3$) δ 7.83 (s, 1H), 4.44-4.37 (m, 1H), 3.13-3.03 (m, 2H), 2.88 (dt, J=13.2, 6.6 Hz, 1H), 2.65-2.55 (m, 1H), 2.03-1.79 (m, 3H), 1.75 (s, 1H), 1.69-1.58 (m, 3H).

Example 64

(S)—N-(Azepan-4-yl)-2,2,2-trifluoroacetamide

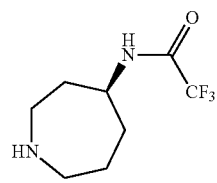 [SMILES: O=C(N[C@H]1CCCNCC1)C(F)(F)F]

Following the procedure for Example 510 starting with (S)-tert-butyl 4-(benzyloxycarbonylamino)azepane-1-carboxylate gave (S)—N-(azepan-4-yl)-2,2,2-trifluoroacetamide as a pale yellow oil (1.35 g, 75% over three steps). $^1$H-NMR (400 MHz, CDCl$_3$) δ 7.86 (s, 1H), 4.44-4.37 (m, 1H), 3.15-3.03 (m, 2H), 2.92-2.81 (m, 1H), 2.67-2.55 (m, 1H), 2.02-1.81 (m, 4H), 1.76-1.56 (m, 3H).

Example 65

N-(1-(1-Ethyl-4-nitro-1H-pyrazol-5-yl)azepan-4-yl)-2,2,2-trifluoroacetamide

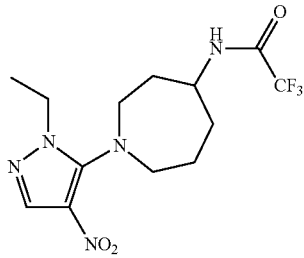 [SMILES: CCn1ncc([N+](=O)[O-])c1N1CCCC(NC(=O)C(F)(F)F)CC1]

Following the procedure for Example 503 starting with 5-chloro-1-ethyl-4-nitro-1H-pyrazole and 2,2,2-trifluoro-N-(hexahydro-1H-azepin-4-yl)-acetamide gave N-(1-(1-ethyl-4-nitro-1H-pyrazol-5-yl)azepan-4-yl)-2,2,2-trifluoroacetamide as a pale yellow gum (0.136 g, 55%). $^1$H-NMR (400 MHz, CDCl$_3$) δ 8.07 (s, 1H), 6.39-6.37 (m, 1H), 4.22-4.19 (m, 1H), 4.12 (q, J=7 Hz, 2H), 3.42-3.35 (m, 1H), 3.27-3.18 (m, 3H), 2.25-2.05 (m, 2H), 2.00-1.75 (m, 4H), 1.47 (t, J=7 Hz, 3H).

Example 66

(R)—N-(1-(1-Ethyl-4-nitro-1H-pyrazol-5-yl)azepan-4-yl)-2,2,2-trifluoroacetamide

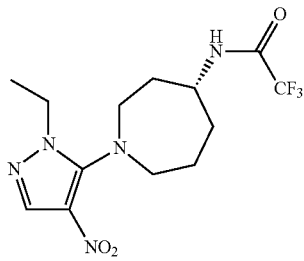

Following the procedure for Example 503 starting with 5-chloro-1-ethyl-4-nitro-1H-pyrazole and (R)-2,2,2-trifluoro-N-(hexahydro-1H-azepin-4-yl)-acetamide (0.1 g, 0.476 mmol) gave (R)—N-(1-(1-ethyl-4-nitro-1H-pyrazol-5-yl)azepan-4-yl)-2,2,2-trifluoroacetamide as a pale yellow gum (0.1 g, 60%). $^1$H-NMR (400 MHz, CDCl$_3$) δ 8.07 (s, 1H), 6.39-6.36 (m, 1H), 4.23-4.19 (m, 1H), 4.12 (q, J=7 Hz, 2H), 3.42-3.35 (m, 1H), 3.27-3.18 (m, 3H), 2.25-2.05 (m, 2H), 2.00-1.75 (m, 4H), 1.47 (t, J=7 Hz, 3H).

Example 67

(S)—N-(1-(1-Ethyl-4-nitro-1H-pyrazol-5-yl)azepan-4-yl)-2,2,2-trifluoroacetamide

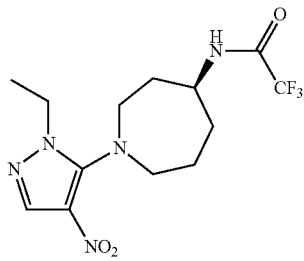 [SMILES: CCn1ncc([N+](=O)[O-])c1N1CCC[C@H](NC(=O)C(F)(F)F)CC1]

Following the procedure for Example 503 starting with 5-chloro-1-ethyl-4-nitro-1H-pyrazole and (S)-2,2,2-trifluoro-N-(hexahydro-1H-azepin-4-yl)-acetamide gave (S)—N-(1-(1-ethyl-4-nitro-1H-pyrazol-5-yl)azepan-4-yl)-2,2,2-trifluoroacetamide as a pale yellow gum (0.12 g, 44%). $^1$H-NMR (400 MHz, CDCl$_3$) δ 8.07 (s, 1H), 6.42-6.40 (m, 1H), 4.22-4.18 (m, 1H), 4.12 (q, J=7 Hz, 2H), 3.42-3.35 (m, 1H), 3.27-3.18 (m, 3H), 2.25-2.05 (m, 2H), 2.00-1.75 (m, 4H), 1.47 (t, J=7 Hz, 3H).

Example 68

(R)—N-(1-(1-Cyclopropylmethyl-4-nitro-1H-pyrazol-5-yl)azepan-4-yl)-2,2,2-trifluoroacetamide

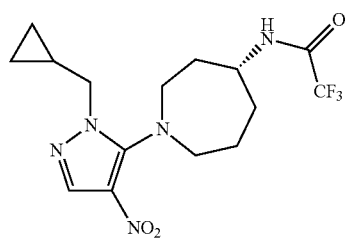 [SMILES: O=C(N[C@@H]1CCCN(c2c([N+](=O)[O-])cnn2CC2CC2)CC1)C(F)(F)F]

Following the procedure for Example 503 starting with 5-chloro-1-cyclopropylmethyl-4-nitro-1H-pyrazole and (R)-2,2,2-trifluoro-N-(hexahydro-1H-azepin-4-yl)-acetamide gave (R)—N-(1-(1-cyclopropylmethyl-4-nitro-1H-pyrazol-5-yl)azepan-4-yl)-2,2,2-trifluoroacetamide as a pale yellow gum (0.98 g, 55%). $^1$H-NMR (400 MHz, CDCl$_3$) δ 8.08 (s, 1H), 6.42-6.39 (m, 1H), 4.22-4.14 (m, 1H), 4.00-3.85 (m, 2H), 3.44-3.32 (m, 1H), 3.30-3.15 (m, 3H), 2.25-2.05 (m, 2H), 2.00-1.75 (m, 4H), 1.30-1.20 (m, 1H), 0.70-0.62 (m, 2H), 0.50-0.35 (m, 2H).

Example 69

(R)—N-(1-(1-Cyclopropyl-4-nitro-1H-pyrazol-5-yl)azepan-4-yl)-2,2,2-trifluoroacetamide

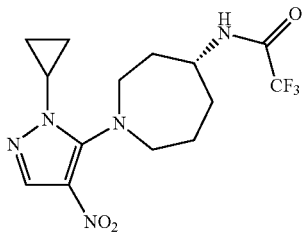 [SMILES: O=C(N[C@@H]1CCCN(c2c([N+](=O)[O-])cnn2C2CC2)CC1)C(F)(F)F]

Following the procedure for Example 503 starting with 5-chloro-1-cyclopropyl-4-nitro-1H-pyrazole and (R)-2,2,2-trifluoro-N-(hexahydro-1H-azepin-4-yl)-acetamide gave (R)—N-(1-(1-cyclopropyl-4-nitro-1H-pyrazol-5-yl)azepan-4-yl)-2,2,2-trifluoroacetamide as a pale yellow gum (0.105 g, 61%). $^1$H-NMR (400 MHz, CDCl$_3$) δ 7.96 (s, 1H), 6.55-6.38 (m, 1H), 4.30-4.15 (m, 1H), 3.65-3.53 (m, 1H), 3.55-3.25 (m, 4H), 2.25-2.05 (m, 6H), 1.35-1.05 (m, 4H).

Example 70 tert-Butyl 2-(2,6-difluorophenyl)-4-(1-ethyl-5-(4-(2,2,2-trifluoroacetamido)azepan-1-yl)-1H-pyrazol-4-ylcarbamoyl)thiazol-5-ylcarbamate

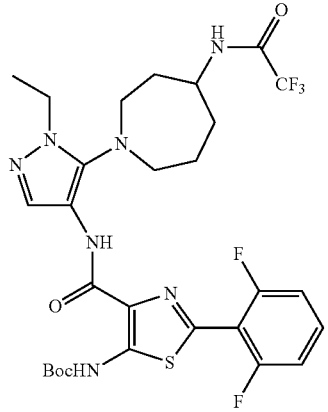 [SMILES: CCn1ncc(NC(=O)c2nc(-c3c(F)cccc3F)sc2NC(=O)OC(C)(C)C)c1N1CCCC(NC(=O)C(F)(F)F)CC1]

A solution of N-(1-(1-ethyl-4-nitro-1H-pyrazol-5-yl)azepan-4-yl)-2,2,2-trifluoroacetamide (136 mg, 0.39 mmol) in MeOH (15 mL) was passed through the H-Cube® (70 bar, 25° C., flow rate: 1 mL/min, 30 mm 10% Pd/C cartridge). The solvent was removed under reduced pressure to afford the crude amine as a purple gum (121 mg). To a solution of this amine in DCM (10 mL) was added 5-(tert-butoxycarbonylamino)-2-(2,6-difluorophenyl)thiazole-4-carboxylic acid (149 mg, 0.42 mmol), HATU (0.43 g, 1.14 mmol) and DIPEA (1 mL, 5.72 mmol). The mixture was stirred at room temperature for 18 hr. Water (30 ml) was added and stirring continued for 15 min. The layers were separated and the aqueous extracted with DCM. The combined organics were passed through a phase separation cartridge and the solvent removed under reduced pressure. Purification of the residue via silica gel column chromatography (0-100% EtOAc/isohexane) gave tert-butyl 2-(2,6-difluorophenyl)-4-(1-ethyl-5-(4-(2,2,2-trifluoroacetamido)azepan-1-yl)-1H-pyrazol-4-ylcarbamoyl)thiazol-5-ylcarbamate as a colourless solid (170 mg, 68%). $^1$H-NMR (400 MHz, CDCl$_3$) δ 10.39 (s, 1H), 8.75 (s, 1H), 7.95 (s, 1H), 7.42-7.33 (m, 1H), 7.12-7.02 (m, 2H), 6.35 (d, J=8 Hz, 1H), 4.25-4.13 (m, 1H), 4.05 (q, J=7 Hz, 2H), 3.45-3.25 (m, 2H), 3.23-3.10 (m, 2H), 2.25-1.65 (m, 6H), 1.56 (s, 9H), 1.45 (t, J=7 Hz, 3H).

Example 71

(R)-tert-Butyl 2-(2,6-difluorophenyl)-4-(1-ethyl-5-(4-(2,2,2-trifluoroacetamido)azepan-1-yl)-1H-pyrazol-4-ylcarbamoyl)thiazol-5-ylcarbamate

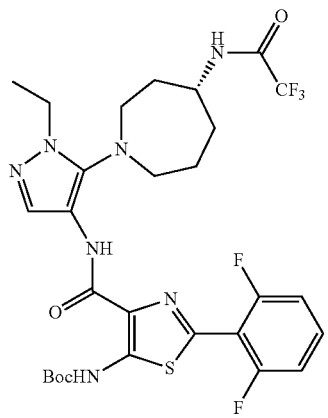 [SMILES: CCn1ncc(NC(=O)c2nc(-c3c(F)cccc3F)sc2NC(=O)OC(C)(C)C)c1N1CCC[C@@H](NC(=O)C(F)(F)F)CC1]

Following the procedure for Example 517 starting with (R)—N-(1-(1-ethyl-4-nitro-1H-pyrazol-5-yl)azepan-4-yl)-2,2,2-trifluoroacetamide and 5-(tert-butoxycarbonylamino)-2-(2,6-difluorophenyl)thiazole-4-carboxylic acid gave (R)-tert-butyl 2-(2,6-difluorophenyl)-4-(1-ethyl-5-(4-(2,2,2-trifluoroacetamido)azepan-1-yl)-1H-pyrazol-4-ylcarbamoyl)thiazol-5-ylcarbamate as a cream solid (0.148 g, 76%). $^1$H-NMR (400 MHz, CDCl$_3$) δ 10.40 (s, 1H), 8.76 (s, 1H), 7.95 (s, 1H), 7.43-7.34 (m, 1H), 7.12-7.02 (m, 2H), 6.37 (d, J=8 Hz, 1H), 4.23-4.16 (m, 1H), 4.05 (q, J=7 Hz, 2H), 3.43-3.31 (m, 2H), 3.25-3.15 (m, 2H), 2.22-2.05 (m, 2H), 2.03-1.89 (m, 2H), 1.89-1.72 (m, 2H), 1.57 (m, 12H).

Example 72

(S)-tert-Butyl 2-(2,6-difluorophenyl)-4-(1-ethyl-5-(4-(2,2,2-trifluoroacetamido)azepan-1-yl)-1H-pyrazol-4-ylcarbamoyl)thiazol-5-ylcarbamate

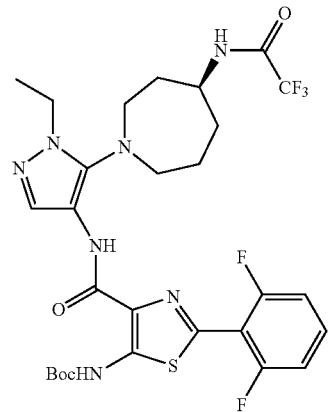 [SMILES: CCn1ncc(NC(=O)c2nc(-c3c(F)cccc3F)sc2NC(=O)OC(C)(C)C)c1N1CCC[C@H](NC(=O)C(F)(F)F)CC1]

Following the procedure for Example 517 starting with (S)—N-(1-(1-ethyl-4-nitro-1H-pyrazol-5-yl)azepan-4-yl)-2,2,2-trifluoroacetamide and 5-(tert-butoxycarbonylamino)-2-(2,6-difluorophenyl)thiazole-4-carboxylic acid gave (S)-tert-butyl 2-(2,6-difluorophenyl)-4-(1-ethyl-5-(4-(2,2,2-trifluoroacetamido)azepan-1-yl)-1H-pyrazol-4-ylcarbamoyl)thiazol-5-ylcarbamate as a cream solid (151 mg, 66%). $^1$H-NMR (400 MHz, CDCl$_3$) δ 10.40 (s, 1H), 8.75 (s, 1H), 7.95 (s, 1H), 7.45-7.34 (m, 1H), 7.12-7.02 (m, 2H), 6.37 (d, J=8 Hz, 1H), 4.23-4.16 (m, 1H), 4.05 (q, J=7 Hz, 2H), 3.43-3.31 (m, 2H), 3.25-3.15 (m, 2H), 2.22-2.05 (m, 2H), 2.03-1.89 (m, 2H), 1.89-1.72 (m, 2H), 1.55 (s, 9H), 1.46 (t, J=7 Hz, 3H).

Example 73

(R)-tert-Butyl 2-(2,6-difluorophenyl)-4-(1-cyclopropylmethyl-5-(4-(2,2,2-trifluoroacetamido)azepan-1-yl)-1H-pyrazol-4-ylcarbamoyl)thiazol-5-ylcarbamate

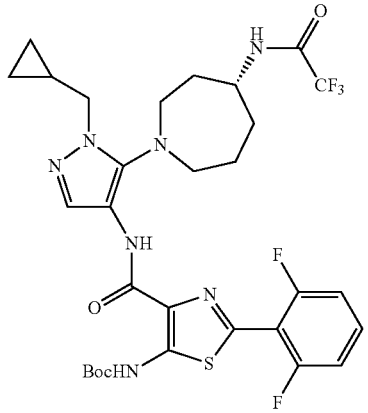 [SMILES: CC(C)(C)OC(=O)Nc1sc(-c2c(F)cccc2F)nc1C(=O)Nc1cnn(CC2CC2)c1N1CCC[C@@H](NC(=O)C(F)(F)F)CC1]

Following the procedure for Example 517 starting with (R)—N-(1-(1-cyclopropylmethyl-4-nitro-1H-pyrazol-5-yl)azepan-4-yl)-2,2,2-trifluoroacetamide and 5-(tert-butoxycarbonylamino)-2-(2,6-difluorophenyl)thiazole-4-carboxylic acid gave (R)-tert-butyl 2-(2,6-difluorophenyl)-4-(1-cyclopropylmethyl-5-(4-(2,2,2-trifluoroacetamido)azepan-1-yl)-1H-pyrazol-4-ylcarbamoyl)thiazol-5-ylcarbamate as a cream solid (136 mg, 77%). ¹H-NMR (400 MHz, CDCl₃) δ 10.39 (s, 1H), 8.75 (s, 1H), 7.95 (s, 1H), 7.41-7.36 (m, 1H), 7.10-7.02 (m, 2H), 6.37 (d, J=8 Hz, 1H), 4.25-4.10 (m, 1H), 3.90-3.83 (m, 2H), 3.43-3.31 (m, 2H), 3.30-3.15 (m, 2H), 2.25-2.05 (m, 2H), 2.03-1.70 (m, 4H), 1.57 (s, 9H) 1.35-1.20 (m, 1H), 0.64-0.59 (m, 2H), 0.43-0.38 (m, 2H).

Example 74

(R)-tert-Butyl 2-(2,6-difluorophenyl)-4-(1-cyclopropyl-5-(4-(2,2,2-trifluoroacetamido)azepan-1-yl)-1H-pyrazol-4-ylcarbamoyl)thiazol-5-ylcarbamate

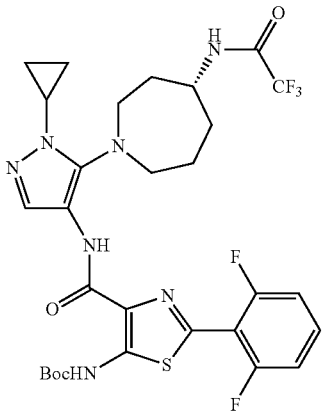 [SMILES: CC(C)(C)OC(=O)Nc1sc(-c2c(F)cccc2F)nc1C(=O)Nc1cnn(C2CC2)c1N1CCC[C@@H](NC(=O)C(F)(F)F)CC1]

Following the procedure for Example 517 starting with (R)—N-(1-(1-cyclopropyl-4-nitro-1H-pyrazol-5-yl)azepan-4-yl)-2,2,2-trifluoroacetamide and 5-(tert-butoxycarbonylamino)-2-(2,6-difluorophenyl)thiazole-4-carboxylic acid gave (R)-tert-butyl 2-(2,6-difluorophenyl)-4-(1-cyclopropyl-5-(4-(2,2,2-trifluoroacetamido)azepan-1-yl)-1H-pyrazol-4-ylcarbamoyl)thiazol-5-ylcarbamate as a cream solid (142 mg, 73%). ¹H-NMR (400 MHz, CDCl₃) δ 10.40 (s, 1H), 8.76 (s, 1H), 7.87 (s, 1H), 7.41-7.34 (m, 1H), 7.10-7.00 (m, 2H), 6.39 (d, J=8 Hz, 1H), 4.25-4.15 (m, 1H), 3.45-3.36 (m, 3H), 3.35-3.15 (m, 2H), 2.25-2.12 (m, 1H), 2.10-1.70 (m, 5H), 1.55 (s, 9H), 1.35-1.15 (m, 2H), 1.10-1.00 (m, 2H).

Example 75

(R)-tert-Butyl 2-(2-fluorophenyl)-4-(1-ethyl-5-(4-(2,2,2-trifluoroacetamido)azepan-1-yl)-1H-pyrazol-4-ylcarbamoyl)thiazol-5-ylcarbamate

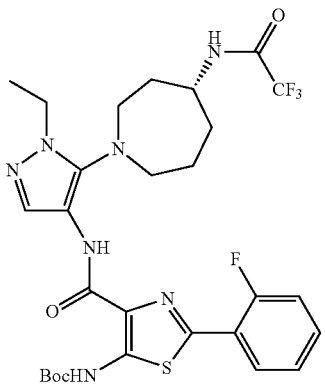 [SMILES: CCn1ncc(NC(=O)c2nc(-c3ccccc3F)sc2NC(=O)OC(C)(C)C)c1N1CCC[C@@H](NC(=O)C(F)(F)F)CC1]

Following the procedure for Example 506 starting with (R)—N-(1-(1-ethyl-4-nitro-1H-pyrazol-5-yl)azepan-4-yl)-2,2,2-trifluoroacetamide and 5-(tert-butoxycarbonylamino)-2-(2-fluorophenyl)thiazole-4-carboxylic acid gave (R)-tert-butyl 2-(2-fluorophenyl)-4-(1-ethyl-5-(4-(2,2,2-trifluoroacetamido)azepan-1-yl)-1H-pyrazol-4-ylcarbamoyl)thiazol-5-ylcarbamate as a cream solid (330 mg, 72%). ¹H-NMR (400 MHz, CDCl₃) δ 10.37 (s, 1H), 8.66 (s, 1H), 8.15-8.05 (m, 1H), 7.45-7.35 (m, 1H), 7.30-7.15 (m, 3H), 6.31 (d, J=8 Hz, 1H), 4.25-4.15 (m, 1H), 4.07 (q, J=7 Hz, 2H), 3.43-3.31 (m, 2H), 3.25-3.15 (m, 2H), 2.25-2.10 (m, 2H), 2.10-1.70 (m, 4H), 1.57 (s, 9H) 1.47 (t, J=7 Hz, 3H).

Example 76

(R)-tert-Butyl 2-(2-fluorophenyl)-4-(1-cyclopropylmethyl-5-(4-(2,2,2-trifluoroacetamido)azepan-1-yl)-1H-pyrazol-4-ylcarbamoyl)thiazol-5-ylcarbamate

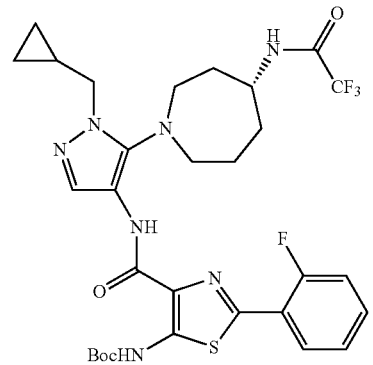 [SMILES: CC(C)(C)OC(=O)Nc1sc(-c2ccccc2F)nc1C(=O)Nc1cnn(CC2CC2)c1N1CCC[C@@H](NC(=O)C(F)(F)F)CC1]

Following the procedure for Example 506 starting with (R)—N-(1-(1-cyclopropylmethyl-4-nitro-1H-pyrazol-5-yl)azepan-4-yl)-2,2,2-trifluoroacetamide 5-(tert-butoxycarbonylamino)-2-(2-fluorophenyl)thiazole-4-carboxylic acid gave (R)-tert-butyl 2-(2-fluorophenyl)-4-(1-cyclopropylmethyl-5-(4-(2,2,2-trifluoroacetamido)azepan-1-yl)-1H-pyrazol-4-ylcarbamoyl)thiazol-5-ylcarbamate as a cream solid (350 mg, 70%). ¹H-NMR (400 MHz, CDCl₃) δ 10.36 (s, 1H), 8.66 (s, 1H), 8.15-8.05 (m, 1H), 7.45-7.35 (m, 1H), 7.28-7.15 (m, 3H), 6.31 (d, J=7.5 Hz, 1H), 4.25-4.15 (m, 1H), 3.95-3.85 (m, 2H), 3.43-3.30 (m, 2H), 3.28-3.15 (m, 2H), 2.25-2.08 (m, 2H), 2.08-1.70 (m, 4H), 1.55 (s, 9H), 1.35-1.20 (m, 1H), 0.70-0.60 (m, 2H), 0.50-0.35 (m, 2H).

Example 77

(R)-tert-Butyl 2-(2-fluorophenyl)-5-(4-(2,2,2-trifluoroacetamido)azepan-1-yl)-1H-pyrazol-4-ylcarbamoyl)thiazol-5-ylcarbamate

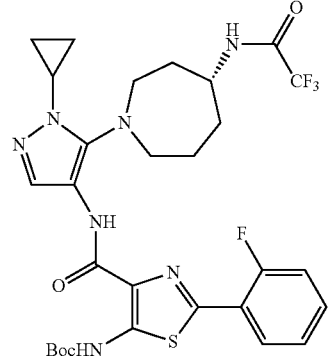 [SMILES: CC(C)(C)OC(=O)Nc1sc(-c2ccccc2F)nc1C(=O)Nc1cnn(C2CC2)c1N1CCC[C@@H](NC(=O)C(F)(F)F)CC1]

Following the procedure for Example 506 starting with (R)—N-(1-(1-cyclopropyl-4-nitro-1H-pyrazol-5-yl)azepan-4-yl)-2,2,2-trifluoroacetamide and 5-(tert-butoxycarbonylamino)-2-(2-fluorophenyl)thiazole-4-carboxylic acid gave (R)-tert-butyl 2-(2-fluorophenyl)-4-(1-cyclopropyl-5-(4-(2,2,2-trifluoroacetamido)azepan-1-yl)-1H-pyrazol-4-ylcarbamoyl)thiazole-5-ylcarbamate as a cream solid (370 mg, 76%). $^1$H-NMR (400 MHz, CDCl$_3$) δ 10.36 (s, 1H), 8.69 (s, 1H), 8.12-8.00 (m, 1H), 7.45-7.30 (m, 1H), 7.28-7.15 (m, 3H), 6.40-6.27 (m, 1H), 4.30-4.15 (m, 1H), 3.43-3.15 (m, 5H), 2.25-1.75 (m, 6H), 1.55 (s, 9H), 1.35-1.15 (m, 2H), 1.10-0.95 (m, 2H).

Example 78 tert-Butyl (1-(4-amino-1-methyl-1H-pyrazol-5-yl)piperidin-4-yl)methylcarbamate

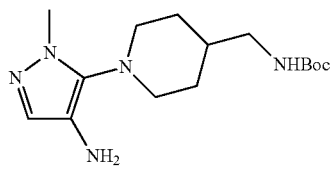

A solution of 5-chloro-1-methyl-4-nitro-1H-pyrazole (1.9 g, 11.77 mmol), 4-(boc-aminomethyl)piperidine (3.78 g, 17.66 mmol) and DIPEA (6.15 mL, 35.31 mmol) in EtOH (20 mL) was heated in a microwave at 130° C. for 1 hr. The solvent was removed under reduced pressure and the residue re-dissolved in DCM. The organic layer was washed with water, passed through a phase separation cartridge and concentrated under reduced pressure. The residue was purified via silica gel column chromatography (0-100% EtOAc/isohexane) to yield tert-butyl (1-(1-methyl-4-nitro-1H-pyrazol-5-yl)piperidin-4-yl)methylcarbamate as a yellow solid (3.95 g, 98%). To a solution of this solid (3.84 g, 11.30 mmol) in MeOH (125 mL) was added 10% Pd/C (0.42 g, 3.96 mmol) and ammonium formate (2.85 g, 45.2 mmol). The mixture was heated at 80° C. for 2.5 hr. The mixture was concentrated under reduced pressure and the residue was re-dissolved in EtOAc and washed with water. The organic layer was passed through a phase separation cartridge and concentrated under reduced pressure to give tert-butyl (1-(4-amino-1-methyl-1H-pyrazol-5-yl)piperidin-4-yl)methylcarbamate as a brown oil (3.49 g, 99%). $^1$H NMR (400 MHz, CDCl$_3$) δ 7.04 (s, 1H), 4.63 (s, 1H), 3.64 (s, 3H), 3.11-3.07 (m, 6H), 2.67 (s, 2H), 1.77 (d, J=12.8 Hz, 2H), 1.45 (s, 9H), 1.39-1.26 (m, 2H). 1H hidden by water peak.

Example 79 tert-Butyl 4-(5-(4-(butyloxycarbonylaminomethyl)piperidin-1-yl)-1-methyl-1H-pyrazol-4-ylcarbamoyl)-2-bromothiazol-5-ylcarbamate

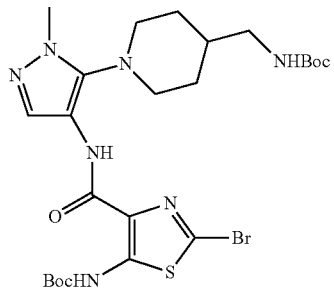 [SMILES: Cn1ncc(NC(=O)c2nc(Br)sc2NC(=O)OC(C)(C)C)c1N1CCC(CNC(=O)OC(C)(C)C)CC1]

A solution of PyBOP (2.84 g, 5.46 mmol) and 2-bromo-5-(tert-butoxycarbonylamino)thiazole-4-carboxylic acid (1.39 g, 4.29 mmol) in DCM (10 mL) was stirred at room temperature for 30 min. A solution of tert-butyl (1-(4-amino-1-methyl-1H-pyrazol-5-yl)piperidin-4-yl)methylcarbamate (1.2 g, 3.90 mmol) and DIPEA (1.1 mL, 6.24 mmol) in DCM (20 mL) was added and the mixture stirred at room temperature for 16 hr. The mixture was diluted with DCM and washed with water. The organic layer was separated, passed through a phase separation cartridge and concentrated under reduced pressure. The residue was purified via silica gel column chromatography (0-100% EtOAc/isohexane) to yield tert-butyl 4-(5-(4-(butyloxycarbonylaminomethyl)piperidin-1-yl)-1-methyl-1H-pyrazol-4-ylcarbamoyl)-2-bromothiazol-5-ylcarbamate as a pink solid (2.32 g, 96%). $^1$H NMR (400 MHz, d$_6$-DMSO) δ 10.62 (s, 1H), 9.64 (s, 1H), 7.23 (s, 1H), 6.86 (t, J=5.8 Hz, 1H), 3.62 (s, 3H), 3.07 (d, J=11.4 Hz, 2H), 2.95 (t, J=11.5 Hz, 2H), 2.87 (t, J=6.3 Hz, 2H), 1.67 (d, J=12.3 Hz, 2H), 1.52 (s, 9H), 1.45 (s, 1H), 1.40 (s, 9H), 1.27-1.16 (m, 2H).

Example 80

5-(tert-Butoxycarbonylamino)-2-(2,6-difluoro-3-methoxyphenyl)thiazole-4-carboxylic acid

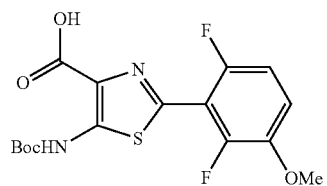 [SMILES: COc1ccc(F)c(-c2nc(C(=O)O)c(NC(=O)OC(C)(C)C)s2)c1F]

Following the procedure for Examples 19-23 starting with 2,6-difluoro-3-methoxybenzoyl chloride gave 5-(tert-butoxycarbonylamino)-2-(2,6-difluoro-3-methoxyphenyl)thiazole-4-carboxylic acid as a pale yellow solid (120 mg, 70%). $^1$H NMR (400 MHz, d$_6$-DMSO) δ 7.32-7.23 (m, 1H), 7.22-7.15 (m, 1H), 3.88 (s, 3H), 1.49 (s, 9H).

Example 81

(R)-Benzyl 1-(4-(5-tert-butoxycarbonyl-amino-2-bromothiazole-4-carboxamido)-1-methyl-1H-pyrazol-5-yl)azepan-4-ylcarbamate

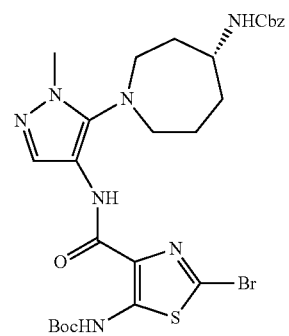 [SMILES: Cn1ncc(NC(=O)c2nc(Br)sc2NC(=O)OC(C)(C)C)c1N1CCC[C@@H](NC(=O)OCc2ccccc2)CC1]

A solution of PyBOP (1.31 g, 2.52 mmol) and 2-bromo-5-(tert-butoxycarbonylamino)thiazole-4-carboxylic acid (0.61 g, 1.89 mmol) in DCM (20 mL) was stirred at room temperature for 30 min. A solution of (R)-benzyl azepan-4-ylcarbamate (0.62 g, 1.80 mmol) and DIPEA (0.5 mL, 2.88 mmol) in DCM (20 mL) was added and the mixture stirred at room temperature for 16 hr. The mixture was diluted with DCM and washed with water. The organic layer was separated, passed through a phase separation cartridge and concentrated under reduced pressure. The residue was purified via silica gel column chromatography (0-100% EtOAc/hexane) to yield (R)-benzyl 1-(4-(5-tert-butoxycarbonyl-amino-2-bromothiazole-4-carboxamido)-1-methyl-1H-pyrazol-5-yl)azepan-4-ylcarbamate as a pink solid (1.04 g, 89%). $^1$H NMR (400 MHz, CDCl$_3$) δ 10.28 (s, 1H), 8.40 (s, 1H), 7.75 (s, 1H), 7.38-7.27 (m, 5H), 5.09 (s, 2H), 5.00-4.92 (m, 1H), 3.91-3.84 (m, 1H), 3.73 (s, 3H), 3.36-3.24 (m, 2H), 3.15-3.04 (m, 2H), 2.19-2.03 (m, 2H), 1.96-1.79 (m, 3H), 1.75-1.63 (m, 1H), 1.52 (s, 9H).

Example 82

(R)-tert-Butyl 2-bromo-4-(1-methyl-5-(4-(2,2,2-trifluoroacetamido)azepan-1-yl)-1H-pyrazol-4-ylcarbamoyl)thiazol-5-ylcarbamate

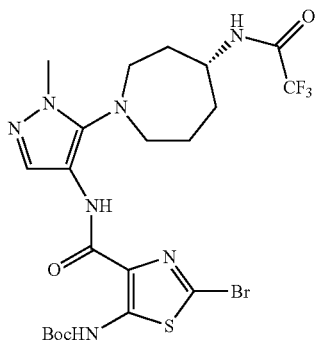 [SMILES: Cn1ncc(NC(=O)c2nc(Br)sc2NC(=O)OC(C)(C)C)c1N1CCC[C@@H](NC(=O)C(F)(F)F)CC1]

Following the procedure for Example 528 starting with 2-bromo-5-(tert-butoxycarbonylamino)thiazole-4-carboxylic acid and (R)—N-(azepan-4-yl)-2,2,2-trifluoroacetamide gave (R)-tert-butyl 2-bromo-4-(1-methyl-5-(4-(2,2,2-trifluoroacetamido)azepan-1-yl)-1H-pyrazol-4-ylcarbamoyl)thiazol-5-ylcarbamate as a salmon solid (500 mg, 74%). $^1$H NMR (400 MHz, CDCl$_3$) δ 10.27 (s, 1H), 8.38 (s, 1H), 7.74 (s, 1H), 6.41 (d, J=8.2 Hz, 1H), 4.23-4.15 (m, 1H), 3.75 (s, 3H), 3.38-3.29 (m, 2H), 3.22-3.08 (m, 2H), 2.22-2.08 (m, 2H), 2.03-1.93 (m, 2H), 1.88-1.69 (m, 2H), 1.52 (s, 9H).

Example 83

(R)4-(benzyloxycarbonylamino)azepane or (S)4-(benzyloxycarbonylamino)azepane

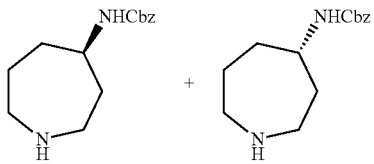 [SMILES: O=C(N[C@@H]1CCCNCC1)OCc1ccccc1 ; O=C(N[C@H]1CCCNCC1)OCc1ccccc1]

To a 250 mL 3-neck-round bottom flask was added tert-butyl 4-aminoazepane-1-carboxylate (8.80 g, 41.0 mmol), triethylamine (29 mL, 0.21 mol) and methylene chloride (20 mL). The mixture was cooled to −20° C. and benzyl chloroformate (8.4 g, 49 mmol) was added dropwise via a syringe over 10 min. The heterogeneous mixture was warmed to room temperature and stirred for 2 h. The reaction was monitored by LCMS and upon completion of the reaction, the solvent was distilled off and the crude product was purified via flash chromatography, heptane/ethyl acetate 10% to 30% to afford a white solid (6.0 g, 42%).

The racemic azepine was resolved using chiral SFC with a Chiralpak OJ-H (100×4.6 mm, 5 micron) column, 15% Methanol/CO$_2$, with a flow rate of 200 ml/min, pressure at 100 bars and at 40° C. for 5 min. to afford the two enantiomers ((R)-tert-butyl 4-(benzyloxycarbonylamino)azepane-1-carboxylate and (S)-tert-butyl 4-(benzyloxycarbonylamino)azepane-1-carboxylate).

To a 100 mL round bottom flask was added one of the enantiomers, dioxane (20 mL) and 12N HCl (4 mL). The mixture was stirred for 2 h and the solvent was distilled off. The product, an HCl salt, (2.2 g, 37%) of isomer 1 and (2.4 g, 40%) of isomer 2 was used directly in the next step.

Table 1 Formula I Compounds 101-157

Example 101

5-amino-2-(2,6-difluorophenyl)-N-(1H-pyrazol-4-yl)thiazole-4-carboxamide 101

Following the procedures as described in Example 113, 1H-pyrazol-4-amine, 5-(tert-butoxycarbonylamino)-2-(2,6-difluorophenyl)thiazole-4-carboxylic acid and HATU were reacted to give 101 as a white solid (63 mg, 78%) over two steps. $^1$H NMR (400 MHz, DMSO) δ 12.51 (s, 1H), 9.71 (s, 1H), 7.95 (s, 1H), 7.74 (s, 1H), 7.65-7.44 (m, 1H), 7.27 (t, J=8.4, 2H). ESIMS m/z=322.0 (M+1)

Example 102

5-amino-2-(2,6-difluorophenyl)-N-(1-methyl-1H-pyrazol-4-yl)thiazole-4-carboxamide 102

Following the procedures as described in Example 113, 1-methyl-1H-pyrazol-4-amine, 5-(tert-butoxycarbonylamino)-2-(2,6-difluorophenyl)thiazole-4-carboxylic acid and HATU were reacted to give 102 as a white solid (45 mg, 70%) over two steps. $^1$H NMR (400 MHz, DMSO) δ 9.78 (s, 1H), 8.00 (d, J=37.3, 1H), 7.70-7.47 (m, 4H), 7.28 (t, J=8.4, 2H), 3.81 (d, J=12.5, 3H). ESIMS m/z=336.1 (M+1)

Example 103

(S)-5-amino-N-(5-(3-aminopiperidin-1-yl)-1H-pyrazol-4-yl)-2-(2,6-difluorophenyl)thiazole-4-carboxamide 103

Following the procedures as described in Example 113, (S)-tert-butyl 1-(4-amino-1H-pyrazol-5-yl)piperidin-3-ylcarbamate, 5-(tert-butoxycarbonylamino)-2-(2,6-difluorophenyl)thiazole-4-carboxylic acid, and HATU were reacted to give 103 as a white solid (27 mg, 23%) over two steps. $^1$H NMR (400 MHz, DMSO) δ 11.90 (s, 1H), 8.48 (s, 1H), 7.86 (s, 1H), 7.54-7.49 (m, 2H), 7.28 (t, J=12 Hz, 2H), 3.19 (d, J=8 Hz, 1H), 3.09 (d, J=8 Hz, 1H), 2.82-2.77 (m, 1H), 2.67-2.60 (m, 1H), 2.43 (t, J=12 Hz, 1H), 1.84-1.81 (m, 1H), 1.75-1.55 (m, 2H), 1.15-1.08 (m, 1H). ESIMS m/z=420.1 (M+1)

Example 104

5-amino-2-(2-fluorophenyl)-N-(1-methyl-5-(piperidin-4-ylmethylamino)-1H-pyrazol-4-yl)thiazole-4-carboxamide 104

Following the procedures as described in Example 113, tert-butyl 4-((4-amino-1-methyl-1H-pyrazol-5-ylamino)methyl)piperidine-1-carboxylate and 5-(tert-butoxycarbonylamino)-2-(2-fluorophenyl)thiazole-4-carboxylic acid, and HATU were reacted to give 104 as a white solid (5.4 mg, 10%) over two steps. $^1$H NMR (400 MHz, DMSO) δ 9.06 (s, 1H), 8.32 (dd, J=15.5, 6.0, 2H), 7.52-7.24 (m, 6H), 4.95 (t, J=6.7, 1H), 3.61 (s, 4H), 2.96 (t, J=22.0, 3H), 2.82 (t, J=6.5, 2H), 1.77 (d, J=12.5, 2H), 1.58 (s, 1H), 1.25-1.04 (m, 2H). ESIMS m/z=430.1 (M+1)

Example 105

5-amino-2-(2,6-difluorophenyl)-N-(1-methyl-5-(piperidin-4-ylmethylamino)-1H-pyrazol-4-yl)thiazole-4-carboxamide 105

Following the procedures as described in Example 113, tert-butyl 4-((4-amino-1-methyl-1H-pyrazol-5-ylamino)methyl)piperidine-1-carboxylate, 5-(tert-butoxycarbonylamino)-2-(2,6-difluorophenyl)thiazole-4-carboxylic acid and HATU were reacted to give 105 as a white solid (4.4 mg, 7.4%) over two steps. $^1$H NMR (400 MHz, DMSO) δ 8.79 (s, 1H), 8.36 (s, 1H), 7.67-7.36 (m, 3H), 7.27 (t, J=8.6, 2H), 4.88 (t, J=6.5, 1H), 3.63-3.55 (m, 4H), 3.01 (d, J=12.2, 2H), 2.80 (t, J=6.5, 2H), 1.76 (d, J=11.1, 2H), 1.55 (s, 1H), 1.24-1.01 (m, 2H). ESIMS m/z=448.1 (M+1)

Example 106

(S)-5-amino-N-(5-(3-aminopiperidin-1-yl)-1-methyl-1H-pyrazol-4-yl)-2-(2,6-difluorophenyl)thiazole-4-carboxamide 106

Following the procedures as described in Example 113, (S)-tert-butyl 1-(1-methyl-4-amino-1H-pyrazol-5-yl)piperidin-3-ylcarbamate, 5-(tert-butoxycarbonylamino)-2-(2,6-difluorophenyl)thiazole-4-carboxylic acid, and HATU were reacted to give 106 as a white solid (32 mg, 11%) over two steps. $^1$H NMR (400 MHz, DMSO) δ 8.80 (s, 1H), 7.60-7.42 (m, 4H), 7.27 (t, J=8.7, 2H), 3.62 (d, J=10.3, 3H), 3.09 (dd, J=11.1, 3.3, 1H), 3.03-2.88 (m, 2H), 2.83 (t, J=8.7, 1H), 2.69 (dd, J=11.0, 8.5, 1H), 1.87-1.64 (m, 2H), 1.55 (d, J=8.9, 1H), 1.17 (dd, J=19.9, 9.3, 1H). ESIMS m/z=434.1 (M+1)

Example 107

(S)-5-amino-N-(5-(3-aminopiperidin-1-yl)-1-methyl-1H-pyrazol-4-yl)-2-(2-fluorophenyl)thiazole-4-carboxamide 107

Following the procedures as described in Example 113, (S)-tert-butyl 1-(1-methyl-4-amino-1H-pyrazol-5-yl)piperidin-3-ylcarbamate, 5-(tert-butoxycarbonylamino)-2-(2-fluorophenyl)thiazole-4-carboxylic acid, and HATU were reacted to give 107 as a white solid (36 mg, 13%) over two steps. $^1$H NMR (400 MHz, DMSO) δ 9.02 (s, 1H), 8.29 (dd, J=8.6, 7.0, 1H), 7.51-7.25 (m, 6H), 3.62 (d, J=13.9, 3H), 3.19-3.06 (m, 1H), 2.96 (dt, J=18.1, 10.4, 2H), 2.81 (d, J=9.0, 1H), 2.69 (dd, J=16.1, 7.5, 1H), 1.75 (dd, J=24.8, 8.7, 2H), 1.63-1.45 (m, 1H), 1.14 (dd, J=19.8, 9.2, 1H). ESIMS m/z=416.1 (M+1)

Example 108

5-amino-N-(5-(4-aminopiperidin-1-yl)-1-methyl-1H-pyrazol-4-yl)-2-(2,6-difluorophenyl)thiazole-4-carboxamide 108

Following the procedures as described in Example 113, tert-butyl 1-(1-methyl-4-amino-1H-pyrazol-5-yl)piperidin-4-ylcarbamate, 5-(tert-butoxycarbonylamino)-2-(2,6-difluorophenyl)thiazole-4-carboxylic acid, and HATU were reacted to give 108 as a white solid (27 mg, 21%) over two steps. $^1$H NMR (400 MHz, DMSO) δ 8.70 (s, 1H), 7.60-7.37 (m, 4H), 7.27 (t, J=8.7, 2H), 3.62 (s, 3H), 3.12-2.92 (m, 4H), 2.66 (dd, J=11.9, 8.2, 1H), 1.77 (d, J=9.5, 2H), 1.36 (td, J=15.3, 4.7, 2H). ESIMS m/z=434.1 (M+1).

Example 109

3-amino-N-(5-(4-aminopiperidin-1-yl)-1-methyl-1H-pyrazol-4-yl)-6-phenylpicolinamide 109

Following the procedures for Example 141, tert-butyl 1-(1-methyl-4-amino-1H-pyrazol-5-yl)piperidin-4-ylcarbamate, 3-amino-6-bromopicolinic acid and phenylboronic acid were converted to 109 as a white solid (9.2 mg, 10%) over three steps. $^1$H NMR (400 MHz, DMSO) δ 9.85 (s, 1H), 8.27 (s, 1H), 8.09 (d, J=7.3, 2H), 7.93 (d, J=8.8, 1H), 7.61 (s, 1H), 7.53-7.27 (m, 4H), 6.99 (s, 2H), 3.66 (d, J=6.5, 3H), 3.14 (dd, J=21.0, 9.8, 3H), 2.92 (s, 2H), 1.90 (d, J=10.4, 2H), 1.68-1.40 (m, 2H). ESIMS m/z=392.1 (M+1)

Example 110

3-amino-N-(5-(4-aminopiperidin-1-yl)-1-methyl-1H-pyrazol-4-yl)-6-(2-fluorophenyl)picolinamide 110

Following the procedures for Example 141, tert-butyl 1-(1-methyl-4-amino-1H-pyrazol-5-yl)piperidin-4-ylcarbamate and 3-amino-6-bromopicolinic acid were converted to 110 as a white solid (12 mg, 11%) over three steps. $^1$H NMR (400 MHz, DMSO) δ 9.81 (s, 1H), 8.06 (td, J=8.1, 1.9, 1H), 7.74 (dd, J=8.7, 2.2, 1H), 7.65 (s, 1H), 7.51-7.21 (m, 5H), 7.06 (s, 2H), 3.65 (d, J=7.3, 3H), 3.16-2.99 (m, 3H), 2.80-2.59 (m, 2H), 1.79 (d, J=9.9, 2H), 1.52-1.16 (m, 2H). ESIMS m/z=410.1 (M+1)

Example 111

(S)-3-amino-N-(5-(3-aminopiperidin-1-yl)-1-methyl-1H-pyrazol-4-yl)-6-(2-fluorophenyl)picolinamide 111

Following the procedures for Example 141, (S)-tert-butyl 1-(4-amino-1-methyl-1H-pyrazol-5-yl)piperidin-3-ylcarbamate and 3-amino-6-bromopicolinic acid were converted to 111 as a white solid (29 mg, 20%) over three steps. $^1$H NMR (400 MHz, DMSO) δ 9.80 (d, J=17.7, 1H), 8.06 (td, J=8.3, 1.9, 1H), 7.74 (dd, J=8.7, 2.2, 1H), 7.64 (d, J=12.2, 1H), 7.48-7.38 (m, 1H), 7.30 (ddd, J=8.1, 7.3, 3.7, 3H), 7.07 (s, 2H), 3.67 (s, 3H), 3.11 (dd, J=10.7, 3.4, 1H), 3.07-2.88 (m, 2H), 2.88-2.74 (m, 1H), 2.74 (s, 1H), 1.77 (ddd, J=33.8, 9.1, 4.0, 2H), 1.57 (dd, J=21.5, 11.7, 1H), 1.22-1.06 (m, 1H). ESIMS m/z=410.1 (M+1)

Example 112

(R)-3-amino-N-(5-(3-aminopiperidin-1-yl)-1-methyl-1H-pyrazol-4-yl)-6-(2-fluorophenyl)picolinamide 112

Following the procedures for Example 141, (R)-tert-butyl 1-(4-amino-1-methyl-1H-pyrazol-5-yl)piperidin-3-ylcarbamate and 3-amino-6-bromopicolinic acid were converted to 112 as a white solid (26 mg, 18%) over three steps. $^1$H NMR (400 MHz, DMSO) δ 9.80 (d, J=17.5, 1H), 8.06 (td, J=8.3, 1.8, 1H), 7.74 (dd, J=8.7, 2.2, 1H), 7.69-7.60 (m, 1H), 7.50-7.37 (m, 1H), 7.37-7.20 (m, 3H), 7.07 (s, 2H), 3.67 (s, 3H), 3.12 (dd, J=10.8, 3.4, 1H), 2.98 (qd, J=11.3, 5.0, 2H), 2.90-2.76 (m, 1H), 2.76-2.63 (m, 1H), 1.93-1.66 (m, 2H), 1.57 (dd, J=21.7, 12.5, 1H), 1.12 (td, J=13.0, 3.6, 1H). ESIMS m/z=410.1 (M+1)

Example 113

5-amino-N-(5-(4-aminoazepan-1-yl)-1-methyl-1H-pyrazol-4-yl)-2-(2,6-difluorophenyl)thiazole-4-carboxamide 113

To a 100 mL round bottom flask containing tert-butyl 1-(4-amino-1-methyl-1H-pyrazol-5-yl)azepan-4-ylcarbamate (410 mg, 1.32 mmol), 5-(tert-butoxycarbonylamino)-2-(2,6-difluorophenyl)thiazole-4-carboxylic acid (496 mg, 1.40 mmol) and HATU (1.51 g, 4.00 mmol) was added methylene chloride (20 mL) and diisopropylethylamine (1.30 g, 10.0 mmol). The reaction mixture was stirred for 24 hr at room temperature and the reaction was monitored by LCMS. Upon completion of the reaction, the solvent was distilled off and the crude material was purified via flash chromatography, heptane/ethyl acetate 20% to 95% to afford yellow oil (598 mg, 71%). In a 50 mL round bottom flask was added the amide (598 mg, 0.923 mmol), dioxane (10 mL) and hydrochloric acid (1 mL, 32.4 mmol). The mixture was stirred at 60° C. for 2 h, and the solvent was distilled off. The crude product was purified via reverse phase HPLC 40% to 80% MeOH in water with 0.1% NH$_4$OH to afford 113 as a white solid (90 mg, 22%). $^1$H NMR (400 MHz, DMSO) $^1$H NMR (400 MHz, DMSO) δ 8.75 (s, 1H), 8.46 (s, 1H), 7.61-7.43 (m, 3H), 7.27 (t, J=8.8, 2H), 3.65 (s, 3H), 3.19-3.04 (m, 6H), 1.99-1.70 (m, 2H), 1.59 (dd, J=14.1, 9.0, 3H). ESIMS m/z=448.1 (M+1)

Example 114

3-amino-N-(5-(4-aminoazepan-1-yl)-1-methyl-1H-pyrazol-4-yl)-6-(2-fluorophenyl)picolinamide 114

Following the procedures as described in Example 141, (R)-benzyl 1-(4-amino-1-methyl-1H-pyrazol-5-yl)azepan-4-ylcarbamate from Example 16, 3-amino-6-bromopicolinic acid, and 2-fluorophenylboronic acid were converted to 114 as a white solid (21 mg, 26%) over three steps. $^1$H NMR (400 MHz, DMSO) δ 9.72 (s, 1H), 8.05 (dd, J=11.3, 4.9, 1H), 7.75 (dd, J=8.8, 2.1, 1H), 7.32 (td, J=7.6, 3.7, 3H), 7.07 (s, 3H), 3.69 (s, 3H), 3.27-3.07 (m, 4H), 2.13-1.51 (m, 7H). ESIMS m/z=424.1 (M+1)

Example 115

5-amino-2-(2,6-difluorophenyl)-N-(1-methyl-5-(piperidin-4-ylmethoxy)-1H-pyrazol-4-yl)thiazole-4-carboxamide 115

Following the procedures as described in Example 113, (S)-tert-butyl 1-(4-amino-1-methyl-1H-pyrazol-5-yl)pyrrolidin-3-ylcarbamate, 5-(tert-butoxycarbonylamino)-2-(2,6-difluorophenyl)thiazole-4-carboxylic acid, and HATU were reacted to give 115 as a white solid (11 mg, 11%) over two steps. $^1$H NMR (400 MHz, DMSO) δ 8.69 (s, 1H), 8.34 (s, 1H), 7.70-7.40 (m, 3H), 7.38 (s, 1H), 7.26 (t, J=8.6, 1H), 3.99 (d, J=6.1, 2H), 3.68-3.54 (m, 3H), 3.04 (d, J=12.5, 3H), 2.70-2.53 (m, 2H), 1.99-1.66 (m, 2H), 1.27 (dd, J=21.3, 12.3, 2H). ESIMS m/z=449.1 (M+1)

Example 116

3-amino-6-(2-fluorophenyl)-N-(1-methyl-5-(piperidin-4-yloxy)-1H-pyrazol-4-yl)picolinamide 116

Following the procedures for Example 141, tert-butyl 4-(4-amino-1-methyl-1H-pyrazol-5-yloxy)piperidine-1-carboxylate and 3-amino-6-bromopicolinic acid were coupled and the intermediate amide was reacted with 2-fluorophenylboronic acid under palladium catalyzed Suzuki conditions to give 116 as a white solid (10 mg, 14%) over three steps. $^1$H NMR (400 MHz, DMSO) δ 9.67 (s, 1H), 8.05 (t, J=7.5, 1H), 7.73 (dd, J=8.8, 1.9, 1H), 7.66-7.38 (m, 3H), 7.38-7.25 (m, 3H), 7.03 (s, 2H), 4.43-4.20 (m, 1H), 3.63 (s, 3H), 2.96-2.79 (m, 2H), 2.39 (dd, J=26.9, 16.6, 2H), 1.92 (d, J=12.0, 2H), 1.55 (td, J=13.2, 3.9, 2H). ESIMS m/z=411.1 (M+1)

Example 117

3-amino-6-(2-fluorophenyl)-N-(1-methyl-5-(piperidin-4-ylmethoxy)-1H-pyrazol-4-yl)picolinamide 117

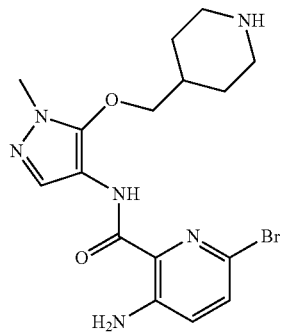 [SMILES: Cn1ncc(NC(=O)c2nc(Br)ccc2N)c1OCC1CCNCC1]

Following the procedures for Example 141, tert-butyl 4-((4-amino-1-methyl-1H-pyrazol-5-yloxy)methyl)piperidine-1-carboxylate and 3-amino-6-bromopicolinic acid were reacted to give 3-amino-6-bromo-N-(1-methyl-5-(piperidin-4-ylmethoxy)-1H-pyrazol-4-yl)picolinamide, which was reacted with 2-fluorophenylboronic acid under palladium catalyzed Suzuki conditions to give 117 as a white solid (6.7 mg, 7.2%) over three steps. $^1$H NMR (400 MHz, DMSO) δ 9.66 (s, 1H), 8.10 (t, J=7.2, 1H), 7.71 (dt, J=37.9, 19.0, 1H), 7.60-7.25 (m, 5H), 7.03 (s, 2H), 3.97 (d, J=6.2, 2H), 3.72-3.42 (m, 3H), 2.76 (t, J=31.9, 2H), 2.36 (t, J=12.2, 2H), 1.88-1.53 (m, 3H), 1.25-0.99 (m, 2H). ESIMS m/z=425.1 (M+1)

Example 118

3-amino-N-(5-(4-aminopiperidin-1-yl)-1-methyl-1H-pyrazol-4-yl)-6-bromopyrazine-2-carboxamide 118

Following the procedures for Example 141, tert-butyl 1-(4-amino-1-methyl-1H-pyrazol-5-yl)piperidin-4-amine was converted to 118 as a white solid (0.83 mg, 0.5%) over two steps. ESIMS m/z=396.1 (M+1)

Example 119

(S)-3-amino-N-(5-(3-aminopiperidin-1-yl)-1-methyl-1H-pyrazol-4-yl)-6-(2-fluorophenyl)pyrazine-2-carboxamide 119

To a 50 mL round bottom flask containing (S)-tert-butyl 1-(4-amino-1-methyl-1H-pyrazol-5-yl)piperidin-3-ylcarbamate (100 mg, 0.34 mmol), 3-amino-6-bromopyrazine-2-carboxylic acid (111 mg, 0.51 mmol) and HATU (0.39 g, 1.02 mmol) was added methylene chloride (10 mL) and diisopropylethylamine (0.18 g, 1.35 mmol). The reaction mixture was stirred for 24 hr at room temperature and the reaction was monitored by LCMS. Upon completion of the reaction, the solvent was distilled off and the crude material was purified via flash chromatography, heptane/ethyl acetate 20% to 95% to afford the coupled product amide as a white solid (153 mg, 91%).

To a 10 mL microwave vial was added the amide (153 mg, 0.31 mmol), 2-fluorophenylboronic acid (130 mg, 0.93 mmol), dichloro[1,1'-bis(diphenylphosphino)ferrocene]palladium(II) (50 mg, 0.062 mmol), a 2M solution of $Na_2CO_3$ (1 mL) and 1,2-dimethoxyethane (3 mL). The mixture was irradiated to 130° C. with a microwave for 30 min and the mixture was cooled, concentrated and purified via flash chromatography, heptane/ethyl acetate 20% to 95% to afford the Boc-aminopiperidine intermediate as a brown oil.

To a 50 mL round bottom flask was added the Boc-aminopiperidine intermediate, dioxane (4 mL) and hydrochloric acid (0.5 mL, 16 mmol). The mixture was stirred at 60° C. for 2 h, and the solvent was distilled off. The crude product was purified via reverse phase HPLC 40% to 80% MeOH in water with 0.1% $NH_4OH$ to afford 119 as obtained as a white solid (9.0 mg, 9.5%) over two steps. $^1$H NMR (400 MHz, DMSO) δ 8.69 (d, J=2.3, 1H), 8.16 (t, J=7.9, 1H), 7.74 (s, 2H), 7.58-7.41 (m, 2H), 7.35 (dd, J=13.7, 5.5, 2H), 3.66 (s, 3H), 3.13 (d, J=7.7, 2H), 3.05-2.76 (m, 4H), 2.70 (dd, J=18.8, 10.2, 1H), 1.89-1.65 (m, 2H), 1.56 (d, J=10.4, 1H), 1.24-1.05 (m, 1H). ESIMS m/z=411.1 (M+1)

Example 120

5-amino-2-(2,6-difluorophenyl)-N-(1-methyl-5-(piperidin-4-yloxy)-1H-pyrazol-4-yl)thiazole-4-carboxamide 120

Following the procedures as described in Example 113, tert-butyl 4-(4-amino-1-methyl-1H-pyrazol-5-yloxy)piperidine-1-carboxylate, 5-(tert-butoxycarbonylamino)-2-(2,6-difluorophenyl)thiazole-4-carboxylic acid, and HATU were reacted to give 120 as a white solid (20 mg, 9.0%) over two steps. $^1$H NMR (400 MHz, DMSO) δ 8.62 (s, 1H), 7.64-7.40 (m, 3H), 7.27 (t, J=8.7, 2H), 4.39-4.11 (m, 1H), 3.60 (s, 3H), 2.94 (dt, J=12.5, 3.9, 2H), 2.50-2.40 (m, 2H), 2.03-1.81 (m, 2H), 1.53 (td, J=13.2, 4.0, 2H). ESIMS m/z=435.1 (M+1).

Example 121

(S)-3-amino-N-(5-(3-aminopiperidin-1-yl)-1-methyl-1H-pyrazol-4-yl)-6-bromopyrazine-2-carboxamide 121

Following the procedures for Example 141, (S)-tert-butyl 1-(4-amino-1-methyl-1H-pyrazol-5-yl)piperidin-3-ylcarbamate was converted to 121 as a white solid (153 mg, 91%) over two steps. ESIMS m/z=396.1 (M+1)

Example 122

3-amino-N-(5-(4-aminopiperidin-1-yl)-1-methyl-1H-pyrazol-4-yl)-6-(2-fluorophenyl)pyrazine-2-carboxamide 122

Following the procedures for Example 141, Boc-protected 1-(4-amino-1-methyl-1H-pyrazol-5-yl)piperidin-4-amine, the title compound was converted to 122 as a white solid (9.0 mg, 9.5%) over three steps. $^1$H NMR (400 MHz, DMSO) δ 8.69 (d, J=2.3, 1H), 8.16 (t, J=7.9, 1H), 7.74 (s, 2H), 7.58-7.41 (m, 2H), 7.35 (dd, J=13.7, 5.5, 2H), 3.66 (s, 3H), 3.13 (d, J=7.7, 2H), 3.05-2.76 (m, 4H), 2.70 (dd, J=18.8, 10.2, 1H), 1.89-1.65 (m, 2H), 1.56 (d, J=10.4, 1H), 1.24-1.05 (m, 1H). ESIMS m/z=411.1 (M+1)

Example 123

(S)-3-amino-N-(5-(3-aminopiperidin-1-yl)-1-methyl-1H-pyrazol-4-yl)-6-chloropyrazine-2-carboxamide 123

Following the procedures for Example 141, (S)-tert-butyl 1-(4-amino-1-methyl-1H-pyrazol-5-yl)piperidin-3-ylcarbamate was converted to 123 as a white solid (4.4 mg, 40%) over two steps. ESIMS m/z=351.1 (M+1)

Example 124

(R)-3-amino-N-(5-(3-aminopyrrolidin-1-yl)-1-methyl-1H-pyrazol-4-yl)-6-(2-fluorophenyl)picolinamide 124

Following the procedures for Example 141, (R)-tert-butyl 1-(4-amino-1-methyl-1H-pyrazol-5-yl)pyrrolidin-3-ylcarbamate and 3-amino-6-bromopicolinic acid were converted to 124 as a white solid (36 mg, 32%) over three steps. $^1$H NMR (400 MHz, DMSO) δ 7.96 (td, J=8.3, 1.7, 1H), 7.81-7.66 (m, 2H), 7.53-7.23 (m, 4H), 7.03 (s, 2H), 3.65 (s, 3H), 3.44 (m, 3H), 2.81 (dt, J=69.2, 34.6, 1H), 1.96 (tt, J=21.1, 10.6, 2H), 1.65 (ddd, J=16.0, 7.6, 4.0, 1H). ESIMS m/z=396.1 (M+1)

Example 125

(S)-3-amino-N-(5-(3-aminopyrrolidin-1-yl)-1-methyl-1H-pyrazol-4-yl)-6-(2-fluorophenyl)picolinamide 125

Following the procedures for Example 141, (S)-tert-butyl 1-(4-amino-1-methyl-1H-pyrazol-5-yl)pyrrolidin-3-ylcarbamate and 3-amino-6-bromopicolinic acid were converted to 125 as a white solid (50 mg, 44%) over three steps. $^1$H NMR (400 MHz, DMSO) δ 7.96 (td, J=8.3, 1.8, 1H), 7.81-7.59 (m, 2H), 7.55-7.12 (m, 4H), 7.03 (s, 2H), 3.65 (s, 3H), 3.44 (m, 4H), 2.85 (dd, J=9.4, 2.8, 1H), 1.96 (tt, J=21.1, 10.6, 1H), 1.77-1.49 (m, 1H). ESIMS m/z=396.1 (M+1)

Example 126

(R)-5-amino-N-(5-(3-aminopyrrolidin-1-yl)-1-methyl-1H-pyrazol-4-yl)-2-(2,6-difluorophenyl)thiazole-4-carboxamide 126

Following the procedures as described in Example 113, (R)-tert-butyl 1-(4-amino-1-methyl-1H-pyrazol-5-yl)pyrrolidin-3-ylcarbamate, 5-(tert-butoxycarbonylamino)-2-(2,6-difluorophenyl)thiazole-4-carboxylic acid, and HATU were reacted to give 126 as a white solid (38 mg, 32%) over two steps. $^1$H NMR (400 MHz, DMSO) δ 7.67 (d, J=19.5, 1H), 7.62-7.45 (m, 3H), 7.28 (t, J=8.7, 2H), 3.63 (s, 3H), 3.53 (s, 1H), 3.20 (dt, J=8.9, 4.4, 2H), 2.84 (d, J=10.2, 2H), 2.05-1.84 (m, 2H), 1.75 (s, 2H). ESIMS m/z=420.1 (M+1)

Example 127

(S)-5-amino-N-(5-(3-aminopyrrolidin-1-yl)-1-methyl-1H-pyrazol-4-yl)-2-(2,6-difluorophenyl)thiazole-4-carboxamide 127

Following the procedures as described in Example 113, (S)-tert-butyl 1-(4-amino-1-methyl-1H-pyrazol-5-yl)pyrrolidin-3-ylcarbamate, 5-(tert-butoxycarbonylamino)-2-(2,6-difluorophenyl)thiazole-4-carboxylic acid, and HATU were reacted to give 127 as a white solid (20 mg, 17%) over two steps. $^1$H NMR (400 MHz, DMSO) δ 7.67 (d, J=19.5, 1H), 7.62-7.45 (m, 3H), 7.28 (t, J=8.7, 2H), 3.63 (s, 3H), 3.53 (s, 1H), 3.20 (dt, J=8.9, 4.4, 2H), 2.84 (d, J=10.2, 2H), 2.05-1.84 (m, 2H), 1.75 (s, 2H). ESIMS m/z=420.1 (M+1)

Example 128

(S)-3-amino-N-(5-(3-(aminomethyl)piperidin-1-yl)-1-methyl-1H-pyrazol-4-yl)-6-(2-fluorophenyl)picolinamide 128

Following the procedures for Example 141, (R)-tert-butyl (1-(4-amino-1-methyl-1H-pyrazol-5-yl)piperidin-3-yl)methylcarbamate, 3-amino-6-bromopicolinic acid were coupled and the intermediate amide was reacted with 2-fluorophenylboronic acid under palladium catalyzed Suzuki conditions to give 128 as a white solid (27 mg, 15%) over three steps. $^1$H NMR (400 MHz, DMSO) δ 9.82 (s, 1H), 8.04 (t, J=8.0, 1H), 7.81-7.60 (m, 2H), 7.38 (ddd, J=22.0, 13.3, 7.2, 5H), 7.07 (s, 4H), 3.68 (s, 3H), 3.15-2.94 (m, 3H), 2.75 (dt, J=17.3, 10.2, 3H), 2.01-1.47 (m, 4H), 1.25-1.01 (m, 1H). ESIMS m/z=424.1 (M+1)

Example 129

(R)-3-amino-N-(5-(3-(aminomethyl)piperidin-1-yl)-1-methyl-1H-pyrazol-4-yl)-6-(2-fluorophenyl)picolinamide 129

Following the procedures for Example 141, (R)-tert-butyl (1-(4-amino-1-methyl-1H-pyrazol-5-yl)piperidin-3-yl)methylcarbamate, 3-amino-6-bromopicolinic acid were coupled and the intermediate amide was reacted with 2-fluorophenylboronic acid under palladium catalyzed Suzuki conditions to give 129 as a white solid (33 mg, 18%) over three steps. $^1$H NMR (400 MHz, DMSO) δ 9.82 (s, 1H), 8.03 (dt, J=9.6, 4.8, 1H), 7.81-7.60 (m, 2H), 7.49-7.20 (m, 4H), 7.07 (s, 2H), 3.67 (s, 3H), 3.30-3.20 (m, 2H), 3.15-2.96 (m, 3H), 2.73 (dd, J=25.7, 14.9, 1H), 1.92-1.44 (m, 4H), 1.03 (dd, J=21.1, 10.1, 1H). ESIMS m/z=424.1 (M+1)

Example 130

3-amino-N-(5-(4-(aminomethyl)piperidin-1-yl)-1-methyl-1H-pyrazol-4-yl)-6-(2-fluorophenyl)picolinamide 130

Following the procedures for Example 141, tert-butyl (1-(4-amino-1H-pyrazol-5-yl)piperidin-4-yl)methylcarbamate, 3-amino-6-bromopicolinic acid were coupled and the intermediate amide was reacted with 2-fluorophenylboronic acid under palladium catalyzed Suzuki conditions to give 130 as a white solid (29 mg, 16%) over three steps. $^1$H NMR (400 MHz, DMSO) δ 9.83 (d, J=16.2, 1H), 8.47 (s, OH), 8.04 (dd, J=15.8, 8.0, 1H), 7.69 (dd, J=37.1, 16.6, 2H), 7.51-7.27 (m, 5H), 7.09 (s, 2H), 3.66 (s, 3H), 3.06 (dd, J=21.6, 10.3, 6H), 1.74 (t, J=17.5, 2H), 1.28 (dd, J=39.1, 27.5, 3H). ESIMS m/z=424.1 (M+1)

Example 131

(S)-5-amino-N-(5-(3-(aminomethyl)piperidin-1-yl)-1-methyl-1H-pyrazol-4-yl)-2-(2,6-difluorophenyl)thiazole-4-carboxamide 131

Following the procedures as described in Example 113, (R)-tert-butyl (1-(4-amino-1-methyl-1H-pyrazol-5-yl)piperidin-3-yl)methylcarbamate, 5-(tert-butoxycarbonylamino)-2-(2,6-difluorophenyl)thiazole-4-carboxylic acid, and HATU were reacted to give 131 as a white solid (12 mg, 6.2%) over two steps. $^1$H NMR (400 MHz, DMSO) δ 8.74 (d, J=4.0, 1H), 7.60-7.42 (m, 4H), 7.28 (t, J=8.8, 2H), 3.63 (d, J=3.3, 3H), 3.24-2.81 (m, 4H), 2.77-2.61 (m, 2H), 1.84-1.42 (m, 4H), 1.03 (d, J=10.6, 1H). ESIMS m/z=448.1 (M+1)

Example 132

R-5-amino-N-(5-(3-(aminomethyl)piperidin-1-yl)-1-methyl-1H-pyrazol-4-yl)-2-(2,6-difluorophenyl)thiazole-4-carboxamide 132

Following the procedures as described in Example 113, (S)-tert-butyl (1-(4-amino-1-methyl-1H-pyrazol-5-yl)piperidin-3-yl)methylcarbamate, 5-(tert-butoxycarbonylamino)-2-(2,6-difluorophenyl)thiazole-4-carboxylic acid, and HATU were reacted to give 132 as a white solid (9.6 mg, 5.0%) over two steps. $^1$H NMR (400 MHz, DMSO) δ 8.74 (d, J=4.0, 1H), 7.60-7.42 (m, 4H), 7.28 (t, J=8.8, 2H), 3.63 (d, J=3.3, 3H), 3.24-2.80 (m, 4H), 2.77-2.61 (m, 2H), 1.82-1.42 (m, 4H), 1.03 (d, J=10.6, 1H). ESIMS m/z=448.1 (M+1)

Example 133

5-amino-N-(5-(4-(aminomethyl)piperidin-1-yl)-1-methyl-1H-pyrazol-4-yl)-2-(2,6-difluorophenyl)thiazole-4-carboxamide 133

Following the procedures as described in Example 113, tert-butyl (1-(4-amino-1H-pyrazol-5-yl)piperidin-4-yl)methylcarbamate, 5-(tert-butoxycarbonylamino)-2-(2,6-difluorophenyl)thiazole-4-carboxylic acid, and HATU were reacted to give 133 as a white solid (40 mg, 21%) over two steps. $^1$H NMR (400 MHz, DMSO) δ 8.76 (d, J=6.8, 1H), 7.62-7.38 (m, 4H), 7.38-7.16 (m, 2H), 3.63 (s, 3H), 3.15-2.94

(m, 5H), 2.88 (t, J=6.4, 1H), 1.86-1.60 (m, 2H), 1.42-1.05 (m, 3H). ESIMS m/z=448.1 (M+1)

Example 134

(S)-3-amino-N-(5-(3-(aminomethyl)pyrrolidin-1-yl)-1-methyl-1H-pyrazol-4-yl)-6-(2-fluorophenyl)picolinamide 134

Following the procedures for Example 141, (S)-tert-butyl (1-(4-amino-1-methyl-1H-pyrazol-5-yl)pyrrolidin-3-yl)methylcarbamate and 3-amino-6-bromopicolinic acid were coupled and the intermediate amide was reacted with 2-fluorophenylboronic acid under palladium catalyzed Suzuki conditions to give 134 as a white solid (76 mg, 48%) over three steps. $^1$H NMR (400 MHz, DMSO) δ 9.75 (s, 1H), 8.05 (t, J=7.9, 1H), 7.73 (dd, J=8.7, 2.0, 1H), 7.57 (s, 1H), 7.49-7.22 (m, 4H), 7.07 (s, 2H), 3.65 (s, 3H), 3.33-3.18 (m, 4H), 3.00 (dd, J=8.8, 6.3, 2H), 2.23 (dt, J=13.9, 7.0, 1H), 1.97 (td, J=12.5, 7.1, 1H), 1.68-1.55 (m, 1H). ESIMS m/z=410.1 (M+1)

Example 135

R-5-amino-N-(5-(3-(aminomethyl)pyrrolidin-1-yl)-1-methyl-1H-pyrazol-4-yl)-2-(2,6-difluorophenyl)thiazole-4-carboxamide 135

Following the procedures as described in Example 113, (R)-tert-butyl (1-(4-amino-1-methyl-1H-pyrazol-5-yl)pyrrolidin-3-yl)methylcarbamate, 5-(tert-butoxycarbonylamino)-2-(2,6-difluorophenyl)thiazole-4-carboxylic acid, and HATU were reacted to give 135 as a white solid (39 mg, 27%) over two steps. $^1$H NMR (400 MHz, DMSO) δ 8.79 (s, 1H), 7.61-7.45 (m, 3H), 7.41 (d, J=5.1, 1H), 7.28 (t, J=8.6, 2H), 3.62 (s, 3H), 3.30-3.20 (m, 4H), 2.97 (dt, J=19.0, 9.5, 1H), 2.61 (d, J=6.9, 1H), 2.34-2.18 (m, 1H), 1.96 (tt, J=29.5, 14.8, 1H), 1.58 (dq, J=14.3, 7.2, 1H). ESIMS m/z=434.1 (M+1)

Example 136

(R)-3-amino-N-(5-(3-(aminomethyl)pyrrolidin-1-yl)-1-methyl-1H-pyrazol-4-yl)-6-(2-fluorophenyl)picolinamide 136

Following the procedures for Example 141, (R)-tert-butyl (1-(4-amino-1-methyl-1H-pyrazol-5-yl)pyrrolidin-3-yl)methylcarbamate and 3-amino-6-bromopicolinic acid were coupled and the intermediate amide was reacted with 2-fluorophenylboronic acid under palladium catalyzed Suzuki conditions to give 136 as a white solid (51 mg, 37%) over three steps. $^1$H NMR (400 MHz, DMSO) δ 9.75 (s, 1H), 8.04 (dd, J=11.3, 4.6, 1H), 7.73 (dd, J=8.7, 2.0, 1H), 7.57 (s, 1H), 7.51-7.23 (m, 4H), 7.07 (s, 2H), 3.65 (s, 3H), 3.30-3.20 (m, 3H), 3.00 (dd, J=8.8, 6.3, 2H), 2.35-2.12 (m, 2H), 1.97 (td, J=12.4, 7.2, 1H), 1.56 (tt, J=40.8, 20.4, 1H). ESIMS m/z=410.1 (M+1)

Example 137

(S)-5-amino-N-(5-(3-(aminomethyl)pyrrolidin-1-yl)-1-methyl-1H-pyrazol-4-yl)-2-(2,6-difluorophenyl)thiazole-4-carboxamide 137

Following the procedures as described in Example 113, (S)-tert-butyl (1-(4-amino-1-methyl-1H-pyrazol-5-yl)pyrrolidin-3-yl)methylcarbamate, 5-(tert-butoxycarbonylamino)-2-(2,6-difluorophenyl)thiazole-4-carboxylic acid, and HATU were reacted to give 137 as a white solid (56 mg, 33%) over two steps. $^1$H NMR (400 MHz, DMSO) δ 8.79 (s, 1H), 7.61-7.45 (m, 3H), 7.41 (d, J=5.1, 1H), 7.28 (t, J=8.6, 2H), 3.62 (s, 3H), 3.31-3.20 (m, 4H), 2.98 (dt, J=19.0, 9.5, 1H), 2.61 (d, J=6.9, 1H), 2.34-2.19 (m, 1H), 1.96 (tt, J=29.5, 14.8, 1H), 1.60 (dq, J=14.3, 7.2, 1H). ESIMS m/z=434.1 (M+1)

Example 138

5-amino-2-(2,6-difluorophenyl)-N-(1-(oxetan-3-yl)-1H-pyrazol-4-yl)thiazole-4-carboxamide 138

Following the procedures as described in Example 113, 1-(oxetan-3-yl)-1H-pyrazol-4-amine, 5-(tert-butoxycarbonylamino)-2-(2,6-difluorophenyl)thiazole-4-carboxylic acid, and HATU were reacted to give 138 as a white solid (10 mg, 9%) over two steps. $^1$H NMR (400 MHz, DMSO) δ 9.93 (s, 1H), 8.36 (s, 1H), 7.86 (s, OH), 7.67-7.41 (m, 1H), 7.28 (t, J=8.4, 1H), 5.46-5.26 (m, 2H), 4.90 (s, 1H), 4.40 (d, J=5.7, 2H). ESIMS m/z=378.0 (M+1)

Example 139

(S)-5-amino-N-(5-(4-aminoazepan-1-yl)-1-methyl-1H-pyrazol-4-yl)-2-(2,6-difluorophenyl)thiazole-4-carboxamide 139

Following the procedures as described in Example 140, (S)-benzyl 1-(4-amino-1-methyl-1H-pyrazol-5-yl)azepan-4-ylcarbamate, 5-(tert-butoxycarbonylamino)-2-(2,6-difluorophenyl)thiazole-4-carboxylic acid, and HATU were reacted to give 139 as a white solid (42 mg, 25%) over two steps. $^1$H NMR (400 MHz, DMSO) δ 8.81 (s, 1H), 7.62-7.44 (m, 4H), 7.28 (t, J=8.7, 2H), 3.66 (d, J=17.1, 3H), 3.21-2.93 (m, 5H), 1.93-1.73 (m, 3H), 1.69-1.40 (m, 3H). ESIMS m/z=448.1 (M+1)

Example 140

R-5-amino-N-(5-(4-aminoazepan-1-yl)-1-methyl-1H-pyrazol-4-yl)-2-(2,6-difluorophenyl)thiazole-4-carboxamide 140

To a 100 mL round bottom flask containing (R)-benzyl 1-(4-amino-1-methyl-1H-pyrazol-5-yl)azepan-4-ylcarbamate from Example 16 (154 mg, 0.45 mmol), 5-(tert-butoxycarbonylamino)-2-(2,6-difluorophenyl)thiazole-4-carboxylic acid (168 mg, 0.47 mmol) and HATU (0.51 g, 1.30 mmol) was added methylene chloride (10 mL) and diisopropylethylamine (0.44 g, 3.40 mmol). The reaction mixture was stirred for 24 hr at room temperature and the reaction was monitored by LCMS. Upon completion of the reaction, the solvent was distilled off and the crude material was purified via flash chromatography, heptane/ethyl acetate 20% to 95% to afford yellow oil (270 mg, 88%).

In a 50 mL round bottom flask was added the amide (270 mg, 0.40 mmol), methylene chloride (8 mL) and a 1M solution of boron tribromide in $CH_2Cl_2$ (1 mL, 1.19 mmol). The mixture was stirred for 5 h, and the solvent was distilled off. The crude product was purified via reverse phase HPLC 40% to 80% MeOH in water with 0.1% $NH_4OH$ to afford 140 as a white solid (50 mg, 33%). $^1$H NMR (400 MHz, DMSO) δ 8.81 (s, 1H), 7.62-7.44 (m, 4H), 7.28 (t, J=8.7, 2H), 3.66 (d, J=17.1, 3H), 3.21-2.93 (m, 5H), 1.93-1.73 (m, 3H), 1.69-1.40 (m, 3H). ESIMS m/z=448.1 (M+1)

Example 141

(R)-3-amino-N-(5-(4-aminoazepan-1-yl)-1-methyl-1H-pyrazol-4-yl)-6-(2-fluorophenyl)pyrazine-2-carboxamide 141

To a 50 mL round bottom flask containing (R)-benzyl 1-(4-amino-1-methyl-1H-pyrazol-5-yl)azepan-4-ylcarbamate from Example 16 (60 mg, 0.17 mmol), 3-amino-6-bromopyrazine-2-carboxylic acid (42 mg, 0.19 mmol) and HATU (0.27 g, 1.30 mmol) was added methylene chloride (10 mL) and diisopropylethylamine (0.18 g, 1.4 mmol). The reaction mixture was stirred for 24 hr at room temperature and the reaction was monitored by LCMS. Upon completion of the reaction, the solvent was distilled off and the crude material was purified via flash chromatography, heptane/ethyl acetate 20% to 95% to afford a white solid (75 mg, 79%).

To a 10 mL microwave vial was added the amide (75 mg, 0.14 mmol), 2-fluorophenylboronic acid (59 mg, 0.42 mmol), dichloro[1,1'-bis(diphenylphosphino)ferrocene]palladium (II) (23 mg, 0.028 mmol), a 2M solution of $Na_2CO_3$ (1 mL) and 1,2-dimethoxyethane (3 mL). The mixture was irradiated to 130° C. with a microwave for 30 min and the mixture was cooled, concentrated and purified via flash chromatography, heptane/ethyl acetate 20% to 95% to afford a brown oil.

To a 50 mL round bottom flask was added the pyrazine bromide, methylene chloride (4 mL) and a 1M solution of boron tribromide in $CH_2Cl_2$ (0.92 mL, 0.9 mmol). The mixture was stirred for 5 h, and the solvent was distilled off. The crude product was purified via reverse phase HPLC 40% to 80% MeOH in water with 0.1% $NH_4OH$ to afford 141 (23 mg, 39%) as a white solid over two steps. $^1$H NMR (400 MHz, DMSO) δ 8.68 (d, J=2.4, 1H), 8.11 (td, J=8.1, 1.8, 1H), 7.76 (s, 2H), 7.57 (d, J=8.1, 1H), 7.47 (dd, J=13.3, 5.7, 1H), 7.42-7.28 (m, 2H), 3.67 (s, 3H), 3.26-2.95 (m, 5H), 1.96-1.73 (m, 3H), 1.54 (ddd, J=14.4, 12.4, 4.9, 3H). ESIMS m/z=425.1 (M+1)

Example 142

(S)-3-amino-N-(5-(4-aminoazepan-1-yl)-1-methyl-1H-pyrazol-4-yl)-6-(2-fluorophenyl)picolinamide 142

Following the procedures for Example 141, (S)-benzyl 1-(4-amino-1-methyl-1H-pyrazol-5-yl)azepan-4-ylcarbamate and 3-amino-6-bromopicolinic acid were converted to 142 as a white solid (54 mg, 69%) over three steps. $^1$H NMR (400 MHz, DMSO) δ 9.73 (s, 1H), 8.05 (t, J=7.3, 1H), 7.74 (dd, J=8.7, 2.1, 1H), 7.60 (s, 1H), 7.50-6.80 (m, 2H), 6.58 (s, 3H), 3.69 (s, 3H), 3.27-3.13 (m, 4H), 1.85 (ddd, J=42.7, 41.6, 18.5, 7H). ESIMS m/z=424.1 (M+1)

Example 143

(S)-3-amino-N-(5-(4-aminoazepan-1-yl)-1-methyl-1H-pyrazol-4-yl)-6-(2-fluorophenyl)pyrazine-2-carboxamide 143

Following the procedures of Example 141, (S)-benzyl 1-(4-amino-1-methyl-1H-pyrazol-5-yl)azepan-4-ylcarbamate was converted to 143 as a white solid (13 mg, 22%) over three steps. $^1$H NMR (400 MHz, DMSO) δ 8.68 (d, J=2.4, 1H), 8.11 (td, J=8.1, 1.8, 1H), 7.76 (s, 2H), 7.57 (d, J=8.1, 1H), 7.47 (dd, J=13.3, 5.7, 1H), 7.42-7.28 (m, 2H), 3.67 (s, 3H), 3.26-2.95 (m, 5H), 1.96-1.73 (m, 3H), 1.54 (ddd, J=14.4, 12.4, 4.9, 3H). ESIMS m/z=425.1 (M+1)

Example 144

R-5-amino-N-(5-(3-aminopiperidin-1-yl)-1-methyl-1H-pyrazol-4-yl)-2-(2,6-difluorophenyl)thiazole-4-carboxamide 144

Following the procedures as described in Example 113, (R)-tert-butyl 1-(1-methyl-4-amino-1H-pyrazol-5-yl)piperidin-3-ylcarbamate, 5-(tert-butoxycarbonylamino)-2-(2,6-difluorophenyl)thiazole-4-carboxylic acid, and HATU were reacted to give 144 as a white solid (32 mg, 11%) over two steps. $^1$H NMR (400 MHz, DMSO) δ 8.81 (s, 1H), 7.63-7.42 (m, 4H), 7.27 (t, J=8.7, 2H), 3.62 (d, J=10.3, 3H), 3.07 (dd, J=11.1, 3.3, 1H), 3.03-2.80 (m, 2H), 2.83 (t, J=8.7, 1H), 2.69 (dd, J=11.0, 8.5, 1H), 1.87-1.64 (m, 2H), 1.55 (d, J=8.9, 1H), 1.17 (dd, J=19.9, 9.3, 1H). ESIMS m/z=434.1 (M+1)

Example 145

(R)-3-amino-N-(5-(4-aminoazepan-1-yl)-1-methyl-1H-pyrazol-4-yl)-6-(2-fluorophenyl)picolinamide 145

Following the procedures for Example 141, (R)-benzyl 1-(4-amino-1-methyl-1H-pyrazol-5-yl)azepan-4-ylcarbamate from Example 16 and 3-amino-6-bromopicolinic acid were converted to 145 as a white solid (21 mg, 26%) over three steps. $^1$H NMR (400 MHz, DMSO) δ 9.72 (s, 1H), 8.05 (dd, J=11.3, 4.9, 1H), 7.75 (dd, J=8.8, 2.1, 1H), 7.32 (td, J=7.6, 3.7, 3H), 7.07 (s, 2H), 3.69 (s, 3H), 3.27-3.07 (m, 4H), 2.13-1.51 (m, 7H). ESIMS m/z=424.1 (M+1)

Example 146

(R)—N-(5-(3-(aminomethyl)piperidin-1-yl)-1-methyl-1H-pyrazol-4-yl)-2-(2,6-difluorophenyl)thiazole-4-carboxamide 146

Following the procedures as described in Example 113 and starting with (R)-tert-butyl (1-(4-amino-1-methyl-1H-pyrazol-5-yl)piperidin-3-yl)methylcarbamate and 2-(2,6-difluorophenyl)thiazole-4-carboxylic acid were converted to 146 as a white solid (9.7 mg, 5.0%) over two steps. $^1$H NMR (400 MHz, DMSO) δ 9.45 (s, 1H), 8.65 (s, 1H), 8.30 (s, 1H), 7.75-7.62 (m, 1H), 7.39 (dd, J=19.2, 10.4, 3H), 3.64 (d, J=7.7, 3H), 3.22 (d, J=11.6, 3H), 3.11-2.92 (m, 3H), 2.82-2.64 (m, 3H), 1.76 (dd, J=38.1, 20.2, 3H), 1.55 (d, J=10.0, 1H), 1.11 (d, J=10.5, 1H). ESIMS m/z=433.1 (M+1)

Example 147

(R)-benzyl 1-(4-(5-amino-2-(2,6-difluorophenyl)thiazole-4-carboxamido)-1-methyl-1H-pyrazol-5-yl)azepan-4-ylcarbamate 147

Following the procedures as described in Example 140 and starting with (S)-benzyl 1-(4-amino-1-methyl-1H-pyrazol-5-yl)azepan-4-ylcarbamate, 5-(tert-butoxycarbonylamino)-2-(2,6-difluorophenyl)thiazole-4-carboxylic acid, and HATU were converted to 147 as a white solid (26 mg, 32%) over two steps. $^1$H NMR (400 MHz, DMSO) δ 8.67 (s, 1H), 7.59-7.42 (m, 4H), 7.29 (dt, J=17.1, 7.3, 7H), 4.99 (s, 2H), 3.65 (s, 4H), 3.28-3.05 (m, 4H), 2.05-1.75 (m, 3H), 1.68 (dd, J=20.2, 10.3, 3H). ESIMS m/z=582.1 (M+1)

Example 148

(R)—N-(5-(4-aminoazepan-1-yl)-1-methyl-1H-pyrazol-4-yl)-2-(2,6-difluorophenyl)thiazole-4-carboxamide 148

Following the procedures as described in Example 140, (R)-benzyl 1-(4-amino-1-methyl-1H-pyrazol-5-yl)azepan-4-ylcarbamate from Example 16, 2-(2,6-difluorophenyl)thiazole-4-carboxylic acid, and HATU were converted to 148 as a white solid (3.6 mg, 2.6%) over two steps. ESIMS m/z=433.1 (M+1)

Example 149

(S)—N-(5-(4-aminoazepan-1-yl)-1-methyl-1H-pyrazol-4-yl)-2-(2,6-difluorophenyl)thiazole-4-carboxamide 149

Following the procedures as described in Example 140, (S)-benzyl 1-(4-amino-1-methyl-1H-pyrazol-5-yl)azepan-4-ylcarbamate, 2-(2,6-difluorophenyl)thiazole-4-carboxylic acid, and HATU were converted to 149 as a white solid (2.1 mg, 1.5%) over two steps. ESIMS m/z=433.1 (M+1)

Example 150

5-amino-N-(5-(6-amino-3-azabicyclo[3.1.0]hexan-3-yl)-1-methyl-1H-pyrazol-4-yl)-2-(2,6-difluorophenyl)thiazole-4-carboxamide 150

Following the procedures as described in Example 113, tert-butyl 3-(4-amino-1-methyl-1H-pyrazol-5-yl)-3-azabicyclo[3.1.0]hexan-6-ylcarbamate, 5-(tert-butoxycarbonylamino)-2-(2,6-difluorophenyl)thiazole-4-carboxylic acid, and HATU were reacted to give 150 as a white solid (30 mg, 32%) over two steps. $^1$H NMR (400 MHz, DMSO) δ 8.64 (s, 1H), 7.64-7.36 (m, 4H), 7.29 (t, J=8.7, 2H), 3.56 (s, 3H), 3.46-3.31 (m, 2H), 3.13 (t, J=15.2, 2H), 1.93 (s, 1H), 1.41 (s, 2H). ESIMS m/z=431.1 (M+1)

Example 151

3-amino-N-(5-(6-amino-3-azabicyclo[3.1.0]hexan-3-yl)-1-methyl-1H-pyrazol-4-yl)-6-(2-fluorophenyl)picolinamide 151

Following the procedures for Example 141, tert-butyl 3-(4-amino-1-methyl-1H-pyrazol-5-yl)-3-azabicyclo[3.1.0]hexan-6-ylcarbamate and 3-amino-6-bromopicolinic acid were coupled and the intermediate amide was reacted with 2-fluorophenylboronic acid under palladium catalyzed Suzuki conditions to give 151 as a white solid (32 mg, 35%) over three steps. $^1$H NMR (400 MHz, DMSO) δ 9.69 (s, 1H), 8.06 (t, J=7.8, 1H), 7.75 (d, J=8.5, 1H), 7.66-7.25 (m, 5H), 7.06 (s, 2H), 3.59 (s, 3H), 3.40 (t, J=10.6, 2H), 3.17 (d, J=8.5, 2H), 2.09 (s, 1H), 1.44 (s, 2H). ESIMS m/z=408.1 (M+1)

Example 152

3-amino-N-(5-(4-aminopiperidin-1-yl)-1-methyl-1H-pyrazol-4-yl)-6-chloropyrazine-2-carboxamide 152

Following the procedures as described in Example 113, tert-butyl carbamate of 1-(4-amino-1-methyl-1H-pyrazol-5-yl)piperidin-4-amine was converted to 152 as a white solid (2.0 mg, 19%) over two steps. ESIMS m/z=351.1 (M+1)

Example 154

5-amino-2-(2,6-difluorophenyl)-N-(1-methyl-5-o-tolyl-1H-pyrazol-4-yl)thiazole-4-carboxamide 154

Following the procedures as described in Example 2 and starting with 1-methyl-5-o-tolyl-1H-pyrazol-4-amine, 154 was obtained as a white solid (33 mg, 19%) over two steps. $^1$H NMR (400 MHz, DMSO) δ 8.37 (s, 1H), 7.88 (s, 1H), 7.54-7.39 (m, 5H), 7.39-7.28 (m, 2H), 7.21 (t, J=8.8, 2H), 3.57 (d, J=7.0, 3H), 2.14 (s, 3H). ESIMS m/z=426.1 (M+1)

Example 155

3-amino-6-(2-fluorophenyl)-N-(1-methyl-5-o-tolyl-1H-pyrazol-4-yl)picolinamide 155

Following the procedures as described in Example 2 and starting with 1-methyl-5-o-tolyl-1H-pyrazol-4-amine and 3-amino-6-bromopicolinic acid, 155 was obtained as a white solid (33 mg, 31%) over three steps. $^1$H NMR (400 MHz, DMSO) δ 9.58 (s, 1H), 8.06 (s, 1H), 7.71 (dd, J=8.8, 2.1, 1H), 7.53 (ddd, J=16.4, 10.9, 4.9, 2H), 7.45-7.33 (m, 4H), 7.24 (ddd, J=22.7, 13.7, 7.7, 3H), 7.08 (s, 2H), 3.63 (s, 3H), 2.15 (s, 3H). ESIMS m/z=402.1 (M+1)

Example 156

3-amino-N-(5-(3-aminophenyl)-1-methyl-1H-pyrazol-4-yl)-6-(2-fluorophenyl)picolinamide 156

Following the procedures as described in Example 2 and starting with tert-butyl 3-(4-amino-1-methyl-1H-pyrazol-5-yl)phenylcarbamate and 3-amino-6-bromopicolinic acid, 156 was obtained as a white solid (44 mg, 42%) over three steps. $^1$H NMR (400 MHz, DMSO) δ 9.95 (s, 1H), 8.09 (s, 1H), 7.73 (dd, J=13.6, 4.7, 2H), 7.39 (dd, J=13.1, 5.4, 1H), 7.37-7.21 (m, 4H), 7.12 (s, 2H), 6.82-6.60 (m, 3H), 5.43 (s, 2H), 3.77 (s, 3H). ESIMS m/z=403.1 (M+1)

Example 157

5-amino-N-(5-(3-aminophenyl)-1-methyl-1H-pyrazol-4-yl)-2-(2,6-difluorophenyl)thiazole-4-carboxamide 157

Following the procedures as described in Example 2 and starting with tert-butyl 3-(4-amino-1-methyl-1H-pyrazol-5-yl)phenylcarbamate, 157 was obtained as a white solid (13 mg, 7.6%) over two steps. $^1$H NMR (400 MHz, DMSO) δ 8.69 (s, 1H), 7.90 (s, 1H), 7.56-7.45 (m, 3H), 7.21 (dt, J=15.5, 8.3, 3H), 6.72-6.54 (m, 3H), 5.28 (s, 2H), 3.74 (s, 3H). ESIMS m/z=427.1 (M+1)

Table 2 Formula I Compounds 158-390

Example 158

(S)-3-amino-N-(5-(3-aminoazepan-1-yl)-1-methyl-1H-pyrazol-4-yl)-6-(2-fluorophenyl)picolinamide 158

Following the procedures as described in Example 23 and starting with tert-butyl azepan-3-ylcarbamate and 3-amino- 6-bromopicolinic acid, 158 was obtained as a white solid (3.8 mg, 4%) over three steps. ESIMS m/z=424.1 (M+1).

Example 159

(R)-5-amino-N-(5-(3-aminoazepan-1-yl)-1-methyl-1H-pyrazol-4-yl)-2-(2,6-difluorophenyl)thiazole-4-carboxamide 159

Following the procedures as described in Examples 1 and 2, starting with tert-butyl azepan-3-ylcarbamate, 159 was obtained as a white solid (4.1 mg, 3%) over two steps. ESIMS m/z=448.1 (M+1).

Example 160

(R)-3-amino-N-(5-(3-aminoazepan-1-yl)-1-methyl-1H-pyrazol-4-yl)-6-(2-fluorophenyl)picolinamide 160

Following the procedures as described in Example 23 and starting with tert-butyl azepan-3-ylcarbamate and 3-amino-6-bromopicolinic acid, 160 was obtained as a white solid (4.5 mg, 5%) over three steps. ESIMS m/z=424.1 (M+1).

Example 161

(S)-5-amino-N-(5-(3-aminoazepan-1-yl)-1-methyl-1H-pyrazol-4-yl)-2-(2,6-difluorophenyl)thiazole-4-carboxamide 161

Following the procedures as described in Examples 1 and 2, starting with tert-butyl azepan-3-ylcarbamate, 161 was obtained as a white solid (2.2 mg, 2%) over two steps. ESIMS m/z=448.1 (M+1).

Example 162

5-amino-2-(2,6-difluorophenyl)-N-(1-methyl-5-(piperazin-1-yl)-1H-pyrazol-4-yl)thiazole-4-carboxamide Following the procedures as described in Examples 1 and 2, starting with tert-butyl piperazine-1-carboxylate, 162 was obtained as a white solid (36 mg, 20%) over two steps. $^1$H NMR (400 MHz, DMSO) δ 8.72 (s, 1H), 7.61-7.46 (m, 3H), 7.41 (s, 1H), 7.27 (t, J=8.7 Hz, 2H), 3.64 (s, 3H), 3.02-2.91 (m, 4H), 2.82-2.74 (m, 4H). ESIMS m/z=420.1 (M+1).

Example 163

3-amino-6-(2-fluorophenyl)-N-(1-methyl-5-(piperazin-1-yl)-1H-pyrazol-4-yl)picolinamide Following the procedures as described in Example 23 and starting with tert-butyl piperazine-1-carboxylate, 163 was obtained as a white solid (19 mg, 21%) over two steps. $^1$H NMR (400 MHz, DMSO) δ 9.81 (s, 1H), 8.25-8.06 (m, 1H), 7.76 (dd, J=8.8, 2.3 Hz, 1H), 7.54 (s, 1H), 7.42 (dd, J=13.0, 5.6 Hz, 1H), 7.31 (tt, J=11.0, 5.6 Hz, 1H), 7.08 (s, 2H), 6.52 (s, 1H), 3.68 (s, 3H), 3.19-3.02 (m, 4H), 2.92 (s, 4H). ESIMS m/z=396.1 (M+1).

Example 164

N-(5-(1,4-diazepan-1-yl)-1-methyl-1H-pyrazol-4-yl)-5-amino-2-(2,6-difluorophenyl)thiazole-4-carboxamide Following the procedures as described in Examples 1 and 2, starting with tert-butyl 1,4-diazepane-1-carboxylate, 164 was obtained as a white solid (36 mg, 20%) over two steps. $^1$H NMR (400 MHz, DMSO) δ 7.90 (s, 1H), 7.65-7.44 (m, 3H), 7.29 (t, J=8.8 Hz, 2H), 3.62 (d, J=10.5 Hz, 3H), 3.16 (t, J=6.0 Hz, 4H), 2.95 (t, J=6.1 Hz, 2H), 2.83 (t, J=5.6 Hz, 2H), 1.48 (s, 2H). ESIMS m/z=434.1 (M+1).

Example 165

5-amino-2-(2,6-difluorophenyl)-N-(1-ethyl-1H-pyrazol-4-yl)thiazole-4-carboxamide 165

Following procedures from Examples 113 and shown in FIG. 5, tert-butyl-2-(2,6-difluorophenyl)-4-(1-ethyl-1H-pyrazol-4-ylcarbamoyl)thiazol-5 ylcarbamate was converted to 165: $^1$H NMR (400 MHz, DMSO) δ 9.70 (s, 1H), 7.99 (s, 1H), 7.64 (s, 1H), 7.56 (t, J=7.5 Hz, 1H), 7.50 (s, 2H), 7.27 (t, J=8.4 Hz, 2H), 4.08 (q, J=7.2 Hz, 2H), 1.35 (t, J=8.0 Hz 3H); MS (ESI) m/z: 350[M+H$^+$]

Example 168

5-amino-2-(2,6-difluorophenyl)-N-(1-methyl-5-(1H-pyrrolo[3,4-c]pyridin-2(3H,3aH,4H,5H,6H,7H,7aH)-yl)-1H-pyrazol-4-yl)thiazole-4-carboxamide 168

Following the procedures as described in Examples 1 and 2, starting with tert-butyl hexahydro-1H-pyrrolo[3,4-c]pyridine-5(6H)-carboxylate, 168 was obtained as a white solid (34 mg, 31%) over two steps. $^1$H NMR (400 MHz, DMSO) δ 8.63 (s, 1H), 7.56-7.42 (m, 4H), 7.26 (t, J=8.7 Hz, 2H), 3.63 (s, 3H), 3.39-3.33 (m, 2H), 3.23-3.17 (m, 1H), 3.09 (dd, J=8.6, 3.9 Hz, 1H), 2.90-2.68 (m, 4H), 2.30 (s, 2H), 1.59 (d, J=5.3 Hz, 2H). ESIMS m/z=460.1 (M+1).

Example 169

5-amino-2-(2-fluorophenyl)-N-(1-methyl-1H-pyrazol-4-yl)thiazole-4-carboxamide 169

Following procedures from Examples 141 and shown in FIG. 5, tert-butyl-2-(2-fluorophenyl)-4-(1-methyl-1H-pyrazol-4-ylcarbamoyl)thiazol-5 ylcarbamate was converted to 169: $^1$H NMR (400 MHz, DMSO) δ 9.86 (s, 1H), 8.39 (t, J=7.8 Hz, 1H), 7.98 (s, 1H), 7.64 (s, 1H), 7.43 (m, 3H), 7.35 (dd, J=13.5, 5.8 Hz, 2H), 3.82 (s, 3H); MS (ESI) m/z: 318 [M+H$^+$]

Example 170

5-amino-2-(2-fluorophenyl)-N-(1-(piperidin-4-yl)-1H-pyrazol-4-yl)thiazole-4-carboxamide 170

Following procedures from Examples 141 and shown in FIG. 5, tert-butyl 2-(2-fluoro-phenyl)-4-(1-(piperidin-4-yl)-1H-pyrazol-4-ylcarbamoyl)thiazol-5-ylcarbamate was converted to 170: $^1$H NMR (400 MHz, DMSO) δ 9.85 (s, 1H), 8.39 (m, 1H), 8.00 (s, 1H), 7.68 (s, 1H), 7.44 (d, J=8.7 Hz, 3H), 7.40-7.30 (m, 2H), 4.16 (m, 1H), 3.04 (d, J=12.6 Hz, 2H), 2.60 (t, J=11.3 Hz, 2H), 1.95 (d, J=11.5 Hz, 2H), 1.75 (dd, J=11.9, 3.9 Hz, 2H); MS (ESI) m/z: 387[M+H$^+$]

Example 172

5-amino-2-(2,6-difluorophenyl)-N-(1-(piperidin-4-yl)-1H-pyrazol-4-yl)thiazole-4-carboxamide 172

Following procedures from Examples 116 and shown in FIG. 5, tert-butyl 2-(2,6-difluorophenyl)-4-(1-(piperidin-4-yl)-1H-pyrazol-4-ylcarbamoyl)thiazol-5-ylcarbamate was converted to 172: $^1$H NMR (400 MHz, DMSO) δ 9.71 (s, 1H), 8.29 (s, 1H), 7.99 (s, 1H), 7.68 (s, 1H), 7.56 (m, 1H), 7.50 (s, 2H), 7.27 (t, J=8.4 Hz, 2H), 4.26-4.10 (m, 1H), 3.11 (d, J=12.5 Hz, 2H), 2.68 (d, J=10.2 Hz, 2H), 1.96 (m, 2H), 1.83 (m, 2H); MS (ESI) m/z: 405[M+H$^+$]

Example 173

5-amino-N-(1-ethyl-1H-pyrazol-4-yl)-2-(2-fluorophenyl)thiazole-4-carboxamide 173

Following procedures from Examples 141 and shown in FIG. 5, tert-butyl-2-(2-fluoro-phenyl)-4-(1-ethyl-1H-pyrazol-4-ylcarbamoyl)thiazol-5 ylcarbamate was converted to 173: $^1$H NMR (400 MHz, DMSO) δ 9.91 (s, 1H), 8.41 (td, J=7.8, 1.6 Hz, 1H), 8.02 (s, 1H), 7.66 (s, 1H), 7.49-7.40 (m, 3H), 7.36 (dd, J=13.0, 7.0 Hz, 2H), 4.11 (q, J=7.3 Hz, 2H), 1.35 (t, J=8.0 Hz 3H); MS (ESI) m/z: 332[M+H$^+$]

Example 174

5-amino-2-(2-fluorophenyl)-N-(1-isopropyl-1H-pyrazol-4-yl)thiazole-4-carboxamide 174

Following procedures from Examples 141 and shown in FIG. 5, tert-butyl-2-(2-fluorophenyl)-4-(1-isopropyl-1H-pyrazol-4-ylcarbamoyl)thiazol-5 ylcarbamate was converted to 174: $^1$H NMR (400 MHz, DMSO) δ 9.90 (s, 1H), 8.41 (td, J=7.8, 1.6 Hz, 1H), 8.03 (s, 1H), 7.66 (s, 1H), 7.48-7.41 (m, 3H), 7.36 (dd, J=13.6, 6.7 Hz, 2H), 4.47 (dt, J=13.3, 6.7 Hz, 1H), 1.41 (d, J=6.7 Hz, 6H); MS (ESI) m/z: 346[M+H$^+$]

Example 175

5-amino-2-(2,6-difluorophenyl)-N-(1-isopropyl-1H-pyrazol-4-yl)thiazole-4-carboxamide 175

Following procedures from Examples 113 and shown in FIG. 5, tert-butyl-2-(2,6-difluorophenyl)-4-(1-isopropyl-1H-pyrazol-4-ylcarbamoyl)thiazol-5 ylcarbamate was converted to 175: $^1$H NMR (400 MHz, DMSO) δ 9.74 (s, 1H), 8.01 (s, 1H), 7.65 (s, 1H), 7.60-7.51 (m, 3H), 7.28 (t, J=8.0 Hz 2H), 4.44 (dt, J=13.3, 6.7 Hz, 1H), 1.39 (d, J=6.7 Hz, 6H); MS (ESI) m/z: 364[M+H$^+$]

Example 176

5-amino-2-(2,6-difluorophenyl)-N-(1-(pyrrolidin-3-yl)-1H-pyrazol-4-yl)thiazole-4-carboxamide 176

Following procedures from Examples 113 and shown in FIG. 5, tert-butyl-2-(2,6-difluorophenyl)-4-(1-(pyrrolidin-3-yl)-1H-pyrazol-4-ylcarbamoyl)thiazol-5-ylcarbamate was converted to 176: $^1$H NMR (400 MHz, DMSO) δ 9.75 (s, 1H), 8.04 (s, 1H), 7.66 (s, 1H), 7.61-7.49 (m, 3H), 7.27 (t, J=8.3 Hz, 2H), 4.75 (m, 1H), 3.12 (dd, J=11.4, 7.0 Hz, 1H), 2.99 (dd, J=17.9, 7.4 Hz, 1H), 2.86 (m, 2H), 2.14 (tt, J=17.7, 8.8 Hz, 1H), 1.98 (dd, J=12.9, 5.4 Hz, 1H); MS (ESI) m/z: 391 [M+H$^+$]

Example 177

5-amino-2-(2-fluorophenyl)-N-(1-(pyrrolidin-3-yl)-1H-pyrazol-4-yl)thiazole-4-carboxamide 177

Following procedures from Examples 141 and shown in FIG. 5, tert-butyl-2-(2-fluoro-phenyl)-4-(1-(pyrrolidin3-yl)-1H-pyrazol-4-ylcarbamoyl)thiazol-5-ylcarbamate was converted to 177: $^1$H NMR (400 MHz, DMSO) δ 9.91 (s, 1H), 8.41 (t, J=7.9 Hz, 1H), 8.07 (s, 1H), 7.67 (s, 1H), 7.44 (m, 3H), 7.36 (dd, J=13.6, 7.0 Hz, 2H), 4.78 (m, 1H), 3.14 (dd, J=11.4, 6.9 Hz, 1H), 3.06-2.97 (m, 1H), 2.93 (dd, J=11.4, 4.4 Hz, 1H), 2.86 (dd, J=15.8, 9.3 Hz, 1H), 2.24-2.10 (m, 1H), 1.98 (td, J=12.7, 5.2 Hz, 1H); MS (ESI) m/z: 373[M+H$^+$]

Example 178

5-amino-N-(1-(cyclopropylmethyl)-1H-pyrazol-4-yl)-2-(2-fluorophenyl)thiazole-4-carboxamide 178

Following procedures from Examples 141 and shown in FIG. 5, tert-butyl-4-(1-cyclo-propylmethyl)-1H-pyrazol-4-ylcarbamoyl) 2-(2-fluorophenyl)thiazol-5-ylcarbamate was converted to 178: $^1$H NMR (400 MHz, DMSO) δ 9.89 (s, 1H), 8.41 (t, J=7.5 Hz, 1H), 8.07 (s, 1H), 7.66 (s, 1H), 7.44 (s, 3H), 7.36 (dd, J=13.6, 6.1 Hz, 2H), 3.95 (d, J=7.1 Hz, 2H), 1.21 (m, 1H), 0.54 (q, J=5.7 Hz, 2H), 0.36 (q, J=4.8 Hz, 2H); MS (ESI) m/z: 358[M+H$^+$]

Example 179

5-amino-N-(1-(cyclopropylmethyl)-1H-pyrazol-4-yl)-2-(2,6-difluorophenyl)thiazole-4-carboxamide 179

Following procedures from Examples 113 and shown in FIG. 5, tert-butyl-4-(1-cyclo-propylmethyl)-1H-pyrazol-4-ylcarbamoyl) 2-(2,6-difluorophenyl)thiazol-5 ylcarbamate was converted to 179: $^1$H NMR (400 MHz, DMSO) δ 9.73 (s, 1H), 8.05 (s, 1H), 7.64 (s, 1H), 7.61-7.53 (m, 1H), 7.51 (m, 2H), 7.27 (t, J=8.4 Hz, 2H), 3.92 (d, J=7.1 Hz, 2H), 1.26-1.12 (m, 1H), 0.52 (q, J=5.8 Hz, 2H), 0.34 (q, J=4.7 Hz, 2H); MS (ESI) m/z: 376[M+H$^+$]

Example 180

(R)-5-amino-2-(2,6-difluorophenyl)-N-(1-(piperidin-3-yl)-1H-pyrazol-4-yl)thiazole-4-carboxamide 180

Following procedures from Examples 113 and shown in FIG. 5, (R)-tert-butyl 2-(2,6-difluorophenyl)-4-(1-(piperidin-3-yl)-1H-pyrazol-4-ylcarbamoyl)thiazol-5-ylcarbamate was converted to 180: $^1$H NMR (400 MHz, DMSO) δ 9.70 (s, 1H), 8.01 (s, 1H), 7.66 (s, 1H), 7.60-7.52 (m, 1H), 7.51 (m, 2H), 7.27 (t, J=8.4 Hz, 2H), 4.06 (t, J=10.4 Hz, 1H), 3.13 (d, J=12.0 Hz, 1H), 2.85 (d, J=11.6 Hz, 1H), 2.74-2.64 (m, 1H), 2.43 (d, J=11.3 Hz, 1H), 2.05 (m, 1H), 1.88-1.75 (m, 1H), 1.69 (d, J=12.8 Hz, 1H), 1.48 (d, J=12.2 Hz, 1H); MS (ESI) m/z: 405[M+H$^+$]

Example 182

(S)-5-amino-2-(2,6-difluorophenyl)-N-(1-(piperidin-3-yl)-1H-pyrazol-4-yl)thiazole-4-carboxamide 182

Following procedures from Examples 113 and shown in FIG. 5, (S)-tert-butyl 2-(2,6-difluorophenyl)-4-(1-(piperidin-3-yl)-1H-pyrazol-4-ylcarbamoyl)thiazol-5-ylcarbamate was converted to 182: $^1$H NMR (400 MHz, DMSO) δ 9.70 (s, 1H), 8.01 (s, 1H), 7.66 (s, 1H), 7.56 (dt, J=13.7, 5.8 Hz, 1H), 7.52 (d, J=11.6 Hz, 2H), 7.27 (t, J=8.4 Hz, 2H), 4.06 (t, J=10.4 Hz, 1H), 3.13 (d, J=11.5 Hz, 1H), 2.85 (d, J=12.4 Hz, 1H), 2.73-2.63 (m, 1H), 2.43 (d, J=11.8 Hz, 1H), 2.05 (m, 1H), 1.81 (m, 1H), 1.69 (d, J=12.8 Hz, 1H), 1.55-1.39 (m, 1H); MS (ESI) m/z: 405[M+H$^+$]

Example 183

5-amino-2-(2,6-difluorophenyl)-N-(1-(2-(dimethylamino)ethyl)-1H-pyrazol-4-yl)thiazole-4-carboxamide 183

Following procedures from Examples 113 and shown in FIG. 5, tert-butyl 2-(2,6-di-fluorophenyl)-4-(1-(2-(dimethylamino)ethyl)-1H-pyrazol-4-ylcarbamoyl)thiazol-5-ylcarbamate was converted to 183: $^1$H NMR (400 MHz, DMSO) δ 9.72 (s, 1H), 8.01 (s, 1H), 7.63 (dd, J=11.7, 5.1 Hz, 1H), 7.60-7.53 (m, 1H), 7.51 (d, J=6.1 Hz, 2H), 7.27 (t, J=8.4 Hz, 2H), 4.13 (t, J=6.5 Hz, 2H), 2.61 (t, J=6.5 Hz, 2H), 2.53-2.16 (s, 6H); MS (ESI) m/z: 393[M+H$^+$]

Example 184

5-amino-2-(2,6-difluorophenyl)-N-(1,5-dimethyl-1H-pyrazol-4-yl)thiazole-4-carboxamide 184

Following procedures from Examples 113 and shown in FIG. 5, tert-butyl-2-(2,6-di-fluorophenyl)-4-(1,5-dimethyl)-1H-pyrazol-4-ylcarbamoyl)thiazol-5-ylcarbamate was converted to 184: $^1$H NMR (400 MHz, DMSO) δ 8.84 (s, 1H), 7.54-7.51 (m, 1H), 7.48 (s, 2H), 7.44 (s, 1H), 7.27 (t, J=8.6 Hz, 2H), 3.71 (s, 3H), 2.16 (s, 3H); MS (ESI) m/z: 350[M+H$^+$]

Example 185

N-(5-(4-aminopiperidin-1-yl)-1-methyl-1H-pyrazol-4-yl)-6-(2-fluorophenyl)pyrazine-2-carboxamide 185

Following procedures as in Example 141, 6-(2-fluorophenyl)-pyrazine-2-carboxylic acid was converted to 185: $^1$H-NMR (DMSO, 500 MHz) δ (ppm): 10.02 (s, 1H), 9.31 (d, J=2.5 Hz, 1H), 9.21 (s, 1H), 8.35-8.36 (m, 1H), 7.51-7.52 (m, 1H), 7.44-7.48 (m, 3H), 3.65 (s, 3H), 3.02-3.11 (m, 4H), 2.62 (m, 1H), 1.74-1.77 (m, 2H), 1.35-1.37 (m, 2H); MS (ESI) m/z: 396 [M+H$^+$]

Example 186

5-amino-2-(2,6-difluorophenyl)-N-(4,5,6,7-tetrahydropyrazolo[1,5-a]pyrimidin-3-yl)thiazole-4-carboxamide 186

Following procedures from Examples 113 and shown in FIG. 5, tert-butyl 2-(2,6-di-fluorophenyl)-4-(4,5,6,7-tetrahydropyrazolo[1,5-a]pyrimidin-3-ylcarbamoyl) thiazole-5-ylcarbamate was converted to 186: $^1$H NMR (400 MHz, DMSO) δ 8.93 (s, 1H), 7.60-7.50 (m, 1H), 7.46 (s, 2H), 7.33-7.20 (m, 3H), 5.74 (s, 1H), 3.96 (t, J=6.0 Hz, 2H), 3.19 (m, 2H), 2.02-1.93 (m, 2H); MS (ESI) m/z: 377[M+H$^+$]

Example 189

5-amino-2-(2,6-difluorophenyl)-N-(5-(4-hydroxyazepan-1-yl)-1-methyl-1H-pyrazol-4-yl)thiazole-4-carboxamide 189

Following procedures from Examples 113 and shown in FIG. 5, tert-butyl 2-(2,6-difluorophenyl)-4-(5-(4-hydroxyazepan-1-yl)-1-methyl-1H-pyrazol-4-ylcarbamoyl)thiazol-5-ylcarbamate was converted to racemic 189: $^1$H NMR (400 MHz, DMSO) δ 8.64 (s, 1H), 7.54 (s, 1H), 7.48 (m, 3H), 7.26 (t, J=8.3 Hz, 2H), 4.44 (d, J=3.7 Hz, 1H), 3.82 (m, 1H), 3.64 (s, 3H), 3.25-3.11 (m, 2H), 3.04 (m, 2H), 1.86 (t, J=10.3 Hz, 2H), 1.73-1.47 (m, 4H); MS (ESI) m/z: 449 [M+H$^+$]

Example 190

(R)—N-(5-(3-aminopiperidin-1-yl)-1-methyl-1H-pyrazol-4-yl)-6-(2-fluorophenyl)pyrazine-2-carboxamide 190

Following procedures as in Example 141, 6-(2-fluorophenyl)-pyrazine-2-carboxylic acid was converted to 190: $^1$H-NMR (DMSO, 500 MHz) δ (ppm): 9.28-9.30 (m, 2H), 8.24-8.27 (m, 1H), 7.58-7.63 (m, 2H), 7.34-7.45 (m, 2H), 3.78 (s, 3H), 3.22-3.25 (m, 1H), 3.07-3.14 (m, 2H), 2.82-2.94 (m, 2H), 1.96-1.92 (m, 1H), 1.84-1.82 (m, 1H), 1.21-1.26 (m, 1H); MS (ESI) m/z: 396 [M+H$^+$]

Example 191

(S)—N-(5-(3-aminopiperidin-1-yl)-1-methyl-1H-pyrazol-4-yl)-6-(2-fluorophenyl)pyrazine-2-carboxamide 191

Following procedures as in Example 141, 6-(2-fluorophenyl)-pyrazine-2-carboxylic acid was converted to 191: $^1$H-NMR (DMSO, 500 MHz) δ (ppm): 9.28-9.30 (m, 2H), 8.24-8.27 (m, 1H), 7.58-7.63 (m, 2H), 7.34-7.45 (m, 2H), 3.78 (s, 3H), 3.22-3.25 (m, 1H), 3.07-3.14 (m, 2H), 2.82-2.94 (m, 2H), 1.96-1.92 (m, 1H), 1.84-1.82 (m, 1H), 1.21-1.26 (m, 1H); MS (ESI) m/z: 396 [M+H$^+$]

Example 192

N-(5-(4-(aminomethyl)piperidin-1-yl)-1-methyl-1H-pyrazol-4-yl)-6-(2-fluorophenyl)pyrazine-2-carboxamide 192

Following procedures as in Example 141, 6-(2-fluorophenyl)-pyrazine-2-carboxylic acid was converted to 192: $^1$H-NMR (DMSO, 500 MHz) δ (ppm): 10.07 (s, 1H), 9.30 (s, 1H), 9.22 (s, 1H), 8.36 (s, 1H), 7.63 (s, 1H), 7.46-7.47 (m, 2H), 7.42 (s, 1H), 7.26-7.30 (m, 2H), 4.13-4.34 (m, 3H), 3.46-3.47 (m, 2H), 3.36-3.37 (m, 2H), 2.98-3.01 (m, 2H), 1.71-1.75 (m, 2H), 1.57-1.58 (m, 1H), 1.23-1.26 (m, 2H); MS (ESI) m/z: 410 [M+H$^+$]

Example 193

N-(5-(4-(2-aminoethyl)piperidin-1-yl)-1-methyl-1H-pyrazol-4-yl)-6-(2-fluorophenyl)pyrazine-2-carboxamide 193

Following procedures as in Example 141, 6-(2-fluorophenyl)-pyrazine-2-carboxylic acid was converted to 193: $^1$H-NMR (DMSO, 500 MHz) δ (ppm): 9.27-9.29 (m, 2H), 8.24-8.25 (m, 1H), 7.60-7.61 (m, 2H), 7.34-7.45 (m, 2H), 3.75 (s, 3H), 3.15-3.19 (m, 4H), 2.79 (t, J=7 Hz, 2H), 1.79 (d, J=12.5 Hz, 2H), 1.38-1.54 (m, 5H); MS (ESI) m/z: 424 [M+H$^+$]

Example 194

N-(5-(1,4-diazepan-1-yl)-1-methyl-1H-pyrazol-4-yl)-6-(2-fluorophenyl)pyrazine-2-carboxamide 194

Following procedures as in Example 141, 6-(2-fluorophenyl)-pyrazine-2-carboxylic acid was converted to 194: $^1$H NMR (CD$_3$OD, 500 MHz) δ 9.27 (s, 1H), 9.22 (d, 1H), 8.10 (d, 1H), 7.92 (s, 1H), 7.40 (m, 1H), 6.9 (m, 1H), 6.8 (m, 1H), 3.76 (s, 3H), 3.32-3.37 (m, 4H), 3.30-3.92 (m, 4H), 1.79 (m, 2H); MS (ESI) m/z: 396 (M+1)

Example 197

(R)-5-amino-N-(5-(4-aminoazepan-1-yl)-1-methyl-1H-pyrazol-4-yl)-2-(2-fluorophenyl)thiazole-4-carboxamide 197

Following procedures as in Example 200, 5-(tert-butoxycarbonylamino)-2-(2-fluorophenyl)thiazole-4-carboxylic acid was converted to 197: $^1$H-NMR (DMSO, 500 MHz) δ (ppm): 8.94 (s, 1H), 8.22 (s, 1H), 7.35-7.51 (m, 6H), 3.65 (s, 3H), 3.04-3.15 (m, 5H), 1.82 (m, 3H), 1.54 (m, 3H); MS (ESI) m/z: 430 [M+H$^+$]

Example 198

N-(5-(4-aminopiperidin-1-yl)-1-methyl-1H-pyrazol-4-yl)-5-(2-fluorophenyl)nicotinamide 198

Following procedures as in Example 141, 5-(2-fluorophenyl)-nicotinic acid was converted to 198: $^1$H-NMR (DMSO, 500 MHz) δ (ppm): 9.82 (s, 1H), 9.09 (s, 1H), 8.94 (s, 1H), 8.43 (s, 1H), 7.71-7.73 (m, 1H), 7.53-7.54 (m, 1H), 7.38-7.43 (m, 2H), 7.27 (s, 1H), 3.57-3.64 (m, 3H), 3.00-3.07 (m, 2H), 2.96-2.98 (m, 2H), 2.61-2.63 (m, 1H), 1.73-1.75 (m, 2H), 1.33-1.35 (m, 2H); MS (ESI) m/z: 395 [M+H$^+$]

Example 200

(R)-5-amino-N-(5-(4-aminoazepan-1-yl)-1-methyl-1H-pyrazol-4-yl)-2-(2,4-difluorophenyl)thiazole-4-carboxamide 200

Step 1: Preparation of [(R)-1-(4-{[5-tert-butoxycarbonylamino-2-(2,4-difluoro-phenyl)-thiazole-4-carbonyl]-amino}-2-methyl-2H-pyrazol-3-yl)-perhydro-azepin-4-yl]-carbamic acid benzyl ester

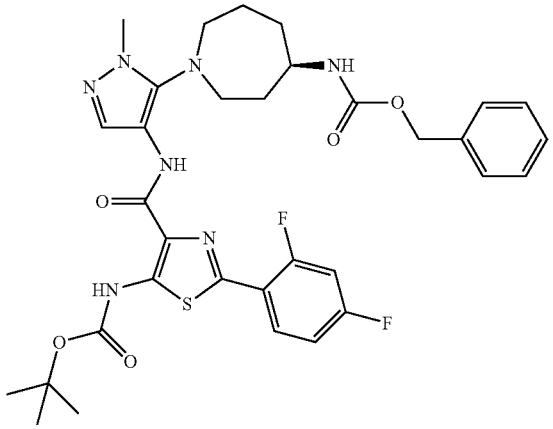 [SMILES: Cn1ncc(NC(=O)c2nc(-c3ccc(F)cc3F)sc2NC(=O)OC(C)(C)C)c1N1CCC[C@@H](NC(=O)OCc2ccccc2)CC1]

In a microwave vial was placed ((R)-1-{4-[(2-bromo-5-tert-butoxycarbonylamino-thiazole-4-carbonyl)-amino]-2-methyl-2H-pyrazol-3-yl}-perhydro-azepin-4-yl)-carbamic acid benzyl ester (78.2 mg, 0.12 mmol), 2-(2,4-difluorophenyl)-4,4,5,5-tetramethyl-1,3,2-dioxaborolane (101.3 mg, 0.42 mmol, 3.5 eq.), cesium carbonate (196.4 mg, 0.60 mmol, 5.0 eq), [1,1'-bis(diphenylphosphino)ferrocene]-dichloropalladium(II), complexed with dichloromethane (1:1) (29.5 mg, 0.036 mmol, 0.30 eq), and anhydrous N,N-dimethylformamide (3.5 mL). The reaction mixture was degassed with N$_2$ for 10 minutes and then subjected to microwave irradiation at 100° C. for 30 minutes. The reaction mixture was diluted with ethyl acetate (50 mL) and then filtered through a pad of Celite. The filtrate was washed with 50% brine/water, water and brine, dried over Na$_2$SO$_4$, filtered, and concentrated under reduced pressure. The crude was purified via flash column chromatography eluted with 40 to 100% ethyl acetate/heptane to give 46.4 mg (56.5%) of desired product as a white solid. $^1$H NMR (400 MHz, CDCl$_3$) δ 10.35 (s, 1H), 8.63 (s, 1H), 8.14-8.04 (m, 1H), 7.82 (s, 1H), 7.31 (s, 5H), 7.03-6.87 (m, 2H), 5.11-5.00 (s, 2H), 4.84-4.74 (m, 1H), 3.95-3.85 (m, 1H), 3.74 (s, 3H), 3.35-3.24 (m, 2H), 3.23-3.11 (m, 2H), 2.18-2.03 (m, 2H), 1.97-1.65 (m, 4H), 1.53 (s, 9H); MS (ESI) m/z: 682.6 [M+H]$^+$.

Step 2: Preparation of title compound 5-amino-2-(2,4-difluoro-phenyl)-thiazole-4-carboxylic acid [5-((R)-4-amino-azepan-1-yl)-1-methyl-1H-pyrazol-4-yl]-amide To a stirred mixture of [(R)-1-(4-{[5-tert-butoxycarbonylamino-2-(2,4-difluoro-phenyl)-thiazole-4-carbonyl]-amino}-2-methyl-2H-pyrazol-3-yl)-perhydro-azepin-4-yl]-carbamic acid benzyl ester (46.0 mg, 0.067 mmol) in anhydrous DCM (4.0 mL) at −10° C. under N$_2$ was added dropwise 1.0 M boron tribromide in DCM (0.22 mL, 0.22 mmol, 3.3 eq.). The reaction mixture was stirred at ambient temperature for 4 h and then cooled to −20° C. Additional 1.0 M Boron tribromide in DCM (0.11 mL, 0.11 mmol, 1.65 eq.) was added dropwise, and the reaction mixture was stirred at ambient temperature for 16 h. The reaction mixture was quenched with saturated aq. NaHCO$_3$ solution and then extracted with ethyl acetate (3×50 mL). The combined organic phases were washed with brine, dried over Na$_2$SO$_4$, filtered, and concentrated under reduced pressure. The crude was purified via reverse phase HPLC to afford 200 (12.7 mg, 42.1%) as a white solid. $^1$H NMR (400 MHz, DMSO) δ 8.93 (s, 1H), 8.39 (s, 1H), 8.33 (dd, J=15.5, 8.8 Hz, 1H), 7.47-7.36 (m, 4H), 7.29 (dd, J=11.6, 5.3 Hz, 1H), 3.66 (s, 3H), 3.26-3.14 (m, 3H), 3.14-3.05 (m, 3H), 2.03-1.89 (m, 2H), 1.88-1.77 (m, 1H), 1.76-1.56 (m, 3H); MS (ESI) m/z: 448.1 [M+H]$^+$

Example 201

5-amino-N-(5-(4-(2-aminoethyl)piperidin-1-yl)-1-methyl-1H-pyrazol-4-yl)-2-(2,6-difluorophenyl)thiazole-4-carboxamide 201

Following procedures as in Example 141, 5-(tert-butoxycarbonylamino)-2-(2,6-difluorophenyl)thiazole-4-carboxylic acid was converted to 201: $^1$H-NMR (DMSO, 500 MHz) δ (ppm): 8.72 (s, 1H), 8.45 (s, 1H), 7.52-7.55 (m, 3H), 7.43 (s, 1H), 7.26-7.30 (m, 2H), 3.59 (s, 3H), 2.99-3.04 (m, 4H), 2.77-2.78 (m, 2H), 1.69-1.71 (m, 2H), 1.43-1.51 (m, 3H), 1.21-1.27 (m, 2H); MS (ESI) m/z: 462 [M+H⁺]

Example 202

(R)-5-amino-N-(5-(4-aminoazepan-1-yl)-1-methyl-1H-pyrazol-4-yl)-2-(2,6-difluoro-4-methoxyphenyl)thiazole-4-carboxamide 202

Step 1: Preparation of [(R)-1-(4-{[5-tert-butoxycarbonylamino-2-(2,6-difluoro-4-methoxyphenyl)-thiazole-4-carbonyl]-amino}-2-methyl-2H-pyrazol-3-yl)-perhydro-azepin-4-yl]-carbamic acid benzyl ester

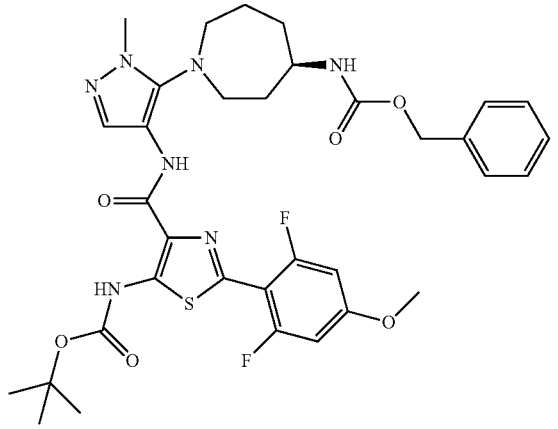 [SMILES: COc1cc(F)c(-c2nc(C(=O)Nc3cnn(C)c3N3CCC[C@@H](NC(=O)OCc4ccccc4)CC3)c(NC(=O)OC(C)(C)C)s2)c(F)c1]

Following the procedure as described in Example 258, step 1, using 2-(2,6-difluoro-4-methoxyphenyl)-4,4,5,5-tetramethyl-1,3,2-dioxaborolane in place of 2-(2,4-difluorophenyl)-4,4,5,5-tetramethyl-1,3,2-dioxaborolane, [(R)-1-(4-{[5-tert-butoxy-carbonylamino-2-(2,6-difluoro-4-methoxyphenyl)-thiazole-4-carbonyl]-amino}-2-methyl-2H-pyrazol-3-yl)-perhydro-azepin-4-yl]-carbamic acid benzyl ester was obtained in 11.9% yield. MS (ESI) m/z: 712.4 [M+H]⁺.

Step 2

A heterogeneous mixture of [(R)-1-(4-{[5-tert-butoxycarbonylamino-2-(2,6-difluoro-4-methoxyphenyl)-thiazole-4-carbonyl]-amino}-2-methyl-2H-pyrazol-3-yl)-perhydro-azepin-4-yl]-carbamic acid benzyl ester (14.5 mg, 0.02 mmol) and 2M aq. HCl (5 mL) was stirred at 100° C. under N₂ for 4 h. The resultant homogeneous reaction was cooled to RT and the water solvent was removed using toluene azeotrope. The crude was redissolved in 9:1 v/v DMF:MeOH (1 mL) and purified via reverse phase HPLC to afford 202 (9.2 mg, 94.3%) as a white solid. ¹H NMR (400 MHz, DMSO) δ 8.75 (broad s, 1H), 8.46 (s, 1H), 7.53 (s, 1H), 7.42 (s, 2H), 6.95 (s, 1H), 6.92 (s, 1H), 3.85 (s, 3H), 3.64 (s, 3H), 3.20-3.04 (m, 6H), 1.95-1.77 (m, 3H), 1.68-1.52 (m, 3H); MS (ESI) m/z: 479.1 [M+H]⁺

Example 203

5-amino-2-(2,6-difluorophenyl)-N-(1-methyl-5-(4-(N-methylacetamido)azepan-1-yl)-1H-pyrazol-4-yl)thiazole-4-carboxamide 203

Following procedures as in Example 141, 5-(tert-butoxycarbonylamino)-2-(2,6-difluorophenyl)thiazole-4-carboxylic acid was converted to 203: ¹H-NMR (DMSO, 500 MHz) δ (ppm): 8.70 (s, 1H), 7.49-7.55 (m, 4H), 7.26-7.29 (m, 2H), 3.66-3.67 (m, 3H), 3.21-3.29 (m, 2H), 3.06-3.08 (m, 2H), 2.70 (s, 2H), 2.57 (s, 3H), 1.90-1.96 (m, 3H), 1.73-1.86 (m, 5H); MS (ESI) m/z: 504 [M+H⁺]

Example 204

5-amino-N-(1-(difluoromethyl)-1H-pyrazol-4-yl)-2-(2,6-difluorophenyl)thiazole-4-carboxamide 204

Following procedures from Examples 113 and shown in FIG. 5, tert-butyl 4-(1-(difluoromethyl)-1H-pyrazol-4-ylcarbamoyl)-2-(2,6-difluorophenyl)thiazol-5-yl carbamate was converted to 204: ¹H NMR (400 MHz, DMSO) δ 10.11 (s, 1H), 8.40 (s, 1H), 8.03 (s, 1H), 7.79 (s, 1H), 7.60 (m, 3H), 7.28 (t, J=8 Hz, 2H); MS (ESI) m/z: 372[M+H⁺]

Example 205

(R)-5-amino-N-(5-(4-aminoazepan-1-yl)-1-methyl-1H-pyrazol-4-yl)-2-(3-(trifluoromethyl)phenyl)thiazole-4-carboxamide 205

Step 1: Preparation of [(R)-1-(4-{[5-tert-butoxycarbonylamino-2-(3-trifluoromethyl-phenyl)-thiazole-4-carbonyl]-amino}-2-methyl-2H-pyrazol-3-yl)-perhydro-azepin-4-yl]-carbamic acid benzyl ester

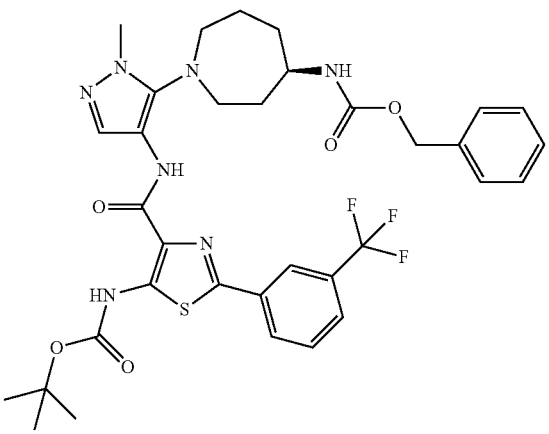 [SMILES: Cn1ncc(NC(=O)c2nc(-c3cccc(C(F)(F)F)c3)sc2NC(=O)OC(C)(C)C)c1N1CCC[C@@H](NC(=O)OCc2ccccc2)CC1]

In a microwave vial was placed ((R)-1-{4-[(2-bromo-5-tert-butoxycarbonylamino-thiazole-4-carbonyl)-amino]-2-methyl-2H-pyrazol-3-yl}-perhydro-azepin-4-yl)-carbamic acid benzyl ester (100.0 mg, 0.154 mmol), 4,4,5,5-tetramethyl-2-(3-trifluoromethyl-phenyl)-1,3,2-dioxaborolane (209.7 mg, 0.77 mmol, 5.0 eq.), sodium carbonate (49.0 mg, 0.46 mmol, 3.0 eq.), potassium acetate (45.4 mg, 0.46 mmol, 3.0 eq.), [1,1'-bis(diphenylphosphino)ferrocene]-dichloropalladium(II), complexed with dichloromethane (1:1) (25.2 mg, 0.03, mmol, 0.20 eq), ACN (9.0 mL), and water (1.9 mL). The reaction mixture was degassed with N₂ for 10 minutes and then subjected to microwave irradiation at 100° C. for 40 minutes. The reaction mixture was diluted with ethyl acetate (50 mL) and then filtered through a pad of Celite. The filtrate was washed with 50% brine/water, water and brine, dried over Na₂SO₄, filtered, and concentrated under reduced pressure. The crude was purified via flash column chromatography eluted with 50 to 100% ethyl acetate/heptane to give 73.5 mg (66.8%) of desired product as an oil. MS (ESI) m/z: 714.4 [M+H]$^+$.

Step 2: Preparation of title compound (R)-5-amino-N-(5-(4-aminoazepan-1-yl)-1-methyl-1H-pyrazol-4-yl)-2-(3-(trifluoromethyl)phenyl)thiazole-4-carboxamide Following the procedure as in Example 202, step 2, using [(R)-1-(4-{[5-tert-butoxycarbonylamino-2-(3-trifluoromethyl-phenyl)-thiazole-4-carbonyl]-amino}-2-methyl-2H-pyrazol-3-yl)-perhydro-azepin-4-yl]-carbamic acid benzyl ester in place of [(R)-1-(4-{[5-tert-butoxycarbonylamino-2-(2,6-difluoro-4-methoxyphenyl)-thiazole-4-carbonyl]-amino}-2-methyl-2H-pyrazol-3-yl)-perhydro-azepin-4-yl]-carbamic acid benzyl ester, 205 was obtained in 64.4% yield as a white solid. $^1$H NMR (400 MHz, DMSO) δ 8.98 (s, 1H), 8.21 (s, 1H), 8.04 (d, J=7.5 Hz, 1H), 7.76-7.66 (m, 2H), 7.53 (broad s, 2H), 7.42 (s, 1H), 3.66 (s, 3H), 3.40-3.10 (m, 7H), 1.99-1.78 (m, 3H), 1.73-1.55 (m, 3H); MS (ESI) m/z: 480.1 [M+H]$^+$ Example 206

(R)-5-amino-N-(5-(4-aminoazepan-1-yl)-1-methyl-1H-pyrazol-4-yl)-2-(4-(trifluoromethyl)phenyl)thiazole-4-carboxamide 206

Step 1: Preparation of (R)-benzyl 1-(4-(5-amino-2-(4-(trifluoromethyl)phenyl)thiazole-4-carboxamido)-1-methyl-1H-pyrazol-5-yl)azepan-4-ylcarbamate

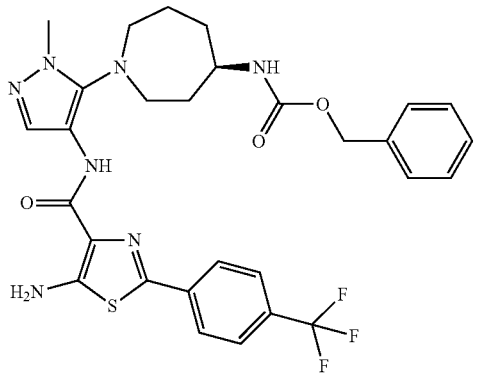 [SMILES: Cn1ncc(NC(=O)c2nc(-c3ccc(C(F)(F)F)cc3)sc2N)c1N1CCC[C@@H](NC(=O)OCc2ccccc2)CC1]

Following the procedure as described in Example 205, step 1, using 4,4,5,5-tetramethyl-2-(4-trifluoromethyl-phenyl)-1,3,2-dioxaborolane in place of 4,4,5,5-tetramethyl-2-(3-trifluoromethyl-phenyl)-1,3,2-dioxaborolane, (R)-benzyl 1-(4-(5-amino-2-(4-(trifluoromethyl)phenyl)thiazole-4-carboxamido)-1-methyl-1H-pyrazol-5-yl)azepan-4-ylcarbamate was obtained in 67.0% yield. MS (ESI) m/z: 614.3 [M+H]$^+$.

Step 2: Preparation of title compound (R)-5-amino-N-(5-(4-aminoazepan-1-yl)-1-methyl-1H-pyrazol-4-yl)-2-(4-(trifluoromethyl)phenyl)thiazole-4-carboxamide Following the procedure as described in Example 200, Step 2, using (R)-benzyl 1-(4-(5-amino-2-(4-(trifluoromethyl)phenyl)thiazole-4-carboxamido)-1-methyl-1H-pyrazol-5-yl)azepan-4-ylcarbamate in place of [(R)-1-(4-{[5-tert-butoxycarbonylamino-2-(2,4-difluoro-phenyl)-thiazole-4-carbonyl]-amino}-2-methyl-2H-pyrazol-3-yl)-perhydro-azepin-4-yl]-carbamic acid benzyl ester, 206 was obtained in 25.2% yield. $^1$H NMR (400 MHz, DMSO) δ 8.90 (s, 1H), 8.04 (d, J=8.1 Hz, 2H), 7.81 (d, J=8.2 Hz, 2H), 7.58 (broad s, 2H), 7.42 (s, 1H), 3.66 (s, 3H), 3.60-3.05 (m, 7H), 2.00-1.80 (m, 3H), 1.76-1.57 (m, 3H); MS (ESI) m/z: 480.1 [M+H]$^+$ Example 208

(R)-5-amino-2-(2,6-difluorophenyl)-N-(1-methyl-5-(4-(N-methylacetamido)azepan-1-yl)-1H-pyrazol-4-yl)thiazole-4-carboxamide 208

Following procedures as in Example 141, 5-(tert-butoxycarbonylamino)-2-(2,6-difluorophenyl)thiazole-4-carboxylic acid was converted to 208: $^1$H-NMR (DMSO, 500 MHz) δ (ppm): 8.70 (s, 1H), 7.49-7.55 (m, 4H), 7.26-7.29 (m, 2H), 3.66-3.67 (m, 3H), 3.21-3.29 (m, 2H), 3.06-3.08 (m, 2H), 2.70 (s, 2H), 2.57 (s, 3H), 1.90-1.96 (m, 3H), 1.73-1.86 (m, 5H); MS (ESI) m/z: 504 [M+H$^+$]

Example 209

5-amino-N-(1-(2-aminoethyl)-1H-pyrazol-4-yl)-2-(2,6-difluorophenyl)thiazole-4-carboxamide 209

Following procedures from Examples 113 and shown in FIG. 5, tert-butyl 4-(1-(2-aminoethyl)-1H-pyrazol-4-ylcarbamoyl)-2-(2,6-difluorophenyl)thiazol-5-ylcarbamate was converted to 209: $^1$H NMR (400 MHz, DMSO) δ 9.74 (s, 1H), 8.26 (s, 1H), 8.02 (s, 1H), 7.69 (s, 1H), 7.56-7.50 (m, 3H), 7.27 (t, J=8.4 Hz, 2H), 4.09 (t, J=6.2 Hz, 2H), 2.97 (t, J=6.2 Hz, 2H); MS (ESI) m/z: 365[M+H$^+$]

Example 210

(R)-5-amino-N-(5-(4-aminoazepan-1-yl)-1-methyl-1H-pyrazol-4-yl)-2-(2-(trifluoromethyl)phenyl)thiazole-4-carboxamide 210

Step 1: Preparation of [(R)-1-(4-{[5-tert-butoxycarbonylamino-2-(2-trifluoromethyl-phenyl)-thiazole-4-carbonyl]-amino}-2-methyl-2H-pyrazol-3-yl)-perhydro-azepin-4-yl]-carbamic acid benzyl ester

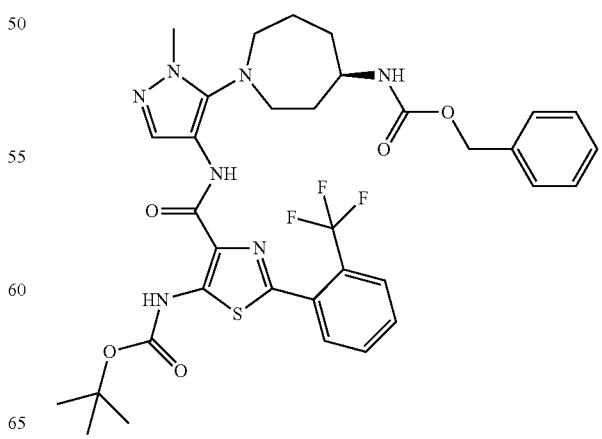

In a microwave vial was placed ((R)-1-{4-[(2-bromo-5-tert-butoxycarbonylamino-thiazole-4-carbonyl)-amino]-2-methyl-2H-pyrazol-3-yl}-perhydro-azepin-4-yl)-carbamic acid benzyl ester (132.7 mg, 0.205 mmol), 4,4,5,5-tetramethyl-2-(2-trifluoromethyl-phenyl)-1,3,2-dioxaborolane (278.3 mg, 1.02 mmol, 5.0 eq.), sodium carbonate (65.0 mg, 0.61 mmol, 3.0 eq.), potassium acetate (60.2 mg, 0.61 mmol, 3.0 eq.), [1,1'-bis(diphenylphosphino)ferrocene]-dichloropalladium(II), complexed with dichloromethane (1:1) (33.4 mg, 0.041, mmol, 0.20 eq), ACN (10 mL), and water (2.5 mL). The reaction mixture was degassed with $N_2$ for 10 minutes and then subjected to microwave irradiation at 100° C. for 40 minutes. The reaction mixture was diluted with ethyl acetate (50 mL) and then filtered through a pad of Celite. The filtrate was washed with 50% brine/water, water and brine, dried over $Na_2SO_4$, filtered, and concentrated under reduced pressure. The crude was purified via flash column chromatography eluted with 50 to 100% ethyl acetate/heptane to give 83.9 mg (57.4%) of desired product as a foam. MS (ESI) m/z: 714.4 [M+H]$^+$.

Step 2: Preparation of title compound (R)-5-amino-N-(5-(4-aminoazepan-1-yl)-1-methyl-1H-pyrazol-4-yl)-2-(2-(trifluoromethyl)phenyl)thiazole-4-carboxamide A heterogeneous mixture of [(R)-1-(4-{[5-tert-butoxycarbonylamino-2-(2-trifluoromethyl-phenyl)-thiazole-4-carbonyl]-amino}-2-methyl-2H-pyrazol-3-yl)-perhydro-azepin-4-yl]-carbamic acid benzyl ester (83.9 mg, 0.117 mmol) in 1,4-dioxane (1.0 mL) and 2M aq. HCl (10 mL) was stirred at 120° C. under $N_2$ for 16 h. The resultant homogeneous reaction was then slowly quenched with saturated aq. $NaHCO_3$ solution and then extracted with ethyl acetate (3×50 mL). The combined organic phases were washed with brine, dried over $Na_2SO_4$, filtered, and concentrated under reduced pressure. The crude was purified via reverse phase HPLC to afford 210 (33.4 mg, 59.2%) as a white solid. $^1$H NMR (400 MHz, DMSO) δ 8.51 (s, 1H), 7.90 (d, J=8.0 Hz, 1H), 7.78 (d, J=4.1 Hz, 2H), 7.68 (dd, J=8.1 Hz, 3.9 Hz, 1H), 7.58 (s, 1H), 7.46 (broad s, 2H), 3.64 (s, 3H), 3.10 (t, J=5.3 Hz, 4H), 3.02-2.90 (m, 1H), 1.89-1.73 (m, 3H), 1.64-1.44 (m, 3H); 2 protons buried in water peak; MS (ESI) m/z: 480.1 [M+H]$^+$ Example 211

(R)-5-amino-N-(5-(4-aminoazepan-1-yl)-1-methyl-1H-pyrazol-4-yl)-2-(2-fluoro-4-methylphenyl)thiazole-4-carboxamide 211

Following the procedures from Example 210 and shown in FIG. 3, using ((R)-1-{4-[(2-bromo-5-tert-butoxycarbonylamino-thiazole-4-carbonyl)-amino]-2-methyl-2H-pyrazol-3-yl}-perhydro-azepin-4-yl)-carbamic acid benzyl ester and 2-fluoro-4-methyl-phenylboronic acid as starting materials, 211 was obtained in 20.5% yield over two steps: $^1$H NMR (400 MHz, DMSO) δ 8.88 (s, 1H), 8.14 (t, J=8.2 Hz, 1H), 7.47 (s, 1H), 7.36 (broad s, 2H), 7.22-7.14 (m, 2H), 3.66 (s, 3H), 3.45-3.05 (m, 7H), 2.36 (s, 3H), 1.98-1.78 (m, 3H), 1.72-1.54 (m, 3H); MS (ESI) m/z: 444.2 [M+H]$^+$ Example 212

(R)—N-(5-(4-aminoazepan-1-yl)-1-methyl-1H-pyrazol-4-yl)-5-fluoro-6-(2-fluorophenyl)picolinamide 212

Following procedures from Examples 141, (R)-benzyl 1-(4-amino-1-methyl-1H-pyrazol-5-yl)azepan-4-ylcarbamate from Example 16 was converted to 212. $^1$H NMR (400 MHz, DMSO) δ 8.23 (dd, J=8.6, 3.8 Hz, 1H), 8.09 (t, J=9.1 Hz, 1H), 7.81 (t, J=7.4 Hz, 1H), 7.67-7.55 (m, 2H), 7.50-7.34 (m, 2H), 3.65 (s, 3H), 3.18-2.99 (m, 5H), 2.91 (t, J=8.7 Hz, 1H), 1.85-1.62 (m, 3H), 1.61-1.34 (m, 3H). MS (ESI) m/z: 427.2 [M+H$^+$].

Example 214

5-amino-2-(2,6-difluorophenyl)-N-(1-(2-(piperidin-1-yl)ethyl)-1H-pyrazol-4-yl)thiazole-4-carboxamide 214

Following procedures from Examples 113 and shown in FIG. 5, tert-butyl 2-(2,6-difluorophenyl)-4-(1-(2-(piperidin-1-yl)ethyl)-1H-pyrazol-4-ylcarbamoyl)thiazol-5-ylcarbamate was converted to 214: $^1$H NMR (400 MHz, DMSO) δ 9.71 (s, 1H), 8.00 (s, 1H), 7.64 (s, 1H), 7.60-7.52 (m, 1H), 7.49 (s, 2H), 7.26 (t, J=8.4 Hz, 2H), 4.14 (t, J=6.7 Hz, 2H), 2.64 (dd, J=14.1, 7.4 Hz, 2H), 2.41-2.31 (m, 4H), 1.52-1.43 (m, 4H), 1.37 (d, J=5.1 Hz, 2H); MS (ESI) m/z: 433[M+H$^+$]

Example 215

5-amino-2-(2,6-difluorophenyl)-N-(1-(2-morpholinoethyl)-1H-pyrazol-4-yl)thiazole-4-carboxamide 215

Following procedures from Examples 113 and shown in FIG. 5, tert-butyl 2-(2,6-difluorophenyl)-4-(1-(2-morpholinoethyl)-1H-pyrazol-4-ylcarbamoyl)thiazol-5-yl carbamate was converted to 215: $^1$H NMR (400 MHz, DMSO) δ 9.71 (s, 1H), 8.01 (s, 1H), 7.65 (s, 1H), 7.60-7.52 (m, 1H), 7.51 (d, J=10.0 Hz, 2H), 7.27 (t, J=8.4 Hz, 2H), 4.17 (t, J=6.6 Hz, 2H), 3.58-3.51 (m, 4H), 2.68 (t, J=6.6 Hz, 2H), 2.42-2.35 (m, 4H); MS (ESI) m/z: 435[M+H$^+$]

Example 216

(R)-5-amino-N-(5-(3-(2-aminoethyl)piperidin-1-yl)-1-methyl-1H-pyrazol-4-yl)-2-(2,6-difluorophenyl)thiazole-4-carboxamide 216

Following procedures as in Example 141, 5-(tert-butoxycarbonylamino)-2-(2,6-difluorophenyl)thiazole-4-carboxylic acid was converted to 216: $^1$H-NMR (DMSO, 500 MHz) δ (ppm): 8.73 (s, 1H), 7.50-7.55 (m, 4H), 7.27 (t, 7.2 Hz, 2H), 3.63 (s, 3H), 2.93-3.08 (m, 3H), 2.66-2.72 (m, 1H), 2.53-2.60 (m, 2H), 1.64-1.82 (m, 3H), 1.50-1.62 (m, 1H), 1.25-1.36 (m, 2H), 0.96-1.06 (m, 1H); MS (ESI) m/z: 462 [M+H$^+$]

Example 217

(S)-5-amino-2-(2,6-difluorophenyl)-N-(1-methyl-5-(2-(pyrrolidin-2-yl)ethylamino)-1H-pyrazol-4-yl)thiazole-4-carboxamide 217

Following procedures as in Example 141, 5-(tert-butoxycarbonylamino)-2-(2,6-difluorophenyl)thiazole-4-carboxylic acid was converted to 217: $^1$H-NMR (CDCl$_3$, 500 MHz) δ (ppm): 8.49 (s, 1H), 7.45 (s, 1H), 7.34-7.38 (m, 1H), 7.01-7.05 (m, 2H), 6.18 (s, 2H), 3.75 (s, 3H), 3.15-3.27 (m, 3H), 3.03-3.07 (m, 1H), 2.89-2.94 (m, 1H), 1.90-1.96 (m, 1H), 1.83-1.86 (d, 15 Hz, 1H), 1.74-1.79 (m, 2H), 1.63-1.68 (m, 1H), 1.38-1.46 (m, 1H); MS (ESI) m/z: 448 [M+H$^+$]

Example 218

5-amino-N-(5-(azepan-1-yl)-1-methyl-1H-pyrazol-4-yl)-2-(2,6-difluorophenyl)thiazole-4-carboxamide 218

Following procedures as in Example 113, tert-butyl 4-(5-(azepan-1-yl)-1-methyl-1H-pyrazol-4-ylcarbamoyl)-2-(2,6-difluorophenyl)thiazol-5-ylcarbamate was converted to 218: $^1$H NMR (400 MHz, DMSO) δ 8.62 (d, J=27.5 Hz, 1H), 7.59 (s, 1H), 7.57-7.43 (m, 3H), 7.33-7.20 (m, 2H), 3.65 (s, 3H), 3.12 (d, J=5.1 Hz, 4H), 1.66 (s, 8H); MS (ESI) m/z: 433.3 [M+H]$^+$

Example 219

(R)—N-(5-(4-aminoazepan-1-yl)-1-methyl-1H-pyrazol-4-yl)-6-(2-fluorophenyl)pyrazine-2-carboxamide 219

Following procedures as in Example 210, 6-(2-fluorophenyl)-pyrazine-2-carboxylic acid was converted to 219: $^1$H-NMR (DMSO, 500 MHz) δ (ppm): 9.30 (s, 1H), 9.23 (s, 1H), 8.26-8.29 (m, 1H), 7.63-7.65 (m, 1H), 7.58 (s, 1H), 7.45-7.49 (m, 2H), 3.67 (s, 3H), 3.12-3.18 (m, 4H), 2.95-2.96 (m, 1H), 1.75-1.83 (m, 4H), 1.43-1.52 (m, 4H); MS (ESI) m/z: 410 [M+H]$^+$

Example 220

(S)—N-(5-(4-aminoazepan-1-yl)-1-methyl-1H-pyrazol-4-yl)-6-(2-fluorophenyl)pyrazine-2-carboxamide 220

Following procedures as in Example 210, 6-(2-fluorophenyl)-pyrazine-2-carboxylic acid was converted to 220: $^1$H-NMR (DMSO, 500 MHz) δ (ppm): 9.30 (s, 1H), 9.23 (s, 1H), 8.26-8.29 (m, 1H), 7.63-7.65 (m, 1H), 7.58 (s, 1H), 7.45-7.49 (m, 2H), 3.67 (s, 3H), 3.12-3.18 (m, 4H), 2.95-2.96 (m, 1H), 1.75-1.83 (m, 4H), 1.43-1.52 (m, 4H); MS (ESI) m/z: 410 [M+H]$^+$

Example 221

(R)-5-amino-2-(2,6-difluorophenyl)-N-(1-methyl-5-(2-(pyrrolidin-2-yl)ethylamino)-1H-pyrazol-4-yl)thiazole-4-carboxamide 221

Following procedures as in Example 141, 5-(tert-butoxycarbonylamino)-2-(2,6-difluorophenyl)thiazole-4-carboxylic acid was converted to 221: $^1$H-NMR (DMSO, 500 MHz) δ (ppm): 8.49 (s, 1H), 7.45 (s, 1H), 7.34-7.38 (m, 1H), 7.01-7.05 (m, 2H), 6.18 (s, 2H), 3.75 (s, 3H), 3.15-3.27 (m, 3H), 3.03-3.07 (m, 1H), 2.89-2.94 (m, 1H), 1.90-1.96 (m, 1H), 1.83-1.86 (d, 15 Hz, 1H), 1.74-1.79 (m, 2H), 1.63-1.68 (m, 1H), 1.38-1.46 (m, 1H); MS (ESI) m/z: 448 [M+H]$^+$

Example 222

(R)-5-amino-N-(5-(4-aminoazepan-1-yl)-1-methyl-1H-pyrazol-4-yl)-2-(4-cyclopropyl-2-fluorophenyl)thiazole-4-carboxamide 222

Following the procedures from Example 210 and shown in FIG. 3, using ((R)-1-{4-[(2-bromo-5-tert-butoxycarbonylamino-thiazole-4-carbonyl)-amino]-2-methyl-2H-pyrazol-3-yl}-perhydro-azepin-4-yl)-carbamic acid benzyl ester and 2-(4-cyclopropyl-2-fluorophenyl)-4,4,5,5-tetramethyl-1,3,2-dioxaborolane as starting materials, 222 was obtained in 37.8% yield over two steps: $^1$H NMR (400 MHz, DMSO) δ 8.86 (s, 1H), 8.10 (t, J=8.2 Hz, 1H), 7.53 (s, 1H), 7.35 (s, 2H), 7.06 (dd, J=19.7, 10.7 Hz, 2H), 3.65 (s, 3H), 3.21-2.99 (m, 5H), 2.05-1.95 (m, 1H), 1.90-1.73 (m, 4H), 1.65-1.47 (m, 3H), 1.06-0.99 (m, 2H), 0.81-0.75 (m, 2H); MS (ESI) m/z: 470.2 [M+H]$^+$

Example 223

(R)-5-amino-N-(5-(4-aminoazepan-1-yl)-1-methyl-1H-pyrazol-4-yl)-2-(2-fluoro-5-methylphenyl)thiazole-4-carboxamide 223

Following procedures from Example 141, (R)-benzyl 1-(4-amino-1-methyl-1H-pyrazol-5-yl)azepan-4-ylcarbamate from Example 16 was converted to 223: $^1$H NMR (400 MHz, DMSO) δ 8.90 (s, 1H), 8.03 (d, J=7.6 Hz, 1H), 7.51 (s, 1H), 7.39 (s, 2H), 7.23 (d, J=9.0 Hz, 2H), 3.65 (s, 3H), 3.19-3.04 (m, 6H), 2.37 (s, 3H), 1.84 (m, 3H), 1.56 (m, 3H). MS (ESI) m/z: 444.2 [M+H]$^+$

Example 224

(S)-5-amino-2-(2,6-difluorophenyl)-N-(5-(4-(dimethylamino)azepan-1-yl)-1-methyl-1H-pyrazol-4-yl)thiazole-4-carboxamide 224

Following procedures as in Example 141, 5-(tert-butoxycarbonylamino)-2-(2,6-difluorophenyl)thiazole-4-carboxylic acid was converted to 224: $^1$H-NMR (DMSO, 500 MHz) δ (ppm): 7.57 (s, 1H), 7.47-7.50 (m, 1H), 7.14-7.17 (m, 2H), 3.75 (s, 3H), 3.36-3.40 (m, 3H), 3.24-3.27 (m, 2H), 2.68 (s, 6H), 1.80-2.11 (m, 6H); MS (ESI) m/z: 476 [M+H]$^+$

Example 225

(R)-5-amino-2-(2,6-difluorophenyl)-N-(5-(4-(dimethylamino)azepan-1-yl)-1-methyl-1H-pyrazol-4-yl)thiazole-4-carboxamide 225

Following procedures as in Example 141, 5-(tert-butoxycarbonylamino)-2-(2,6-difluorophenyl)thiazole-4-carboxylic acid was converted to 225: $^1$H-NMR (DMSO, 500 MHz) δ (ppm): $^1$H-NMR (DMSO, 500 MHz) δ (ppm): 7.57 (s, 1H), 7.50-7.47 (m, 1H), 7.17-7.14 (m, 2H), 3.75 (s, 3H), 3.40-3.36 (m, 3H), 3.27-3.24 (m, 2H), 2.68 (s, 6H), 2.11-1.80 (m, 6H); MS (ESI) m/z: 476 [M+H]$^+$

Example 226

(R)-5-amino-N-(5-(4-aminoazepan-1-yl)-1-methyl-1H-pyrazol-4-yl)-2-(2,5-difluorophenyl)thiazole-4-carboxamide 226

Following procedures as in Example 200, 5-(tert-butoxycarbonylamino)-2-(2,5-difluorophenyl)thiazole-4-carboxylic acid was converted to 226: $^1$H-NMR (DMSO, 500 MHz) δ (ppm): 9.11 (s, 1H), 7.57 (s, 1H), 8.11-8.12 (m, 1H), 7.40-7.48 (m, 3H), 7.27-7.29 (m, 1H), 3.65 (s, 3H), 3.08-3.18 (m, 4H), 2.95-3.01 (m, 1H), 1.75-1.83 (m, 3H), 1.39-1.58 (m, 3H); MS (ESI) m/z: 448 [M+H]$^+$

Example 227

(R)—N-(5-(4-acetamidoazepan-1-yl)-1-methyl-1H-pyrazol-4-yl)-5-amino-2-(2,6-difluorophenyl)thiazole-4-carboxamide 227

In a 40 mL sealed vial was added (R)-tert-butyl 4-(5-(4-Cbz-aminoazepan-1-yl)-1-methyl-1H-pyrazol-4-ylcarbamoyl)-2-(2,6-difluorophenyl)thiazol-5-ylcarbamate (220 mg, 0.32 mmol, prepared according to Example 140 Step 1), 1,4-cyclohexadiene (0.18 mL, 1.94 mmol) and ethanol (12 mL). 10% Pd/C (35.0 mg, 0.033 mmol) was added and the reaction vial was vacuum purged with nitrogen three times. The reaction mixture was then stirred at 95° C. under nitrogen for 2 h. After cooling down to room temperature, the reaction mixture was filtered through Celite and rinsed thoroughly with methanol. The solvent was distilled off under reduced pressure to give the crude product (R)-tert-butyl 4-(5-(4-aminoazepan-1-yl)-1-methyl-1H-pyrazol-4-ylcarbamoyl)-2-(2,6-difluorophenyl)thiazol-5-ylcarbamate (180 mg, 84%).

In a 50 mL round bottom flask was added the above product (148 mg, 0.27 mmol), acetic acid (0.02 mL, 0.35 mmol) and HATU (0.308 mg, 0.81 mmol). Methylene chloride (6 mL) and diisopropylethylamine (0.33 mL, 1.89 mmol) were added and the reaction mixture was stirred at room temperature for 2 h upon which the reaction was complete by LCMS. The solvent was distilled off and the crude material was purified via flash chromatography, methylene chloride/methanol (with 1% ammonium hydroxide) 0% to 10% to afford (R)-tert-butyl 4-(5-(4-acetamidoazepan-1-yl)-1-methyl-1H-pyrazol-4-ylcarbamoyl)-2-(2,6-difluorophenyl)thiazol-5-ylcarbamate (17 mg, 11%).

The above product (17 mg, 0.03 mmol) was stirred with 4.0M HCl in dioxane at room temperature overnight. The reaction was monitored by LCMS. Upon completion of the reaction, the solvent was distilled off and the residue was basified with saturated sodium bicarbonate. The aqueous solution was extracted with ethyl acetate 3x. The combined organic layers were dried over sodium sulfate, filtered and concentrated. The crude product was purified via reverse phase HPLC to afford 227 (5.9 mg, 42%). $^1$H NMR (400 MHz, DMSO) δ 8.66 (s, 1H), 7.74 (d, J=7.5 Hz, 1H), 7.50 (d, J=19.7 Hz, 4H), 7.26 (t, J=8.7 Hz, 2H), 3.84 (s, 1H), 3.66 (s, 3H), 3.14 (m, 5H), 1.96-1.79 (m, 3H), 1.76 (s, 3H), 1.72-1.51 (m, 3H). MS (ESI) m/z: 490.2 [M+H$^+$].

Example 228

5-amino-N-(5-(3-(2-aminoethyl)piperidin-1-yl)-1-methyl-1H-pyrazol-4-yl)-2-(2,6-difluorophenyl)thiazole-4-carboxamide 228

Following procedures as in Example 141, 5-(tert-butoxycarbonylamino)-2-(2,6-difluorophenyl)thiazole-4-carboxylic acid was converted to 228: $^1$H-NMR (DMSO, 500 MHz) δ (ppm): 8.73 (s, 1H), 7.50-7.55 (m, 4H), 7.27 (t, 7.2 Hz, 2H), 3.64 (s, 3H), 2.93-3.08 (m, 3H), 2.68-2.72 (m, 1H), 2.54-2.66 (m, 2H), 1.64-1.82 (m, 3H), 1.50-1.62 (m, 1H), 1.28-1.42 (m, 2H), 0.96-1.08 (m, 1H); MS (ESI) m/z: 462 [M+H$^+$]

Example 229

(R)—N-(5-(4-aminoazepan-1-yl)-1-methyl-1H-pyrazol-4-yl)-5-fluoro-6-phenylpicolinamide 229

Following procedures from Example 141, (R)-benzyl 1-(4-amino-1-methyl-1H-pyrazol-5-yl)azepan-4-ylcarbamate from Example 16 was converted to (R)-benzyl 1-(4-(5-fluoro-6-phenylpicolinamido)-1-methyl-1H-pyrazol-5-yl)azepan-4-ylcarbamate.

In a 40 mL sealed vial was added (R)-benzyl 1-(4-(5-fluoro-6-phenylpicolinamido)-1-methyl-1H-pyrazol-5-yl)azepan-4-ylcarbamate (62 mg, 0.11 mmol), 1,4-cyclohexadiene (0.11 mL, 1.14 mmol) and ethanol (7 mL). 10% Pd/C (18.2 mg, 0.017 mmol) was added and the reaction vial was vacuum purged with nitrogen three times. The reaction mixture was then stirred at 95° C. under nitrogen for 2 h. After cooling down to room temperature, the reaction mixture was filtered through Celite and rinsed thoroughly with methanol. The solvent was distilled off under reduced pressure to give the crude product which was purified via reverse phase HPLC to afford 229. $^1$H NMR (400 MHz, DMSO) δ 8.40 (s, 1H), 8.18-7.98 (m, 4H), 7.68-7.48 (m, 3H), 3.68 (s, 3H), 3.25-3.03 (m, 5H), 2.02-1.75 (m, 3H), 1.74-1.51 (m, 3H). MS (ESI) m/z: 409.2 [M+H$^+$].

Example 230

5-amino-2-(2,6-difluorophenyl)-N-(1-methyl-5-((tetrahydro-2H-pyran-4-yl)methoxy)-1H-pyrazol-4-yl)thiazole-4-carboxamide 230

Step 1: 1-Methyl-4-nitro-5-((tetrahydro-2H-pyran-4-yl)methoxy)-1H-pyrazole

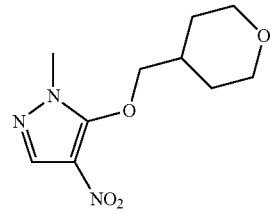 [SMILES: Cn1ncc([N+](=O)[O-])c1OCC1CCOCC1]

To a solution of 5-chloro-1-methyl-4-nitro-1H-pyrazole (0.2 g, 1.24 mmol) and tetrahydro-2H-pyran-4-yl-methanol (0.223 g, 1.92 mmol) in DMF (20 mL) cooled to 0° C. was added sodium hydride (60% dispersion in mineral oil, 0.128 g, 3.2 mmol) portionwise. The mixture was warmed to room temperature and stirred for 1 hr. The mixture was concentrated under reduced pressure and the residue dissolved in EtOAc. The organic layer was washed with water, separated and passed through a phase separator cartridge. The solvent was removed under reduced pressure and the crude product was purified via silica gel column chromatography (0-80% EtOAc/isohexane) to give 1-methyl-4-nitro-5-((tetrahydro-2H-pyran-4-yl)methoxy)-1H-pyrazole as a clear oil (143 mg, 48%). $^1$H NMR (400 MHz, CDCl$_3$) δ 7.98 (s, 1H), 4.28 (d, J=6.3 Hz, 2H), 4.07-3.96 (m, 4H), 3.71 (s, 3H), 2.22-2.09 (m, 1H), 1.82-1.62 (m, 4H)

Step 2

A solution of 1-methyl-4-nitro-5-((tetrahydro-2H-pyran-4-yl)methoxy)-1H-pyrazole (0.143 g, 0.59 mmol) in MeOH (15 mL) was passed through the H-Cube® (70 bar, 60° C., flow rate: 1 mL/min, 30 mm 10% Pd/C cartridge). The solvent was removed under reduced pressure to afford the crude amine as a brown oil (0.115 g, 0.54 mmol). To a solution of this amine in DCM (8 mL) was added 5-(tert-butoxycarbonylamino)-2-(2,6-difluorophenyl)thiazole-4-carboxylic acid (0.206 g, 0.58 mmol), HATU (0.615 g, 1.62 mmol) and DIPEA (0.66 mL, 3.78 mmol). The mixture was stirred at room temperature for 18 hr. Water (30 ml) was added and stirring continued for 15 min. The layers were separated and the aqueous extracted with DCM. The combined organics were passed through a phase separation cartridge and the solvent removed under reduced pressure. Purification of the residue via silica gel column chromatography (0-100% EtOAc/isohexane) gave tert-butyl 2-(2,6-difluorophenyl)-4-(1-methyl-5-((tetrahydro-2H-pyran-4-yl)methoxy)-1H-pyrazol-4-ylcarbamoyl)thiazol-5-ylcarbamate as a yellow solid (0.22 g, 69%). This solid (0.129 g, 0.25 mmol) was stirred in HCl in 1,4-dioxane (4.0 M, 4 mL) at room temperature for 18 hr. The solvents were removed under reduced pressure and the crude residue was re-dissolved in MeOH and loaded onto an SCX column. The column was washed with MeOH and 0.3 M ammonia in MeOH to yield a coloured foam. Further purification via silica gel column chromatography (0-100% EtOAc/isohexane) gave 230 as a white solid (70 mg, 67%). $^1$H NMR (400 MHz, CDCl$_3$) δ 8.26 (s, 1H), 7.62 (s, 1H), 7.37-7.28 (m, 1H), 7.07-6.97 (m, 2H), 6.15 (s, 2H), 4.02 (d, J=6.5 Hz, 2H), 3.96 (dd, J=11.5, 4.5 Hz, 2H), 3.69 (s, 3H), 3.43-3.35 (m, 2H), 2.11-1.98 (m, 1H), 1.75-1.69 (m, 2H), 1.51-1.38 (m, 2H). LCMS (ES+) m/z 450 (M+1)

Example 231

5-amino-2-(2,6-difluorophenyl)-N-(1-methyl-5-(1-methylpiperidin-4-yl)-1H-pyrazol-4-yl)thiazole-4-carboxamide 231

Step 1: 1-Methyl-4-(1-methyl-4-nitro-1H-pyrazol-5-yl)-1,2,3,6-tetrahydropyridine

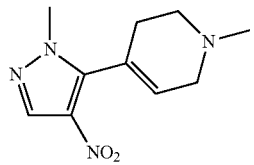

5-Chloro-1-methyl-4-nitro-1H-pyrazole (0.2 g, 1.24 mmol), 1-methyl-1,2,3,6 tetrahydropyridine-4-boronic acid pinacol ester (0.553 g, 2.48 mmol) and Pd(dppf)$_2$Cl$_2$ (0.02 g, 0.025 mmol) were suspended in degassed MeCN (5 mL). Aqueous Na$_2$CO$_3$/KOAc solution (1:1, 1.1 M, 1.5 mL) was added and the mixture was heated at 130° C. in a microwave for 40 min. A further portion of Pd(dppf)$_2$Cl$_2$ (0.1 g, 0.12 mmol) was added and the mixture was heated at 130° C. for a further 90 min. The solvents were removed under reduced pressure and the crude residue dissolved in EtOAc and water. The mixture was extracted with EtOAc and the combined organic layers passed through a phase separator cartridge. The solvent was removed under reduced pressure and the crude product was purified via silica gel column chromatography (0-10% MeOH/DCM) to give 1-methyl-4-(1-methyl-4-nitro-1H-pyrazol-5-yl)-1,2,3,6-tetrahydropyridine as a brown oil (44 mg, 16%). $^1$H NMR (400 MHz, CDCl$_3$) δ 8.08 (s, 1H), 5.89-5.86 (m, 1H), 3.82 (s, 3H), 3.19 (q, J=3.0 Hz, 2H), 2.74 (q, J=5.5 Hz, 2H), 2.47-2.39 (m, 5H)

Step 2

Following the procedure for Example 230, starting with 1-methyl-4-(1-methyl-4-nitro-1H-pyrazol-5-yl)-1,2,3,6-tetrahydropyridine (0.111 g, 0.5 mmol) gave 231 as a beige solid (75 mg, 35% over three steps). $^1$H NMR (400 MHz, CDCl$_3$) δ 8.35 (s, 1H), 7.63 (s, 1H), 7.37-7.24 (m, 1H), 7.01 (t, J=8.5 Hz, 2H), 6.14 (s, 2H), 3.86 (s, 3H), 3.03-2.93 (m, 2H), 2.73-2.62 (m, 1H), 2.30 (s, 3H), 2.15-1.97 (m, 4H), 1.86 (d, J=12.0 Hz, 2H). LCMS (ES+) m/z 433 (M+1)

Example 232

(R)-5-amino-2-(2,6-difluorophenyl)-N-(1-methyl-5-(tetrahydrofuran-3-yloxy)-1H-pyrazol-4-yl)thiazole-4-carboxamide 232

Step 1: (R)-1-Methyl-4-nitro-5-(tetrahydrofuran-3-yloxy)-1H-pyrazole

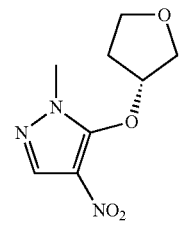

Following the procedure for Example 230 starting with 5-chloro-1-methyl-4-nitro-1H-pyrazole and (R)-(−)-3-hydroxy tetrahydrofuran gave (R)-1-methyl-4-nitro-5-(tetrahydrofuran-3-yloxy)-1H-pyrazole as a clear oil (90 mg, 34%). $^1$H NMR (400 MHz, CDCl$_3$) δ 8.01 (s, 1H), 5.65 (q, J=3.4 Hz, 1H), 4.10 (q, J=8.0 Hz, 1H), 4.02-3.87 (m, 2H), 3.81 (dd, J=11.3, 3.4 Hz, 1H), 3.71 (s, 3H), 2.26 (td, J=7.3, 3.4 Hz, 2H)

Step 2

Following the procedure for Example 230, starting with (R)-1-methyl-4-nitro-5-(tetrahydrofuran-3-yloxy)-1H-pyrazole gave 232 as a white solid (70 mg, 38% over three steps). $^1$H NMR (400 MHz, CDCl$_3$) δ 8.26 (s, 1H), 7.60 (s, 1H), 7.37-7.28 (m, 1H), 7.08-6.98 (m, 2H), 6.15 (s, 2H), 5.10-5.06 (m, 1H), 4.10-3.99 (m, 2H), 3.94-3.86 (m, 1H), 3.82 (dd, J=10.8, 4.0 Hz, 1H), 3.68 (s, 3H), 2.28-2.09 (m, 2H). LCMS (ES+) m/z 422 (M+1)

Example 233

(S)-5-amino-2-(2,6-difluorophenyl)-N-(1-methyl-5-(tetrahydrofuran-3-yloxy)-1H-pyrazol-4-yl)thiazole-4-carboxamide 233

Step 1: (S)-1-Methyl-4-nitro-5-(tetrahydrofuran-3-yloxy)-1H-pyrazole

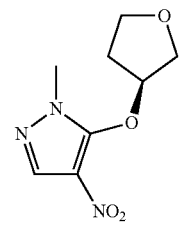

5-Chloro-1-methyl-4-nitro-1H-pyrazole and (S)-(+)-3-hydroxy tetrahydrofuran gave (S)-1-methyl-4-nitro-5-(tetrahydrofuran-3-yloxy)-1H-pyrazole as a clear oil (52 mg, 20%). $^1$H NMR (400 MHz, CDCl$_3$) δ 8.01 (s, 1H), 5.65 (q, J=3.4 Hz, 1H), 4.10 (q, J=8.0 Hz, 1H), 4.02-3.87 (m, 2H), 3.84-3.76 (m, 1H), 3.71 (s, 3H), 2.26 (td, J=7.3, 3.4 Hz, 2H)

Step 2

Following the procedure for Example 230, starting with (S)-1-methyl-4-nitro-5-(tetrahydrofuran-3-yloxy)-1H-pyrazole gave 233 as a white solid (60 mg, 59% over three steps). $^1$H NMR (400 MHz, CDCl$_3$) δ 8.26 (s, 1H), 7.60 (s, 1H), 7.37-7.28 (m, 1H), 7.08-6.98 (m, 2H), 6.15 (s, 2H), 5.08 (dd, J=5.5, 4.0 Hz, 1H), 4.10-3.99 (m, 2H), 3.90 (td, J=8.5, 4.0 Hz, 1H), 3.82 (dd, J=11.0, 4.0 Hz, 1H), 3.68 (s, 3H), 2.28-2.09 (m, 2H), 2.28-2.09. LCMS (ES+) m/z 422 (M+1)

Example 234

(R)—N-(5-(4-aminoazepan-1-yl)-1-methyl-1H-pyrazol-4-yl)-6-cyclopentyl-5-fluoropicolinamide 234

Following procedures from Example 229, (R)-benzyl 1-(4-amino-1-methyl-1H-pyrazol-5-yl)azepan-4-ylcarbamate from Example 16 was converted to 234. $^1$H NMR (400 MHz, DMSO) δ 9.54 (br, 1H), 8.00 (dd, J=8.4, 3.9 Hz, 1H), 7.88-7.80 (m, 1H), 7.71 (s, 1H), 3.68 (s, 3H), 3.55-3.45 (m, 1H), 3.22-3.09 (m, 4H), 3.05-2095 (m, 1H), 2.12-1.45 (m, 14H). MS (ESI) m/z: 401.2 [M+H$^+$].

Example 235

(R)—N-(5-(4-aminoazepan-1-yl)-1-methyl-1H-pyrazol-4-yl)-6-(5-(dimethylcarbamoyl)-2-fluorophenyl)-5-fluoropicolinamide 235

Following procedures from Example 229, (R)-benzyl 1-(4-amino-1-methyl-1H-pyrazol-5-yl)azepan-4-ylcarbamate from Example 16 was converted to 235. $^1$H NMR (400 MHz, DMSO) δ 8.24 (dd, J=8.6, 3.9 Hz, 1H), 8.10 (t, J=9.1 Hz, 1H), 7.86 (dd, J=6.9, 1.9 Hz, 1H), 7.68 (dd, J=7.2, 4.2 Hz, 1H), 7.57 (s, 1H), 7.54-7.41 (m, 1H), 3.64 (s, 3H), 3.19-3.04 (m, 4H), 2.99 (s, 6H), 2.93-2.84 (m, 1H), 1.82-1.64 (m, 3H), 1.55-1.45 (m, 3H). MS (ESI) m/z: 498.2 [M+H$^+$].

Example 236

(R)—N-(5-(4-aminoazepan-1-yl)-1-methyl-1H-pyrazol-4-yl)-6-cyclopentenyl-5-fluoropicolinamide 236

Following procedures from Example 229, (R)-benzyl 1-(4-amino-1-methyl-1H-pyrazol-5-yl)azepan-4-ylcarbamate from Example 16 was converted to 236. $^1$H NMR (400 MHz, DMSO) δ 9.55 (s, 1H), 8.01 (dd, J=8.5, 3.7 Hz, 1H), 7.91 (dd, J=11.2, 8.5 Hz, 1H), 7.68 (s, 1H), 6.80 (s, 1H), 3.67 (s, 4H), 3.22-3.07 (m, 6H), 3.07-2.92 (m, 4H), 2.66 (d, J=7.0 Hz, 3H), 2.04-1.92 (m, 3H), 1.90-1.41 (m, 13H). MS (ESI) m/z: 399.2 [M+H$^+$].

Example 237

(R)—N-(5-(4-aminoazepan-1-yl)-1-methyl-1H-pyrazol-4-yl)-5-(trifluoromethyl)picolinamide 237

Following procedures from Example 229, (R)-benzyl 1-(4-amino-1-methyl-1H-pyrazol-5-yl)azepan-4-ylcarbamate from Example 16 was converted to 237. $^1$H NMR (400 MHz, DMSO) δ 9.11 (s, 1H), 8.46 (d, J=8.2 Hz, 1H), 8.28 (d, J=8.2 Hz, 1H), 7.54 (s, 1H), 3.65 (s, 3H), 3.21-2.94 (m, 6H), 1.89-1.68 (m, 3H), 1.63-1.44 (m, 3H). MS (ESI) m/z: 383.2 [M+H$^+$].

Example 238

(R)—N-(5-(4-aminoazepan-1-yl)-1-methyl-1H-pyrazol-4-yl)-6-(2,6-difluorophenyl)-5-fluoropicolinamide 238

Following procedures from Example 229, (R)-benzyl 1-(4-amino-1-methyl-1H-pyrazol-5-yl)azepan-4-ylcarbamate from Example 16 was converted 238. $^1$H NMR (400 MHz, DMSO) δ 8.30 (dd, J=8.7, 4.1 Hz, 1H), 8.17 (t, J=8.9 Hz, 1H), 7.71 (dd, J=15.1, 8.3 Hz, 1H), 7.64 (d, J=14.2 Hz, 1H), 7.36 (t, J=8.2 Hz, 2H), 3.64 (s, 3H), 3.17-2.99 (m, 4H), 2.94-2.82 (m, 1H), 1.80-1.60 (m, 3H), 1.59-1.33 (m, 3H). MS (ESI) m/z: 445.2 [M+H$^+$].

Example 239

5-amino-2-(2,6-difluorophenyl)-N-(1-methyl-5-morpholino-1H-pyrazol-4-yl)thiazole-4-carboxamide 239

Step 1:
4-(1-Methyl-4-nitro-1H-pyrazol-5-yl)morpholine

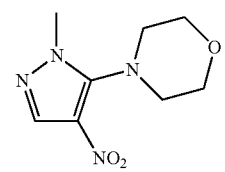

5-Chloro-1-methyl-4-nitro-1H-pyrazole and morpholine gave 4-(1-methyl-4-nitro-1H-pyrazol-5-yl)morpholine as a pale yellow solid (200 mg, 78%). $^1$H NMR (400 MHz, CDCl$_3$) δ 8.04 (s, 1H), 3.86 (t, J=4.6 Hz, 4H), 3.81 (s, 3H), 3.23 (t, J=4.6 Hz, 4H)

Step 2

Following the procedure for Example 230, starting with 4-(1-methyl-4-nitro-1H-pyrazol-5-yl)morpholine gave 239 as a dark cream solid (76 mg, 38% over three steps). $^1$H NMR (400 MHz, CDCl$_3$) δ 8.47 (s, 1H), 7.72 (s, 1H), 7.38-7.24 (m, 1H), 7.03 (t, J=8.8 Hz, 2H), 6.13 (s, 2H), 3.83 (t, J=4.3 Hz, 4H), 3.77 (s, 3H), 3.16 (t, J=4.3 Hz, 4H). LCMS (ES+) m/z 421 (M+1)

Example 240

(R)-5-amino-2-(2,6-difluorophenyl)-N-(5-(3-hydroxypyrrolidin-1-yl)-1-methyl-1H-pyrazol-4-yl)thiazole-4-carboxamide 240

Step 1: (R)-1-(1-Methyl-4-nitro-1H-pyrazol-5-yl)pyrrolidin-3-ol

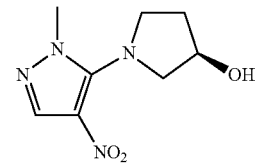

5-Chloro-1-methyl-4-nitro-1H-pyrazole and (R)-(+)-3-hydroxypyrrolidine gave (R)-1-(1-methyl-4-nitro-1H-pyrazol-5-yl)pyrrolidin-3-ol as a yellow solid (264 mg, 100%). $^1$H NMR (400 MHz, CDCl$_3$) δ 8.05 (s, 1H), 4.64-4.59 (m, 1H), 3.78 (s, 3H), 3.71-3.59 (m, 2H), 3.39 (td, J=8.8, 3.4 Hz, 1H), 3.24 (dt, J=10.2, 1.6 Hz, 1H), 2.34-2.23 (m, 1H), 2.15-2.03 (m, 2H)

Step 2

Following the procedure for Example 230, starting with (R)-1-(1-methyl-4-nitro-1H-pyrazol-5-yl)pyrrolidin-3-ol gave 240 as an off-white foam (48 mg, 20% over three steps). $^1$H NMR (400 MHz, CDCl$_3$) δ 9.55 (s, 1H), 7.91 (s, 1H), 7.36-7.30 (m, 1H), 7.07-7.00 (m, 2H), 6.23 (s, 2H), 4.51 (s, 1H), 3.75 (s, 3H), 3.49-3.28 (m, 4H), 3.26-3.22 (m, 1H), 2.09-2.07 (m, 2H). LCMS (ES+) m/z 421 (M+1)

Example 241

5-amino-N-(5-(4-aminoazepan-1-yl)-1-ethyl-1H-pyrazol-4-yl)-2-(2,6-difluorophenyl)thiazole-4-carboxamide 241

A solution of tert-butyl 2-(2,6-difluorophenyl)-4-(1-ethyl-5-(4-(2,2,2-trifluoroacetamido)azepan-1-yl)-1H-pyrazol-4-ylcarbamoyl)thiazol-5-ylcarbamate (0.17 g, 0.26 mmol) in HCl in 1,4-dioxane (4 M, 5 mL) was allowed to stand at room temperature for 40 hr. The reaction mixture was concentrated under reduced pressure and the residue dissolved in 50% aqueous MeOH (20 mL). K$_2$CO$_3$ (1.22 g, 8.84 mmol) was added and the mixture heated at 60° C. for 3 hr. The mixture was allowed to cool, concentrated to approximately 5 mL and extracted with DCM. The combined organic layers were passed through a phase separation cartridge and the solvent removed under reduced pressure. Purification of the residue by passing through an SCX column washing with DCM and MeOH and eluting with 1 N ammonia in MeOH gave 241 as a cream solid (118 mg, 99%). $^1$H-NMR (400 MHz, CDCl$_3$) δ 8.67 (s, 1H), 7.92 (s, 1H), 7.36-7.28 (m, 1H), 7.06-6.97 (m, 2H), 6.14 (s, 2H), 4.05 (q, J=7 Hz, 2H), 3.29-3.12 (m, 5H), 2.02-1.88 (m, 3H), 1.75-1.60 (m, 3H), 1.43 (t, J=7 Hz, 3H). RNH$_2$ not seen. LCMS (ES+) m/z 462.0 (M+1).

Example 242

(S)-5-amino-2-(2,6-difluorophenyl)-N-(5-(3-hydroxypyrrolidin-1-yl)-1-methyl-1H-pyrazol-4-yl)thiazole-4-carboxamide 242

Step 1: (S)-1-(1-Methyl-4-nitro-1H-pyrazol-5-yl)pyrrolidin-3-ol

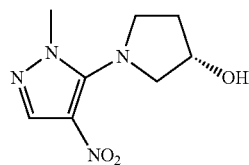

Following Example 231, 5-Chloro-1-methyl-4-nitro-1H-pyrazole and (S)-(−)-3-hydroxypyrrolidine gave (S)-1-(1-methyl-4-nitro-1H-pyrazol-5-yl)pyrrolidin-3-ol (250 mg, 96%). $^1$H NMR (400 MHz, CDCl$_3$) δ 8.05 (s, 1H), 4.64-4.59 (m, 1H), 3.78 (s, 3H), 3.71-3.59 (m, 2H), 3.39 (td, J=8.8, 3.4 Hz, 1H), 3.24 (dt, J=10.2, 1.6 Hz, 1H), 2.34-2.23 (m, 1H), 2.14-2.04 (m, 2H)

Step 2

Following the procedure for Example 230, starting with (S)-1-(1-methyl-4-nitro-1H-pyrazol-5-yl)pyrrolidin-3-ol gave 242 as a off-white solid (20 mg, 16% over three steps). $^1$H NMR (400 MHz, CDCl$_3$) δ 9.55 (s, 1H), 7.91 (s, 1H), 7.36-7.31 (m, 1H), 7.05 (t, J=8.8 Hz, 2H), 6.23 (s, 2H), 4.51 (s, 1H), 3.75 (s, 3H), 3.50-3.20 (m, 5H), 2.09-2.07 (m, 2H). LCMS (ES+) m/z 421 (M+1)

Example 243

5-amino-2-(2,6-difluorophenyl)-N-(1-methyl-5-(tetrahydro-2H-pyran-4-yl)-1H-pyrazol-4-yl)thiazole-4-carboxamide 243

Step 1: 5-(3,6-Dihydro-2H-pyran-4-yl)-1-methyl-4-nitro-1H-pyrazole

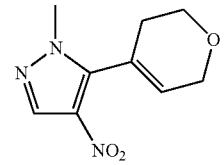

Following Example 231, reaction of 5-chloro-1-methyl-4-nitro-1H-pyrazole and 3,6-dihydro-2H-pyran-4-boronic acid pinacol ester gave 5-(3,6-dihydro-2H-pyran-4-yl)-1-methyl-4-nitro-1H-pyrazole (167 mg, 65%). $^1$H NMR (400 MHz, CDCl$_3$) δ 8.09 (s, 1H), 5.99-5.94 (m, 1H), 4.37 (q, J=2.8 Hz, 2H), 3.99 (t, J=5.3 Hz, 2H), 3.84 (s, 3H), 2.40-2.35 (m, 2H)

Step 2

A solution of 5-(3,6-dihydro-2H-pyran-4-yl)-1-methyl-4-nitro-1H-pyrazole (80 mg, 0.38 mmol) in MeOH (20 mL) was passed through the H-Cube® (30 bar, 25° C., flow rate: 1 mL/min, 30 mm 10% Pd/C cartridge). The solvent was removed under reduced pressure to afford crude 1-methyl-5-(tetrahydro-2H-pyran-4-yl)-1H-pyrazol-4-amine as a light yellow oil (64 mg, 0.35 mmol). To a solution of this amine (60 mg, 0.33 mmol) in DCM (20 mL) was added DIPEA (0.5 mL, 2.87 mmol), PyBOP (0.34 g, 0.66 mmol) and 5-(tert-butoxycarbonylamino)-2-(2,6-difluorophenyl)thiazole-4-carboxylic acid (124 mg, 0.35 mmol) and the mixture was stirred at room temperature for 18 hr. The mixture was diluted with DCM and washed with water. The organic layer was separated, dried over MgSO$_4$ and the solvent removed under reduced pressure. Purification via silica gel column chromatography (0-80% EtOAc/isohexane) gave tert-butyl 2-(2,6-difluorophenyl)-4-(1-methyl-5-(tetrahydro-2H-pyran-4-yl)-1H-pyrazol-4-ylcarbamoyl)thiazol-5-ylcarbamate as an off-white solid (102 mg, 59%). This solid (100 mg, 0.19 mmol) was stirred in HCl in 1,4-dioxane (4.0 M, 1.9 mL) at room temperature for 18 hr. The solvents were removed under reduced pressure and the crude residue was re-dissolved in MeOH and loaded onto an SCX column. The column was washed with MeOH and 7 N ammonia in MeOH to yield 301 as a peach solid (59 mg, 73%). $^1$H NMR (400 MHz, CDCl$_3$) δ 8.42 (s, 1H), 7.69 (s, 1H), 7.34-7.29 (m, 1H), 7.02 (t, J=8.7 Hz, 2H), 6.11 (s, 2H), 4.09 (dd, J=11.6, 4.2 Hz, 2H), 3.88 (s, 3H), 3.50 (t, J=11.6 Hz, 2H), 3.02-2.95 (m, 1H), 2.17-2.08 (m, 2H), 1.78 (d, J=13.4 Hz, 2H). LCMS (ES+) m/z 420 (M+1)

Example 244

5-amino-N-(1-methyl-1H-pyrazol-4-yl)-2-(3-morpholinophenyl)thiazole-4-carboxamide 244

Following Example 278, Suzuki coupling of (tert-butyl 2-bromo-4-(1-methyl-1H-pyrazol-4-ylcarbamoyl)thiazole-5-ylcarbamate and 3-morpholinophenylboronic acid gave 244 as a beige solid (56 mg, 59% over two steps). $^1$H NMR (400 MHz, CDCl$_3$) δ 8.65 (s, 1H), 7.96 (s, 1H), 7.53 (s, 1H), 7.25-6.95 (m, 4H), 6.07 (s, 2H), 3.92-3.88 (m, 7H), 3.24 (t, J=5 Hz, 4H). LCMS (ES+) m/z 385 (M+1)

Example 245

5-amino-2-(2,6-difluorophenyl)-N-(5-(4-fluoropiperidin-1-yl)-1-methyl-1H-pyrazol-4-yl)thiazole-4-carboxamide 245

Step 1: 4-Fluoro-1-(1-methyl-4-nitro-1H-pyrazol-5-yl)piperidine

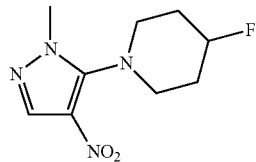 [SMILES: Cn1ncc([N+](=O)[O-])c1N1CCC(F)CC1]

Reaction of 5-chloro-1-methyl-4-nitro-1H-pyrazole and 4-fluoropiperidine hydrochloride gave 4-fluoro-1-(1-methyl-4-nitro-1H-pyrazol-5-yl)piperidine as a white solid (280 mg, 99%). $^1$H NMR (400 MHz, CDCl$_3$) δ 8.02 (s, 1H), 4.86 (dtt, J=47.9, 7.1, 3.6 Hz, 1H), 3.77 (s, 3H), 3.37 (d, J=9.4 Hz, 2H), 3.20-3.12 (m, 2H), 2.16-2.06 (m, 1H), 2.07-1.92 (m, 3H)

Step 2

Following the procedure for Example 243 starting with 4-fluoro-1-(1-methyl-4-nitro-1H-pyrazol-5-yl)piperidine gave 245 as a brown foam (146 mg, 59% over three steps). $^1$H NMR (400 MHz, CDCl$_3$) δ 8.50 (s, 1H), 7.74 (s, 1H), 7.32 (tt, J=8.5, 6.0 Hz, 1H), 7.06-7.00 (m, 2H), 6.12 (s, 2H), 4.88-4.71 (m, 1H), 3.75 (s, 2H), 3.33 (s, 3H), 3.11-3.03 (m, 2H), 2.11-1.94 (m, 4H). LCMS (ES+) m/z 437 (M+1)

Example 246

5-amino-2-(2,6-difluorophenyl)-N-(5-(4,4-difluoropiperidin-1-yl)-1-methyl-1H-pyrazol-4-yl)thiazole-4-carboxamide 246

Step 1: 4,4-Difluoro-1-(1-methyl-4-nitro-1H-pyrazol-5-yl)piperidine

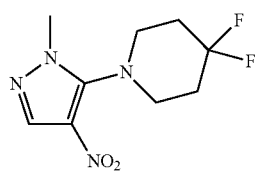 [SMILES: Cn1ncc([N+](=O)[O-])c1N1CCC(F)(F)CC1]

Reaction of 5-chloro-1-methyl-4-nitro-1H-pyrazole and 4,4 di-fluoropiperidine hydrochloride gave 4,4-difluoro-1-(1-methyl-4-nitro-1H-pyrazol-5-yl)piperidine as a white solid (289 mg, 97%). $^1$H NMR (400 MHz, CDCl$_3$) δ 8.03 (s, 1H), 3.79 (s, 3H), 3.36-3.31 (m, 4H), 2.22-2.09 (m, 4H)

Step 2

Following the procedure for Example 243 starting with 4,4-difluoro-1-(1-methyl-4-nitro-1H-pyrazol-5-yl)piperidine gave 246 as a yellow foam (130 mg, 57% over three steps). $^1$H NMR (400 MHz, CDCl$_3$) δ 8.50 (s, 1H), 7.75 (s, 1H), 7.32 (tt, J=8.5, 6.0 Hz, 1H), 7.08-6.99 (m, 2H), 6.11 (s, 2H), 3.76 (s, 3H), 3.27 (t, J=5.5 Hz, 4H), 2.20-2.07 (m, 4H). LCMS (ES+) m/z 455 (M+1)

Example 247

(S)-5-amino-2-(2,6-difluorophenyl)-N-(5-(3-fluoropyrrolidin-1-yl)-1-methyl-1H-pyrazol-4-yl)thiazole-4-carboxamide 247

Step 1: (S)-5-(3-Fluoropyrrolidin-1-yl)-1-methyl-4-nitro-1H-pyrazole

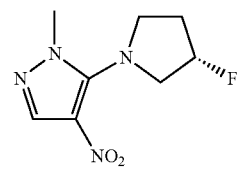

Reaction of 5-chloro-1-methyl-4-nitro-1H-pyrazole and (S)-3-fluoropyrrolidine gave (S)-5-(3-fluoropyrrolidin-1-yl)-1-methyl-4-nitro-1H-pyrazole as a yellow solid (220 g, 83%). $^1$H NMR (400 MHz, CDCl$_3$) δ 8.05 (s, 1H), 5.48-5.31 (m, 1H), 3.79 (s, 3H), 3.73-3.57 (m, 2H), 3.49-3.37 (m, 2H), 2.46-2.27 (m, 2H)

Step 2

Following the procedure for Example 243 starting with (S)-5-(3-fluoropyrrolidin-1-yl)-1-methyl-4-nitro-1H-pyrazole gave 247 as a light brown foam (35 mg, 18% over three steps). $^1$H NMR (400 MHz, CDCl$_3$) δ 8.39 (s, 1H), 7.73 (s, 1H), 7.36-7.27 (m, 1H), 7.07-6.97 (m, 2H), 6.13 (s, 2H), 5.37-5.19 (m, 1H), 3.75 (s, 3H), 3.64-3.43 (m, 3H), 3.38-3.31 (m, 1H), 2.34-2.13 (m, 2H). LCMS (ES+) m/z 423 (M+1)

Example 248

(R)-5-amino-2-(2,6-difluorophenyl)-N-(5-(3-fluoropyrrolidin-1-yl)-1-methyl-1H-pyrazol-4-yl)thiazole-4-carboxamide 248

Step 1: (R)-5-(3-Fluoropyrrolidin-1-yl)-1-methyl-4-nitro-1H-pyrazole

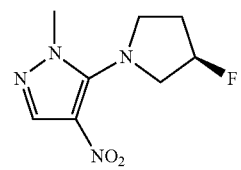

Reaction of 5-chloro-1-methyl-4-nitro-1H-pyrazole and (R)-3-fluoropyrrolidine gave (R)-5-(3-fluoropyrrolidin-1-yl)-1-methyl-4-nitro-1H-pyrazole as a yellow solid (153 mg, 58%). $^1$H NMR (400 MHz, CDCl$_3$) δ 8.06 (s, 1H), 5.48-5.31 (m, 1H), 3.79 (s, 3H), 3.73-3.57 (m, 2H), 3.48-3.37 (m, 2H), 2.46-2.27 (m, 2H)

Step 2

Following the procedure for Example 243 starting with (R)-5-(3-fluoropyrrolidin-1-yl)-1-methyl-4-nitro-1H-pyrazole gave 248 as light brown solid (50 mg, 29% over three steps). $^1$H NMR (400 MHz, CDCl$_3$) δ 8.39 (s, 1H), 7.73 (s, 1H), 7.36-7.28 (m, 1H), 7.06-6.96 (m, 2H), 6.14 (s, 2H), 5.41-5.21 (m, 1H), 3.75 (s, 3H), 3.64-3.43 (m, 3H), 3.38-3.31 (m, 1H), 2.34-2.14 (m, 2H). LCMS (ES+) m/z 423 (M+1)

Example 249

5-amino-2-(2,6-difluorophenyl)-N-(1-methyl-5-(piperidin-1-yl)-1H-pyrazol-4-yl)thiazole-4-carboxamide 249

Step 1:
1-(1-Methyl-4-nitro-1H-pyrazol-5-yl)piperidine

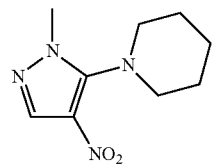

Reaction of 5-chloro-1-methyl-4-nitro-1H-pyrazole and piperidine gave 1-(1-methyl-4-nitro-1H-pyrazol-5-yl)piperidine as a white solid (232 mg, 89%). $^1$H NMR (400 MHz, CDCl$_3$) δ 8.00 (s, 1H), 3.74 (s, 3H), 3.18-3.12 (m, 4H), 1.74-1.63 (m, 6H)

Step 2

Following the procedure for Example 243 starting with 1-(1-methyl-4-nitro-1H-pyrazol-5-yl)piperidine gave 249 as a light brown foam (129 mg, 50% over three steps). $^1$H NMR (400 MHz, CDCl$_3$) δ 8.56 (s, 1H), 7.77 (s, 1H), 7.36-7.27 (m, 1H), 7.08-6.98 (m, 2H), 6.13 (s, 2H), 3.72 (s, 3H), 3.09 (t, J=5.0 Hz, 4H), 1.73-1.65 (m, 4H), 1.62-1.55 (m, 2H). LCMS (ES+) m/z 419 (M+1)

Example 250

5-amino-N-(5-(4-(aminomethyl)piperidin-1-yl)-1-methyl-1H-pyrazol-4-yl)-2-(3-cyanophenyl)thiazole-4-carboxamide 250

Following Example 278, Suzuki coupling of tert-butyl 4-(5-(4-(butyloxycarbonylaminomethyl)piperidin-1-yl)-1-methyl-1H-pyrazol-4-ylcarbamoyl)-2-bromothiazol-5-ylcarbamate and 3-cyanophenyl boronic acid gave 250 as a pale brown solid (36 mg, 42% over two steps). $^1$H NMR (400 MHz, d$_6$-DMSO) δ 9.09 (s, 1H), 8.42 (s, 1H), 8.11 (d, J=7.9 Hz, 1H), 7.86 (d, J=7.9 Hz, 1H), 7.68 (t, J=7.9 Hz, 1H), 7.56 (s, 2H), 7.33 (s, 1H), 3.66 (s, 3H), 3.16-2.99 (m, 4H), 2.47 (d, J=5.7 Hz, 2H), 1.82-1.73 (m, 4H), 1.30-1.17 (m, 3H). LCMS (ES+) m/z 437 (M+1)

Example 251

5-amino-N-(5-(4-(aminomethyl)piperidin-1-yl)-1-methyl-1H-pyrazol-4-yl)-2-(3-fluorophenyl)thiazole-4-carboxamide 251

Following Example 278, Suzuki coupling of tert-butyl 4-(5-(4-(butyloxycarbonylaminomethyl)piperidin-1-yl)-1-methyl-1H-pyrazol-4-ylcarbamoyl)-2-bromothiazol-5-ylcarbamate and 3-phenylboronic acid gave 251 as a brown solid (22 mg, 25% over two steps). $^1$H NMR (400 MHz, d$_6$-DMSO) δ 9.00 (s, 1H), 7.79 (dt, J=10.3, 2.0 Hz, 1H), 7.63 (d, J=7.8 Hz, 1H), 7.56-7.48 (m, 3H), 7.36 (s, 1H), 7.26 (td, J=8.5, 2.6 Hz, 1H), 3.66 (s, 3H), 3.15-3.00 (m, 4H), 2.48 (d, J=5.7 Hz, 2H), 1.78 (d, J=11.9 Hz, 4H), 1.30-1.20 (m, 3H). LCMS (ES+) m/z 430 (M+1)

Example 252

5-amino-N-(5-(3-(2-aminoethyl)pyrrolidin-1-yl)-1-methyl-1H-pyrazol-4-yl)-2-(2,6-difluorophenyl)thiazole-4-carboxamide 252 tert-Butyl 2-(1-(4-amino-1-methyl-1H-pyrazol-5-yl)pyrrolidin-3-yl)ethylcarbamate was prepared according to Example 2. Using this amine, 252 was prepared according to Example 140. $^1$H NMR (400 MHz, DMSO) δ 8.64 (br, 1H), 7.61-7.38 (m, 4H), 7.26 (t, J=8.7 Hz, 2H), 3.62 (s, 3H), 2.87 (t, J=8.3 Hz, 1H), 2.38-2.17 (m, 2H), 2.09-1.97 (m, 1H), 1.56-1.42 (m, 3H). MS (ESI) m/z: 448.2 [M+H$^+$].

Example 253

(R)-5-amino-N-(5-(4-aminoazepan-1-yl)-1-methyl-1H-pyrazol-4-yl)-2-(2-fluoro-5-(trifluoromethyl)phenyl)thiazole-4-carboxamide 253

Following procedures from Example 141, (R)-benzyl 1-(4-amino-1-methyl-1H-pyrazol-5-yl)azepan-4-ylcarbamate from Example 16 was converted to 253. $^1$H NMR (400 MHz, DMSO) δ 9.10 (br, 1H), 8.63 (d, J=6.7 Hz, 1H), 7.86-7.74 (m, 1H), 7.66-7.56 (m, 1H), 7.51 (br, 2H), 7.44 (s, 1H), 3.65 (s, 3H), 3.23-3.04 (m, 4H), 3.00-2.93 (m, 1H), 1.86-1.75 (m, 3H), 1.67-1.42 (m, 3H). MS (ESI) m/z: 498.2 [M+H$^+$].

Example 254

N-(5-((1S,4S)-2,5-diazabicyclo[2.2.1]heptan-2-yl)-1-methyl-1H-pyrazol-4-yl)-5-amino-2-(2,6-difluorophenyl)thiazole-4-carboxamide 254

5-((1S,4S)-2,5-Diazabicyclo[2.2.1]heptan-2-yl)-1-methyl-1H-pyrazol-4-amine was prepared according to Example 2. Using this amine, 254 was prepared according to Example 140. $^1$H NMR (400 MHz, DMSO) δ 9.70 (s, 1H), 7.56 (d, J=14.8 Hz, 1H), 7.54-7.40 (m, 3H), 7.32-7.18 (m, 2H), 3.86 (s, 1H), 3.62 (s, 3H), 3.30-3.20 (m, 3H), 2.87 (d, J=9.6 Hz, 1H), 2.78 (d, J=8.5 Hz, 1H), 1.91 (d, J=9.4 Hz, 1H), 1.64 (d, J=9.4 Hz, 1H). MS (ESI) m/z: 432.1 [M+H$^+$].

Example 255

5-amino-2-(2,6-difluorophenyl)-N-(1-methyl-5-(pyrrolidin-3-yl)-1H-pyrazol-4-yl)thiazole-4-carboxamide 255

Step 1: tert-Butyl 2-(2,6-difluorophenyl)-4-(1-methyl-5-(tert-butyloxycarbonylpyrrolidin-3-yl)-1H-pyrazol-4-ylcarbamoyl)thiazol-5-ylcarbamate

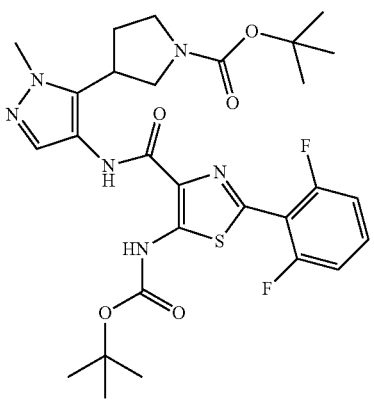 [SMILES: Cn1ncc(NC(=O)c2nc(-c3c(F)cccc3F)sc2NC(=O)OC(C)(C)C)c1C1CCN(C(=O)OC(C)(C)C)C1]

5-Chloro-1-methyl-4-nitro-1H-pyrazole (0.2 g, 1.24 mmol), tert-butyl 3-(4,4,5,5-tetramethyl-1,3,2-dioxaborolan-2-yl)-2,5-dihydro-1H-pyrrole-1-carboxylate (0.437 g, 1.48 mmol) and aqueous Na$_2$CO$_3$/KOAc solution (1:1, 1.1 M, 1.5 mL) were suspended in MeCN (5 mL). The mixture was degassed under a stream of nitrogen for 5 min. Pd(dppf)$_2$Cl$_2$ (0.1 g, 0.123 mmol) was added and the mixture was heated at 130° C. in a microwave for 90 min. A further portion of Pd(dppf)$_2$Cl$_2$ (50 mg, 0.06 mmol) was added and the mixture was heated at 130° C. for a further 90 min. The solvents were removed under reduced pressure and the crude residue partitioned between EtOAc and water. The organic layer was separated, dried over MgSO$_4$ and concentrated under reduced pressure. The crude product was purified via silica gel column chromatography (40-60% EtOAc/isohexane) to give the intermediate nitro-pyrazole as a yellow oil (76 mg, 21%). A solution of this oil (70 mg, 0.23 mmol) in MeOH (20 mL) was passed through the H-Cube® (50 bar, 20° C., flow rate: 1 mL/min, 30 mm 10% Pd/C cartridge). The solvent was removed under reduced pressure to afford tert-butyl 3-(1-methyl-4-nitro-1H-pyrazol-5-yl)pyrrolidine-1-carboxylate as a yellow viscous oil (55 mg, 87%). To a solution of this oil (55 mg, 0.21 mmol) in DCM (20 mL) and DIPEA (0.5 mL) was added PyBOP (161 mg, 0.31 mmol) and 5-(tert-butoxycarbonylamino)-2-(2,6-difluorophenyl)thiazole-4-carboxylic acid (77 mg, 0.22 mmol) and the mixture was stirred at room temperature for 18 hr. The mixture was diluted with DCM and washed with water. The organic layer was separated, dried over MgSO$_4$ and the solvent removed under reduced pressure. Purification via silica gel column chromatography (75% EtOAc/isohexane) gave tert-butyl 2-(2,6-difluorophenyl)-4-(1-methyl-5-(tert-butyloxycarbonylpyrrolidin-3-yl)-1H-pyrazol-4-ylcarbamoyl)thiazol-5-ylcarbamate as a pale yellow glass (44 mg, 35%). $^1$H NMR (400 MHz, CDCl$_3$) δ 10.32 (s, 1H), 8.70-8.50 (m, 2H), 7.80-7.70 (m, 1H), 7.89-7.82 (m, 1H), 7.05 (t, J=8.7 Hz, 2H), 3.89 (s, 3H), 3.85-3.32 (m, 5H), 2.43-2.25 (m, 2H), 1.54 (s, 18H)

Step 2

Acidic deprotection of the two Boc groups of tert-butyl 2-(2,6-difluorophenyl)-4-(1-methyl-5-(tert-butyloxycarbonylpyrrolidin-3-yl)-1H-pyrazol-4-ylcarbamoyl)thiazol-5-ylcarbamate gave 255 as a peach foam (19 mg, 65%). $^1$H NMR (400 MHz, CDCl$_3$) δ 11.79 (s, 1H), 8.18 (s, 1H), 7.34-7.28 (m, 1H), 7.05-6.98 (m, 2H), 6.24 (s, 2H), 3.84 (s, 3H), 3.49-3.44 (m, 1H), 3.38-3.32 (m, 2H), 3.07 (dd, J=9.5, 6.5 Hz, 1H), 2.96-2.91 (m, 1H), 2.27-2.22 (m, 1H), 1.90-1.82 (m, 1H). Alkyl NH not seen. LCMS (ES+) m/z 405 (M+1)

Example 256

5-amino-N-(5-(4-(aminomethyl)piperidin-1-yl)-1-methyl-1H-pyrazol-4-yl)-2-cyclopentenylthiazole-4-carboxamide 256

Following Example 278, Suzuki coupling of tert-butyl 4-(5-(4-(butyloxycarbonylaminomethyl)piperidin-1-yl)-1-methyl-1H-pyrazol-4-ylcarbamoyl)-2-bromothiazol-5-ylcarbamate and cyclopent-1-ene-1-boronic acid gave 256 as an off-white solid (23 mg, 29% over two steps). $^1$H NMR (400 MHz, d$_6$-DMSO) δ 8.60 (s, 1H), 7.46 (s, 1H), 7.36 (s, 2H), 6.21 (t, J=2.4 Hz, 1H), 3.66 (s, 3H), 3.12-2.97 (m, 4H), 2.75 (t, J=7.3 Hz, 2H), 2.54 (s, 2H), 2.48 (d, J=5.9 Hz, 2H), 2.03-1.93 (m, 2H), 1.84-1.74 (m, 4H), 1.33-1.16 (m, 3H). LCMS (ES+) m/z 402 (M+1)

Example 257

(E)-5-amino-N-(5-(4-(aminomethyl)piperidin-1-yl)-1-methyl-1H-pyrazol-4-yl)-2-(2-cyclohexylvinyl)thiazole-4-carboxamide 257

Following Example 278, Suzuki coupling of tert-butyl 4-(5-(4-(butyloxycarbonylaminomethyl)piperidin-1-yl)-1-methyl-1H-pyrazol-4-ylcarbamoyl)-2-bromothiazol-5-ylcarbamate and trans-(2-cyclohexylvinyl)boronic acid gave 257 as an off-white solid (17 mg, 20% over two steps). $^1$H NMR (400 MHz, d$_6$-DMSO) δ 8.70 (s, 1H), 7.36 (s, 2H), 7.31 (s, 1H), 6.40 (dd, J=16.0, 1.3 Hz, 1H), 6.20 (dd, J=16.0, 6.7 Hz, 1H), 3.63 (s, 3H), 3.10-2.96 (m, 6H), 2.47 (d, J=5.9 Hz, 2H), 2.21-2.10 (m, 1H), 1.83-1.71 (m, 7H), 1.35-1.13 (m, 8H). LCMS (ES+) m/z 444 (M+1)

Example 258

5-amino-2-(2,6-difluorophenyl)-N-(1-methyl-5-(1,2,3,6-tetrahydropyridin-4-yl)-1H-pyrazol-4-yl)thiazole-4-carboxamide 258

Step 1: tert-Butyl 4-(1-methyl-4-nitro-1H-pyrazol-5-yl)-5,6-dihydropyridine-1(2H)-carboxylate

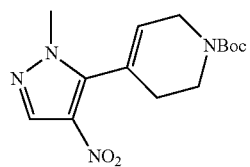 [SMILES: Cn1ncc([N+](=O)[O-])c1C1=CCN(C(=O)OC(C)(C)C)CC1]

Following Example 231, reaction of 5-chloro-1-methyl-4-nitro-1H-pyrazole and tert-butyl 4-(4,4,5,5-tetramethyl-1,3,2-dioxaborolan-2-yl)-5,6-dihydropyridine-1(2H)-carboxylate gave tert-butyl 4-(1-methyl-4-nitro-1H-pyrazol-5-yl)-5,6-dihydropyridine-1(2H)-carboxylate (310 mg, 80%). $^1$H NMR (400 MHz, CDCl$_3$) δ 8.08 (s, 1H), 5.89 (s br, 1H), 4.14 (s br, 2H), 3.81 (s, 3H), 3.73-3.67 (m, 2H), 2.37 (s br, 2H), 1.27 (s) and 1.24 (s) (9H)

Step 2: tert-butyl 4-(4-amino-1-methyl-1H-pyrazol-5-yl)-5,6-dihydropyridine-1(2H)-carboxylate

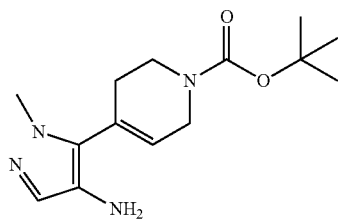 [SMILES: CN/C(C1=CCN(C(=O)OC(C)(C)C)CC1)=C(/N)C=N]

To a solution of tert-butyl 4-(1-methyl-4-nitro-1H-pyrazol-5-yl)-5,6-dihydropyridine-1(2H)-carboxylate (0.15 g, 0.48 mmol) in ethanol (10 mL) and water (1 mL) was added ammonium chloride (0.131 g, 2.44 mmol) and iron powder (0.109 g, 1.95 mmol). The mixture was heated at 100° C. for 1 hr. The mixture was cooled and filtered through celite and washed with EtOAc. The organic layer was washed with water, separated and dried over MgSO$_4$. The solvent was removed under reduced pressure to yield tert-butyl 4-(4-amino-1-methyl-1H-pyrazol-5-yl)-5,6-dihydropyridine-1(2H)-carboxylate as a brown oil (86 mg, 64%).

Step 3: tert-butyl 2-(2,6-difluorophenyl)-4-(1-methyl-5-(tert-butyloxycarbonyl-1,2,3,6-tetrahydropyridin-4-yl)-1H-pyrazol-4-ylcarbamoyl)thiazol-5-ylcarbamate

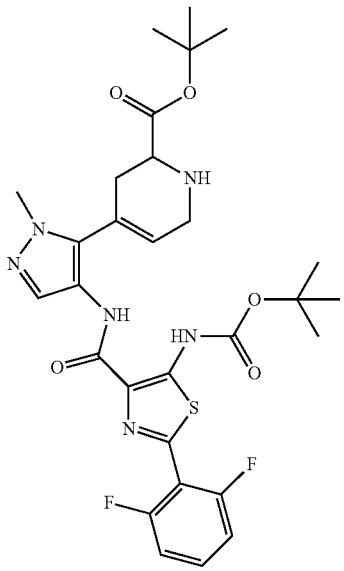 [SMILES: Cn1ncc(NC(=O)c2nc(-c3c(F)cccc3F)sc2NC(=O)OC(C)(C)C)c1C1=CCNC(C(=O)OC(C)(C)C)C1]

To a solution of tert-butyl 4-(4-amino-1-methyl-1H-pyrazol-5-yl)-5,6-dihydropyridine-1(2H)-carboxylate (85 mg, 0.31 mmol) in DCM (20 mL) was added DIPEA (0.5 mL, 2.87 mmol), PyBOP (0.238 g, 0.46 mmol) and 5-(tert-butoxycarbonylamino)-2-(2,6-difluorophenyl)thiazole-4-carboxylic acid (0.114 g, 0.32 mmol) and the mixture was stirred at room temperature for 18 hr. The mixture was diluted with DCM and washed with water. The organic layer was separated, dried over MgSO$_4$ and the solvent removed under reduced pressure. Purification via silica gel column chromatography (0-75% EtOAc/isohexane) gave tert-butyl 2-(2,6-difluorophenyl)-4-(1-methyl-5-(tert-butyloxycarbonyl-1,2,3,6-tetrahydropyridin-4-yl)-1H-pyrazol-4-ylcarbamoyl)thiazol-5-ylcarbamate as a white solid (54 mg, 29%).

Step 4 tert-butyl 2-(2,6-difluorophenyl)-4-(1-methyl-5-(tert-butyloxycarbonyl-1,2,3,6-tetrahydropyridin-4-yl)-1H-pyrazol-4-ylcarbamoyl)thiazol-5-ylcarbamate (0.10 g, 0.16 mmol) was dissolved in MeOH (3 mL) and HCl in 1,4-dioxane (4.0 M, 3 mL) was added. The mixture was stirred at room temperature for 18 hr. The solvents were removed under reduced pressure and the crude residue was re-dissolved in MeOH and loaded onto an SCX column. The column was washed with MeOH and eluted with 7 N ammonia in MeOH to give 258 as a yellow solid (64 mg, 95%). $^1$H NMR (400 MHz, CDCl$_3$) δ 8.69 (s, 1H), 8.06 (s, 1H), 7.36-7.29 (m, 1H), 7.02 (t, J=8.9 Hz, 2H), 6.12 (s, 2H), 6.01 (s, 1H), 3.82 (s, 3H), 3.61 (d, J=3.4 Hz, 2H), 3.14 (t, J=5.5 Hz, 2H), 2.34 (s, 3H). LCMS (ES+) m/z 417 (M+1)

Example 259

5-amino-2-(2,6-difluorophenyl)-N-(5-((3S,4S)-3,4-dihydroxypyrrolidin-1-yl)-1-methyl-1H-pyrazol-4-yl)thiazole-4-carboxamide 259

Step 1: (3S,4S)-1-(1-Methyl-4-nitro-1H-pyrazol-5-yl)pyrrolidine-3,4-diol

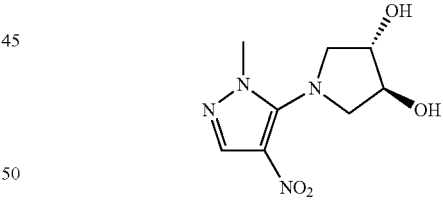

Reaction of 5-chloro-1-methyl-4-nitro-1H-pyrazole and (3S,4S)-pyrrolidine-3,4-diol gave (3S,4S)-1-(1-methyl-4-nitro-1H-pyrazol-5-yl)pyrrolidine-3,4-diol as a bright yellow solid (258 mg, 91%). $^1$H NMR (400 MHz, d$_4$-MeOD) δ 8.04 (s, 1H), 4.27-4.22 (m, 2H), 3.98 (dd, J=10.0, 4.4 Hz, 2H), 3.84 (s, 3H), 3.31-3.25 (m, 2H)

Step 2

Following the procedure for Example 243 starting with (3S,4S)-1-(1-methyl-4-nitro-1H-pyrazol-5-yl)pyrrolidine-3,4-diol gave 259 as a yellow solid (27 mg, 5% over three steps). $^1$H NMR (400 MHz, CDCl$_3$) δ 9.45 (s, 1H), 7.85 (s, 1H), 7.39-7.30 (m, 1H), 7.11-6.99 (m, 2H), 6.22 (s, 2H), 4.30 (d, J=3.5 Hz, 2H), 3.76 (s, 3H), 3.69 (dd, J=11.5, 3.5 Hz, 2H), 3.28 (d, J=11.5 Hz, 2H), 2.76 (s, 2H). LCMS (ES+) m/z 437 (M+1)

Example 260

5-amino-2-(2,6-difluorophenyl)-N-(1-methyl-5-((tetrahydro-2H-pyran-4-yl)methylamino)-1H-pyrazol-4-yl)thiazole-4-carboxamide 260

Step 1: 1-Methyl-4-nitro-N-((tetrahydro-2H-pyran-4-yl)methyl)-1H-pyrazol-5-amine

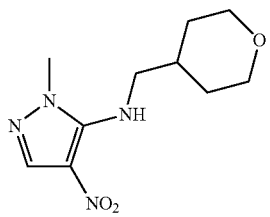 [SMILES: Cn1ncc([N+](=O)[O-])c1NCC1CCOCC1]

Reaction of 5-chloro-1-methyl-4-nitro-1H-pyrazole and (tetrahydro-2H-pyran-4-yl)methanamine gave 1-methyl-4-nitro-N-((tetrahydro-2H-pyran-4-yl)methyl)-1H-pyrazol-5-amine as an off-white solid (277 mg, 93%). ¹H NMR (400 MHz, CDCl₃) δ 7.88 (d, J=1.6 Hz, 1H), 6.75 (s, 1H), 4.01 (dd, J=11.6, 4.3 Hz, 2H), 3.85 (d, J=1.0 Hz, 3H), 3.44-3.32 (m, 4H), 1.90-1.76 (m, 1H), 1.75-1.68 (m, 2H), 1.38 (qd, J=12.4, 4.4 Hz, 2H)

Step 2

Following the procedure for Example 243 starting with 1-methyl-4-nitro-N-((tetrahydro-2H-pyran-4-yl)methyl)-1H-pyrazol-5-amine gave 260 as a yellow solid (99 mg, 19% over three steps). ¹H NMR (400 MHz, d₆-DMSO) δ 8.84 (s, 1H), 7.64-7.49 (m, 3H), 7.45 (s, 1H), 7.30 (t, J=8.5 Hz, 2H), 4.90 (t, J=6.5 Hz, 1H), 3.76 (dd, J=11.5, 4.0 Hz, 2H), 3.62 (s, 3H), 3.17 (t, J=11.5 Hz, 2H), 2.82 (t, J=6.5 Hz, 2H), 1.69-1.55 (m, 3H), 1.20-1.08 (m, 2H). LCMS (ES+) m/z 449 (M+1)

Example 261

5-amino-2-(2,6-difluorophenyl)-N-(5-(dimethylamino)-1-methyl-1H-pyrazol-4-yl)thiazole-4-carboxamide 261

Step 1: N,N,1-Trimethyl-4-nitro-1H-pyrazol-5-amine

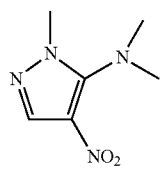

Reaction of 5-chloro-1-methyl-4-nitro-1H-pyrazole and dimethylamine gave N,N,1-trimethyl-4-nitro-1H-pyrazol-5-amine as a yellow solid (210 g, 100%). ¹H NMR (400 MHz, CDCl₃) δ 8.01 (s, 1H), 3.75 (s, 3H), 2.90 (s, 6H)

Step 2

Following the procedure for Example 243 starting with N,N,1-trimethyl-4-nitro-1H-pyrazol-5-amine gave 261 as a light brown solid (0.26 g, 54% over three steps). ¹H NMR (400 MHz, CDCl₃) δ 8.48 (s, 1H), 7.75 (s, 1H), 7.39-7.29 (m, 1H), 7.09-6.99 (m, 2H), 6.18 (s, 2H), 3.75 (s, 3H), 2.87 (s, 6H). LCMS (ES+) m/z 379 (M+1)

Example 262

5-amino-N-(5-(cyclohexyloxy)-1-methyl-1H-pyrazol-4-yl)-2-(2,6-difluorophenyl)thiazole-4-carboxamide 262

Step 1: 5-(Cyclohexyloxy)-1-methyl-4-nitro-1H-pyrazole

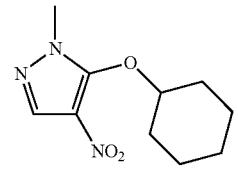 [SMILES: Cn1ncc([N+](=O)[O-])c1OC1CCCCC1]

Following the procedure for Example 230 reaction of 5-chloro-1-methyl-4-nitro-1H-pyrazole and cyclohexanol gave 5-(cyclohexyloxy)-1-methyl-4-nitro-1H-pyrazole as off-white solid (132 mg, 47%). ¹H NMR (400 MHz, CDCl₃) δ 7.99 (s, 1H), 4.76-4.67 (m, 1H), 3.70 (s, 3H), 2.10-2.02 (m, 2H), 1.85-1.78 (m, 2H), 1.64-1.52 (m, 2H), 1.43-1.22 (m, 3H), 0.96-0.81 (m, 1H)

Step 2

Following the procedure for Example 243 starting with 5-(cyclohexyloxy)-1-methyl-4-nitro-1H-pyrazole gave 262 as a light brown solid (157 mg, 41% over three steps). ¹H NMR (400 MHz, CDCl₃) δ 8.39 (s, 1H), 7.80 (s, 1H), 7.38-7.29 (m, 1H), 7.09-6.99 (m, 2H), 6.18 (s, 2H), 4.21-4.12 (m, 1H), 3.71 (s, 3H), 2.09-1.98 (m, 3H), 1.86-1.78 (m, 2H), 1.66-1.50 (m, 3H), 1.39-1.25 (m, 2H). LCMS (ES+) m/z 434 (M+1)

Example 263

5-amino-2-(2,6-difluorophenyl)-N-(1-methyl-5-(piperidin-4-yl)-1H-pyrazol-4-yl)thiazole-4-carboxamide 263

Following the procedure for Example 243 starting with tert-butyl 4-(1-methyl-4-nitro-1H-pyrazol-5-yl)-5,6-dihydropyridine-1(2H)-carboxylate gave 263 as an orange solid (28 mg, 18% over three steps). ¹H NMR (400 MHz, d₆-DMSO) δ 8.77 (s, 1H), 7.61-7.48 (m, 3H), 7.46 (s, 1H), 7.30 (t, J=8.8 Hz, 2H), 3.80 (s, 3H), 3.09 (d, J=12.3 Hz, 2H), 2.97-2.87 (m, 1H), 2.66 (t, J=12.3 Hz, 2H), 1.92-1.68 (m, 4H). Alkyl NH not seen. LCMS (ES+) m/z 419 (M+1). LCMS (ES+) m/z 488 (M+1)

Example 264

5-amino-N-(5-(4-(aminomethyl)piperidin-1-yl)-1-(cyclopropylmethyl)-1H-pyrazol-4-yl)-2-(2,6-difluorophenyl)thiazole-4-carboxamide 264

Step 1: tert-Butyl (1-(1-(cyclopropylmethyl)-4-nitro-1H-pyrazol-5-yl)piperidin-4-yl)methylcarbamate

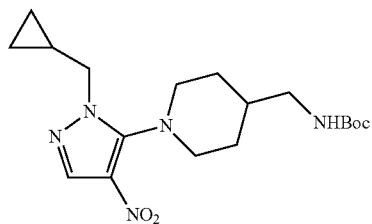 [SMILES: CC(C)(C)OC(=O)NCC1CCN(c2c([N+](=O)[O-])cnn2CC2CC2)CC1]

Reaction of 5-chloro-1-cyclopropylmethyl-4-nitro-1H-pyrazole and tert-butyl piperidin-4-ylmethylcarbamate gave tert-butyl (1-(1-(cyclopropylmethyl)-4-nitro-1H-pyrazol-5-yl)piperidin-4-yl)methylcarbamate as a pale yellow gum (0.57 g, 95%). $^1$H NMR (400 MHz, CDCl$_3$) δ 8.07-8.03 (m, 1H), 4.63 (s, 1H), 3.91 (d, J=7.1 Hz, 2H), 3.40-3.32 (m, 2H), 3.13-3.06 (m, 2H), 2.95 (d, J=11.5 Hz, 2H), 1.81 (d, J=12.9 Hz, 2H), 1.46 (s, 9H), 1.42-1.14 (m, 3H), 0.95-0.82 (m, 1H), 0.63-0.57 (m, 2H), 0.42-0.35 (m, 2H)

Step 2

Following the procedures of Example 230, tert-butyl (1-(1-(cyclopropylmethyl)-4-nitro-1H-pyrazol-5-yl)piperidin-4-yl)methylcarbamate was converted to 264 as a cream solid (125 mg, 53% over three steps). $^1$H NMR (400 MHz, d$_6$-DMSO) δ 8.75 (s, 1H), 7.62-7.52 (m, 4H), 7.36-7.28 (m, 2H), 3.83 (d, J=6.8 Hz, 2H), 3.07 (d, J=7.8 Hz, 4H), 2.60 (d, J=6.8 Hz, 2H), 1.80 (d, J=12.4 Hz, 2H), 1.50-1.40 (m, 1H), 1.30-1.20 (m, 3H), 0.55-0.48 (m, 2H), 0.40-0.34 (m, 2H). Alkyl NH$_2$ not seen. LCMS (ES+) m/z 488 (M+1)

Example 265

5-amino-N-(5-(4-(aminomethyl)piperidin-1-yl)-1-methyl-1H-pyrazol-4-yl)-2-cyclohexenylthiazole-4-carboxamide 265

Following Example 278, Suzuki coupling of tert-butyl 4-(5-(4-(butyloxycarbonylaminomethyl)piperidin-1-yl)-1-methyl-1H-pyrazol-4-ylcarbamoyl)-2-bromothiazol-5-ylcarbamate and cyclohex-1-ene-1-boronic acid gave 265 as a pale brown solid (21 mg, 26% over two steps). $^1$H NMR (400 MHz, d$_6$-DMSO) δ 8.61 (s, 1H), 7.43 (s, 1H), 7.26 (s, 2H), 6.25 (s br, 1H), 3.64 (s, 3H), 3.07-2.94 (m, 4H), 2.47 (d, J=6.1 Hz, 4H), 2.19 (s, 2H), 1.77 (d, J=12.2 Hz, 2H), 1.73-1.58 (m, 4H), 1.34-1.14 (m, 3H). Alkyl NH$_2$ not seen. LCMS (ES+) m/z 416 (M+1)

Example 266

(E)-5-Amino-N-(5-(4-(aminomethyl)piperidin-1-yl)-1-methyl-1H-pyrazol-4-yl)-2-cycloheptenylthiazole-4-carboxamide 266

Following the procedure for Example 337 starting with tert-butyl 4-(5-(4-(butyloxycarbonylaminomethyl)piperidin-1-yl)-1-methyl-1H-pyrazol-4-ylcarbamoyl)-2-bromothiazol-5-ylcarbamate and 1-cycloheptenylboronic acid pinacol ester gave 266 as a pale brown solid (25 mg, 28%). $^1$H NMR (400 MHz, d$_6$-DMSO) δ 8.64 (s, 1H), 7.43 (s, 1H), 7.29 (s, 2H), 6.38 (t, J=6.7 Hz, 1H), 3.64 (s, 3H), 3.08-2.94 (m, 4H), 2.78 (d, J=8.2 Hz, 2H), 2.47 (d, J=6.2 Hz, 2H), 2.35-2.20 (m, 2H), 1.82-1.72 (m, 4H), 1.56-1.49 (m, 4H), 1.33-1.11 (m, 3H). LCMS (ES+) m/z 430 (M+1).

Example 267

5-amino-N-(5-(4-(aminomethyl)piperidin-1-yl)-1-methyl-1H-pyrazol-4-yl)-2-(3-ethylphenyl)thiazole-4-carboxamide 267

Following Example 278, Suzuki coupling of tert-butyl 4-(5-(4-(butyloxycarbonylaminomethyl)piperidin-1-yl)-1-methyl-1H-pyrazol-4-ylcarbamoyl)-2-bromothiazol-5-ylcarbamate and 3-ethylphenyl boronic acid gave 267 as an off-white solid (25 mg, 29% over two steps). $^1$H NMR (400 MHz, d$_6$-DMSO) δ 8.89 (s, 1H), 7.71 (s, 1H), 7.61 (d, J=7.8 Hz, 1H), 7.43-7.33 (m, 4H), 7.26 (d, J=7.8 Hz, 1H), 3.64 (s, 3H), 3.14-2.98 (m, 4H), 2.67 (q, J=7.6 Hz, 2H), 2.46 (d, J=5.7 Hz, 2H), 1.77 (d, J=11.7 Hz, 2H), 1.32-1.19 (m, 6H). Alkyl NH$_2$ not seen. LCMS (ES+) m/z 440 (M+1)

Example 268

5-amino-N-(5-(4-(aminomethyl)piperidin-1-yl)-1-methyl-1H-pyrazol-4-yl)-2-(3-methoxyphenyl)thiazole-4-carboxamide 268

Following Example 278, Suzuki coupling of tert-butyl 4-(5-(4-(butyloxycarbonylaminomethyl)piperidin-1-yl)-1-methyl-1H-pyrazol-4-ylcarbamoyl)-2-bromothiazol-5-ylcarbamate and 3-methoxyphenyl boronic acid gave 268 as a brown solid (153 mg, 17% over two steps). $^1$H NMR (400 MHz, d$_6$-DMSO) δ 8.92 (s, 1H), 7.47-7.29 (m, 6H), 6.98 (d, J=7.7 Hz, 1H), 3.84 (s, 3H), 3.64 (s, 3H), 3.12-2.95 (m, 4H), 2.47 (d, J=6.0 Hz, 2H), 1.76 (d, J=11.7 Hz, 2H), 1.30-1.17 (m, 3H). Alkyl NH$_2$ not seen. LCMS (ES+) m/z 442 (M+1)

Example 269

5-amino-N-(5-(4-(aminomethyl)piperidin-1-yl)-1-methyl-1H-pyrazol-4-yl)-2-(2-isopropylphenyl)thiazole-4-carboxamide 269

Following Example 278, Suzuki coupling of tert-butyl 4-(5-(4-(butyloxycarbonylaminomethyl)piperidin-1-yl)-1-methyl-1H-pyrazol-4-ylcarbamoyl)-2-bromothiazol-5-ylcarbamate and 3-isopropylbenzene boronic acid gave 269 as a red gum (38 mg, 41% over two steps). $^1$H NMR (400 MHz, d$_6$-DMSO) δ 8.55 (s, 1H), 7.54-7.33 (m, 6H), 7.28 (t, J=7.5 Hz, 1H), 3.71 (t, J=9.2 Hz, 1H), 3.62 (s, 3H), 3.11-2.93 (m, 4H), 2.42 (d, J=5.4 Hz, 2H), 1.73 (d, J=11.3 Hz, 2H), 1.27-1.21 (m, 9H). Alkyl NH₂ not seen. LCMS (ES+) m/z 454 (M+1)

Example 270

5-amino-N-(5-(4-(aminomethyl)piperidin-1-yl)-1-isopropyl-1H-pyrazol-4-yl)-2-(2,6-difluorophenyl)thiazole-4-carboxamide 270

Step 1: tert-Butyl (1-(1-isopropyl-4-nitro-1H-pyrazol-5-yl)piperidin-4-yl)methylcarbamate

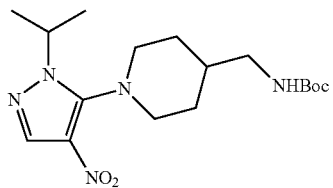 [SMILES: CC(C)n1ncc([N+](=O)[O-])c1N1CCC(CNC(=O)OC(C)(C)C)CC1]

Reaction of 5-chloro-1-isopropyl-4-nitro-1H-pyrazole and tert-butyl piperidin-4-ylmethylcarbamate gave tert-butyl (1-(1-isopropyl-4-nitro-1H-pyrazol-5-yl)piperidin-4-yl)methylcarbamate as a pale yellow solid (0.45 g, 92%). ¹H NMR (400 MHz, CDCl₃) δ 8.06 (s, 1H), 4.78 (hep, J=6.7 Hz, 1H), 4.64 (s, 1H), 3.42-3.29 (m, 2H), 3.11 (t, J=6.6 Hz, 2H), 2.95-2.87 (m, 2H), 2.05 (s, 1H), 1.81 (d, J=12.8 Hz, 2H), 1.46 (s, 9H), 1.43 (d, J=6.7 Hz, 6H), 1.37 (dd, J=12.1, 4.3 Hz, 2H)

Step 2

Following the procedure for Example 230 starting with tert-butyl (1-(1-isopropyl-4-nitro-1H-pyrazol-5-yl)piperidin-4-yl)methylcarbamate gave 270 as a cream solid (78 mg, 40% over three steps). ¹H NMR (400 MHz, d₆-DMSO) δ 8.71 (s, 1H), 7.61 (s, 1H), 7.57-7.48 (m, 3H), 7.35-7.23 (m, 2H), 4.61-4.51 (m, 1H), 3.35-3.31 (m, 2H), 3.10-2.99 (m, 2H), 2.52-2.45 (m, 2H), 1.90-1.72 (m, 2H), 1.35 (d, J=6.6 Hz, 6H), 1.29-1.16 (m, 3H). Alkyl NH₂ not seen. LCMS (ES+) m/z 476 (M+1)

Example 271

5-amino-2-(2,6-difluorophenyl)-N-(5-((2-hydroxyethyl)(methyl)amino)-1-methyl-1H-pyrazol-4-yl)thiazole-4-carboxamide 271

Step 1: 2-(Methyl(1-methyl-4-nitro-1H-pyrazol-5-yl)amino)ethanol

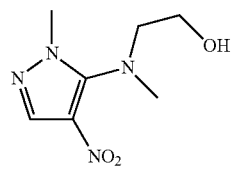

Reaction of 5-chloro-1-methyl-4-nitro-1H-pyrazole and 2-(methylamino)ethanol gave 2-(methyl(1-methyl-4-nitro-1H-pyrazol-5-yl)amino)ethanol as a yellow oil (0.2 g, 81%). ¹H NMR (400 MHz, CDCl₃) δ 8.04 (s, 1H), 3.79 (s, 3H), 3.72 (q, J=5.4 Hz, 2H), 3.33 (t, J=5.4 Hz, 2H), 2.93 (s, 3H), 1.91 (t, J=5.4 Hz, 1H)

Step 2

Following the procedure for Example 243 starting with 2-(methyl(1-methyl-4-nitro-1H-pyrazol-5-yl)amino)ethanol gave 271 as a peach solid (60 mg, 30% over three steps). ¹H NMR (400 MHz, CDCl₃) δ 8.91 (s, 1H), 7.77 (s, 1H), 7.37-7.29 (m, 1H), 7.03 (t, J=8.9 Hz, 2H), 6.17 (s, 2H), 3.75 (s, 5H), 3.26 (t, J=4.9 Hz, 2H), 2.92 (s, 3H), 2.82 (s br, 1H). LCMS (ES+) m/z 409 (M+1)

Example 272

(S)-5-amino-2-(2,6-difluorophenyl)-N-(1-methyl-5-(piperidin-3-yloxy)-1H-pyrazol-4-yl)thiazole-4-carboxamide 272

Step 1: (S)-tert-Butyl 3-(1-methyl-4-nitro-1H-pyrazol-5-yloxy)piperidine-1-carboxylate

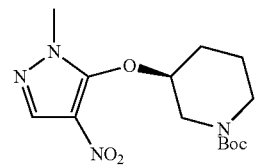 [SMILES: Cn1ncc([N+](=O)[O-])c1O[C@H]1CCCN(C(=O)OC(C)(C)C)C1]

Following the procedure for Example 230, reaction of 5-chloro-1-methyl-4-nitro-1H-pyrazole and (S)-tert-butyl 3-hydroxypiperidine-1-carboxylate gave (S)-tert-butyl 3-(1-methyl-4-nitro-1H-pyrazol-5-yloxy)piperidine-1-carboxylate as a pale yellow oil (0.35 g, 97%). ¹H NMR (400 MHz, CDCl₃) δ 8.01 (s, 1H), 5.15-4.85 (m, 1H), 3.84-3.72 (m, 2H), 3.69 (s, 3H), 3.41 (d, J=14.2 Hz, 1H), 3.30-3.13 (m, 1H), 2.11-2.02 (m, 1H), 1.94-1.82 (m, 2H), 1.63-1.52 (m, 1H), 1.42 (s, 9H)

Step 2

Following the procedure for Example 243 starting with (S)-tert-butyl 3-(1-methyl-4-nitro-1H-pyrazol-5-yloxy)piperidine-1-carboxylate gave 272 as an off-white foam (86 mg, 43% over three steps). ¹H NMR (400 MHz, CDCl₃) δ 9.22 (s, 1H), 7.83 (s, 1H), 7.36-7.29 (m, 1H), 7.02 (t, J=8.6 Hz, 2H), 6.19 (s, 2H), 4.21 (s, 1H), 3.71 (s, 3H), 3.02 (s, 2H), 2.90-2.72 (m, 2H), 2.00-1.85 (m, 3H), 1.55-1.40 (m, 1H). Alkyl NH not seen. LCMS (ES+) m/z 435 (M+1)

Example 273

(R)-5-amino-2-(3-(3-(aminomethyl)pyrrolidin-1-yl)phenyl)-N-(1-methyl-1H-pyrazol-4-yl)thiazole-4-carboxamide 273

Step 1: (R)-tert-Butyl 2-(3-(3-(butyloxycarbonylaminomethyl)pyrrolidin-1-yl)phenyl)-4-(1-methyl-1H-pyrazol-4-ylcarbamoyl)thiazol-5-ylcarbamate

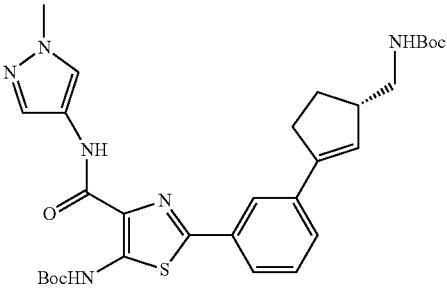 [SMILES: Cn1cc(NC(=O)c2nc(-c3cccc(C4=C[C@@H](CNC(=O)OC(C)(C)C)CC4)c3)sc2NC(=O)OC(C)(C)C)cn1]

1,3-Dibromobenzene (0.2 g, 0.85 mmol), (R)-tert-butyl pyrrolidin-3-ylmethylcarbamate (0.17 g, 0.85 mmol), Pd$_2$(dba)$_3$ (39 mg, 0.04 mmol), BINAP (40 mg, 0.06 mmol) and sodium tert-butoxide (98 mg, 1.02 mmol) were suspended in toluene (2 mL). The mixture was heated at 80° C. for 16 hr. The mixture was cooled and diluted with water and EtOAc. The organic layer was separated, passed through a phase separator cartridge and concentrated under reduced pressure. Purification via silica gel column chromatography (0-100% EtOAc/isohexane) gave (R)-tert-butyl (1-(3-bromophenyl)pyrrolidin-3-yl)methylcarbamate as a yellow oil (0.179 g, 59%). This oil (0.179 g, 0.5 mmol) was suspended in 1,4-dioxane (2 mL). Bis-pinacolato-diboron (0.166 g, 0.66 mmol), potassium acetate (65 mg, 0.66 mmol) and Pd(dppf)Cl$_2$ (20 mg, 0.025 mmol) were added and the mixture was heated at 100° C. for 16 h. The solution was cooled, diluted with DCM and filtered through celite. The solvent was removed under reduced pressure to afford crude (R)-tert-butyl (1-(3-(4,4,5,5-tetramethyl-1,3,2-dioxaborolan-2-yl)phenyl)pyrrolidin-3-yl)methylcarbamate as a brown oil. A mixture of this oil (0.5 mmol), tert-butyl 2-bromo-4-(1-methyl-1H-pyrazol-4-ylcarbamoyl)thiazol-5-ylcarbamate (0.177 g, 0.44 mmol), Na$_2$CO$_3$ (0.7 mL, 2M aq. solution, 1.32 mmol) in DME (4.3 mL) was degassed by gently bubbling nitrogen through the mixture for 15 min. [1,1'-Bis(diphenylphosphino)ferrocene]dichloro-palladium(II) (72 mg, 0.09 mmol) was added and the mixture degassed for a further 10 min before being heated in a microwave at 130° C. for 40 min. The solvents were removed under reduced pressure and the residue purified via silica gel column chromatography (0-100% EtOAc/isohexane) to yield (R)-tert-butyl 2-(3-(3-(butyloxycarbonylaminomethyl)pyrrolidin-1-yl)phenyl)-4-(1-methyl-1H-pyrazol-4-ylcarbamoyl)thiazol-5-ylcarbamate as a yellow oil (86 mg, 33%). $^1$H NMR (400 MHz, CDCl$_3$) δ 10.38 (s, 1H), 8.90 (s, 1H), 7.98 (s, 1H), 7.58 (s, 1H), 7.00 (s, 1H), 6.63-6.57 (m, 1H), 4.71-4.69 (m, 1H), 3.92 (s, 3H), 3.59-3.36 (m, 5H), 2.67-2.46 (m, 1H), 2.14-2.13 (m, 1H), 1.84-1.80 (m, 1H), 1.55 (s, 9H), 1.54 (s, 9H). Three protons not seen Step 2

Acidic deprotection of (R)-tert-butyl 2-(3-(3-(butyloxycarbonylaminomethyl)pyrrolidin-1-yl)phenyl)-4-(1-methyl-1H-pyrazol-4-ylcarbamoyl)thiazol-5-ylcarbamate gave 273 as an off-white solid (143 mg, 20%). $^1$H NMR (400 MHz, d$_6$-DMSO) δ 9.84 (s, 1H), 8.03 (s, 1H), 7.70 (s, 1H), 7.48 (s, 2H), 7.27 (dd, J=8, 7.5 Hz, 1H), 7.12 (dd, J=7.5, 6 Hz, 1H), 7.03-6.97 (m, 1H), 6.61 (dd, J=8, 2 Hz, 1H), 3.86 (s, 3H), 3.51-3.31 (m, 3H), 3.14-3.05 (m, 2H), 2.67 (dd, J=7, 3 Hz, 1H), 2.41-2.30 (m, 1H), 2.18-2.08 (m, 1H), 1.84-1.74 (m, 1H). Alkyl NH$_2$ not seen. LCMS (ES+) m/z 398 (M+1)

Example 274

5-amino-N-(1-methyl-1H-pyrazol-4-yl)-2-(3-(piperazin-1-yl)phenyl)thiazole-4-carboxamide 274

Following Example 278, Suzuki coupling of tert-butyl 2-bromo-4-(1-methyl-1H-pyrazol-4-ylcarbamoyl)thiazol-5-ylcarbamate and tert-butyl 4-(3-(4,4,5,5-tetramethyl-1,3,2-dioxaborolan-2-yl)phenyl)piperazine-1-carboxylate gave 274 as a pale brown solid (18 mg, 19% over two steps). $^1$H NMR (400 MHz, d$_6$-DMSO) δ 9.82 (s, 1H), 7.99 (s, 1H), 7.65 (s, 1H), 7.45 (s, 3H), 7.28 (dd, J=8, 7.5 Hz, 1H), 7.19 (d, J=7.5 Hz, 1H), 6.96 (dd, J=8, 2.5 Hz, 1H), 3.82 (s, 3H), 3.14 (t, J=5 Hz, 4H), 2.86 (t, J=5 Hz, 4H). Alkyl NH not seen. LCMS (ES+) m/z 384 (M+1)

Example 275

5-amino-N-(5-(4-(aminomethyl)piperidin-1-yl)-1-methyl-1H-pyrazol-4-yl)-2-(2-carbamoylphenyl)thiazole-4-carboxamide 275

Following Example 278, Suzuki coupling of tert-butyl 4-(5-(4-(butyloxycarbonylaminomethyl)piperidin-1-yl)-1-methyl-1H-pyrazol-4-ylcarbamoyl)-2-bromothiazol-5-ylcarbamate and 2-cyanophenylboronic acid gave 275 as a yellow solid (26 mg, 29% over two steps). $^1$H NMR (400 MHz, d$_4$-MeOD) δ 7.71 (d, J=7.5 Hz, 1H), 7.57-7.46 (m, 4H), 3.72 (s, 3H), 3.22-3.11 (m, 4H), 2.61 (d, J=6.5 Hz, 2H), 1.84 (d, J=12.1 Hz, 2H), 1.61-1.50 (m, 1H), 1.42-1.29 (m, 2H). LCMS (ES+) m/z 455 (M+1)

Example 276

5-amino-N-(5-(4-(aminomethyl)piperidin-1-yl)-1-methyl-1H-pyrazol-4-yl)-2-(3-(dimethylamino)phenyl)thiazole-4-carboxamide 276

Following Example 278, Suzuki coupling of tert-butyl 4-(5-(4-(butyloxycarbonylaminomethyl)piperidin-1-yl)-1-methyl-1H-pyrazol-4-ylcarbamoyl)-2-bromothiazol-5-ylcarbamate and 3-(dimethylamino)phenylboronic acid gave 276 as an off-white solid (34 mg, 37% over two steps). $^1$H NMR (400 MHz, d$_4$-MeOD) δ 7.37-7.34 (m, 1H), 7.30 (s, 1H), 7.26 (t, J=8.0 Hz, 1H), 7.07 (d, J=7.6 Hz, 1H), 6.82 (dd, J=8.3, 2.6 Hz, 1H), 3.69 (s, 3H), 3.13-3.04 (m, 4H), 2.97 (s, 6H), 2.58 (d, J=6.5 Hz, 2H), 1.80 (d, J=12.5 Hz, 2H), 1.52-1.39 (m, 1H), 1.32 (qd, J=11.8, 4.7 Hz, 2H). LCMS (ES+) m/z 455 (M+1)

Example 277

5-Amino-N-(5-(4-(aminomethyl)piperidin-1-yl)-1-methyl-1H-pyrazol-4-yl)-2-(2,5-dichlorophenyl)thiazole-4-carboxamide 277

Following Example 278, Suzuki coupling of tert-butyl 4-(5-(4-(butyloxycarbonylaminomethyl)piperidin-1-yl)-1-methyl-1H-pyrazol-4-ylcarbamoyl)-2-bromothiazol-5-ylcarbamate and 2,5-dichlorobenzeneboronic acid gave 277 as an off-white solid (19 mg, 19%). $^1$H NMR (400 MHz, d$_4$-MeOD) δ 8.39 (d, J=2.6 Hz, 1H), 7.51 (d, J=8.6 Hz, 1H), 7.48 (s, 1H), 7.37 (dd, J=8.6, 2.6 Hz, 1H), 3.73 (s, 3H), 3.24-3.11 (m, 4H), 2.60 (d, J=6.6 Hz, 2H), 1.85 (d, J=12.5 Hz, 2H), 1.55-1.44 (m, 1H), 1.36 (qd, J=11.9, 4.4 Hz, 2H). LCMS (ES+) m/z 464 (M+1).

Example 278

5-amino-N-(5-(4-(aminomethyl)piperidin-1-yl)-1-methyl-1H-pyrazol-4-yl)-2-(4-hydroxy-2-(trifluoromethyl)phenyl)thiazole-4-carboxamide 278

A mixture of tert-butyl 4-(5-(4-(butyloxycarbonylaminomethyl)piperidin-1-yl)-1-methyl-1H-pyrazol-4-ylcarbamoyl)-2-bromothiazol-5-ylcarbamate (0.123 g, 0.20 mmol), Na$_2$CO$_3$ (42 mg, 0.40 mmol) and 4-hydroxy-2-(trifluoromethyl)benzeneboronic acid (66 mg, 0.32 mmol) in DME (1.5 mL) and water (0.5 mL) was degassed by gently bubbling nitrogen through the mixture for 15 min. [1,1'-Bis(diphenylphosphino)ferrocene]dichloro-palladium(II) (16 mg, 0.02 mmol) was then added and the mixture degassed for a further 10 min before being heated in a microwave at 130° C. for 40 min. The solvents were removed under reduced pressure and the residue purified via silica gel column chromatography (0-100% EtOAc/isohexane). The isolated intermediate was dissolved in a solution of HCl in 1,4-dioxane (4 M, 2 mL) and stirred at room temperature for 16 hr. The solvent was removed under reduced pressure and the residue purified by preparative HPLC to yield 278 as a pale brown solid (48 mg, 48%). $^1$H NMR (400 MHz, $d_4$-MeOD) δ 7.59 (s, 1H), 7.44 (d, J=8.5 Hz, 1H), 7.15 (d, J=2.5 Hz, 1H), 6.98 (dd, J=8.5, 2.5 Hz, 1H), 3.72 (s, 3H), 3.22-3.10 (m, 4H), 2.71 (d, J=6.8 Hz, 2H), 1.85 (d, J=12.6 Hz, 2H), 1.66-1.55 (m, 1H), 1.47-1.33 (m, 2H). LCMS (ES+) m/z 496 (M+1).

Example 279

5-amino-N-(5-(4-(aminomethyl)piperidin-1-yl)-1-methyl-1H-pyrazol-4-yl)-2-(5-fluoro-2-(trifluoromethyl)phenyl)thiazole-4-carboxamide 279

Following Example 278, Suzuki coupling of tert-butyl 4-(5-(4-(butyloxycarbonylaminomethyl)piperidin-1-yl)-1-methyl-1H-pyrazol-4-ylcarbamoyl)-2-bromothiazol-5-ylcarbamate and 5-fluoro-2-(trifluoromethyl)phenylboronic acid gave 279 as a brown solid (54 mg, 55% over two steps). $^1$H NMR (400 MHz, $d_4$-MeOD) 7.94 (dd, J=8.9, 5.4 Hz, 1H), 7.60-7.50 (m, 2H), 7.40 (td, J=8.3, 2.6 Hz, 1H), 3.73 (s, 3H), 3.21-3.09 (m, 4H), 2.63 (d, J=6.6 Hz, 2H), 1.84 (d, J=12.5 Hz, 2H), 1.57-1.48 (m, 1H), 1.38 (qd, J=11.8, 4.7 Hz, 2H). LCMS (ES+) m/z 498 (M+1)

Example 280

5-amino-N-(5-(4-(aminomethyl)piperidin-1-yl)-1-methyl-1H-pyrazol-4-yl)-2-(4-methoxy-2-(trifluoromethyl)phenyl)thiazole-4-carboxamide 280

Following the procedure for Example 337 starting with tert-butyl 4-(5-(4-(butyloxycarbonylaminomethyl)piperidin-1-yl)-1-methyl-1H-pyrazol-4-ylcarbamoyl)-2-bromothiazol-5-ylcarbamate and 4-methoxy-2-(trifluoromethyl)benzeneboronic acid gave 280 as a brown solid (56 mg, 54%). $^1$H NMR (400 MHz, $d_4$-MeOD) δ 7.65 (d, J=8.6 Hz, 1H), 7.58 (s, 1H), 7.37 (d, J=2.6 Hz, 1H), 7.27 (dd, J=8.6, 2.6 Hz, 1H), 3.94 (s, 3H), 3.72 (s, 3H), 3.19-3.06 (m, 4H), 2.62 (d, J=6.5 Hz, 2H), 1.84 (d, J=12.5 Hz, 2H), 1.57-1.46 (m, 1H), 1.37 (qd, J=11.7, 4.9 Hz, 2H). LCMS (ES+) m/z 510 (M+1).

Example 281

5-amino-N-(5-(4-(aminomethyl)piperidin-1-yl)-1-methyl-1H-pyrazol-4-yl)-2-(2-cyclohexylethyl)thiazole-4-carboxamide 281

A mixture of tert-butyl 4-(5-(4-(butyloxycarbonylaminomethyl)piperidin-1-yl)-1-methyl-1H-pyrazol-4-ylcarbamoyl)-2-bromothiazol-5-ylcarbamate (0.203 g, 0.33 mmol), Na$_2$CO$_3$ (70 mg, 0.66 mmol) and trans-(2-cyclohexylvinyl)boronic acid (0.102 g, 0.66 mmol) in DME (1.5 mL) and water (0.5 mL) was degassed by gently bubbling nitrogen through the mixture for 15 min. [1,1'-Bis(diphenylphosphino)ferrocene]dichloro-palladium(II) (27 mg, 0.033 mmol) was then added and the mixture degassed for a further 10 min before being heated in a microwave at 130° C. for 45 min. The reaction mixture was diluted with water and extracted with EtOAc. The combined organic extracts were passed through a phase separator cartridge and concentrated under reduced pressure. The residue was purified via silica gel column chromatography (0-100% EtOAc/isohexane) to afford (E)-tert-butyl 4-(5-(4-(butyloxycarbonylaminomethyl)piperidin-1-yl)-1-methyl-1H-pyrazol-4-ylcarbamoyl)-2-(2-cyclohexylvinyl)thiazol-5-ylcarbamate as a brown gum (0.144 g, 68%). A solution of this gum (0.142 g, 0.22 mmol) in MeOH (5 mL) and acetic acid (0.5 mL) was passed through the H-Cube® (70 bar, 70° C., flow rate: 1 mL/min, 30 mm 10% Pd/C cartridge). The solvent was removed under reduced pressure to afford crude tert-butyl 4-(5-(4-(butyloxycarbonylaminomethyl)piperidin-1-yl)-1-methyl-1H-pyrazol-4-ylcarbamoyl)-2-(2-cyclohexylethyl)thiazol-5-ylcarbamate as a clear gum (0.122 g, 99%). This gum (0.122 g, 0.188 mmol) was stirred in HCl in 1,4-dioxane (4.0 M, 2 mL) at room temperature for 18 hr. The solvents were removed under reduced pressure and the crude residue was re-dissolved in MeOH and loaded onto an SCX column. The column was washed with MeOH and 7 N ammonia in MeOH to yield 281 as a pink solid (39 mg, 63%). $^1$H NMR (400 MHz, $d_4$-MeOD) δ 7.43 (s, 1H), 3.71 (s, 3H), 3.21-3.06 (m, 4H), 2.86 (t, J=7.8 Hz, 2H), 2.62 (d, J=6.6 Hz, 2H), 1.87-1.59 (m, 9H), 1.58-1.45 (m, 1H), 1.43-1.15 (m, 6H), 0.99 (q, J=11.9 Hz, 2H). LCMS (ES+) m/z 446 (M+1)

Example 282

5-amino-N-(5-(4-(aminomethyl)piperidin-1-yl)-1-methyl-1H-pyrazol-4-yl)-2-cyclohexylthiazole-4-carboxamide 282

Following the procedure for Example 281, Suzuki coupling of tert-butyl 4-(5-(4-(butyloxycarbonylaminomethyl)piperidin-1-yl)-1-methyl-1H-pyrazol-4-ylcarbamoyl)-2-bromothiazol-5-ylcarbamate and cyclohex-1-ene-1-boronic acid gave 282 (44 mg, 51% over three steps). $^1$H NMR (400 MHz, $d_4$-MeOD) δ 7.45 (s, 1H), 3.71 (s, 3H), 3.21-3.08 (m, 4H), 2.85-2.76 (m, 1H), 2.64 (d, J=6.6 Hz, 2H), 2.09 (d, J=12.1 Hz, 2H), 1.90-1.81 (m, 4H), 1.76 (d, J=13.0 Hz, 1H), 1.59-1.25 (m, 8H). LCMS (ES+) m/z 418 (M+1)

Example 283

5-amino-N-(5-(4-(aminomethyl)piperidin-1-yl)-1-methyl-1H-pyrazol-4-yl)thiazole-4-carboxamide 283

A solution of tert-butyl 4-(5-(4-(butyloxycarbonylaminomethyl)piperidin-1-yl)-1-methyl-1H-pyrazol-4-ylcarbamoyl)-2-bromothiazol-5-ylcarbamate (0.15 g, 0.244 mmol) in MeOH (5 mL) and acetic acid (0.5 mL) was passed through the H-Cube® (70 bar, 70° C., flow rate: 1 mL/min, 30 mm 10% Pd/C cartridge). The solvent was removed under reduced pressure to afford crude tert-butyl 4-(5-(4-(butyloxycarbonylaminomethyl)piperidin-1-yl)-1-methyl-1H-pyrazol-4-ylcarbamoyl)thiazol-5-ylcarbamate as a clear gum (98 mg, 96%). This gum (97 mg, 0.182 mmol) was stirred in HCl in 1,4-dioxane (4.0 M, 2 mL) at room temperature for 18 hr. The solvents were removed under reduced pressure and the crude residue was re-dissolved in MeOH and loaded onto an SCX column. The column was washed with MeOH and 7 N ammonia in MeOH to give 283 as an off-white solid (39 mg, 84%). $^1$H NMR (400 MHz, $d_4$-MeOD) δ 7.97 (s, 1H), 7.44 (s, 1H), 3.71 (s, 3H), 3.21-3.07 (m, 4H), 2.65 (d, J=6.6 Hz, 2H), 1.83 (d, J=12.5 Hz, 2H), 1.60-1.47 (m, 1H), 1.43-1.30 (m, 2H). LCMS (ES+) m/z 336 (M+1)

Example 284

(R)-5-amino-2-(2,6-difluorophenyl)-N-(1-methyl-5-(piperidin-3-yloxy)-1H-pyrazol-4-yl)thiazole-4-carboxamide 284

Step 1: (R)-tert-Butyl 3-(1-methyl-4-nitro-1H-pyrazol-5-yloxy)piperidine-1-carboxylate

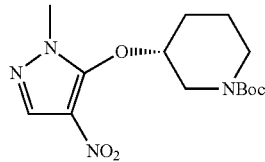

Following the procedure for Example 230, reaction of 5-chloro-1-methyl-4-nitro-1H-pyrazole and (R)-tert-butyl 3-hydroxypiperidine-1-carboxylate gave (R)-tert-butyl 3-(1-methyl-4-nitro-1H-pyrazol-5-yloxy)piperidine-1-carboxylate as a pale yellow oil (0.34 g, 93%). ¹H NMR (400 MHz, CDCl₃) δ 8.01 (s, 1H), 5.15-4.85 (m, 1H), 3.84-3.72 (m, 2H), 3.69 (s, 3H), 3.41 (d, J=14.2 Hz, 1H), 3.30-3.13 (m, 1H), 2.11-2.02 (m, 1H), 1.94-1.82 (m, 2H), 1.63-1.52 (m, 1H), 1.42 (s, 9H)

Step 2

Following the procedure for Example 243, (R)-tert-butyl 3-(1-methyl-4-nitro-1H-pyrazol-5-yloxy)piperidine-1-carboxylate was converted to 284 (145 mg, 68% over three steps). ¹H NMR (400 MHz, CDCl₃) δ 9.29 (s, 1H), 7.86 (s, 1H), 7.38-7.23 (m, 1H), 7.02 (t, J=8.6 Hz, 2H), 6.18 (s, 2H), 4.18 (s, 1H), 3.71 (s, 3H), 3.08-2.90 (m, 2H), 2.85-2.70 (m, 1H), 2.81-2.71 (m, 1H), 2.00-1.87 (s, 3H), 1.50-1.35 (m, 1H). Alkyl NH not seen. LCMS (ES+) m/z 435 (M+1)

Example 285

5-amino-2-(3-(4-(aminomethyl)piperidin-1-yl)phenyl)-N-(1-methyl-1H-pyrazol-4-yl)thiazole-4-carboxamide 285

Step 1: tert-Butyl 2-(3-(4-(butyloxycarbonylaminomethyl)piperidin-1-yl)phenyl)-4-(1-methyl-1H-pyrazol-4-ylcarbamoyl)thiazol-5-ylcarbamate

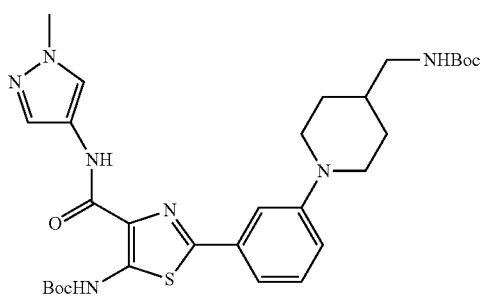 [SMILES: Cn1cc(NC(=O)c2nc(-c3cccc(N4CCC(CNC(=O)OC(C)(C)C)CC4)c3)sc2NC(=O)OC(C)(C)C)cn1]

Following the procedure for Example 273 starting with 1,3-dibromobenzene and tert-butyl piperidin-4-ylmethylcarbamate and tert-butyl 2-bromo-4-(1-methyl-1H-pyrazol-4-ylcarbamoyl)thiazol-5-ylcarbamate gave tert-butyl 2-(3-(4-(butyloxycarbonyl-aminomethyl)piperidin-1-yl)phenyl)-4-(1-methyl-1H-pyrazol-4-ylcarbamoyl)thiazol-5-ylcarbamate as a yellow oil (138 mg, 71%). ¹H NMR (400 MHz, CDCl₃) δ 10.37 (s, 1H), 8.89 (s, 1H), 7.98 (s, 1H), 7.59 (s, 1H), 7.42 (s, 1H), 7.39-7.36 (m, 1H), 7.31 (t, J=7.9 Hz, 1H), 7.03-6.97 (m, 1H), 4.61-4.61 (m, 1H), 3.92 (s, 3H), 3.80-3.75 (m, 2H), 3.14-3.01 (m, 2H), 2.79-2.74 (m, 2H), 1.89-1.79 (m, 2H), 1.56-1.53 (m, 18H), 1.43-1.40 (m, 2H). One proton not seen Step 2

Deprotection of tert-butyl 2-(3-(4-(butyloxycarbonylaminomethyl)piperidin-1-yl)phenyl)-4-(1-methyl-1H-pyrazol-4-ylcarbamoyl)thiazol-5-ylcarbamate under acidic conditions gave 285 as an off-white solid (12 mg, 17%). ¹H NMR (400 MHz, d₆-DMSO) δ 9.80 (s, 1H), 7.98 (s, 1H), 7.65-7.63 (m, 1H), 7.46-7.42 (m, 3H), 7.27 (t, J=7.8 Hz, 1H), 7.17 (d, J=7.8 Hz, 1H), 6.98 (dd, J=7.8, 2.4 Hz, 1H), 3.86-3.75 (m, 5H), 2.70 (dd, J=12.9, 10.7 Hz, 2H), 2.50-2.42 (m, 2H), 1.86-1.72 (m, 4H), 1.42-1.35 (m, 1H), 1.23 (qd, J=12.1, 3.9 Hz, 2H). LCMS (ES+) m/z 412 (M+1)

Example 286

5-amino-N-(5-(4,4-difluoroazepan-1-yl)-1-methyl-1H-pyrazol-4-yl)-2-(2,6-difluorophenyl)thiazole-4-carboxamide 286

Step 1: 4,4-Difluoro-1-(1-methyl-4-nitro-1H-pyrazol-5-yl)azepane

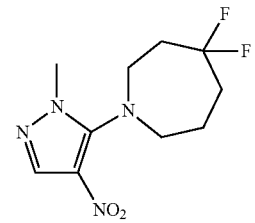 [SMILES: Cn1ncc([N+](=O)[O-])c1N1CCCC(F)(F)CC1]

Reaction of 5-chloro-1-methyl-4-nitro-1H-pyrazole and 4,4-difluoroazepane gave 4,4-difluoro-1-(1-methyl-4-nitro-1H-pyrazol-5-yl)azepane as a white solid (0.41 g, 100%). ¹H NMR (400 MHz, CDCl₃) δ 8.04 (s, 1H), 3.79 (s, 3H), 3.39-3.23 (m, 4H), 2.35-2.20 (m, 4H), 2.00-1.92 (m, 2H)

Step 2

Following the procedure for Example 243 starting with 4,4-difluoro-1-(1-methyl-4-nitro-1H-pyrazol-5-yl)azepane gave 286 as a white solid (90 mg, 12% over three steps). ¹H NMR (400 MHz, CDCl₃) δ 8.54 (s, 1H), 7.84 (s, 1H), 7.32 (tt, J=8.5, 6.0 Hz, 1H), 7.05-6.98 (m, 2H), 6.12 (s, 2H), 3.75 (s, 3H), 3.30-3.23 (m, 4H), 2.33-2.18 (m, 4H), 1.95-1.87 (m, 2H). LCMS (ES+) m/z 469 (M+1)

Example 287

5-Amino-2-(2,6-difluorophenyl)-N-(5-(3,3-difluoropiperidin-1-yl)-1-methyl-1H-pyrazol-4-yl)thiazole-4-carboxamide 287

To a solution of tert-butyl 2-(2,6-difluorophenyl)-4-(5-(3,3-difluoropiperidin-1-yl)-1-methyl-1H-pyrazol-4-ylcarbamoyl)thiazol-5-ylcarbamate (57 mg, 0.1 mmol) in MeOH (2 mL) was added HCl in 1,4-dioxane (4 M, 5 mL). After stirring at room temperature for 18 hr the mixture was concentrated under reduced pressure. Purification via preparative HPLC gave 287 as a white solid (29 mg, 63%). $^1$H NMR (400 MHz, CDCl$_3$) δ 8.40 (s, 1H), 7.65 (s, 1H), 7.37-7.28 (m, 1H), 7.06-6.99 (m, 2H), 6.13 (s, 2H), 3.75 (s, 3H), 3.32 (t, J=11.0 Hz, 2H), 3.17-3.12 (m, 2H), 2.08-1.95 (m, 2H), 1.92-1.84 (m, 2H). LCMS (ES+) m/z 455.0 (M+1).

Example 288

5-amino-2-(2,6-difluorophenyl)-N-(1-methyl-5-(3-oxopiperazin-1-yl)-1H-pyrazol-4-yl)thiazole-4-carboxamide 288

Step 1: 4-(1-Methyl-4-nitro-1H-pyrazol-5-yl)piperazin-2-one

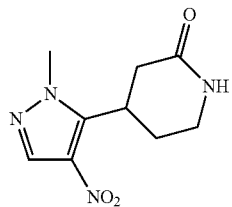

Reaction of 5-chloro-1-methyl-4-nitro-1H-pyrazole and piperazin-2-one gave 4-(1-methyl-4-nitro-1H-pyrazol-5-yl)piperazin-2-one as a white solid (166 mg, 100%). $^1$H NMR (400 MHz, d$_6$-DMSO) δ 8.21 (s, 1H), 8.09 (s, 1H), 3.78 (s, 3H), 3.44-3.30 (m, 6H)

Step 2

Following the procedure for Example 243 starting with 4-(1-methyl-4-nitro-1H-pyrazol-5-yl)piperazin-2-one gave 288 as a white solid (15 mg, 5% over three steps). $^1$H NMR (400 MHz, CDCl$_3$) δ 8.54 (s, 1H), 7.84 (s, 1H), 7.32 (tt, J=8.5, 6.0 Hz, 1H), 7.05-6.98 (m, 2H), 6.12 (s, 2H), 3.75 (s, 3H), 3.30-3.23 (m, 2H), 2.33-2.18 (m, 2H), 1.95-1.87 (m, 2H). LCMS (ES+) m/z 434 (M+1)

Example 289

5-amino-N-(5-(4-(aminomethyl)piperidin-1-yl)-1-methyl-1H-pyrazol-4-yl)-2-cyclopentylthiazole-4-carboxamide 289

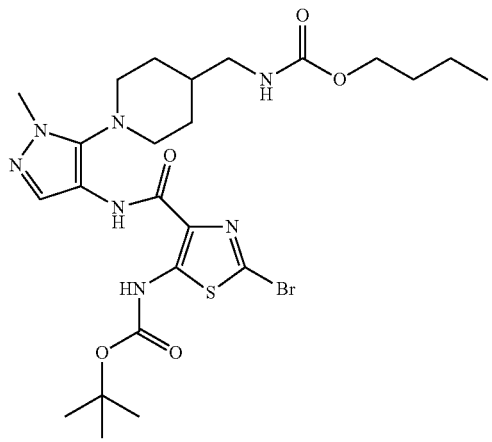 [SMILES: CCCCOC(=O)NCC1CCN(c2c(NC(=O)c3nc(Br)sc3NC(=O)OC(C)(C)C)cnn2C)CC1]

A mixture of tert-butyl 4-(5-(4-(butyloxycarbonylaminomethyl)piperidin-1-yl)-1-methyl-1H-pyrazol-4-ylcarbamoyl)-2-bromothiazol-5-ylcarbamate (0.200 g, 0.62 mmol), Na$_2$CO$_3$ (0.200 g, 1.86 mmol) and cyclopent-1-ene boronic acid (0.208 g, 1.86 mmol) in DME (3 mL) and water (1 mL) was degassed by gently bubbling nitrogen through the mixture for 15 min. [1,1'-Bis(diphenylphosphino)ferrocene]dichloro-palladium(II) (76 mg, 0.09 mmol) was then added and the mixture degassed for a further 10 min before being heated at 80° C. for 16 hr. The reaction mixture was diluted with water and extracted with EtOAc. The aqueous layer was acidified to pH 5 with citric acid and extracted with DCM. The combined organic extracts were passed through a phase separator cartridge and concentrated under reduced pressure to give 5-(tert-butyloxycarbonylamino)-2-cyclopentenylthiazole-4-carboxylic acid as a black solid (0.190 g, 99%). This acid (0.184 g, 0.59 mmol) was added to a solution of 5-(4-(aminomethyl)piperidin-1-yl)-1-methyl-1H-pyrazol-4-amine (0.108 g, 0.35 mmol), DIPEA (0.097 mL, 0.56 mmol) and PyBOP (0.255 g, 0.49 mmol) in DCM (6 mL) and the mixture was stirred at room temperature for 18 hr. The mixture was diluted with DCM and washed with water. The organic layer was separated, dried over MgSO$_4$ and the solvent removed under reduced pressure. Purification via silica gel column chromatography (0-10% MeOH/DCM) gave tert-butyl 4-(5-(4-(butyloxycarbonylaminomethyl)piperidin-1-yl)-1-methyl-1H-pyrazol-4-ylcarbamoyl)-2-cyclopentenylthiazol-5-ylcarbamate as a brown solid (0.165 g, 78%). A solution of this solid (0.162 g, 0.27 mmol) in MeOH (5 mL) and acetic acid (0.4 mL) was passed through the H-Cube® (70 bar, 70° C., flow rate: 1 mL/min, 30 mm 10% Pd/C cartridge). The solvent was removed under reduced pressure to afford crude tert-butyl 4-(5-(4-(butyloxycarbonylaminomethyl)piperidin-1-yl)-1-methyl-1H-pyrazol-4-ylcarbamoyl)-2-cyclopentylthiazol-5-ylcarbamate as a clear gum (84 mg, 51%). This gum (81 mg, 0.13 mmol) was stirred in HCl in 1,4-dioxane (4 M, 2 mL) at room temperature for 18 hr. The solvents were removed under reduced pressure and the crude residue was re-dissolved in MeOH and loaded onto an SCX column. The column was washed with MeOH and eluted with 7 N ammonia in MeOH. The residue was further purified via silica gel column chromatography (0-10% MeOH/DCM) to afford 289 as a yellow solid (19 mg, 35%). $^1$H NMR (400 MHz, d$_4$-MeOD) δ 7.46 (s, 1H), 3.71 (s, 3H), 3.30-3.23 (m, 1H), 3.21-3.08 (m, 4H), 2.62 (d, J=6.6 Hz, 2H), 2.17-2.07 (m, 2H), 1.89-1.66 (m, 8H), 1.58-1.45 (m, 1H), 1.44-1.29 (m, 2H). LCMS (ES+) m/z 404 (M+1)

Example 290

5-amino-N-(5-(4-(aminomethyl)piperidin-1-yl)-1-methyl-1H-pyrazol-4-yl)-2-(tetrahydro-2H-pyran-2-yl)thiazole-4-carboxamide 290

Following the procedure for Example 281, tert-butyl 4-(5-(4-(butyloxycarbonylaminomethyl)piperidin-1-yl)-1-methyl-1H-pyrazol-4-ylcarbamoyl)-2-bromothiazol-5-ylcarbamate and 3,4-dihydro-2H-pyran-6-boronic acid pinacol ester gave 290 as a yellow solid (27 mg, 20% over three steps). $^1$H NMR (400 MHz, d$_4$-MeOD) δ 7.34 (s, 1H), 4.46-4.41 (m, 1H), 4.02-3.95 (m, 1H), 3.63 (s, 3H), 3.67-3.51 (m, 1H), 3.12-2.97 (m, 4H), 2.53 (d, J=6.6 Hz, 2H), 2.07-1.98 (m, 1H), 1.97-1.79 (m, 1H), 1.76 (d, J=12.5 Hz, 2H), 1.68-1.53 (m, 4H), 1.49-1.36 (m, 1H), 1.36-1.21 (m, 2H). LCMS (ES+) m/z 420 (M+1)

Example 291

(R)-5-amino-N-(5-(4-aminoazepan-1-yl)-1-methyl-1H-pyrazol-4-yl)-2-(5-cyclopropyl-2-fluoro-3-methylphenyl)thiazole-4-carboxamide 291

Step 1: 2-(5-bromo-2-fluoro-3-methylphenyl)-6-methyl-1,3,6,2-dioxazaborocane-4,8-dione

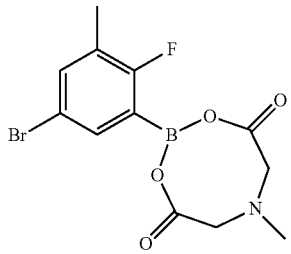 [SMILES: Cc1cc(Br)cc(B2OC(=O)CN(C)CC(=O)O2)c1F]

To a 50 mL round bottom flask equipped with a stir bar was added 5-bromo-2-fluoro-3-methylphenylboronic acid (1.0 g, 4.3 mmol), N-methyliminodiacetic acid (0.76 g, 5.2 mmol), toluene (8 mL) and DMSO (2 mL). The flask was fitted with a Dean-Stark trap and the Dean-Stark trap was fitted with a reflux condenser. The mixture was heated to reflux with azeotropic removal of water for 4.5 h. The solution was concentrated in vacuo. The residue was absorbed on Celite in vacuo from an acetone suspension and the resulting powder was subjected to Isco flash chromatography eluted with 0 to 70% acetonitrile in ether to give 2-(5-bromo-2-fluoro-3-methylphenyl)-6-methyl-1,3,6,2-dioxazaborocane-4,8-dione (1.26 g, 86%).

Step 2: 2-(5-cyclopropyl-2-fluoro-3-methylphenyl)-6-methyl-1,3,6,2-dioxazaborocane-4,8-dione

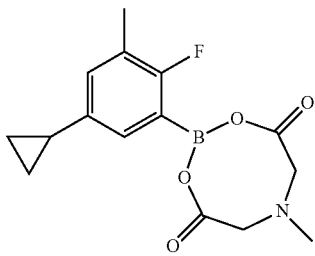 [SMILES: Cc1cc(C2CC2)cc(B2OC(=O)CN(C)CC(=O)O2)c1F]

In a microwave reaction vessel equipped with stir bar was charged 2-(5-bromo-2-fluoro-3-methylphenyl)-6-methyl-1,3,6,2-dioxazaborocane-4,8-dione (300 mg, 0.9 mmol), cyclopropylboronic acid (220 mg, 2.6 mmol), palladium acetate (14 mg, 0.06 mmol), S-Phos (50 mg, 0.12 mmol) and potassium phosphate (560 mg, 2.6 mmol). Degassed toluene (15 mL) was added. The reaction was heated under microwave at 120° C. for 15 min. LCMS indicated completion of the reaction. The mixture was diluted with acetonitrile and filtered through a pad of Celite and washed with copious amount of acetonitrile. The filtrate was concentrated in vacuo and the residue was absorbed on Celite from an acetone solution. The resulting powder was subjected to Isco flash chromatography eluted with 0 to 70% acetonitrile in ether to give a light yellow oil, 2-(5-cyclopropyl-2-fluoro-3-methylphenyl)-6-methyl-1,3,6,2-dioxazaborocane-4,8-dione (167 mg, 60%).

Step 3: (R)-tert-butyl 4-(5-(4-Cbz-aminoazepan-1-yl)-1-methyl-1H-pyrazol-4-ylcarbamoyl)-2-(5-cyclopropyl-2-fluoro-3-methylphenyl)thiazol-5-ylcarbamate

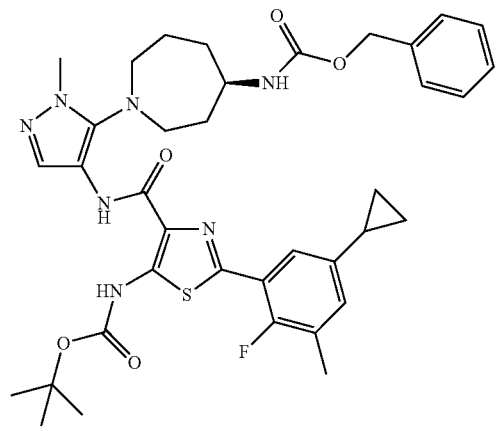 [SMILES: Cc1cc(C2CC2)cc(-c2nc(C(=O)Nc3cnn(C)c3N3CCC[C@@H](NC(=O)OCc4ccccc4)CC3)c(NC(=O)OC(C)(C)C)s2)c1F]

In a microwave reaction vessel, (R)-tert-butyl 4-(5-(4-Cbz-aminoazepan-1-yl)-1-methyl-1H-pyrazol-4-ylcarbamoyl)-2-bromothiazol-5-ylcarbamate (130 mg, 0.2 mmol), 2-(5-cyclopropyl-2-fluoro-3-methylphenyl)-6-methyl-1,3,6,2-dioxazaborocane-4,8-dione (167 mg, 0.55 mmol), S-Phos (13.2 mg, 0.032 mmol) and palladium acetate (3.6 mg, 0.016 mmol) were dissolved in 1,4-dioxane (4.0 mL). The cap was closed and the reaction vessel was vacuum purged with nitrogen three times. Potassium phosphate (3.0M aq., 0.27 mL, 0.81 mmol, degassed before use) was added and mixture was stirred at room temperature for 10 min before heated under microwave at 120° C. for 20 min. The mixture was diluted with methanol and filtered through a pad of Celite and washed with copious amount of methylene chloride. The filtrate was concentrated in vacuo and purified on flash chromatography (Isco Co.) eluted with 0 to 5% methanol in methylene chloride to give (R)-tert-butyl 4-(5-(4-Cbz-aminoazepan-1-yl)-1-methyl-1H-pyrazol-4-ylcarbamoyl)-2-(5-cyclopropyl-2-fluoro-3-methylphenyl)thiazol-5-ylcarbamate (82 mg, 57%).

Step 4

To a 25 mL round bottom flask was added the (R)-tert-butyl 4-(5-(4-Cbz-aminoazepan-1-yl)-1-methyl-1H-pyrazol-4-ylcarbamoyl)-2-(5-cyclopropyl-2-fluoro-3-methylphenyl)thiazol-5-ylcarbamate (82 mg, 0.11 mmol), methylene chloride (4 mL) and a 1M solution of boron tribromide in $CH_2Cl_2$ (0.46 mL, 0.46 mmol). The mixture was stirred at room temperature overnight. The solvent was distilled off and the residue was basified with saturated sodium bicarbonate. The aqueous solution was extracted with ethyl acetate 3×. The combined organic layers were dried over sodium sulfate, filtered and concentrated. The crude product was purified via reverse phase HPLC to afford 291 (2.8 mg, 5%). MS (ESI) m/z: 484.2 [M+H$^+$].

Example 292

(R)—N-(5-(4-aminoazepan-1-yl)-1-methyl-1H-pyrazol-4-yl)-6-bromopicolinamide 292

Following procedures from Examples 141, (R)-benzyl 1-(4-amino-1-methyl-1H-pyrazol-5-yl)azepan-4-ylcarbamate from Example 16 was converted to 292. ¹H NMR (400 MHz, DMSO) δ 8.10 (d, J=7.5 Hz, 1H), 7.99 (t, J=7.7 Hz, 1H), 7.90 (d, J=7.9 Hz, 1H), 7.56 (s, 1H), 3.66 (s, 3H), 3.20-3.03 (m, 5H), 1.95-1.76 (m, 3H), 1.73-1.48 (m, 3H). MS (ESI) m/z: 393.1/395.1 [M+H⁺].

Example 293

(R)—N-(5-(4-aminoazepan-1-yl)-1-methyl-1H-pyrazol-4-yl)-6-(2-fluorophenyl)picolinamide 293

Following procedures from Examples 141, (R)-benzyl 1-(4-amino-1-methyl-1H-pyrazol-5-yl)azepan-4-ylcarbamate from Example 16 was converted to 293. ¹H NMR (400 MHz, DMSO) δ 8.21-8.07 (m, 3H), 8.04 (d, J=7.6 Hz, 1H), 7.68 (s, 1H), 7.63-7.51 (m, 1H), 7.47-7.32 (m, 2H), 3.67 (s, 3H), 3.21-3.04 (m, 5H), 2.96 (td, J=8.8, 4.4 Hz, 1H), 1.79 (ddd, J=24.4, 13.7, 5.6 Hz, 4H), 1.66-1.39 (m, 4H). MS (ESI) m/z: 409.2 [M+H⁺].

Example 294

5-amino-2-(2,6-difluorophenyl)-N-(1-methyl-5-(3-oxo-1,4-diazepan-1-yl)-1H-pyrazol-4-yl)thiazole-4-carboxamide 294

Step 1: 4-(1-Methyl-4-nitro-1H-pyrazol-5-yl)-1,4-diazepan-2-one

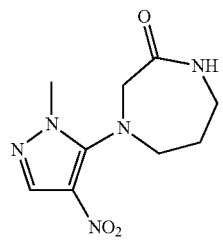 [SMILES: Cn1ncc([N+](=O)[O-])c1N1CCCNC(=O)C1]

Reaction of 5-chloro-1-methyl-4-nitro-1H-pyrazole and 1,4-diazepan-2-one gave 4-(1-methyl-4-nitro-1H-pyrazol-5-yl)-1,4-diazepan-2-one as an off-white solid (0.27 g, 92%). ¹H NMR (400 MHz, CDCl₃) δ 8.02 (s, 1H), 6.10 (s, 1H), 3.95-3.86 (m, 2H), 3.80 (s, 3H), 3.51-3.44 (m, 2H), 3.43-3.37 (m, 2H), 2.04-1.97 (m, 2H)

Step 2

Following the procedure for Example 243 starting with 4-(1-methyl-4-nitro-1H-pyrazol-5-yl)-1,4-diazepan-2-one gave 294 as a white solid (67 mg, 11% over three steps). ¹H NMR (400 MHz, CDCl₃) δ 8.47 (s, 1H), 7.71 (s, 1H), 7.33 (tt, J=8.5, 6.0 Hz, 1H), 7.06-6.99 (m, 2H), 6.12 (s, 2H), 5.94 (t, J=6.0 Hz, 1H), 3.77 (s, 3H), 3.48-3.42 (m, 2H), 3.33-3.26 (m, 4H), 2.82-2.76 (m, 2H). LCMS (ES+) m/z 448 (M+1)

Example 295

5-amino-2-(2,6-difluorophenyl)-N-(5-(3-fluoropiperidin-1-yl)-1-methyl-1H-pyrazol-4-yl)thiazole-4-carboxamide 295

Step 1: 3-Fluoro-1-(1-methyl-4-nitro-1H-pyrazol-5-yl)piperidine

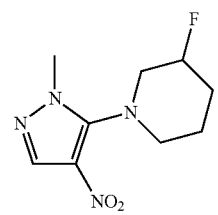 [SMILES: Cn1ncc([N+](=O)[O-])c1N1CCCC(F)C1]

Reaction of 5-chloro-1-methyl-4-nitro-1H-pyrazole and 3-fluoropiperidine hydrochloride gave 3-fluoro-1-(1-methyl-4-nitro-1H-pyrazol-5-yl)piperidine as a yellow oil (0.27 g, 97%). ¹H NMR (400 MHz, CDCl₃) δ 8.02 (s, 1H), 4.88-4.71 (m, 1H), 3.79 (s, 3H), 3.47 (ddd, J=29.8, 12.8, 2.1 Hz, 1H), 3.32-3.15 (m, 2H), 3.07-2.99 (m, 1H), 2.11-1.99 (m, 2H), 1.95-1.76 (m, 1H), 1.74-1.62 (m, 1H)

Step 2

Following the procedure for Example 243 starting with 3-fluoro-1-(1-methyl-4-nitro-1H-pyrazol-5-yl)piperidine gave 295 as a white solid (19 mg, 3% over three steps). ¹H NMR (400 MHz, CDCl₃) δ 8.46 (s, 1H), 7.71 (s, 1H), 7.37-7.28 (m, 1H), 7.08-6.98 (m, 2H), 6.12 (s, 2H), 4.83-4.65 (m, 1H), 3.74 (s, 3H), 3.37 (ddd, J=22.0, 12.0, 3.0 Hz, 1H), 3.27-3.19 (m, 1H), 3.14-3.08 (m, 2H), 2.02-1.83 (m, 3H), 1.71-1.63 (m, 1H). LCMS (ES+) m/z 437 (M+1)

Example 296

5-amino-2-(2,6-difluorophenyl)-N-(1-methyl-5-(4-methylpiperazin-1-yl)-1H-pyrazol-4-yl)thiazole-4-carboxamide 296

Step 1: 1-Methyl-4-(1-methyl-4-nitro-1H-pyrazol-5-yl)piperazine

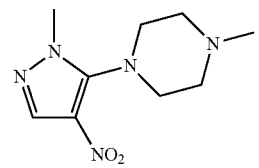 [SMILES: CN1CCN(c2c([N+](=O)[O-])cnn2C)CC1]

Reaction of 5-chloro-1-methyl-4-nitro-1H-pyrazole and N-methyl piperazine gave 1-methyl-4-(1-methyl-4-nitro-1H-pyrazol-5-yl)piperazine as an oil (0.18 g, 65%). ¹H NMR (400 MHz, CDCl₃) δ 8.02 (s, 1H), 3.77 (s, 3H), 3.26 (t, J=4.6 Hz, 4H), 2.60-2.53 (m, 4H), 2.38 (s, 3H)

295

Step 2

Following the procedure for Example 243 starting with 1-methyl-4-(1-methyl-4-nitro-1H-pyrazol-5-yl)piperazine gave 296 as a beige solid (19 mg, 3% over three steps). $^1$H NMR (400 MHz, CDCl$_3$) δ 8.43 (s, 1H), 7.69 (s, 1H), 7.36-7.28 (m, 1H), 7.06-6.97 (m, 2H), 6.12 (s, 2H), 3.75 (s, 3H), 3.18 (t, J=4.5 Hz, 4H), 2.53-2.59 (m, 4H), 2.36 (s, 3H). LCMS (ES+) m/z 434 (M+1)

Example 297

5-Amino-N-(5-(4-(aminomethyl)piperidin-1-yl)-1-methyl-1H-pyrazol-4-yl)-2-(5-fluoro-2-hydroxyphenyl)thiazole-4-carboxamide 297

Following the procedure for Example 278 starting with tert-butyl 4-(5-(4-(butyloxycarbonylaminomethyl)piperidin-1-yl)-1-methyl-1H-pyrazol-4-ylcarbamoyl)-2-bromothiazol-5-ylcarbamate and 5-fluoro-2-hydroxyphenylboronic acid gave 297 as an off-white solid (18 mg, 20%). $^1$H NMR (400 MHz, d$_4$-MeOD) δ 7.64 (dd, J=9.6, 3.1 Hz, 1H), 7.49 (s, 1H), 6.96 (td, J=4.8, 3.1 Hz, 1H), 6.90 (dd, J=9.6, 4.8 Hz, 1H), 3.74 (s, 3H), 3.27-3.12 (m, 4H), 2.66 (d, J=6.5 Hz, 2H), 1.86 (d, J=12.5 Hz, 2H), 1.69-1.42 (m, 1H), 1.45-1.36 (m, 2H). LCMS (ES+) m/z 446 (M+1).

Example 298

5-amino-N-(5-(4-(aminomethyl)piperidin-1-yl)-1-methyl-1H-pyrazol-4-yl)-2-(5-cyano-2-fluorophenyl)thiazole-4-carboxamide 298

Following Example 278, Suzuki coupling of tert-butyl 4-(5-(4-(butyloxycarbonylaminomethyl)piperidin-1-yl)-1-methyl-1H-pyrazol-4-ylcarbamoyl)-2-bromothiazol-5-ylcarbamate and 5-cyano-2-fluorophenylboronic acid gave 298 as a yellow solid (32 mg, 35% over two steps). $^1$H NMR (400 MHz, d$_4$-MeOD) 8.75 (dd, J=6.9, 2.2 Hz, 1H), 7.80-7.75 (m, 1H), 7.51-7.45 (m, 2H), 3.74 (s, 3H), 3.25-3.11 (m, 4H), 2.60 (d, J=6.6 Hz, 2H), 1.87 (d, J=12.5 Hz, 2H), 1.53-1.49 (m, 1H), 1.43-1.32 (m, 2H). LCMS (ES+) m/z 455 (M+1)

Example 299

5-amino-N-(5-(4-(aminomethyl)piperidin-1-yl)-1-methyl-1H-pyrazol-4-yl)-2-cycloheptylthiazole-4-carboxamide 299

Following the procedure for Example 281 starting with tert-butyl 4-(5-(4-(butyloxycarbonylaminomethyl)piperidin-1-yl)-1-methyl-1H-pyrazol-4-ylcarbamoyl)-2-bromothiazol-5-ylcarbamate and 1-cycloheptenylboronic acid pinacol ester gave 299 as an off-white solid (24 mg, 30% over three steps). $^1$H NMR (400 MHz, d$_4$-MeOD) δ 7.46 (s, 1H), 3.72 (s, 3H), 3.21-3.08 (m, 4H), 3.07-2.96 (m, 1H), 2.66 (d, J=6.7 Hz, 2H), 2.18-2.09 (m, 2H), 1.85-1.46 (m, 13H), 1.44-1.30 (m, 2H). LCMS (ES+) m/z 432 (M+1)

Example 300

5-amino-N-(5-(4-cyanopiperidin-1-yl)-1-methyl-1H-pyrazol-4-yl)-2-(2,6-difluorophenyl)thiazole-4-carboxamide 300

Step 1: 1-(1-Methyl-4-nitro-1H-pyrazol-5-yl)piperidine-4-carbonitrile

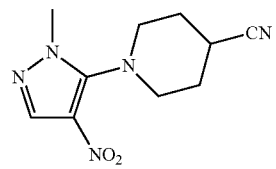 [SMILES: Cn1ncc([N+](=O)[O-])c1N1CCC(C#N)CC1]

Reaction of 5-chloro-1-methyl-4-nitro-1H-pyrazole and 4-cyanopiperidine gave 1-(1-methyl-4-nitro-1H-pyrazol-5-yl)piperidine-4-carbonitrile as an off-white solid (0.23 g, 79%). $^1$H NMR (400 MHz, CDCl$_3$) δ 8.03 (s, 1H), 3.78 (s, 3H), 3.35-3.19 (m, 4H), 2.88-2.79 (m, 1H), 2.19-2.11 (m, 2H), 2.06-1.95 (m, 2H)

Step 2

Following the procedure for Example 243 starting with 1-(1-methyl-4-nitro-1H-pyrazol-5-yl)piperidine-4-carbonitrile gave 300 as a white solid (14 mg, 3% over three steps). $^1$H NMR (400 MHz, CDCl$_3$) δ 8.48 (s, 1H), 7.72 (s, 1H), 7.36-7.29 (m, 1H), 7.09-7.00 (m, 2H), 6.11 (s, 2H), 3.74 (s, 3H), 3.31-3.24 (m, 2H), 3.17-3.09 (m, 2H), 2.78-2.70 (m, 1H), 2.14-1.96 (m, 4H). LCMS (ES+) m/z 444 (M+1)

Example 301

5-amino-N-(5-(4-(aminomethyl)piperidin-1-yl)-1-methyl-1H-pyrazol-4-yl)-2-(3-isopropylphenyl)thiazole-4-carboxamide 301

Following Example 278, Suzuki coupling of tert-butyl 4-(5-(4-(butyloxycarbonylaminomethyl)piperidin-1-yl)-1-methyl-1H-pyrazol-4-ylcarbamoyl)-2-bromothiazol-5-ylcarbamate and 3-isopropylbenzeneboronic acid gave 301 as the mono-formate salt as a red gum (38 mg, 41% over two steps). $^1$H NMR (400 MHz, d$_6$-DMSO with D$_2$O) δ 8.35 (s, 1H), 7.70 (s, 1H), 7.58 (d, J=7.7 Hz, 1H), 7.37 (t, J=7.7 Hz, 1H), 7.32-7.25 (m, 2H), 3.62 (s, 3H), 3.10 (d, J=11.5 Hz, 2H), 3.04-2.88 (m, 3H), 2.72 (d, J=6.9 Hz, 2H), 1.73 (d, J=12.6 Hz, 2H), 1.64-1.58 (m, 1H), 1.34-1.24 (m, 2H), 1.22 (d, J=6.9 Hz, 6H). LCMS (ES+) m/z 454 (M+1)

Example 302

(R)-3-amino-N-(5-(4-aminoazepan-1-yl)-1-methyl-1H-pyrazol-4-yl)picolinamide 302

Following procedures from Example 229, (R)-benzyl 1-(4-amino-1-methyl-1H-pyrazol-5-yl)azepan-4-ylcarbamate from Example 16 was converted to 302. $^1$H NMR (400 MHz, DMSO) δ 9.74 (br, 1H), 7.84 (d, J=4.1 Hz, 1H), 7.55 (s, 1H), 7.28 (dd, J=8.4, 4.2 Hz, 1H), 7.20 (d, J=8.4 Hz, 1H), 6.85 (br, 2H), 3.64 (s, 3H), 3.20-2.93 (m, 5H), 1.88-1.75 (m, 3H), 1.70-1.41 (m, 3H). MS (ESI) m/z: 330.2 [M+H$^+$].

Example 303

(R)—N-(5-(4-aminoazepan-1-yl)-1-methyl-1H-pyrazol-4-yl)-5-fluoropicolinamide 303

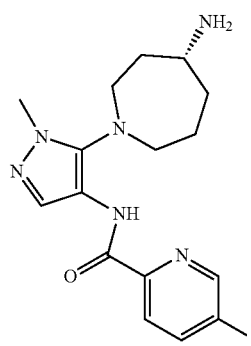

Following procedures from Examples 140, (R)-benzyl 1-(4-amino-1-methyl-1H-pyrazol-5-yl)azepan-4-ylcarbamate from Example 16 was converted to 303. $^1$H NMR (400 MHz, DMSO) δ 8.70 (d, J=2.8 Hz, 1H), 8.17 (dd, J=8.7, 4.7 Hz, 1H), 7.94 (td, J=8.7, 2.8 Hz, 1H), 7.48 (s, 1H), 3.65 (s, 3H), 3.20-2.96 (m, 6H), 1.92-1.70 (m, 3H), 1.64-1.42 (m, 3H). MS (ESI) m/z: 333.2 [M+H$^+$].

Example 304

5-amino-N-(5-(4-(aminomethyl)piperidin-1-yl)-1-methyl-1H-pyrazol-4-yl)-2-cyclopropylthiazole-4-carboxamide 304

Step 1: 5-(tert-Butoxycarbonylamino)-2-cyclopropylthiazole-4-carboxylic acid

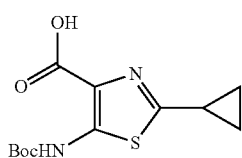 [SMILES: CC(C)(C)OC(=O)Nc1sc(C2CC2)nc1C(=O)O]

Reaction of ethyl 2-amino-2-cyanoacetate and cyclopropanecarbonyl chloride gave 5-(tert-butoxycarbonylamino)-2-cyclopropylthiazole-4-carboxylic acid as a yellow solid (0.31 g, 14% over four steps). $^1$H NMR (400 MHz, d$_6$-DMSO) δ 9.97 (s, 1H), 2.32-2.24 (m, 1H), 1.49 (s, 9H), 1.09-1.03 (m, 2H), 0.95-0.89 (m, 2H). OH not seen

Step 2

To a solution of 5-(4-(aminomethyl)piperidin-1-yl)-1-methyl-1H-pyrazol-4-amine (99 mg, 0.32 mmol) in DCM (6 mL) was added DIPEA (0.09 mL, 0.51 mmol), PyBOP (0.233 g, 0.44 mmol) and 5-(tert-butoxycarbonylamino)-2-cyclopropylthiazole-4-carboxylic acid (95 mg, 0.34 mmol) and the mixture was stirred at room temperature for 18 hr. The mixture was diluted with DCM and washed with water. The organic layer was separated, dried over MgSO$_4$ and the solvent removed under reduced pressure. Purification via silica gel column chromatography (0-10% MeOH/DCM) gave tert-butyl 4-(5-(4-(butyloxycarbonyl-aminomethyl)piperidin-1-yl)-1-methyl-1H-pyrazol-4-ylcarbamoyl)-2-cyclopropylthiazol-5-ylcarbamate as a red gum (0.131 g, 71%). This gum (0.127 g, 0.22 mmol) was stirred in HCl in 1,4-dioxane (4.0 M, 2 mL) at room temperature for 18 hr. The solvents were removed under reduced pressure and the crude residue purified by preparative HPLC to afford 304 as a white solid (41 mg, 50%). $^1$H NMR (400 MHz, d$_4$-MeOD) δ 7.43 (s, 1H), 3.71 (s, 3H), 3.20-3.05 (m, 4H), 2.61 (d, J=6.6 Hz, 2H), 2.17-2.08 (m, 1H), 1.84 (d, J=12.6 Hz, 2H), 1.57-1.45 (m, 1H), 1.35 (qd, J=11.9, 4.4 Hz, 2H), 1.09-1.02 (m, 2H), 0.98-0.92 (m, 2H). LCMS (ES+) m/z 376 (M+1)

Example 305

5-amino-N-(5-(4-(aminomethyl)piperidin-1-yl)-1-methyl-1H-pyrazol-4-yl)-2-cyclobutylthiazole-4-carboxamide 305

Step 1: 5-(tert-Butoxycarbonylamino)-2-cyclobutylthiazole-4-carboxylic acid

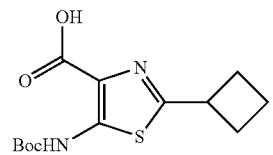 [SMILES: CC(C)(C)OC(=O)Nc1sc(C2CCC2)nc1C(=O)O]

Following the procedure for Examples 19-23 starting with ethyl 2-amino-2-cyanoacetate and cyclobutane carbonyl chloride gave 5-(tert-butoxycarbonylamino)-2-cyclobutylthiazole-4-carboxylic acid as a brown gum (0.24 g, 10% over four steps). $^1$H NMR (400 MHz, d$_6$-DMSO) δ 3.69-3.61 (m, 1H), 2.35-2.27 (m, 2H), 2.24-2.17 (m, 2H), 2.02-1.94 (m, 1H), 1.87-1.82 (m, 1H), 1.46 (s, 9H). NH and OH not seen

Step 2

Following the procedure for Example 304 starting with 5-(4-(aminomethyl)piperidin-1-yl)-1-methyl-1H-pyrazol-4-amine and 5-(tert-butoxycarbonylamino)-2-cyclobutylthiazole-4-carboxylic acid gave 305 as a white solid (44 mg, 37% over two steps). $^1$H NMR (400 MHz, d$_4$-MeOD) δ 7.45 (s, 1H), 3.75-3.62 (m, 4H), 3.23-3.07 (m, 4H), 2.60 (d, J=6.5 Hz, 2H), 2.47-2.29 (m, 4H), 2.17-2.01 (m, 1H), 2.00-1.90 (m, 1H), 1.84 (d, J=12.5 Hz, 2H), 1.56-1.43 (m, 1H), 1.36 (qd, J=11.9, 4.4 Hz, 2H). LCMS (ES+) m/z 390 (M+1)

Example 306

5-amino-2-(2,6-difluorophenyl)-N-(1-methyl-5-(piperidin-4-ylamino)-1H-pyrazol-4-yl)thiazole-4-carboxamide 306

Step 1: tert-Butyl 4-(1-methyl-4-nitro-1H-pyrazol-5-ylamino)piperidine-1-carboxylate

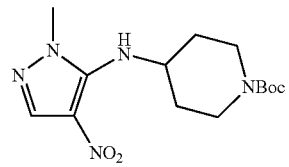

Reaction of 5-chloro-1-methyl-4-nitro-1H-pyrazole and tert-butyl 4-aminopiperidine-1-carboxylate gave tert-butyl 4-(1-methyl-4-nitro-1H-pyrazol-5-ylamino)piperidine-1-carboxylate as a pale yellow solid (0.23 g, 57%). $^1$H NMR (400 MHz, CDCl$_3$) δ 7.91 (s, 1H), 6.40 (d, J=9.8 Hz, 1H), 4.06-3.95 (m, 2H), 3.81 (s, 3H), 3.70-3.59 (m, 1H), 3.05-2.93 (m, 2H), 2.00-1.92 (m, 2H), 1.60-1.50 (m, 2H), 1.49 (s, 9H)

Step 2

Following the procedure for Example 243 starting with tert-butyl 4-(1-methyl-4-nitro-1H-pyrazol-5-ylamino)piperidine-1-carboxylate gave 306 as a beige solid (90 mg, 60% over three steps). $^1$H NMR (400 MHz, CDCl$_3$) δ 8.45 (s, 1H), 7.48 (s, 1H), 7.41-7.23 (m, 1H), 7.02 (t, J=8.8 Hz, 2H), 6.17 (s, 2H), 3.75 (s, 3H), 7.74-3.68 (m, 1H), 3.08 (d, J=12.4 Hz, 2H), 3.00-2.85 (m, 1H), 2.58 (t, J=11.8 Hz, 2H), 1.92 (d, J=13.7 Hz, 2H), 1.37 (q, J=11.8 Hz, 2H). Alkyl NH not seen. LCMS (ES+) m/z 434 (M+1)

Example 307

5-amino-2-(2,6-difluorophenyl)-N-(2,3-dihydro-1H-imidazo[1,2-b]pyrazol-7-yl)thiazole-4-carboxamide 307

Step 1: tert-Butyl 7-nitro-2,3-dihydro-1H-pyrazolo[1,5-a]imidazole-1-carboxylate

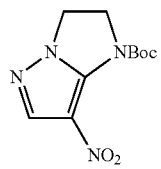

To a solution of 2,3-dihydro-1H-pyrazolo[1,5-a]imidazole (1 g, 9.17 mmol) in conc. H$_2$SO$_4$ (aq.) at 0° C. was added conc. HNO$_3$ (aq.) portion-wise over 15 min. The reaction was warmed to room temperature and the mixture was stirred for 18 h. The mixture was poured into ice water (200 mL) with stirring. The product was extracted into DCM and the combined organics were washed with saturated aqueous NaHCO$_3$. The organic layer was separated, passed through a phase separator cartridge and concentrated under reduced pressure. The crude residue was triturated with diethyl ether to yield 7-nitro-2,3-dihydro-1H-pyrazolo[1,5-a]imidazole as a pale brown solid (0.52 g, 34%). Sodium hydride (60% dispersion in mineral oil, 0.065 g, 1.62 mmol) was added in 2 portions to a stirred solution of 7-nitro-2,3-dihydro-1H-pyrazolo[1,5-a]imidazole (0.21 g, 1.35 mmol) in anhydrous DMF (10 mL) at room temperature under a nitrogen atmosphere. The mixture was stirred for 10 min. before di-tert-butyl dicarbonate (0.68 mL, 2.75 mmol) was added. The reaction was stirred for 45 min. Water (5 mL) was added dropwise and the mixture concentrated under reduced pressure. The residue was diluted with water and the product extracted into diethyl ether. The combined organics were dried over MgSO$_4$ and concentrated under reduced pressure. The crude residue was purified via silica gel chromatography (0-100% EtOAc/isohexane) to give tert-butyl 7-nitro-2,3-dihydro-1H-pyrazolo[1,5-c]imidazole-1-carboxylate as a grey solid (0.22 g, 63%). $^1$H NMR (400 MHz, CDCl$_3$) δ 7.89 (s, 1H), 4.60-4.53 (m, 2H), 4.38-4.30 (m, 2H), 1.50 (s, 9H)

Step 2

Following the procedure for Example 230 starting with tert-butyl 7-nitro-2,3-dihydro-1H-pyrazolo[1,5-c]imidazole-1-carboxylate gave 307 as a cream solid (26 mg, 8% over three steps). $^1$H NMR (400 MHz, d$_6$-DMSO) δ 9.20 (s, 1H), 7.65-7.45 (m, 3H), 7.36 (s, 1H), 7.27 (t, J=8.7 Hz, 2H), 5.26 (s, 1H), 4.06 (t, J=7.9 Hz, 2H), 3.84 (t, J=7.9 Hz, 2H). LCMS (ES+) m/z 363 (M+1)

Example 308

(R)-5-amino-N-(5-(4-aminoazepan-1-yl)-1-methyl-1H-pyrazol-4-yl)-2-(5-bromo-2-fluorophenyl)thiazole-4-carboxamide 308

Following procedures from Examples 140, (R)-benzyl 1-(4-amino-1-methyl-1H-pyrazol-5-yl)azepan-4-ylcarbamate from Example 16 and the product of Example 27, 2-(5-bromo-2-fluorophenyl)-5-(tert-butoxycarbonylamino)thiazole-4-carboxylic acid, were converted to 308. $^1$H NMR (400 MHz, DMSO) δ 9.05 (s, 1H), 8.45 (dd, J=6.7, 2.5 Hz, 1H), 7.66-7.55 (m, 1H), 7.48 (s, 2H), 7.43 (s, 1H), 7.36 (dd, J=11.2, 8.9 Hz, 1H), 3.65 (s, 4H), 3.21-2.93 (m, 7H), 1.84 (dd, J=8.2, 3.6 Hz, 3H), 1.72-1.39 (m, 3H). MS (ESI) m/z: 508.1/510.1 [M+H$^+$].

Example 309

(R)—N-(5-(4-aminoazepan-1-yl)-1-methyl-1H-pyrazol-4-yl)picolinamide 309

Following procedures from Examples 140, (R)-benzyl 1-(4-amino-1-methyl-1H-pyrazol-5-yl)azepan-4-ylcarbamate from Example 16 was converted to 309. $^1$H NMR (400 MHz, DMSO) δ 9.86 (s, 1H), 8.71 (d, J=4.6 Hz, 1H), 8.40 (s, 1H), 8.16-7.97 (m, 2H), 7.71-7.58 (m, 1H), 7.48 (s, 1H), 3.67 (s, 5H), 3.25-2.98 (m, 8H), 2.04-1.51 (m, 7H). MS (ESI) m/z: 315.2 [M+H$^+$].

Example 310

(R)-5-amino-N-(5-(4-aminoazepan-1-yl)-1-isopropyl-1H-pyrazol-4-yl)-2-(2,6-difluorophenyl)thiazole-4-carboxamide 310

Step 1: 5-Chloro-1-isopropyl-4-nitro-1H-pyrazole

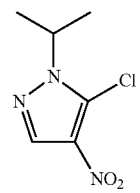

Chlorination of 1-isopropyl-4-nitro-1H-pyrazole gave 5-chloro-1-isopropyl-4-nitro-1H-pyrazole as a colourless solid (1.43 g, 75%). ¹H NMR (400 MHz, CDCl₃) δ 8.18 (s, 1H), 4.80-4.72 (m, 1H), 1.53 (d, J=6.4 Hz, 6H).

Step 2: (R)-2,2,2-Trifluoro-N-(1-(1-isopropyl-4-nitro-1H-pyrazol-5-yl)azepan-4-yl)acetamide

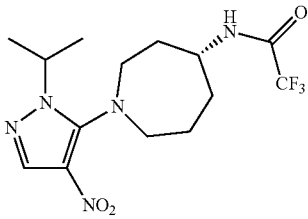 [SMILES: CC(C)n1ncc([N+](=O)[O-])c1N1CCC[C@@H](NC(=O)C(F)(F)F)CC1]

Reaction of 5-chloro-1-isopropyl-4-nitro-1H-pyrazole and (R)—N-(azepan-4-yl)-2,2,2-trifluoroacetamide gave (R)-2,2,2-trifluoro-N-(1-(1-isopropyl-4-nitro-1H-pyrazol-5-yl)azepan-4-yl)acetamide as a pale yellow gum (90 mg, 52%). ¹H NMR (400 MHz, CDCl₃) δ 8.08 (s, 1H), 6.39 (s, 1H), 4.83-4.70 (m, 1H), 4.24-4.17 (m, 1H), 3.45-3.32 (m, 1H), 3.28-3.12 (m, 3H), 2.23-2.02 (m, 2H), 2.00-1.80 (m, 4H), 1.54-1.44 (m, 6H)

Step 3

Following the procedure for Example 230 starting with (R)-2,2,2-trifluoro-N-(1-(1-isopropyl-4-nitro-1H-pyrazol-5-yl)azepan-4-yl)acetamide gave 310 as a cream fluffy solid (65 mg, 52% over three steps). ¹H NMR (400 MHz, d₄-MeOD) δ 7.75 (s, 1H), 7.52-7.43 (m, 1H), 7.21-7.10 (m, 2H), 4.78-4.67 (m, 1H), 3.37-3.22 (m, 4H), 3.18-3.08 (m, 1H), 2.08-1.88 (m, 3H), 1.87-1.63 (m, 3H), 1.46 (d, J=4.2 Hz, 3H), 1.45 (d, J=4.2 Hz, 3H). LCMS (ES+) m/z 476 (M+1)

Example 311

(R)-5-Amino-N-(5-(4-aminoazepan-1-yl)-1-cyclopropyl-1H-pyrazol-4-yl)-2-(2,6-difluorophenyl)thiazole-4-carboxamide 311

Following the procedure for Example 241 starting with (R)-tert-butyl 2-(2-fluorophenyl)-4-(1-cyclopropyl-5-(4-(2,2,2-trifluoroacetamido)azepan-1-yl)-1H-pyrazol-4-ylcarbamoyl)thiazol-5-ylcarbamate gave 311 as a cream solid (90 mg, 90%). ¹H-NMR (400 MHz, d₄-MeOD) δ 7.62 (s, 1H), 7.53-7.43 (m, 1H), 7.21-7.11 (m, 2H), 3.55-3.49 (m, 1H), 3.36-3.32 (m, 4H), 3.20-3.09 (m, 1H), 2.09-1.89 (m, 3H), 1.90-1.64 (m, 3H), 1.18-1.03 (m, 4H). LCMS (ES+) m/z 474.0 (M+1).

Example 312

(R)-5-Amino-N-(5-(4-aminoazepan-1-yl)-1-cyclopropylmethyl-1H-pyrazol-4-yl)-2-(2,6-difluorophenyl)thiazole-4-carboxamide 312

Following the procedure for Example 241 starting with (R)-tert-butyl 2-(2-fluorophenyl)-4-(1-cyclopropylmethyl-5-(4-(2,2,2-trifluoroacetamido)azepan-1-yl)-1H-pyrazol-4-ylcarbamoyl)thiazol-5-ylcarbamate gave 312 as a cream solid (90 mg, 91%). ¹H-NMR (400 MHz, d₄-MeOD) δ 7.76-7.70 (s, 1H), 7.53-7.43 (m, 1H), 7.21-7.10 (m, 2H), 3.92 (d, J=7 Hz, 2H), 3.33-3.21 (m, 4H), 3.16-3.05 (m, 1H), 2.06-1.86 (m, 3H), 1.86-1.61 (m, 3H), 1.38-1.24 (m, 1H), 0.63-0.56 (m, 2H), 0.49-0.39 (m, 2H). LCMS (ES+) m/z 488.0 (M+1).

Example 313

(S)-5-Amino-N-(5-(4-aminoazepan-1-yl)-1-ethyl-1H-pyrazol-4-yl)-2-(2,6-difluorophenyl)thiazole-4-carboxamide 313

Following the procedure for Example 241 starting with (S)-tert-butyl 2-(2-fluorophenyl)-4-(1-ethyl-5-(4-(2,2,2-trifluoroacetamido)azepan-1-yl)-1H-pyrazol-4-ylcarbamoyl)thiazol-5-ylcarbamate gave 313 as a pale yellow solid (90 mg, 85%). ¹H-NMR (400 MHz, d₄-MeOD) δ 7.71 (s, 1H), 7.52-7.43 (m, 1H), 7.20-7.11 (m, 2H), 4.10 (q, J=7 Hz, 2H), 3.32-3.17 (m, 4H), 3.16-3.05 (m, 1H), 2.06-1.86 (m, 3H), 1.86-1.62 (m, 3H), 1.47-1.38 (t, J=7 Hz, 3H). LCMS (ES+) m/z 462.0 (M+1).

Example 314

5-Amino-N-(5-(4-(aminomethyl)piperidin-1-yl)-1-methyl-1H-pyrazol-4-yl)-2-(5-chloro-2-fluorophenyl)thiazole-4-carboxamide 314

Following the procedure for Example 278 starting with tert-butyl 4-(5-(4-(butyloxycarbonylaminomethyl)piperidin-1-yl)-1-methyl-1H-pyrazol-4-ylcarbamoyl)-2-bromothiazol-5-ylcarbamate and 5-chloro-2-fluorophenylboronic acid gave 314 as a grey solid (29.2 mg, 31%). ¹H NMR (400 MHz, d₄-MeOD) δ 8.34 (dd, J=6.4, 2.7 Hz, 1H), 7.47 (s, 1H), 7.43-7.37 (m, 1H), 7.27 (dd, J=10.9, 8.8 Hz, 1H), 3.74 (s, 3H), 3.27-3.11 (m, 4H), 2.63 (d, J=6.6 Hz, 2H), 1.86 (d, J=12.6 Hz, 2H), 1.56-1.47 (m, 1H), 1.38 (qd, J=11.9, 4.4 Hz, 2H). LCMS (ES+) m/z 480 (M+1).

Example 315

(S)-5-amino-2-(3-(3-(aminomethyl)pyrrolidin-1-yl)phenyl)-N-(1-methyl-1H-pyrazol-4-yl)thiazole-4-carboxamide 315

Step 1: (S)-tert-Butyl 2-(3-(3-(butyloxycarbonylaminomethyl)pyrrolidin-1-yl)phenyl)-4-(1-methyl-1H-pyrazol-4-ylcarbamoyl)thiazol-5-ylcarbamate

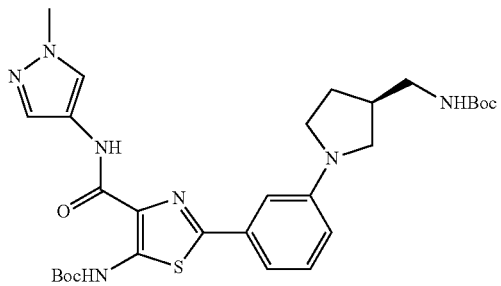 [SMILES: Cn1cc(NC(=O)c2nc(-c3cccc(N4CC[C@@H](CNC(=O)OC(C)(C)C)C4)c3)sc2NC(=O)OC(C)(C)C)cn1]

Following the procedure for Example 273 starting with 1,3-dibromobenzene and (R)-tert-butyl pyrrolidin-3-ylmethylcarbamate and tert-butyl 2-bromo-4-(1-methyl-1H-pyrazol-4-ylcarbamoyl)thiazol-5-ylcarbamate gave (S)-tert-butyl 2-(3-(3-(butyloxycarbonylaminomethyl)pyrrolidin-1-yl)phenyl)-4-(1-methyl-1H-pyrazol-4-ylcarbamoyl)thiazol-5-ylcarbamate as a yellow gum (71 mg, 16%). LCMS (ES+) m/z 598 (M+1)

Step 2

Acidic deprotection of (S)-tert-butyl 2-(3-(3-(butyloxycarbonylaminomethyl)pyrrolidin-1-yl)phenyl)-4-(1-methyl-1H-pyrazol-4-ylcarbamoyl)thiazol-5-ylcarbamate gave the mono-formate salt of 315 as a pale brown solid (30 mg, 65%). $^1$H NMR (400 MHz, d$_6$-DMSO with D$_2$O) δ 8.40 (s, 1H), 7.96 (s, 1H), 7.63 (s, 1H), 7.24 (t, J=7.9 Hz, 1H), 7.06 (d, J=7.9 Hz, 1H), 6.98 (s, 1H), 6.57 (d, J=7.9 Hz, 1H), 3.79 (s, 3H), 3.47 (t, J=8.6 Hz, 1H), 3.43-3.35 (m, 1H), 3.34-3.27 (m, 1H), 3.07 (dd, J=9.8, 6.9 Hz, 1H), 2.86 (d, J=7.3 Hz, 2H), 2.55-2.48 (m, 1H), 2.19-2.13 (m, 1H), 1.79-1.73 (m, 1H). LCMS (ES+) m/z 398 (M+1)

Example 316

5-amino-2-(3-(3-aminopyrrolidin-1-yl)phenyl)-N-(1-methyl-1H-pyrazol-4-yl)thiazole-4-carboxamide 316

Step 1: tert-Butyl 2-(3-(3-(butyloxycarbonyl aminopyrrolidin-1-yl)phenyl)-4-(1-methyl-1H-pyrazol-4-ylcarbamoyl)thiazol-5-ylcarbamate

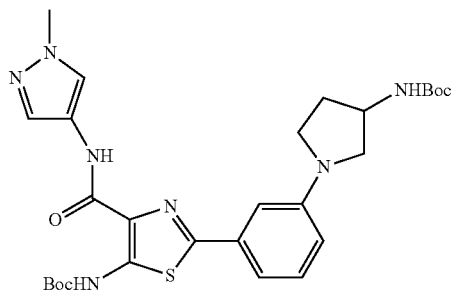 [SMILES: Cn1cc(NC(=O)c2nc(-c3cccc(N4CCC(NC(=O)OC(C)(C)C)C4)c3)sc2NC(=O)OC(C)(C)C)cn1]

Following the procedure for Example 273 starting with 1,3-dibromobenzene and tert-butyl pyrrolidin-3-ylcarbamate and tert-butyl 2-bromo-4-(1-methyl-1H-pyrazol-4-ylcarbamoyl)thiazol-5-ylcarbamate gave tert-butyl 2-(3-(3-(butyloxycarbonyl aminopyrrolidin-1-yl)phenyl)-4-(1-methyl-1H-pyrazol-4-ylcarbamoyl)thiazol-5-ylcarbamate as a yellow gum (105 mg, 22%). LCMS (ES+) m/z 584 (M+1)

Step 2

Acidic deprotection of tert-butyl 2-(3-(3-(butyloxycarbonyl aminopyrrolidin-1-yl)phenyl)-4-(1-methyl-1H-pyrazol-4-ylcarbamoyl)thiazol-5-ylcarbamate gave 316 as an off-white solid (38 mg, 55%). $^1$H NMR (400 MHz, d$_6$-DMSO) δ 7.93 (s, 1H), 7.62 (s, 1H), 7.22 (t, J=7.9 Hz, 1H), 7.01 (d, J=7.9 Hz, 1H), 6.95 (s, 1H), 6.54 (dd, J=7.9, 2.4 Hz, 1H), 3.78 (s, 3H), 3.55-3.49 (m, 1H), 3.46 (dd, J=9.5, 6.4 Hz, 1H), 3.41-3.35 (m, 1H), 3.28-3.23 (m, 1H), 2.94 (dd, J=9.4, 5.1 Hz, 1H), 2.14-2.09 (m, 1H), 1.77-1.71 (m, 1H). Exchangeable protons not visible. LCMS (ES+) m/z 384 (M+1)

Example 317

3-amino-6-bromo-N-(1-methyl-1H-pyrazol-4-yl)picolinamide 317

1-Methyl-4-nitro-1H-pyrazole (1.62 g, 12.7 mmol) was dissolved in methanol (250 mL) and hydrogenated on H-Cube at 60 bar hydrogen pressure and 70° C. to give 1-methyl-1H-pyrazol-4-amine (1.23 g, 99%).

To a 100 mL round bottom flask containing 1-methyl-1H-pyrazol-4-amine (700 mg, 7.0 mmol), 3-amino-6-bromopicolinic acid (1.86 g, 8.5 mmol) and PyBop (4.12 g, 8.0 mmol) was added methylene chloride (30 mL) and diisopropylethylamine (3.8 mL, 21.6 mmol). The reaction mixture was stirred for 24 hr at room temperature and the reaction was monitored by LCMS. Upon completion of the reaction, the solvent was distilled off and the crude material was purified via flash chromatography, heptane/ethyl acetate 0% to 100% to afford a yellow solid. A fraction of it was purified via reverse phase HPLC to afford 317. $^1$H NMR (400 MHz, DMSO) δ 10.25 (s, 1H), 8.03 (s, 1H), 7.70 (s, 1H), 7.43 (d, J=8.7 Hz, 1H), 7.19 (d, J=8.7 Hz, 1H), 7.02 (br, 2H), 3.81 (s, 3H). MS (ESI) m/z: 296.0/298.0 [M+H$^+$].

Example 318

3-amino-N-(1-methyl-1H-pyrazol-4-yl)-6-(3-(piperidin-1-yl)phenyl)picolinamide 318

To a microwave reaction vial was added 317 from Example 317 (150 mg, 0.51 mmol), 3-(piperidin-1-yl)phenylboronic acid (312 mg, 1.52 mmol), dichloro[1,1'-bis(diphenylphosphino)ferrocene]palladium(II) (41 mg, 0.051 mmol), a 1M solution of Na$_2$CO$_3$ (0.76 mL), a 1M solution of potassium acetate (0.76 mL) and acetonitrile (11 mL). The mixture was irradiated to 120° C. with a microwave for 30 min and cooled to room temperature. It was filtered through Celite and thoroughly washed with methylene chloride. The filtrate was concentrated and the residue was purified via flash chromatography, 0 to 7% methanol in methylene chloride (with 1% ammonium hydroxide). The product was further purified via reverse phase HPLC to afford 318. $^1$H NMR (400 MHz, DMSO) δ 10.34 (s, 1H), 8.07 (s, 1H), 7.86 (d, J=8.7 Hz, 1H), 7.71 (s, 1H), 7.59-7.43 (m, 2H), 7.34-7.17 (m, 2H), 7.03-6.84 (m, 3H), 3.83 (s, 3H), 3.26-3.18 (m, 4H), 1.73-1.48 (m, 7H). MS (ESI) m/z: 377.2 [M+H$^+$].

Example 319

5-amino-2-(2,6-difluorophenyl)-N-(1-methyl-5-(1,4-oxazepan-4-yl)-1H-pyrazol-4-yl)thiazole-4-carboxamide 319

Step 1: 4-(1-Methyl-4-nitro-1H-pyrazol-5-yl)-1,4-oxazepane

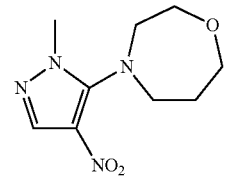 [SMILES: Cn1ncc([N+](=O)[O-])c1N1CCCOCC1]

Reaction of 5-chloro-1-methyl-4-nitro-1H-pyrazole and 1,4-oxazepane gave 4-(1-methyl-4-nitro-1H-pyrazol-5-yl)-1,4-oxazepane as a yellow oil (72 mg, 52%). $^1$H NMR (400 MHz, CDCl$_3$) δ 8.03 (s, 1H), 3.94 (t, J=5.6 Hz, 2H), 3.88-3.84 (m, 2H), 3.80 (s, 3H), 3.40-3.35 (m, 4H), 2.07-1.99 (m, 2H)

Step 2

Following the procedure for Example 243 starting with 4-(1-methyl-4-nitro-1H-pyrazol-5-yl)-1,4-oxazepane gave 319 as a beige solid (53 mg, 45% over three steps). ¹H NMR (400 MHz, CDCl₃) δ 8.67 (s, 1H), 7.85 (s, 1H), 7.38-7.23 (m, 1H), 7.03 (t, J=8.8 Hz, 2H), 6.14 (s, 2H), 3.96 (t, J=5.7 Hz, 2H), 3.83 (t, J=4.5 Hz, 2H), 3.76 (s, 3H), 3.35 (t, J=6.0 Hz, 4H), 2.05-1.96 (m, 2H). LCMS (ES+) m/z 435 (M+1)

Example 320

5-amino-2-(2,6-difluorophenyl)-N-(1-methyl-5-(5-oxo-1,4-diazepan-1-yl)-1H-pyrazol-4-yl)thiazole-4-carboxamide 320

Step 1: 1-(1-Methyl-4-nitro-1H-pyrazol-5-yl)-1,4-diazepan-5-one

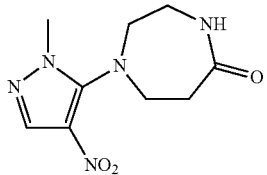

Reaction of 5-chloro-1-methyl-4-nitro-1H-pyrazole and 1,4-diazepan-5-one gave 1-(1-methyl-4-nitro-1H-pyrazol-5-yl)-1,4-diazepan-5-one as a yellow oil (173 mg, 58%). ¹H NMR (400 MHz, CDCl₃) δ 8.03 (s, 1H), 6.35 (s, 1H), 3.82 (s, 3H), 3.53-3.47 (m, 2H), 3.38-3.31 (m, 4H), 2.83-2.78 (m, 2H)

Step 2

Following the procedure for Example 243 starting with 1-(1-methyl-4-nitro-1H-pyrazol-5-yl)-1,4-diazepan-5-one gave 320 as a white solid (98 mg, 26% over three steps). ¹H NMR (400 MHz, d₆-DMSO) δ 8.82 (s, 1H), 7.65 (t, J=5.5 Hz, 1H), 7.60-7.47 (m, 3H), 7.41 (s, 1H), 7.31-7.24 (m, 2H), 3.67 (s, 3H), 3.27-3.21 (m, 2H), 3.18-3.10 (m, 5H), 2.57-2.48 (m, 1H). LCMS (ES+) m/z 448 (M+1)

Example 321

5-amino-2-(2,6-difluorophenyl)-N-(5-(4-(2-hydroxyethyl)piperazin-1-yl)-1-methyl-1H-pyrazol-4-yl)thiazole-4-carboxamide 321

Step 1: 2-(4-(1-Methyl-4-nitro-1H-pyrazol-5-yl)piperazin-1-yl)ethanol

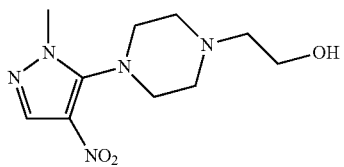

Reaction of 5-chloro-1-methyl-4-nitro-1H-pyrazole and 2-(piperazin-1-yl)ethanol gave 2-(4-(1-methyl-4-nitro-1H-pyrazol-5-yl)piperazin-1-yl)ethanol as a cream solid (0.30 g, 95%). ¹H NMR (400 MHz, CDCl₃) δ 8.03 (s, 1H), 3.78 (s, 3H), 3.67 (t, J=5.3 Hz, 2H), 3.26 (t, J=4.6 Hz, 4H), 2.72-2.62 (m, 6H). OH not seen Step 2

Following the procedure for Example 243 starting with 2-(4-(1-methyl-4-nitro-1H-pyrazol-5-yl)piperazin-1-yl)ethanol gave 321 as a light peach solid (165 mg, 67% over three steps). ¹H NMR (400 MHz, CDCl₃) δ 8.61 (s, 1H), 7.82 (s, 1H), 7.35-7.29 (m, 1H), 7.08-7.01 (m, 2H), 6.12 (s, 2H), 3.74 (s, 3H), 3.65 (t, J=5.3 Hz, 2H), 3.21 (t, J=4.5 Hz, 4H), 2.69-2.60 (m, 6H). OH not seen. LCMS (ES+) m/z 464 (M+1)

Example 322

(S)-5-amino-2-(3-(3-hydroxypyrrolidin-1-yl)phenyl)-N-(1-methyl-1H-pyrazol-4-yl)thiazole-4-carboxamide 322

Step 1: (S)-tert-butyl 2-(3-(3-hydroxypyrrolidin-1-yl)phenyl)-4-(1-methyl-1H-pyrazol-4-ylcarbamoyl)thiazol-5-ylcarbamate

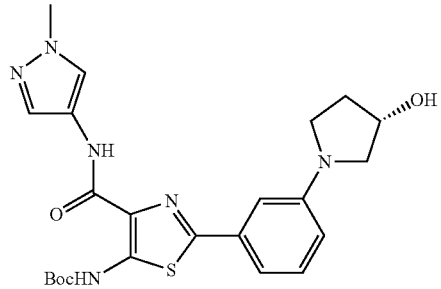 [SMILES: Cn1cc(NC(=O)c2nc(-c3cccc(N4CC[C@H](O)C4)c3)sc2NC(=O)OC(C)(C)C)cn1]

Following the procedure for Example 273 starting with 1,3-dibromobenzene and (S)-pyrrolidin-3-ol and tert-butyl 2-bromo-4-(1-methyl-1H-pyrazol-4-ylcarbamoyl)thiazol-5-ylcarbamate gave (S)-tert-butyl 2-(3-(3-hydroxypyrrolidin-1-yl)phenyl)-4-(1-methyl-1H-pyrazol-4-ylcarbamoyl)thiazol-5-ylcarbamate as a yellow solid (110 mg, 40%). LCMS (ES+) m/z 485 (M+1)

Step 2

Acidic deprotection of (S)-tert-butyl 2-(3-(3-hydroxypyrrolidin-1-yl)phenyl)-4-(1-methyl-1H-pyrazol-4-ylcarbamoyl)thiazol-5-ylcarbamate gave 322 as an off-white solid (25 mg, 29%). ¹H NMR (400 MHz, d₆-DMSO with D₂O) δ 7.95 (s, 1H), 7.62 (s, 1H), 7.22 (t, J=7.9 Hz, 1H), 7.01 (d, J=7.7 Hz, 1H), 6.96 (s, 1H), 6.55 (dd, J=8.3, 2.3 Hz, 1H), 4.42 (s, 1H), 3.78 (s, 3H), 3.45 (dd, J=10.4, 4.8 Hz, 1H), 3.42-3.26 (m, 2H), 3.13 (d, J=10.4 Hz, 1H), 2.10-1.99 (m, 1H), 1.94-1.87 (m, 1H). LCMS (ES+) m/z 385 (M+1)

Example 323

(R)-5-Amino-N-(5-(4-aminoazepan-1-yl)-1-methyl-1H-pyrazol-4-yl)-2-(4-methoxy-2-(trifluoromethyl)phenyl)thiazole-4-carboxamide 323

A mixture of (R)-benzyl 1-(4-(5-tert-butoxycarbonylamino-2-bromothiazole-4-carboxamido)-1-methyl-1H-pyrazol-5-yl)azepan-4-ylcarbamate (130 mg, 0.20 mmol), Na₂CO₃ (42 mg, 0.40 mmol) and 4-methoxy-2-(trifluoromethyl)phenylboronic acid (70 mg, 0.32 mmol) in DME (1.5 mL) and water (0.5 mL) was degassed by gently bubbling nitrogen through the mixture for 15 min. [1,1'-Bis(diphenylphosphino)ferrocene]dichloro-palladium(II) (16 mg, 0.020 mmol) was then added and the mixture degassed for a further 10 min before being heated in a microwave at 130° C. for 35 min. The solvents were removed under reduced pressure and the residue purified via silica gel column chromatography (0-100% EtOAc/isohexane). The isolated intermediate was dissolved in DCM (2 mL) and a 1M solution of boron tribromide in DCM (0.6 mL, 0.60 mmol) was added. The mixture was stirred at room temperature for 6 hr. The mixture was concentrated under reduced pressure and the residue purified by preparative HPLC to yield 323 as a brown solid (23 mg, 22%). $^1$H NMR (400 MHz, d$_6$-DMSO) δ 8.53 (s, 1H), 7.71 (d, J=8.6 Hz, 1H), 7.60 (s, 1H), 7.42-7.29 (m, 4H), 3.90 (s, 3H), 3.65 (s, 3H), 3.13-3.04 (m, 4H), 3.01-2.91 (m, 1H), 1.86-1.75 (m, 3H), 1.64-1.46 (m, 3H). LCMS (ES+) m/z 510 (M+1).

Example 324

(R)-5-Amino-N-(5-(4-aminoazepan-1-yl)-1-methyl-1H-pyrazol-4-yl)-2-(3-fluorophenyl)thiazole-4-carboxamide 324

Following the procedure for Example 323 starting with (R)-benzyl 1-(4-(5-tert-butoxycarbonyl-amino-2-bromothiazole-4-carboxamido)-1-methyl-1H-pyrazol-5-yl)azepan-4-ylcarbamate and 3-fluorophenylboronic acid gave 324 as a pale brown solid (26 mg, 29%). $^1$H NMR (400 MHz, d$_6$-DMSO) δ 8.91 (s, 1H), 7.73 (d, J=10.3 Hz, 1H), 7.62 (d, J=7.8 Hz, 1H), 7.55-7.47 (m, 4H), 7.24 (td, J=7.8, 2.6 Hz, 1H), 3.66 (s, 3H), 3.24-3.02 (m, 5H), 1.88-1.79 (m, 3H), 1.64-1.46 (m, 3H). LCMS (ES+) m/z 430 (M+1).

Example 325

3-amino-N-(1-methyl-1H-pyrazol-4-yl)-6-(3-morpholinophenyl)picolinamide 325

Following the procedures described in Example 318, 325 was obtained. $^1$H NMR (400 MHz, DMSO) δ 10.35 (s, 1H), 8.07 (s, 1H), 7.88 (d, J=8.8 Hz, 1H), 7.72 (s, 1H), 7.59 (d, J=12.1 Hz, 2H), 7.35-7.21 (m, 2H), 6.94 (d, J=5.3 Hz, 3H), 3.83 (s, 3H), 3.80-3.69 (m, 4H), 3.25-3.12 (m, 4H). MS (ESI) m/z: 379.2 [M+H$^+$].

Example 326

(R)-5-amino-N-(5-(4-aminoazepan-1-yl)-1-methyl-1H-pyrazol-4-yl)pyrimidine-4-carboxamide 326

Step 1: ethyl 5-amino-2-chloropyrimidine-4-carboxylate

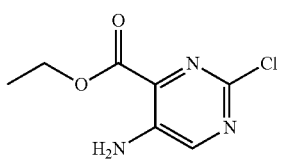

In a Parr hydrogenator, ethyl 2,6-dichloro-5-nitropyrimidine-4-carboxylate (2.16 g, 8.12 mmol), 10% Pd/C (2.0 g, 0.94 mmol), magnesium monoxide (1.60 g, 39.7 mmol) and 1,4-dioxane (100 mL) were charged. The hydrogenation was allowed to go at room temperature under 50-60 psi for 2 days while monitored by LCMS. The reaction mixture was filtered through Celite and washed with methanol. The filtrate was concentrated and purified via flash chromatography eluting with 50 to 100% ethyl acetate in heptane to give ethyl 5-amino-2-chloropyrimidine-4-carboxylate (0.90 g, 55%).

Step 2: 5-amino-2-chloropyrimidine-4-carboxylic acid

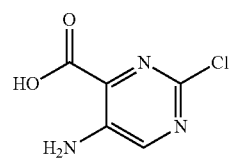 [SMILES: Nc1cnc(Cl)nc1C(=O)O]

Ethyl 5-amino-2-chloropyrimidine-4-carboxylate (0.90 g, 4.0 mmol) was dissolved in THF (22 mL). To it water (8 mL) and 1M lithium hydroxide (11 mL, 11 mmol) were added and the mixture was stirred at room temperature for 6 h. The reaction was then acidified to pH6 with 6N HCl (1.15 mL) and concentrated in vacuo to remove organic solvent. The solid was collected by filtration and washed with water to give 5-amino-2-chloropyrimidine-4-carboxylic acid as a yellow solid (434 mg, 60%).

Step 3: (R)-benzyl 1-(4-(5-amino-2-chloropyrimidine-4-carboxamido)-1-methyl-1H-pyrazol-5-yl)azepan-4-ylcarbamate

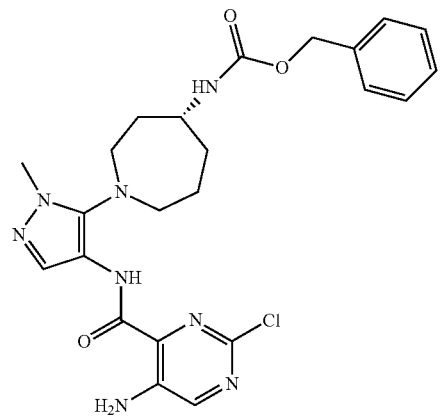 [SMILES: Cn1ncc(NC(=O)c2nc(Cl)ncc2N)c1N1CCC[C@@H](NC(=O)OCc2ccccc2)CC1]

Following the procedure from Example 140, (R)-benzyl 1-(4-amino-1-methyl-1H-pyrazol-5-yl)azepan-4-ylcarbamate from Example 16 and 5-amino-2-chloropyrimidine-4-carboxylic acid were converted to (R)-benzyl 1-(4-(5-amino-2-chloropyrimidine-4-carboxamido)-1-methyl-1H-pyrazol-5-yl)azepan-4-ylcarbamate.

Step 4

In a 40 mL sealed vial was added (R)-benzyl 1-(4-(5-amino-2-chloropyrimidine-4-carboxamido)-1-methyl-1H-pyrazol-5-yl)azepan-4-ylcarbamate (140 mg, 0.28 mmol), 1,4-cyclohexadiene (0.16 mL, 1.68 mmol) and ethanol (12 mL). 10% Pd/C (30 mg, 0.028 mmol) was added and the reaction vial was vacuum purged with nitrogen three times. The reaction mixture was then stirred at 95° C. under nitrogen for 2 h. LCMS indicated de-chlorinated product as the malor product. After cooling down to room temperature, the reaction mixture was filtered through Celite and rinsed thoroughly with methanol. The solvent was distilled off under reduced pressure to give the crude product which was purified via reverse phase HPLC to afford 326. ¹H NMR (400 MHz, DMSO) δ 8.48 (s, 1H), 8.46 (s, 1H), 7.51 (s, 1H), 6.88 (s, 3H), 3.65 (s, 4H), 3.19-2.89 (m, 9H), 1.93-1.69 (m, 4H), 1.69-1.41 (m, 4H). MS (ESI) m/z: 331.2 [M+H⁺].

Example 327

(R)-5-amino-2-(2,6-difluorophenyl)-N-(1-methyl-5-(4-(methylamino)azepan-1-yl)-1H-pyrazol-4-yl)thiazole-4-carboxamide 327

Following procedures as in Example 141, 5-(tert-butoxycarbonylamino)-2-(2,6-difluorophenyl)thiazole-4-carboxylic acid was converted to 327: ¹H-NMR (DMSO, 500 MHz) δ (ppm): 8.79 (s, 1H), 7.51 (m, 4H), 7.26 (t, 8.5 Hz, 2H), 3.64 (s, 3H), 3.18 (m, 1H), 3.10 (m, 3H), 2.81 (s, 1H), 2.30 (s, 3H), 1.92-1.90 (m, 3H), 1.57 (m, 3H); MS (ESI) m/z: 462 [M+H⁺]

Example 328

(S)-5-amino-2-(2,6-difluorophenyl)-N-(1-methyl-5-(4-(methylamino)azepan-1-yl)-1H-pyrazol-4-yl)thiazole-4-carboxamide 328

Following procedures as in Example 141, 5-(tert-butoxycarbonylamino)-2-(2,6-difluorophenyl)thiazole-4-carboxylic acid was converted to 328: ¹H-NMR (DMSO, 500 MHz) δ (ppm): 8.77 (s, 1H), 7.51 (m, 4H), 7.27 (t, 8.5 Hz, 2H), 3.64 (s, 3H), 3.21 (m, 1H), 3.17 (m, 3H), 2.81 (s, 1H), 2.30 (s, 3H), 1.92-1.90 (m, 3H), 1.60 (m, 3H); MS (ESI) m/z: 462 [M+H⁺]

Example 329

3-amino-N-(1-methyl-1H-pyrazol-4-yl)-6-(3-(pyrrolidin-1-yl)phenyl)picolinamide 329

Following the procedures described in Example 318, 329 was obtained. ¹H NMR (400 MHz, DMSO) δ 10.32 (s, 1H), 8.07 (s, 1H), 7.83 (d, J=8.7 Hz, 1H), 7.73 (s, 1H), 7.38-7.18 (m, 3H), 7.16 (s, 1H), 6.92 (s, 2H), 6.55 (d, J=8.0 Hz, 1H), 3.83 (s, 3H), 3.33 (t, J=6.3 Hz, 4H), 1.98 (t, J=6.4 Hz, 4H). MS (ESI) m/z: 363.1 [M+H⁺].

Example 330

(R)-5-amino-N-(5-(4-aminoazepan-1-yl)-1-methyl-1H-pyrazol-4-yl)-2-(2-fluorophenyl)pyrimidine-4-carboxamide 330

Following the procedure from Example 326, (R)-benzyl 1-(4-amino-1-methyl-1H-pyrazol-5-yl)azepan-4-ylcarbamate from Example 16 was converted to (R)-benzyl 1-(4-(5-amino-2-chloropyrimidine-4-carboxamido)-1-methyl-1H-pyrazol-5-yl)azepan-4-ylcarbamate.
Following the procedure from Example 229, (R)-benzyl 1-(4-(5-amino-2-chloropyrimidine-4-carboxamido)-1-methyl-1H-pyrazol-5-yl)azepan-4-ylcarbamate was converted to 330. ¹H NMR (400 MHz, DMSO) δ 8.63 (s, 1H), 8.07 (td, J=8.1, 1.7 Hz, 1H), 7.72 (s, 1H), 7.55-7.39 (m, 1H), 7.32 (dd, J=14.1, 7.3 Hz, 2H), 7.07 (br, 2H), 3.67 (s, 3H), 3.20-3.06 (m, 4H), 3.03-2.89 (m, 1H), 1.89-1.72 (m, 3H), 1.70-1.42 (m, 3H). MS (ESI) m/z: 425.1 [M+H⁺].

Example 331

3-amino-N-(1-methyl-1H-pyrazol-4-yl)-6-(3-(piperazin-1-yl)phenyl)picolinamide 331 tert-Butyl 4-(3-(5-amino-6-(1-methyl-1H-pyrazol-4-ylcarbamoyl)pyridin-2-yl)phenyl)piperazine-1-carboxylate was prepared following the procedures described in Example 318, and treated with 4M HCl in dioxane at room temperature to give 331, purified by reverse phase HPLC. ¹H NMR (400 MHz, DMSO) δ 10.35 (s, 1H), 8.07 (s, 1H), 7.86 (d, J=8.8 Hz, 1H), 7.72 (s, 1H), 7.54 (d, J=7.2 Hz, 2H), 7.34-7.18 (m, 2H), 6.92 (d, J=12.1 Hz, 3H), 3.83 (s, 3H), 3.20-3.06 (m, 4H), 2.93-2.79 (m, 4H). MS (ESI) m/z: 378.1 [M+H⁺].

Example 332

(R)-5-amino-N-(5-(azepan-4-ylamino)-1-methyl-1H-pyrazol-4-yl)-2-(2,6-difluorophenyl)thiazole-4-carboxamide 332

Step 1: (R)-tert-Butyl 4-(1-methyl-4-nitro-1H-pyrazol-5-ylamino)azepane-1-carboxylate

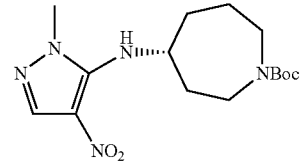 [SMILES: Cn1ncc([N+](=O)[O-])c1N[C@@H]1CCCN(C(=O)OC(C)(C)C)CC1]

A solution of (R)-tert-butyl 4-(benzyloxycarbonylamino)azepane-1-carboxylate from Examples 63 and 83 (3.25 g, 9.85 mmol) in MeOH (100 mL) was stirred at room temperature under an atmospheric pressure of hydrogen gas in the presence of 10% Pd/C (1 g) for 1.5 hr. The mixture was filtered through celite and the solvent removed under reduced pressure to afford (R)-tert-butyl 4-(2,2,2-trifluoroacetamido)azepane-1-carboxylate as a pale grey oil (2 g, 100%). A solution of this oil (0.145 g, 0.68 mmol) in ethanol (3 mL) was added to 5-chloro-1-methyl-4-nitro-1H-pyrazole (0.1 g, 0.62 mmol). DIPEA (1 mL) was added and the reaction mixture was heated at 130° C. in the microwave for 1 hr followed by a further 3×90 min at 140° C. The solvent was removed under reduced pressure and the crude material was purified via silica gel chromatography (60% EtOAc/isohexane) to afford (R)-tert-butyl 4-(1-methyl-4-nitro-1H-pyrazol-5-ylamino)azepane-1-carboxylate as a yellow oil (148 mg, 71%). ¹H NMR (400 MHz, CDCl₃) δ 7.90 (s, 1H), 6.60-6.50 (m, 1H), 3.80 (s, 3H), 3.79-3.67 (m, 1H), 3.60-3.52 (m, 1H), 3.49-3.44 (m, 1H), 3.44-3.22 (m, 2H), 2.25-2.10 (m, 1H), 2.05-1.62 (m, 5H), 1.48 (s, 9H)

Step 2

Following the procedure for Example 243 starting with (R)-tert-butyl 4-(1-methyl-4-nitro-1H-pyrazol-5-ylamino)azepane-1-carboxylate gave 332 as an orange foam (107 mg, 65% over three steps). ¹H NMR (400 MHz, CDCl₃) δ 8.49 (s, 1H), 7.54 (s, 1H), 7.37-7.30 (m, 1H), 7.06-6.98 (m, 2H), 6.16 (s, 2H), 3.90 (d, J=8.9 Hz, 1H), 3.73 (s, 3H), 3.29-3.22 (m, 1H), 3.03-2.69 (m, 4H), 2.01-1.46 (m, 6H). Alkyl NH not seen. LCMS (ES+) m/z 448 (M+1)

Example 333

5-amino-2-(2,6-difluorophenyl)-N-(1-(2-(piperidin-4-yl)ethyl)-2,3-dihydro-1H-imidazo[1,2-b]pyrazol-7-yl)thiazole-4-carboxamide 333

Step 1: tert-Butyl 4-(2-(7-nitro-2,3-dihydro-1H-pyrazolo[1,5-c]imidazol-1-yl)ethyl)piperidine-1-carboxylate

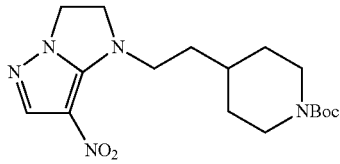 [SMILES: CC(C)(C)OC(=O)N1CCC(CCN2CCn3ncc([N+](=O)[O-])c32)CC1]

Sodium hydride (60% dispersion in mineral oil, 39 mg, 0.97 mmol) was added portionwise to a stirred solution of 7-nitro-2,3-dihydro-1H-pyrazolo[1,5-a]imidazole (0.125 g, 0.81 mmol) in anhydrous THF (10 mL) at room temperature under a nitrogen atmosphere. The mixture was stirred for 10 min. before a solution of tert-butyl 4-(2-(tosyloxy)ethyl)piperidine-1-carboxylate (0.31 g, 0.81 mmol) in THF (5 mL) was added portionwise over 10 min. The reaction was stirred for 6 hr at room temperature followed by 18 hr at 50° C. Further sodium hydride (60% dispersion in mineral oil, 39 mg, 0.97 mmol) was added and stirring continued at 60° C. for a further 24 h. The reaction was cooled and water was added dropwise. The mixture was extracted with EtOAc and the combined organics were dried over MgSO$_4$ and concentrated under reduced pressure. The crude residue was purified via silica gel chromatography (0-100% EtOAc/isohexane) to give tert-butyl 4-(2-(7-nitro-2,3-dihydro-1H-pyrazolo[1,5-c]imidazol-1-yl)ethyl)piperidine-1-carboxylate as a yellow oil (50 mg, 17%). $^1$H NMR (400 MHz, CDCl$_3$) δ 7.83 (s, 1H), 4.24-4.16 (m, 2H), 4.25-3.97 (m, 2H), 3.83-3.77 (s, 2H), 3.27 (s, 2H), 3.22 (t, J=6.8 Hz, 2H), 2.72-2.62 (s, 2H), 1.73-1.65 (m, 3H), 1.46-1.44 (m, 9H) 1.40-1.05 (m, 2H)

Step 2

Following the procedure for Example 230 starting with tert-butyl 4-(2-(7-nitro-2,3-dihydro-1H-pyrazolo[1,5-c]imidazol-1-yl)ethyl)piperidine-1-carboxylate gave 333 as a cream solid (13 mg, 20% over three steps). $^1$H NMR (400 MHz, d$_4$-MeOD) δ 7.54-7.45 (m, 1H), 7.33 (s, 1H), 7.22-7.12 (m, 2H), 4.18-4.08 (m, 2H), 3.85-3.72 (m, 2H), 3.30-3.12 (m, 4H), 2.95-2.82 (m, 2H), 1.93 (d, J=14.0 Hz, 2H), 1.81-1.69 (m, 1H), 1.59 (dd, J=14.0, 6.9 Hz, 2H), 1.42-1.27 (m, 2H). LCMS (ES+) m/z 474 (M+1)

Example 334

5-amino-2-(2,6-difluorophenyl)-N-(5-((3aR,6aS)-hexahydropyrrolo[3,4-c]pyrrol-2(1H)-yl)-1-methyl-1H-pyrazol-4-yl)thiazole-4-carboxamide 334

Step 1: (3aR,6aS)-tert-Butyl 5-(1-methyl-4-nitro-1H-pyrazol-5-yl)hexahydropyrrolo[3,4-c]pyrrole-2(1H)-carboxylate

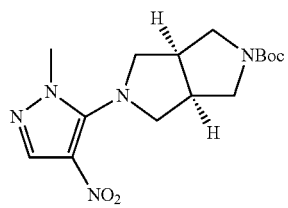

Reaction of 5-chloro-1-methyl-4-nitro-1H-pyrazole and (3aR,6aS)-tert-butyl hexahydropyrrolo[3,4-c]pyrrole-2(1H)-carboxylate gave (3aR,6aS)-tert-butyl 5-(1-methyl-4-nitro-1H-pyrazol-5-yl)hexahydropyrrolo[3,4-c]pyrrole-2(1H)-carboxylate as a yellow oil (0.36 g, 86%). $^1$H NMR (400 MHz, CDCl$_3$) δ 8.05 (s, 1H), 3.75 (s, 3H), 3.73-3.55 (m, 4H), 3.42-3.33 (m, 2H), 3.17-3.04 (m, 4H), 1.48 (s, 9H)

Step 2

Following the procedure for Example 243 starting with (3aR,6aS)-tert-butyl 5-(1-methyl-4-nitro-1H-pyrazol-5-yl)hexahydropyrrolo[3,4-c]pyrrole-2(1H)-carboxylate gave 334 as the mono-formate salt as an off-white solid (52 mg, 37%). $^1$H NMR (400 MHz, d$_6$-DMSO) δ 8.84 (s, 1H), 8.37 (s, 1H), 7.61-7.46 (m, 3H), 7.37 (s, 1H), 7.32-7.23 (m, 2H), 3.65 (s, 3H), 3.34-3.26 (m, 2H), 3.21-3.18 (m, 2H), 3.00 (d, J=9.3 Hz, 2H), 2.79-2.69 (m, 4H). Alkyl NH not seen. LCMS (ES+) m/z 446 (M+1)

Example 335

5-amino-2-(2,6-difluorophenyl)-N-(1-methyl-5-(methyl(piperidin-4-yl)amino)-1H-pyrazol-4-yl)thiazole-4-carboxamide 335

Step 1: tert-Butyl 4-(methyl(1-methyl-4-nitro-1H-pyrazol-5-yl)amino)piperidine-1-carboxylate

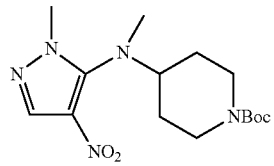 [SMILES: CN(c1c([N+](=O)[O-])cnn1C)C1CCN(C(=O)OC(C)(C)C)CC1]

Reaction of 5-chloro-1-methyl-4-nitro-1H-pyrazole and tert-butyl 4-(methylamino)piperidine-1-carboxylate gave tert-butyl 4-(methyl(1-methyl-4-nitro-1H-pyrazol-5-yl)amino)piperidine-1-carboxylate (75 mg, 36%). $^1$H NMR (400 MHz, CDCl$_3$) δ 8.07 (s, 1H), 4.15-4.05 (m, 2H), 3.75 (s, 3H), 3.32 (tt, J=11.1, 3.9 Hz, 1H), 2.81 (s, 3H), 2.72 (t, J=12.9 Hz, 2H), 1.79-1.70 (m, 2H), 1.48 (s, 9H), 1.40-1.25 (m, 2H)

Step 2

Following the procedure for Example 243 starting with tert-butyl 4-(methyl(1-methyl-4-nitro-1H-pyrazol-5-yl)amino)piperidine-1-carboxylate gave 335 as a yellow solid (45 mg, 55% over three steps). $^1$H NMR (400 MHz, CDCl$_3$) δ 8.60 (s, 1H), 7.97 (s, 1H), 7.35-7.28 (m, 1H), 7.02 (t, J=8.9 Hz, 2H), 6.11 (s, 2H), 3.73 (s, 3H), 3.12 (d, J=12.4 Hz, 2H), 3.05-3.01 (m, 1H), 2.85 (s, 3H), 2.68-2.58 (m, 2H), 1.89-1.82 (m, 2H), 1.55-1.42 (m, 2H). Alkyl NH not seen. LCMS (ES+) m/z 448 (M+1)

Example 336

(R)-5-Amino-N-(5-(4-aminoazepan-1-yl)-1-ethyl-1H-pyrazol-4-yl)-2-(2,6-difluorophenyl)thiazole-4-carboxamide 336

Following the procedure for Example 241 starting with (R)-tert-butyl 2-(2-fluorophenyl)-4-(1-ethyl-5-(4-(2,2,2-trifluoroacetamido)azepan-1-yl)-1H-pyrazol-4-ylcarbamoyl)thiazol-5-ylcarbamate gave, after preparative HPLC, 336 as a cream solid (31 mg, 30%). $^1$H-NMR (400 MHz, d$_4$-MeOD) δ 7.69 (s, 1H), 7.50-7.40 (m, 1H), 7.19-7.09 (m, 2H), 4.08 (q, J=7 Hz, 2H), 3.30-3.16 (m, 4H), 3.14-3.05 (m, 1H), 2.05-1.84 (m, 3H), 1.83-1.61 (m, 3H), 1.44-1.35 (m, 3H). LCMS (ES+) m/z 462.0 (M+1).

Example 337

(R)-5-Amino-N-(5-(4-aminoazepan-1-yl)-1-methyl-1H-pyrazol-4-yl)-2-cyclopentenylthiazole-4-carboxamide 337

Following the procedure for Example 350 starting with (R)-tert-butyl 2-bromo-4-(1-methyl-5-(4-(2,2,2-trifluoroacetamido)-azepan-1-yl)-1H-pyrazol-4-ylcarbamoyl)thiazol-5-ylcarbamate and cyclopent-1-ene-1-boronic acid gave 397 as an orange solid (8 mg, 14%). $^1$H NMR (400 MHz, d$_4$-MeOD) δ 7.48 (s, 1H), 6.13 (t, J=2.5 Hz, 1H), 3.67 (s, 3H), 3.22-3.17 (m, 3H), 3.10-3.03 (m, 1H), 2.77-2.70 (m, 2H), 2.53-2.47 (m, 2H), 2.03-1.81 (m, 6H), 1.73-1.58 (m, 3H). LCMS (ES+) m/z 402 (M+1).

Example 338

(R)-5-Amino-N-(5-(4-aminoazepan-1-yl)-1-methyl-1H-pyrazol-4-yl)-2-cyclohexenylthiazole-4-carboxamide 338

Following the procedure for Example 350 starting with (R)-tert-butyl 2-bromo-4-(1-methyl-5-(4-(2,2,2-trifluoroacetamido)-azepan-1-yl)-1H-pyrazol-4-ylcarbamoyl)thiazol-5-ylcarbamate and cyclohex-1-ene-1-boronic acid gave 338 as a white solid (17.1 mg, 33%). $^1$H NMR (400 MHz, d$_4$-MeOD) δ 7.58 (s, 1H), 6.31 (t, J=4.1 Hz, 1H), 3.74 (s, 3H), 3.30-3.24 (m, 3H), 3.13-3.07 (m, 1H), 2.64-2.45 (m, 2H), 2.28-2.24 (m, 2H), 2.04-1.88 (m, 3H), 1.83-1.66 (m, 8H). LCMS (ES+) m/z 416 (M+1).

Example 339

(R,E)-5-Amino-N-(5-(4-aminoazepan-1-yl)-1-methyl-1H-pyrazol-4-yl)-2-cycloheptenylthiazole-4-carboxamide 339

Following the procedure for Example 350 starting with (R)-tert-butyl 2-bromo-4-(1-methyl-5-(4-(2,2,2-trifluoroacetamido)-azepan-1-yl)-1H-pyrazol-4-ylcarbamoyl)thiazol-5-ylcarbamate and 1-cycloheptenylboronic acid pinacol ester gave 339 as an orange solid (7.0 mg, 14%). $^1$H NMR (400 MHz, d$_4$-MeOD) δ 7.57 (s, 1H), 6.46 (t, J=6.7 Hz, 1H), 3.74 (s, 3H), 3.31-3.22 (m, 4H), 3.14-3.06 (m, 1H), 2.88-2.82 (m, 2H), 2.39-2.32 (m, 2H), 2.05-1.56 (m, 12H). LCMS (ES+) m/z 430 (M+1)

Example 340

5-amino-N-(5-((cis-4-aminocyclohexylamino)-1-methyl-1H-pyrazol-4-yl)-2-(2,6-difluorophenyl)thiazole-4-carboxamide 340

Following the procedures from Example 2, tert-butyl cis-4-(4-amino-1-methyl-1H-pyrazol-5-ylamino)cyclohexylcarbamate was prepared.

Following the procedures from Example 140, tert-butyl (cis-4-(4-amino-1-methyl-1H-pyrazol-5-ylamino)cyclohexylcarbamate was converted to 340. $^1$H NMR (400 MHz, DMSO) δ 8.89 (s, 1H), 7.59-7.38 (m, 4H), 7.26 (t, J=8.6 Hz, 2H), 4.58 (d, J=7.4 Hz, 1H), 3.61 (s, 3H), 2.97 (br, 1H), 2.76 (br, 1H), 1.53 (dt, J=17.3, 7.0 Hz, 9H). MS (ESI) m/z: 448.2 [M+H$^+$].

Example 341

(S)-3-amino-6-(3-(3-aminopiperidin-1-yl)phenyl)-N-(1-methyl-1H-pyrazol-4-yl)picolinamide 341

Step 1: (S)-tert-butyl 1-(3-(4,4,5,5-tetramethyl-1,3,2-dioxaborolan-2-yl)phenyl)piperidin-3-ylcarbamate

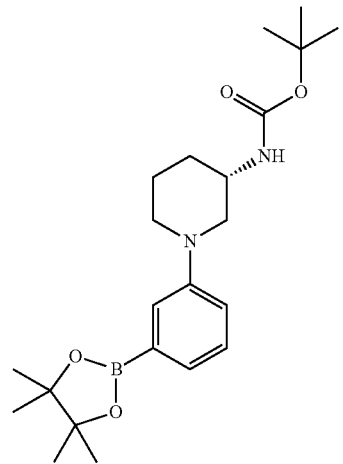 [SMILES: CC(C)(C)OC(=O)N[C@H]1CCCN(c2cccc(B3OC(C)(C)C(C)(C)O3)c2)C1]

A solution of tert-butyl N-[(3S)-3-piperidyl]carbamate (533 mg, 2.66 mmol), 1,3-dibromobenzene (878 mg, 3.72 mmol), (+/−)-BINAP (171 mg, 0.266 mmol), Pd$_2$(dba)$_3$ (122 mg, 0.133 mmol) and sodium tert-butoxide (277 mg, 2.79 mmol) in toluene (25 mL) was heated at 85° C. overnight. The reaction mixture was filtered through Celite and washed thoroughly with EA. The crude product was purified via flash chromatography eluted with 0 to 100% ethyl acetate in heptane to give (S)-tert-butyl 1-(3-(4,4,5,5-tetramethyl-1,3,2-dioxaborolan-2-yl)phenyl)piperidin-3-ylcarbamate.

Step 2

Following the procedure from Example 331, 3-amino-6-bromo-N-(1-methyl-1H-pyrazol-4-yl)picolinamide was converted to 341. $^1$H NMR (400 MHz, DMSO) δ 10.34 (s, 1H), 8.08 (s, 1H), 7.85 (d, J=8.7 Hz, 1H), 7.72 (s, 1H), 7.56 (s, 1H), 7.51 (d, J=7.7 Hz, 1H), 7.28 (t, J=8.4 Hz, 2H), 7.01-6.80 (m, 3H), 3.83 (s, 3H), 3.72 (d, J=9.2 Hz, 1H), 3.63 (d, J=12.2 Hz, 1H), 2.89-2.77 (m, 1H), 2.77-2.63 (m, 1H), 1.90-1.83 (m, 1H), 1.80-1.72 (m, 1H), 1.65-1.53 (m, 1H), 1.27-1.09 (m, 1H). MS (ESI) m/z: 392.2 [M+H⁺].

Example 342

(S)-3-amino-6-(3-(3-aminopyrrolidin-1-yl)phenyl)-N-(1-methyl-1H-pyrazol-4-yl)picolinamide 342

Following the procedure from Example 341, 3-amino-6-bromo-N-(1-methyl-1H-pyrazol-4-yl)picolinamide was converted to 342. ¹H NMR (400 MHz, DMSO) δ 10.32 (s, 1H), 8.07 (s, 1H), 7.83 (d, J=8.7 Hz, 1H), 7.73 (s, 1H), 7.38-7.17 (m, 3H), 7.11 (s, 1H), 6.92 (s, 2H), 6.50 (d, J=8.1 Hz, 1H), 3.83 (s, 3H), 3.66-3.56 (m, 1H), 3.56-3.41 (m, 3H), 2.99 (dd, J=9.3, 4.7 Hz, 1H), 2.11 (td, J=12.9, 6.4 Hz, 1H), 1.74 (td, J=12.8, 6.6 Hz, 1H). MS (ESI) m/z: 378.2 [M+H⁺].

Example 343

(R)-3-amino-6-(3-(3-aminopiperidin-1-yl)phenyl)-N-(1-methyl-1H-pyrazol-4-yl)picolinamide 343

Following the procedure from Example 341, 3-amino-6-bromo-N-(1-methyl-1H-pyrazol-4-yl)picolinamide was converted to 343. ¹H NMR (400 MHz, DMSO) δ 10.34 (s, 1H), 8.08 (s, 1H), 7.85 (d, J=8.7 Hz, 1H), 7.72 (s, 1H), 7.60-7.44 (m, 2H), 7.28 (t, J=8.1 Hz, 2H), 7.00-6.80 (m, 3H), 3.83 (s, 3H), 3.72 (d, J=11.8 Hz, 1H), 3.63 (d, J=12.0 Hz, 1H), 2.93-2.59 (m, 3H), 1.95-1.69 (m, 2H), 1.65-1.52 (m, 1H), 1.31-1.07 (m, 1H). MS (ESI) m/z: 392.2 [M+H⁺].

Example 344

(R)-5-amino-N-(5-(4-aminoazepan-1-yl)-1-methyl-1H-pyrazol-4-yl)-2-methylthiazole-4-carboxamide 344

Following procedures from Examples 140, (R)-benzyl 1-(4-amino-1-methyl-1H-pyrazol-5-yl)azepan-4-ylcarbamate from Example 16 was converted to 344. ¹H NMR (400 MHz, DMSO) δ 8.70 (s, 1H), 7.44 (s, 1H), 7.03 (s, 2H), 3.62 (s, 4H), 3.18-2.96 (m, 7H), 2.44 (d, J=8.4 Hz, 4H), 1.94-1.72 (m, 4H), 1.68-1.42 (m, 4H). MS (ESI) m/z: 350.2 [M+H⁺].

Example 345

(R)-3-amino-6-(3-(3-aminopyrrolidin-1-yl)phenyl)-N-(1-methyl-1H-pyrazol-4-yl)picolinamide 345

Following the procedure from Example 341, 3-amino-6-bromo-N-(1-methyl-1H-pyrazol-4-yl)picolinamide was converted to Example 345. ¹H NMR (400 MHz, DMSO) δ 10.32 (s, 1H), 8.07 (s, 1H), 7.83 (d, J=8.7 Hz, 1H), 7.73 (s, 1H), 7.38-7.15 (m, 3H), 7.11 (s, 1H), 6.92 (s, 2H), 6.50 (d, J=7.9 Hz, 1H), 3.83 (s, 3H), 3.64-3.54 (m, 1H), 3.54-3.40 (m, 3H), 2.99 (dd, J=9.3, 4.7 Hz, 1H), 2.11 (dt, J=12.5, 6.4 Hz, 1H), 1.74 (td, J=12.7, 6.4 Hz, 1H). MS (ESI) m/z: 378.2 [M+H⁺].

Example 346

5-amino-N-(5-((cis-3-aminocyclohexylamino)-1-methyl-1H-pyrazol-4-yl)-2-(2,6-difluorophenyl)thiazole-4-carboxamide 346

Following the procedures provided in Example 340, racemic 346 was obtained. The cis diastereoisomers were isolated via chiral preparative HPLC. ¹H NMR (400 MHz, DMSO) δ 7.61-7.40 (m, 4H), 7.27 (t, J=8.6 Hz, 2H), 4.64 (d, J=7.8 Hz, 1H), 3.60 (s, 3H), 2.87-2.73 (m, 1H), 1.96 (d, J=11.7 Hz, 1H), 1.78 (d, J=11.8 Hz, 1H), 1.65 (t, J=15.1 Hz, 2H), 1.21-0.78 (m, 4H). MS (ESI) m/z: 448.2 [M+H⁺].

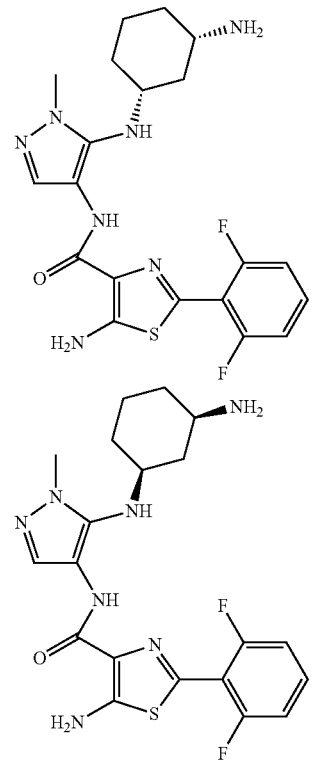

Example 347

5-amino-2-(2,6-difluorophenyl)-N-(5-(4-(2,4-dimethoxybenzylamino)cyclohexyl)-1-methyl-1H-pyrazol-4-yl)thiazole-4-carboxamide 347

Following procedures from Examples 113 and shown in FIG. 5, tert-butyl 2-(2,6-di-fluorophenyl)-4-(5-(4-(2,4-dimethoxybenzylamino)cyclohexyl)-1-methyl-1H-pyrazol-4-ylcarbamoyl)thiazol-5-ylcarbamate was converted to 347: ¹H NMR (400 MHz, DMSO) δ 8.76 (s, 1H), 8.30 (s, 1H), 7.53 (s, 1H), 7.45 (m, 3H), 7.20 (m, 2H), 7.06 (d, J=8.3 Hz, 1H), 6.42 (d, J=2.1 Hz, 1H), 6.29 (dd, J=8.3, 2.1 Hz, 1H), 3.78 (s, 3H), 3.75 (m, 2H), 3.70 (m, 5H), 3.51 (s, 3H), 2.77 (m, 2H), 2.14-2.04 (m, 2H), 1.80 (d, J=12.8 Hz, 2H), 1.49 (t, J=14.4 Hz, 2H); MS (ESI) m/z: 583[M+H⁺]

Example 348

5-amino-2-(2,6-difluorophenyl)-N-(1-(piperidin-4-ylmethyl)-2,3-dihydro-1H-imidazo[1,2-b]pyrazol-7-yl)thiazole-4-carboxamide 348

Step 1: tert-Butyl 4-((7-nitro-2,3-dihydro-1H-pyrazolo[1,5-a]imidazol-1-yl)methyl)piperidine-1-carboxylate

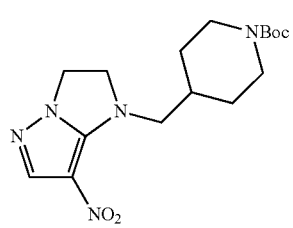 [SMILES: CC(C)(C)OC(=O)N1CCC(CN2CCn3ncc([N+](=O)[O-])c32)CC1]

Following the procedure for Example 333 starting with 7-nitro-2,3-dihydro-1H-pyrazolo[1,5-a]imidazole and tert-butyl 4-(tosyloxymethyl)piperidine-1-carboxylate gave tert-butyl 4-((7-nitro-2,3-dihydro-1H-pyrazolo[1,5-c]imidazol-1-yl)methyl)piperidine-1-carboxylate as a pale yellow solid (40 mg, 23%). $^1$H NMR (400 MHz, CDCl$_3$) δ 7.82 (s, 1H), 4.26-4.02 (m, 6H), 3.77-3.61 (m, 2H), 2.71 (s, 2H), 1.92-1.67 (m, 3H), 1.47-1.45 (m, 9H), 1.32-1.11 (m, 2H)

Step 2

Following the procedure for Example 230 starting with tert-butyl 4-((7-nitro-2,3-dihydro-1H-pyrazolo[1,5-c]imidazol-1-yl)methyl)piperidine-1-carboxylate gave 348 as the mono-formate salt as an off-white foam (41 mg, 11% over three steps). $^1$H NMR (400 MHz, d$_4$-MeOD) δ 8.55 (s, 1H), 7.54-7.45 (m, 1H), 7.31 (s, 1H), 7.19-7.10 (m, 2H), 4.15 (t, J=7.8 Hz, 2H), 3.86 (t, J=7.8 Hz, 2H), 3.38-3.30 (m, 2H), 3.10-3.00 (m, 2H), 2.88 (td, J=12.8, 2.9 Hz, 2H), 2.07-1.89 (m, 3H), 1.45-1.30 (m, 2H). LCMS (ES+) m/z 460 (M+1)

Example 349

5-amino-N-(5-(3-aminopropylamino)-1-methyl-1H-pyrazol-4-yl)-2-(2,6-difluorophenyl)thiazole-4-carboxamide 349

Step 1: tert-Butyl 3-(1-methyl-4-nitro-1H-pyrazol-5-ylamino)propylcarbamate

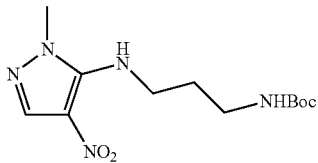 [SMILES: Cn1ncc([N+](=O)[O-])c1NCCCNC(=O)OC(C)(C)C]

Following Example 58, reaction of 5-chloro-1-methyl-4-nitro-1H-pyrazole and tert-butyl 3-aminopropylcarbamate gave tert-butyl 3-(1-methyl-4-nitro-1H-pyrazol-5-ylamino)propylcarbamate as a pale yellow gum (1.27 g, 85%). $^1$H NMR (400 MHz, CDCl$_3$) δ 7.88 (s, 1H), 6.75 (s br, 1H), 4.67 (s br, 1H), 3.84 (s, 3H), 3.54 (q, J=6.6 Hz, 2H), 3.27 (q, J=6.6 Hz, 2H), 1.90-1.79 (m, 2H), 1.44 (s, 9H)

Step 2

Following the procedure for Example 230 starting with tert-butyl 3-(1-methyl-4-nitro-1H-pyrazol-5-ylamino)propylcarbamate gave 349 as the mono-formate salt as an off-white foam (19 mg, 5% over three steps). $^1$H NMR (400 MHz, d$_4$-MeOD) δ 8.56 (s, 1H), 7.55-7.43 (m, 1H), 7.43 (s, 1H), 7.21-7.11 (m, 2H), 3.70 (s, 3H), 3.28-3.21 (m, 2H), 3.06-2.97 (m, 2H), 1.93-1.82 (m, 2H). LCMS (ES+) m/z 408 (M+1)

Example 350

(R)-5-amino-N-(5-(4-aminoazepan-1-yl)-1-methyl-1H-pyrazol-4-yl)-2-(2,5-dichlorophenyl)thiazole-4-carboxamide 350

A mixture of (R)-tert-butyl 2-bromo-4-(1-methyl-5-(4-(2,2,2-trifluoroacetamido)-azepan-1-yl)-1H-pyrazol-4-ylcarbamoyl)thiazol-5-ylcarbamate (122 mg, 0.20 mmol), Na$_2$CO$_3$ (42 mg, 0.40 mmol) and 2,5-dichlorobenzeneboronic acid (38 mg, 0.20 mmol) in DME (1.5 mL) and water (0.5 mL) was degassed by gently bubbling nitrogen through the mixture for 15 min. [1,1'-Bis(diphenylphosphino)ferrocene]dichloro-palladium(II) (16 mg, 0.020 mmol) was added and the mixture degassed for a further 10 min before being heated in a microwave at 130° C. for 35 min. Water was added and the mixture extracted with EtOAc. The combined organic layers were passed through a phase separation cartridge and concentrated under reduced pressure. The residue was purified via silica gel column chromatography (0-100% EtOAc/isohexane). The isolated intermediate was dissolved in a mixture of DCM (1.5 mL) and TFA (0.5 mL) and stirred at room temperature for 6 hr. The solvents were removed under reduced pressure and the residue dissolved in a mixture of MeOH/water (3 mL, 1:1) and K$_2$CO$_3$ (55 mg, 0.40 mmol) added. The mixture was heated at 60° C. for 3 hr. The mixture was concentrated under reduced pressure and the residue purified by preparative HPLC to yield 350 as a yellow solid (12 mg, 29%). $^1$H NMR (400 MHz, d$_4$-MeOD) δ 8.35 (d, J=2.6 Hz, 1H), 7.56 (s, 1H), 7.52 (d, J=8.6 Hz, 1H), 7.39 (dd, J=8.6, 2.6 Hz, 1H), 3.76 (s, 3H), 3.35-3.31 (m, 4H), 3.11-3.09 (m, 1H), 2.04-1.91 (m, 3H), 1.76-1.67 (m, 3H). LCMS (ES+) m/z 480 (M+1).

Example 351

5-Amino-N-(5-(5-amino-4,4-difluoroazepan-1-yl)-1-methyl-1H-pyrazol-4-yl)-2-(2,6-difluorophenyl)thiazole-4-carboxamide 351

HCl in 1,4-dioxane (4 M, 2 mL) was added to a solution of Example 55 (20 mg, 0.03 mmol) in MeOH (0.5 mL). This mixture was stirred at room temperature for 18 hr. The solvents were removed under reduced pressure and the crude product re-dissolved in MeOH/water (1:1, 5 mL). K$_2$CO$_3$ (0.3 g, 7, 2.2 mmol) was added and the mixture heated and stirred at 60° C. for 3 hr before being cooled to room temperature. The mixture was concentrated under reduced pressure and the residue purified by preparative HPLC to yield 351 as a white solid (4 mg, 25%). $^1$H NMR (400 MHz, CDCl$_3$) δ 9.02 (s, 1H), 7.88 (s, 1H), 7.37-7.28 (m, 1H), 7.08-6.98 (m, 2H), 6.15 (s, 2H), 3.73 (s, 3H), 3.39-3.13 (m, 6H), 2.46-2.34 (m, 1H), 2.22-2.03 (m, 2H), 1.99-1.89 (m, 1H), 1.83-1.78 (m, 1H). LCMS (ES+) m/z 484.0 (M+1).

Example 352

5-Amino-N-(5-((3-aminopropyl)(methyl)amino)-1-methyl-1H-pyrazol-4-yl)-2-(2,6-difluorophenyl)thiazole-4-carboxamide 352

Following the procedure for Example 287 starting from tert-butyl 2-(2,6-difluorophenyl)-4-(5-(tert-butyl-(3-methylamino)propylcarbamoyl-3-yl)-1-methyl-1H-pyrazol-4-ylcarbamoyl)thiazol-5-ylcarbamate gave 352 as the monoformate salt as pale brown solid (134 mg, 73%). $^1$H-NMR (400 MHz, d$_4$-MeOD) δ 8.56 (s, 1H), 7.60 (s, 1H), 7.53-7.44 (m, 1H), 7.18-7.11 (m, 2H), 3.75 (s, 3H), 3.20 (t, J=7.5 Hz, 2H), 2.95 (t, J=7.5 Hz, 2H), 2.87 (s, 3H), 1.88-1.77 (m, 2H). LCMS (ES+) m/z 422.0 (M+1).

Example 353

5-amino-2-(2,6-difluorophenyl)-N-(1-(2-fluoroethyl)-1H-pyrazol-4-yl)thiazole-4-carboxamide 353

Step 1: 1-(2-Fluoroethyl)-4-nitro-1H-pyrazole

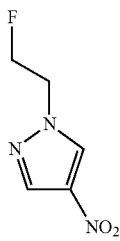

1-Bromo-2-fluoroethane (5 g, 38.5 mmol) was added to a stirred mixture of 4-nitro-1H-pyrazole (4.35 g, 38.5 mmol) and $K_2CO_3$ (13.3 g, 96.3 mmol) in MeCN (120 mL). The mixture was stirred at room temperature for 30 min and then heated to 50° C. for 18 hr. The mixture was cooled and the solid filtered and washed with MeCN. The filtrate was concentrated under reduced pressure and the crude residue purified via silica gel chromatography (0-100% EtOAc/isohexane) to give 1-(2-fluoroethyl)-4-nitro-1H-pyrazole as a colourless solid (5.13 g, 84%). $^1$H NMR (400 MHz, $CDCl_3$) δ 8.24 (s, 1H), 8.11 (s, 1H), 4.89-4.72 (m, 2H), 4.57-4.40 (m, 2H)

Step 2

Following the procedure for Example 230 starting with 1-(2-fluoroethyl)-4-nitro-1H-pyrazole gave 353 as a cream solid (137 mg, 50% yield over three steps). $^1$H NMR (400 MHz, $d_4$-MeOD) δ 8.07 (s, 1H), 7.73 (d, J=0.7 Hz, 1H), 7.53-7.42 (m, 1H), 7.18-7.09 (m, 2H), 4.75 (dt, J=47.2, 4.8 Hz, 2H), 4.43 (dt, J=26.7, 4.8 Hz, 2H). LCMS (ES+) m/z 368 (M+1)

Example 354

5-Amino-N-(5-(4-(aminomethyl)piperidin-1-yl)-1-methyl-1H-pyrazol-4-yl)-2-(2,6-difluoro-3-methoxyphenyl)thiazole-4-carboxamide 354

A solution of PyBOP (211 mg, 0.406 mmol) and 5-(tert-butoxycarbonylamino)-2-(2,6-difluoro-3-methoxyphenyl)thiazole-4-carboxylic acid (118 mg, 0.31 mmol) in DCM (3 mL) was stirred at room temperature for 30 min. A solution of tert-butyl (1-(4-amino-1-methyl-1H-pyrazol-5-yl)piperidin-4-yl)methylcarbamate (89 mg, 0.29 mmol) and DIPEA (81 μL, 0.46 mmol) in DCM (3 mL) was added and the mixture stirred at room temperature for 16 hr. The mixture was diluted with DCM and washed with water. The organic layer was separated, passed through a phase separation cartridge and concentrated under reduced pressure. The residue was purified via silica gel column chromatography (0-100% EtOAc/isohexane). The isolated intermediate was re-dissolved in DCM (10 mL) and TFA (2 mL) added. The mixture was stirred at room temperature for 3 hr. The mixture was concentrated under reduced pressure and the residue purified by preparative HPLC to yield 354 as a white solid (31 mg, 42%). $^1$H NMR (400 MHz, $d_4$-MeOD) δ 7.58 (s, 1H), 7.37-6.99 (m, 1H), 7.06 (t, J=10.0 Hz, 1H), 3.93 (s, 3H), 3.73 (s, 3H), 3.29-3.04 (m, 4H), 2.65 (d, J=6.5 Hz, 2H), 1.85 (d, J=12.4 Hz, 2H), 1.70-1.42 (m, 1H), 1.48-1.21 (m, 2H). LCMS (ES+) m/z 478 (M+1).

Example 355

(R)-5-Amino-N-(5-(4-aminoazepan-1-yl)-1-methyl-1H-pyrazol-4-yl)-2-(2-cyanophenyl)thiazole-4-carboxamide 355

A mixture of (R)-tert-butyl 2-bromo-4-(1-methyl-5-(4-(2,2,2-trifluoroacetamido)azepan-1-yl)-1H-pyrazol-4-ylcarbamoyl)thiazol-5-ylcarbamate (122 mg, 0.20 mmol), potassium fluoride dihydrate (62 mg, 0.66 mmol) and 2-cyanophenylboronic acid (88 mg, 0.60 mmol) in THF (3 mL) was degassed by gently bubbling nitrogen through the mixture for 15 min. Tris(dibenzylideneacetone)dipalladium/tri-tert-butyl phosphonium tetrafluoroborate mixture (mole ratio: 1/1.2) (24 mg, 0.020 mmol) was then added and the mixture degassed for a further 10 min before being heated in a microwave at 80° C. for 2 hr. Water was added and the mixture extracted with EtOAc. The combined organic layers were passed through a phase separation cartridge and concentrated under reduced pressure. The residue was purified via silica gel column chromatography (0-100% EtOAc/isohexane). The isolated intermediate was dissolved in a mixture of DCM (1.5 mL) and TFA (0.5 mL) and stirred at room temperature for 4 hr. The solvents were removed under reduced pressure and the residue dissolved in MeOH/water (3 mL, 3:1) and $K_2CO_3$ (66 mg, 0.48 mmol) added. The mixture was heated at 80° C. for 6 hr. The solvents were removed under reduced pressure and the residue purified by preparative HPLC to yield 355 as an orange solid (36 mg, 51%). $^1$H NMR (400 MHz, $d_4$-MeOD) δ 7.87 (d, J=7.8 Hz, 1H), 7.81 (d, J=7.8 Hz, 1H), 7.74 (t, J=7.8 Hz, 1H), 7.68 (s, 1H), 7.55 (t, J=7.8 Hz, 1H), 3.75 (s, 3H), 3.40-3.26 (m, 4H), 3.18-3.10 (m, 1H), 2.05-1.86 (m, 3H), 1.87-1.67 (m, 3H). LCMS (ES+) m/z 437 (M+1).

Example 356

5-amino-N-(1-methyl-1H-pyrazol-4-yl)-2-(3-(morpholinomethyl)phenyl)thiazole-4-carboxamide 356

Step 1: tert-Butyl 2-bromo-4-(1-methyl-1H-pyrazol-4-ylcarbamoyl)thiazol-5-ylcarbamate

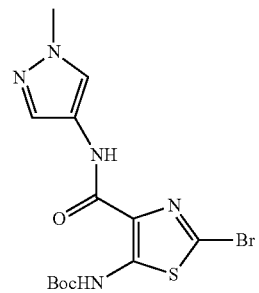

Coupling of 1-methyl-1H-pyrazol-4-amine and 2-bromo-5-(tert-butoxycarbonylamino)thiazole-4-carboxylic acid gave tert-butyl 2-bromo-4-(1-methyl-1H-pyrazol-4-ylcarbamoyl)thiazol-5-ylcarbamate (0.32 g, 74%). $^1$H NMR (400 MHz, $CDCl_3$) δ 10.31 (s, 1H), 8.62 (s, 1H), 7.91 (s, 1H), 7.54 (s, 1H), 3.90 (s, 3H), 1.53 (s, 9H)

Step 2

Following Example 278, Suzuki coupling of tert-butyl 2-bromo-4-(1-methyl-1H-pyrazol-4-ylcarbamoyl)thiazol-5-ylcarbamate and 3-(4-morpholinomethyl)phenylboronic acid pinacol ester gave 356 as an off-white solid (31 mg, 36% over two steps). $^1$H NMR (400 MHz, d$_6$-DMSO) δ 9.80 (s, 1H), 7.98 (s, 1H), 7.80-7.73 (m, 2H), 7.65 (s, 1H), 7.49-7.38 (m, 3H), 7.35 (d, J=7.6 Hz, 1H), 3.82 (s, 3H), 3.60 (t, J=4.5 Hz, 4H), 3.53 (s, 2H), 2.45-2.33 (m, 4H). LCMS (ES+) m/z 399 (M+1)

Example 357

(R)-5-amino-N-(5-(4-aminoazepan-1-yl)-1-methyl-1H-pyrazol-4-yl)-2-(5-fluoro-2-hydroxyphenyl)thiazole-4-carboxamide 357

Following Example 278, Suzuki coupling of (R)-benzyl 1-(4-(5-amino-2-bromothiazole-4-carboxamido)-1-methyl-1H-pyrazol-5-yl)azepan-4-ylcarbamate and 5-fluoro-2-hydroxyphenylboronic acid gave 357 as a yellow solid (12 mg, 21% over two steps). $^1$H NMR (400 MHz, d$_6$-DMSO with D$_2$O) δ 7.80 (dd, J=10.1, 3.3 Hz, 1H), 7.42 (s, 1H), 6.94 (td, J=8.5, 3.4 Hz, 1H), 6.77 (dd, J=9.0, 4.9 Hz, 1H), 3.63 (s, 3H), 3.23-3.04 (m, 6H), 1.93-1.76 (m, 3H), 1.68-1.51 (m, 3H). LCMS (ES+) m/z 446 (M+1)

Example 358

(R)-5-Amino-N-(5-(4-aminoazepan-1-yl)-1-methyl-1H-pyrazol-4-yl)-2-(5-cyano-2-fluorophenyl)thiazole-4-carboxamide 358

Following the procedure for Example 323 starting with (R)-benzyl 1-(4-(5-tert-butoxycarbonyl-amino-2-bromothiazole-4-carboxamido)-1-methyl-1H-pyrazol-5-yl)azepan-4-ylcarbamate and 5-cyano-2-fluorophenylboronic acid gave 358 as a yellow solid (30 mg, 89%). $^1$H NMR (400 MHz, d$_6$-DMSO) δ 9.13 (s, 1H), 8.81 (dd, J=7.0, 2.2 Hz, 1H), 7.95-7.90 (m, 1H), 7.62 (dd, J=11.3, 8.6 Hz, 1H), 7.53 (s, 2H), 7.40 (s, 1H), 3.66 (s, 3H), 3.21-3.08 (m, 4H), 3.14-2.86 (m, 1H), 1.86-1.77 (m, 3H), 1.59-1.50 (m, 3H). LCMS (ES+) m/z 455 (M+1).

Example 359

(S)—N-(5-(4-aminoazepan-1-yl)-1-methyl-1H-pyrazol-4-yl)-5-fluoro-6-(2-fluorophenyl)picolinamide 359

Following procedures from Examples 141, (S)-benzyl 1-(4-amino-1-methyl-1H-pyrazol-5-yl)azepan-4-ylcarbamate was converted to 359. $^1$H NMR (400 MHz, DMSO) δ 8.23 (dd, J=8.6, 3.8 Hz, 1H), 8.09 (t, J=9.1 Hz, 1H), 7.81 (t, J=7.4 Hz, 1H), 7.67-7.55 (m, 2H), 7.50-7.34 (m, 2H), 3.65 (s, 3H), 3.18-2.99 (m, 5H), 2.91 (t, J=8.7 Hz, 1H), 1.85-1.62 (m, 3H), 1.61-1.34 (m, 3H). MS (ESI) m/z: 427.2 [M+H$^+$].

Example 360

5-amino-N-(5-((trans-4-aminocyclohexylamino)-1-methyl-1H-pyrazol-4-yl)-2-(2,6-difluorophenyl)thiazole-4-carboxamide 360

Following the procedures provided in Example 340, 360 was obtained. $^1$H NMR (400 MHz, DMSO) δ 8.83 (s, 1H), 7.64-7.38 (m, 4H), 7.26 (t, J=8.6 Hz, 2H), 4.53 (d, J=7.5 Hz, 1H), 3.60 (s, 3H), 2.72 (m, 1H), 1.80 (d, J=11.8 Hz, 2H), 1.71 (d, J=11.9 Hz, 2H), 1.19 (dd, J=23.9, 10.8 Hz, 2H), 0.98 (q, J=10.7 Hz, 2H). MS (ESI) m/z: 448.2 [M+H$^+$].

Example 361

5-amino-2-(2,6-difluorophenyl)-N-(5-(4-hydroxycyclohexyl)-1-methyl-1H-pyrazol-4-yl)thiazole-4-carboxamide 361

5-Amino-2-(2,6-difluorophenyl)-N-(1-methyl-5-(4-oxocyclohexyl)-1H-pyrazol-4-yl)thiazole-4-carboxamide (57 mg, 0.13 mmol), prepared according to the procedures provided in Example 347, was dissolved in methanol (2 mL). Sodium borohydride (15.1 mg, 0.40 mmol) was added. The mixture was stirred at RT for 1 h, quenched with sat. NaHCO3 and extracted with ethyl acetate three times. Combined organic layers were concentrated and purified via reverse phase HPLC to give 361. $^1$H NMR (400 MHz, DMSO) δ 8.69 (s, 1H), 7.61-7.48 (m, 2H), 7.46 (s, 2H), 7.26 (dd, J=14.5, 5.8 Hz, 2H), 4.57 (d, J=4.4 Hz, 1H), 3.76 (s, 3H), 3.50-3.34 (m, 1H), 3.02 (td, J=6.6, 4.0 Hz, 1H), 2.84-2.60 (m, 1H), 1.91 (d, J=9.9 Hz, 2H), 1.84-1.59 (m, 5H), 1.37-1.17 (m, 2H). MS (ESI) m/z: 434.2 [M+H$^+$].

Example 362

5-amino-N-(5-((trans-3-aminocyclohexylamino)-1-methyl-1H-pyrazol-4-yl)-2-(2,6-difluorophenyl)thiazole-4-carboxamide 362

Following the procedures provided in Examples 340 and 346, racemic 362 was obtained. The trans diastereoisomers were isolated via chiral preparative HPLC. $^1$H NMR (400 MHz, DMSO) δ 8.88 (s, 1H), 7.63-7.38 (m, 4H), 7.26 (t, J=8.6 Hz, 2H), 4.50 (d, J=8.0 Hz, 1H), 3.61 (s, 3H), 3.05 (d, J=3.1 Hz, 1H), 1.68-1.03 (m, 10H). MS (ESI) m/z: 448.2 [M+H$^+$].

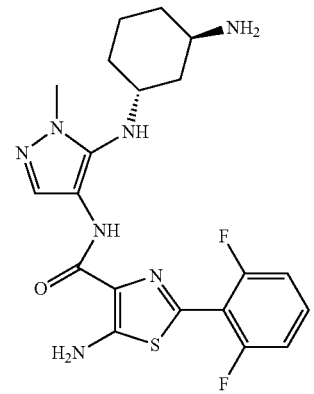

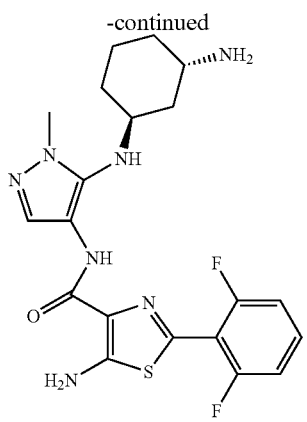

Example 363

5-amino-N-(1-benzyl-1H-pyrazol-4-yl)-2-(2,6-difluorophenyl)thiazole-4-carboxamide 363

Following the procedure for Example 304 starting with 1-benzyl-1H-pyrazol-4-amine gave 363 as a pale orange gum (114 mg, 37% over two steps) $^1$H NMR (400 MHz, $d_4$-MeOD) δ 8.06 (d, J=0.7 Hz, 1H), 7.71 (d, J=0.7 Hz, 1H), 7.52-7.42 (m, 1H), 7.40-7.26 (m, 5H), 7.17-7.08 (m, 2H), 5.32 (s, 2H). LCMS (ES+) m/z 412 (M+1)

Example 364

(R)-5-Amino-N-(5-(4-aminoazepan-1-yl)-1-ethyl-1H-pyrazol-4-yl)-2-(2-fluorophenyl)thiazole-4-carboxamide 364

Following the procedure for Example 241 starting with (R)-tert-butyl 2-(2-fluorophenyl)-4-(1-ethyl-5-(4-(2,2,2-trifluoroacetamido)azepan-1-yl)-1H-pyrazol-4-ylcarbamoyl)thiazol-5-ylcarbamate gave, after preparative HPLC, 364 as a brown solid (25 mg, 9%). $^1$H NMR (400 MHz, $d_6$-DMSO) δ 8.91 (s, 1H), 8.30-8.23 (m, 1H), 7.59 (s, 1H), 7.50-7.42 (m, 3H), 7.42-7.30 (m, 2H), 4.05-3.92 (m, 2H), 3.22-2.99 (m, 7H), 1.93-1.77 (m, 3H), 1.64-1.47 (m, 3H), 1.34 (t, J=7 Hz, 3H). LCMS (ES+) m/z 444.0 (M+1).

Example 365

(R)-5-Amino-N-(5-(4-aminoazepan-1-yl)-1-cyclopropyl-1H-pyrazol-4-yl)-2-(2-fluorophenyl)thiazole-4-carboxamide 365

Following the procedure for Example 241 starting with (R)-tert-butyl 2-(2-fluorophenyl)-4-(1-cyclopropyl-5-(4-(2,2,2-trifluoroacetamido)azepan-1-yl)-1H-pyrazol-4-ylcarbamoyl)thiazol-5-ylcarbamate gave, after preparative HPLC, 365 as a brown solid (147 mg, 58%). $^1$H-NMR (400 MHz, $d_6$-DMSO) δ 8.90 (s, 1H), 8.30-8.20 (m, 1H), 7.53 (s, 1H), 7.49-7.41 (m, 3H), 7.40-7.33 (m, 2H), 3.60-3.50 (m, 1H), 3.28-3.13 (m, 4H), 3.06 (s, 1H), 1.93-1.83 (m, 3H), 1.70-1.50 (m, 5H), 1.10-1.00 (m, 2H), 1.00-0.91 (m, 2H). LCMS (ES+) m/z 456.0 (M+1).

Example 366

(R)-5-Amino-N-(5-(4-aminoazepan-1-yl)-1-cyclopropylmethyl-1H-pyrazol-4-yl)-2-(2-fluorophenyl)thiazole-4-carboxamide 366

Following the procedure for Example 241 starting with (R)-tert-butyl 2-(2-fluorophenyl)-4-(1-cyclopropylmethyl-5-(4-(2,2,2-trifluoroacetamido)azepan-1-yl)-1H-pyrazol-4-ylcarbamoyl)thiazol-5-ylcarbamate gave, after preparative HPLC, 366 as the monoformate salt as a brown solid (109 mg, 40%). $^1$H-NMR (400 MHz, $d_6$-DMSO) δ 8.95 (s, 1H), 8.44 (s, 1H), 8.32-8.27 (m, 1H), 8.29 (m, 1H), 7.50-7.32 (m, 5H), 3.89-3.78 (m, 2H), 3.24-3.06 (m, 7H), 2.06-1.89 (m, 3H), 1.89-1.80 (m, 1H), 1.77-1.57 (m, 2H), 1.31-1.19 (m, 1H), 0.56-0.48 (m, 2H), 0.43-0.33 (m, 2H). LCMS (ES+) m/z 470.0 (M+1)

Example 367

5-amino-N-(1-(3-aminopropyl)-2,3-dihydro-1H-imidazo[1,2-b]pyrazol-7-yl)-2-(2,6-difluorophenyl)thiazole-4-carboxamide 367

Step 1: tert-Butyl 3-(7-nitro-2,3-dihydro-1H-pyrazolo[1,5-a]imidazol-1-yl)propylcarbamate

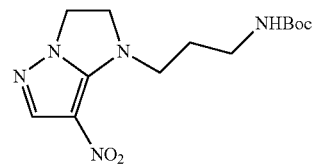

Sodium hydride (60% dispersion in mineral oil, 0.3 g, 7.5 mmol) was added portion-wise to a stirred solution of 2,3-dihydro-1H-pyrazolo[1,5-a]imidazole (0.68 g, 6.19 mmol) in anhydrous DMF (5 mL) at room temperature under a nitrogen atmosphere. The mixture was cooled to 0° C. and stirred for 15 min before a solution of tert-butyl 3-bromopropylcarbamate (1.47 g, 6.19 mmol) in DMF (5 mL) was added portion-wise over 5 min. The reaction was warmed to room temperature and stirred for 66 hr at room temperature. Water (5 mL) was added dropwise and the mixture was concentrated under reduced pressure. More water was added and the mixture was extracted with EtOAc. The combined organics were dried over MgSO$_4$ and concentrated under reduced pressure. The crude residue was purified via silica gel chromatography (0-100% EtOAc/isohexane) to give tert-butyl 3-(2,3-dihydro-1H-pyrazolo[1,5-a]imidazol-1-yl)propylcarbamate as an orange oil (0.51 g, 31%). To a solution of this oil in conc. H$_2$SO$_4$ at 0° C. was added conc. HNO$_3$ portionwise over 5 min. The reaction was warmed to room temperature and the mixture was stirred for 18 h. The mixture was re-cooled to 0° C., poured into ice water with stirring and basified with 40% aq. NaOH. The product was extracted into DCM and the combined organics were dried over MgSO$_4$ and concentrated under reduced pressure to afford 3-(7-nitro-2,3-dihydro-1H-pyrazolo[1,5-a]imidazol-1-yl)propan-1-amine as a brown gum. This gum was dissolved in DCM (30 mL) and DIPEA (1 mL) and di-tert-butyl dicarbonate (0.5 g, 2.3 mmol) were added. The mixture was stirred at room temperature for 2 hr. The solvents were removed under reduced pressure and the residue was purified via silica gel chromatography (0-100% EtOAc/isohexane) to give tert-butyl 3-(7-nitro-2,3-dihydro-1H-pyrazolo[1,5-a]imidazol-1-yl)propylcarbamate as a pale yellow gum (100 mg, 17% over two steps). $^1$H NMR (400 MHz, CDCl$_3$) δ 7.82 (s, 1H), 4.82 (s br, 1H), 4.26-4.16 (m, 2H), 4.12-4.00 (m, 2H), 3.84-3.72 (m, 2H), 3.23 (q, J=6.6 Hz, 2H), 1.89-1.78 (m, 2H), 1.44 (s, 9H)

Step 2

Following the procedure for Example 243 starting with tert-butyl 3-(7-nitro-2,3-dihydro-1H-pyrazolo[1,5-c]imidazol-1-yl)propylcarbamate gave 367 as the mono-formate salt as an off-white foam (58 mg, 46% over three steps). ¹H NMR (400 MHz, d₆-DMSO) δ 8.44 (s, 1H), 7.59-7.50 (m, 3H), 7.31-7.22 (m, 2H), 7.21 (s, 1H), 4.08 (t, J=7.8 Hz, 2H), 3.71 (t, J=7.8 Hz, 2H), 3.08 (t, J=6.4 Hz, 2H), 2.84 (t, J=6.4 Hz, 2H), 1.77-1.68 (m, 2H). LCMS (ES+) m/z 420 (M+1)

Example 368

(S)-5-amino-N-(5-(4-aminoazepan-1-yl)-1-methyl-1H-pyrazol-4-yl)-2-(2-fluorophenyl)pyrimidine-4-carboxamide 368

Following the procedures from Example 330, (S)-benzyl 1-(4-amino-1-methyl-1H-pyrazol-5-yl)azepan-4-ylcarbamate was converted to 368. ¹H NMR (400 MHz, DMSO) δ 8.63 (s, 1H), 8.38 (br, 1H), 8.12 (dd, J=8.2, 6.5 Hz, 1H), 7.66 (s, 1H), 7.52-7.45 (m, 1H), 7.36-7.30 (m, 2H), 7.07 (br, 2H), 3.69 (s, 3H), 3.19 (dd, J=8.8, 3.6 Hz, 10H), 2.04-1.76 (m, 3H), 1.67 (t, J=8.5 Hz, 3H). MS (ESI) m/z: 425.2 [M+H⁺].

Example 369

5-amino-N-(5-(4-aminocyclohexyl)-1-methyl-1H-pyrazol-4-yl)-2-(2,6-difluorophenyl)thiazole-4-carboxamide 369

Step 1: tert-butyl 2-(2,6-difluorophenyl)-4-(1-methyl-5-(4-oxocyclohexyl)-1H-pyrazol-4-ylcarbamoyl)thiazol-5-ylcarbamate

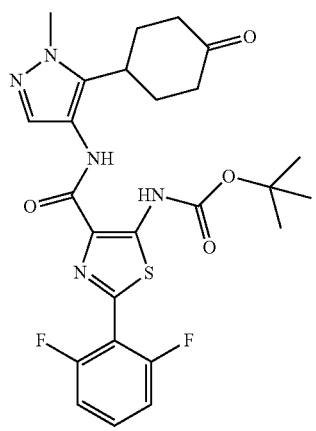 [SMILES: Cn1ncc(NC(=O)c2nc(-c3c(F)cccc3F)sc2NC(=O)OC(C)(C)C)c1C1CCC(=O)CC1]

In a 50 mL round bottom flask, 5-amino-2-(2,6-difluorophenyl)-N-(1-methyl-5-(4-oxocyclohexyl)-1H-pyrazol-4-yl)thiazole-4-carboxamide (235 mg, 0.54 mmol, prepared according to the procedures provided in Example 347 was dissolved in anhydrous THF (10 mL). Di-tert-butyl-di-carbonate (143 mg, 0.65 mmol) and DMAP (68 mg, 0.54 mmol) were added and the mixture was stirred at room temperature for 45 min. The reaction was concentrated and purified via flash chromatography (0 to 100% ethyl acetate in heptane) to give tert-butyl 2-(2,6-difluorophenyl)-4-(1-methyl-5-(4-oxocyclohexyl)-1H-pyrazol-4-ylcarbamoyl)thiazol-5-ylcarbamate (68 mg, 23%)

Step 2: tert-butyl 2-(2,6-difluorophenyl)-4-(5-(4-hydroxycyclohexyl)-1-methyl-1H-pyrazol-4-ylcarbamoyl)thiazol-5-ylcarbamate

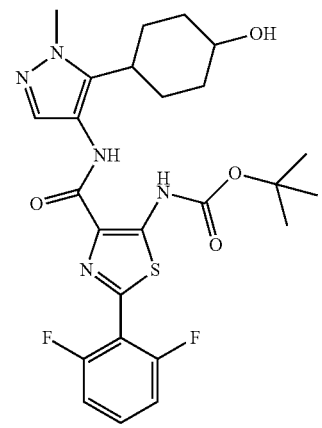 [SMILES: Cn1ncc(NC(=O)c2nc(-c3c(F)cccc3F)sc2NC(=O)OC(C)(C)C)c1C1CCC(O)CC1]

tert-Butyl 2-(2,6-difluorophenyl)-4-(1-methyl-5-(4-oxocyclohexyl)-1H-pyrazol-4-ylcarbamoyl)thiazol-5-ylcarbamate (68 mg, 0.13 mmol) was dissolved in methanol (3 mL) and sodium borohydride (16 mg, 0.39 mmol) was added. The mixture was stirred at RT for 30 min then quenched with sat. NaHCO3 and extracted with ethyl acetate three times. Combined organic layers were dried over sodium sulfate, filtered and concentrated to give the crude tert-butyl 2-(2,6-difluorophenyl)-4-(5-(4-hydroxycyclohexyl)-1-methyl-1H-pyrazol-4-ylcarbamoyl)thiazol-5-ylcarbamate (58 mg, 85%).

Step 3: tert-butyl 4-(5-(4-azidocyclohexyl)-1-methyl-1H-pyrazol-4-ylcarbamoyl)-2-(2,6-difluorophenyl)thiazol-5-ylcarbamate

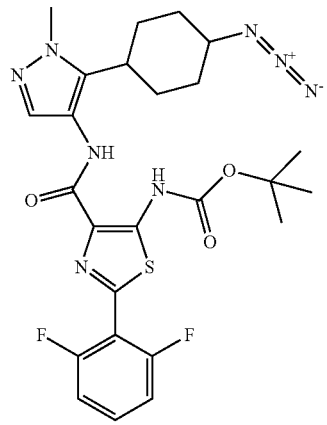 [SMILES: Cn1ncc(NC(=O)c2nc(-c3c(F)cccc3F)sc2NC(=O)OC(C)(C)C)c1C1CCC(N=[N+]=[N-])CC1]

tert-Butyl 2-(2,6-difluorophenyl)-4-(5-(4-hydroxycyclohexyl)-1-methyl-1H-pyrazol-4-ylcarbamoyl)thiazol-5-ylcarbamate (58 mg, 0.11 mmol) was dissolved in methylene chloride (3 mL) and THF (1.5 mL). Triethylamine (33 mg, 0.33 mmol) and methanesulfonyl chloride (19 mg, 0.16 mmol) were added and the mixture was stirred at room temperature for 2.5 h. The reaction was diluted with ethyl acetate (50 mL), washed with sat. sodium bicarbonate and brine and concentrated in vacuo (65 mg). The residue was dissolved in NMP (3.0 mL) and sodium azide (21.4 mg, 0.33 mmol) was added. The mixture was stirred at 85° C. overnight. After cooling to room temperature, the reaction was diluted with ethyl acetate, washed with water and brine, dried over sodium sulfate and concentrated in vacuo. The residue was purified via flash chromatography, eluted with 0 to 100% ethyl acetate in heptane to give tert-butyl 4-(5-(4-azidocyclohexyl)-1-methyl-1H-pyrazol-4-ylcarbamoyl)-2-(2,6-difluorophenyl)thiazol-5-ylcarbamate (18 mg, 30%).

Step 4: tert-butyl 4-(5-(4-aminocyclohexyl)-1-methyl-1H-pyrazol-4-ylcarbamoyl)-2-(2,6-difluorophenyl)thiazol-5-ylcarbamate

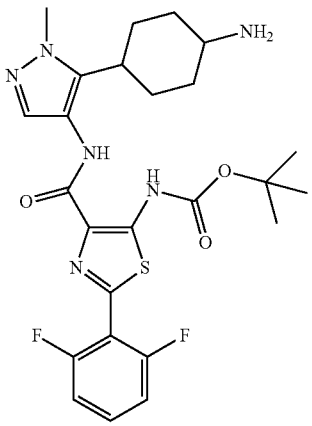

tert-Butyl 4-(5-(4-azidocyclohexyl)-1-methyl-1H-pyrazol-4-ylcarbamoyl)-2-(2,6-difluorophenyl)thiazol-5-ylcarbamate (18 mg, 0.032 mmol) was dissolved in THF (2 mL) and water (0.5 mL). Triphenylphosphine (21.5 mg, 0.083 mmol) was added and the mixture was heated at 60° C. overnight. After cooling to room temperature, the reaction was quenched with water and extracted with methylene chloride three times to give the crude product tert-butyl 4-(5-(4-aminocyclohexyl)-1-methyl-1H-pyrazol-4-ylcarbamoyl)-2-(2,6-difluorophenyl)thiazol-5-ylcarbamate.

Step 5 tert-Butyl 4-(5-(4-aminocyclohexyl)-1-methyl-1H-pyrazol-4-ylcarbamoyl)-2-(2,6-difluorophenyl)thiazol-5-ylcarbamate was stirred with 4.0M HCl in dioxane (5 mL) for 2 h. Solvent was removed in vacuo, and the residue was basified with sat. sodium bicarbonate and extracted with ethyl acetate 3x. Combined organic layers were concentrated and purified via reverse phase HPLC to give 369. $^1$H NMR (400 MHz, DMSO) δ 8.82 (s, 1H), 8.35 (s, 1H), 7.60-7.36 (m, 3H), 7.27 (t, J=8.7 Hz, 1H), 3.80 (s, 3H), 2.77 (t, J=12.3 Hz, 1H), 2.13-1.94 (m, 2H), 1.67 (dt, J=29.6, 13.3 Hz, 5H). MS (ESI) m/z: 433.2 [M+H$^+$].

Example 370

(S)-5-amino-N-(5-(azepan-4-ylamino)-1-methyl-1H-pyrazol-4-yl)-2-(2,6-difluorophenyl)thiazole-4-carboxamide 370

Step 1: (S)-tert-Butyl 4-(1-methyl-4-nitro-1H-pyrazol-5-ylamino)azepane-1-carboxylate

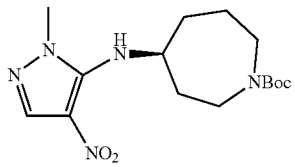 [SMILES: Cn1ncc([N+](=O)[O-])c1N[C@H]1CCCN(C(=O)OC(C)(C)C)CC1]

Following the procedure for Example 332 starting with (S)-tert-butyl 4-(benzyloxycarbonylamino)azepane-1-carboxylate and 5-chloro-1-methyl-4-nitro-1H-pyrazole gave (S)-tert-butyl 4-(1-methyl-4-nitro-1H-pyrazol-5-ylamino)azepane-1-carboxylate as a yellow viscous oil (103 mg, 49%). $^1$H NMR (400 MHz, CDCl$_3$) δ 7.90 (s, 1H), 6.60-6.50 (m, 1H), 3.80 (s, 3H), 3.79-3.67 (m 1H), 3.60-3.52 (m, 1H), 3.49-3.44 (m, 1H), 3.44-3.22 (m, 2H), 2.25-2.10 (m, 1H), 2.05-1.62 (m, 5H), 1.48 (s, 9H)

Step 2

Following the procedure for Example 243 starting with (S)-tert-butyl 4-(1-methyl-4-nitro-1H-pyrazol-5-ylamino)azepane-1-carboxylate gave 370 as a cream solid (35 mg, 27% over three steps). $^1$H NMR (400 MHz, CDCl$_3$) δ 8.46 (s, 1H), 8.41 (s br, 1H), 7.46 (s, 1H), 7.34-7.30 (m, 1H), 7.06-6.98 (m, 3H), 6.21 (s br, 1H), 3.73 (s, 3H), 3.28-3.20 (m, 2H), 3.15-3.00 (m, 2H), 3.00-2.90 (m, 1H), 2.15-2.08 (m, 1H), 2.05-1.85 (m, 3H), 1.70-1.60 (m, 2H). Alkyl NH not seen. LCMS (ES+) m/z 448 (M+1)

Example 371

5-amino-N-(5-(2-(aminomethyl)morpholino)-1-methyl-1H-pyrazol-4-yl)-2-(2,6-difluorophenyl)thiazole-4-carboxamide 371

Step 1: tert-Butyl (4-(1-methyl-4-nitro-1H-pyrazol-5-yl)morpholin-2-yl)methylcarbamate

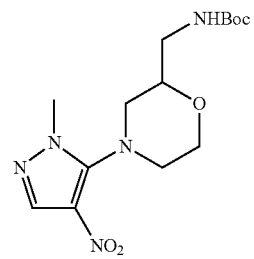 [SMILES: Cn1ncc([N+](=O)[O-])c1N1CCOC(CNC(=O)OC(C)(C)C)C1]

Reaction of 5-chloro-1-methyl-4-nitro-1H-pyrazole and tert-butyl morpholin-2-ylmethylcarbamate gave tert-butyl (4-(1-methyl-4-nitro-1H-pyrazol-5-yl)morpholin-2-yl)methylcarbamate as a yellow oil (196 mg, 93%). $^1$H NMR (400 MHz, CDCl$_3$) δ 8.04 (s, 1H), 4.92 (s br, 1H), 4.00 (dd, J=11.3, 2.9 Hz, 1H), 3.90-3.68 (m, 5H), 3.57 (td, J=11.6, 3.2 Hz, 1H), 3.38-3.24 (m, 2H), 3.15 (ddd, J=14.1, 7.1, 5.1 Hz, 1H), 2.86 (d, J=11.8 Hz, 1H), 2.77 (d, J=11.8 Hz, 1H), 1.45 (s, 9H)

Step 2 tert-Butyl (4-(1-methyl-4-nitro-1H-pyrazol-5-yl)morpholin-2-yl)methylcarbamate was deprotected under acidic conditions. Following the procedure for Example 243 starting with (4-(1-methyl-4-nitro-1H-pyrazol-5-yl)morpholin-2-yl)methanamine gave 371 as a cream solid (102 mg, 41% over three steps). $^1$H NMR (400 MHz, CDCl$_3$) δ 8.47 (s, 1H), 7.74 (s, 1H), 7.39-7.24 (m, 1H), 7.07-6.99 (m, 2H), 6.15 (s, 2H), 3.99 (dd, J=11.3, 2.8 Hz, 1H), 3.87-3.73 (m, 4H), 3.62 (ddt, J=9.5, 7.3, 3.2 Hz, 1H), 3.33 (td, J=11.3, 3.2 Hz, 1H), 3.12-2.87 (m, 3H), 2.85-2.70 (m, 2H). LCMS (ES+) m/z 450 (M+1)

Example 372

(R)-5-amino-N-(5-(4-aminoazepan-1-yl)-1-methyl-1H-pyrazol-4-yl)-2-(5-chloro-2-fluorophenyl)thiazole-4-carboxamide 372

Following the procedures from Examples 140, (R)-benzyl 1-(4-amino-1-methyl-1H-pyrazol-5-yl)azepan-4-ylcarbamate from Example 16 was converted to Boc and Cbz protected intermediate. This intermediate was heated with 3N aqueous HCl (12 mL) for 4 h and concentrated under reduced pressure. The residue was basified with sat. sodium bicarbonate, extracted with ethyl acetate, and purified via reverse phase PHLC to give 372. $^1$H NMR (400 MHz, DMSO) δ 9.04 (s, 1H), 8.33 (dd, J=6.5, 2.6 Hz, 1H), 7.53-7.35 (m, 5H), 3.65 (s, 3H), 3.22-2.91 (m, 6H), 1.83 (d, J=10.6 Hz, 4H), 1.69-1.40 (m, 5H). MS (ESI) m/z: 464.2 [M+H$^+$].

Example 373

(R)-5-amino-N-(5-(4-aminoazepan-1-yl)-1-methyl-1H-pyrazol-4-yl)-2-(3-bromo-2-fluorophenyl)thiazole-4-carboxamide 373

Following the procedures from Example 372, 373 was obtained. $^1$H NMR (400 MHz, DMSO) δ 8.92 (s, 1H), 8.25 (t, J=6.9 Hz, 1H), 7.73 (t, J=6.7 Hz, 1H), 7.49 (s, 3H), 7.30 (t, J=8.0 Hz, 1H), 6.59 (s, 1H), 3.65 (s, 3H), 3.13 (dd, J=34.5, 22.1 Hz, 6H), 1.94-1.74 (m, 3H), 1.70-1.39 (m, 3H). MS (ESI) m/z: 508.1/510.1 [M+H$^+$].

Example 374

(S)-5-amino-2-(2,6-difluorophenyl)-N-(5-(4-hydroxyazepan-1-yl)-1-methyl-1H-pyrazol-4-yl)thiazole-4-carboxamide 374

Example 375

(R)-5-amino-2-(2,6-difluorophenyl)-N-(5-(4-hydroxyazepan-1-yl)-1-methyl-1H-pyrazol-4-yl)thiazole-4-carboxamide 375

The racemic compound 189 from Example 189 was resolved on chiral preparative HPLC to separate the (S) enantiomer 374 and the (R) enantiomer 375. $^1$H NMR (400 MHz, DMSO) δ 8.63 (s, 1H), 7.58-7.39 (m, 4H), 7.26 (t, J=8.7 Hz, 2H), 4.43 (d, J=3.7 Hz, 1H), 3.91-3.74 (m, 1H), 3.64 (s, 3H), 3.24-3.09 (m, 2H), 3.09-2.93 (m, 2H), 2.07 (s, 1H), 1.87 (dd, J=18.2, 10.9 Hz, 3H), 1.75-1.46 (m, 3H). MS (ESI) m/z: 449.2 [M+H$^+$].

Example 376

5-amino-N-(5-(4-hydroxyazepan-1-yl)-1-methyl-1H-pyrazol-4-yl)-2-(pyridin-2-yl)thiazole-4-carboxamide 376

Following the procedures from Example 140, 1-(4-amino-1-methyl-1H-pyrazol-5-yl)azepan-4-ol, prepared according to the procedures from Example 189, and 5-(tert-butoxycarbonylamino)-2-(yridine-2-yl)thiazole-4-carboxylic acid from Example 31 were converted to 376. $^1$H NMR (400 MHz, DMSO) δ 8.79 (s, 1H), 8.54 (d, J=4.7 Hz, 1H), 8.14 (d, J=7.9 Hz, 1H), 7.89 (t, J=7.6 Hz, 1H), 7.54 (m, 3H), 7.43-7.34 (m, 1H), 4.58 (d, J=3.6 Hz, 1H), 3.90-3.82 (m, 1H), 3.66 (s, 3H), 3.24-2.99 (m, 4H), 2.00-1.55 (m, 6H). MS (ESI) m/z: 414.2 [M+H$^+$].

Example 377

(R)-5-amino-N-(5-(4-aminoazepan-1-yl)-1-methyl-1H-pyrazol-4-yl)-2-(2,3-difluorophenyl)thiazole-4-carboxamide 377

Following the procedures from Example 140, (R)-benzyl 1-(4-amino-1-methyl-1H-pyrazol-5-yl)azepan-4-ylcarbamate from Example 16 and 5-(tert-butoxycarbonylamino)-2-(2,3-difluorophenyl)thiazole-4-carboxylic acid from Example 42 were converted to 377. $^1$H NMR (400 MHz, DMSO) δ 8.92 (br, 1H), 8.06 (t, J=7.2 Hz, 1H), 7.62-7.39 (m, 4H), 7.34 (dd, J=13.1, 7.8 Hz, 1H), 3.66 (s, 4H), 3.20-3.01 (m, 5H), 1.92-1.76 (m, 3H), 1.71-1.47 (m, 3H). MS (ESI) m/z: 448.2 [M+H$^+$].

Example 378

5-amino-N-(5-(trans-3-aminocyclohexyl)-1-methyl-1H-pyrazol-4-yl)-2-(2,6-difluorophenyl)thiazole-4-carboxamide 378

Step 1: tert-butyl N-[3-(2-methyl-4-nitro-pyrazol-3-yl)cyclohex-2-en-1-yl]carbamate

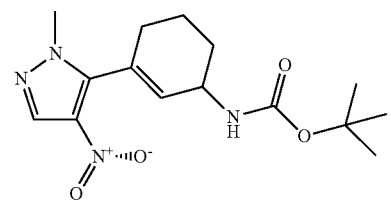

5-Chloro-1-methyl-4-nitropyrazole (100 mg, 0.62 mmol), tert-butyl N-[3-(4,4,5,5-tetramethyl-1,3,2-dioxaborolan-2-yl)cyclohex-2-en-1-yl]carbamate (240 mg, 0.74 mmol), dichloro[1,1'-bis(diphenylphosphino)ferrocene]palladium (II) (45 mg, 0.061 mmol), a 1M solution of Na$_2$CO$_3$ (0.93 mL), a 1M solution of potassium acetate (0.93 mL) and acetonitrile (6 mL) were charged in a microwave reaction vial, The mixture was irradiated to 140° C. with a microwave for 30 min and cooled to room temperature. It was filtered through Celite and thoroughly washed with methanol. The filtrate was concentrated and the residue was purified via flash chromatography, 0 to 100% ethyl acetate in heptane to give tert-butyl N-[3-(2-methyl-4-nitro-pyrazol-3-yl)cyclohex-2-en-1-yl]carbamate (98 mg, 49%)

Step 2: tert-butyl N-[3-(4-amino-2-methyl-pyrazol-3-yl)cyclohexyl]carbamate

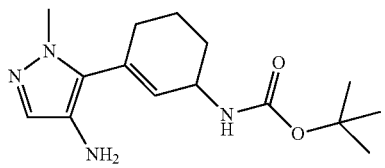 [SMILES: Cn1ncc(N)c1C1=CC(NC(=O)OC(C)(C)C)CCC1]

tert-Butyl N-[3-(2-methyl-4-nitro-pyrazol-3-yl)cyclohex-2-en-1-yl]carbamate was dissolved in methanol (100 mL) and hydrogenated on H-Cube at 60° C. and 60 bar hydrogen pressure to give tert-butyl N-[3-(4-amino-2-methyl-pyrazol-3-yl)cyclohexyl]carbamate.

Step 3: tert-butyl-3-(4-(5-Boc-amino-2-(2,6-difluorophenyl)thiazole-4-carboxamido)-1-methyl-1H-pyrazol-5-yl)cyclohexylcarbamate

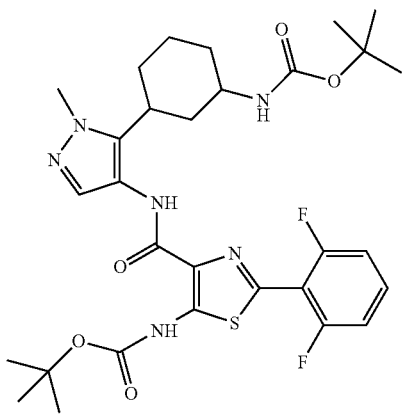 [SMILES: Cn1ncc(NC(=O)c2nc(-c3c(F)cccc3F)sc2NC(=O)OC(C)(C)C)c1C1CCCC(NC(=O)OC(C)(C)C)C1]

Following the procedures from Example 140, tert-butyl N-[3-(4-amino-2-methyl-pyrazol-3-yl)cyclohexyl]carbamate and 5-(tert-butoxycarbonylamino)-2-(2,6-difluorophenyl)thiazole-4-carboxylic acid from Example 25 were converted to tert-butyl-3-(4-(5-Boc-amino-2-(2,6-difluorophenyl)thiazole-4-carboxamido)-1-methyl-1H-pyrazol-5-yl)cyclohexylcarbamate. Trans and cis diastereoisomers were separated by flash chromatography eluted with 0 to 100% ethyl acetate in heptane. The Rf value for trans and cis isomers were 0.64 and 0.53, respectively.

Step 4

The above trans isomer was stirred with 4.0M HCl in dioxane (4 mL) for 3 h. The reaction was concentrated and the residue was basified with saturated sodium bicarbonate and extracted with ethyl acetate 3×. The combined organic layers were dried over sodium sulfate, filtered and concentrated. The crude product was further purified on reverse phase HPLC to give 378. $^1$H NMR (400 MHz, DMSO) δ 8.40 (s, 1H), 7.60-7.39 (m, 1H), 7.27 (t, J=8.7 Hz, 2H), 3.78 (s, 3H), 3.50-3.45 m, 1H), 3.30-3.20 (m, 1H), 2.04-1.44 (m, 8H). MS (ESI) m/z: 433.2 [M+H$^+$]

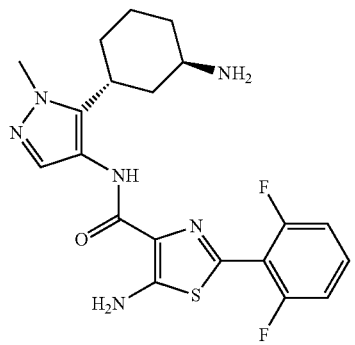

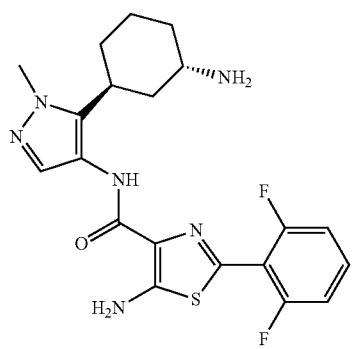

Example 379

5-amino-N-(5-(cis-3-aminocyclohexyl)-1-methyl-1H-pyrazol-4-yl)-2-(2,6-difluorophenyl)thiazole-4-carboxamide 379

The cis isomer from the preparation of Example 378 was stirred with 4.0M HCl in dioxane (4 mL) for 3 h. The reaction was concentrated and the residue was basified with saturated sodium bicarbonate and extracted with ethyl acetate 3×. The combined organic layers were dried over sodium sulfate, filtered and concentrated. The crude product was further purified on reverse phase HPLC to give 379. $^1$H NMR (400 MHz, DMSO) δ 8.70 (s, 1H), 7.62-7.37 (m, 4H), 7.26 (t, J=8.8 Hz, 2H), 3.77 (s, 3H), 2.84 (t, J=12.4 Hz, 1H), 2.74-2.60 (m, 1H), 1.85-1.70 (m, 4H), 1.62-1.50 (m, 1H), 1.45-1.35 (m, 2H), 1.08-0.98 (m, 1H). MS (ESI) m/z: 433.2 [M+H$^+$]

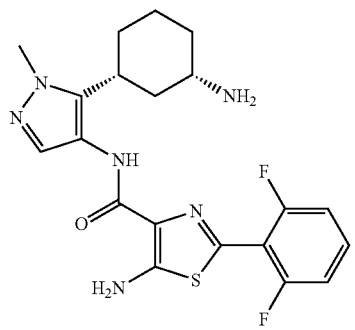

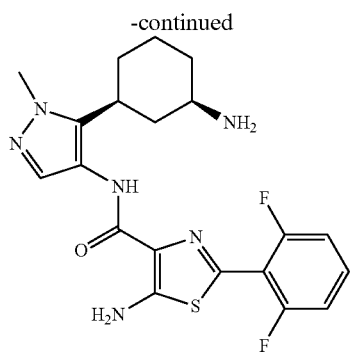

Example 380

(R)-5-amino-N-(5-(4-aminoazepan-1-yl)-1-methyl-1H-pyrazol-4-yl)-2-(pyridin-2-yl)thiazole-4-carboxamide 380

Following the procedures from Example 140, (R)-benzyl 1-(4-amino-1-methyl-1H-pyrazol-5-yl)azepan-4-ylcarbamate from Example 16 and 5-(tert-butoxycarbonylamino)-2-(2,6-difluorophenyl)thiazole-4-carboxylic acid from Example 25 were converted to 380. $^1$H NMR (400 MHz, DMSO) δ 8.85 (s, 1H), 8.54 (d, J=4.7 Hz, 1H), 8.14 (d, J=8.0 Hz, 1H), 7.91 (td, J=7.8, 1.5 Hz, 1H), 7.62-7.43 (m, 3H), 7.38 (dd, J=6.9, 5.2 Hz, 1H), 3.65 (s, 3H), 3.22-2.98 (m, 5H), 1.99-1.74 (m, 3H), 1.72-1.49 (m, 3H). MS (ESI) m/z: 413.2 [M+H$^+$]

Example 381

(R)-5-amino-N-(5-(4-aminoazepan-1-yl)-1-methyl-1H-pyrazol-4-yl)-2-(2-fluoro-3-methylphenyl)thiazole-4-carboxamide 381

Boc and Cbz protected intermediate of 373 from Example 373, was subjected to standard Suzuki conditions, following procedures in Example 141 with methyl boronic acid to give the methylated intermediate. Deprotection according to procedures for Example 373, gave 381. $^1$H NMR (400 MHz, DMSO) δ 8.89 (s, 1H), 8.07 (t, J=7.2 Hz, 1H), 7.52 (s, 1H), 7.40 (s, 2H), 7.32 (t, J=6.9 Hz, 1H), 7.22 (t, J=7.7 Hz, 1H), 6.74 (s, 1H), 3.65 (s, 4H), 3.23-2.95 (m, 8H), 2.31 (s, 3H), 1.95-1.72 (m, 4H), 1.72-1.44 (m, 4H). MS (ESI) m/z: 444.2 [M+H$^+$].

Example 382

(R)-5-amino-N-(5-(4-aminoazepan-1-yl)-1-methyl-1H-pyrazol-4-yl)-2-(3-cyclopropyl-2-fluorophenyl)thiazole-4-carboxamide 382

Step 1: tricyclopropylbismuthane

Trichlorobismuthane (1.25 g; 3.96 mmol) was dissolved in anhydrous THF (50 mL) and cooled to −10° C. Cyclopropylmagnesium bromide (0.5M in THF, 15 mmol; 30 mL) was added via dropping funnel over 30 min, keeping the temperature at −10° C. The reaction mixture was stirred at RT for 1 h then heated at 70° C. for 30 min, at which time a black precipitate was observed. After cooling to RT, the solution was cannulated under nitrogen over a degassed biphasic solution of brine (100 ml) and ether (100 ml). The heterogeneous solution was stirred for 5 min, transferred to a separatory funnel and diluted with ether (50 ml). The organic phase was collected, dried over sodium sulfate, filtered and concentrated under reduced pressure to give a yellow oily solid. Ether (25 ml) was added followed by hexane (25 ml). The mixture was sonicated, cooled to 0° C., and filtered to collect the light yellow solid, tricyclopropylbismuthane (770 mg, 58%).

Step 2: (R)-tert-butyl 4-(5-(4-Cbz-aminoazepan-1-yl)-1-methyl-1H-pyrazol-4-ylcarbamoyl)-2-(3-cyclopropyl-2-fluorophenyl)thiazol-5-ylcarbamate

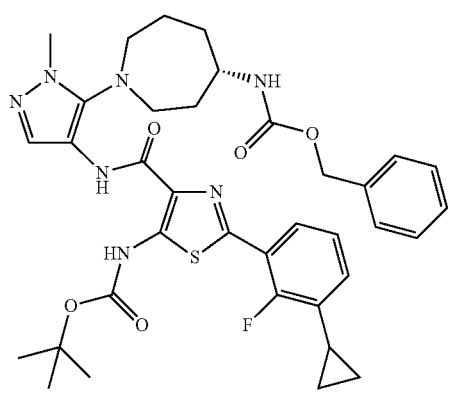 [SMILES: Cn1ncc(NC(=O)c2nc(-c3cccc(C4CC4)c3F)sc2NC(=O)OC(C)(C)C)c1N1CCC[C@H](NC(=O)OCc2ccccc2)CC1]

In a 40 mL reaction vial, the Boc and Cbz protected intermediate of compound 373, tert-butyl N-[4-[[5-[(4R)-4-(benzyloxycarbonylamino)azepan-1-yl]-1-methyl-pyrazol-4-yl]carbamoyl]-2-(3-bromo-2-fluoro-phenyl)thiazol-5-yl]carbamate (200 mg; 0.2693 mmol):

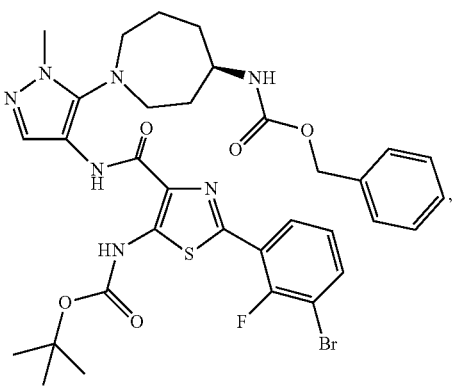 [SMILES: Cn1ncc(NC(=O)c2nc(-c3cccc(Br)c3F)sc2NC(=O)OC(C)(C)C)c1N1CCC[C@@H](NC(=O)OCc2ccccc2)CC1]

tricyclopropylbismuthane (134 mg, 0.4039 mmol), palladium(0) tetrakis(triphenylphosphine) (31 mg, 0.027 mmol), potassium carbonate (75 mg, 0.54 mmol) and DMF (3 mL) were mixed. The reaction vial was vacuum purged and filled with nitrogen. The vial was sealed and heated at 90° C. overnight. The mixture was cooled to RT, diluted with sat. sodium bicarbonate and extracted with ethyl acetate (2×). The combined organic layers were back washed with sat. sodium bicarbonate and brine, dried over sodium sulfate, filtered and concentrated. The crude product was purified via flash chromatography, eluted with 0 to 7% methanol in DCM to give (R)-tert-butyl 4-(5-(4-Cbz-aminoazepan-1-yl)-1-methyl-1H-pyrazol-4-ylcarbamoyl)-2-(3-cyclopropyl-2-fluorophenyl)thiazol-5-ylcarbamate (104 mg, 55%).

Step 3

(R)-tert-butyl 4-(5-(4-Cbz-aminoazepan-1-yl)-1-methyl-1H-pyrazol-4-ylcarbamoyl)-2-(3-cyclopropyl-2-fluorophenyl)thiazol-5-ylcarbamate was heated with 3N aqueous HCl (6 mL) overnight. Only Boc deprotection was observed. The reaction was concentrated under reduced pressure and the residue was re-dissolved in methanol (100 mL). The methanol solution was hydrogenated on H-Cube at 40° C. and 30 bar hydrogen pressure. The solution was concentrated and purified via reverse phase PHLC to give 382. $^1$H NMR (400 MHz, DMSO) δ 8.89 (br, 1H), 8.03 (t, J=6.9 Hz, 1H), 7.52 (s, 1H), 7.40 (br, 2H), 7.21 (t, J=7.8 Hz, 1H), 7.02 (t, J=6.9 Hz, 1H), 3.65 (s, 3H), 3.22-2.95 (m, 5H), 2.12 (ddd, J=13.7, 8.5, 5.2 Hz, 2H), 1.84 (t, J=9.5 Hz, 3H), 1.70-1.42 (m, 3H), 1.05-0.93 (m, 2H), 0.82-0.68 (m, 2H). MS (ESI) m/z: 470.2 [M+H$^+$].

Example 383

(R)-5-amino-N-(5-(4-aminoazepan-1-yl)-1-methyl-1H-pyrazol-4-yl)-2-(3-ethyl-2-fluorophenyl)thiazole-4-carboxamide 383

Step 1: tert-butyl N-[4-[[5-[(4R)-4-(benzyloxycarbonylamino)azepan-1-yl]-1-methyl-pyrazol-4-yl]carbamoyl]-2-(2-fluoro-3-vinyl-phenyl)thiazol-5-yl]carbamate

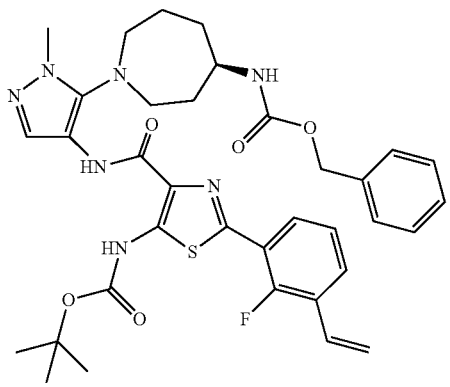 [SMILES: C=Cc1cccc(-c2nc(C(=O)Nc3cnn(C)c3N3CCC[C@@H](NC(=O)OCc4ccccc4)CC3)c(NC(=O)OC(C)(C)C)s2)c1F]

The Boc and Cbz protected intermediate of compound 373 from Example 373, tert-butyl N-[4-[[5-[(4R)-4-(benzyloxycarbonylamino)azepan-1-yl]-1-methyl-pyrazol-4-yl]carbamoyl]-2-(3-bromo-2-fluoro-phenyl)thiazol-5-yl]carbamate, (158 mg; 0.213 mmol), 4,4,5,5-tetramethyl-2-vinyl-1,3,2-dioxaborolane (98 mg, 0.11 mmol), dichloro[1,1'-bis(diphenylphosphino)ferrocene]palladium(II) (16 mg, 0.021 mmol), a 1M solution of Na$_2$CO$_3$ (0.32 mL), a 1M solution of potassium acetate (0.32 mL) and acetonitrile (3.5 mL) were charged in a microwave reaction vial. The mixture was irradiated to 130° C. with a microwave for 30 min and cooled to room temperature. It was filtered through Celite and thoroughly washed with methanol. The filtrate was concentrated and the residue was purified via flash chromatography, 0 to 100% ethyl acetate in heptane to give tert-butyl N-[4-[[5-[(4R)-4-(benzyloxycarbonylamino)azepan-1-yl]-1-methyl-pyrazol-4-yl]carbamoyl]-2-(2-fluoro-3-vinyl-phenyl)thiazol-5-yl]carbamate.

Step 2 tert-butyl N-[4-[[5-[(4R)-4-(benzyloxycarbonylamino)azepan-1-yl]-1-methyl-pyrazol-4-yl]carbamoyl]-2-(2-fluoro-3-vinyl-phenyl)thiazol-5-yl]carbamate (51 mg, 0.086 mmol) was dissolved in methanol (50 mL) and hydrogenated on H-Cube at 60° C. and 50 bar hydrogen pressure to reduce the double bond. The solution was concentrated and the residue was dissolved in DCM (5 mL). 1.0M solution of boron tribromide in methylene chloride (0.35 ml, 0.35 mmol) was added and the mixture was stirred for 2 h. The solvent was distilled off and the residue was purified via reverse phase HPLC to afford 383. MS (ESI) m/z: 458.3 [M+H$^+$].

Example 384

5-amino-N-(1-(2,2-difluoroethyl)-1H-pyrazol-4-yl)-2-(2,6-difluorophenyl)thiazole-4-carboxamide 384

Step 1: 1-(2,2-difluoroethyl)-4-nitro-pyrazole

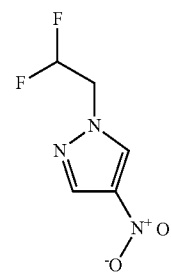

4-Nitro-1H-pyrazole (150 mg, 1.33 mmol) and 1,1-difluoro-2-iodo-ethane (509 mg, 2.65 mmol) were dissolved in acetonitrile (5 mL). Cesium carbonate (917 mg, 2.79 mmol) was added and the mixture was heated at 100° C. for 40 min. After cooling down to room temperature, the reaction was diluted with sat. ammonium chloride and extracted with methylene chloride (3×). The combined organic layers were dried over sodium sulfate, filtered and the filtrate was concentrated to give 1-(2,2-difluoroethyl)-4-nitro-pyrazole (237 mg) as a light yellow solid.

Step 2: 1-(2,2-difluoroethyl)pyrazol-4-amine

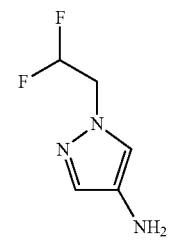

1-(2,2-difluoroethyl)-4-nitro-pyrazole (235 mg, 1.33 mmol) was dissolved in methanol (50 mL) and hydrogenated on H-Cube at 50° C. and 40 bar pressure to give 1-(2,2-difluoroethyl)pyrazol-4-amine (183 mg, 93%).

Step 3: tert-butyl 4-(1-(2,2-difluoroethyl)-1H-pyrazol-4-ylcarbamoyl)-2-(2,6-difluorophenyl)thiazol-5-ylcarbamate

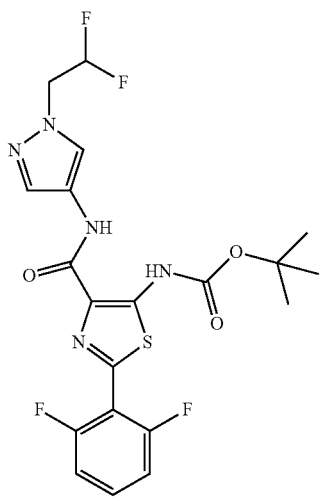 [SMILES: CC(C)(C)OC(=O)Nc1sc(-c2c(F)cccc2F)nc1C(=O)Nc1cnn(CC(F)F)c1]

1-(2,2-difluoroethyl)pyrazol-4-amine (183 mg, 1.24 mmol) and 5-(tert-butoxycarbonylamino)-2-(2,6-difluorophenyl)thiazole-4-carboxylic acid from Example 25 were converted to tert-butyl 4-(1-(2,2-difluoroethyl)-1H-pyrazol-4-ylcarbamoyl)-2-(2,6-difluorophenyl)thiazol-5-ylcarbamate according to the procedure provided in Example 140.

Step 4 tert-butyl 4-(1-(2,2-difluoroethyl)-1H-pyrazol-4-ylcarbamoyl)-2-(2,6-difluorophenyl)thiazol-5-ylcarbamate was stirred with 4.0M HCl in dioxane overnight. The reaction was concentrated and the residue was basified with sat. sodium bicarbonate. The mixture was extracted with ethyl acetate (3×), concentrated and purified on reverse phase HPLC to afford the title compound 384. $^1$H NMR (400 MHz, DMSO) δ 9.82 (s, 1H), 8.10 (s, 1H), 7.74 (s, 1H), 7.62-7.39 (m, 3H), 7.26 (dd, J=14.3, 5.9 Hz, 2H), 6.32 (tt, J=54.9, 3.7 Hz, 1H), 4.58 (td, J=15.1, 3.8 Hz, 2H). MS (ESI) m/z: 386.3 [M+H$^+$].

Example 385

5-amino-2-(2,6-difluorophenyl)-N-(1-propyl-1H-pyrazol-4-yl)thiazole-4-carboxamide 385

Following the procedures provided in Example 384, 1-propyl-1H-pyrazol-4-amine and 5-(tert-butoxycarbonylamino)-2-(2,6-difluorophenyl)thiazole-4-carboxylic acid from Example 25 were converted to 385. $^1$H NMR (400 MHz, DMSO) δ 9.70 (s, 1H), 7.98 (s, 1H), 7.65 (s, 1H), 7.62-7.42 (m, 3H), 7.26 (dd, J=14.2, 5.8 Hz, 2H), 4.01 (t, J=6.9 Hz, 2H), 1.76 (dd, J=14.4, 7.2 Hz, 2H), 0.83 (t, J=7.4 Hz, 3H). MS (ESI) m/z: 364.1 [M+H$^+$].

Example 386

5-amino-2-(2,6-difluorophenyl)-N-(1-(2-hydroxyethyl)-1H-pyrazol-4-yl)thiazole-4-carboxamide 386

Following the procedures provided in Example 384, 2-(4-amino-1H-pyrazol-1-yl)ethanol and 5-(tert-butoxycarbonylamino)-2-(2,6-difluorophenyl)thiazole-4-carboxylic acid from Example 25 were converted to 386. MS (ESI) m/z: 366.1 [M+H$^+$]

Example 387

N-(5-(1,4-diazepan-1-yl)-1-methyl-1H-pyrazol-4-yl)-3-amino-6-(2-fluorophenyl)picolinamide 387

Following the procedures as described in Example 23 and starting with tert-butyl 1,4-diazepane-1-carboxylate, 387 was obtained as a white solid (22 mg, 23%) over two steps. $^1$H NMR (400 MHz, DMSO) δ 9.97 (s, 1H), 8.07 (dd, J=11.2, 4.9 Hz, 1H), 7.73 (dd, J=8.7, 2.2 Hz, 1H), 7.56 (d, J=12.9 Hz, 2H), 7.50-7.27 (m, 4H), 7.07 (s, 2H), 6.50 (d, J=18.1 Hz, 1H), 3.69 (d, J=18.7 Hz, 3H), 3.42-3.35 (m, 2H), 3.25 (t, J=5.9 Hz, 2H), 3.19-3.03 (m, 4H), 1.93 (dd, J=10.8, 5.8 Hz, 2H). ESIMS m/z=410.1 (M+1).

Example 388

3-amino-6-(2-fluorophenyl)-N-(1-methyl-5-(1H-pyrrolo[3,4-c]pyridin-2(3H,3aH,4H,5H,6H,7H,7aH)-yl)-1H-pyrazol-4-yl)picolinamide 388

Following the procedures as described in Example 23 and starting with tert-butyl hexahydro-1H-pyrrolo[3,4-c]pyridine-5(6H)-carboxylate, 388 was obtained as a white solid (21 mg, 25%) over two steps. $^1$H NMR (400 MHz, DMSO) δ 8.63 (s, 1H), 7.56-7.42 (m, 4H), 7.26 (t, J=8.7 Hz, 2H), 3.63 (s, 3H), 3.39-3.33 (m, 2H), 3.23-3.17 (m, 1H), 3.09 (dd, J=8.6, 3.9 Hz, 1H), 2.90-2.68 (m, 4H), 2.30 (s, 2H), 1.59 (d, J=5.3 Hz, 2H). ESIMS m/z=436.1 (M+1).

Example 389

5-Amino-N-(5-(4-(aminomethyl)piperidin-1-yl)-1-methyl-1H-pyrazol-4-yl)-2-(4-cyanophenyl)thiazole-4-carboxamide 389

Following Example 278, Suzuki coupling of tert-butyl 4-(5-(4-(butyloxycarbonylaminomethyl)piperidin-1-yl)-1-methyl-1H-pyrazol-4-ylcarbamoyl)-2-bromothiazol-5-ylcarbamate and 4-cyanophenyl boronic acid gave 389 as a green solid (26 mg 30% over two steps). $^1$H NMR (400 MHz, d$_6$-DMSO) δ 9.01 (s, 1H), 8.01 (d, J=8.3 Hz, 2H), 7.90 (d, J=8.3 Hz, 2H), 7.62 (s, 2H), 7.31 (s, 1H), 3.62 (s, 3H), 3.12-2.96 (m, 4H), 2.45 (d, J=5.6 Hz, 2H), 2.20-1.80 (m, 2H), 1.74 (d, J=11.6 Hz, 2H), 1.26-1.14 (m, 3H). LCMS (ES+) m/z 437 (M+1)

Example 390

5-Amino-N-(5-(4-(aminomethyl)piperidin-1-yl)-1-methyl-1H-pyrazol-4-yl)-2-(5-fluoro-2-methoxyphenyl)thiazole-4-carboxamide 390

Following Example 278, Suzuki coupling of tert-butyl 4-(5-(4-(butyloxycarbonylaminomethyl)piperidin-1-yl)-1-methyl-1H-pyrazol-4-ylcarbamoyl)-2-bromothiazol-5-ylcarbamate and 5-fluoro-2-methoxyphenyl boronic acid gave 390 as a pale brown solid (24 mg, 26% over two steps). $^1$H NMR (400 MHz, d$_6$-DMSO) δ 9.12 (s, 1H), 8.19 (d, J=10.0 Hz, 1H), 7.36 (d, J=2.1 Hz, 1H), 7.28 (d, J=7.1 Hz, 1H), 7.26-7.22 (m, 2H), 3.99 (s, 3H), 3.67 (s, 3H), 3.16-3.00 (m, 4H), 2.47 (d, J=5.6 Hz, 2H), 1.78 (d, J=11.5 Hz, 2H), 1.30-1.17 (m, 3H). LCMS (ES+) m/z 460 (M+1)

Example 901

Pim Kinase Binding Activity

PIM-1, -2, and -3 enzymes were generated as fusion proteins expressed in bacteria and purified by IMAC column chromatography (Sun, X., Chiu, J. F., and He, Q. Y. (2005) Expert Rev. Proteomics, 2:649-657). A fluorescent-labeled Pim-specific peptide substrate, was custom synthesized by American Peptide Company (Sunnyvale, Calif.). Reaction Buffer contained 10 mM HEPES, pH 7.2, 10 mM $MgCl_2$, 0.01% Tween 20, 2 mM DTT. Termination Buffer contained 190 mM HEPES, pH 7.2, 0.015% Brij-35, 0.2% Coating Reagent 3 (Caliper Life Sciences, Hopkinton, Mass.), 20 mM EDTA. Separation Buffer contained 100 mM HEPES, pH 7.2, 0.015% Brij-35, 0.1% Coating Reagent 3, 1:200 Coating Reagent 8 (Caliper Life Sciences, Hopkinton, Mass.), 10 mM EDTA and 5% DMSO.

PIM reactions were carried out in a final volume of 10 μL per well in a 384-well plate. A standard enzymatic reaction, initiated by the addition of 5 μL 2×ATP and test compound to 5 μL of 2× enzyme and FAM-peptide, contained 20 pM PIM1, 50 pM PIM2, or 55 pM PIM3, 1 μM FAM-peptide, and 10 μM ATP, in Reaction Buffer. After 90 minutes of incubation at room temperature, the phosphorylation reaction was stopped by the addition of 10 μL Termination Buffer. The product and substrate in each independent reaction were separated on a 12-sipper microfluidic chip (Caliper Life Sciences, Hopkinton, Mass.) run on a Caliper LC3000® (Caliper Life Sciences, Hopkinton, Mass.). The separation of product and substrate was optimized by choosing voltages and pressure using Caliper's Optimizer software (Hopkinton, Mass.). The separation conditions used a downstream voltage of −500V, an upstream voltage of −2150V, and a screening pressure of −1.2 psi. The product and substrate fluorophore were excited at 488 nm and detected at 530 nm. Substrate conversion was calculated from the electropherogram using HTS Well Analyzer software (Caliper Life Sciences, Hopkinton, Mass.). Ki values for the test compound were calculated.

| No. | PIM1 LC3K (KI) μM | PIM2 LC3K (KI) μM | PIM3 LC3K (KI) μM |
|---|---|---|---|
| 102 | 0.016 | 0.110 | 0.0088 |
| 103 | 0.0065 | 0.0551 | 0.00489 |
| 105 | 0.00454 | 0.148 | 0.00577 |
| 107 | 0.00122 | 0.0201 | 0.000575 |
| 109 | 0.000762 | 0.0411 | 0.00263 |
| 112 | 0.000246 | 0.00249 | 0.00034 |
| 113 | 2.70E−05 | 0.000316 | 2.20E−05 |
| 114 | 0.000115 | 0.00165 | 0.000159 |
| 115 | 0.00114 | 0.0461 | 0.00108 |
| 116 | 0.00436 | 0.0262 | 0.00497 |
| 119 | 0.000274 | 0.00213 | 0.000305 |
| 120 | 0.00197 | 0.0283 | 0.0011 |
| 121 | 0.0388 | 0.154 | 0.0681 |
| 122 | 0.000281 | 0.0147 | 0.000962 |
| 123 | 0.137 | 0.587 | 0.215 |
| 124 | 0.00192 | 0.0285 | 0.00379 |
| 129 | 0.000343 | 0.0102 | 0.00133 |
| 135 | 0.000506 | 0.0106 | 0.000344 |
| 140 | 2.40E−05 | 0.000167 | 1.00E−05 |
| 141 | — | 0.00352 | 0.000295 |
| 142 | 0.000368 | 0.00313 | 0.000245 |
| 220 | 0.022 | 0.581 | 0.0342 |
| 231 | 0.00765 | 0.201 | 0.00526 |
| 238 | 0.000897 | 0.0173 | 0.00248 |
| 263 | 0.0104 | 0.185+ | 0.00612 |
| 328 | 0.000096 | 0.00437 | 0.000176 |
| 353 | 0.0119 | 0.038 | 0.019 |
| 364 | 0.020 | 0.124 | 0.024 |
| 369 | 0.000462 | 0.0125 | 0.000735 |

Example 902

In Vitro Cell Proliferation Potency Assays

BaF3 parental line was obtained from the DSMZ repository. BaF3 lines transfected with PIM 1 or PIM2 were generated. Mouse IL-3 was purchased from R&D Systems. G418 was purchased from Clontech. Media for BaF3 parental line contained RPMI, 10% FBS, 2 mM L-Glutamine, 2 ng/mL mIL-3. Media for BaF3 PIM1 & 2 lines contained RPMI, 10% FBS, 2 mM L-Glutamine, 250 μg/mL. Media for MM1.S (multiple myeloma cells) line contained RPMI, 10% FBS, 2 mM L-Glutamine.

BaF3, a murine interleukin-3 dependent pro-B cell line, parental cells, BaF3 PIM1 cells, BaF3 PIM2 cells, and MM1.S (multiple myeloma) cells were seeded at 2 k/well, 5 k/well, 5 k/well, and 10 k/well respectively, in a 384-well plate, at 45 μL/well. Test compound was added at 5 μL/well. BaF3 cells (parental and transfected) were incubated overnight, while MM1.S cells were incubated for 72 hours at 37° C., 5% $CO_2$. Cell Titer Glo Reagent (Promega) was added at 50 μL/well, the plates were incubated for 30 minutes, and their luminescence read on an HT Analyst. $IC_{50}/EC_{50}$ values for the test compound were calculated.

Representative compounds of the present invention were tested as described above and found to exhibit a $Ki/IC_{50}/EC_{50}$ as shown below.

| No. | Prolif BaF3 IL3 (IC50) μM | Prolif BaF3 PIM1 (IC50) μM | Prolif MM1S ATP (EC50) μM |
|---|---|---|---|
| 103 | 10.6 | 7.3 | 9.1 |
| 106 | 6.6 | 3.8 | 4.2 |
| 108 | 4.3 | 0.615 | 8.2 |
| 110 | 12 | 1.5 | 16.1 |
| 111 | 13.2 | 4.2 | 7.1 |
| 113 | 11.3 | 0.123 | 10 |
| 114 | 5.5 | 2.3 | |
| 115 | 6.2 | 4.5 | |
| 117 | >25 | 4.9 | |
| 119 | 5.2 | 1.3 | |
| 120 | 25 | 7.8 | |
| 122 | 11.9 | 1.1 | |
| 129 | 21.5 | 5.1 | |
| 133 | 25 | 0.258 | |
| 134 | 7.8 | 1.4 | |
| 135 | 9.3 | 0.66 | |
| 136 | 5.9 | 0.634 | |
| 140 | 7.4 | 0.0147 | |
| 141 | 1.1 | 0.219 | |
| 143 | 1.1 | 0.377 | |
| 145 | 3.8 | 1 | |

I claim:

1. A method of treating cancer comprising administering a therapeutically effective amount of a compound to a patient wherein the compound is selected from Formula I:

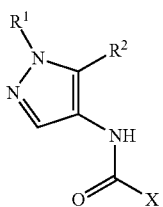

and stereoisomers, geometric isomers, tautomers, or pharmaceutically acceptable salts thereof, wherein:
$R^1$ is H, $C_1$-$C_{12}$ alkyl, $C_2$-$C_{12}$ alkenyl, $C_2$-$C_{12}$ alkynyl, $C_6$-$C_{20}$ aryl, $C_3$-$C_{12}$ carbocyclyl, $C_2$-$C_{20}$ heterocyclyl, or $C_1$-$C_{20}$ heteroaryl;
$R^2$ is H, $C_2$-$C_{20}$ heterocyclyl, $C_1$-$C_{20}$ heteroaryl, —($C_1$-$C_{20}$ heteroaryl)-($C_2$-$C_{20}$ heterocyclyl), $C_6$-$C_{20}$ aryl, $C_3$-$C_{12}$ carbocyclyl, $NR^4R^5$ or $OR^4$;
X is selected from the structures:

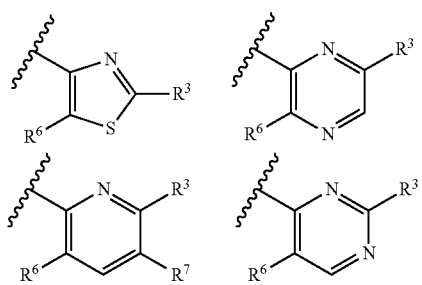

where the wavy line indicates the site of attachment;
$R^3$ is $C_6$-$C_{20}$ aryl, —($C_6$-$C_{20}$ arylene)-($C_2$-$C_{20}$ heterocyclyl), —($C_6$-$C_{20}$ arylene)-($C_1$-$C_{12}$ alkylene)-($C_2$-$C_{20}$ heterocyclyl), $C_3$-$C_{12}$ carbocyclyl, $C_2$-$C_{20}$ heterocyclyl, or $C_1$-$C_{20}$ heteroaryl;
$R^4$ and $R^5$ are independently selected from H, $C_1$-$C_{12}$ alkyl, $C_6$-$C_{20}$ aryl, $C_3$-$C_{12}$ carbocyclyl, $C_2$-$C_{20}$ heterocyclyl, $C_1$-$C_{20}$ heteroaryl, —($C_1$-$C_{12}$ alkylene)-($C_6$-$C_{20}$ aryl), —($C_1$-$C_{12}$ alkylene)-($C_3$-$C_{12}$ carbocyclyl), —($C_1$-$C_{12}$ alkylene)-($C_2$-$C_{20}$ heterocyclyl), —($C_1$-$C_{12}$ alkylene)-($C_1$-$C_{20}$ heteroaryl); or $R^4$ and $R^5$ together form $C_2$-$C_{20}$ heterocyclyl or $C_1$-$C_{20}$ heteroaryl;
$R^6$ is H or —$NH_2$;
$R^7$ is H, F, $CH_2F$, $CHF_2$, and $CF_3$; and
where alkyl, alkenyl, alkynyl, alkylene, carbocyclyl, heterocyclyl, aryl, and heteroaryl are optionally substituted with one or more groups independently selected from F, Cl, Br, I, —$CH_3$, —$CH_2CH_3$, —$CH(CH_3)_2$, —$CH_2CH(CH_3)_2$, —$CH_2NH_2$, —$CH_2CH_2NH_2$, —$CH_2CHCH_2NH_2$, —$CH_2CH(CH_3)NH_2$, —$CH_2OH$, —$CH_2CH_2OH$, —$C(CH_3)_2OH$, —$CH(OH)CH(CH_3)_2$, —$C(CH_3)_2CH_2OH$, $CH_2CH_2SO_2CH_3$, —CN, —$CF_3$, —$CO_2H$, —$COCH_3$, —$CO_2CH_3$, —$CO_2C(CH_3)_3$, —$COCH(OH)CH_3$, —$CONH_2$, —$CONHCH_3$, —$CON(CH_3)_2$, —$C(CH_3)_2CONH_2$, —$NO_2$, —$NH_2$, —$NHCH_3$, —$N(CH_3)_2$, —$NHCOCH_3$, —$N(CH_3)COCH_3$, —$NHS(O)_2CH_3$, —$N(CH_3)C(CH_3)_2CONH_2$, —$N(CH_3)CH_2CH_2S(O)_2CH_3$, =O, —OH, —$OCH_3$, —$S(O)_2N(CH_3)_2$, —$SCH_3$, —$CH_2OCH_3$, —$S(O)_2CH_3$, cyclopropyl, cyclobutyl, cyclopentyl, cyclohexyl, cycloheptyl, azetidinyl, azepanyl, oxetanyl, pyrrolidinyl, piperazinyl, piperidinyl, (piperidin-4-yl) ethyl), pyranyl, (piperidin-4-ylmethyl), morpholinomethyl, and morpholino;

wherein the cancer is selected from multiple myeloma, leukemia, lymphoma, prostate cancer, pancreatic cancer, and hepatocellular carcinoma.

2. The method of claim 1 wherein the cancer is multiple myeloma.

3. The method of claim 1 wherein $R^1$ is $C_1$-$C_{12}$ alkyl.

4. The method of claim 1 wherein $R^2$ is $NR^4R^5$, and $R^4$ and $R^5$ together form $C_2$-$C_{20}$ heterocyclyl or $C_1$-$C_{20}$ heteroaryl.

5. The method of claim 4 wherein $R^2$ is selected from the structures:

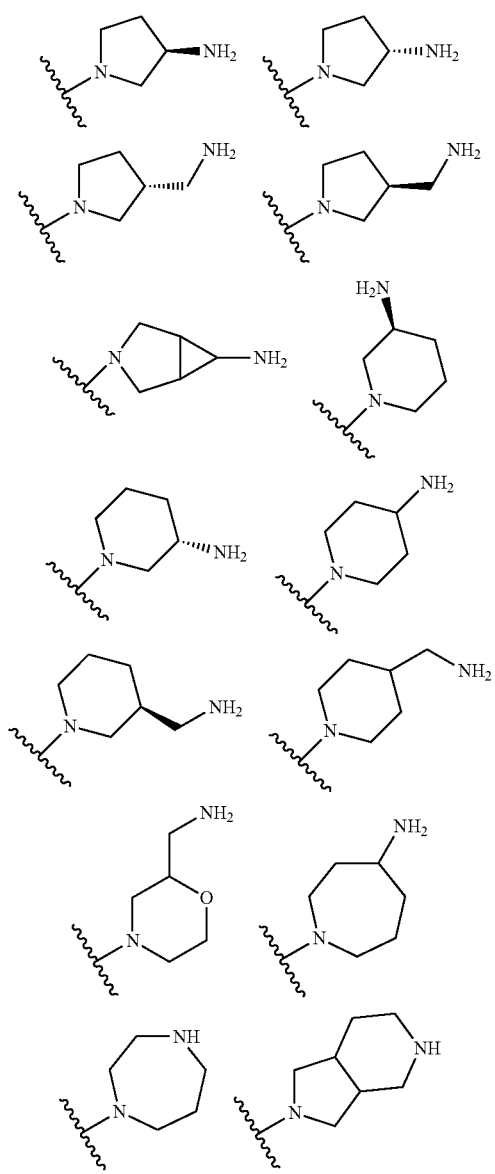

where the wavy line indicates the site of attachment.

6. The method of claim 1 wherein R² is selected from the structures:

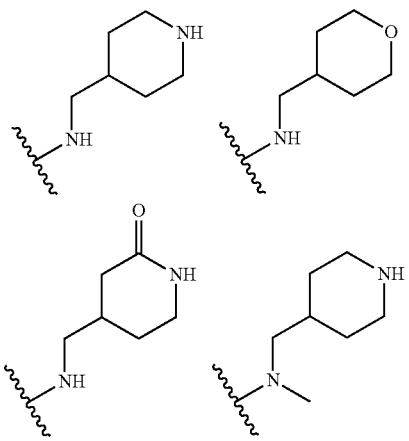

where the wavy line indicates the site of attachment.

7. The method of claim 1 wherein R² is OR⁴.

8. The method of claim 7 wherein R² is selected from the structures:

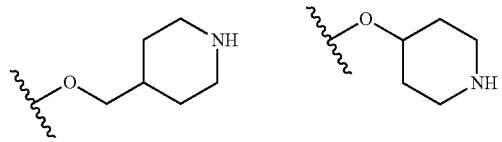 [SMILES: *OCC1CCNCC1 ; *OC1CCNCC1]

where the wavy line indicates the site of attachment.

9. The method of claim 1 wherein R³ is $C_6$-$C_{20}$ aryl.

10. The method of claim 9 wherein R³ is phenyl substituted with one or more F.

11. The method of claim 1 wherein the compound has the structure of Formula Ia:

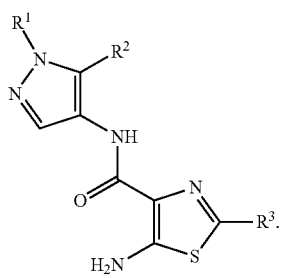

12. The method of claim 1 wherein the compound has the structure of Formula Ib:

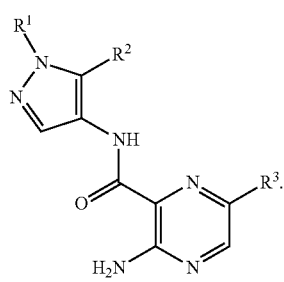

13. The method of claim 1 wherein the compound has the structure of Formula Ic:

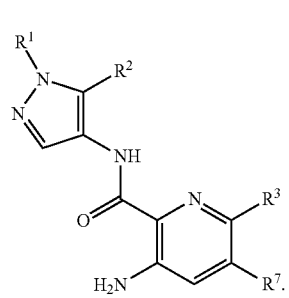

14. The method of claim 1 wherein the compound has the structure of Formula Id:

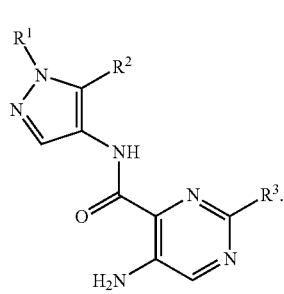

15. The method of claim 1 wherein the compound is selected from
- 5-amino-2-(2,6-difluorophenyl)-N-(1H-pyrazol-4-yl)thiazole-4-carboxamide;
- 5-amino-2-(2,6-difluorophenyl)-N-(1-methyl-1H-pyrazol-4-yl)thiazole-4-carboxamide;
- (S)-5-amino-N-(5-(3-aminopiperidin-1-yl)-1H-pyrazol-4-yl)-2-(2,6-difluorophenyl)thiazole-4-carboxamide;
- 5-amino-2-(2-fluorophenyl)-N-(1-methyl-5-(piperidin-4-ylmethylamino)-1H-pyrazol-4-yl)thiazole-4-carboxamide;
- 5-amino-2-(2,6-difluorophenyl)-N-(1-methyl-5-(piperidin-4-ylmethylamino)-1H-pyrazol-4-yl)thiazole-4-carboxamide;
- (S)-5-amino-N-(5-(3-aminopiperidin-1-yl)-1-methyl-1H-pyrazol-4-yl)-2-(2,6-difluorophenyl)thiazole-4-carboxamide;
- (S)-5-amino-N-(5-(3-aminopiperidin-1-yl)-1-methyl-1H-pyrazol-4-yl)-2-(2-fluorophenyl)thiazole-4-carboxamide;
- 5-amino-N-(5-(4-aminopiperidin-1-yl)-1-methyl-1H-pyrazol-4-yl)-2-(2,6-difluorophenyl)thiazole-4-carboxamide;
- 3-amino-N-(5-(4-aminopiperidin-1-yl)-1-methyl-1H-pyrazol-4-yl)-6-phenylpicolinamide;
- 3-amino-N-(5-(4-aminopiperidin-1-yl)-1-methyl-1H-pyrazol-4-yl)-6-(2-fluorophenyl)picolinamide;
- (S)-3-amino-N-(5-(3-aminopiperidin-1-yl)-1-methyl-1H-pyrazol-4-yl)-6-(2-fluorophenyl)picolinamide;
- (R)-3-amino-N-(5-(3-aminopiperidin-1-yl)-1-methyl-1H-pyrazol-4-yl)-6-(2-fluorophenyl)picolinamide;
- 5-amino-N-(5-(4-aminoazepan-1-yl)-1-methyl-1H-pyrazol-4-yl)-2-(2,6-difluorophenyl)thiazole-4-carboxamide;

3-amino-N-(5-(4-aminoazepan-1-yl)-1-methyl-1H-pyrazol-4-yl)-6-(2-fluorophenyl)picolinamide;
5-amino-2-(2,6-difluorophenyl)-N-(1-methyl-5-(piperidin-4-ylmethoxy)-1H-pyrazol-4-yl)thiazole-4-carboxamide;
3-amino-6-(2-fluorophenyl)-N-(1-methyl-5-(piperidin-4-yloxy)-1H-pyrazol-4-yl)picolinamide;
3-amino-6-(2-fluorophenyl)-N-(1-methyl-5-(piperidin-4-ylmethoxy)-1H-pyrazol-4-yl)picolinamide;
(S)-3-amino-N-(5-(3-aminopiperidin-1-yl)-1-methyl-1H-pyrazol-4-yl)-6-(2-fluorophenyl)pyrazine-2-carboxamide;
5-amino-2-(2,6-difluorophenyl)-N-(1-methyl-5-(piperidin-4-yloxy)-1H-pyrazol-4-yl)thiazole-4-carboxamide;
3-amino-N-(5-(4-aminopiperidin-1-yl)-1-methyl-1H-pyrazol-4-yl)-6-(2-fluorophenyl)pyrazine-2-carboxamide;
(R)-3-amino-N-(5-(3-aminopyrrolidin-1-yl)-1-methyl-1H-pyrazol-4-yl)-6-(2-fluorophenyl)picolinamide;
(S)-3-amino-N-(5-(3-aminopyrrolidin-1-yl)-1-methyl-1H-pyrazol-4-yl)-6-(2-fluorophenyl)picolinamide;
(R)-5-amino-N-(5-(3-aminopyrrolidin-1-yl)-1-methyl-1H-pyrazol-4-yl)-2-(2,6-difluorophenyl)thiazole-4-carboxamide;
(S)-5-amino-N-(5-(3-aminopyrrolidin-1-yl)-1-methyl-1H-pyrazol-4-yl)-2-(2,6-difluorophenyl)thiazole-4-carboxamide;
(S)-3-amino-N-(5-(3-(aminomethyl)piperidin-1-yl)-1-methyl-1H-pyrazol-4-yl)-6-(2-fluorophenyl)picolinamide;
(R)-3-amino-N-(5-(3-(aminomethyl)piperidin-1-yl)-1-methyl-1H-pyrazol-4-yl)-6-(2-fluorophenyl)picolinamide;
3-amino-N-(5-(4-(aminomethyl)piperidin-1-yl)-1-methyl-1H-pyrazol-4-yl)-6-(2-fluorophenyl)picolinamide;
(S)-5-amino-N-(5-(3-(aminomethyl)piperidin-1-yl)-1-methyl-1H-pyrazol-4-yl)-2-(2,6-difluorophenyl)thiazole-4-carboxamide;
(R)-5-amino-N-(5-(3-(aminomethyl)piperidin-1-yl)-1-methyl-1H-pyrazol-4-yl)-2-(2,6-difluorophenyl)thiazole-4-carboxamide;
5-amino-N-(5-(4-(aminomethyl)piperidin-1-yl)-1-methyl-1H-pyrazol-4-yl)-2-(2,6-difluorophenyl)thiazole-4-carboxamide;
(S)-3-amino-N-(5-(3-(aminomethyl)pyrrolidin-1-yl)-1-methyl-1H-pyrazol-4-yl)-6-(2-fluorophenyl)picolinamide;
(R)-5-amino-N-(5-(3-(aminomethyl)pyrrolidin-1-yl)-1-methyl-1H-pyrazol-4-yl)-2-(2,6-difluorophenyl)thiazole-4-carboxamide;
(R)-3-amino-N-(5-(3-(aminomethyl)pyrrolidin-1-yl)-1-methyl-1H-pyrazol-4-yl)-6-(2-fluorophenyl)picolinamide;
(S)-5-amino-N-(5-(3-(aminomethyl)pyrrolidin-1-yl)-1-methyl-1H-pyrazol-4-yl)-2-(2,6-difluorophenyl)thiazole-4-carboxamide;
5-amino-2-(2,6-difluorophenyl)-N-(1-(oxetan-3-yl)-1H-pyrazol-4-yl)thiazole-4-carboxamide;
(S)-5-amino-N-(5-(4-aminoazepan-1-yl)-1-methyl-1H-pyrazol-4-yl)-2-(2,6-difluorophenyl)thiazole-4-carboxamide;
(R)-5-amino-N-(5-(4-aminoazepan-1-yl)-1-methyl-1H-pyrazol-4-yl)-2-(2,6-difluorophenyl)thiazole-4-carboxamide;
(R)-3-amino-N-(5-(4-aminoazepan-1-yl)-1-methyl-1H-pyrazol-4-yl)-6-(2-fluorophenyl)pyrazine-2-carboxamide;
(S)-3-amino-N-(5-(4-aminoazepan-1-yl)-1-methyl-1H-pyrazol-4-yl)-6-(2-fluorophenyl)picolinamide;
(S)-3-amino-N-(5-(4-aminoazepan-1-yl)-1-methyl-1H-pyrazol-4-yl)-6-(2-fluorophenyl)pyrazine-2-carboxamide;
(R)-5-amino-N-(5-(3-aminopiperidin-1-yl)-1-methyl-1H-pyrazol-4-yl)-2-(2,6-difluorophenyl)thiazole-4-carboxamide;
(R)-3-amino-N-(5-(4-aminoazepan-1-yl)-1-methyl-1H-pyrazol-4-yl)-6-(2-fluorophenyl)picolinamide;
(R)—N-(5-(3-(aminomethyl)piperidin-1-yl)-1-methyl-1H-pyrazol-4-yl)-2-(2,6-difluorophenyl)thiazole-4-carboxamide;
(R)—N-(5-(4-aminoazepan-1-yl)-1-methyl-1H-pyrazol-4-yl)-2-(2,6-difluorophenyl)thiazole-4-carboxamide;
(S)—N-(5-(4-aminoazepan-1-yl)-1-methyl-1H-pyrazol-4-yl)-2-(2,6-difluorophenyl)thiazole-4-carboxamide;
5-amino-N-(5-(6-amino-3-azabicyclo[3.1.0]hexan-3-yl)-1-methyl-1H-pyrazol-4-yl)-2-(2,6-difluorophenyl)thiazole-4-carboxamide;
3-amino-N-(5-(6-amino-3-azabicyclo[3.1.0]hexan-3-yl)-1-methyl-1H-pyrazol-4-yl)-6-(2-fluorophenyl)picolinamide;
5-amino-2-(2,6-difluorophenyl)-N-(1-methyl-5-o-tolyl-1H-pyrazol-4-yl)thiazole-4-carboxamide;
3-amino-6-(2-fluorophenyl)-N-(1-methyl-5-o-tolyl-1H-pyrazol-4-yl)picolinamide;
3-amino-N-(5-(3-aminophenyl)-1-methyl-1H-pyrazol-4-yl)-6-(2-fluorophenyl)picolinamide; and
5-amino-N-(5-(3-aminophenyl)-1-methyl-1H-pyrazol-4-yl)-2-(2,6-difluorophenyl)thiazole-4-carboxamide.

16. The method of claim 1 wherein the compound is selected from
(S)-3-amino-N-(5-(3-aminoazepan-1-yl)-1-methyl-1H-pyrazol-4-yl)-6-(2-fluorophenyl)picolinamide;
(R)-5-amino-N-(5-(3-aminoazepan-1-yl)-1-methyl-1H-pyrazol-4-yl)-2-(2,6-difluorophenyl)thiazole-4-carboxamide;
(R)-3-amino-N-(5-(3-aminoazepan-1-yl)-1-methyl-1H-pyrazol-4-yl)-6-(2-fluorophenyl)picolinamide;
(S)-5-amino-N-(5-(3-aminoazepan-1-yl)-1-methyl-1H-pyrazol-4-yl)-2-(2,6-difluorophenyl)thiazole-4-carboxamide;
5-amino-2-(2,6-difluorophenyl)-N-(1-methyl-5-(piperazin-1-yl)-1H-pyrazol-4-yl)thiazole-4-carboxamide;
3-amino-6-(2-fluorophenyl)-N-(1-methyl-5-(piperazin-1-yl)-1H-pyrazol-4-yl)picolinamide;
N-(5-(1,4-diazepan-1-yl)-1-methyl-1H-pyrazol-4-yl)-5-amino-2-(2,6-difluorophenyl)thiazole-4-carboxamide;
5-amino-2-(2,6-difluorophenyl)-N-(1-ethyl-1H-pyrazol-4-yl)thiazole-4-carboxamide;
5-amino-2-(2,6-difluorophenyl)-N-(1-methyl-5-(1H-pyrrolo[3,4-c]pyridin-2(3H,3 aH,4H,5H,6H,7H,7aH)-yl)-1H-pyrazol-4-yl)thiazole-4-carboxamide;
5-amino-2-(2-fluorophenyl)-N-(1-methyl-1H-pyrazol-4-yl)thiazole-4-carboxamide;
5-amino-2-(2-fluorophenyl)-N-(1-(piperidin-4-yl)-1H-pyrazol-4-yl)thiazole-4-carboxamide;
5-amino-2-(2,6-difluorophenyl)-N-(1-(piperidin-4-yl)-1H-pyrazol-4-yl)thiazole-4-carboxamide;
5-amino-N-(1-ethyl-1H-pyrazol-4-yl)-2-(2-fluorophenyl)thiazole-4-carboxamide;
5-amino-2-(2-fluorophenyl)-N-(1-isopropyl-1H-pyrazol-4-yl)thiazole-4-carboxamide;
5-amino-2-(2,6-difluorophenyl)-N-(1-isopropyl-1H-pyrazol-4-yl)thiazole-4-carboxamide;

5-amino-2-(2,6-difluorophenyl)-N-(1-(pyrrolidin-3-yl)-1H-pyrazol-4-yl)thiazole-4-carboxamide;
5-amino-2-(2-fluorophenyl)-N-(1-(pyrrolidin-3-yl)-1H-pyrazol-4-yl)thiazole-4-carboxamide;
5-amino-N-(1-(cyclopropylmethyl)-1H-pyrazol-4-yl)-2-(2-fluorophenyl)thiazole-4-carboxamide;
5-amino-N-(1-(cyclopropylmethyl)-1H-pyrazol-4-yl)-2-(2,6-difluorophenyl)thiazole-4-carboxamide;
(R)-5-amino-2-(2,6-difluorophenyl)-N-(1-(piperidin-3-yl)-1H-pyrazol-4-yl)thiazole-4-carboxamide;
(S)-5-amino-2-(2,6-difluorophenyl)-N-(1-(piperidin-3-yl)-1H-pyrazol-4-yl)thiazole-4-carboxamide;
5-amino-2-(2,6-difluorophenyl)-N-(1-(2-(dimethylamino)ethyl)-1H-pyrazol-4-yl)thiazole-4-carboxamide;
N-(5-(4-aminopiperidin-1-yl)-1-methyl-1H-pyrazol-4-yl)-6-(2-fluorophenyl)pyrazine-2-carboxamide;
N-(5-(1,4-diazepan-1-yl)-1-methyl-1H-pyrazol-4-yl)-3-amino-6-(2-fluorophenyl)picolinamide;
N-(3-(4-aminopiperidin-1-yl)-1H-pyrazol-4-yl)-6-(2-fluorophenyl)pyrazine-2-carboxamide;
5-amino-2-(2,6-difluorophenyl)-N-(5-(4-hydroxyazepan-1-yl)-1-methyl-1H-pyrazol-4-yl)thiazole-4-carboxamide;
(R)—N-(5-(3-aminopiperidin-1-yl)-1-methyl-1H-pyrazol-4-yl)-6-(2-fluorophenyl)pyrazine-2-carboxamide;
(S)—N-(5-(3-aminopiperidin-1-yl)-1-methyl-1H-pyrazol-4-yl)-6-(2-fluorophenyl)pyrazine-2-carboxamide;
N-(5-(4-(aminomethyl)piperidin-1-yl)-1-methyl-1H-pyrazol-4-yl)-6-(2-fluorophenyl)pyrazine-2-carboxamide;
N-(5-(4-(2-aminoethyl)piperidin-1-yl)-1-methyl-1H-pyrazol-4-yl)-6-(2-fluorophenyl)pyrazine-2-carboxamide;
N-(5-(1,4-diazepan-1-yl)-1-methyl-1H-pyrazol-4-yl)-6-(2-fluorophenyl)pyrazine-2-carboxamide;
(R)—N-(5-(3-aminoazepan-1-yl)-1-methyl-1H-pyrazol-4-yl)-6-(2-fluorophenyl)pyrazine-2-carboxamide;
(S)—N-(5-(3-aminoazepan-1-yl)-1-methyl-1H-pyrazol-4-yl)-6-(2-fluorophenyl)pyrazine-2-carboxamide;
(R)-5-amino-N-(5-(4-aminoazepan-1-yl)-1-methyl-1H-pyrazol-4-yl)-2-(2-fluorophenyl)thiazole-4-carboxamide;
N-(5-(4-aminopiperidin-1-yl)-1-methyl-1H-pyrazol-4-yl)-5-(2-fluorophenyl)nicotinamide;
5-amino-2-(2,6-difluorophenyl)-N-(5-(4-(dimethylamino)azepan-1-yl)-1-methyl-1H-pyrazol-4-yl)thiazole-4-carboxamide;
(R)-5-amino-N-(5-(4-aminoazepan-1-yl)-1-methyl-1H-pyrazol-4-yl)-2-(2,4-difluorophenyl)thiazole-4-carboxamide;
5-amino-N-(5-(4-(2-aminoethyl)piperidin-1-yl)-1-methyl-1H-pyrazol-4-yl)-2-(2,6-difluorophenyl)thiazole-4-carboxamide;
(R)-5-amino-N-(5-(4-aminoazepan-1-yl)-1-methyl-1H-pyrazol-4-yl)-2-(2,6-difluoro-4-methoxyphenyl)thiazole-4-carboxamide;
5-amino-2-(2,6-difluorophenyl)-N-(1-methyl-5-(4-(N-methylacetamido)azepan-1-yl)-1H-pyrazol-4-yl)thiazole-4-carboxamide;
5-amino-N-(1-(difluoromethyl)-1H-pyrazol-4-yl)-2-(2,6-difluorophenyl)thiazole-4-carboxamide;
(R)-5-amino-N-(5-(4-aminoazepan-1-yl)-1-methyl-1H-pyrazol-4-yl)-2-(3-(trifluoromethyl)phenyl)thiazole-4-carboxamide;
(R)-5-amino-N-(5-(4-aminoazepan-1-yl)-1-methyl-1H-pyrazol-4-yl)-2-(4-(trifluoromethyl)phenyl)thiazole-4-carboxamide;
(R)-5-amino-2-(2,6-difluorophenyl)-N-(1-methyl-5-(4-(N-methylacetamido)azepan-1-yl)-1H-pyrazol-4-yl)thiazole-4-carboxamide;
5-amino-N-(1-(2-aminoethyl)-1H-pyrazol-4-yl)-2-(2,6-difluorophenyl)thiazole-4-carboxamide;
(R)-5-amino-N-(5-(4-aminoazepan-1-yl)-1-methyl-1H-pyrazol-4-yl)-2-(2-(trifluoromethyl)phenyl)thiazole-4-carboxamide;
(R)-5-amino-N-(5-(4-aminoazepan-1-yl)-1-methyl-1H-pyrazol-4-yl)-2-(2-fluoro-4-methylphenyl)thiazole-4-carboxamide;
(R)—N-(5-(4-aminoazepan-1-yl)-1-methyl-1H-pyrazol-4-yl)-5-fluoro-6-(2-fluorophenyl)picolinamide;
5-amino-2-(2,6-difluorophenyl)-N-(1-(2-(piperidin-1-yl)ethyl)-1H-pyrazol-4-yl)thiazole-4-carboxamide;
5-amino-2-(2,6-difluorophenyl)-N-(1-(2-morpholinoethyl)-1H-pyrazol-4-yl)thiazole-4-carboxamide;
(R)-5-amino-N-(5-(3-(2-aminoethyl)piperidin-1-yl)-1-methyl-1H-pyrazol-4-yl)-2-(2,6-difluorophenyl)thiazole-4-carboxamide;
(S)-5-amino-2-(2,6-difluorophenyl)-N-(1-methyl-5-(2-(pyrrolidin-2-yl)ethylamino)-1H-pyrazol-4-yl)thiazole-4-carboxamide;
5-amino-N-(5-(azepan-1-yl)-1-methyl-1H-pyrazol-4-yl)-2-(2,6-difluorophenyl)thiazole-4-carboxamide;
(R)—N-(5-(4-aminoazepan-1-yl)-1-methyl-1H-pyrazol-4-yl)-6-(2-fluorophenyl)pyrazine-2-carboxamide;
(S)—N-(5-(4-aminoazepan-1-yl)-1-methyl-1H-pyrazol-4-yl)-6-(2-fluorophenyl)pyrazine-2-carboxamide;
(R)-5-amino-2-(2,6-difluorophenyl)-N-(1-methyl-5-(2-(pyrrolidin-2-yl)ethylamino)-1H-pyrazol-4-yl)thiazole-4-carboxamide;
(R)-5-amino-N-(5-(4-aminoazepan-1-yl)-1-methyl-1H-pyrazol-4-yl)-2-(4-cyclopropyl-2-fluorophenyl)thiazole-4-carboxamide;
(R)-5-amino-N-(5-(4-aminoazepan-1-yl)-1-methyl-1H-pyrazol-4-yl)-2-(2-fluoro-5-methylphenyl)thiazole-4-carboxamide;
(S)-5-amino-2-(2,6-difluorophenyl)-N-(5-(4-(dimethylamino)azepan-1-yl)-1-methyl-1H-pyrazol-4-yl)thiazole-4-carboxamide;
(R)-5-amino-2-(2,6-difluorophenyl)-N-(5-(4-(dimethylamino)azepan-1-yl)-1-methyl-1H-pyrazol-4-yl)thiazole-4-carboxamide;
(R)-5-amino-N-(5-(4-aminoazepan-1-yl)-1-methyl-1H-pyrazol-4-yl)-2-(2,5-difluorophenyl)thiazole-4-carboxamide;
(R)—N-(5-(4-acetamidoazepan-1-yl)-1-methyl-1H-pyrazol-4-yl)-5-amino-2-(2,6-difluorophenyl)thiazole-4-carboxamide;
5-amino-N-(5-(3-(2-aminoethyl)piperidin-1-yl)-1-methyl-1H-pyrazol-4-yl)-2-(2,6-difluorophenyl)thiazole-4-carboxamide;
(R)—N-(5-(4-aminoazepan-1-yl)-1-methyl-1H-pyrazol-4-yl)-5-fluoro-6-phenylpicolinamide;
5-amino-2-(2,6-difluorophenyl)-N-(1-methyl-5-((tetrahydro-2H-pyran-4-yl)methoxy)-1H-pyrazol-4-yl)thiazole-4-carboxamide;
5-amino-2-(2,6-difluorophenyl)-N-(1-methyl-5-(1-methylpiperidin-4-yl)-1H-pyrazol-4-yl)thiazole-4-carboxamide;
(R)-5-amino-2-(2,6-difluorophenyl)-N-(1-methyl-5-(tetrahydrofuran-3-yloxy)-1H-pyrazol-4-yl)thiazole-4-carboxamide;

(S)-5-amino-2-(2,6-difluorophenyl)-N-(1-methyl-5-(tetrahydrofuran-3-yloxy)-1H-pyrazol-4-yl)thiazole-4-carboxamide;

(R)—N-(5-(4-aminoazepan-1-yl)-1-methyl-1H-pyrazol-4-yl)-6-cyclopentyl-5-fluoropicolinamide;

(R)—N-(5-(4-aminoazepan-1-yl)-1-methyl-1H-pyrazol-4-yl)-6-(5-(dimethylcarbamoyl)-2-fluorophenyl)-5-fluoropicolinamide;

(R)—N-(5-(4-aminoazepan-1-yl)-1-methyl-1H-pyrazol-4-yl)-6-cyclopentenyl-5-fluoropicolinamide;

(R)—N-(5-(4-aminoazepan-1-yl)-1-methyl-1H-pyrazol-4-yl)-6-(2,6-difluorophenyl)-5-fluoropicolinamide;

5-amino-2-(2,6-difluorophenyl)-N-(1-methyl-5-morpholino-1H-pyrazol-4-yl)thiazole-4-carboxamide;

(R)-5-amino-2-(2,6-difluorophenyl)-N-(5-(3-hydroxypyrrolidin-1-yl)-1-methyl-1H-pyrazol-4-yl)thiazole-4-carboxamide;

5-amino-N-(5-(4-aminoazepan-1-yl)-1-ethyl-1H-pyrazol-4-yl)-2-(2,6-difluorophenyl)thiazole-4-carboxamide;

(S)-5-amino-2-(2,6-difluorophenyl)-N-(5-(3-hydroxypyrrolidin-1-yl)-1-methyl-1H-pyrazol-4-yl)thiazole-4-carboxamide;

5-amino-2-(2,6-difluorophenyl)-N-(1-methyl-5-(tetrahydro-2H-pyran-4-yl)-1H-pyrazol-4-yl)thiazole-4-carboxamide;

5-amino-N-(1-methyl-1H-pyrazol-4-yl)-2-(3-morpholinophenyl)thiazole-4-carboxamide;

5-amino-2-(2,6-difluorophenyl)-N-(5-(4-fluoropiperidin-1-yl)-1-methyl-1H-pyrazol-4-yl)thiazole-4-carboxamide;

5-amino-2-(2,6-difluorophenyl)-N-(5-(4,4-difluoropiperidin-1-yl)-1-methyl-1H-pyrazol-4-yl)thiazole-4-carboxamide;

(S)-5-amino-2-(2,6-difluorophenyl)-N-(5-(3-fluoropyrrolidin-1-yl)-1-methyl-1H-pyrazol-4-yl)thiazole-4-carboxamide;

(R)-5-amino-2-(2,6-difluorophenyl)-N-(5-(3-fluoropyrrolidin-1-yl)-1-methyl-1H-pyrazol-4-yl)thiazole-4-carboxamide;

5-amino-2-(2,6-difluorophenyl)-N-(1-methyl-5-(piperidin-1-yl)-1H-pyrazol-4-yl)thiazole-4-carboxamide;

5-amino-N-(5-(4-(aminomethyl)piperidin-1-yl)-1-methyl-1H-pyrazol-4-yl)-2-(3-cyanophenyl)thiazole-4-carboxamide;

5-amino-N-(5-(4-(aminomethyl)piperidin-1-yl)-1-methyl-1H-pyrazol-4-yl)-2-(3-fluorophenyl)thiazole-4-carboxamide;

5-amino-N-(5-(3-(2-aminoethyl)pyrrolidin-1-yl)-1-methyl-1H-pyrazol-4-yl)-2-(2,6-difluorophenyl)thiazole-4-carboxamide;

(R)-5-amino-N-(5-(4-aminoazepan-1-yl)-1-methyl-1H-pyrazol-4-yl)-2-(2-fluoro-5-(trifluoromethyl)phenyl)thiazole-4-carboxamide;

N-(5-((1S,4S)-2,5-diazabicyclo[2.2.1]heptan-2-yl)-1-methyl-1H-pyrazol-4-yl)-5-amino-2-(2,6-difluorophenyl)thiazole-4-carboxamide;

5-amino-2-(2,6-difluorophenyl)-N-(1-methyl-5-(pyrrolidin-3-yl)-1H-pyrazol-4-yl)thiazole-4-carboxamide;

5-amino-N-(5-(4-(aminomethyl)piperidin-1-yl)-1-methyl-1H-pyrazol-4-yl)-2-cyclopentenylthiazole-4-carboxamide;

5-amino-2-(2,6-difluorophenyl)-N-(1-methyl-5-(1,2,3,6-tetrahydropyridin-4-yl)-1H-pyrazol-4-yl)thiazole-4-carboxamide;

5-amino-2-(2,6-difluorophenyl)-N-(5-((3S,4S)-3,4-dihydroxypyrrolidin-1-yl)-1-methyl-1H-pyrazol-4-yl)thiazole-4-carboxamide;

5-amino-2-(2,6-difluorophenyl)-N-(1-methyl-5-((tetrahydro-2H-pyran-4-yl)methylamino)-1H-pyrazol-4-yl)thiazole-4-carboxamide;

5-amino-2-(2,6-difluorophenyl)-N-(5-(dimethylamino)-1-methyl-1H-pyrazol-4-yl)thiazole-4-carboxamide;

5-amino-N-(5-(cyclohexyloxy)-1-methyl-1H-pyrazol-4-yl)-2-(2,6-difluorophenyl)thiazole-4-carboxamide;

5-amino-2-(2,6-difluorophenyl)-N-(1-methyl-5-(piperidin-4-yl)-1H-pyrazol-4-yl)thiazole-4-carboxamide;

5-amino-N-(5-(4-(aminomethyl)piperidin-1-yl)-1-(cyclopropylmethyl)-1H-pyrazol-4-yl)-2-(2,6-difluorophenyl)thiazole-4-carboxamide;

5-amino-N-(5-(4-(aminomethyl)piperidin-1-yl)-1-methyl-1H-pyrazol-4-yl)-2-cyclohexenylthiazole-4-carboxamide;

5-amino-N-(5-(4-(aminomethyl)piperidin-1-yl)-1-methyl-1H-pyrazol-4-yl)-2-cycloheptenylthiazole-4-carboxamide;

5-amino-N-(5-(4-(aminomethyl)piperidin-1-yl)-1-methyl-1H-pyrazol-4-yl)-2-(3-ethylphenyl)thiazole-4-carboxamide;

5-amino-N-(5-(4-(aminomethyl)piperidin-1-yl)-1-methyl-1H-pyrazol-4-yl)-2-(3-methoxyphenyl)thiazole-4-carboxamide;

5-amino-N-(5-(4-(aminomethyl)piperidin-1-yl)-1-methyl-1H-pyrazol-4-yl)-2-(2-isopropylphenyl)thiazole-4-carboxamide;

5-amino-N-(5-(4-(aminomethyl)piperidin-1-yl)-1-isopropyl-1H-pyrazol-4-yl)-2-(2,6-difluorophenyl)thiazole-4-carboxamide;

5-amino-2-(2,6-difluorophenyl)-N-(5-((2-hydroxyethyl)(methyl)amino)-1-methyl-1H-pyrazol-4-yl)thiazole-4-carboxamide;

(S)-5-amino-2-(2,6-difluorophenyl)-N-(1-methyl-5-(piperidin-3-yloxy)-1H-pyrazol-4-yl)thiazole-4-carboxamide;

(R)-5-amino-2-(3-(3-(aminomethyl)pyrrolidin-1-yl)phenyl)-N-(1-methyl-1H-pyrazol-4-yl)thiazole-4-carboxamide;

5-amino-N-(1-methyl-1H-pyrazol-4-yl)-2-(3-(piperazin-1-yl)phenyl)thiazole-4-carboxamide;

5-amino-N-(5-(4-(aminomethyl)piperidin-1-yl)-1-methyl-1H-pyrazol-4-yl)-2-(2-carbamoylphenyl)thiazole-4-carboxamide;

5-amino-N-(5-(4-(aminomethyl)piperidin-1-yl)-1-methyl-1H-pyrazol-4-yl)-2-(3-(dimethylamino)phenyl)thiazole-4-carboxamide;

5-amino-N-(5-(4-(aminomethyl)piperidin-1-yl)-1-methyl-1H-pyrazol-4-yl)-2-(2,5-dichlorophenyl)thiazole-4-carboxamide;

5-amino-N-(5-(4-(aminomethyl)piperidin-1-yl)-1-methyl-1H-pyrazol-4-yl)-2-(4-hydroxy-2-(trifluoromethyl)phenyl)thiazole-4-carboxamide;

5-amino-N-(5-(4-(aminomethyl)piperidin-1-yl)-1-methyl-1H-pyrazol-4-yl)-2-(5-fluoro-2-(trifluoromethyl)phenyl)thiazole-4-carboxamide;

5-amino-N-(5-(4-(aminomethyl)piperidin-1-yl)-1-methyl-1H-pyrazol-4-yl)-2-(4-methoxy-2-(trifluoromethyl)phenyl)thiazole-4-carboxamide;

5-amino-N-(5-(4-(aminomethyl)piperidin-1-yl)-1-methyl-1H-pyrazol-4-yl)-2-cyclohexylthiazole-4-carboxamide;

(R)-5-amino-2-(2,6-difluorophenyl)-N-(1-methyl-5-(piperidin-3-yloxy)-1H-pyrazol-4-yl)thiazole-4-carboxamide;

5-amino-2-(3-(4-(aminomethyl)piperidin-1-yl)phenyl)-N-(1-methyl-1H-pyrazol-4-yl)thiazole-4-carboxamide;

5-amino-N-(5-(4,4-difluoroazepan-1-yl)-1-methyl-1H-pyrazol-4-yl)-2-(2,6-difluorophenyl)thiazole-4-carboxamide;

5-amino-2-(2,6-difluorophenyl)-N-(5-(3,3-difluoropiperidin-1-yl)-1-methyl-1H-pyrazol-4-yl)thiazole-4-carboxamide;

5-amino-2-(2,6-difluorophenyl)-N-(1-methyl-5-(3-oxopiperazin-1-yl)-1H-pyrazol-4-yl)thiazole-4-carboxamide;

5-amino-N-(5-(4-(aminomethyl)piperidin-1-yl)-1-methyl-1H-pyrazol-4-yl)-2-cyclopentylthiazole-4-carboxamide;

5-amino-N-(5-(4-(aminomethyl)piperidin-1-yl)-1-methyl-1H-pyrazol-4-yl)-2-(tetrahydro-2H-pyran-2-yl)thiazole-4-carboxamide;

(R)-5-amino-N-(5-(4-aminoazepan-1-yl)-1-methyl-1H-pyrazol-4-yl)-2-(5-cyclopropyl-2-fluoro-3-methylphenyl)thiazole-4-carboxamide;

(R)—N-(5-(4-aminoazepan-1-yl)-1-methyl-1H-pyrazol-4-yl)-6-(2-fluorophenyl)picolinamide;

5-amino-2-(2,6-difluorophenyl)-N-(1-methyl-5-(3-oxo-1,4-diazepan-1-yl)-1H-pyrazol-4-yl)thiazole-4-carboxamide;

5-amino-2-(2,6-difluorophenyl)-N-(5-(3-fluoropiperidin-1-yl)-1-methyl-1H-pyrazol-4-yl)thiazole-4-carboxamide;

5-amino-2-(2,6-difluorophenyl)-N-(1-methyl-5-(4-methylpiperazin-1-yl)-1H-pyrazol-4-yl)thiazole-4-carboxamide;

5-amino-N-(5-(4-(aminomethyl)piperidin-1-yl)-1-methyl-1H-pyrazol-4-yl)-2-(5-fluoro-2-hydroxyphenyl)thiazole-4-carboxamide;

5-amino-N-(5-(4-(aminomethyl)piperidin-1-yl)-1-methyl-1H-pyrazol-4-yl)-2-(5-cyano-2-fluorophenyl)thiazole-4-carboxamide;

5-amino-N-(5-(4-(aminomethyl)piperidin-1-yl)-1-methyl-1H-pyrazol-4-yl)-2-cycloheptylthiazole-4-carboxamide;

5-amino-N-(5-(4-cyanopiperidin-1-yl)-1-methyl-1H-pyrazol-4-yl)-2-(2,6-difluorophenyl)thiazole-4-carboxamide;

5-amino-N-(5-(4-(aminomethyl)piperidin-1-yl)-1-methyl-1H-pyrazol-4-yl)-2-(3-isopropylphenyl)thiazole-4-carboxamide;

5-amino-N-(5-(4-(aminomethyl)piperidin-1-yl)-1-methyl-1H-pyrazol-4-yl)-2-cyclopropylthiazole-4-carboxamide;

5-amino-N-(5-(4-(aminomethyl)piperidin-1-yl)-1-methyl-1H-pyrazol-4-yl)-2-cyclobutylthiazole-4-carboxamide;

5-amino-2-(2,6-difluorophenyl)-N-(1-methyl-5-(piperidin-4-ylamino)-1H-pyrazol-4-yl)thiazole-4-carboxamide;

(R)-5-amino-N-(5-(4-aminoazepan-1-yl)-1-methyl-1H-pyrazol-4-yl)-2-(5-bromo-2-fluorophenyl)thiazole-4-carboxamide;

(R)-5-amino-N-(5-(4-aminoazepan-1-yl)-1-isopropyl-1H-pyrazol-4-yl)-2-(2,6-difluorophenyl)thiazole-4-carboxamide;

(R)-5-amino-N-(5-(4-aminoazepan-1-yl)-1-cyclopropyl-1H-pyrazol-4-yl)-2-(2,6-difluorophenyl)thiazole-4-carboxamide;

(R)-5-amino-N-(5-(4-aminoazepan-1-yl)-1-(cyclopropylmethyl)-1H-pyrazol-4-yl)-2-(2,6-difluorophenyl)thiazole-4-carboxamide;

(S)-5-amino-N-(5-(4-aminoazepan-1-yl)-1-ethyl-1H-pyrazol-4-yl)-2-(2,6-difluorophenyl)thiazole-4-carboxamide;

5-amino-N-(5-(4-(aminomethyl)piperidin-1-yl)-1-methyl-1H-pyrazol-4-yl)-2-(5-chloro-2-fluorophenyl)thiazole-4-carboxamide;

(S)-5-amino-2-(3-(3-(aminomethyl)pyrrolidin-1-yl)phenyl)-N-(1-methyl-1H-pyrazol-4-yl)thiazole-4-carboxamide;

5-amino-2-(3-(3-aminopyrrolidin-1-yl)phenyl)-N-(1-methyl-1H-pyrazol-4-yl)thiazole-4-carboxamide;

3-amino-N-(1-methyl-1H-pyrazol-4-yl)-6-(3-(piperidin-1-yl)phenyl)picolinamide;

5-amino-2-(2,6-difluorophenyl)-N-(1-methyl-5-(1,4-oxazepan-4-yl)-1H-pyrazol-4-yl)thiazole-4-carboxamide;

5-amino-2-(2,6-difluorophenyl)-N-(1-methyl-5-(5-oxo-1,4-diazepan-1-yl)-1H-pyrazol-4-yl)thiazole-4-carboxamide;

5-amino-2-(2,6-difluorophenyl)-N-(5-(4-(2-hydroxyethyl)piperazin-1-yl)-1-methyl-1H-pyrazol-4-yl)thiazole-4-carboxamide;

(S)-5-amino-2-(3-(3-hydroxypyrrolidin-1-yl)phenyl)-N-(1-methyl-1H-pyrazol-4-yl)thiazole-4-carboxamide;

(R)-5-amino-N-(5-(4-aminoazepan-1-yl)-1-methyl-1H-pyrazol-4-yl)-2-(4-methoxy-2-(trifluoromethyl)phenyl)thiazole-4-carboxamide;

(R)-5-amino-N-(5-(4-aminoazepan-1-yl)-1-methyl-1H-pyrazol-4-yl)-2-(3-fluorophenyl)thiazole-4-carboxamide;

3-amino-N-(1-methyl-1H-pyrazol-4-yl)-6-(3-morpholinophenyl)picolinamide;

(R)-5-amino-2-(2,6-difluorophenyl)-N-(1-methyl-5-(4-(methylamino)azepan-1-yl)-1H-pyrazol-4-yl)thiazole-4-carboxamide;

(S)-5-amino-2-(2,6-difluorophenyl)-N-(1-methyl-5-(4-(methylamino)azepan-1-yl)-1H-pyrazol-4-yl)thiazole-4-carboxamide;

3-amino-N-(1-methyl-1H-pyrazol-4-yl)-6-(3-(pyrrolidin-1-yl)phenyl)picolinamide;

(R)-5-amino-N-(5-(4-aminoazepan-1-yl)-1-methyl-1H-pyrazol-4-yl)-2-(2-fluorophenyl)pyrimidine-4-carboxamide;

3-amino-N-(1-methyl-1H-pyrazol-4-yl)-6-(3-(piperazin-1-yl)phenyl)picolinamide;

(R)-5-amino-N-(5-(azepan-4-ylamino)-1-methyl-1H-pyrazol-4-yl)-2-(2,6-difluorophenyl)thiazole-4-carboxamide;

5-amino-2-(2,6-difluorophenyl)-N-(5-((3aR,6aS)-hexahydropyrrolo[3,4-c]pyrrol-2(1H)-yl)-1-methyl-1H-pyrazol-4-yl)thiazole-4-carboxamide;

5-amino-2-(2,6-difluorophenyl)-N-(1-methyl-5-(methyl(piperidin-4-yl)amino)-1H-pyrazol-4-yl)thiazole-4-carboxamide;

(R)-5-amino-N-(5-(4-aminoazepan-1-yl)-1-ethyl-1H-pyrazol-4-yl)-2-(2,6-difluorophenyl)thiazole-4-carboxamide;

(R)-5-amino-N-(5-(4-aminoazepan-1-yl)-1-methyl-1H-pyrazol-4-yl)-2-cyclopentenylthiazole-4-carboxamide;

(R)-5-amino-N-(5-(4-aminoazepan-1-yl)-1-methyl-1H-pyrazol-4-yl)-2-cyclohexenylthiazole-4-carboxamide;

(R)-5-amino-N-(5-(4-aminoazepan-1-yl)-1-methyl-1H-pyrazol-4-yl)-2-cycloheptenylthiazole-4-carboxamide;

5-amino-N-(5-((1s,4s)-4-aminocyclohexylamino)-1-methyl-1H-pyrazol-4-yl)-2-(2,6-difluorophenyl)thiazole-4-carboxamide;

(S)-3-amino-6-(3-(3-aminopiperidin-1-yl)phenyl)-N-(1-methyl-1H-pyrazol-4-yl)picolinamide;

(S)-3-amino-6-(3-(3-aminopyrrolidin-1-yl)phenyl)-N-(1-methyl-1H-pyrazol-4-yl)picolinamide;
(R)-3-amino-6-(3-(3-aminopiperidin-1-yl)phenyl)-N-(1-methyl-1H-pyrazol-4-yl)picolinamide;
(R)-3-amino-6-(3-(3-aminopyrrolidin-1-yl)phenyl)-N-(1-methyl-1H-pyrazol-4-yl)picolinamide;
5-amino-N-(5-((cis-3-aminocyclohexylamino)-1-methyl-1H-pyrazol-4-yl)-2-(2,6-difluorophenyl)thiazole-4-carboxamide;
5-amino-N-(5-(3-aminopropylamino)-1-methyl-1H-pyrazol-4-yl)-2-(2,6-difluorophenyl)thiazole-4-carboxamide;
(R)-5-amino-N-(5-(4-aminoazepan-1-yl)-1-methyl-1H-pyrazol-4-yl)-2-(2,5-dichlorophenyl)thiazole-4-carboxamide;
5-amino-N-(5-((3-aminopropyl)(methyl)amino)-1-methyl-1H-pyrazol-4-yl)-2-(2,6-difluorophenyl)thiazole-4-carboxamide;
5-amino-2-(2,6-difluorophenyl)-N-(1-(2-fluoroethyl)-1H-pyrazol-4-yl)thiazole-4-carboxamide;
5-amino-N-(5-(4-(aminomethyl)piperidin-1-yl)-1-methyl-1H-pyrazol-4-yl)-2-(2,6-difluoro-3-methoxyphenyl)thiazole-4-carboxamide;
(R)-5-amino-N-(5-(4-aminoazepan-1-yl)-1-methyl-1H-pyrazol-4-yl)-2-(2-cyanophenyl)thiazole-4-carboxamide;
5-amino-N-(1-methyl-1H-pyrazol-4-yl)-2-(3-(morpholinomethyl)phenyl)thiazole-4-carboxamide;
(R)-5-amino-N-(5-(4-aminoazepan-1-yl)-1-methyl-1H-pyrazol-4-yl)-2-(5-fluoro-2-hydroxyphenyl)thiazole-4-carboxamide;
(R)-5-amino-N-(5-(4-aminoazepan-1-yl)-1-methyl-1H-pyrazol-4-yl)-2-(5-cyano-2-fluorophenyl)thiazole-4-carboxamide;
(S)—N-(5-(4-aminoazepan-1-yl)-1-methyl-1H-pyrazol-4-yl)-5-fluoro-6-(2-fluorophenyl)picolinamide;
5-amino-N-(5-((1r,4r)-4-aminocyclohexylamino)-1-methyl-1H-pyrazol-4-yl)-2-(2,6-difluorophenyl)thiazole-4-carboxamide;
5-amino-2-(2,6-difluorophenyl)-N-(5-(4-hydroxycyclohexyl)-1-methyl-1H-pyrazol-4-yl)thiazole-4-carboxamide;
5-amino-N-(5-((trans-3-aminocyclohexylamino)-1-methyl-1H-pyrazol-4-yl)-2-(2,6-difluorophenyl)thiazole-4-carboxamide;
(R)-5-amino-N-(5-(4-aminoazepan-1-yl)-1-ethyl-1H-pyrazol-4-yl)-2-(2-fluorophenyl)thiazole-4-carboxamide;
(R)-5-amino-N-(5-(4-aminoazepan-1-yl)-1-cyclopropyl-1H-pyrazol-4-yl)-2-(2-fluorophenyl)thiazole-4-carboxamide;
(R)-5-amino-N-(5-(4-aminoazepan-1-yl)-1-(cyclopropylmethyl)-1H-pyrazol-4-yl)-2-(2-fluorophenyl)thiazole-4-carboxamide;
(S)-5-amino-N-(5-(4-aminoazepan-1-yl)-1-methyl-1H-pyrazol-4-yl)-2-(2-fluorophenyl)pyrimidine-4-carboxamide;
5-amino-N-(5-(4-aminocyclohexyl)-1-methyl-1H-pyrazol-4-yl)-2-(2,6-difluorophenyl)thiazole-4-carboxamide;
(S)-5-amino-N-(5-(azepan-4-ylamino)-1-methyl-1H-pyrazol-4-yl)-2-(2,6-difluorophenyl)thiazole-4-carboxamide;
5-amino-N-(5-(2-(aminomethyl)morpholino)-1-methyl-1H-pyrazol-4-yl)-2-(2,6-difluorophenyl)thiazole-4-carboxamide;
(R)-5-amino-N-(5-(4-aminoazepan-1-yl)-1-methyl-1H-pyrazol-4-yl)-2-(5-chloro-2-fluorophenyl)thiazole-4-carboxamide;
(R)-5-amino-N-(5-(4-aminoazepan-1-yl)-1-methyl-1H-pyrazol-4-yl)-2-(3-bromo-2-fluorophenyl)thiazole-4-carboxamide;
(S)-5-amino-2-(2,6-difluorophenyl)-N-(5-(4-hydroxyazepan-1-yl)-1-methyl-1H-pyrazol-4-yl)thiazole-4-carboxamide;
(R)-5-amino-2-(2,6-difluorophenyl)-N-(5-(4-hydroxyazepan-1-yl)-1-methyl-1H-pyrazol-4-yl)thiazole-4-carboxamide;
5-amino-N-(5-(4-hydroxyazepan-1-yl)-1-methyl-1H-pyrazol-4-yl)-2-(pyridin-2-yl)thiazole-4-carboxamide;
(R)-5-amino-N-(5-(4-aminoazepan-1-yl)-1-methyl-1H-pyrazol-4-yl)-2-(2,3-difluorophenyl)thiazole-4-carboxamide;
5-amino-N-(5-(trans-3-aminocyclohexyl)-1-methyl-1H-pyrazol-4-yl)-2-(2,6-difluorophenyl)thiazole-4-carboxamide;
5-amino-N-(5-(cis-3-aminocyclohexyl)-1-methyl-1H-pyrazol-4-yl)-2-(2,6-difluorophenyl)thiazole-4-carboxamide;
(R)-5-amino-N-(5-(4-aminoazepan-1-yl)-1-methyl-1H-pyrazol-4-yl)-2-(pyridin-2-yl)thiazole-4-carboxamide;
(R)-5-amino-N-(5-(4-aminoazepan-1-yl)-1-methyl-1H-pyrazol-4-yl)-2-(2-fluoro-3-methylphenyl)thiazole-4-carboxamide;
(R)-5-amino-N-(5-(4-aminoazepan-1-yl)-1-methyl-1H-pyrazol-4-yl)-2-(3-cyclopropyl-2-fluorophenyl)thiazole-4-carboxamide;
(R)-5-amino-N-(5-(4-aminoazepan-1-yl)-1-methyl-1H-pyrazol-4-yl)-2-(3-ethyl-2-fluorophenyl)thiazole-4-carboxamide;
5-amino-N-(1-(2,2-difluoroethyl)-1H-pyrazol-4-yl)-2-(2,6-difluorophenyl)thiazole-4-carboxamide;
5-amino-2-(2,6-difluorophenyl)-N-(1-propyl-1H-pyrazol-4-yl)thiazole-4-carboxamide;
5-amino-2-(2,6-difluorophenyl)-N-(1-(2-hydroxyethyl)-1H-pyrazol-4-yl)thiazole-4-carboxamide;
N-(5-(1,4-diazepan-1-yl)-1-methyl-1H-pyrazol-4-yl)-3-amino-6-(2-fluorophenyl)picolinamide;
3-amino-6-(2-fluorophenyl)-N-(1-methyl-5-(1H-pyrrolo[3,4-c]pyridin-2(3H,3aH,4H,5H,6H,7H,7aH)-yl)-1H-pyrazol-4-yl)picolinamide;
5-Amino-N-(5-(4-(aminomethyl)piperidin-1-yl)-1-methyl-1H-pyrazol-4-yl)-2-(4-cyanophenyl)thiazole-4-carboxamide;
5-Amino-N-(5-(4-(aminomethyl)piperidin-1-yl)-1-methyl-1H-pyrazol-4-yl)-2-(5-fluoro-2-methoxyphenyl)thiazole-4-carboxamide;
(R)-5-amino-N-(5-(4-aminoazepan-1-yl)-1-methyl-1H-pyrazol-4-yl)-2-(3-cyclopropyl-2-fluorophenyl)thiazole-4-carboxamide;
(R)-5-amino-N-(5-(4-aminoazepan-1-yl)-1-cyclopropyl-1H-pyrazol-4-yl)-2-cyclopentenylthiazole-4-carboxamide;
(R)-5-amino-N-(5-(4-aminoazepan-1-yl)-1-ethyl-1H-pyrazol-4-yl)-2-cyclopentenylthiazole-4-carboxamide;
5-amino-N-(5-(4-amino-3-fluoroazepan-1-yl)-1-methyl-1H-pyrazol-4-yl)-2-(2,6-difluorophenyl)thiazole-4-carboxamide;
(R)-5-amino-N-(5-(4-aminoazepan-1-yl)-1-methyl-1H-pyrazol-4-yl)-2-(3-ethyl-2-fluorophenyl)thiazole-4-carboxamide;
5-amino-2-(2,6-difluorophenyl)-N-(1-(2,2,2-trifluoroethyl)-1H-pyrazol-4-yl)thiazole-4-carboxamide;

(R)-5-amino-N-(5-(4-aminoazepan-1-yl)-1-cyclopropyl-1H-pyrazol-4-yl)-2-(2,5-difluorophenyl)thiazole-4-carboxamide;
5-amino-2-(2,6-difluorophenyl)-N-(1-(2-methoxyethyl)-1H-pyrazol-4-yl)thiazole-4-carboxamide;
(R)-5-amino-N-(5-(4-aminoazepan-1-yl)-1-ethyl-1H-pyrazol-4-yl)-2-(2-fluoro-5-methylphenyl)thiazole-4-carboxamide;
5-amino-N-(5-((4S,5S)-4-amino-5-fluoroazepan-1-yl)-1-methyl-1H-pyrazol-4-yl)-2-(2,6-difluorophenyl)thiazole-4-carboxamide;
5-amino-N-(5-((4S,5R)-4-amino-5-fluoroazepan-1-yl)-1-methyl-1H-pyrazol-4-yl)-2-(2,6-difluorophenyl)thiazole-4-carboxamide;
(R)-5-amino-N-(5-(4-aminoazepan-1-yl)-1-methyl-1H-pyrazol-4-yl)-2-(2-fluoro-3-isopropylphenyl)thiazole-4-carboxamide;
(R)-5-amino-N-(5-(4-aminoazepan-1-yl)-1-cyclopropyl-1H-pyrazol-4-yl)-2-(2-fluoro-5-methylphenyl)thiazole-4-carboxamide;
(R)-5-amino-N-(5-(4-aminoazepan-1-yl)-1-ethyl-1H-pyrazol-4-yl)-2-(2,5-difluorophenyl)thiazole-4-carboxamide;
(R)-5-amino-N-(5-(4-aminoazepan-1-yl)-1-(cyclopropylmethyl)-1H-pyrazol-4-yl)-2-(2-fluoro-5-methylphenyl)thiazole-4-carboxamide;
(R)-5-amino-N-(5-(4-aminoazepan-1-yl)-1-methyl-1H-pyrazol-4-yl)-2-(5-cyclopropyl-2-fluorophenyl)thiazole-4-carboxamide;
5-amino-2-(2,6-difluorophenyl)-N-(1-(2-(methylsulfonyl)ethyl)-1H-pyrazol-4-yl)thiazole-4-carboxamide;
(R)-5-amino-N-(5-(4-aminoazepan-1-yl)-1-methyl-1H-pyrazol-4-yl)-2-(5-ethyl-2-fluorophenyl)thiazole-4-carboxamide;
5-amino-2-(2,6-difluorophenyl)-N-(1-methyl-5-(5-(trifluoromethyl)-1,4-diazepan-1-yl)-1H-pyrazol-4-yl)thiazole-4-carboxamide;
(R)-5-amino-N-(5-(4-aminoazepan-1-yl)-1-(cyclopropylmethyl)-1H-pyrazol-4-yl)-2-(2,5-difluorophenyl)thiazole-4-carboxamide;
5-amino-N-(5-(6,6-difluoro-1,4-diazepan-1-yl)-1-methyl-1H-pyrazol-4-yl)-2-(2,6-difluorophenyl)thiazole-4-carboxamide;
5-amino-2-(2-fluorophenyl)-N-(5-(4-hydroxy-4-methylazepan-1-yl)-1-methyl-1H-pyrazol-4-yl)thiazole-4-carboxamide;
N-(5-(1,4-diazepan-1-yl)-1-(2,2-difluoroethyl)-1H-pyrazol-4-yl)-5-amino-2-(2,6-difluorophenyl)thiazole-4-carboxamide;
5-amino-2-(2,6-difluorophenyl)-N-(1-(oxetan-3-ylmethyl)-1H-pyrazol-4-yl)thiazole-4-carboxamide;
5-amino-N-(5-(5-amino-4,4-difluoroazepan-1-yl)-1-methyl-1H-pyrazol-4-yl)-2-(2,6-difluorophenyl)thiazole-4-carboxamide;
(R)-5-amino-N-(5-(4-aminoazepan-1-yl)-1-(2,2-difluoroethyl)-1H-pyrazol-4-yl)-2-(2-fluoro-5-methylphenyl)thiazole-4-carboxamide;
N-(5-(1,4-diazepan-1-yl)-1-(2,2-difluoroethyl)-1H-pyrazol-4-yl)-5-amino-2-(2-fluoro-5-methylphenyl)thiazole-4-carboxamide;
N-(5-(1,4-diazepan-1-yl)-1-(2,2-difluoroethyl)-1H-pyrazol-4-yl)-5-amino-2-(2,5-difluorophenyl)thiazole-4-carboxamide;
5-amino-N-(5-(3-aminoazepan-1-yl)-1-(2,2-difluoroethyl)-1H-pyrazol-4-yl)-2-(2,6-difluorophenyl)thiazole-4-carboxamide;
5-amino-N-(1-cyclobutyl-1H-pyrazol-4-yl)-2-(2,6-difluorophenyl)thiazole-4-carboxamide; and
5-amino-2-(2,6-difluorophenyl)-N-(1-methyl-5-(6-methyl-1,4-diazepan-1-yl)-1H-pyrazol-4-yl)thiazole-4-carboxamide.

\* \* \* \* \*